US012173018B2

(12) United States Patent
Burns et al.

(10) Patent No.: US 12,173,018 B2
(45) Date of Patent: Dec. 24, 2024

(54) PENICILLIN-BINDING PROTEIN INHIBITORS

(71) Applicant: VenatoRx Pharmaceuticals, Inc., Malvern, PA (US)

(72) Inventors: Christopher J. Burns, Malvern, PA (US); Denis Daigle, Street, MD (US); Guo-Hua Chu, Exton, PA (US); Jodie Hamrick, New Holland, PA (US); Steven A. Boyd, Chester Springs, PA (US); Allison L Zulli, Chesterbrook, PA (US); Eugen F. Mesaros, Wallingford, PA (US); Stephen M. Condon, Glenmoore, PA (US); Robert E. Lee Trout, Collegeville, PA (US); Cullen L. Myers, Exton, PA (US); Zhenrong Xu, Chalfont, PA (US)

(73) Assignee: VENATORX PHARMACEUTICALS, INC., Malvern, PA (US)

( * ) Notice: Subject to any disclaimer, the term of this patent is extended or adjusted under 35 U.S.C. 154(b) by 964 days.

(21) Appl. No.: 17/057,593

(22) PCT Filed: May 23, 2019

(86) PCT No.: PCT/US2019/033813
§ 371 (c)(1),
(2) Date: Nov. 20, 2020

(87) PCT Pub. No.: WO2019/226931
PCT Pub. Date: Nov. 28, 2019

(65) Prior Publication Data
US 2021/0198288 A1 Jul. 1, 2021

Related U.S. Application Data

(60) Provisional application No. 62/772,056, filed on Nov. 27, 2018, provisional application No. 62/676,793, filed on May 25, 2018.

(51) Int. Cl.
*A61P 31/04* (2006.01)
*C07F 5/02* (2006.01)

(52) U.S. Cl.
CPC .............. *C07F 5/025* (2013.01); *A61P 31/04* (2018.01)

(58) Field of Classification Search
CPC ....................................................... C07F 5/025
See application file for complete search history.

(56) References Cited

U.S. PATENT DOCUMENTS

| | | | |
|---|---|---|---|
| 4,427,690 A | 1/1984 | Cole et al. | |
| 7,271,186 B1 | 9/2007 | Shoichet et al. | |
| 7,714,159 B2 | 5/2010 | Pickersgill et al. | |
| 8,283,467 B2 | 10/2012 | Ammoscato et al. | |
| 8,680,136 B2 | 3/2014 | Hirst et al. | |
| 8,912,169 B2 | 12/2014 | Burns et al. | |
| 9,040,504 B2 | 5/2015 | Burns et al. | |
| 9,101,638 B2 | 8/2015 | Reddy et al. | |
| 9,376,454 B2 | 6/2016 | Burns et al. | |
| 9,403,850 B2 | 8/2016 | Burns et al. | |
| 9,422,314 B2 | 8/2016 | Burns et al. | |
| 9,511,142 B2 | 12/2016 | Burns et al. | |
| 9,637,504 B2 | 5/2017 | Burns et al. | |
| 9,642,869 B2 | 5/2017 | Reddy et al. | |
| 9,771,382 B2 | 9/2017 | Burns et al. | |
| 9,783,555 B2 | 10/2017 | Burns et al. | |
| 9,802,966 B2 | 10/2017 | Burns et al. | |
| 9,828,391 B2 | 11/2017 | Burns et al. | |
| 9,926,336 B2 | 3/2018 | Burns et al. | |
| 9,944,658 B2 | 4/2018 | Burns et al. | |
| 9,963,467 B2 | 5/2018 | Reddy et al. | |
| 10,125,152 B2 | 11/2018 | Burns et al. | |
| 10,206,937 B2 | 2/2019 | Reddy et al. | |
| 10,214,547 B2 | 2/2019 | Burns et al. | |
| 10,294,247 B2 | 5/2019 | Burns et al. | |
| 10,294,248 B2 | 5/2019 | Burns et al. | |
| 10,399,996 B2 | 9/2019 | Burns et al. | |
| 10,464,952 B2 | 11/2019 | Burns et al. | |
| 10,479,805 B2 | 11/2019 | Wu et al. | |
| 10,669,290 B2 | 6/2020 | Burns et al. | |
| 10,889,600 B2 | 1/2021 | Amann et al. | |
| 2009/0156518 A1 | 6/2009 | Zhang | |
| 2010/0056478 A1 | 3/2010 | Desarbre et al. | |
| 2010/0120715 A1 | 5/2010 | Burns et al. | |
| 2010/0286092 A1 | 11/2010 | Burns et al. | |

(Continued)

FOREIGN PATENT DOCUMENTS

| CN | 1965838 A | 5/2007 |
|---|---|---|
| CN | 105801610 A | 7/2016 |

(Continued)

OTHER PUBLICATIONS

PCT/US2022/021883 International Search Report and Written Opinion dated May 17, 2022.
Contreras-Martel et al. Structure-guided design of cell wall biosynthesis inhibitors that overcome β-lactam resistance in *Staphylococcus aureus* (MRSA). ACS Chem Biol 6(7):943-951 (2011).
Inglis et al. Synthesis and evaluation of 3-(dihydroxyboryl)benzoic acids as D,D-carboxypeptidase R39 inhibitors. J Med Chem 52:6097-6106 (2009).
U.S. Appl. No. 16/616,294 Office Action dated Jun. 18, 2021.
Woon et al. Structure guided development of potent reversibly binding penicillin binding protein inhibitors. ACS Med Chem Lett 2(1):219-223 (2011).

(Continued)

*Primary Examiner* — Svetlana M Ivanova
(74) *Attorney, Agent, or Firm* — WILSON SONSINI GOODRICH & ROSATI

(57) ABSTRACT

Described herein are certain boron-containing compounds, compositions, preparations and their use as modulators of the transpeptidase function of bacterial penicillin-binding proteins and as antibacterial agents. In some embodiments, the compounds described herein inhibit penicillin-binding proteins. In certain embodiments, the compounds described herein are useful in the treatment of bacterial infections.

17 Claims, No Drawings

(56) References Cited

U.S. PATENT DOCUMENTS

| | | |
|---|---|---|
| 2010/0292185 A1 | 11/2010 | Burns et al. |
| 2010/0317621 A1 | 12/2010 | Burns et al. |
| 2011/0294777 A1 | 12/2011 | Blizzard et al. |
| 2012/0040932 A1 | 2/2012 | Hirst et al. |
| 2014/0171390 A1 | 6/2014 | Burns et al. |
| 2014/0194385 A1 | 7/2014 | Reddy et al. |
| 2014/0194386 A1 | 7/2014 | Burns et al. |
| 2015/0094472 A1 | 4/2015 | Hecker et al. |
| 2015/0291630 A1 | 10/2015 | Burns et al. |
| 2015/0361107 A1 | 12/2015 | Trout |
| 2015/0361108 A1 | 12/2015 | Burns et al. |
| 2017/0073360 A1 | 3/2017 | Burns et al. |
| 2017/0145037 A1 | 5/2017 | Burns et al. |
| 2017/0281639 A1 | 10/2017 | Kawasaki et al. |
| 2017/0342092 A1 | 11/2017 | Burns et al. |
| 2018/0002351 A1 | 1/2018 | Hecker et al. |
| 2018/0273552 A1 | 9/2018 | Burns et al. |
| 2020/0010485 A1 | 1/2020 | Burns et al. |
| 2020/0055877 A1 | 2/2020 | Burns et al. |
| 2020/0102331 A1 | 4/2020 | Burns et al. |
| 2020/0157123 A1 | 5/2020 | Burns et al. |
| 2020/0317698 A1 | 10/2020 | Burns et al. |
| 2020/0361962 A1 | 11/2020 | Burns et al. |
| 2021/0163506 A1 | 6/2021 | Amann et al. |
| 2022/0002322 A1 | 1/2022 | Burns et al. |
| 2022/0054513 A1 | 3/2022 | Hamrick et al. |
| 2022/0125812 A1 | 4/2022 | Burns et al. |
| 2023/0114728 A1 | 4/2023 | Burns et al. |

FOREIGN PATENT DOCUMENTS

| | | |
|---|---|---|
| EP | 2152279 A2 | 2/2010 |
| KR | 20130064004 A | 6/2013 |
| RU | 2012107163 A | 9/2013 |
| WO | WO-2005004799 A2 | 1/2005 |
| WO | WO-2009064413 A1 | 5/2009 |
| WO | WO-2009064414 A1 | 5/2009 |
| WO | WO-2009124167 A1 | 10/2009 |
| WO | WO-2010030810 A1 | 3/2010 |
| WO | WO-2010050468 A1 | 5/2010 |
| WO | WO-2010056827 A1 | 5/2010 |
| WO | WO-2010130708 A1 | 11/2010 |
| WO | WO-2012021455 A1 | 2/2012 |
| WO | WO-2013014497 A1 | 1/2013 |
| WO | WO-2013053372 A1 | 4/2013 |
| WO | WO-2013092979 A1 | 6/2013 |
| WO | WO-2013122888 A2 | 8/2013 |
| WO | WO-2014086664 A1 | 6/2014 |
| WO | WO-2014089365 A1 | 6/2014 |
| WO | WO-2014107535 A1 | 7/2014 |
| WO | WO-2014107536 A1 | 7/2014 |
| WO | WO-2014110442 A1 | 7/2014 |
| WO | WO-2014151958 A1 | 9/2014 |
| WO | WO-2015157618 A1 | 10/2015 |
| WO | WO-2015171398 A1 | 11/2015 |
| WO | WO-2015171430 A1 | 11/2015 |
| WO | WO-2015179308 A1 | 11/2015 |
| WO | WO-2015191907 A1 | 12/2015 |
| WO | WO-2016003929 A1 | 1/2016 |
| WO | WO-2016100043 A1 | 6/2016 |
| WO | WO-2017044828 A1 | 3/2017 |
| WO | WO-2017100537 A1 | 6/2017 |
| WO | WO-2018027062 A1 | 2/2018 |
| WO | WO-2018165048 A1 | 9/2018 |
| WO | WO-2018218154 A1 | 11/2018 |
| WO | WO-2018218190 A1 | 11/2018 |
| WO | WO-2019226931 A1 | 11/2019 |
| WO | WO-2020056048 A1 | 3/2020 |
| WO | WO-2020112542 A1 | 6/2020 |
| WO | WO-2020205932 A1 | 10/2020 |
| WO | WO-2021108023 A1 | 6/2021 |
| WO | WO-2022250776 A1 | 12/2022 |

OTHER PUBLICATIONS

Burns et al. Accession No. 2014:955904. STN International Caplus database, (Columbus, Ohio) (2014).

Bertsche et al. In vitro murein peptidoglycan synthesis by dimers of the bifunctional transglycosylase-transpeptidase PBP1B from *Escherichia coli*. J Biol Chem 280(45):38096-38101 (2005).

Born et al. In vitro synthesis of cross-linked murein and its attachment to sacculi by PBP1A from *Escherichia coli*. J Biol Chem 281(37):26985-26993 (2006).

Brasholz et al. An Expedient and Short Synthesis of a 6-Iodo Isocoumarin Building Block for the Rubromycin Family and its First Palladium-Catalyzed Couplings. Synlett 2004(15):2736-2738 (2004).

Burns et al. Caplus AN 2014-1130723 (1 pg.) (2014).

Bush et al. Updated functional classification of β-lactamases. Antimicrob Agents Chemother 54(3):969-976 (2010) (Epub: Dec. 7, 2009).

Dudley et al. Caplus 2013:1302853 (WO2013/122888).

Eidam et al. Design, synthesis, crystal structures, and antimicrobial activity of sulfonamide boronic acids as β-lactamase inhibitors. J. Med. Chem. 53(21):7852-7863 (2010).

Hanaki et al. TOC-39, a novel parenteral broad-spectrum cephalosporin with excellent activity against methicillin-resistant *Staphylococcus aureus*. Antimicrobial Agents and Chemotherapy 39(5):1120-1126 (1995).

Hardy et al. The Chemistry of Some 2-Aminothiazol-4-ylacetic Acid Derivatives and the Synthesis of Derived Penicillins. J Chem Soc Perkin Trans 1:1227-1235 (1984).

Ishikura et al. Synthesis and structure-activity relationships of 7 beta-[(Z)-2-(2-aminothiazol-4-yl)-3-(substituted)-2-propenoyl-amino]-3-desacetoxymethylcephalosporins. J. Antibiotics 47:453-465 (1994).

Jacoby. β-lactamase classification and amino acid sequences for TEM, SHV, and OXA extended-spectrum and inhibitor resistant enzymes. Lahey Clinic, [cited May 14, 2014] Available from: http://www.lahey.org/Studies/.

Katsube et al. Cefiderocol, a Siderophore Cephalosporin for Gram-Negative Bacterial Infections: Pharmacokinetics and Safety in Subjects With Renal Impairment. J Clin Pharmacol 57(5):584-591 (2017).

King et al. Molecular Mechanism of Avibactam-Mediated β-Lactamase Inhibition. ACS Infect Dis 1(4):175-84 (2015).

Lima et al. Bioisosterism: A Useful Strategy for Molecular Modification and Drug Design. Current Medicinal Chemistry 12:23-49 (2005).

Martin et al. Rational design and synthesis of a highly effective transition state analog inhibitor of the RTEM-1 β-lactamase. Tetrahedron Lett. 36:8399-8402 (1995).

Matteson. Boronic esters in asymmetric synthesis. J Org Chem 78:10009-10023 (2013).

Matteson et al. Synthesis of 1-amino-2-phenylethane-1-boronic acid derivatives. Organometallics 3:614-18 (1984).

Molander et al. Synthesis and Suzuki-Miyaura cross-coupling reactions of potassium Boc-protected aminomethyltrifluoroborate with aryl and hetaryl halides. Organic Letters 13(15):3956-3959 (2011).

Morandi et al. Structure-based optimization of cephalothin-analogue boronic acids as β-lactamase inhibitors. Bioorg. Med. Chem. 16(3):1195-1205 (2008) (Epub: Nov. 7, 2007).

Ness et al. Structure-based design guides the improved efficacy of deacylation transition state analogue inhibitors of TEM-1 β-lactamase. Biochemistry 39(18):5312-5321 (2000).

Page. The kinetics of non-stoichiometric bursts of beta-lactam hydrolysis catalysed by class C beta-lactamases. Biochem J 295:295-304 (1993).

Patani et al. Bioisosterism: A Rational Approach in Drug Design. Chemical Reviews 96:3147-3176 (1996).

Payne et al. Comparative activities of clavulanic acid, sulbactam, and tazobactam against clinically important β-lactamases. Antimicrobial Agents and Chemotherapy 38(4):767-772 (1994).

PCT/US2018/034660 International Search Report and Written Opinion dated Sep. 14, 2018.

PCT/US2018/034722 International Search Report and Written Opinion dated Sep. 14, 2018.

PCT/US2019/033813 International Search Report and Written Opinion dated Sep. 10, 2019.

(56) References Cited

OTHER PUBLICATIONS

Powers et al. Structure-based approach for binding site identification on AmpC β-lactamase. J. Med. Chem. 45(15):3222-3234 (2002).

Powers et al. Structures of ceftazidime and its transition-state analogue in complex with AmpC β-lactamase: implications for resistance mutations and inhibitor design. Biochemistry 40(31):9207-9214 (2001).

Pub Chem Substance Record for SID 197433672. https://pubchem.ncbi.nim.nih/substance/197433672. Created Aug. 18, 2014. Retrieved Jan. 10, 2017 (5 pgs).

Reddy et al. Caplus 2014:1118372 (2014) (2 pgs.).

Saulnier et al. An efficient method for the synthesis of guanidino prodrugs. Bioorganic & Medicinal Chemistry Letters. 4(16): 1985-1990 (1994).

U.S. Appl. No. 16/616,294 Office Action dated Feb. 8, 2021.

Watkins et al. Novel β-lactamase inhibitors: a therapeutic hope against the scourge of multi-drug resistance. © Dec. 24, 2013. Accessed Jul. 7, 2018. (18 pgs) (2013).

Weston et al. Structure-based enhancement of boronic acid-based inhibitors of AmpC β-lactamase. J. Med. Chem. 41(23):4577-4586 (1998).

Winkler et al. Design and exploration of novel boronic acid inhibitors reveals important interactions with a clavulanic acid-resistant sulfhydryl-variable (SHV) β-lactamase. J Med Chem 56:1084-1097 (2013) (Publication Date (Web): Dec. 19, 2012).

Burns et al. Penicillin-binding protein inhibitors. Database accession No. 2019:2257399. Chemical Abstract Service, Columbus, Ohio, US (Nov. 28, 2019).

Co-pending U.S. Appl. No. 18/563,292, inventors Burns; Christopher J. et al., filed on Nov. 21, 2023.

Hinkle et al. In Vitro Evaluation of Cefoperazone. Antimicrob Agents Chemother 17(3):423-427 (1980).

U.S. Appl. No. 17/057,593 Office Action dated Jan. 24, 2024.

Krajnc et al., Bicyclic boronate VNRX-5133 inhibits metallo- and serine-beta-lactamases. Journal of Medicinal Chemistry 62(18):8544-8556 (2019).

PCT/US2020/052439 International Search Report and Written Opinion dated Dec. 31, 2020.

PENICILLIN-BINDING PROTEIN INHIBITORS

CROSS-REFERENCE

This patent application is a national stage entry of PCT/US2019/033813, filed on May 23, 2019, which claims the benefit of U.S. Provisional Application No. 62/676,793, filed May 25, 2018 and U.S. Provisional Application No. 62/772,056, filed Nov. 27, 2018; which are incorporated herein by reference in their entirety.

STATEMENT AS TO FEDERALLY SPONSORED RESEARCH

This invention was made with the support of the United States government under SBIR Grant number 5R43AI094827 by the National Institutes of Health (NIH), Federal Award 6 IDSEP16030-01-02, subaward 4500002377, awarded by the Health and Human Services Office of the Assistant Secretary for Preparedness and Response (HHS/ASPR) under the CARB-X Pass Through Entity, and contract HDTRA117C0070, awarded by the Defense Threat Reduction Agency (DTRA) of the Department of Defense. The government has certain rights in the invention.

BACKGROUND OF THE INVENTION

Antibiotics are the most effective drugs for curing bacteria-related infectious diseases clinically. They are incredibly valuable therapeutic options that are currently losing efficacy due to the evolution and spread of drug resistance genes, leading to multidrug resistance bacterial organisms. Among the different classes of antibiotics, the penicillin-binding protein-targeting beta-lactams (e.g. penicillins, cephalosporins, and carbapenems) are the most widely used antibiotic class because they have a strong bactericidal effect and low associated toxicity.

Penicillin Binding Proteins (PBPs) are a family of essential bacterial enzymes involved in the synthesis of peptidoglycan, the major structural polymer found in the bacterial cell wall. Beta-lactam antibiotics bind with high affinity to PBPs and inhibit their transpeptidase function, resulting in disruption of peptidoglycan cell wall synthesis and rapid cell lysis of actively dividing bacteria. As there are no close mammalian homologues to PBPs, and beta-lactams are well-regarded for their safety and efficacy, PBPs represent an ideal target for antibacterials.

SUMMARY OF THE INVENTION

Described herein are compounds that inhibit the activity of penicillin-binding proteins, the bacterial enzyme class targeted by the beta lactam antibiotics and do provide significant antibacterial activity in vitro.

Also provided herein are compounds of Formula (Ia) or (Ib), or a pharmaceutically acceptable salt, solvate, stereoisomer, tautomer, N-oxide, dimer, or trimer thereof:

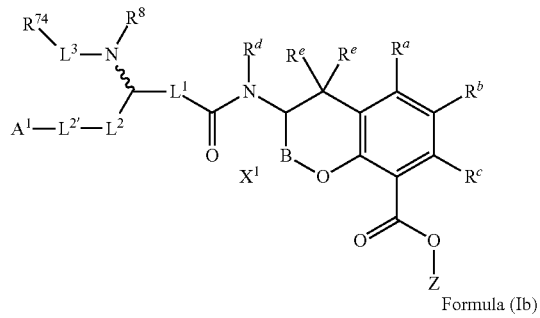

Formula (Ia)

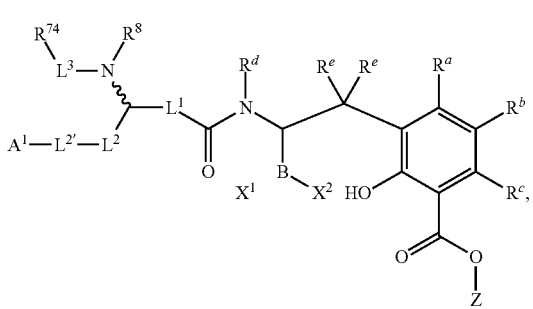

Formula (Ib)

wherein:
$L^1$ is —$(CR^1R^2)_n$—;
$L^2$ is —$(CR^1R^2)_m$—;
$L^{2'}$ is absent, —C(=O)NH—, —NHC(=O)—, or —CH$_2$NH—;
$L^3$ is —C(=O)—, —S(=O)—, or —S(=O)$_2$—;
$A^1$ is

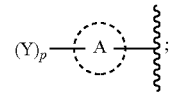

Ring A is a 6-membered aryl or a 6-membered heteroaryl;
each $R^1$ and $R^2$ is independently hydrogen, halogen, optionally substituted alkyl, —OH, —OR$^{34}$, —SR$^{35}$, —NR$^{32}$R$^{33}$, —NR$^{32}$C(=O)R$^{34}$, —C(=O)NR$^{32}$R$^{33}$, —NR$^{32}$S(=O)$_2$R$^{34}$, —C(=O)OH, —C(=O)OR$^{34}$, optionally substituted cycloalkyl, optionally substituted heterocycloalkyl, optionally substituted aryl, or optionally substituted heteroaryl; or
$R^1$ and $R^2$ are taken together with the carbon to which they are attached to form an optionally substituted cycloalkyl;
$R^8$ is hydrogen, optionally substituted alkyl, optionally substituted cycloalkyl, optionally substituted heterocycloalkyl, optionally substituted aryl, or optionally substituted heteroaryl;
each $R^{20}$ and $R^{21}$ is independently hydrogen, halogen, or optionally substituted alkyl;
$R^{22}$ and $R^{23}$ are independently hydrogen or optionally substituted alkyl; or
$R^{22}$ and $R^{23}$ are taken together with the nitrogen to which they are attached to form an optionally substituted heterocycloalkyl;
$R^{24}$ is optionally substituted alkyl, optionally substituted cycloalkyl, optionally substituted heterocycloalkyl, optionally substituted aryl, or optionally substituted heteroaryl;

$R^{25}$ is hydrogen, optionally substituted alkyl, optionally substituted cycloalkyl, optionally substituted heterocycloalkyl, optionally substituted aryl, or optionally substituted heteroaryl;

each $R^{30}$, $R^{31}$, $R^{50}$, and $R^{51}$ is independently hydrogen, halogen, optionally substituted alkyl, optionally substituted cycloalkyl, optionally substituted heterocycloalkyl, optionally substituted aryl, optionally substituted heteroaryl, —OH, —OR$^{24}$, —SR$^{25}$, —NR$^{22}$R$^{23}$, —NR$^{22}$C(=O)R$^{24}$, —C(=O)NR$^{22}$R$^{23}$, —NR$^{22}$S(=O)$_2$R$^{24}$, —C(=O)OH, or —C(=O)OR$^{24}$; or $R^{30}$ and $R^{31}$, or $R^{50}$ and $R^{51}$ are taken together with the carbon atom to which they are attached to form an optionally substituted cycloalkyl; or two $R^{30}$ or two $R^{50}$ on adjacent carbons are taken together to form an alkenyl; or two $R^{30}$ and two $R^{31}$, or two $R^{50}$ and two R on adjacent carbons are taken together to form an alkynyl;

$R^{32}$, $R^{33}$, $R^{52}$, $R^{53}$, $R^{82}$, and $R^{83}$ are independently hydrogen, optionally substituted alkyl, optionally substituted cycloalkyl, optionally substituted heterocycloalkyl, optionally substituted aryl, optionally substituted heteroaryl, (poly-ethylene-glycol)-ethyl, optionally substituted saccharide, —CN, —OH, —S(=O)$_2$R$^{24}$, —S(=O)$_2$NR$^{22}$R$^{23}$, or —C(=O)R$^{24}$; or $R^{32}$ and $R^{33}$, or $R^{52}$ and $R^{53}$, or $R^{82}$ and $R^{83}$ are taken together with the nitrogen to which they are attached to form an optionally substituted heterocycloalkyl;

$R^{34}$, $R^{54}$, and $R^{84}$ are independently optionally substituted alkyl, optionally substituted cycloalkyl, optionally substituted heterocycloalkyl, optionally substituted aryl, or optionally substituted heteroaryl;

$R^{35}$ and $R^{55}$ are independently hydrogen, optionally substituted alkyl, optionally substituted cycloalkyl, optionally substituted heterocycloalkyl, optionally substituted aryl, or optionally substituted heteroaryl;

$R^{36}$ and $R^{56}$ are independently hydrogen, —OH, —OR$^{24}$, —CN, —NO$_2$, —NR$^{22}$R$^{23}$, or optionally substituted alkyl;

Z is hydrogen, $R^{61}$, —(R$^{60}$)$_q$OR$^{61}$, —(R$^{60}$)$_q$O(R$^{60}$)$_q$OR$^{61}$, —R$^{60}$C(=O)R$^{61}$, —R$^{60}$OC(=O)OR$^{61}$, —R$^{60}$OC(=O)NHR$^{61}$, —R$^{60}$OC(=O)N(R$^{61}$)$_2$, optionally substituted alkyloxyalkyl, optionally substituted acyloxyalkyl, optionally substituted alkyloxycarbonyloxyalkyl, optionally substituted cycloalkyloxycarbonyloxyalkyl, optionally substituted aryloxycarbonyloxyalkyl, or optionally substituted alkyl-[1,3]dioxol-2-one;

each $R^{60}$ is independently —CH$_2$—, —CH(CH$_3$)—, —C(CH$_3$)$_2$—, or optionally substituted 1,1'-cyclopropylene;

each $R^{61}$ is independently optionally substituted alkyl, optionally substituted cycloalkyl, optionally substituted heterocycloalkyl, optionally substituted aryl, or optionally substituted heteroaryl; or two $R^{61}$ are taken together with the nitrogen to which they are attached to form an optionally substituted heterocycloalkyl;

$R^{74}$ is optionally substituted alkyl, optionally substituted cycloalkyl, optionally substituted heterocycloalkyl, optionally substituted aryl, optionally substituted heteroaryl, optionally substituted cycloalkylalkyl, optionally substituted heterocycloalkylalkyl, optionally substituted aralkyl, optionally substituted heteroaralkyl, —OH, —OR$^{54}$, —NR$^{82}$R$^{83}$, —C(=O)OH, or —C(=O)OR$^{54}$;

$R^a$, $R^b$, and $R^c$ are independently hydrogen, halogen, cyano, optionally substituted alkyl, optionally substituted cycloalkyl, optionally substituted heterocycloalkyl, optionally substituted aryl, optionally substituted heteroaryl, —OH, —OR$^{54}$, —O(CR$^{50}$R$^{51}$)$_w$NR$^{52}$R$^{53}$, —O(CR$^{50}$R$^{51}$)$_v$OH, —O(CR$^{50}$R$^{51}$)$_w$OR$^{54}$, —O(CR$^{50}$R$^{51}$)$_v$C(=O)OH, —O(CR$^{50}$R$^{51}$)$_v$C(=O)OR$^{54}$, —O(CR$^{50}$R$^{51}$)$_v$C(=O)NR$^{52}$R$^{53}$, —NR$^{52}$R$^{53}$, —NR$^{52}$(CR$^{50}$R$^{51}$)$_w$NR$^{52}$R$^{53}$, —NR$^{52}$(CR$^{50}$R$^{51}$)$_v$C(=O)OH, NR$^{52}$(CR$^{50}$R$^{51}$)$_v$C(=O)OR$^{54}$, —NR$^{52}$(CR$^{50}$R$^{51}$)$_v$C(=O)NR$^{52}$R$^{53}$, —NR$^{52}$S(=O)$_{1,2}$R$^{54}$, —S(=O)$_{1,2}$R$^{54}$, —SR$^{55}$, —S(CR$^{50}$R$^{51}$)$_v$NR$^{52}$C(=NR$^{56}$)NR$^{52}$R$^{53}$, —S(CR$^{50}$R$^{51}$)$_v$NR$^{52}$CR$^{50}$(=NR$^{56}$), —S(CR$^{50}$R$^{51}$)$_v$C(=NR$^{56}$)NR$^{52}$R$^{53}$, —S(CR$^{50}$R$^{51}$)$_v$OH, —S(CR$^{50}$R$^{51}$)$_w$OR$^{54}$, —S(CR$^{50}$R$^{51}$)$_w$NR$^{52}$R$^{53}$, —S(CR$^{50}$R$^{51}$)$_v$C(=O)OH, —S(CR$^{50}$R$^{51}$)$_v$C(=O)OR$^{54}$, —S(CR$^{50}$R$^{51}$)$_v$C(=O)NR$^{52}$R$^{53}$, —C(=O)H, —C(=O)R$^{54}$, —C(=O)OH, —C(=O)OR$^{54}$, —C(=O)NR$^{52}$R$^{53}$, —(CR$^{50}$R$^{51}$)$_v$N(R$^{52}$)(CR$^{50}$R$^{51}$)$_v$C(=O)OH, —(CR$^{50}$R$^{51}$)$_v$OH, —(CR$^{50}$R$^{51}$)$_v$OR$^{54}$, —(CR$^{50}$R$^{51}$)$_v$C(=O)OH, —(CR$^{50}$R$^{51}$)$_v$C(=O)OR$^{54}$, —(CR$^{50}$R$^{51}$)$_v$C(=O)NR$^{52}$R$^{53}$, —(CR$^{50}$R$^{51}$)$_v$OC(=O)R$^{54}$, —(CR$^{50}$R$^{51}$)$_v$SR$^{55}$, —(CR$^{50}$R$^{51}$)$_v$NR$^{52}$C(=NR$^{56}$), —(CR$^{50}$R$^{51}$)$_v$NR$^{52}$R$^{53}$, —(CR$^{50}$R$^{51}$)$_v$C(=NR$^{56}$)NR$^{52}$R$^{53}$, —(CR$^{50}$R$^{51}$)$_v$C(=O)NR$^{52}$R$^{53}$, —(CR$^{50}$R$^{51}$)$_v$heterocycloalkyl, or —(CR$^{50}$R$^{51}$)$_v$heteroaryl;

$R^d$ is hydrogen, —CN, —OH, —S(=O)$_2$R$^{24}$, —S(=O)$_2$NR$^{22}$R$^{23}$, —(CR$^{20}$R$^{21}$)$_v$C(=O)OH, —C(=O)R$^{24}$ optionally substituted alkyl, optionally substituted cycloalkyl, optionally substituted heterocycloalkyl, optionally substituted aryl, optionally substituted heteroaryl, (poly-ethylene-glycol)-ethyl, or an optionally substituted saccharide;

each $R^e$ is independently hydrogen, —CN, —OH, optionally substituted alkyl, or optionally substituted cycloalkyl;

$R^X$ is optionally substituted alkyl or optionally substituted cycloalkyl;

$X^1$ and $X^2$ are independently —OH, —OR$^X$, or F; or $X^1$ and $X^2$ are taken together with the boron atom to which they are attached to form a cyclic boronate ester;

each Y is independently halogen, optionally substituted alkyl, optionally substituted cycloalkyl, optionally substituted heterocycloalkyl, optionally substituted aryl, optionally substituted heteroaryl, -heteroaryl-NR$^{32}$R$^{33}$, -heterocycloalkyl-NR$^{32}$R$^{33}$, -heteroaryl-N(R$^{32}$)C(=NR$^{32}$)NR$^{32}$R$^{33}$, -heterocycloalkyl-N(R$^{32}$)C(=NR$^{32}$)NR$^{32}$R$^{33}$, —OH, —OR$^{34}$, —O(CR$^{30}$R$^{31}$)$_w$OH, —O(CR$^{30}$R$^{31}$)OR$^{34}$, —O(CR$^{30}$R$^{31}$)$_w$NR$^{32}$R$^{33}$, —O(CR$^{30}$R$^{31}$)$_v$NR$^{32}$C(=O)R$^{34}$, —O(CR$^{30}$R$^{31}$)$_w$NR$^{32}$C(=O)OR$^{34}$, —O(CR$^{30}$R$^{31}$)$_w$NR$^{32}$C(=O)NR$^{32}$R$^{33}$, —O(CR$^{30}$R$^{31}$)$_w$C(=O)NR$^{32}$R$^{33}$, —O(CR$^{30}$R$^{31}$)$_w$NR$^{32}$S(=O)$_{0,1,2}$R$^{34}$, —O(CR$^{30}$R$^{31}$)$_w$NR$^{32}$S(=O)$_{0,1,2}$NR$^{32}$R$^{33}$, —O(CR$^{30}$R$^{31}$)$_w$S(=O)$_{0,1,2}$R$^{34}$, —O(CR$^{30}$R$^{31}$)$_w$S(=O)$_{0,1,2}$NR$^{32}$R$^{33}$, —O(CR$^{30}$R$^{31}$)$_v$C(=NR$^{36}$)NR$^{32}$R$^{33}$, —O(CR$^{30}$R$^{31}$)$_w$N(R$^{32}$)C(=NR$^{36}$)R$^{34}$, —O(CR$^{30}$R$^{31}$)$_v$C(=NR$^{36}$)NR$^{32}$C(=NR$^{36}$)NR$^{32}$R$^{33}$, —O(CR$^{30}$R$^{31}$)$_w$N(R$^{32}$)C(=NR$^{36}$)NR$^{32}$R$^{33}$, —O(CR$^{30}$R$^{31}$)$_w$S(=O)$_{0,1,2}$R$^{34}$, —O(CR$^{30}$R$^{31}$)$_w$S(=O)$_{0,1,2}$NR$^{32}$R$^{33}$, —OC(=O)R$^{34}$, —OC(=O)(CR$^{30}$R$^{31}$)$_w$NR$^{32}$R$^{33}$, —OC(=O)NR$^{32}$R$^{33}$, —OC(=O)OR$^{34}$, —OC(=O)NR$^{32}$(CR$^{30}$R$^{31}$)$_w$NR$^{32}$R$^{33}$, —O-heteroaryl, —O-heterocycloalkyl, —O(CR$^{30}$R$^{31}$)$_v$heteroaryl, —O(CR$^{30}$R$^{31}$)$_v$heterocycloalkyl, —O(CR³⁰R³¹)$_w$NR³²-heteroaryl, —O(CR³⁰R³¹)$_w$NR³²-heterocycloalkyl, —O(CR³⁰R³¹)$_w$O-heterocycloalkyl, —NR³²R³³, —NR³²(CR³⁰R³¹)$_w$NR³²R³³, —NR³²(CR³⁰R³¹)$_v$OH, —NR³²(CR³⁰R³¹) OR³⁴, —NR³²C(=O)R³⁴, —NR³²C(=O)OR³⁴, —N(R³²)$_v$C(=O)(CR³⁰R³¹)$_w$NR³²R³³, —NR³²C(=O)NR³²R³³, —NR³²C(=O)NR³² (CR³⁰R³¹)$_w$NR³²R³³, —NR³²(CR³⁰R³¹)$_w$S(=O)$_{0,1,2}$R³⁴, —NR³²(CR³⁰R³¹)$_w$S(=O)$_{0,1,2}$NR³²R³³, —NR³²(CR³⁰R³¹)$_w$NR³²R³³S(=O)$_{0,1,2}$R³⁴, —NR³²(CR³⁰R³¹)$_w$NR³²S(=O)$_{0,1,2}$NR³²R³³, —NR³²C(=NR³⁶)NR³²R³³, —N(R³²)C(=NR³⁶)R³⁴, —NR³²(CR³⁰R³¹)$_w$N(R³²)C(=NR³⁶)R³⁴, —NR³²(CR³⁰R³¹)$_v$C(=NR³⁶)NR³²R³³, —NR³²(CR³⁰R³¹)$_w$N(R³²)C(=NR³⁶)NR³²R³³, —NR³²(CR³⁰R³¹)$_w$NR³²C(=O)NR³²R³³, NR³² (CR³⁰R³¹)$_w$NR³²C(=O)OR³⁴, —NR³² S(=O)$_{0,1,2}$NR³²R³³, —NR³²S(=O)$_{0,1,2}$R³⁴, —NR³² (CR³⁰R³¹)$_v$CO₂H, —NR³²(CR³⁰R³¹)$_v$CO₂R³⁴, —NR³²(CR³⁰R³¹)$_v$C(=O)NR³²R³³, —N(R³²)-heteroaryl- NR³²R³³, —N(R³²)-heterocycloalkyl-NR³²R³³, —NR³²(CR³⁰R³¹)$_v$heteroaryl, —NR³² (CR³⁰R³¹)$_v$heterocycloalkyl, —NR³²(CR³⁰R³¹)$_w$NR³²-heteroaryl, —NR³²(CR³⁰R³¹)$_w$NR³²-heterocycloalkyl, —CN, —(CR³⁰R³¹)$_v$CN, —(CR³⁰R³¹)$_v$NR³²R³³, —(CR³⁰R³¹)$_v$OH, —(CR³⁰R³¹)$_w$OR³⁴, —(CR³⁰R³¹)$_v$OC(=O)R³⁴, —(CR³⁰R³¹)$_v$OC(=O)NR³²R³³, —(CR³⁰R³¹)$_v$O(CR³⁰R³¹)$_v$OR³⁴, —(CR³⁰R³¹)$_v$O(CR³⁰R³¹)$_v$OH, —(CR³⁰R³¹)$_v$O(CR³⁰R³¹)NR³²R³³, —(CR³⁰R³¹)$_v$NR³²(CR³⁰R³¹)$_v$OH, —(CR³⁰R³¹)$_w$NR³²(CR³⁰R³¹)$_w$OR³⁴, —(CR³⁰R³¹)$_v$C(=O)NR³²R³³, —(CR³⁰R³¹)$_v$C(=O)OH, —(CR³⁰R³¹)$_v$C(=O)OR³⁴, —(CR³⁰R³¹)$_v$C(=O)NR³²(CR³⁰R³¹)$_w$NR³²R³³, —(CR³⁰R³¹)$_v$C(=O)NR³² (CR³⁰R³¹)$_w$OR³⁴, —(CR³⁰R³¹)$_w$N(R³²)$_v$C(=O)R³⁴, —(CR³⁰R³¹)$_w$N(R³²)$_v$C(=O)OR³⁴, —(CR³⁰R³¹)$_w$N(R³²)$_v$C(=O)NR³²R³³, —(CR³⁰R³¹)$_w$N(R³²)$_v$C(=O)(CR³⁰R³¹)$_w$NR³²R³³, —(CR³⁰R³¹)$_w$N(R³²)S(=O)$_{0,1,2}$R³⁴, —(CR³⁰R³¹)$_w$N(R³²)S(=O)$_{0,1,2}$NR³²R³³, —(CR³⁰R³¹)$_w$S(=O)$_{0,1,2}$NR³²R³³, —(CR³⁰R³¹)$_w$NR³²(CR³⁰R³¹)$_w$NR³²R³³, —(CR³⁰R³¹)$_w$N(R³²)CH(=NR³⁶), —(CR³⁰R³¹)$_w$N(R³²)C(=NR³⁶)R³⁴, —(CR³⁰R³¹)$_w$C(=NR³⁶)NR³²R³³, —(CR³⁰R³¹)$_w$N(R³²)C(=NR³⁶)NR³²R³³, —(CR³⁰R³¹)$_v$C(=NR³⁶)NR³²C(=NR³⁶)NR³²R³³, —(CR³⁰R³¹)$_v$heteroaryl-NR³²R³³, —(CR³⁰R³¹)$_v$heterocycloalkyl-NR³²R³³, —(CR³⁰R³¹)$_v$heteroaryl-N(R³²)C(=NR³⁶)NR³²R³³, —(CR³⁰R³¹)$_v$heterocycloalkyl-N(R³²)C(=NR³⁶)NR³²R³³, —(CR³⁰R³¹)$_v$heteroaryl, —(CR³⁰R³¹)$_v$heterocycloalkyl, —C(=O)OH, —C(=O)OR³⁴, —C(=O)NR³²R³³, —C(=O)NR³²(CR³⁰R³¹)$_w$NR³²R³³, —C(=O)NR³²(CR³⁰R³¹)$_w$OH, —C(=O)NR³²(CR³⁰R³¹)$_w$OR³⁴, —C(=NR³⁶)NR³²R³³, —C(=NR³⁶)NR³²C(=O)R³⁴, —S(=O)$_{1,2}$R³⁴, —SR³⁵, —S(=O)$_{0,1,2}$(CR³⁰R³¹)$_w$NR³²R³³, —S(=O)$_{0,1,2}$(CR³⁰R³¹)$_w$OH, —S(=O)$_{0,1,2}$(CR³⁰R³¹)$_v$OR³⁴, —S(=O)$_{0,1,2}$NR³²R³³, —S(=O)$_{0,1,2}$NR³²(CR³⁰R³¹)$_w$NR³²R³³, —S(=O)$_{0,1,2}$(CR³⁰R³¹)$_w$N(R³²)C(=NR³⁶)R³⁴, —S(=O)$_{0,1,2}$(CR³⁰R³¹)$_v$C(=NR³⁶)NR³²R³³, —S(=O)$_{0,1,2}$(CR³⁰R³¹)$_w$N(R³²)C(=NR³⁶)$_w$NR³²R³³, —S(=O)$_{0,1,2}$(CR³⁰R³¹)$_v$C(=NR³⁶)NR³²C(=NR³⁶)NR³²R³³, —Si(R³⁴)₃, —NR³²R³³R³⁴⁺Q⁻, —(CR³⁰R³¹)$_v$NR³²R³³R³⁴⁺Q⁻, —NR³²(CR³⁰R³¹)$_w$NR³²R³³R³⁴⁺Q⁻, —NR³²R³⁴⁺ (CR³⁰R³¹)$_w$NR³²R³³R³⁴⁺Q⁻₂, —(CR³⁰R³¹)$_v$(T)⁺Q⁻, or —O(CR³⁰R³¹)$_w$NR³²R³³R³⁴⁺Q⁻;

or two Ys taken together with the atoms to which they are attached to form an optionally substituted cycloalkyl or an optionally substituted heterocycloalkyl;

T is pyridin-1-yl, pyrimidin-1-yl, or thiazol-3-yl;

Q is a pharmaceutically acceptable counterion;

n is 0-3;

m is 0-3;

p is 1-3;

each q is independently 2-6;

each v is independently 1-5; and each w is independently 2-5.

Also provided herein are compounds of Formula (IIa) or (IIb), or a pharmaceutically acceptable salt, solvate, stereoisomer, tautomer, N-oxide, dimer, or trimer thereof:

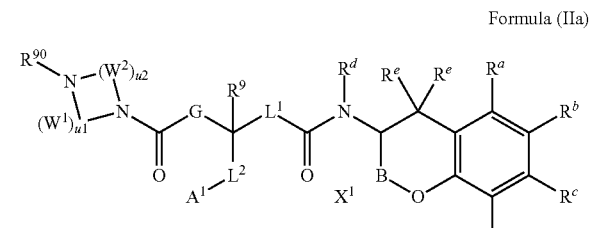

Formula (IIa)

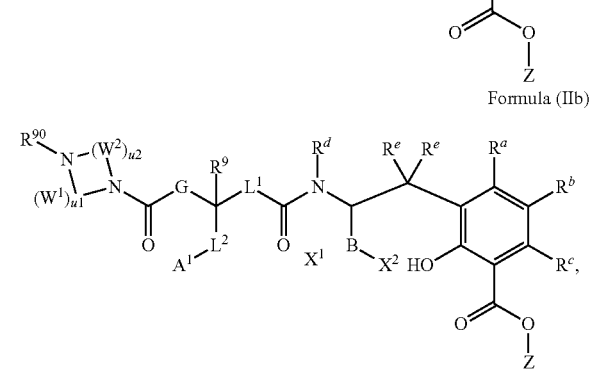

Formula (IIb)

wherein:

G is —NR⁸—, —C(R¹⁰)₂—, or —C(R¹⁰)₂NR⁸—;

L¹ is —(CR¹R²)$_n$—;

L² is —(CR¹R²)$_m$—;

A¹ is

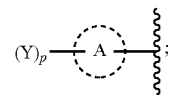

Ring A is a 6-membered aryl or a 6-membered heteroaryl;

R¹, R², and R⁹ are independently hydrogen, halogen, optionally substituted alkyl, —OH, —OR³⁴, —SR³⁵, —NR³²R³³, —NR³²C(=O)R³⁴, —C(=O)NR³²R³³, —NR³²S(=O)₂R³⁴, —C(=O)OH, —C(=O)OR³⁴, optionally substituted cycloalkyl, optionally substituted heterocycloalkyl, optionally substituted aryl, or optionally substituted heteroaryl; or R¹ and R² are taken together with the carbon to which they are attached to form an optionally substituted cycloalkyl or an optionally substituted heterocycloalkyl;

R$^8$ is hydrogen, optionally substituted alkyl, optionally substituted cycloalkyl, optionally substituted heterocycloalkyl, optionally substituted aryl, or optionally substituted heteroaryl; or R$^8$ and R$^9$ are taken together with the atoms to which they are attached to form an optionally substituted heterocycloalkyl;

each R$^{10}$ is independently hydrogen, halogen, or optionally substituted alkyl;

each R$^{20}$ and R$^{21}$ is independently hydrogen, halogen, or optionally substituted alkyl;

R$^{22}$ and R$^{23}$ are independently hydrogen or optionally substituted alkyl; or R$^{22}$ and R$^{23}$ are taken together with the nitrogen to which they are attached to form an optionally substituted heterocycloalkyl;

R$^{24}$ is optionally substituted alkyl, optionally substituted cycloalkyl, optionally substituted heterocycloalkyl, optionally substituted aryl, or optionally substituted heteroaryl;

R$^{25}$ is hydrogen, optionally substituted alkyl, optionally substituted cycloalkyl, optionally substituted heterocycloalkyl, optionally substituted aryl, or optionally substituted heteroaryl;

each R$^{30}$, R$^{31}$, R$^{50}$, and R$^{51}$ is independently hydrogen, halogen, optionally substituted alkyl, optionally substituted cycloalkyl, optionally substituted heterocycloalkyl, optionally substituted aryl, optionally substituted heteroaryl, —OH, —OR$^{24}$, —SR$^{25}$, —NR$^{22}$R$^{23}$, —NR$^{22}$C(=O)R$^{24}$, —C(=O)NR$^{22}$R$^{23}$, —NR$^{22}$S(=O)$_2$R$^{24}$, —C(=O)OH, or —C(=O)OR$^{24}$; or R$^{30}$ and R$^{31}$, or R$^{50}$ and R$^{51}$ are taken together with the carbon atom to which they are attached to form an optionally substituted cycloalkyl; or two R$^{30}$ or two R$^{50}$ on adjacent carbons are taken together to form an alkenyl; or two R$^{30}$ and two R$^{31}$, or two R$^{50}$ and two R$^{51}$ on adjacent carbons are taken together to form an alkynyl;

R$^{32}$, R$^{33}$, R$^{52}$, and R$^{53}$ are independently hydrogen, optionally substituted alkyl, optionally substituted cycloalkyl, optionally substituted heterocycloalkyl, optionally substituted aryl, optionally substituted heteroaryl, (poly-ethylene-glycol)-ethyl, optionally substituted saccharide, —CN, —OH, —S(=O)$_2$R$^{24}$, —S(=O)$_2$NR$^{22}$R$^{23}$, or —C(=O)R$^{24}$; or R$^{32}$ and R$^{33}$, or R$^{52}$ and R$^{53}$ are taken together with the nitrogen to which they are attached to form an optionally substituted heterocycloalkyl;

R$^{34}$, and R$^{54}$ are independently optionally substituted alkyl, optionally substituted cycloalkyl, optionally substituted heterocycloalkyl, optionally substituted aryl, or optionally substituted heteroaryl;

R$^{35}$ and R$^{55}$ are independently hydrogen, optionally substituted alkyl, optionally substituted cycloalkyl, optionally substituted heterocycloalkyl, optionally substituted aryl, or optionally substituted heteroaryl;

R$^{36}$ and R$^{56}$ are independently hydrogen, —OH, —OR$^{24}$, —CN, —NO$_2$, —NR$^{22}$R$^{23}$, or optionally substituted alkyl;

each R$^{60}$ is independently —CH$_2$—, —CH(CH$_3$)—, —C(CH$_3$)$_2$—, or optionally substituted 1,1'-cyclopropylene;

each R$^{61}$ is independently optionally substituted alkyl, optionally substituted cycloalkyl, optionally substituted heterocycloalkyl, optionally substituted aryl, or optionally substituted heteroaryl; or two R$^{61}$ are taken together with the nitrogen to which they are attached to form an optionally substituted heterocycloalkyl;

each W$^1$ and W$^2$ is independently —C(=O)— or —C(R$^{91}$)$_2$—;

R$^{90}$ is hydrogen, —OH, optionally substituted alkyl, optionally substituted alkoxy, optionally substituted cycloalkyl, optionally substituted heterocycloalkyl, optionally substituted aryl, optionally substituted heteroaryl, optionally substituted cycloalkylalkyl, optionally substituted heterocycloalkylalkyl, optionally substituted aralkyl, optionally substituted heteroaralkyl, —S(=O)$_2$R$^{24}$, —S(=O)$_2$NR$^{22}$R$^{23}$, or —C(=O)R$^{24}$.

each R$^{91}$ is independently hydrogen, halogen, —OH, —CN, NH$_2$, NO$_2$, optionally substituted alkyl, optionally substituted alkoxy, optionally substituted cycloalkyl, optionally substituted heterocycloalkyl, optionally substituted aryl, or optionally substituted heteroaryl;

R$^a$, R$^b$, and R$^c$ are independently hydrogen, halogen, cyano, optionally substituted alkyl, optionally substituted cycloalkyl, optionally substituted heterocycloalkyl, optionally substituted aryl, optionally substituted heteroaryl, —OH, —OR$^{54}$, —O(CR$^{50}$R$^{51}$)$_w$NR$^{52}$R$^{53}$, —O(CR$^{50}$R$^{51}$)$_w$OH, —O(CR$^{50}$R$^{51}$)$_w$OR$^{54}$, —O(CR$^{50}$R$^{51}$)$_v$C(=O)OH, —O(CR$^{50}$R$^{51}$)$_v$C(=O)OR$^{54}$, —O(CR$^{50}$R$^{51}$)$_v$C(=O)NR$^{52}$R$^{53}$, —NR$^{52}$R$^{53}$, —NR$^{52}$(CR$^{50}$R$^{51}$)$_w$NR$^{52}$R$^{53}$, —NR$^{52}$(CR$^{50}$R$^{51}$)$_v$C(=O)OH, —NR$^{52}$(CR$^{50}$R$^{51}$)$_v$C(=O)OR$^{54}$, —NR$^{52}$(CR$^{50}$R$^{51}$)$_v$C(=O)NR$^{52}$R$^{53}$, —NR$^{52}$S(=O)$_{1,2}$R$^{54}$, —S(=O)$_{1,2}$R$^{54}$, —SR$^{55}$, —S(CR$^{50}$R$^{51}$)$_w$NR$^{52}$C(=NR$^{56}$)NR$^{52}$R$^{53}$, —S(CR$^{50}$R$^{51}$)NR$^{52}$CR$^{50}$(=NR$^{56}$), —S(CR$^{50}$R$^{51}$)$_v$C(=NR$^{56}$)NR$^{52}$R$^{53}$, —S(CR$^{50}$R$^{51}$)$_w$OH, —S(CR$^{50}$R$^{51}$)$_w$OR$^{54}$, —S(CR$^{50}$R$^{51}$) NR$^{52}$R$^{53}$, —S(CR$^{50}$R$^{51}$)$_v$C(=O)OH, —S(CR$^{50}$R$^{51}$)$_v$C(=O)OR$^{54}$, —S(CR$^{50}$R$^{51}$)$_v$C(=O)NR$^{52}$R$^{53}$, —C(=O)H, —C(=O)R$^{54}$, —C(=O)OH, —C(=O)OR$^{54}$, —C(=O)NR$^{52}$R$^{53}$, —(CR$^{50}$R$^{51}$)$_v$N(R$^{52}$)(CR$^{50}$R$^{51}$)$_v$C(=O)OH, —(CR$^{50}$R$^{51}$)$_v$OH, —(CR$^{50}$R$^{51}$)$_v$OR$^{54}$, —(CR$^{50}$R$^{51}$)$_v$C(=O)OH, —(CR$^{50}$R$^{51}$)$_v$C(=O)OR$^{54}$, —(CR$^{50}$R$^{51}$)$_v$C(=O) NR$^{52}$R$^{53}$, —(CR$^{50}$R$^{51}$)$_v$OC(=O)R$^{54}$, —(CR$^{50}$R$^{51}$)$_v$SR$^{55}$, —(CR$^{50}$R$^{51}$)$_v$NR$^{52}$C(=NR$^{56}$), —(CR$^{50}$R$^{51}$)$_w$NR$^{52}$R$^{53}$, —(CR$^{50}$R$^{51}$)$_v$C(=NR$^{56}$) NR$^{52}$R$^{53}$, —(CR$^{50}$R$^{51}$)$_v$C(=O)NR$^{52}$R$^{53}$, —(CR$^{50}$R$^{51}$)$_v$heterocycloalkyl, or —(CR$^{50}$R$^{51}$)$_v$heteroaryl;

R$^d$ is hydrogen, —CN, —OH, —S(=O)$_2$R$^{24}$, —S(=O)$_2$NR$^{22}$R$^{23}$, —(CR$^{20}$R$^{21}$)$_v$C(=O)OH, —C(=O)R$^{24}$, optionally substituted alkyl, optionally substituted cycloalkyl, optionally substituted heterocycloalkyl, optionally substituted aryl, optionally substituted heteroaryl, (poly-ethylene-glycol)-ethyl, or an optionally substituted saccharide;

each R$^e$ is independently hydrogen, —CN, —OH, optionally substituted alkyl, or optionally substituted cycloalkyl;

R$^X$ is optionally substituted alkyl or optionally substituted cycloalkyl;

X$^1$ and X$^2$ are independently —OH, —OR$^X$, or F; or

X$^1$ and X$^2$ are taken together with the boron atom to which there are attached to form a cyclic boronate ester;

each Y is independently halogen, optionally substituted alkyl, optionally substituted cycloalkyl, optionally substituted heterocycloalkyl, optionally substituted aryl, optionally substituted heteroaryl, -heteroaryl-NR$^{32}$R$^{33}$, -heterocycloalkyl-NR$^{32}$R$^{33}$, -heteroaryl-N(R$^{32}$)C(=NR$^{32}$)NR$^{32}$R$^{33}$, -heterocycloalkyl-N(R$^{32}$)C(=NR$^{32}$)NR$^{32}$R$^{33}$, —OH, —OR$^{34}$, —O(CR$^{30}$ $R^{31})_w OH$, $-O(CR^{30}R^{31})_w OR^{34}$, $-O(CR^{30}R^{31})_w NR^{32}R^{33}$, $-O(CR^{30}R^{31})_w NR^{32}C(=O)R^{34}$, $-O(CR^{30}R^{31})_v NR^{32}C(=O)OR^{34}$, $-O(CR^{30}R^{31})_w NR^{32}C(=O)NR^{32}R^{33}$, $-O(CR^{30}R^{31})_v C(=O)NR^{32}R^{33}$, $-O(CR^{30}R^{31})_w NR^{32}S(=O)_{0,1,2}R^{34}$, $-O(CR^{30}R^{31})_w NR^{32}S(=O)_{0,1,2}NR^{32}R^{33}$, $-O(CR^{30}R^{31})_w S(=O)_{0,1,2}R^{34}$, $-O(CR^{30}R^{31})_w S(=O)_{0,1,2}NR^{32}R^{33}$, $-O(CR^{30}R^{31})_v C(=NR^{36})NR^{32}R^{33}$, $-O(CR^{30}R^{31})_v N(R^{32})C(=NR^{36})R^{34}$, $-O(CR^{30}R^{31})_v C(=NR^{36})NR^{32}C(=NR^{36})NR^{32}R^{33}$, $-O(CR^{30}R^{31})_w N(R^{32})C(=NR^{36})NR^{32}R^{33}$, $-O(CR^{30}R^{31})_w S(=O)_{0,1,2}R^{34}$, $-O(CR^{30}R^{31})_w S(=O)_{0,1,2}NR^{32}R^{33}$, $-OC(=O)R^{34}$, $-OC(=O)(CR^{30}R^{31})_v NR^{32}R^{33}$, $-OC(=O)NR^{32}R^{33}$, $-OC(=O)OR^{34}$, $-OC(=O)NR^{32}(CR^{30}R^{31})_w NR^{32}R^{33}$, —O-heteroaryl, —O-heterocycloalkyl, $-O(CR^{30}R^{31})_v$heteroaryl, $-O(CR^{30}R^{31})_v$heterocycloalkyl, $-O(CR^{30}R^{31})_w NR^{32}$-heteroaryl, $-O(CR^{30}R^{31})_w NR^{32}$-heterocycloalkyl, $-O(CR^{30}R^{31})_w O$-heterocycloalkyl, $-NR^{32}R^{33}$, $-NR^{32}(CR^{30}R^{31})_v NR^{32}R^{33}$, $-NR^{32}(CR^{30}R^{31})_v OH$, $-NR^{32}(CR^{30}R^{31})_w OR^{34}$, $-NR^{32}C(=O)R^{34}$, $-NR^{32}C(=O)OR^{34}$, $-N(R^{32})_v C(=O)(CR^{30}R^{31})_w NR^{32}R^{33}$, $-NR^{32}C(=O)NR^{32}R^{33}$, $-NR^{32}C(=O)NR^{32}(CR^{30}R^{31})_w NR^{32}R^{33}$, $-NR^{32}(CR^{30}R^{31})_w$ $S(=O)_{0,1,2}R^{34}$, $-NR^{32}(CR^{30}R^{31})_w$ $S(=O)_{0,1,2}NR^{32}R^{33}$, $-NR^{32}(CR^{30}R^{31})_w NR^{32}R^{33}S(=O)_{0,1,2}R^{34}$, $-NR^{32}(CR^{30}R^{31})_w NR^{32}S(=O)_{0,1,2}NR^{32}R^{33}$, $-NR^{32}C(=NR^{36})NR^{32}R^{33}$, $-N(R^{32})C(=NR^{36})R^{34}$, $-NR^{32}(CR^{30}R^{31})_w N(R^{32})C(=NR^{36})R^{34}$, $-NR^{32}(CR^{30}R^{31})_v C(=NR^{36})NR^{32}R^{33}$, $-NR^{32}(CR^{30}R^{31})_w N(R^{32})C(=NR^{36})NR^{32}R^{33}$, $-NR^{32}(CR^{30}R^{31})_w NR^{32}C(=O)NR^{32}R^{33}$, $-NR^{32}(CR^{30}R^{31})_w NR^{32}C(=O)OR^{34}$, $-NR^{32}S(=O)_{0,1,2}NR^{32}R^{33}$, $-NR^{32}S(=O)_{0,1,2}R^{34}$, $-NR^{32}(CR^{30}R^{31})_v CO_2H$, $-NR^{32}(CR^{30}R^{31})_v CO_2R^{34}$, $-NR^{32}(CR^{30}R^{31})_v C(=O)NR^{32}R^{33}$, $-N(R^{32})$-heteroaryl-$NR^{32}R^{33}$, $-N(R^{32})$-heterocycloalkyl-$NR^{32}R^{33}$, $-NR^{32}(CR^{30}R^{31})_v$heteroaryl, $-NR^{32}(CR^{30}R^{31})_v$heterocycloalkyl, $-NR^{32}(CR^{30}R^{31})_w NR^{32}$-heteroaryl, $-NR^{32}(CR^{30}R^{31})_w NR^{32}$-heterocycloalkyl, $-CN$, $-(CR^{30}R^{31})CN$, $-(CR^{30}R^{31})_w NR^{32}R^{33}$, $-(CR^{30}R^{31})_w OH$, $-(CR^{30}R^{31})_v OR^{34}$, $-(CR^{30}R^{31})_v OC(=O)R^{34}$, $-(CR^{30}R^{31})_v OC(=O)NR^{32}R^{33}$, $-(CR^{30}R^{31})_v O(CR^{30}R^{31})_w OR^{34}$, $-(CR^{30}R^{31})_v O(CR^{30}R^{31})_v OH$, $(CR^{30}R^{31})_v O(CR^{30}R^{31})_w NR^{32}R^{33}$, $-(CR^{30}R^{31})_v NR^{32}(CR^{30}R^{31})_w OH$, $-(CR^{30}R^{31})_v NR^{32}(CR^{30}R^{31})_w OR^{34}$, $-(CR^{30}R^{31})_v C(=O)NR^{32}R^{33}$, $-(CR^{30}R^{31})_v C(=O)OH$, $-(CR^{30}R^{31})_v C(=O)OR^{34}$, $-(CR^{30}R^{31})_v C(=O)NR^{32}(CR^{30}R^{31})_w NR^{32}R^{33}$, $-(CR^{30}R^{31})_v C(=O)NR^{32}(CR^{30}R^{31})_w OR^{34}$, $-(CR^{30}R^{31})_w N(R^{32})_v C(=O)R^{34}$, $-(CR^{30}R^{31})N(R^{32})_v C(=O)OR^{34}$, $-(CR^{30}R^{31})_w N(R^{32})_v C(=O)NR^{32}R^{33}$, $-(CR^{30}R^{31})_w N(R^{32})C(=O)(CR^{30}R^{31})_w NR^{32}R^{33}$, $-(CR^{30}R^{31})_w N(R^{32})S(=O)_{0,1,2}R^{34}$, $-(CR^{30}R^{31})_w N(R^{32})S(=O)_{0,1,2}NR^{32}R^{33}$, $-(CR^{30}R^{31})_w N(R^{32})S(=O)_{0,1,2}NR^{32}R^{33}$, $-(CR^{30}R^{31})_v NR^{32}(CR^{30}R^{31})_w NR^{32}R^{33}$, $-(CR^{30}R^{31})_v N(R^{32})CH(=NR^{36})$, $-(CR^{30}R^{31})_v N(R^{32})C(=NR^{36})R^{34}$, $-(CR^{30}R^{31})_v C(=NR^{36})NR^{32}R^{33}$, $-(CR^{30}R^{31})_w N(R^{32})C(=NR^{36})NR^{32}R^{33}$, $-(CR^{30}R^{31})_v C(=NR^{36})NR^{32}C(=NR^{36})NR^{32}R^{33}$, $-(CR^{30}R^{31})_v$heteroaryl-$NR^{32}R^{33}$, $-(CR^{30}R^{31})_v$heterocycloalkyl-$NR^{32}R^{33}$, $-(CR^{30}R^{31})_v$heteroaryl-$N(R^{32})C(=NR^{36})NR^{32}R^{33}$, $-(CR^{30}R^{31})_v$heterocycloalkyl-$N(R^{32})C(=NR^{36})NR^{32}R^{33}$, $-(CR^{30}R^{31})_v$heteroaryl, $-(CR^{30}R^{31})_v$heterocycloalkyl, $-C(=O)OH$, $-C(=O)OR^{34}$, $-C(=O)NR^{32}R^{33}$, $-C(=O)NR^{32}(CR^{30}R^{31})_w NR^{32}R^{33}$, $-C(=O)NR^{32}(CR^{30}R^{31})_w OH$, $-C(=O)NR^{32}(CR^{30}R^{31})_v OR^{34}$, $-C(=NR^{36})NR^{32}R^{33}$, $-C(=NR^{36})NR^{32}C(=O)R^{34}$, $-S(=O)_{1,2}R^{34}$, $-SR^{35}$, $-S(=O)_{0,1,2}(CR^{30}R^{31})_w NR^{32}R^{33}$, $-S(=O)_{0,1,2}(CR^{30}R^{31})_w OH$, $-S(=O)_{0,1,2}(CR^{30}R^{31})_v OR^{34}$, $-S(=O)_{0,1,2}NR^{32}R^{33}$, $-S(=O)_{0,1,2}NR^{32}(CR^{30}R^{31})_w NR^{32}R^{33}$, $-S(=O)_{0,1,2}(CR^{30}R^{31})_w N(R^{32})C(=NR^{36})R^{34}$, $-S(=O)_{0,1,2}(CR^{30}R^{31})_v C(=NR^{36})NR^{32}R^{33}$, $-S(=O)_{0,1,2}(CR^{30}R^{31})_w N(R^{32})C(=NR^{36})NR^{32}R^{33}$, $-S(=O)_{0,1,2}(CR^{30}R^{31})_v C(=NR^{36})NR^{32}C(=NR^{36})NR^{32}R^{33}$, $-Si(R^{34})_3$, $-NR^{32}R^{33}R^{34+}Q^-$, $-(CR^{30}R^{31})_w NR^{32}R^{33}R^{34+}Q^-$, $-NR^{32}(CR^{30}R^{31})_w NR^{32}R^{33}R^{34+}Q^-$, $-NR^{32}R^{34+}(CR^{30}R^{31})_w NR^{32}R^{33}R^{34+}Q^-_2$, $-(CR^{30}R^{31})_v(T)^+Q^-$, or $-O(CR^{30}R^{31})_w NR^{32}R^{33}R^{34+}Q^-$;

or two Ys are taken together with the atoms to which they are attached to form an optionally substituted cycloalkyl or an optionally substituted heterocycloalkyl;

Z is hydrogen, $R^{61}$, $-(R^{60})_q OR^{61}$, $-(R^{60})_q O(R^{60})_q OR^{61}$, $-R^{60}OC(=O)R^{61}$, $-R^{60}OC(=O)OR^{61}$, $-R^{60}OC(=O)NHR^{61}$, $-R^{60}OC(=O)N(R^{61})_2$, optionally substituted alkyloxyalkyl, optionally substituted acyloxyalkyl, optionally substituted alkyloxycarbonyloxyalkyl, optionally substituted cycloalkyloxycarbonyloxyalkyl, optionally substituted aryloxycarbonyloxyalkyl, or optionally substituted alkyl-[1,3]dioxol-2-one;

T is pyridin-1-yl, pyrimidin-1-yl, or thiazol-3-yl;

Q is a pharmaceutically acceptable counterion;

n is 0-3;

m is 0-3;

p is 1-3;

each q is independently 2-6;

u1 is 1-3;

u2 is 1-3;

each v is independently 1-5; and each w is independently 2-5.

Also disclosed herein is a pharmaceutical composition comprising a compound disclosed herein and a pharmaceutically acceptable excipient.

Also disclosed herein is a method of treating a bacterial infection in a subject, comprising administering to the subject an effective amount of a compound disclosed herein, or a pharmaceutically acceptable salt, solvate, stereoisomer, tautomer, N-oxide, dimer, or trimer thereof, or a pharmaceutical composition comprising a compound disclosed herein and a pharmaceutically acceptable excipient.

Also disclosed herein is method of inhibiting a bacterial penicillin binding protein in a human infected with a bacterial infection, comprising contacting said bacterial penicillin binding protein with an effective amount of compound disclosed herein, or a pharmaceutically acceptable salt, solvate, stereoisomer, tautomer, N-oxide, dimer, or trimer thereof, or a pharmaceutical composition comprising a compound disclosed herein and a pharmaceutically acceptable excipient.

INCORPORATION BY REFERENCE

All publications, patents, and patent applications mentioned in this specification are herein incorporated by reference to the same extent as if each individual publication, patent, or patent application was specifically and individually indicated to be incorporated by reference.

DETAILED DESCRIPTION OF THE INVENTION

Over the decades of clinical use of beta-lactam antibiotics, bacteria have evolved resistance mechanisms that compromise beta-lactam utility, including production of easily transferable, broad-spectrum beta-lactamases that are able to efficiently hydrolyze the beta lactam ring. These enzymes, now counting >1300 variants, have spread throughout Enterobacteriaceae. The rapid spread of this mechanism of bacterial resistance severely limits beta-lactam therapeutic options.

Novel non-beta-lactam compounds that inhibit the transpeptidase function of PBPs and are not degraded by beta-lactamases would represent a major advance in the treatment of resistant bacterial infections, essentially circumventing >70 years of bacterial evolution to protect the function of the penicillin-binding proteins in cell wall biosynthesis. The present invention is directed to certain boron-based compounds (boronic acids and cyclic boronic acid esters) which are PBP inhibitors and antibacterial compounds. The compounds and their pharmaceutically acceptable salts are useful for the treatment of bacterial infections, particularly antibiotic resistant bacterial infections. Some embodiments include compounds, compositions, pharmaceutical compositions, use, and preparation thereof.

Definitions

In the following description, certain specific details are set forth in order to provide a thorough understanding of various embodiments. However, one skilled in the art will understand that the invention may be practiced without these details. In other instances, well-known structures have not been shown or described in detail to avoid unnecessarily obscuring descriptions of the embodiments. Unless the context requires otherwise, throughout the specification and claims which follow, the word "comprise" and variations thereof, such as, "comprises" and "comprising" are to be construed in an open, inclusive sense, that is, as "including, but not limited to." Further, headings provided herein are for convenience only and do not interpret the scope or meaning of the claimed invention.

Reference throughout this specification to "one embodiment" or "an embodiment" means that a particular feature, structure or characteristic described in connection with the embodiment is included in at least one embodiment. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments. Also, as used in this specification and the appended claims, the singular forms "a," "an," and "the" include plural referents unless the content clearly dictates otherwise. It should also be noted that the term "or" is generally employed in its sense including "and/or" unless the content clearly dictates otherwise.

The term "antibiotic" refers to a compound or composition which decreases the viability of a microorganism, or which inhibits the growth or proliferation of a microorganism. The phrase "inhibits the growth or proliferation" means increasing the generation time (i.e., the time required for the bacterial cell to divide or for the population to double) by at least about 2-fold. Preferred antibiotics are those which can increase the generation time by at least about 10-fold or more (e.g., at least about 100-fold or even indefinitely, as in total cell death). As used in this disclosure, an antibiotic is further intended to include an antimicrobial, bacteriostatic, or bactericidal agent. Examples of antibiotics suitable for use with respect to the present invention include penicillins, cephalosporins, and carbapenems.

The term "β-lactam antibiotic" refers to a compound with antibiotic properties that contains a β-lactam functionality. Non-limiting examples of β-lactam antibiotics useful with respect to the invention include penicillins, cephalosporins, penems, carbapenems, and monobactams.

The term "β-lactamase" denotes a protein capable of inactivating a β-lactam antibiotic. The β-lactamase can be an enzyme which catalyzes the hydrolysis of the β-lactam ring of a β-lactam antibiotic. Of particular interest herein are microbial β-lactamases. The β-lactamase may be, for example, a serine β-lactamase or a metallo-β-lactamase.

"Amino" refers to the —$NH_2$ substituent.

"Oxo" refers to the =O substituent.

"Oxime" refers to the =N—OH substituent.

"Thioxo" refers to the =S substituent.

"Alkyl" refers to a linear or branched hydrocarbon chain, which is fully saturated. Alkyl may have from one to thirty carbon atoms. An alkyl comprising up to 30 carbon atoms is referred to as a $C_1$-$C_{30}$ alkyl, likewise, for example, an alkyl comprising up to 12 carbon atoms is a $C_1$-$C_{12}$ alkyl. An alkyl comprising up to 6 carbons is a $C_1$-$C_6$ alkyl. Alkyl groups include, but are not limited to, C1-$C_{30}$ alkyl, $C_1$-$C_{20}$ alkyl, $C_1$-$C_{15}$ alkyl, $C_1$-$C_{10}$ alkyl, $C_1$-$C_8$ alkyl, $C_1$-$C_6$ alkyl, $C_1$-$C_4$ alkyl, $C_1$-$C_3$ alkyl, $C_1$-$C_2$ alkyl, $C_2$-$C_8$ alkyl, $C_3$-$C_8$ alkyl, $C_4$-$C_8$ alkyl, and $C_5$-$C_{12}$ alkyl. In some embodiments, the alkyl group is C1-$C_6$ alkyl. Representative alkyl groups include, but are not limited to, methyl, ethyl, n-propyl, 1-methylethyl (isopropyl), n-butyl, i-butyl, s-butyl, n-pentyl, 1,1-dimethylethyl (t-butyl), 2-ethylpropyl, and the like. Representative linear alkyl groups include, but are not limited to, methyl, ethyl, n-propyl, n-butyl, n-pentyl and the like. In some embodiments, the alkyl is substituted with an optionally substituted aryl to form an optionally substituted aralkyl. In some embodiments, the alkyl is substituted with an optionally substituted heteroaryl to form an optionally substituted heteroarylalkyl. In some embodiments, the alkyl is substituted with an optionally substituted cycloalkyl to form an optionally substituted cycloalkylalkyl. In some embodiments, the alkyl is substituted with an optionally substituted heterocycloalkyl to form an optionally substituted heterocycloalkylalkyl. In some embodiments, the alkyl group is optionally substituted with oxo, halogen, amino, nitrile, nitro, hydroxyl, haloalkyl, alkoxy, aryl, cycloalkyl, heterocycloalkyl, heteroaryl, and the like. In some embodiments, the alkyl is optionally substituted with oxo, halogen, —CN, —$CF_3$, —OH, —OMe, —$NH_2$, or —$NO_2$. In some embodiments, the alkyl is optionally substituted with oxo, halogen, —CN, —$CF_3$, —OH, or —OMe. In some embodiments, the alkyl is optionally substituted with halogen.

"Alkenyl" refers to a straight or branched hydrocarbon chain, containing at least one carbon-carbon double bond. In certain embodiments, alkenyl comprises two to twelve ($C_2$-$C_{12}$ alkenyl) carbon atoms, or two to eight carbon atoms ($C_2$-$C_8$ alkenyl), or two to six carbon atoms ($C_2$-$C_6$ alkenyl) or two to four carbon atoms ($C_2$-$C_4$ alkenyl). The alkenyl may be attached to the rest of the molecule by a single bond, for example, ethenyl (i.e., vinyl), prop-1-enyl (i.e., allyl), but-1-enyl, pent-1-enyl, penta-1,4-dienyl, and the like. Alkenyl may be attached to the rest of the molecule by a double bond, e.g., =CH$_2$, =CH(CH$_2$)$_3$CH$_3$. In some embodiments, the alkenyl group is optionally substituted with oxo, halogen, amino, nitrile, nitro, hydroxyl, haloalkyl, alkoxy, aryl, cycloalkyl, heterocycloalkyl, heteroaryl, and the like. In some embodiments, the alkenyl is optionally substituted with oxo, halogen, —CN, —CF$_3$, —OH, —OMe, —NH$_2$, or —NO$_2$. In some embodiments, the alkenyl is optionally substituted with oxo, halogen, —CN, —CF$_3$, —OH, or —OMe. In some embodiments, the alkenyl is optionally substituted with halogen.

"Alkynyl" refers to a straight or branched hydrocarbon chain group, containing at least one carbon-carbon triple bond. In certain embodiments, alkynyl comprises two to twelve (C$_2$-C$_{12}$ alkynyl) carbon atoms, or two to eight carbon atoms (C$_2$-C$_8$ alkynyl), or two to six carbon atoms (C$_2$-C$_6$ alkynyl) or two to four carbon atoms (C$_2$-C$_4$ alkynyl). The alkynyl may be attached to the rest of the molecule by a single bond, for example, ethynyl, propynyl, butynyl, pentynyl, hexynyl, and the like. In some embodiments, the alkynyl group is optionally substituted with oxo, halogen, amino, nitrile, nitro, hydroxyl, haloalkyl, alkoxy, aryl, cycloalkyl, heterocycloalkyl, heteroaryl, and the like. In some embodiments, the alkynyl is optionally substituted with oxo, halogen, —CN, —CF$_3$, —OH, —OMe, —NH$_2$, or —NO$_2$. In some embodiments, the alkynyl is optionally substituted with oxo, halogen, —CN, —CF$_3$, —OH, or —OMe. In some embodiments, the alkynyl is optionally substituted with halogen.

"Alkylene" or "alkylene chain" refers to a straight or branched divalent hydrocarbon chain linking the rest of the molecule to a radical group, consisting solely of carbon and hydrogen, containing no unsaturation and having, for example, from one to twelve carbon atoms (C$_1$-C$_{12}$ alkylene), e.g., methylene, ethylene, propylene, n-butylene, and the like. The alkylene chain is attached to the rest of the molecule through a single bond and to the radical group through a single bond. The points of attachment of the alkylene chain to the rest of the molecule and to the radical group are through one carbon in the alkylene chain or through any two carbons within the chain. In certain embodiments, an alkylene comprises one to eight carbon atoms (C$_1$-C$_8$ alkylene), or one to five carbon atoms (C$_1$-C$_5$ alkylene), or one to four carbon atoms (C$_1$-C$_4$ alkylene), or one to three carbon atoms (C$_1$-C$_3$ alkylene), or one to two carbon atoms (C$_1$-C$_2$ alkylene). In other embodiments, an alkylene comprises one carbon atom (C$_1$ alkylene), or two carbon atoms (C$_2$ alkylene). In certain embodiments, an alkylene comprises two to five carbon atoms (e.g., C$_2$-C$_5$ alkylene). In some embodiments, the alkylene is optionally substituted with oxo, halogen, —CN, —CF$_3$, —OH, —OMe, —NH$_2$, or —NO$_2$. In some embodiments, the alkylene is optionally substituted with oxo, halogen, —CN, —CF$_3$, —OH, or —OMe. In some embodiments, the alkylene is optionally substituted with halogen.

"Alkoxy" refers to a radical of the formula —O-alkyl where alkyl is as defined herein. Unless stated otherwise specifically in the specification, an alkoxy group may be optionally substituted as described above for alkyl.

"Aryl" refers to an aromatic monocyclic hydrocarbon or aromatic multicyclic hydrocarbon ring system by removing a hydrogen atom from a ring carbon atom. Aryl may include cycles with six to eighteen carbon atoms, where at least one of the rings in the ring system is aromatic, i.e., it contains a cyclic, delocalized (4n+2) π-electron system in accordance with the Hückel theory. In some embodiments, the aryl is a monocyclic, bicyclic, tricyclic or tetracyclic ring system, which may include fused ring system (when fused with a cycloalkyl or heterocycloalkyl ring, the aryl is bonded through an aromatic ring atom). In some embodiments, the aryl is a 6 to 10-membered aryl. In some embodiments, the aryl is a 6-membered aryl. In some embodiments, the aryl is a 10-membered aryl. The ring system from which aryl groups are derived include, but are not limited to, groups such as benzene, fluorene, indane, indene, tetralin and naphthalene. In some embodiments, the aryl is optionally substituted with halogen, amino, nitrile, nitro, hydroxyl, alkyl, haloalkyl, alkoxy, aryl, aralkyl, cycloalkyl, heterocycloalkyl, heteroaryl, and the like. In some embodiments, the aryl is optionally substituted with halogen, —CN, -Me, -Et, —CF$_3$, —OH, —OMe, —NH$_2$, —NO$_2$, or cyclopropyl. In some embodiments, the aryl is optionally substituted with oxo, halogen, —CN, -Me, -Et, —CF$_3$, —OH, —OMe, or cyclopropyl. In some embodiments, the aryl is optionally substituted with halogen.

"Aryloxy" refers to a radical bonded through an oxygen atom of the formula —O-aryl, where aryl is as described above.

"Aralkyl" refers to a radical of the formula —R$^h$-aryl where R$^h$ is an alkylene chain as defined above, for example, methylene, ethylene, and the like. The alkylene chain part of the aralkyl radical is optionally substituted as described above for an alkylene chain. The aryl part of the aralkyl radical is optionally substituted as described above for an aryl group.

"Boronate ester" refers to —B(OR$^k$)$_2$ wherein each R$^k$ are independently hydrogen, optionally substituted alkyl, optionally substituted cycloalkyl, optionally substituted heterocycloalkyl, optionally substituted aryl, optionally substituted heteroaryl, (poly ethylene glycol) ethyl, or an optionally substituted saccharide provided that they are not both hydrogen. In some embodiments, each R$^k$ is alkyl. In some embodiments, two R$^k$ may be taken together with the atom to which they are attached to form an optionally substituted heterocycle or a cyclic boronate ester. In some embodiments, the cyclic boronate ester is formed from pinanediol, pinacol, 1,2-ethanediol, 1,3-propanediol, 1,2-propanediol, 2,3-butanediol, 1,2-diisopropylethandiol, 5,6-decanediol, 1,2-dicyclohexylethanediol, diethanolamine, 1,2-diphenyl-1,2-ethanediol, 2,6,6-trimethylbicyclo[3.1.1]heptane-2,3-diol, or (1S,2S,3R,5S)-2,6,6-trimethylbicyclo[3.1.1]heptane-2,3-diol.

"Cycloalkyl" refers to a saturated or partially unsaturated, monocyclic or polycyclic hydrocarbon. In certain embodiments, the cycloalkyl includes fused (when fused with an aryl or a heteroaryl ring, the cycloalkyl is bonded through a non-aromatic ring atom) or bridged ring systems. In certain embodiments, the cycloalkyl comprises from three to twenty carbon atoms (C$_3$-C$_{20}$ cycloalkyl), or three to ten carbon atoms (C$_3$-C$_{10}$ cycloalkyl), or three to eight carbon atoms (C$_3$-C$_8$ cycloalkyl), or three to six carbon atoms (C$_3$-C$_6$ cycloalkyl). In some embodiments, the cycloalkyl is a 3- to 6-membered cycloalkyl. In some embodiments, the cycloalkyl is a 3- to 8-membered cycloalkyl. Examples of monocyclic cycloalkyls include, e.g., cyclopropyl, cyclobutyl, cyclopentyl, cyclohexyl, cycloheptyl, and cyclooctyl. Polycyclic cycloalkyl include, for example, adamantyl, norbornyl (i.e., bicyclo[2.2.1]heptanyl), norbornenyl, decalinyl, 7,7-dimethyl-bicyclo[2.2.1]heptanyl, and the like. In some embodiments, the cycloalkyl is optionally substituted with oxo, halogen, amino, nitrile, nitro, hydroxyl, alkyl, haloalkyl, alkoxy, aryl, aralkyl, cycloalkyl, heterocycloalkyl, heteroaryl, and the like. In some embodiments, the cycloalkyl is optionally substituted with oxo, halogen, —CN, -Me, -Et, —CF$_3$, —OH, —OMe, —NH$_2$, —NO$_2$, or cyclopropyl. In some embodiments, the cycloalkyl is optionally substituted with oxo, halogen, —CN, -Me, -Et, —CF$_3$, —OH, —OMe, or cyclopropyl. In some embodiments, the cycloalkyl is optionally substituted with halogen.

"Cycloalkylalkyl" refers to a radical of the formula —R$^h$-cycloalkyl where R$^h$ is an alkylene chain as defined above. The alkylene chain and the cycloalkyl radical are optionally substituted as described above.

"Halo" or "halogen" refers to bromo, chloro, fluoro, or iodo. In some embodiments, halogen refers to chloro or fluoro.

"Heterocycloalkyl" refers to a saturated or partially unsaturated ring that comprises two to twenty carbon atoms and at least one heteroatom. In certain embodiments, the heteroatoms are independently selected from N, O, Si, P, B, and S atoms. In certain embodiments, the heteroatoms are independently selected from N, O, and S atoms. The heterocycloalkyl may be selected from monocyclic or bicyclic, fused (when fused with an aryl or a heteroaryl ring, the heterocycloalkyl is bonded through a non-aromatic ring atom) or bridged ring systems. The heteroatoms in the heterocycloalkyl are optionally oxidized. One or more nitrogen atoms, if present, are optionally quaternized. The heterocycloalkyl is partially or fully saturated. The heterocycloalkyl is attached to the rest of the molecule through any atom of the heterocycloalkyl, valence permitting, such as any carbon or nitrogen atoms of the heterocycloalkyl. In certain embodiments, the heterocycloalkyl comprises from two to twenty carbon atoms (C$_2$-C$_{20}$ heterocycloalkyl), or two to ten carbon atoms (C$_2$-C$_{10}$ heterocycloalkyl), or two to eight carbon atoms (C$_2$-C$_8$ heterocycloalkyl), or two to six carbon atoms (C$_2$-C$_6$ heterocycloalkyl). In some embodiments, the heterocycloalkyl is a 3- to 6-membered heterocycloalkyl. In some embodiments, the heterocycloalkyl is a 3- to 8-membered heterocycloalkyl. In some embodiments, the heterocycloalkyl is a 5- to 6-membered heterocycloalkyl. In some embodiments, the heterocycloalkyl is a 5-membered heterocycloalkyl. In some embodiments, the heterocycloalkyl is a 6-membered heterocycloalkyl. Examples of heterocycloalkyl include, but are not limited to, azetidinyl, aziridyl, dioxolanyl, thienyl[1,3]dithianyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, piperidinyl, piperazinyl, 4-piperidonyl, pyrrolidinyl, pyrazolidinyl, quinuclidinyl, thiazolidinyl, tetrahydrofuryl, trithianyl, tetrahydropyranyl, thiomorpholinyl, thiamorpholinyl, 1-oxo-thiomorpholinyl, and 1,1-dioxothiomorpholinyl. In some embodiments, the heterocycloalkyl is optionally substituted with oxo, halogen, amino, nitrile, nitro, hydroxyl, alkyl, haloalkyl, alkoxy, aryl, aralkyl, cycloalkyl, heterocycloalkyl, heteroaryl, and the like. In some embodiments, the heterocycloalkyl is optionally substituted with oxo, halogen, —CN, -Me, -Et, —CF$_3$, —OH, —OMe, —NH$_2$, —NO$_2$, or cyclopropyl. In some embodiments, the heterocycloalkyl is optionally substituted with oxo, halogen, —CN, -Me, -Et, —CF$_3$, —OH, —OMe, or cyclopropyl. In some embodiments, the heterocycloalkyl is optionally substituted with halogen.

"Heterocycloalkylalkyl" refers to a radical of the formula —R$^h$-heterocycloalkyl where R$^h$ is an alkylene chain as defined above. If the heterocycloalkyl is a nitrogen-containing heterocycloalkyl, the heterocycloalkyl is optionally attached to the alkyl radical at the nitrogen atom. The alkylene chain of the heterocycloalkylalkyl radical is optionally substituted as defined above for an alkylene chain. The heterocycloalkyl part of the heterocycloalkylalkyl radical is optionally substituted as defined above for a heterocycloalkyl group.

"Heteroaryl" refers to a 5- to 14-membered ring system comprising hydrogen atoms, one to thirteen carbon atoms, one to six heteroatoms selected from the group consisting of nitrogen, oxygen, phosphorous and sulfur, and at least one aromatic ring. In some embodiments, the heteroaryl is a 5- or 6-membered heteroaryl. In some embodiments, the heteroaryl is a 5-membered heteroaryl. In some embodiments, the heteroaryl is a 6-membered heteroaryl. In some embodiments, the heteroaryl is a monocyclic, bicyclic, tricyclic or tetracyclic ring system, which may include fused ring systems (when fused with a cycloalkyl or heterocycloalkyl ring, the heteroaryl is bonded through an aromatic ring atom); and the nitrogen, carbon or sulfur atoms in the heteroaryl may be optionally oxidized; the nitrogen atom may be optionally quaternized. In some embodiments, the heteroaryl is a 5- to 10-membered heteroaryl. In some embodiments, the heteroaryl is a 10-membered heteroaryl. Examples include, but are not limited to, azepinyl, acridinyl, benzimidazolyl, benzothiazolyl, benzindolyl, benzodioxolyl, benzofuranyl, benzooxazolyl, benzothiazolyl, benzothiadiazolyl, benzo[b][1,4]dioxepinyl, 1,4-benzodioxanyl, benzonaphthofuranyl, benzoxazolyl, benzodioxolyl, benzodioxinyl, benzopyranyl, benzopyranonyl, benzofuranyl, benzofuranonyl, benzothienyl (benzothiophenyl), benzotriazolyl, benzo[4,6]imidazo[1,2-a]pyridinyl, carbazolyl, cinnolinyl, dibenzofuranyl, dibenzothiophenyl, furanyl, furanonyl, isothiazolyl, imidazolyl, indazolyl, indolyl, indazolyl, isoindolyl, indolinyl, isoindolinyl, isoquinolyl, indolizinyl, isoxazolyl, naphthyridinyl, oxadiazolyl, 2-oxoazepinyl, oxazolyl, oxiranyl, 1-oxidopyridinyl, 1-oxidopyrimidinyl, 1-oxidopyrazinyl, 1-oxidopyridazinyl, 1-phenyl-1H-pyrrolyl, phenazinyl, phenothiazinyl, phenoxazinyl, phthalazinyl, pteridinyl, purinyl, pyrrolyl, pyrazolyl, pyridinyl, pyrazinyl, pyrimidinyl, pyridazinyl, quinazolinyl, quinoxalinyl, quinolinyl, quinuclidinyl, isoquinolinyl, tetrahydroquinolinyl, thiazolyl, thiadiazolyl, triazolyl, tetrazolyl, triazinyl, and thiophenyl (i.e., thienyl). In some embodiments, the heteroaryl is optionally substituted with halogen, amino, nitrile, nitro, hydroxyl, alkyl, haloalkyl, alkoxy, aryl, aralkyl, cycloalkyl, heterocycloalkyl, heteroaryl, and the like. In some embodiments, the heteroaryl is optionally substituted with halogen, —CN, -Me, -Et, —CF$_3$, —OH, —OMe, —NH$_2$, —NO$_2$, or cyclopropyl. In some embodiments, the heteroaryl is optionally substituted with halogen, —CN, -Me, -Et, —CF$_3$, —OH, —OMe, or cyclopropyl. In some embodiments, the heteroaryl is optionally substituted with halogen.

The term "optional" or "optionally" means that the subsequently described event or circumstance may or may not occur, and that the description includes instances where said event or circumstance occurs and instances in which it does not. For example, "optionally substituted alkyl" means either "alkyl" or "substituted alkyl" as defined above. Further, an optionally substituted group may be un-substituted (e.g., —CH$_2$CH$_3$), fully substituted (e.g., —CF$_2$CF$_3$), mono-substituted (e.g., —CH$_2$CH$_2$F) or substituted at a level anywhere in-between fully substituted and mono-substituted (e.g., —CH$_2$CHF$_2$, —CH$_2$CF$_3$, —CF$_2$CH$_3$, —CFHCHF$_2$, etc). It will be understood by those skilled in the art with respect to any group containing one or more substituents that such groups are not intended to introduce any substitution or substitution patterns (e.g., substituted alkyl includes optionally substituted cycloalkyl groups, which in turn are defined as including optionally substituted alkyl groups, potentially ad infinitum) that are sterically impractical and/or synthetically non-feasible. Thus, any substituents described should generally be understood as having a maximum molecular weight of about 1,000 daltons, and more typically, up to about 500 daltons.

An "effective amount" or "therapeutically effective amount" refers to an amount of a compound administered to a mammalian subject, either as a single dose or as part of a series of doses, which is effective to produce a desired therapeutic effect.

"Treatment" of an individual (e.g. a mammal, such as a human) or a cell is any type of intervention used in an attempt to alter the natural course of the individual or cell. In some embodiments, treatment includes administration of a pharmaceutical composition, subsequent to the initiation of a pathologic event or contact with an etiologic agent and includes stabilization of the condition (e.g., condition does not worsen) or alleviation of the condition. In some embodiments, treatment also includes prophylactic treatment (e.g., administration of a composition described herein when an individual is suspected to be suffering from a bacterial infection).

Compounds

Described herein are compounds that modulate the activity of beta-lactamase. In some embodiments, the compounds described herein inhibit beta-lactamase. In some embodiments, the compounds described herein inhibit penicillin binding protein. In certain embodiments, the compounds described herein are useful in the treatment of bacterial infections. In some embodiments, the bacterial infection is an upper or lower respiratory tract infection, a urinary tract infection, an intra-abdominal infection, or a skin infection. In some embodiments, the bacterial infection is uncomplicated or complicated urinary tract infections, uncomplicated or complicated gonorrhea, upper or lower respiratory tract infections, skin or skin structure infections, intra-abdominal infections, central nervous system infections, blood stream infections, or systemic infections.

Also disclosed herein is a compound of Formula (Ia) or (Ib), or a pharmaceutically acceptable salt, solvate, stereoisomer, tautomer, N-oxide, dimer, or trimer thereof:

Formula (Ia)

Formula (Ib)

wherein:
$L^1$ is —$(CR^1R^2)_n$—;
$L^2$ is —$(CR^1R^2)_m$—;
$L^{2'}$ is absent, —C(=O)NH—, —NHC(=O)—, or —CH$_2$NH—;
$L^3$ is —C(=O)—, —S(=O)—, or —S(=O)$_2$—;
$A^1$ is hydrogen,

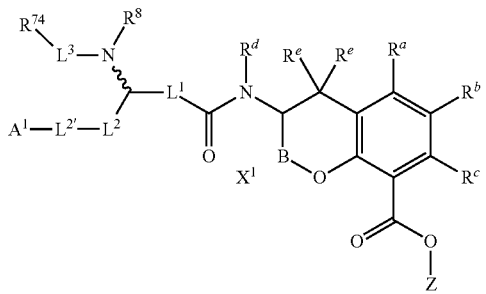

or Y

Ring A is cycloalkyl, heterocycloalkyl, aryl, or heteroaryl;
each $R^1$ and $R^2$ is independently hydrogen, halogen, optionally substituted alkyl, —OH, —OR$^{34}$, —SR$^{35}$, —NR$^{32}$R$^{33}$, —NR$^{32}$C(=O)R$^{34}$, —C(=O)NR$^{32}$R$^{33}$, —NR$^{32}$S(=O)$_2$R$^{34}$, —C(=O)OH, —C(=O)OR$^{34}$, optionally substituted cycloalkyl, optionally substituted heterocycloalkyl, optionally substituted aryl, or optionally substituted heteroaryl; or
$R^1$ and $R^2$ are taken together with the carbon to which they are attached to form an optionally substituted cycloalkyl;
$R^8$ is hydrogen, optionally substituted alkyl, optionally substituted cycloalkyl, optionally substituted heterocycloalkyl, optionally substituted aryl, or optionally substituted heteroaryl;
each $R^{20}$ and $R^{21}$ is independently hydrogen, halogen, or optionally substituted alkyl;
$R^{22}$ and $R^{23}$ are independently hydrogen or optionally substituted alkyl; or
$R^{22}$ and $R^{23}$ are taken together with the nitrogen to which they are attached to form an optionally substituted heterocycloalkyl;
$R^{24}$ is optionally substituted alkyl, optionally substituted cycloalkyl, optionally substituted heterocycloalkyl, optionally substituted aryl, or optionally substituted heteroaryl;
$R^{25}$ is hydrogen, optionally substituted alkyl, optionally substituted cycloalkyl, optionally substituted heterocycloalkyl, optionally substituted aryl, or optionally substituted heteroaryl;
each $R^{30}$, $R^{31}$, $R^{50}$, and $R^{51}$ is independently hydrogen, halogen, optionally substituted alkyl, optionally substituted cycloalkyl, optionally substituted heterocycloalkyl, optionally substituted aryl, optionally substituted heteroaryl, —OH, —OR$^{24}$, —SR$^{25}$, —NR$^{22}$R$^{23}$, —NR$^{22}$C(=O)R$^{24}$, —C(=O)NR$^{22}$R$^{23}$, —NR$^{22}$S(=O)$_2$R$^{24}$, —C(=O)OH, or —C(=O)OR$^{24}$; or
$R^{30}$ and $R^{31}$, or $R^{50}$ and $R^{51}$ are taken together with the carbon atom to which they are attached to form an optionally substituted cycloalkyl; or
two $R^{30}$ or two $R^{50}$ on adjacent carbons are taken together to form an alkenyl; or
two $R^{30}$ and two $R^{31}$, or two $R^{50}$ and two $R^{51}$ on adjacent carbons are taken together to form an alkynyl;
$R^{32}$, $R^{33}$, $R^{52}$, $R^{53}$, $R^2$, and $R^3$ are independently hydrogen, optionally substituted alkyl, optionally substituted cycloalkyl, optionally substituted heterocycloalkyl, optionally substituted aryl, optionally substituted heteroaryl, (poly-ethylene-glycol)-ethyl, optionally substituted saccharide, —CN, —OH, —S(=O)$_2$R$^{24}$, —S(=O)$_2$NR$^{22}$R$^{23}$, or —C(=O)R$^{24}$; or $R^{32}$ and $R^{33}$, or $R^{52}$ and $R^{53}$, or $R^{82}$ and $R^{83}$ are taken together with the nitrogen to which they are attached to form an optionally substituted heterocycloalkyl;

$R^{34}$, $R^{54}$, and $R^{84}$ are independently optionally substituted alkyl, optionally substituted cycloalkyl, optionally substituted heterocycloalkyl, optionally substituted aryl, or optionally substituted heteroaryl;

$R^{35}$ and $R^{55}$ are independently hydrogen, optionally substituted alkyl, optionally substituted cycloalkyl, optionally substituted heterocycloalkyl, optionally substituted aryl, or optionally substituted heteroaryl;

$R^{36}$ and $R^{56}$ are independently hydrogen, —OH, —OR$^{24}$, —CN, —NO$_2$, —NR$^{22}$R$^{23}$, or optionally substituted alkyl;

Z is hydrogen, $R^{61}$, —(R$^{60}$)$_q$OR$^{61}$, —(R$^{60}$)$_q$O(R$^{60}$)$_q$OR$^{61}$, —R$^{60}$OC(=O)R$^{61}$, —R$^{60}$OC(=O)OR$^{61}$, —R$^{60}$OC(=O)NHR$^{61}$, —R$^{60}$OC(=O)N(R$^{61}$)$_2$, optionally substituted alkyloxyalkyl, optionally substituted acyloxyalkyl, optionally substituted alkyloxycarbonyloxyalkyl, optionally substituted cycloalkyloxycarbonyloxyalkyl, optionally substituted aryloxycarbonyloxyalkyl, or optionally substituted alkyl-[1,3]dioxol-2-one;

each $R^{60}$ is independently —CH$_2$—, —CH(CH$_3$)—, —C(CH$_3$)$_2$—, or optionally substituted 1,1'-cyclopropylene;

each $R^{61}$ is independently optionally substituted alkyl, optionally substituted cycloalkyl, optionally substituted heterocycloalkyl, optionally substituted aryl, or optionally substituted heteroaryl; or two $R^{61}$ are taken together with the nitrogen to which they are attached to form an optionally substituted heterocycloalkyl;

$R^{74}$ is optionally substituted alkyl, optionally substituted cycloalkyl, optionally substituted heterocycloalkyl, optionally substituted aryl, optionally substituted heteroaryl, optionally substituted cycloalkylalkyl, optionally substituted heterocycloalkylalkyl, optionally substituted aralkyl, optionally substituted heteroaralkyl, —OH, —OR$^{84}$, —NR$^{82}$R$^{83}$, —C(=O)OH, or —C(=O)OR$^{84}$;

$R^a$, $R^b$, and $R^c$ are independently hydrogen, halogen, cyano, optionally substituted alkyl, optionally substituted cycloalkyl, optionally substituted heterocycloalkyl, optionally substituted aryl, optionally substituted heteroaryl, —OH, —OR$^{54}$, —O(CR$^{30}$R$^{31}$)$_w$NR$^{52}$R$^{53}$, —O(CR$^{50}$R$^{51}$)$_v$OH, —O(CR$^{50}$R$^{51}$)$_v$OR$^{54}$, —O(CR$^{50}$R$^{51}$)$_v$C(=O)OH, —O(CR$^{50}$R$^{51}$)$_v$C(=O)OR$^{54}$, —O(CR$^{50}$R$^{51}$)$_v$C(=O)NR$^{52}$R$^{53}$, —NR$^{52}$R$^{53}$, —NR$^{52}$(CR$^{50}$R$^{51}$)$_w$NR$^{52}$R$^{53}$, —NR$^{52}$(CR$^{50}$R$^{51}$)$_v$C(=O)OH, —NR$^{52}$(CR$^{50}$R$^{51}$)$_v$C(=O)OR$^{54}$, —NR$^{52}$(CR$^{50}$R$^{51}$)$_v$C(=O)NR$^{52}$R$^{53}$, —NR$^{52}$S(=O)$_{1,2}$R$^{54}$, —S(=O)$_{1,2}$R$^{54}$, —SR$^{55}$, —S(CR$^{50}$R$^{51}$)$_v$NR$^{52}$C(=NR$^{56}$)NR$^{52}$R$^{53}$, —S(CR$^{50}$R$^{51}$)NR$^{52}$CR$^{50}$(=NR$^{56}$), —S(CR$^{50}$R$^{51}$)$_v$C(=NR$^{56}$)NR$^{52}$R$^{53}$, —S(CR$^{50}$R$^{51}$)$_w$OH, —S(CR$^{50}$R$^{51}$)$_w$OR$^{54}$, —S(CR$^{50}$R$^{51}$) NR$^{52}$R$^{53}$, —S(CR$^{50}$R$^{51}$)$_v$C(=O)OH, —S(CR$^{50}$R$^{51}$)$_v$C(=O)OR$^{54}$, —S(CR$^{50}$R$^{51}$)$_v$C(=O)NR$^{52}$R$^{53}$, —C(=O)H, —C(=O)R$^{54}$, —C(=O)OH, —C(=O)OR$^{54}$, —C(=O)NR$^{52}$R$^{53}$, —(CR$^{50}$R$^{51}$)$_v$N(R$^{52}$)(CR$^{50}$R$^{51}$)$_v$C(=O)OH, —(CR$^{50}$R$^{51}$)$_v$OH, —(CR$^{50}$R$^{51}$)$_v$OR$^{54}$, —(CR$^{50}$R$^{51}$)$_v$C(=O)OH, —(CR$^{50}$R$^{51}$)$_v$C(=O)OR$^{54}$, —(CR$^{50}$R$^{51}$)$_v$C(=O)NR$^{52}$R$^{53}$, —(CR$^{50}$R$^{51}$)$_v$OC(=O)R$^{54}$, —(CR$^{50}$R$^{51}$)$_v$SR$^{55}$, —(CR$^{50}$R$^{51}$)$_v$NR$^{52}$C(=NR$^{56}$), —(CR$^{50}$R$^{51}$)$_v$NR$^{52}$R$^{53}$, —(CR$^{50}$R$^{51}$)$_v$C(=NR$^{56}$) NR$^{52}$R$^{53}$, —(CR$^{50}$R$^{51}$)$_v$C(=O)NR$^{52}$R$^{53}$, —(CR$^{50}$R$^{51}$)$_v$heterocycloalkyl, or —(CR$^{50}$R$^{51}$)$_v$heteroaryl;

$R^d$ is hydrogen, —CN, —OH, —S(=O)$_2$R$^{24}$, —S(=O)$_2$NR$^{22}$R$^{23}$, —(CR$^{20}$R$^{21}$)$_v$C(=O)OH, —C(=O)R$^{24}$, optionally substituted alkyl, optionally substituted cycloalkyl, optionally substituted heterocycloalkyl, optionally substituted aryl, optionally substituted heteroaryl, (poly-ethylene-glycol)-ethyl, or an optionally substituted saccharide;

each $R^e$ is independently hydrogen, —CN, —OH, optionally substituted alkyl, or optionally substituted cycloalkyl;

$R^X$ is optionally substituted alkyl or optionally substituted cycloalkyl;

$X^1$ and $X^2$ are independently —OH, —OR$^X$, or F; or $X^1$ and $X^2$ are taken together with the boron atom to which they are attached to form a cyclic boronate ester;

each Y is independently halogen, optionally substituted alkyl, optionally substituted cycloalkyl, optionally substituted heterocycloalkyl, optionally substituted aryl, optionally substituted heteroaryl, -heteroaryl-NR$^{32}$R$^{33}$, -heterocycloalkyl-NR$^{32}$R$^{33}$, -heteroaryl-N(R$^{32}$)C(=NR$^{32}$)NR$^{32}$R$^{33}$, -heterocycloalkyl-N(R$^{32}$)C(=NR$^{32}$)NR$^{32}$R$^{33}$, —OH, —OR$^{34}$, —O(CR$^{30}$R$^{31}$)$_w$OH, —O(CR$^{30}$R$^{31}$)$_w$OR$^{34}$, —O(CR$^{30}$R$^{31}$)$_w$NR$^{32}$R$^{33}$, —O(CR$^{30}$R$^{31}$)$_w$NR$^{32}$C(=O)R$^{34}$, —O(CR$^{30}$R$^{31}$)$_w$NR$^{32}$C(=O)OR$^{34}$, —O(CR$^{30}$R$^{31}$)$_w$NR$^{32}$C(=O)NR$^{32}$R$^{33}$, —O(CR$^{30}$R$^{31}$)$_v$C(=O)NR$^{32}$R$^{33}$, —O(CR$^{30}$R$^{31}$)$_w$NR$^{32}$S(=O)$_{0,1,2}$R$^{34}$, —O(CR$^{30}$R$^{31}$)$_w$NR$^{32}$S(=O)$_{0,1,2}$NR$^{32}$R$^{33}$, —O(CR$^{30}$R$^{31}$)$_w$S(=O)$_{0,1,2}$R$^{34}$, —O(CR$^{30}$R$^{31}$)$_w$S(=O)$_{0,1,2}$NR$^{32}$R$^{33}$, —O(CR$^{30}$R$^{31}$)$_v$C(=NR$^{36}$)NR$^{32}$R$^{33}$, —O(CR$^{30}$R$^{31}$)$_w$N(R$^{32}$)C(=NR$^{36}$)R$^{34}$, —O(CR$^{30}$R$^{31}$)$_v$C(=NR$^{36}$)NR$^{32}$C(=NR$^{36}$)NR$^{32}$R$^{33}$, —O(CR$^{30}$R$^{31}$)$_w$N(R$^{32}$)C(=NR$^{36}$)NR$^{32}$R$^{33}$, —O(CR$^{30}$R$^{31}$)$_w$S(=O)$_{0,1,2}$R$^{34}$, —O(CR$^{30}$R$^{31}$)$_w$S(=O)$_{0,1,2}$NR$^{32}$R$^{33}$, —OC(=O)R$^{34}$, —OC(=O)(CR$^{30}$R$^{31}$)$_v$NR$^{32}$R$^{33}$, —OC(=O)NR$^{32}$R$^{33}$, —OC(=O)OR$^{34}$, —OC(=O)NR$^{32}$(CR$^{30}$R$^{31}$)$_w$NR$^{32}$R$^{33}$, —O-heteroaryl, —O-heterocycloalkyl, —O(CR$^{30}$R$^{31}$)$_v$heteroaryl, —O(CR$^{30}$R$^{31}$)$_v$heterocycloalkyl, —O(CR$^{30}$R$^{31}$)$_w$NR$^{32}$-heteroaryl, —O(CR$^{30}$R$^{31}$)$_w$NR$^{32}$-heterocycloalkyl, —O(CR$^{30}$R$^{31}$)$_w$O-heterocycloalkyl, —NR$^{32}$R$^{33}$, —NR$^{32}$(CR$^{30}$R$^{31}$)$_w$NR$^{32}$R$^{33}$, —NR$^{32}$(CR$^{30}$R$^{31}$)$_w$OH, —NR$^{32}$(CR$^{30}$R$^{31}$)$_w$OR$^{34}$, —NR$^{32}$C(=O)R$^{34}$, —NR$^{32}$C(=O)OR$^{34}$, —N(R$^{32}$)$_v$C(=O)(CR$^{30}$R$^{31}$)$_w$NR$^{32}$R$^{33}$, —NR$^{32}$C(=O)NR$^{32}$R$^{33}$, —NR$^{32}$C(=O)NR$^{32}$(CR$^{30}$R$^{31}$)$_w$NR$^{32}$R$^{33}$, —NR$^{32}$(CR$^{30}$R$^{31}$)$_w$S(=O)$_{0,1,2}$R$^{34}$, —NR$^{32}$(CR$^{30}$R$^{31}$)$_w$S(=O)$_{0,1,2}$NR$^{32}$R$^{33}$, —NR$^{32}$(CR$^{30}$R$^{31}$)$_w$NR$^{32}$R$^{33}$S(=O)$_{0,1,2}$R$^{34}$, —NR$^{32}$(CR$^{30}$R$^{31}$)$_w$NR$^{32}$S(=O)$_{0,1,2}$NR$^{32}$R$^{33}$, —NR$^{32}$C(=NR$^{36}$)NR$^{32}$R$^{33}$, —N(R$^{32}$)C(=NR$^{36}$)R$^{34}$, —NR$^{32}$(CR$^{30}$R$^{31}$)$_w$N(R$^{32}$)C(=NR$^{36}$)R$^{34}$, —NR$^{32}$(CR$^{30}$R$^{31}$)$_v$C(=NR$^{36}$)NR$^{32}$R$^{33}$, NR$^{32}$(CR$^{30}$R$^{31}$)$_w$N(R$^{32}$)C(=NR$^{36}$)NR$^{32}$R$^{33}$, —NR$^{32}$(CR$^{30}$R$^{31}$)$_w$NR$^{32}$C(=O)NR$^{32}$R$^{33}$, —NR$^{32}$(CR$^{30}$R$^{31}$)$_w$NR$^{32}$C(=O)OR$^{34}$, —NR$^{32}$S(=O)$_{0,1,2}$NR$^{32}$R$^{33}$, —NR$^{32}$S(=O)$_{0,1,2}$R$^{34}$, —NR$^{32}$(CR$^{30}$R$^{31}$)$_v$CO$_2$H, —NR$^{32}$(CR$^{30}$R$^{31}$)$_v$CO$_2$R$^{34}$, —NR$^{32}$(CR$^{30}$R$^{31}$)$_v$C(=O)NR$^{32}$R$^{33}$, —N(R$^{32}$)-heteroaryl- NR$^{32}$R$^{33}$, —N(R$^{32}$)-heterocycloalkyl-NR$^{32}$R$^{33}$, —NR$^{32}$(CR$^{30}$R$^{31}$)$_v$heteroaryl, —NR$^{32}$(CR$^{30}$R$^{31}$)$_v$heterocycloalkyl, —NR$^{32}$(CR$^{30}$R$^{31}$)$_w$NR$^{32}$-heteroaryl, —NR$^{32}$(CR$^{30}$R$^{31}$)$_w$NR$^{32}$-heterocycloalkyl, —CN, —(CR$^{30}$R$^{31}$)$_v$CN, —(CR$^{30}$ $R^{31})_w NR^{32}R^{33}$, —$(CR^{30}R^{31})_w OH$, —$(CR^{30}R^{31})_v OR^{34}$, —$(CR^{30}R^{31})_v OC(=O)R^{34}$, —$(CR^{30}R^{31})_v OC(=O)NR^{32}R^{33}$, —$(CR^{30}R^{31})_v O(CR^{30}R^{31})_v OR^{34}$, —$(CR^{30}R^{31})_v O(CR^{30}R^{31})_w OH$, —$(CR^{30}R^{31})_v O(CR^{30}R^{31})_w NR^{32}R^{33}$, —$(CR^{30}R^{31})_w NR^{32}(CR^{30}R^{31})_w OH$, —$(CR^{30}R^{31})_v NR^{32}(CR^{30}R^{31})_v OR^{34}$, —$(CR^{30}R^{31})_v C(=O)NR^{32}R^{33}$, —$(CR^{30}R^{31})_v C(=O)OH$, —$(CR^{30}R^{31})_v C(=O)OR^{34}$, —$(CR^{30}R^{31})_v C(=O)NR^{32}(CR^{30}R^{31})_w NR^{32}R^{33}$, —$(CR^{30}R^{31})_v C(=O)NR^{32}(CR^{30}R^{31})_w OR^{34}$, —$(CR^{30}R^{31})_w N(R^{32})_v C(=O)R^{34}$, —$(CR^{30}R^{31})_v N(R^{32})_v C(=O)OR^{34}$, —$(CR^{30}R^{31})_w N(R^{32})_v C(=O)NR^{32}R^{33}$, —$(CR^{30}R^{31})_w N(R^{32})C(=O)(CR^{30}R^{31})_w NR^{32}R^{33}$, —$(CR^{30}R^{31})_w N(R^{32})S(=O)_{0,1,2}R^{34}$, —$(CR^{30}R^{31})_w N(R^{32})S(=O)_{0,1,2}NR^{32}R^{33}$, —$(CR^{30}R^{31})_w S(=O)_{0,1,2}NR^{32}R^{33}$, —$(CR^{30}R^{31})_v NR^{32}(CR^{30}R^{31})_w NR^{32}R^{33}$, —$(CR^{30}R^{31})_v N(R^{32})CH(=NR^{36})$, —$(CR^{30}R^{31})_w N(R^{32})C(=NR^{36})R^{34}$, —$(CR^{30}R^{31})_v C(=NR^{36})NR^{32}R^{33}$, —$(CR^{30}R^{31})_v N(R^{32})C(=NR^{36})NR^{32}R^{33}$, —$(CR^{30}R^{31})_v C(=NR^{36})NR^{32}C(=NR^{36})NR^{32}R^{33}$, —$(CR^{30}R^{31})_v$ heteroaryl-$NR^{32}R^{33}$, —$(CR^{30}R^{31})_v$ heterocycloalkyl-$NR^{32}R^{33}$, —$(CR^{30}R^{31})_v$ heteroaryl-$N(R^{32})C(=NR^{36})NR^{32}R^{33}$, —$(CR^{30}R^{31})_v$ heterocycloalkyl-$N(R^{32})C(=NR^{36})NR^{32}R^{33}$, —$(CR^{30}R^{31})$ heteroaryl, —$(CR^{30}R^{31})$ heterocycloalkyl, —$C(=O)OH$, —$C(=O)OR^{34}$, —$C(=O)NR^{32}R^{33}$, —$C(=O)NR^{32}(CR^{30}R^{31})_w NR^{32}R^{33}$, —$C(=O)NR^{32}(CR^{30}R^{31})_w OH$, —$C(=O)NR^{32}(CR^{30}R^{31})_w OR^{34}$, —$C(=NR^{36})NR^{32}R^{33}$, —$C(=NR^{36})NR^{32}C(=O)R^{34}$, —$S(=O)_{1,2}R^{34}$, —$SR^{35}$, —$S(=O)_{0,1,2}(CR^{30}R^{31})_v NR^{32}R^{33}$, —$S(=O)_{0,1,2}(CR^{30}R^{31})_w OH$, —$S(=O)_{0,1,2}(CR^{30}R^{31})_v OR^{34}$, —$S(=O)_{0,1,2}NR^{32}R^{33}$, —$S(=O)_{0,1,2}NR^{32}(CR^{30}R^{31})_w NR^{32}R^{33}$, —$S(=O)_{0,1,2}(CR^{30}R^{31})_w N(R^{32})C(=NR^{36})R^{34}$, —$S(=O)_{0,1,2}(CR^{30}R^{31})_v C(=NR^{36})NR^{32}R^{33}$, —$S(=O)_{0,1,2}(CR^{30}R^{31})_w N(R^{32})C(=NR^{36})NR^{32}R^{33}$, —$S(=O)_{0,1,2}(CR^{30}R^{31})_v C(=NR^{36})NR^{32}C(=NR^{36})NR^{32}R^{33}$, —$Si(R^{34})_3$, —$NR^{32}R^{33}R^{34+}Q^-$, —$(CR^{30}R^{31})_w NR^{32}R^{33}R^{34+}Q^-$, —$NR^{32}(CR^{30}R^{31})_w NR^{32}R^{33}R^{34+}Q^-$, —$NR^{32}R^{34+}(CR^{30}R^{31})_w NR^{32}R^{33}R^{34+}Q^-_2$, —$(CR^{30}R^{31})_v(T)^+ Q^-$, or —$O(CR^{30}R^{31})_w NR^{32}R^{33}R^{34+}Q^-$;

or two Ys are taken together with the atoms to which they are attached to form an optionally substituted cycloalkyl or an optionally substituted heterocycloalkyl;

T is pyridin-1-yl, pyrimidin-1-yl, or thiazol-3-yl;
Q is a pharmaceutically acceptable counterion;
n is 0-3;
m is 0-3;
p is 0-3;
each q is independently 2-6;
each v is independently 1-5; and
each w is independently 2-5.

In some embodiments of a compound of Formula (Ia) or (Ib), $L^3$ is —$C(=O)$— or —$S(=O)_2$—. In some embodiments of a compound of Formula (Ia) or (Ib), $L^3$ is —$C(=O)$—. In some embodiments of a compound of Formula (Ia) or (Ib), $L^3$ is —$S(=O)_2$—. In some embodiments of a compound of Formula (Ia) or (Ib), $L^3$ is —$S(=O)$—.

In some embodiments of a compound of Formula (Ia) or (Ib), $L^2$ is absent. In some embodiments of a compound of Formula (Ia) or (Ib), $L^2$ is —$C(=O)NH$—, or —$NHC(=O)$—. In some embodiments of a compound of Formula (Ia) or (Ib), $L^2$ is —$CH_2NH$—.

In some embodiments of a compound of Formula (Ia) or (Ib), $R^8$ is hydrogen or optionally substituted alkyl. In some embodiments of a compound of Formula (Ia) or (Ib), $R^8$ is hydrogen.

In some embodiments of a compound of Formula (Ia) or (Ib), $R^{74}$ is optionally substituted alkyl, optionally substituted heterocycloalkyl, optionally substituted heteroaryl, optionally substituted heteroaralkyl, —$NR^{82}R^{83}$, or —$C(=O)OR^{84}$. In some embodiments of a compound of Formula (Ia) or (Ib), $R^{74}$ is optionally substituted heteroaryl. In some embodiments of a compound of Formula (Ia) or (Ib), the heteroaryl is thiazole, pyridine, or pyrimidine. In some embodiments of a compound of Formula (Ia) or (Ib), $R^{74}$ is optionally substituted heterocycloalkyl. In some embodiments of a compound of Formula (Ia) or (Ib), the heterocycloalkyl is piperazine, morpholine, or imidazolidine. In some embodiments of a compound of Formula (Ia) or (Ib), $R^{74}$ is optionally substituted piperazine.

In some embodiments of a compound of Formula (Ia) or (Ib), $R^{74}$ is —$NR^{82}R^{83}$.

In some embodiments of a compound of Formula (Ia) or (Ib), $R^{82}$ and $R^{83}$ are independently hydrogen, optionally substituted alkyl, or optionally substituted heteroaryl. In some embodiments of a compound of Formula (Ia) or (Ib), $R^{82}$ and $R^{83}$ are independently hydrogen or optionally substituted alkyl. In some embodiments of a compound of Formula (Ia) or (Ib), $R^{82}$ and $R^{83}$ are both optionally substituted alkyl. In some embodiments of a compound of Formula (Ia) or (Ib), $R^{82}$ is hydrogen and and $R^{83}$ optionally substituted alkyl or optionally substituted heteroaryl.

In some embodiments of a compound of Formula (Ia) or (Ib), $R^{82}$ and $R^{83}$ are taken together with the nitrogen to which they are attached to form an optionally substituted heterocycloalkyl. In some embodiments of a compound of Formula (Ia) or (Ib), the heterocycloalkyl is piperazine, morpholine, or imidazolidine. In some embodiments of a compound of Formula (Ia) or (Ib), $R^{74}$ is optionally substituted piperazine.

In some embodiments of a compound of Formula (Ia) or (Ib), $R^{74}$ is

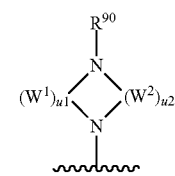

wherein:
each $W^1$ and $W^2$ is independently —$C(=O)$— or —$C(R^{91})_2$—;
$R^{90}$ is hydrogen, —OH, optionally substituted alkyl, optionally substituted alkoxy, optionally substituted cycloalkyl, optionally substituted heterocycloalkyl, optionally substituted aryl, optionally substituted heteroaryl, optionally substituted cycloalkylalkyl, optionally substituted heterocycloalkylalkyl, optionally substituted aralkyl, optionally substituted heteroaralkyl, —$S(=O)_2R^{24}$, —$S(=O)_2NR^{22}R^{23}$, or —$C(=O)R^{24}$.
each $R^{91}$ is independently hydrogen, halogen, —OH, —CN, $NH_2$, $NO_2$, optionally substituted alkyl, optionally substituted alkoxy, optionally substituted cycloalkyl, optionally substituted heterocycloalkyl, optionally substituted aryl, or optionally substituted heteroaryl;

or one $R^{90}$ and $R^{91}$ are taken together with the atoms to which they are attached to form an optionally substituted cycloalkyl or an optionally substituted heterocycloalkyl;
u1 is 1-3; and
u2 is 1-3.

In some embodiments of a compound of Formula (Ia) or (Ib), $R^{74}$ is

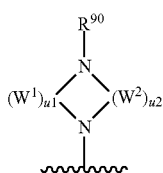

wherein:
each $W^1$ and $W^2$ is independently —C(═O)— or —C($R^{91}$)$_2$—;
$R^{90}$ is hydrogen, —OH, optionally substituted alkyl, optionally substituted alkoxy, optionally substituted cycloalkyl, optionally substituted heterocycloalkyl, optionally substituted aryl, optionally substituted heteroaryl, optionally substituted cycloalkylalkyl, optionally substituted heterocycloalkylalkyl, optionally substituted aralkyl, optionally substituted heteroaralkyl, —S(═O)$_2$R$^{24}$, —S(═O)$_2$NR$^{22}$R$^{23}$, or —C(═O)R$^{24}$.
each $R^{91}$ is independently hydrogen, halogen, —OH, —CN, NH$_2$, NO$_2$, optionally substituted alkyl, optionally substituted alkoxy, optionally substituted cycloalkyl, optionally substituted heterocycloalkyl, optionally substituted aryl, or optionally substituted heteroaryl;
u1 is 1-3; and
u2 is 1-3.

In some embodiments of a compound of Formula (Ia) or (Ib), u1 is 1. In some embodiments of a compound of Formula (Ia) or (Ib), u1 is 2. In some embodiments of a compound of Formula (Ia) or (Ib), u1 is 3. In some embodiments of a compound of Formula (Ia) or (Ib), u1 is 1. In some embodiments of a compound of Formula (Ia) or (Ib), u1 is 2. In some embodiments of a compound of Formula (Ia) or (Ib), u1 is 3. In some embodiments of a compound of Formula (Ia) or (Ib), u2 is 1. In some embodiments of a compound of Formula (Ia) or (Ib), u2 is 2. In some embodiments of a compound of Formula (Ia) or (Ib), u2 is 3. In some embodiments of a compound of Formula (Ia) or (Ib), u1 is 1 and u2 is 1. In some embodiments of a compound of Formula (Ia) or (Ib), u1 is 2 and u2 is 1. In some embodiments of a compound of Formula (Ia) or (Ib), u1 is 2 and u2 is 2. In some embodiments of a compound of Formula (Ia) or (Ib), u1 is 1 and u2 is 3. In some embodiments of a compound of Formula (Ia) or (Ib), u1 is 2 and u2 is 3. In some embodiments of a compound of Formula (Ia) or (Ib), u1 is 3 and u2 is 3.

In some embodiments of a compound of Formula (Ia) or (Ib), u1 is 2; each $W^1$ is —C($R^{91}$)$_2$—; u2 is 2; and each $W^2$ is —C(═O)—. In some embodiments of a compound of Formula (Ia) or (Ib), u1 is 2; each $W^1$ is —C($R^{91}$)$_2$—; u2 is 1; and $W^2$ is —C(═O)—. In some embodiments of a compound of Formula (Ia) or (Ib), u1 is 2; each $W^1$ is —C($R^{91}$)$_2$—; u2 is 2; and one $W^2$ is —C($R^{91}$)$_2$— and one $W^2$ is —C(═O)—. In some embodiments of a compound of Formula (Ia) or (Ib), u1 is 2; one $W^1$ is —C($R^{91}$)$_2$— and one $W^1$ is —C(═O)—; u2 is 2; and one $W^2$ is —C($R^{91}$)$_2$— and one $W^2$ is —C(═O)—.

In some embodiments of a compound of Formula (Ia) or (Ib), $R^{90}$ is hydrogen, optionally substituted alkyl, optionally substituted cycloalkyl, optionally substituted aralkyl, —S(═O)$_2$R$^{24}$, or —C(═O)R$^{24}$. In some embodiments of a compound of Formula (Ia) or (Ib), $R^{90}$ is optionally substituted alkyl. In some embodiments of a compound of Formula (Ia) or (Ib), $R^{90}$ is —H, —OH,

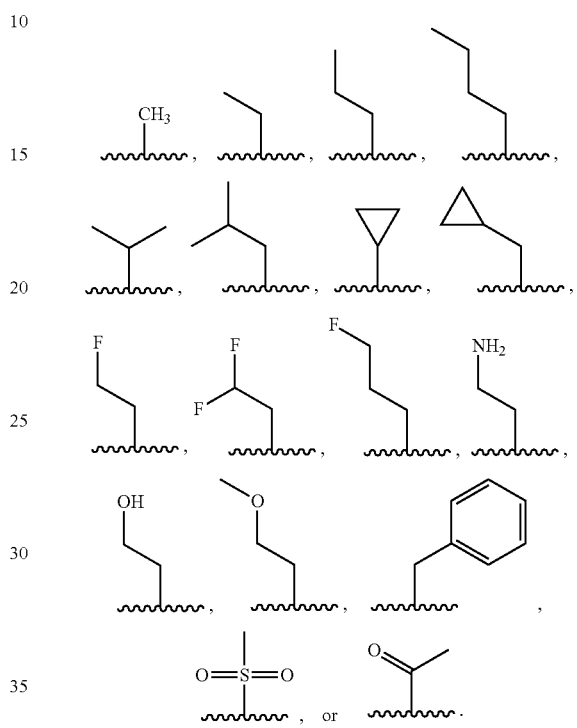

In some embodiments of a compound of Formula (Ia) or (Ib), $R^{90}$ is ethyl.

In some embodiments of a compound of Formula (Ia) or (Ib), each $R^{91}$ is independently hydrogen, halogen, or optionally substituted alkyl. In some embodiments of a compound of Formula (Ia) or (Ib), each $R^{91}$ is hydrogen.

In some embodiments of a compound of Formula (Ia) or (Ib), $R^{74}$ is selected from:

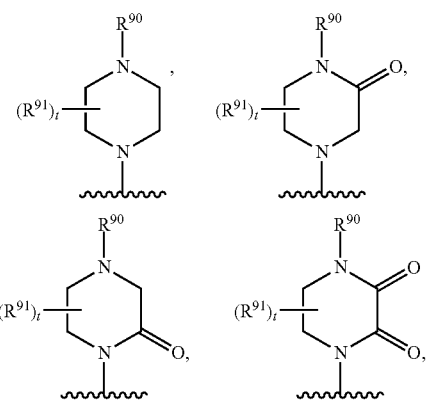

25

-continued

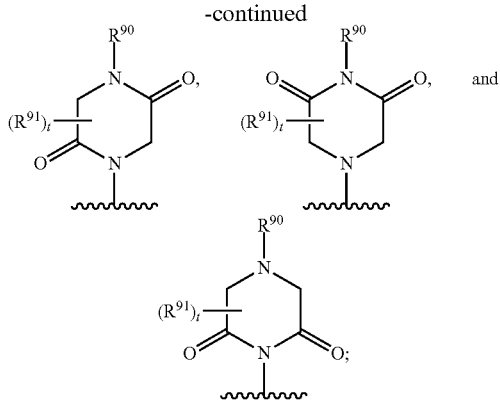

wherein
R$^{90}$ is hydrogen, —OH, optionally substituted alkyl, optionally substituted alkoxy, optionally substituted cycloalkyl, optionally substituted heterocycloalkyl, optionally substituted aryl, optionally substituted heteroaryl, optionally substituted cycloalkylalkyl, optionally substituted heterocycloalkylalkyl, optionally substituted aralkyl, optionally substituted heteroaralkyl, —S(=O)$_2$R$^{24}$, —S(=O)$_2$NR$^{22}$R$^{23}$, or —C(=O)R$^{24}$.
each R$^{91}$ is independently hydrogen, halogen, —OH, —CN, NH$_2$, NO$_2$, optionally substituted alkyl, optionally substituted alkoxy, optionally substituted cycloalkyl, optionally substituted heterocycloalkyl, optionally substituted aryl, or optionally substituted heteroaryl; and
t is 1-4.

In some embodiments of a compound of Formula (Ia) or (Ib), R$^{74}$ is:

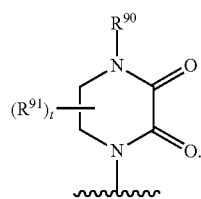

In some embodiments of a compound of Formula (Ia) or (Ib), t is 0. In some embodiments of a compound of Formula (Ia) or (Ib), t is 1. In some embodiments of a compound of Formula (Ia) or (Ib), t is 2. In some embodiments of a compound of Formula (Ia) or (Ib), t is 3. In some embodiments of a compound of Formula (Ia) or (Ib), t is 4.

In some embodiments of a compound of Formula (Ia) or (Ib), R$^{90}$ is hydrogen, optionally substituted alkyl, optionally substituted cycloalkyl, optionally substituted aralkyl, or —S(=O)$_2$R$^{24}$. In some embodiments of a compound of Formula (Ia) or (Ib), R$^{90}$ is hydrogen, optionally substituted alkyl, optionally substituted cycloalkyl, or optionally substituted aralkyl. In some embodiments of a compound of Formula (Ia) or (Ib), R$^{90}$ is optionally substituted alkyl. In some embodiments of a compound of Formula (Ia) or (Ib), R$^{90}$ is alkyl optionally substituted with halogen, cycloalkyl, —NH$_2$, —OH, or —OMe. In some embodiments of a compound of Formula (Ia) or (Ib), R$^{90}$ is methyl, ethyl, propyl, or butyl. In some embodiments of a compound of Formula (Ia) or (Ib), R$^{90}$ is ethyl.

26

In some embodiments of a compound of Formula (Ia) or (Ib), R$^{90}$ is —H, —OH,

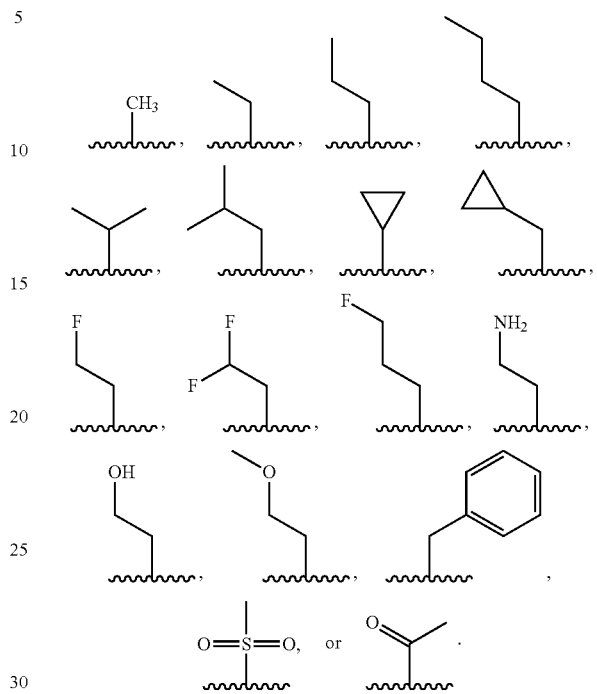

In some embodiments of a compound of Formula (Ia) or (Ib), each R$^{91}$ is independently hydrogen, halogen, or optionally substituted alkyl. In some embodiments of a compound of Formula (Ia) or (Ib), each R$^{91}$ is independently hydrogen or halogen. In some embodiments of a compound of Formula (Ia) or (1b), each R$^{91}$ is hydrogen.

In some embodiments of a compound of Formula (Ia) or (Ib), R$^{74}$ is:

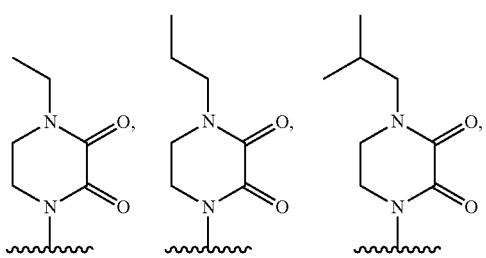

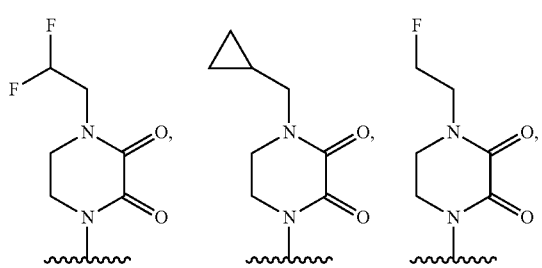

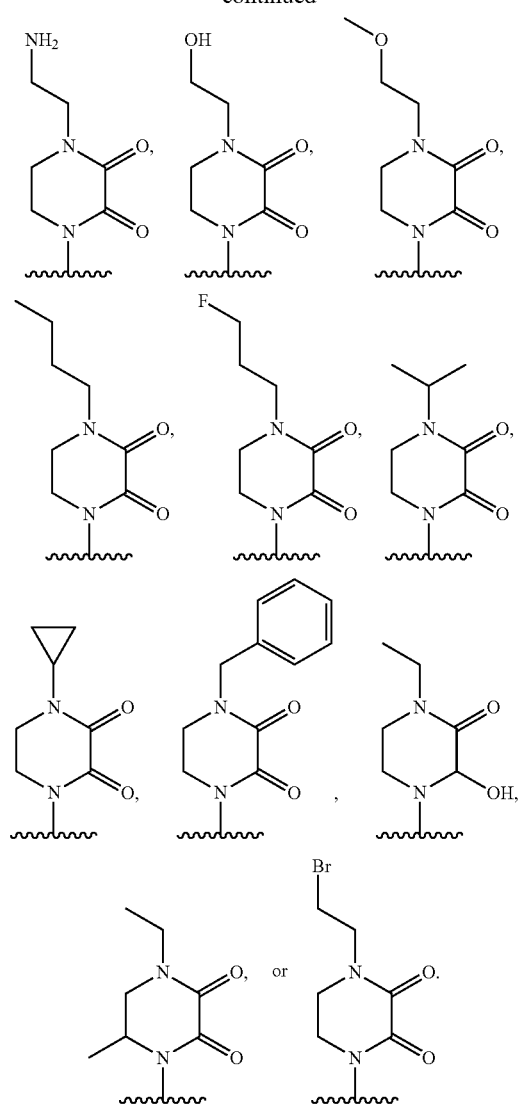
In some embodiments of a compound of Formula (Ia) or (Ib), $R^{74}$ is:
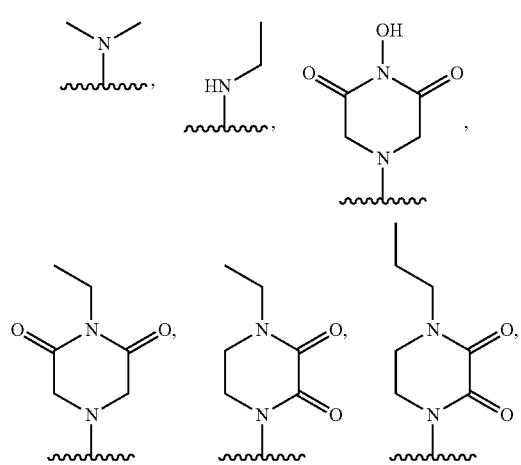
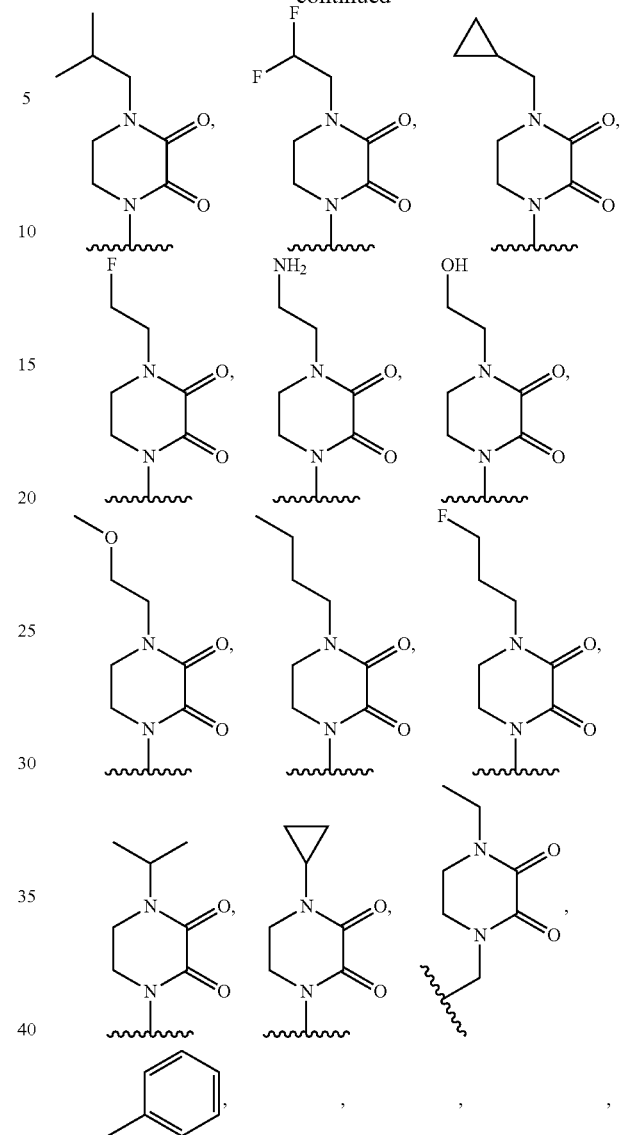
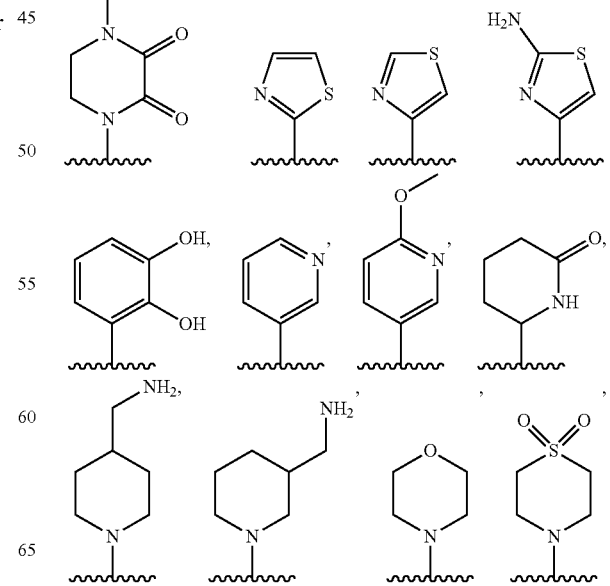

-continued
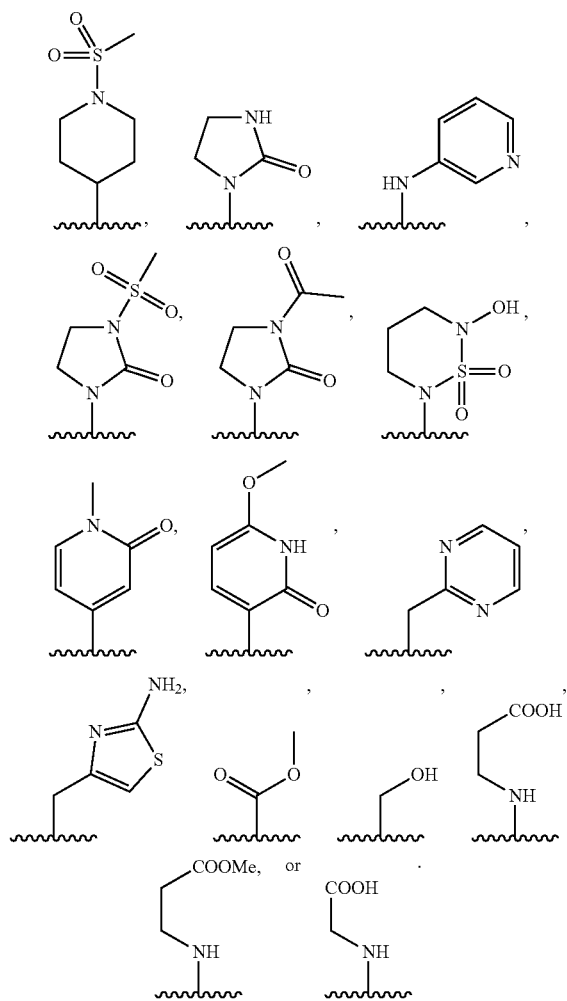
In some embodiments of a compound of Formula (Ia) or (Ib), $R^{74}$ is:
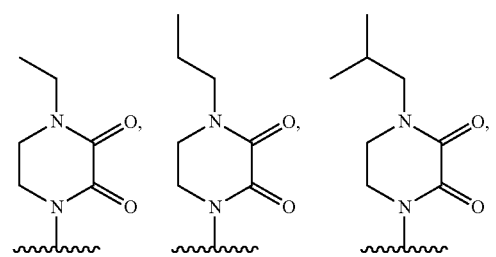
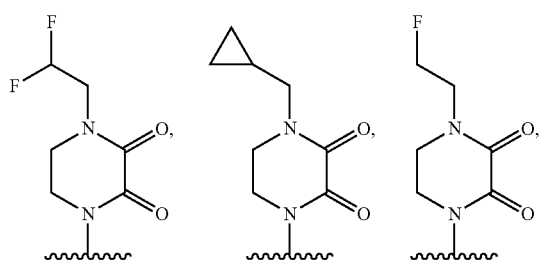
-continued
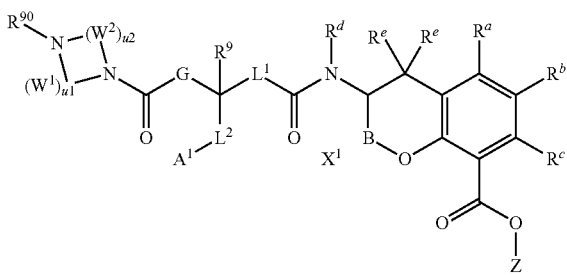
In some embodiments of a compound of Formula (Ia) or (Ib), $R^{74}$ is
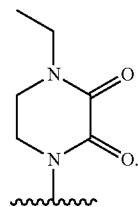
Also disclosed herein is a compound of Formula (IIa) or (IIb), or a pharmaceutically acceptable salt, solvate, stereoisomer, tautomer, N-oxide, dimer, or trimer thereof:
Formula (IIa)

-continued

Formula (IIb)

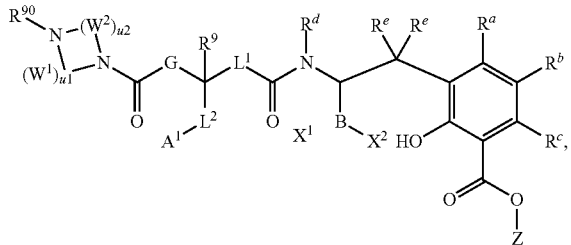

wherein:
G is —NR$^8$—, —C(R$^{10}$)$_2$—, or —C(R$^{10}$)$_2$NR$^8$—;
L$^1$ is —(CR$^1$R$^2$)$_n$—;
L$^2$ is —(CR$^1$R$^2$)$_m$—;
A$^1$ is hydrogen

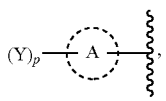

or Y;
Ring A is cycloalkyl, heterocycloalkyl, aryl, or heteroaryl;
R$^1$, R$^2$, and R$^9$ are independently hydrogen, halogen, optionally substituted alkyl, —OH, —OR$^{34}$, —SR$^{35}$, —NR$^{32}$R$^{33}$, —NR$^{32}$C(=O)R$^{34}$, —C(=O)NR$^{32}$R$^{33}$, —NR$^{32}$S(=O)$_2$R$^{34}$, —C(=O)OH, —C(=O)OR$^{34}$, optionally substituted cycloalkyl, optionally substituted heterocycloalkyl, optionally substituted aryl, or optionally substituted heteroaryl; or
R$^1$ and R$^2$ are taken together with the carbon to which they are attached to form an optionally substituted cycloalkyl or an optionally substituted heterocycloalkyl;
R$^8$ is hydrogen, optionally substituted alkyl, optionally substituted cycloalkyl, optionally substituted heterocycloalkyl, optionally substituted aryl, or optionally substituted heteroaryl; or
R$^8$ and R$^9$ are taken together with the atoms to which they are attached to form an optionally substituted heterocycloalkyl;
each R$^{10}$ is independently hydrogen, halogen, or optionally substituted alkyl;
each R$^{20}$ and R$^{21}$ is independently hydrogen, halogen, or optionally substituted alkyl;
R$^{22}$ and R$^{23}$ are independently hydrogen or optionally substituted alkyl; or
R$^{22}$ and R$^{23}$ are taken together with the nitrogen to which they are attached to form an optionally substituted heterocycloalkyl;
R$^{24}$ is optionally substituted alkyl, optionally substituted cycloalkyl, optionally substituted heterocycloalkyl, optionally substituted aryl, or optionally substituted heteroaryl;
R$^{25}$ is hydrogen, optionally substituted alkyl, optionally substituted cycloalkyl, optionally substituted heterocycloalkyl, optionally substituted aryl, or optionally substituted heteroaryl; each R$^{30}$, R$^{31}$, R$^{50}$, and R$^{51}$ is independently hydrogen, halogen, optionally substituted alkyl, optionally substituted cycloalkyl, optionally substituted heterocycloalkyl, optionally substituted aryl, optionally substituted heteroaryl, —OH, —OR$^{24}$, —SR$^{25}$, —NR$^{22}$R$^{23}$, —NR$^{22}$C(=O)R$^{24}$, —C(=O)NR$^{22}$R$^{23}$, —NR$^{22}$S(=O)$_2$R$^{24}$, —C(=O)OH, or —C(=O)OR$^{24}$; or
R$^{30}$ and R$^{31}$, or R$^{50}$ and R$^{51}$ are taken together with the carbon atom to which they are attached to form an optionally substituted cycloalkyl; or
two R$^{30}$ or two R$^{50}$ on adjacent carbons are taken together to form an alkenyl; or
two R$^{30}$ and two R$^{31}$, or two R$^{50}$ and two R$^{51}$ on adjacent carbons are taken together to form an alkynyl;
R$^{32}$, R$^{33}$, R$^{52}$, and R$^{53}$ are independently hydrogen, optionally substituted alkyl, optionally substituted cycloalkyl, optionally substituted heterocycloalkyl, optionally substituted aryl, optionally substituted heteroaryl, (poly-ethylene-glycol)-ethyl, optionally substituted saccharide, —CN, —OH, —S(=O)$_2$R$^{24}$, —S(=O)$_2$NR$^{22}$R$^{23}$, or —C(=O)R$^{24}$; or
R$^{32}$ and R$^{33}$, or R$^{52}$ and R$^{53}$ are taken together with the nitrogen to which they are attached to form an optionally substituted heterocycloalkyl;
R$^{34}$, and R$^{54}$ are independently optionally substituted alkyl, optionally substituted cycloalkyl, optionally substituted heterocycloalkyl, optionally substituted aryl, or optionally substituted heteroaryl;
R$^{35}$ and R$^{55}$ are independently hydrogen, optionally substituted alkyl, optionally substituted cycloalkyl, optionally substituted heterocycloalkyl, optionally substituted aryl, or optionally substituted heteroaryl;
R$^{36}$ and R$^{56}$ are independently hydrogen, —OH, —OR$^{24}$, —CN, —NO$_2$, —NR$^{22}$R$^{23}$, or optionally substituted alkyl;
each R$^{60}$ is independently —CH$_2$—, —CH(CH$_3$)—, —C(CH$_3$)$_2$—, or optionally substituted 1,1'-cyclopropylene;
each R$^{61}$ is independently optionally substituted alkyl, optionally substituted cycloalkyl, optionally substituted heterocycloalkyl, optionally substituted aryl, or optionally substituted heteroaryl; or
two R$^{61}$ are taken together with the nitrogen to which they are attached to form an optionally substituted heterocycloalkyl;
each W$^1$ and W$^2$ is independently —C(=O)— or —C(R$^{91}$)$_2$—;
R$^{90}$ is hydrogen, —OH, optionally substituted alkyl, optionally substituted alkoxy, optionally substituted cycloalkyl, optionally substituted heterocycloalkyl, optionally substituted aryl, optionally substituted heteroaryl, optionally substituted cycloalkylalkyl, optionally substituted heterocycloalkylalkyl, optionally substituted aralkyl, optionally substituted heteroaralkyl, —S(=O)$_2$R$^{24}$, —S(=O)$_2$NR$^{22}$R$^{23}$, or —C(=O)R$^4$.
each R$^{91}$ is independently hydrogen, halogen, —OH, —CN, NH$_2$, NO$_2$, optionally substituted alkyl, optionally substituted alkoxy, optionally substituted cycloalkyl, optionally substituted heterocycloalkyl, optionally substituted aryl, or optionally substituted heteroaryl;
or one R$^{90}$ and R$^{91}$ are taken together with the atoms to which they are attached to form an optionally substituted cycloalkyl or an optionally substituted heterocycloalkyl;
R$^a$, R$^b$, and R$^c$ are independently hydrogen, halogen, cyano, optionally substituted alkyl, optionally substituted cycloalkyl, optionally substituted heterocycloalkyl, optionally substituted aryl, optionally substituted heteroaryl, —OH, —OR$^{54}$, —O(CR$^{50}$R$^{51}$)$_w$NR$^{52}$R$^{53}$, —O(CR$^{50}$R$^{51}$)$_v$OH, —O(CR$^{50}$R$^{51}$)$_w$OR$^{54}$, —O(CR$^{50}$R$^{51}$)$_v$C(=O)OH, —O(CR$^{50}$R$^{51}$)$_v$C(=O)

OR$^{54}$, —O(CR$^{50}$R$^{51}$)$_v$C(=O)NR$^{52}$R$^{53}$, —NR$^{52}$R$^{53}$, —NR$^{52}$(CR$^{50}$R$^{51}$)$_w$NR$^{52}$R$^{53}$, —NR$^{52}$(CR$^{50}$R$^{51}$)$_v$C(=O)OH, —NR$^{52}$(CR$^{50}$R$^{51}$)$_v$C(=O)OR$^{54}$, —NR$^{52}$(CR$^{50}$R$^{51}$)$_v$C(=O)NR$^{52}$R$^{53}$, —NR$^{52}$S(=O)$_{1,2}$R$^{54}$, —S(=O)$_{1,2}$R$^{54}$, —SR$^{55}$, —S(CR$^{50}$R$^{51}$)$_v$NR$^{52}$C(=NR$^{56}$)NR$^{52}$R$^{53}$, —S(CR$^{50}$R$^{51}$)NR$^{52}$CR$^{50}$(=NR$^{56}$), —S(CR$^{50}$R$^{51}$)$_v$C(=NR$^{56}$)NR$^{52}$R$^{53}$, —S(CR$^{50}$R$^{51}$)$_v$OH, —S(CR$^{50}$R$^{51}$)$_w$OR$^{54}$, —S(CR$^{50}$R$^{51}$) NR$^{52}$R$^{53}$, —S(CR$^{50}$R$^{51}$)$_v$C(=O)OH, —S(CR$^{50}$R$^{51}$)$_v$C(=O)OR$^{54}$, —S(CR$^{50}$R$^{51}$)$_v$C(=O)NR$^{52}$R$^{53}$, —C(=O)H, —C(=O)R$^{54}$, —C(=O)OH, —C(=O)OR$^{54}$, —C(=O)NR$^{52}$R$^{53}$, —(CR$^{50}$R$^{51}$)$_v$N(R$^{52}$)(CR$^{50}$R$^{51}$)$_v$C(=O)OH, —(CR$^{50}$R$^{51}$)$_v$OH, —(CR$^{50}$R$^{51}$)$_v$OR$^{54}$, —(CR$^{50}$R$^{51}$)$_v$C(=O)OH, —(CR$^{50}$R$^{51}$)$_v$C(=O)OR$^{54}$, —(CR$^{50}$R$^{51}$)$_v$C(=O)NR$^{52}$R$^{53}$, —(CR$^{50}$R$^{51}$)$_v$OC(=O)R$^{54}$, —(CR$^{50}$R$^{51}$)$_v$SR$^{55}$, —(CR$^{50}$R$^{51}$)$_v$NR$^{52}$C(=NR$^{56}$), —(CR$^{50}$R$^{51}$)$_v$NR$^{52}$R$^{53}$, —(CR$^{50}$R$^{51}$)$_v$C(=NR$^{56}$)NR$^{52}$R$^{53}$, —(CR$^{50}$R$^{51}$)$_v$C(=O)NR$^{52}$R$^{53}$, —(CR$^{50}$R$^{51}$)$_v$heterocycloalkyl, or —(CR$^{50}$R$^{51}$)$_v$heteroaryl;

R$^d$ is hydrogen, —CN, —OH, —S(=O)$_2$R$^{24}$, —S(=O)$_2$NR$^{22}$R$^{23}$, —(CR$^{20}$R$^{21}$)$_v$C(=O)OH, —C(=O)R$^{24}$ optionally substituted alkyl, optionally substituted cycloalkyl, optionally substituted heterocycloalkyl, optionally substituted aryl, optionally substituted heteroaryl, (poly-ethylene-glycol)-ethyl, or an optionally substituted saccharide;

each R$^e$ is independently hydrogen, —CN, —OH, optionally substituted alkyl, or optionally substituted cycloalkyl;

R$^X$ is optionally substituted alkyl or optionally substituted cycloalkyl;

X$^1$ and X$^2$ are independently —OH, —OR$^X$, or F; or

X$^1$ and X$^2$ are taken together with the boron atom to which there are attached to form a cyclic boronate ester;

each Y is independently halogen, optionally substituted alkyl, optionally substituted cycloalkyl, optionally substituted heterocycloalkyl, optionally substituted aryl, optionally substituted heteroaryl, -heteroaryl-NR$^{32}$R$^{33}$, -heterocycloalkyl-NR$^{32}$R$^{33}$, -heteroaryl-N(R$^{32}$)C(=NR$^{32}$)NR$^{32}$R$^{33}$, -heterocycloalkyl-N(R$^{32}$)C(=NR$^{32}$)NR$^{32}$R$^{33}$, —OH, —OR$^{34}$, —O(CR$^{30}$R$^{31}$)$_v$OH, —O(CR$^{30}$R$^{31}$) OR$^{34}$, —O(CR$^{30}$R$^{31}$)$_v$NR$^{32}$R$^{33}$, —O(CR$^{30}$R$^{31}$)$_v$NR$^{32}$C(=O)R$^{34}$, —O(CR$^{30}$R$^{31}$)$_w$NR$^{32}$C(=O)OR$^{34}$, —O(CR$^{30}$R$^{31}$)$_w$NR$^{32}$C(=O)NR$^{32}$R$^{33}$, —O(CR$^{30}$R$^{31}$)$_w$C(=O) NR$^{32}$R$^{33}$, —O(CR$^{30}$R$^{31}$)$_w$NR$^{32}$S(=O)$_{0,1,2}$R$^{34}$, —O(CR$^{30}$R$^{31}$)$_v$NR$^{32}$S(=O)$_{0,1,2}$NR$^{32}$R$^{33}$, —O(CR$^{30}$R$^{31}$)$_w$S(=O)$_{0,1,2}$R$^{34}$, —O(CR$^{30}$R$^{31}$)$_w$S(=O)$_{0,1,2}$NR$^{32}$R$^{33}$, —O(CR$^{30}$R$^{31}$)$_v$C(=NR$^{36}$) NR$^{32}$R$^{33}$, —O(CR$^{30}$R$^{31}$)$_w$N(R$^{32}$)C(=NR$^{36}$)R$^{34}$, —O(CR$^{30}$R$^{31}$)$_v$C(=NR$^{36}$)NR$^{32}$C(=NR$^{36}$)NR$^{32}$R$^{33}$, —O(CR$^{30}$R$^{31}$)$_v$N(R$^{32}$)C(=NR$^{36}$)NR$^{32}$R$^{33}$, —O(CR$^{30}$R$^{31}$)$_w$S(=O)$_{0,1,2}$R$^{34}$, —O(CR$^{30}$R$^{31}$)$_w$S(=O)$_{0,1,2}$NR$^{32}$R$^{33}$, —OC(=O)R$^{34}$, —OC(=O)(CR$^{30}$R$^{31}$)$_w$NR$^{32}$R$^{33}$, —OC(=O)NR$^{32}$R$^{33}$, —OC(=O)OR$^{34}$, —OC(=O)NR$^{32}$(CR$^{30}$R$^{31}$)$_w$NR$^{32}$R$^{33}$, —O-heteroaryl, —O-heterocycloalkyl, —O(CR$^{30}$R$^{31}$)$_v$heteroaryl, —O(CR$^{30}$R$^{31}$)$_v$heterocycloalkyl, —O(CR$^{30}$R$^{31}$)$_w$NR$^{32}$-heteroaryl, —O(CR$^{30}$R$^{31}$)$_w$NR$^{32}$-heterocycloalkyl, —O(CR$^{30}$R$^{31}$)$_w$O-heterocycloalkyl, —NR$^{32}$R$^{33}$, —NR$^{32}$(CR$^{30}$R$^{31}$)$_w$NR$^{32}$R$^{33}$, —NR$^{32}$(CR$^{30}$R$^{31}$)$_v$OR$^{34}$, —NR$^{32}$C(=O)R$^{34}$, —NR$^{32}$C(=O)OR$^{34}$, —N(R$^{32}$)$_v$C(=O)(CR$^{30}$R$^{31}$)$_w$NR$^{32}$R$^{33}$, —NR$^{32}$C(=O)NR$^{32}$R$^{33}$, —NR$^{32}$C(=O)NR$^{32}$(CR$^{30}$R$^{31}$)$_w$NR$^{32}$R$^{33}$, —NR$^{32}$(CR$^{30}$R$^{31}$)$_w$S(=O)$_{0,1,2}$R$^{34}$, —NR$^{32}$(CR$^{30}$R$^{31}$)$_w$S(=O)$_{0,1,2}$NR$^{32}$R$^{33}$, —NR$^{32}$(CR$^{30}$R$^{31}$)$_w$NR$^{32}$R$^{33}$S(=O)$_{0,1,2}$R$^{34}$, —NR$^{32}$(CR$^{30}$R$^{31}$)$_w$NR$^{32}$S(=O)$_{0,1,2}$NR$^{32}$R$^{33}$, —NR$^{32}$(CR$^{30}$R$^{31}$)$_w$NR$^{32}$S(=O)$_{0,1,2}$NR$^{32}$R$^{33}$, —NR$^{32}$C(=NR$^{36}$)NR$^{32}$R$^{33}$, —N(R$^{32}$)C(=NR$^{36}$)R$^{34}$, —NR$^{32}$(CR$^{30}$R$^{31}$)$_w$N(R$^{32}$)C(=NR$^{36}$)R$^{34}$, —NR$^{32}$(CR$^{30}$R$^{31}$)$_v$C(=NR$^{36}$)NR$^{32}$R$^{33}$, —NR$^{32}$(CR$^{30}$R$^{31}$)$_w$N(R$^{32}$)C(=NR$^{36}$)NR$^{32}$R$^{33}$, —NR$^{32}$(CR$^{30}$R$^{31}$)$_w$NR$^{32}$C(=O)NR$^{32}$R$^{33}$, —NR$^{32}$(CR$^{30}$R$^{31}$)$_w$NR$^{32}$C(=O)OR$^{34}$, —NR$^{32}$S(=O)$_{0,1,2}$NR$^{32}$R$^{33}$, —NR$^{32}$S(=O)$_{0,1,2}$R$^{34}$, —NR$^{32}$(CR$^{30}$R$^{31}$)$_v$CO$_2$H, —NR$^{32}$(CR$^{30}$R$^{31}$)$_v$CO$_2$R$^{34}$, —NR$^{32}$(CR$^{30}$R$^{31}$)$_v$C(=O)NR$^{32}$R$^{33}$, —N(R$^{32}$)-heteroaryl-NR$^{32}$R$^{33}$, —N(R$^{32}$)-heterocycloalkyl-NR$^{32}$R$^{33}$, —NR$^{32}$(CR$^{30}$R$^{31}$)$_v$heteroaryl, —NR$^{32}$(CR$^{30}$R$^{31}$)$_v$heterocycloalkyl, —NR$^{32}$(CR$^{30}$R$^{31}$)$_w$NR$^{32}$-heteroaryl, —NR$^{32}$(CR$^{30}$R$^{31}$)$_w$NR$^{32}$-heterocycloalkyl, —CN, —(CR$^{30}$R$^{31}$)$_v$CN, —(CR$^{30}$R$^{31}$)$_v$NR$^{32}$R$^{33}$, —(CR$^{30}$R$^{31}$)$_w$OH, —(CR$^{30}$R$^{31}$)$_v$OR$^{34}$, —(CR$^{30}$R$^{31}$)$_v$OC(=O)R$^{34}$, —(CR$^{30}$R$^{31}$)$_v$OC(=O) NR$^{32}$R$^{33}$, —(CR$^{30}$R$^{31}$)$_v$O(CR$^{30}$R$^{31}$)$_v$OR$^{34}$, —(CR$^{30}$R$^{31}$)$_v$O(CR$^{30}$R$^{31}$)$_v$OH, —(CR$^{30}$R$^{31}$)$_v$O(CR$^{30}$R$^{31}$)NR$^{32}$R$^{33}$, —(CR$^{30}$R$^{31}$)$_v$NR$^{32}$(CR$^{30}$R$^{31}$)$_w$OH, —(CR$^{30}$R$^{31}$)$_v$NR$^{32}$(CR$^{30}$R$^{31}$)$_w$OR$^{34}$, —(CR$^{30}$R$^{31}$)$_v$C(=O)NR$^{32}$R$^{33}$, —(CR$^{30}$R$^{31}$)$_v$C(=O) OH, —(CR$^{30}$R$^{31}$)$_v$C(=O)OR$^{34}$, —(CR$^{30}$R$^{31}$)$_v$C(=O) NR$^{32}$(CR$^{30}$R$^{31}$)$_w$NR$^{32}$R$^{33}$, —(CR$^{30}$R$^{31}$)$_v$C(=O)NR$^{32}$(CR$^{30}$R$^{31}$)$_w$OR$^{34}$, —(CR$^{30}$R$^{31}$)$_v$N(R$^{32}$)$_v$C(=O)R$^{34}$, —(CR$^{30}$R$^{31}$)$_v$N(R$^{32}$)$_v$C(=O)OR$^{34}$, —(CR$^{30}$R$^{31}$)$_v$N(R$^{32}$)$_v$C(=O)NR$^{32}$R$^{33}$, —(CR$^{30}$R$^{31}$)$_w$N(R$^{32}$)$_v$C(=O)(CR$^{30}$R$^{31}$)$_w$NR$^{32}$R$^{33}$, —(CR$^{30}$R$^{31}$)$_w$N(R$^{32}$)S(=O)$_{0,1,2}$R$^{34}$, —(CR$^{30}$R$^{31}$)$_w$N(R$^{32}$)S(=O)$_{0,1,2}$NR$^{32}$R$^{33}$, —(CR$^{30}$R$^{31}$)$_w$NR$^{32}$(CR$^{30}$R$^{31}$)$_w$NR$^{32}$R$^{33}$, —(CR$^{30}$R$^{31}$)$_w$N(R$^{32}$)CH(=NR$^{36}$), —(CR$^{30}$R$^{31}$)$_w$N(R$^{32}$)C(=NR$^{36}$)R$^{34}$, —(CR$^{30}$R$^{31}$)$_v$C(=NR$^{36}$)NR$^{32}$R$^{33}$, —(CR$^{30}$R$^{31}$)$_w$N(R$^{32}$)C(=NR$^{36}$)NR$^{32}$R$^{33}$, —(CR$^{30}$R$^{31}$)$_v$C(=NR$^{36}$)NR$^{32}$C(=NR$^{36}$)NR$^{32}$R$^{33}$, —(CR$^{30}$R$^{31}$)$_v$heteroaryl-NR$^{32}$R$^{33}$, —(CR$^{30}$R$^{31}$)$_v$heterocycloalkyl-NR$^{32}$R$^{33}$, —(CR$^{30}$R$^{31}$)$_v$heteroaryl-N(R$^{32}$)C(=NR$^{36}$)NR$^{32}$R$^{33}$, —(CR$^{30}$R$^{31}$)$_v$heterocycloalkyl-N(R$^{32}$)C(=NR$^{36}$) NR$^{32}$R$^{33}$, —(CR$^{30}$R$^{31}$)$_v$heteroaryl, —(CR$^{30}$R$^{31}$)$_v$heterocycloalkyl, —C(=O)OH, —C(=O)OR$^{34}$, —C(=O)NR$^{32}$R$^{33}$, —C(=O)NR$^{32}$(CR$^{30}$R$^{31}$)$_w$NR$^{32}$R$^{33}$, —C(=O)NR$^{32}$(CR$^{30}$R$^{31}$)$_w$OH, —C(=O)NR$^{32}$(CR$^{30}$R$^{31}$)$_v$OR$^{34}$, —C(=NR$^{36}$)NR$^{32}$R$^{33}$, —C(=NR$^{36}$)NR$^{32}$C(=O)R$^{34}$, —S(=O)$_{1,2}$R$^{34}$, —SR$^{35}$, —S(=O)$_{0,1,2}$(CR$^{30}$R$^{31}$)$_v$NR$^{32}$R$^{33}$, —S(=O)$_{0,1,2}$(CR$^{30}$R$^{31}$)$_w$OH, —S(=O)$_{0,1,2}$(CR$^{30}$R$^{31}$) OR$^{34}$, —S(=O)$_{0,1,2}$NR$^{32}$R$^{33}$, —S(=O)$_{0,1,2}$NR$^{32}$(CR$^{30}$R$^{31}$)$_w$NR$^{32}$R$^{33}$, —S(=O)$_{0,1,2}$(CR$^{30}$R$^{31}$)$_w$N(R$^{32}$)C(=NR$^{36}$)R$^{34}$, —S(=O)$_{0,1,2}$(CR$^{30}$R$^{31}$)$_v$C(=NR$^{36}$)NR$^{32}$R$^{33}$, —S(=O)$_{0,1,2}$(CR$^{30}$R$^{31}$)$_w$N(R$^{32}$)C(=NR$^{36}$)NR$^{32}$R$^{33}$, —S(=O)$_{0,1,2}$(CR$^{30}$R$^{31}$)$_v$C(=NR$^{36}$)NR$^{32}$C(=NR$^{36}$)NR$^{32}$R$^{33}$, —Si(R$^{34}$)$_3$, —NR$^{32}$R$^{33}$R$^{34+}$Q$^-$, —(CR$^{30}$R$^{31}$)$_w$NR$^{32}$R$^{33}$R$^{34+}$Q$^-$, —NR$^{32}$(CR$^{30}$R$^{31}$)$_w$NR$^{32}$R$^{33}$R$^{34+}$Q$^-$, —NR$^{32}$R$^{34+}$(CR$^{30}$R$^{31}$)$_w$NR$^{32}$R$^{33}$R$^{34+}$Q$^-_2$, —(CR$^{30}$R$^{31}$)$_v$(T)$^+$Q$^-$, or —O(CR$^{30}$R$^{31}$)$_w$NR$^{32}$R$^{33}$R$^{34+}$Q$^-$;

or two Ys are taken together with the atoms to which they are attached to form an optionally substituted cycloalkyl or an optionally substituted heterocycloalkyl;

Z is hydrogen, R$^{61}$, —(R$^{60}$)$_q$OR$^{61}$, —(R$^{60}$)$_q$O(R$^{60}$)$_q$OR$^{61}$, —R$^{60}$OC(=O)R$^{61}$, —R$^{60}$OC(=O)OR$^{61}$, —R$^{60}$OC(=O)NHR$^{61}$, —R$^{60}$OC(=O)N(R$^{61}$)$_2$, optionally substituted alkyloxyalkyl, optionally substituted acyloxyalkyl, optionally substituted alkyloxycarbonyloxyalkyl, optionally substituted cycloalkyloxycarbonyloxyalkyl, optionally substituted aryloxycarbonyloxyalkyl, or optionally substituted alkyl-[1,3]dioxol-2-one;

T is pyridin-1-yl, pyrimidin-1-yl, or thiazol-3-yl;
Q is a pharmaceutically acceptable counterion;
n is 0-3;
m is 0-3;
p is 0-3;
each q is independently 2-6;
u1 is 1-3;
u2 is 1-3;
each v is independently 1-5; and
each w is independently 2-5.

Also disclosed herein is a compound of Formula (IIa) or (IIb), or a pharmaceutically acceptable salt, solvate, stereoisomer, tautomer, N-oxide, dimer, or trimer thereof:

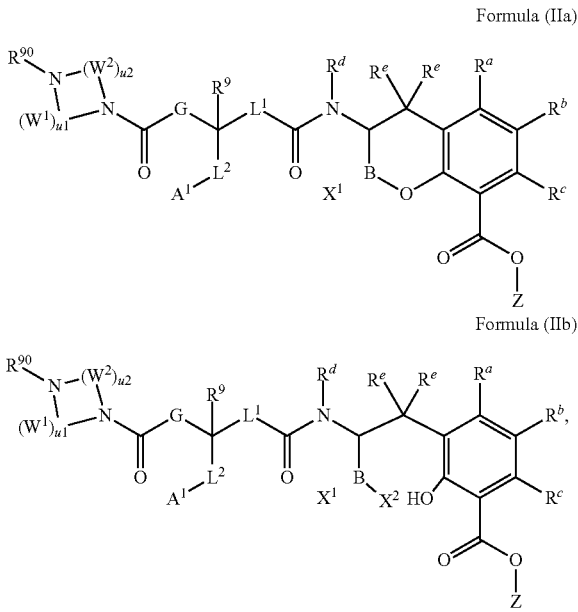

Formula (IIa)

Formula (IIb)

wherein:
G is $-NR^8-$, $-C(R^{10})_2-$, or $-C(R^{10})_2NR^8-$;
$L^1$ is $-(CR^1R^2)_n-$;
$L^2$ is $-(CR^1R^2)_m-$;
$A^1$ is hydrogen,

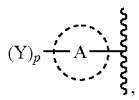

or Y;
Ring A is cycloalkyl, heterocycloalkyl, aryl, or heteroaryl;
$R^1$, $R^2$, and $R^9$ are independently hydrogen, halogen, optionally substituted alkyl, $-OH$, $-OR^{34}$, $-SR^{35}$, $-NR^{32}R^{33}$, $-NR^{32}C(=O)R^{34}$, $-C(=O)NR^{32}R^{33}$, $-NR^{32}S(=O)_2R^{34}$, $-C(=O)OH$, $-C(=O)OR^{34}$, optionally substituted cycloalkyl, optionally substituted heterocycloalkyl, optionally substituted aryl, or optionally substituted heteroaryl; or $R^1$ and $R^2$ are taken together with the carbon to which they are attached to form an optionally substituted cycloalkyl or an optionally substituted heterocycloalkyl;
$R^8$ is hydrogen, optionally substituted alkyl, optionally substituted cycloalkyl, optionally substituted heterocycloalkyl, optionally substituted aryl, or optionally substituted heteroaryl; or
$R^8$ and $R^9$ are taken together with the atoms to which they are attached to form an optionally substituted heterocycloalkyl;
each $R^{10}$ is independently hydrogen, halogen, or optionally substituted alkyl;
each $R^{20}$ and $R^{21}$ is independently hydrogen, halogen, or optionally substituted alkyl;
$R^{22}$ and $R^{23}$ are independently hydrogen or optionally substituted alkyl; or
$R^{22}$ and $R^{23}$ are taken together with the nitrogen to which they are attached to form an optionally substituted heterocycloalkyl;
$R^{24}$ is optionally substituted alkyl, optionally substituted cycloalkyl, optionally substituted heterocycloalkyl, optionally substituted aryl, or optionally substituted heteroaryl;
$R^{25}$ is hydrogen, optionally substituted alkyl, optionally substituted cycloalkyl, optionally substituted heterocycloalkyl, optionally substituted aryl, or optionally substituted heteroaryl;
each $R^{30}$, $R^{31}$, $R^{50}$, and $R^{51}$ is independently hydrogen, halogen, optionally substituted alkyl, optionally substituted cycloalkyl, optionally substituted heterocycloalkyl, optionally substituted aryl, optionally substituted heteroaryl, $-OH$, $-OR^{24}$, $-SR^{25}$, $-NR^{22}R^{23}$, $-NR^{22}C(=O)R^{24}$, $-C(=O)NR^{22}R^{23}$, $-NR^{22}S(=O)_2R^{24}$, $-C(=O)OH$, or $-C(=O)OR^{24}$; or
$R^{30}$ and $R^{31}$, or $R^{50}$ and $R^{51}$ are taken together with the carbon atom to which they are attached to form an optionally substituted cycloalkyl; or
two $R^{30}$ or two $R^{50}$ on adjacent carbons are taken together to form an alkenyl; or
two $R^{30}$ and two $R^{31}$, or two $R^{50}$ and two $R^{51}$ on adjacent carbons are taken together to form an alkynyl;
$R^{32}$, $R^{33}$, $R^{52}$, and $R^{53}$ are independently hydrogen, optionally substituted alkyl, optionally substituted cycloalkyl, optionally substituted heterocycloalkyl, optionally substituted aryl, optionally substituted heteroaryl, (poly-ethylene-glycol)-ethyl, optionally substituted saccharide, $-CN$, $-OH$, $-S(=O)_2R^{24}$, $-S(=O)_2NR^{22}R^{23}$, or $-C(=O)R^{24}$; or
$R^{32}$ and $R^{33}$, or $R^{52}$ and $R^{53}$ are taken together with the nitrogen to which they are attached to form an optionally substituted heterocycloalkyl;
$R^{34}$, and $R^{54}$ are independently optionally substituted alkyl, optionally substituted cycloalkyl, optionally substituted heterocycloalkyl, optionally substituted aryl, or optionally substituted heteroaryl;
$R^{35}$ and $R^{55}$ are independently hydrogen, optionally substituted alkyl, optionally substituted cycloalkyl, optionally substituted heterocycloalkyl, optionally substituted aryl, or optionally substituted heteroaryl;
$R^{36}$ and $R^{56}$ are independently hydrogen, $-OH$, $-OR^{24}$, $-CN$, $-NO_2$, $-NR^{22}R^{23}$, or optionally substituted alkyl;
each $R^{60}$ is independently $-CH_2-$, $-CH(CH_3)-$, $-C(CH_3)_2-$, or optionally substituted 1,1'-cyclopropylene;
each $R^{61}$ is independently optionally substituted alkyl, optionally substituted cycloalkyl, optionally substituted heterocycloalkyl, optionally substituted aryl, or optionally substituted heteroaryl; or two $R^{61}$ are taken together with the nitrogen to which they are attached to form an optionally substituted heterocycloalkyl;

each $W^1$ and $W^2$ is independently —C(=O)— or —C($R^{91}$)$_2$—;

$R^{90}$ is hydrogen, —OH, optionally substituted alkyl, optionally substituted alkoxy, optionally substituted cycloalkyl, optionally substituted heterocycloalkyl, optionally substituted aryl, optionally substituted heteroaryl, optionally substituted cycloalkylalkyl, optionally substituted heterocycloalkylalkyl, optionally substituted aralkyl, optionally substituted heteroaralkyl, —S(=O)$_2R^{24}$, —S(=O)$_2$N$R^{22}R^{23}$, or —C(=O)$R^{24}$.

each $R^{91}$ is independently hydrogen, halogen, —OH, —CN, NH$_2$, NO$_2$, optionally substituted alkyl, optionally substituted alkoxy, optionally substituted cycloalkyl, optionally substituted heterocycloalkyl, optionally substituted aryl, or optionally substituted heteroaryl;

$R^a$, $R^b$, and $R^c$ are independently hydrogen, halogen, cyano, optionally substituted alkyl, optionally substituted cycloalkyl, optionally substituted heterocycloalkyl, optionally substituted aryl, optionally substituted heteroaryl, —OH, —O$R^{54}$, —O(C$R^{50}R^{51}$)$_w$N$R^{52}R^{53}$, —O(C$R^{50}R^{51}$)$_v$OH, —O(C$R^{50}R^{51}$)O$R^{54}$, —O(C$R^{50}R^{51}$)$_v$C(=O)OH, —O(C$R^{50}R^{51}$)$_v$C(=O)O$R^{54}$, —O(C$R^{50}R^{51}$)$_v$C(=O)N$R^{52}R^{53}$, —N$R^{52}R^{53}$, —N$R^{52}$(C$R^{50}R^{51}$)$_w$N$R^{52}R^{53}$, —N$R^{52}$(C$R^{50}R^{51}$)$_v$C(=O)OH, —N$R^{52}$(C$R^{50}R^{51}$)$_w$C(=O)O$R^{54}$, —N$R^{52}$(C$R^{50}R^{51}$)$_v$C(=O)N$R^{52}R^{53}$, —N$R^{52}$S(=O)$_{1,2}R^{54}$, —S(=O)$_{1,2}R^{54}$, —S$R^{55}$, —S(C$R^{50}R^{51}$)$_w$N$R^{52}$C(=N$R^{56}$)N$R^{52}R^{53}$, —S(C$R^{50}R^{51}$)$_w$C$R^{50}$(=N$R^{56}$), —S(C$R^{50}R^{51}$)$_v$C(=N$R^{56}$)N$R^{52}R^{53}$, —S(C$R^{50}R^{51}$)$_w$OH, —S(C$R^{50}R^{51}$)$_w$O$R^{54}$, —S(C$R^{50}R^{51}$) N$R^{52}R^{53}$, —S(C$R^{50}R^{51}$)$_v$C(=O)OH, —S(C$R^{50}R^{51}$)$_v$C(=O)O$R^{54}$, —S(C$R^{50}R^{51}$)$_v$C(=O) N$R^{52}R^{53}$, —C(=O)H, —C(=O)$R^{54}$, —C(=O)OH, —C(=O)O$R^{54}$, —C(=O)N$R^{52}R^{53}$, —(C$R^{50}R^{51}$)$_v$N (R$^{52}$)(C$R^{50}R^{51}$)$_v$C(=O)OH, —(C$R^{50}R^{51}$)$_v$OH, —(C$R^{50}R^{51}$)$_v$O$R^{54}$, —(C$R^{50}R^{51}$)$_v$C(=O)OH, —(C$R^{50}R^{51}$)$_v$C(=O)O$R^{54}$, —(C$R^{50}R^{51}$)$_v$C(=O) N$R^{52}R^{53}$, —(C$R^{50}R^{51}$)$_v$OC(=O)O$R^{54}$, —(C$R^{50}R^{51}$)$_v$S$R^{55}$, —(C$R^{50}R^{51}$)$_v$N$R^{52}$C(=N$R^{16}$), —(C$R^{50}R^{51}$)$_v$N$R^{52}R^{53}$, —(C$R^{50}R^{51}$)$_v$C(=N$R^{56}$) N$R^{52}R^{53}$, —(C$R^{50}R^{51}$)$_v$C(=O)N$R^{52}R^{53}$, —(C$R^{50}$ R$^{51}$)$_v$heterocycloalkyl, or —(C$R^{50}R^{51}$)$_v$heteroaryl;

$R^d$ is hydrogen, —CN, —OH, —S(=O)$_2R^{24}$, —S(=O)$_2$N$R^{22}R^{23}$, —(C$R^{20}R^{21}$)$_v$C(=O)OH, —C(=O)$R^{24}$, optionally substituted alkyl, optionally substituted cycloalkyl, optionally substituted heterocycloalkyl, optionally substituted aryl, optionally substituted heteroaryl, (poly-ethylene-glycol)-ethyl, or an optionally substituted saccharide;

each $R^e$ is independently hydrogen, —CN, —OH, optionally substituted alkyl, or optionally substituted cycloalkyl;

$R^X$ is optionally substituted alkyl or optionally substituted cycloalkyl;

$X^1$ and $X^2$ are independently —OH, —O$R^X$, or F; or $X^1$ and $X^2$ are taken together with the boron atom to which there are attached to form a cyclic boronate ester;

each Y is independently halogen, optionally substituted alkyl, optionally substituted cycloalkyl, optionally substituted heterocycloalkyl, optionally substituted aryl, optionally substituted heteroaryl, -heteroaryl-N$R^{32}R^{33}$, -heterocycloalkyl-N$R^{32}R^{33}$, -heteroaryl-N(R$^{32}$)C(=N$R^{32}$)N$R^{32}R^{33}$, -heterocycloalkyl-N(R$^{32}$)C(=N$R^{32}$)N$R^{32}R^{33}$, —OH, —O$R^{34}$, —O(C$R^{30}$ R$^{31}$)$_w$OH, —O(C$R^{30}R^{31}$)$_v$O$R^{34}$, —O(C$R^{30}$ R$^{31}$)$_w$N$R^{32}R^{33}$, —O(C$R^{30}R^{31}$)$_v$N$R^{32}$C(=O)$R^{34}$, —O(C$R^{30}R^{31}$)$_w$N$R^{32}$C(=O)O$R^{34}$, —O(C$R^{30}$ R$^{31}$)$_w$N$R^{32}$C(=O)N$R^{32}R^{33}$, —O(C$R^{30}R^{31}$)$_w$C(=O) N$R^{32}R^{33}$, —O(C$R^{30}R^{31}$)$_w$N$R^{32}$S(=O)$_{0,1,2}R^{34}$, —O(C$R^{30}R^{31}$)$_w$N$R^{32}$S(=O)$_{0,1,2}$N$R^{32}R^{33}$, —O(C$R^{30}R^{31}$)$_w$S(=O)$_{0,1,2}R^{34}$, —O(C$R^{30}R^{31}$)$_w$S(=O)$_{0,1,2}$N$R^{32}R^{33}$, —O(C$R^{30}R^{31}$)$_w$C(=N$R^{36}$) N$R^{32}R^{33}$, —O(C$R^{30}R^{31}$)$_w$N(R$^{32}$)C(=N$R^{36}$)$R^{34}$, —O(C$R^{30}R^{31}$)$_w$C(=N$R^{36}$)N$R^{32}$C(=N$R^{36}$)N$R^{32}R^{33}$, —O(C$R^{30}R^{31}$)$_w$N(R$^{32}$)C(=N$R^{36}$)N$R^{32}R^{33}$, —O(C$R^{30}R^{31}$)$_w$S(=O)$_{0,1,2}R^{34}$, —O(C$R^{30}R^{31}$)$_w$S(=O)$_{0,1,2}$N$R^{32}R^{33}$, —OC(=O)$R^{34}$, —OC(=O)(C$R^{30}R^{31}$)$_w$N$R^{32}R^{33}$, —OC(=O)N$R^{32}R^{33}$, —OC(=O)O$R^{34}$, —OC(=O)N$R^{32}$(C$R^{30}R^{31}$)$_w$N$R^{32}R^{33}$, —O-heteroaryl, —O-heterocycloalkyl, —O(C$R^{30}$ R$^{31}$)$_v$heteroaryl, —O(C$R^{30}R^{31}$)$_v$heterocycloalkyl, —O(C$R^{30}R^{31}$)$_w$N$R^{32}$-heteroaryl, —O(C$R^{30}$ R$^{31}$)$_w$N$R^{32}$-heterocycloalkyl, —O(C$R^{30}R^{31}$)$_w$O-heterocycloalkyl, —N$R^{32}R^{33}$, —N$R^{32}$(C$R^{30}$ R$^{31}$)$_w$N$R^{32}R^{33}$, —N$R^{32}$(C$R^{30}R^{31}$)$_w$OH, —N$R^{32}$(C$R^{30}R^{31}$)$_v$O$R^{34}$, —N$R^{32}$C(=O)$R^{34}$, —N$R^{32}$C(=O)O$R^{34}$, —N(R$^{32}$)$_v$C(=O)(C$R^{30}R^{31}$)$_w$N$R^{32}R^{33}$, —N$R^{32}$C(=O)N$R^{32}R^{33}$, —N$R^{32}$C(=O)N$R^{32}$(C$R^{30}R^{31}$)$_w$N$R^{32}R^{33}$, —N$R^{32}$(C$R^{30}R^{31}$)$_w$S(=O)$_{0,1,2}R^{34}$, —N$R^{32}$(C$R^{30}R^{31}$)$_w$S(=O)$_{0,1,2}$N$R^{32}R^{33}$, —N$R^{32}$(C$R^{30}R^{31}$)$_w$N$R^{32}R^{33}$S(=O)$_{0,1,2}R^{34}$, —N$R^{32}$(C$R^{30}R^{31}$)$_w$N$R^{32}$S(=O)$_{0,1,2}$N$R^{32}R^{33}$, —N$R^{32}$C(=N$R^{36}$)N$R^{32}R^{33}$, —N(R$^{32}$)C(=N$R^{36}$)$R^{34}$, —N$R^{32}$(C$R^{30}R^{31}$)$_w$N(R$^{32}$)C(=N$R^{36}$)$R^{34}$, —N$R^{32}$(C$R^{30}R^{31}$)$_w$C(=N$R^{36}$)N$R^{32}R^{33}$, —N$R^{32}$(C$R^{30}R^{31}$)$_w$N(R$^{32}$)C(=N$R^{36}$)N$R^{32}R^{33}$, —N$R^{32}$(C$R^{30}R^{31}$)$_w$N$R^{32}$C(=O)N$R^{32}R^{33}$, —N$R^{32}$(C$R^{30}$ R$^{31}$)$_w$N$R^{32}$C(=O)O$R^{34}$, —N$R^{32}$S(=O)$_{0,1,2}$N$R^{32}R^{33}$, —N$R^{32}$S(=O)$_{0,1,2}R^{34}$, —N$R^{32}$(C$R^{30}R^{31}$)$_v$CO$_2$H, —N$R^{32}$(C$R^{30}R^{31}$)$_v$CO$_2R^{34}$, —N$R^{32}$(C$R^{30}R^{31}$)$_v$C(=O)N$R^{32}R^{33}$, —N(R$^{32}$)-heteroaryl-N$R^{32}R^{33}$, —N(R$^{32}$)-heterocycloalkyl-N$R^{32}R^{33}$, —N$R^{32}$(C$R^{30}R^{31}$)$_v$heteroaryl, —N$R^{32}$(C$R^{30}R^{31}$)$_v$heterocycloalkyl, —N$R^{32}$(C$R^{30}R^{31}$)$_w$N$R^{32}$-heteroaryl, —N$R^{32}$(C$R^{30}R^{31}$)$_w$N$R^{32}$-heterocycloalkyl, —CN, —(C$R^{30}R^{31}$)$_v$CN, —(C$R^{30}R^{31}$)$_v$N$R^{32}R^{33}$, —(C$R^{30}R^{31}$)$_v$OH, —(C$R^{30}R^{31}$)$_w$O$R^{34}$, —(C$R^{30}$ R$^{31}$)$_v$OC(=O)$R^{34}$, —(C$R^{30}R^{31}$)$_v$OC(=O)N$R^{32}R^{33}$, —(C$R^{30}R^{31}$)$_v$O(C$R^{30}R^{31}$)$_v$O$R^{34}$, —(C$R^{30}R^{31}$)$_v$O(C$R^{30}R^{31}$)$_w$OH, —(C$R^{30}R^{31}$)$_v$O(C$R^{30}R^{31}$)$_w$N$R^{32}R^{33}$, —(C$R^{30}R^{31}$)$_w$N$R^{32}$(C$R^{30}R^{31}$)$_w$OH, —(C$R^{30}$ R$^{31}$)$_w$N$R^{32}$(C$R^{30}R^{31}$)$_v$O$R^{34}$, —(C$R^{30}R^{31}$)$_v$C(=O) N$R^{32}R^{33}$, —(C$R^{30}R^{31}$)$_v$C(=O)OH, —(C$R^{30}R^{31}$)$_v$C(=O)O$R^{34}$, —(C$R^{30}R^{31}$)$_v$C(=O)N$R^{32}$(C$R^{30}$ R$^{31}$)$_w$N$R^{32}R^{33}$, —(C$R^{30}R^{31}$)$_v$C(=O)N$R^{32}$(C$R^{30}$ R$^{31}$)$_v$O$R^{34}$, —(C$R^{30}R^{31}$)$_w$N(R$^{32}$)$_v$C(=O)$R^{34}$, —(C$R^{30}R^{31}$)$_w$N(R$^{32}$)$_v$C(=O)O$R^{34}$, —(C$R^{30}R^{31}$)$_w$N (R$^{32}$)$_v$C(=O)N$R^{32}R^{33}$, —(C$R^{30}R^{31}$)$_w$N(R$^{32}$)$_v$C(=O)(C$R^{30}R^{31}$)$_w$N$R^{32}R^{33}$, —(C$R^{30}R^{31}$)$_w$N(R$^{32}$)S(=O)$_{0,1,2}R^{34}$, —(C$R^{30}R^{31}$)$_w$N(R$^{32}$)S(=O)$_{0,1,2}$N$R^{32}R^{33}$, —(C$R^{30}R^{31}$)$_w$N$R^{32}$(C$R^{30}$ R$^{31}$)$_w$N$R^{32}R^{33}$, —(C$R^{30}R^{31}$)$_w$N(R$^{32}$)CH(=N$R^{36}$), —(C$R^{30}R^{31}$)$_w$N(R$^{32}$)C(=N$R^{36}$)$R^{34}$, —(C$R^{30}R^{31}$)$_v$C(=N$R^{36}$)N$R^{32}R^{33}$, —(C$R^{30}R^{31}$)$_w$N(R$^{32}$)C(=N$R^{36}$) N$R^{32}R^{33}$, —(C$R^{30}R^{31}$)$_v$C(=N$R^{36}$)N$R^{32}$C(=N$R^{36}$) N$R^{32}R^{33}$, —(C$R^{30}R^{31}$)$_v$heteroaryl-N$R^{32}R^{33}$, —(C$R^{30}R^{31}$)$_v$heterocycloalkyl-N$R^{32}R^{33}$, —(C$R^{30}$ R$^{31}$)$_v$heteroaryl-N(R$^{32}$)C(=N$R^{36}$)N$R^{32}R^{33}$, —(CR$^{30}$R$^{31}$)$_v$heterocycloalkyl-N(R$^{32}$)C(=NR$^{36}$)NR$^{32}$R$^{33}$, —(CR$^{30}$R$^{31}$)heteroaryl, —(CR$^{30}$R$^{31}$)heterocycloalkyl, —C(=O)OH, —C(=O)OR$^{34}$, —C(=O)NR$^{32}$R$^{33}$, —C(=O)NR$^{32}$(CR$^{30}$R$^{31}$)$_w$NR$^{32}$R$^{33}$, —C(=O)NR$^{32}$(CR$^{30}$R$^{31}$)$_w$OH, —C(=O)NR$^{32}$(CR$^{30}$R$^{31}$)$_v$OR$^{34}$, —C(=NR$^{36}$)NR$^{32}$R$^{33}$, —C(=NR$^{36}$)NR$^{32}$C(=O)R$^{34}$, —S(=O)$_{1,2}$R$^{34}$, —SR$^{35}$, —S(=O)$_{0,1,2}$(CR$^{30}$R$^{31}$)$_v$NR$^{32}$R$^{33}$, —S(=O)$_{0,1,2}$(CR$^{30}$R$^{31}$)$_w$OH, —S(=O)$_{0,1,2}$(CR$^{30}$R$^{31}$)OR$^{34}$, —S(=O)$_{0,1,2}$NR$^{32}$R$^{33}$, —S(=O)$_{0,1,2}$NR$^{32}$(CR$^{30}$R$^{31}$)$_w$NR$^{32}$R$^{33}$, —S(=O)$_{0,1,2}$(CR$^{30}$R$^{31}$)$_w$N(R$^{32}$)C(=NR$^{36}$)R$^{34}$, —S(=O)$_{0,1,2}$(CR$^{30}$R$^{31}$)$_v$C(=NR$^{36}$)NR$^{32}$R$^{33}$, —S(=O)$_{0,1,2}$(CR$^{30}$R$^{31}$)$_w$N(R$^{32}$)C(=NR$^{36}$)NR$^{32}$R$^{33}$, —S(=O)$_{0,1,2}$(CR$^{30}$R$^{31}$)$_v$C(=NR$^{36}$)NR$^{32}$C(=NR$^{36}$)NR$^{32}$R$^{33}$, —Si(R$^{34}$)$_3$, —NR$^{32}$R$^{33}$R$^{34+}$Q$^-$, —(CR$^{30}$R$^{31}$)$_w$NR$^{32}$R$^{33}$R$^{34+}$Q$^-$, —NR$^{32}$(CR$^{30}$R$^{31}$)$_w$NR$^{32}$R$^{33}$R$^{34+}$Q$^-$, —NR$^{32}$R$^{34+}$(CR$^{30}$R$^{31}$)$_w$NR$^{32}$R$^{33}$R$^{34+}$Q$^-_2$, —(CR$^{30}$R$^{31}$)$_v$(T)$^+$Q$^-$, or —O(CR$^{30}$R$^{31}$)$_w$NR$^{32}$R$^{33}$R$^{34+}$Q$^-$;

or two Ys are taken together with the atoms to which they are attached to form an optionally substituted cycloalkyl or an optionally substituted heterocycloalkyl;

Z is hydrogen, R$^{61}$, —(R$^{60}$)$_q$OR$^{61}$, —(R$^{60}$)$_q$O(R$^{60}$)$_q$OR$^{61}$, —R$^{60}$OC(=O)R$^{61}$, —R$^{60}$OC(=O)OR$^{61}$, —R$^{60}$OC(=O)NHR$^{61}$, —R$^{60}$OC(=O)N(R$^{61}$)$_2$, optionally substituted alkyloxyalkyl, optionally substituted acyloxyalkyl, optionally substituted alkyloxycarbonyloxyalkyl, optionally substituted cycloalkyloxycarbonyloxyalkyl, optionally substituted aryloxycarbonyloxyalkyl, or optionally substituted alkyl-[1,3]dioxol-2-one;

T is pyridin-1-yl, pyrimidin-1-yl, or thiazol-3-yl;
Q is a pharmaceutically acceptable counterion;
n is 0-3;
m is 0-3;
p is 0-3;
each q is independently 2-6;
u1 is 1-3;
u2 is 1-3;
each v is independently 1-5; and
each w is independently 2-5.

In some embodiments of a compound of Formula (IIa) or (IIb), G is —NR$^8$— or —CH$_2$NR$^8$—. In some embodiments of a compound of Formula (IIa) or (IIb), G is —CH$_2$—. In some embodiments of a compound of Formula (IIa) or (IIb), G is —NR$^8$—. In some embodiments of a compound of Formula (IIa) or (IIb), G is —CH$_2$NR$^8$—. In some embodiments of a compound of Formula (IIa) or (IIb), R$^9$ is hydrogen or optionally substituted alkyl. In some embodiments of a compound of Formula (IIa) or (IIb), R$^9$ is optionally substituted alkyl. In some embodiments of a compound of Formula (IIa) or (IIb), R$^9$ is methyl. In some embodiments of a compound of Formula (IIa) or (IIb), R$^9$ is hydrogen. In some embodiments of a compound of Formula (IIa) or (IIb), and R$^9$ are taken together with the atoms to which they are attached to form an optionally substituted heterocycloalkyl. In some embodiments of a compound of Formula (IIa) or (IIb), and R$^9$ are taken together with the atoms to which they are attached to form an optionally substituted heterocycloalkyl selected from pyrrolidine or azetidine. In some embodiments of a compound of Formula (IIa) or (IIb), G is —NR$^8$— and the heterocycloalkyl formed when R$^8$ and R$^9$ are taken together with the atoms to which they are attached is pyrrolidine. In some embodiments of a compound of Formula (IIa) or (IIb), G is —CH$_2$NR$^8$— and the heterocycloalkyl formed when R$^8$ and R$^9$ are taken together with the atoms to which they are attached is azetidine.

In some embodiments the compound of Formula (IIa) or (IIb) is of Formula (IIa-1) or (IIb-1), or a pharmaceutically acceptable salt, solvate, stereoisomer, tautomer, N-oxide, dimer, or trimer thereof

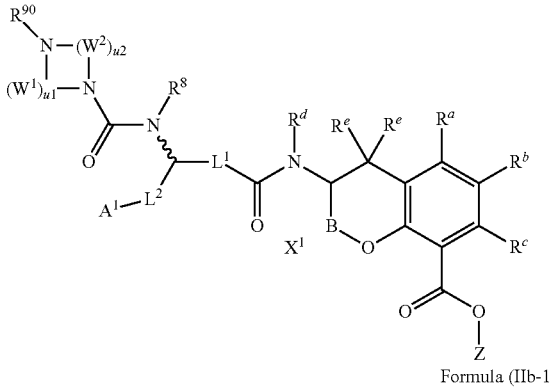

Formula (IIa-1)

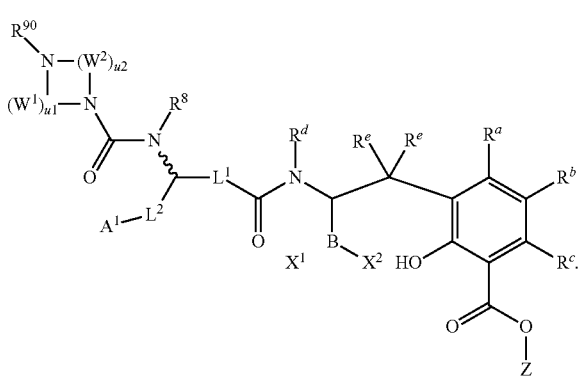

Formula (IIb-1)

In some embodiments of a compound of Formula (IIa), (IIa-1), (IIb), or (IIb-1), u1 is 1. In some embodiments of a compound of Formula (IIa), (IIa-1), (IIb), or (IIb-1), u1 is 2. In some embodiments of a compound of Formula (IIa), (IIa-1), (IIb), or (IIb-1), u1 is 3. In some embodiments of a compound of Formula (IIa), (IIa-1), (IIb), or (IIb-1), u1 is 1. In some embodiments of a compound of Formula (IIa), (IIa-1), (IIb), or (IIb-1), u1 is 2. In some embodiments of a compound of Formula (IIa), (IIa-1), (IIb), or (IIb-1), u1 is 3. In some embodiments of a compound of Formula (IIa), (IIa-1), (IIb), or (IIb-1), u2 is 1. In some embodiments of a compound of Formula (IIa), (IIa-1), (IIb), or (IIb-1), u2 is 2. In some embodiments of a compound of Formula (IIa), (IIa-1), (IIb), or (IIb-1), u2 is 3. In some embodiments of a compound of Formula (IIa), (IIa-1), (IIb), or (IIb-1), u1 is 1 and u2 is 1. In some embodiments of a compound of Formula (IIa), (IIa-1), (IIb), or (IIb-1), u1 is 2 and u2 is 1. In some embodiments of a compound of Formula (IIa), (IIa-1), (IIb), or (IIb-1), u1 is 2 and u2 is 2. In some embodiments of a compound of Formula (IIa), (IIa-1), (IIb), or (IIb-1), u1 is 1 and u2 is 3. In some embodiments of a compound of Formula (IIa), (IIa-1), (IIb), or (IIb-1), u1 is 2 and u2 is 3. In some embodiments of a compound of Formula (IIa), (IIa-1), (IIb), or (IIb-1), u1 is 3 and u2 is 3.

In some embodiments of a compound of Formula (IIa), (IIa-1), (IIb), or (IIb-1), u1 is 2; each W$^1$ is —C(R$^{91}$)$_2$—; u2 is 2; and each W² is —C(=O)—. In some embodiments of a compound of Formula (IIa), (IIa-1), (IIb), or (IIb-1), u1 is 2; each W¹ is —C(R⁹¹)₂—; u2 is 1; and W² is —C(=O)—. In some embodiments of a compound of Formula (IIa), (IIa-1), (IIb), or (IIb-1), u1 is 2; each W¹ is —C(R⁹¹)₂—; u2 is 2; and one W² is —C(R⁹¹)₂— and one W² is —C(=O)—. In some embodiments of a compound of Formula (IIa), (IIa-1), (IIb), or (IIb-1), u1 is 2; one W¹ is —C(R⁹¹)₂— and one W¹ is —C(=O)—; u2 is 2; and one W² is —C(R⁹¹)₂— and one W² is —C(=O)—. In some embodiments of a compound of Formula (IIa), (IIa-1), (IIb), or (IIb-1),

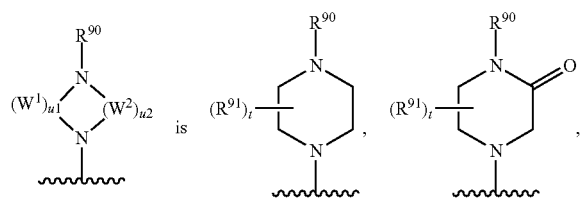

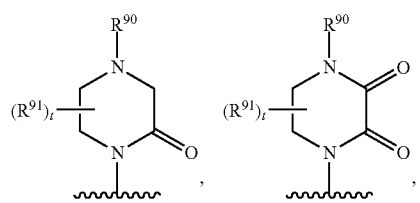

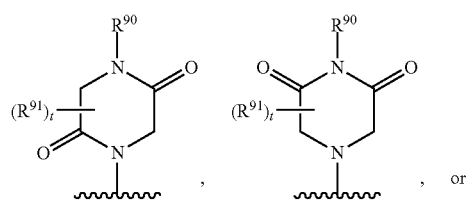

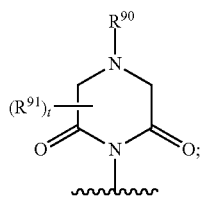

wherein t is 1-4. In some embodiments of a compound of Formula (IIa), (IIa-1), (IIb), or (IIb-1),

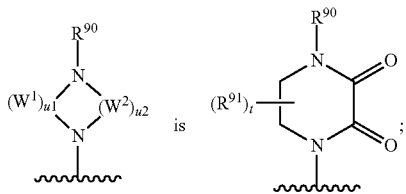

wherein t is 1-4. In some embodiments of a compound of Formula (IIa), (IIa-1), (IIb), or (IIb-1),

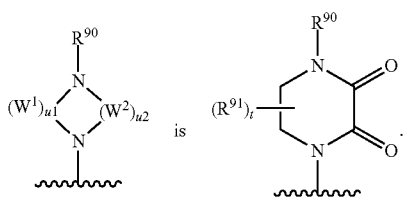

In some embodiments of a compound of Formula (IIa), (IIa-1), (IIb), or (IIb-1), R⁹⁰ is hydrogen, optionally substituted alkyl, optionally substituted cycloalkyl, optionally substituted aralkyl, —S(=O)₂R²⁴, or —C(=O)R²⁴. In some embodiments of a compound of Formula (IIa), (IIa-1), (IIb), or (IIb-1), R⁹⁰ is optionally substituted alkyl. In some embodiments of a compound of Formula (IIa), (IIa-1), (IIb), or (IIb-1), R⁹⁰ is —H, —OH,

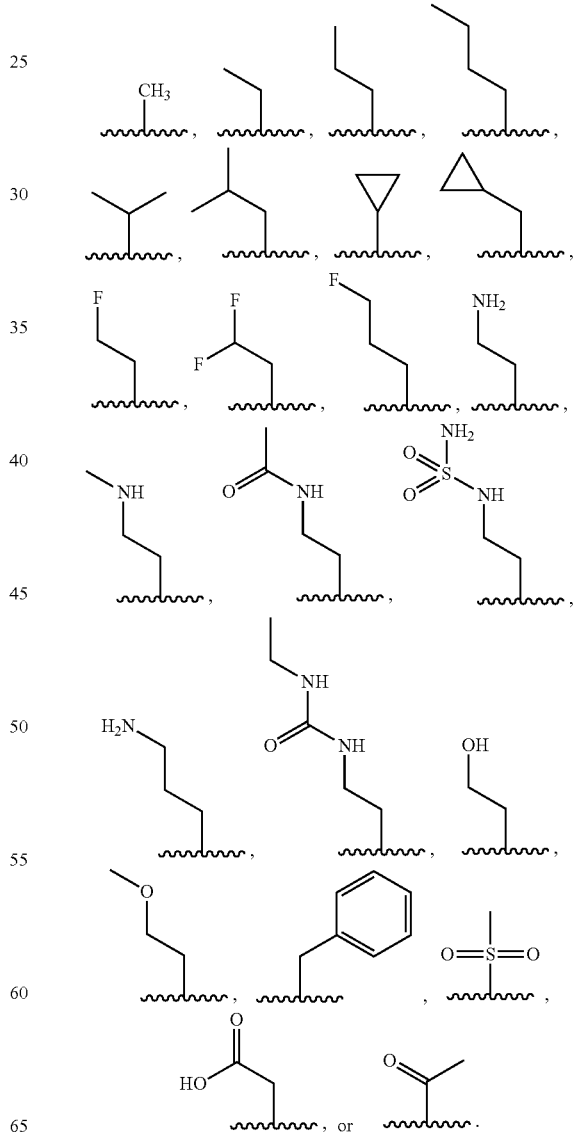

In some embodiments of a compound of Formula (IIa), (IIa-1), (IIb), or (IIb-1), $R^{90}$ is —H, —OH,

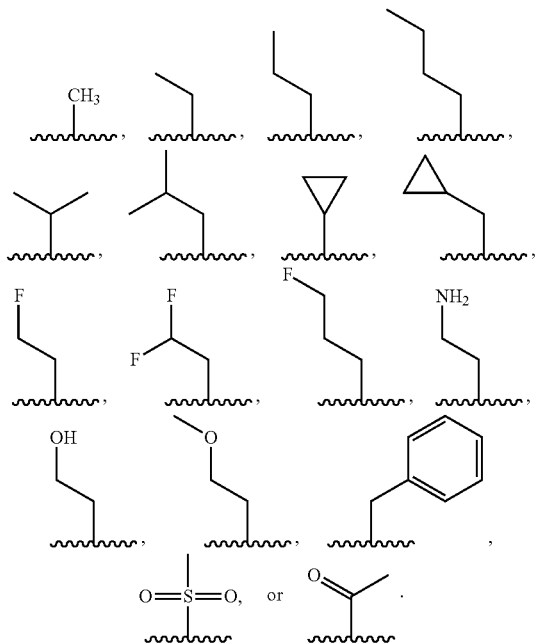

In some embodiments of a compound of Formula (IIa), (IIa-1), (IIb), or (IIb-1), $R^{90}$ is ethyl.

In some embodiments of a compound of Formula (IIa), (IIa-1), (IIb), or (IIb-1), each $R^{91}$ is independently hydrogen, halogen, or optionally substituted alkyl. In some embodiments of a compound of Formula (IIa), (IIa-1), (IIb), or (IIb-1), each $R^{91}$ is hydrogen.

In some embodiments of a compound of Formula (Ia), (IIa), (IIa-1), (Ib), (IIb), or (IIb-1), $A^1$ is

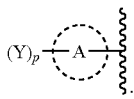

In some embodiments of a compound of Formula (Ia), (IIa), (IIa-1), (Ib), (IIb), or (IIb-1), Ring A is cyclopropane, cyclobutane, cyclopentane, cyclohexane, cycloheptane, cyclooctane, cyclopentene, cyclohexene, cycloheptene, and cyclooctene, wherein the olefin functionality of the cyclopentene, cyclohexene, cycloheptene, and cyclooctene is not directly attached to an oxygen, sulfur, or nitrogen substituent. In some embodiments of a compound of Formula (Ia), (IIa), (IIa-1), (Ib), (IIb), or (IIb-1), Ring A is cyclopropane, cyclobutane, cyclopentane, or cyclohexane.

In some embodiments of a compound of Formula (Ia), (IIa), (IIa-1), (Ib), (IIb), or (IIb-1), Ring A is azetidine, aziridine, oxirane, oxetane, thietane, pyrrolidine, oxazolidine, isoxazolidine, thiazolidine, isothiazolidine, imidazolidine, pyrazolidine, 2,5-dihydro-1H-pyrrole, 3,4-dihydro-2H-pyrrole, 4,5-dihydrooxazole, 4,5-dihydroisoxazole, 4,5-dihydrothiazole, 4,5-dihydroisothiazole, 4,5-dihydro-1H-pyrazole, 4,5-dihydro-1H-imidazole, 2,5-dihydro-1H-pyrrole, piperidine, morpholine, thiomorpholine, tetrahydrothiopyran, tetrahydropyran, tetrahydrofuran, 1,4-oxathiane, piperazine, hexahydropyrimidine, hexahydropyridazine, 1,4,5,6-tetrahydropyrimidine, 1,3-oxazinane, 5,6-dihydro-4H-1,3-oxazine, 1,3-thiazinane, 5,6-dihydro-4H-1,3-thiazine, 1,4,5,6-tetrahydropyridazine, 1,2,3,6-tetrahydropyrazine, 1,2,3,6-tetrahydropyridine, 1,2,3,6-tetrahydropyridazine, azepane, 1,3-oxazepane, 1,4-oxazepane, 1,3-diazepane, 1,4-diazepane, 1,3-thiazepane, 1,4-thiazepane, diazepane, oxazepane, thiazepane, 3,4,5,6-tetrahydro-2H-azepine, 4,5,6,7-tetrahydro-1H-1,3-diazepine, 4,5,6,7-tetrahydro-1,3-oxazepine, 4,5,6,7-tetrahydro-1,3-thiazepine, 2,3,4,7-tetrahydro-1H-1,3-diazepine, or 2,3,4,7-tetrahydro-1,3-oxazepine. In some embodiments of a compound of Formula (Ia), (IIa), (IIa-1), (Ib), (IIb), or (IIb-1), Ring A is pyrrolidine, piperidine, morpholine, or piperazine. In some embodiments of a compound of Formula (Ia), (IIa), (IIa-1), (Ib), (IIb), or (IIb-1), Ring A is a 5-membered heterocycloalkyl bearing at least one nitrogen atom. In some embodiments of a compound of Formula (Ia), (IIa), (IIa-1), (Ib), (IIb), or (IIb-1), Ring A is a 5-membered heterocycloalkyl bearing at least one oxygen atom. In some embodiments of a compound of Formula (Ia), (IIa), (IIa-1), (Ib), (IIb), or (IIb-1), Ring A is a 5-membered heterocycloalkyl bearing at least one oxygen atom and one nitrogen atom.

In some embodiments of a compound of Formula (Ia), (IIa), (IIa-1), (Ib), (IIb), or (IIb-1), Ring A is benzene, naphthalene, pyridine, pyrimidine, pyrazine, pyridazine, triazine, thiophene, furan, pyrrole, pyrazole, triazole, tetrazole, imidazole, thiazole, isothiazole, oxazole, isoxazole, indole, thiadiazole, oxadiazole, indazole, azaindole, azaindazole, indolizine, imidazopyridine, pyrazolo-pyridine, thiazolo-pyridine, pyrrolo-pyrimidine, thieno-pyrazole, benzimidazole, benzothiazole, benzoxazole, benzofuran, benzisoxazole, benzisothiazole, quinoline, isoquinoline, quinoxaline, quinazoline, cinnoline, benzotriazine, napthyridine, pyridopyrimidine, pyrido-pyrazine, pyridopyridazine, isoxazolo-pyridine, or oxazolo-pyridine. In some embodiments of a compound of Formula (Ia), (IIa), (IIa-1), (Ib), (IIb), or (IIb-1), Ring A is benzene, pyridine, thiazole, triazole, tetrazole, oxadiazole, or thiadiazole. In some embodiments of a compound of Formula (Ia), (IIa), (IIa-1), (Ib), (IIb), or (IIb-1), Ring A is benzene, pyridine, thiazole, triazole, tetrazole, imidazole, oxadiazole, or thiadiazole. In some embodiments of a compound of Formula (Ia), (IIa), (IIa-1), (Ib), (IIb), or (IIb-1), Ring A is thiazole. In some embodiments of a compound of Formula (Ia), (IIa), (IIa-1), (Ib), (IIb), or (IIb-1), Ring A is not thiazole. In some embodiments of a compound of Formula (Ia), (IIa), (IIa-1), (Ib), (IIb), or (IIb-1), Ring A is benzene. In some embodiments of a compound of Formula (Ia), (IIa), (IIa-1), (Ib), (IIb), or (IIb-1), Ring A is benzene and p is 1-3. In some embodiments of a compound of Formula (Ia), (IIa), (IIa-1), (Ib), (IIb), or (IIb-1), Ring A is 6-membered aryl or 6-membered heteroaryl. In some embodiments of a compound of Formula (Ia), (IIa), (IIa-1), (Ib), (IIb), or (IIb-1), Ring A is 6-membered aryl or 6-membered heteroaryl and p is 1-3. In some embodiments of a compound of Formula (Ia), (IIa), (IIa-1), (Ib), (IIb), or (IIb-1), Ring A is 6-membered aryl or 6-membered heteroaryl and p is 1-4. In some embodiments of a compound of Formula (Ia), (IIa), (IIa-1), (Ib), (IIb), or (IIb-1), Ring A is thiophene, furan, pyrrole, pyrazole, triazole, tetrazole, imidazole, isothiazole, oxazole, isoxazole, thiadiazole, and oxadiazole. In some embodiments of a compound of Formula (Ia), (IIa), (IIa-1), (Ib), (IIb), or (IIb-1), Ring A is naphthalene, pyridine, pyrimidine, pyrazine, pyridazine, triazine, indole, indazole, azaindole, azaindazole, indolizine, imidazopyridine, pyrazolo-pyridine, thiazolo-pyridine, pyrrolo-pyrimidine, thieno-pyrazole, benzimidazole, benzothiazole, benzoxazole, benzofuran, benzisoxazole, benzisothiazole, quinoline, isoquinoline, quinoxaline, quinazoline, cinnoline, benzotriazine, napthyridine, pyrido-pyrimidine, pyrido-pyrazine, pyridopyridazine, isoxazolo-pyridine, or oxazolo-pyridine. In some embodiments of a compound of Formula (Ia), (IIa), (IIa-1), (Ib), (IIb), or (IIb-1), Ring A is pyridine, pyrimidine, pyrazine, or pyridazine. In some embodiments of a compound of Formula (Ia), (IIa), (IIa-1), (Ib), (IIb), or (IIb-1), Ring A is pyridine. In some embodiments of a compound of Formula (Ia), (IIa), (IIa-1), (Ib), (IIb), or (IIb-1), Ring A is benzene or pyridine.

In some embodiments of a compound of Formula (Ia), (IIa), (IIa-1), (Ib), (IIb), or (IIb-1), Ring A is a 5-membered heteroaryl bearing at least two nitrogen atoms. In some embodiments of a compound of Formula (Ia), (IIa), (IIa-1), (Ib), (IIb), or (IIb-1), Ring A is a 5-membered heteroaryl bearing at least three nitrogen atoms. In some embodiments of a compound of Formula (Ia), (IIa), (IIa-1), (Ib), (IIb), or (IIb-1), Ring A is a 5-membered heteroaryl bearing four nitrogen atoms. In some embodiments of a compound of Formula (Ia), (IIa), (IIa-1), (Ib), (IIb), or (IIb-1), Ring A is a 5-membered heteroaryl bearing only nitrogen atoms as heteroatoms. In some embodiments of a compound of Formula (Ia), (IIa), (IIa-1), (Ib), (IIb), or (IIb-1), Ring A is a 5-membered heteroaryl bearing at least one oxygen atom. In some embodiments of a compound of Formula (Ia), (IIa), (IIa-1), (Ib), (IIb), or (IIb-1), Ring A is a 5-membered heteroaryl bearing at least one sulfur atom.

In some embodiments of a compound of Formula (Ia), (IIa), (IIa-1), (Ib), (IIb), or (IIb-1), at least one Y is halogen, alkyl, optionally substituted heteroaryl, —OH, —OR$^{34}$, —O(CR$^{30}$R$^{31}$)$_w$OH, —O(CR$^{30}$R$^{31}$)$_w$OR$^{34}$, —O(CR$^{30}$R$^{31}$)$_w$NR$^{32}$R$^{33}$, —O(CR$^{30}$R$^{31}$)$_w$NR$^{32}$C(=O)R$^{34}$, —O(CR$^{30}$R$^{31}$)$_w$NR$^{32}$C(=O)OR$^{34}$, —O(CR$^{30}$R$^{31}$)$_w$NR$^{32}$C(=O)NR$^{32}$R$^{33}$, —O(CR$^{30}$R$^{31}$)$_w$C(=O)NR$^{32}$R$^{33}$, —O(CR$^{30}$R$^{31}$)$_v$C(=NR$^{36}$)NR$^{32}$R$^{33}$, —O(CR$^{30}$R$^{31}$)$_w$N(R$^{32}$)C(=NR$^{36}$)R$^{34}$, —O(CR$^{30}$R$^{31}$)$_v$C(=NR$^{36}$)NR$^{32}$C(=NR$^{36}$)NR$^{32}$R$^{33}$, —O(CR$^{30}$R$^{31}$)$_w$N(R$^{32}$)C(=NR$^{36}$)NR$^{32}$R$^{33}$, —NR$^{32}$R$^{33}$, —NR$^{32}$(CR$^{30}$R$^{31}$)$_w$NR$^{32}$R$^{33}$, —NR$^{32}$(CR$^{30}$R$^{31}$)$_w$OH, —NR$^{32}$(CR$^{30}$R$^{31}$)$_w$OR$^{34}$, —NR$^{32}$C(=O)R$^{34}$, —NR$^{32}$C(=O)OR$^{34}$, —N(R$^{32}$)C(=O)(CR$^{30}$R$^{31}$)$_w$NR$^{32}$R$^{33}$, —NR$^{32}$C(=O)NR$^{32}$R$^{33}$, —NR$^{32}$C(=O)NR$^{32}$(CR$^{30}$R$^{31}$)$_w$NR$^{32}$R$^{33}$, —NR$^{32}$C(=NR$^{36}$)NR$^{32}$R$^{33}$, —N(R$^{32}$)C(=NR$^{36}$)R$^{34}$, —NR$^{32}$(CR$^{30}$R$^{31}$)$_w$N(R$^{32}$)C(=NR$^{36}$)R$^{34}$, —NR$^{32}$(CR$^{30}$R$^{31}$)$_v$C(=NR$^{36}$)NR$^{32}$R$^{33}$, —NR$^{32}$(CR$^{30}$R$^{31}$)$_w$N(R$^{32}$)C(=NR$^{36}$)NR$^{32}$R$^{33}$, —NR$^{32}$(CR$^{30}$R$^{31}$)$_w$NR$^{32}$C(=O)NR$^{32}$R$^{33}$, NR$^{32}$(CR$^{30}$R$^{31}$)$_w$NR$^{32}$C(=O)OR$^{34}$, —NR$^{32}$(CR$^{30}$R$^{31}$)$_v$CO$_2$H, —NR$^{32}$(CR$^{30}$R$^{31}$)$_v$CO$_2$R$^{34}$, —NR$^{32}$(CR$^{30}$R$^{31}$)$_v$C(=O)NR$^{32}$R$^{33}$, —N(R$^{32}$)-heteroaryl-NR$^{32}$R$^{33}$, —N(R$^{32}$)-heterocycloalkyl-NR$^{32}$R$^{33}$, —NR$^{32}$(CR$^{30}$R$^{31}$)$_v$heteroaryl, —NR$^{32}$(CR$^{30}$R$^{31}$)$_v$heterocycloalkyl, —CN, —(CR$^{30}$R$^{31}$)$_v$CN, —(CR$^{30}$R$^{31}$)$_w$NR$^{32}$R$^{33}$, —(CR$^{30}$R$^{31}$)$_w$OH, —(CR$^{30}$R$^{31}$)$_w$OR$^{34}$, —(CR$^{30}$R$^{31}$)$_v$OC(=O)R$^{34}$, —(CR$^{30}$R$^{31}$)$_v$OC(=O)NR$^{32}$R$^{33}$, —(CR$^{30}$R$^{31}$)$_v$O(CR$^{30}$R$^{31}$)$_w$OR$^{34}$, —(CR$^{30}$R$^{31}$)$_v$O(CR$^{30}$R$^{31}$)$_w$OH, —(CR$^{30}$R$^{31}$)$_v$O(CR$^{30}$R$^{31}$)$_w$NR$^{32}$R$^{33}$, —(CR$^{30}$R$^{31}$)$_w$NR$^{32}$(CR$^{30}$R$^{31}$)$_w$OH, —(CR$^{30}$R$^{31}$)$_w$NR$^{32}$(CR$^{30}$R$^{31}$)$_w$OR$^{34}$, —(CR$^{30}$R$^{31}$)$_v$C(=O)NR$^{32}$R$^{33}$, —(CR$^{30}$R$^{31}$)$_v$C(=O)OH, —(CR$^{30}$R$^{31}$)$_v$C(=O)OR$^{34}$, —(CR$^{30}$R$^{31}$)$_v$C(=O)NR$^{32}$(CR$^{30}$R$^{31}$)$_w$NR$^{32}$R$^{33}$, —(CR$^{30}$R$^{31}$)$_v$C(=O)NR$^{32}$(CR$^{30}$R$^{31}$)$_w$OR$^{34}$, —(CR$^{30}$R$^{31}$)$_v$N(R$^{32}$)$_v$C(=O)R$^{34}$, —(CR$^{30}$R$^{31}$)$_v$N(R$^{32}$)$_v$C(=O)OR$^{34}$, —(CR$^{30}$R$^{31}$)$_v$N(R$^{32}$)$_v$C(=O)NR$^{32}$R$^{33}$, —(CR$^{30}$R$^{31}$)$_v$N(R$^{32}$)$_v$C(=O)(CR$^{30}$R$^{31}$)$_w$NR$^{32}$R$^{33}$, —(CR$^{30}$R$^{31}$)$_w$NR$^{32}$(CR$^{30}$R$^{31}$)$_w$NR$^{32}$R$^{33}$, —(CR$^{30}$R$^{31}$)$_w$N(R$^{32}$)CH(=NR$^{36}$), —(CR$^{30}$R$^{31}$)$_v$N(R$^{32}$)C(=NR$^{36}$)R$^{34}$, —(CR$^{30}$R$^{31}$)$_v$C(=NR$^{36}$)NR$^{32}$R$^{33}$, —(CR$^{30}$R$^{31}$)$_v$N(R$^{32}$)C(=NR$^{36}$)NR$^{32}$R$^{33}$, —(CR$^{30}$R$^{31}$)$_v$C(=NR$^{36}$)NR$^{32}$C(=NR$^{36}$)NR$^{32}$R$^{33}$, —(CR$^{30}$R$^{31}$)$_v$heteroaryl-NR$^{32}$R$^{33}$, —C(=O)OH, —C(=O)OR$^{34}$, —C(=O)NR$^{32}$R$^{33}$, —C(=O)NR$^{32}$(CR$^{30}$R$^{31}$)$_w$NR$^{32}$R$^{33}$, —C(=O)NR$^{32}$(CR$^{30}$R$^{31}$)$_w$OH, —C(=O)NR$^{32}$(CR$^{30}$R$^{31}$)$_w$OR$^{34}$, —C(=NR$^{36}$)NR$^{32}$R$^{33}$, —C(=NR$^{36}$)NR$^{32}$C(=O)R$^{34}$, or SR$^{35}$.

In some embodiments of a compound of Formula (Ia), (IIa), (IIa-1), (Ib), (IIb), or (IIb-1), each Y is independently halogen, alkyl, optionally substituted heteroaryl, —OH, —OR$^{34}$, —NR$^{32}$R$^{33}$, —NR$^{32}$(CR$^{30}$R$^{31}$)$_w$NR$^{32}$R$^{33}$, —NR$^{32}$(CR$^{30}$R$^{31}$)$_v$OH, —NR$^{32}$(CR$^{30}$R$^{31}$)$_v$OR$^{34}$, —NR$^{32}$C(=O)R$^{34}$, —NR$^{32}$C(=O)OR$^{34}$, —N(R$^{32}$)$_v$C(=O)(CR$^{30}$R$^{31}$)$_w$NR$^{32}$R$^{33}$, —NR$^{32}$C(=O)NR$^{32}$R$^{33}$, —NR$^{32}$C(=O)NR$^{32}$(CR$^{30}$R$^{31}$)$_w$NR$^{32}$R$^{33}$, —NR$^{32}$C(=NR$^{36}$)NR$^{32}$R$^{33}$, —N(R$^{32}$)C(=NR$^{36}$)R$^{34}$, —NR$^{32}$(CR$^{30}$R$^{31}$)$_w$N(R$^{32}$)C(=NR$^{36}$)R$^{34}$, —NR$^{32}$(CR$^{30}$R$^{31}$)$_v$C(=NR$^{36}$)NR$^{32}$R$^{33}$, —NR$^{32}$(CR$^{30}$R$^{31}$)$_w$N(R$^{32}$)C(=NR$^{36}$)NR$^{32}$R$^{33}$, —NR$^{32}$(CR$^{30}$R$^{31}$)$_w$NR$^{32}$C(=O)NR$^{32}$R$^{33}$, NR$^{32}$(CR$^{30}$R$^{31}$)$_w$NR$^{32}$C(=O)OR$^{34}$, —NR$^{32}$(CR$^{30}$R$^{31}$)$_v$CO$_2$H, —NR$^{32}$(CR$^{30}$R$^{31}$)$_v$CO$_2$R$^{34}$, —NR$^{32}$(CR$^{30}$R$^{31}$)$_v$C(=O)NR$^{32}$R$^{33}$, —NR$^{32}$(CR$^{30}$R$^{31}$)$_v$heteroaryl, —NR$^{32}$(CR$^{30}$R$^{31}$)heterocycloalkyl, —(CR$^{30}$R$^{31}$)$_w$NR$^{32}$R$^{33}$, —(CR$^{30}$R$^{31}$)$_v$OC(=O)NR$^{32}$R$^{33}$, —(CR$^{30}$R$^{31}$)$_v$O(CR$^{30}$R$^{31}$)$_w$NR$^{32}$R$^{33}$, —(CR$^{30}$R$^{31}$)$_v$C(=O)NR$^{32}$R$^{33}$, —(CR$^{30}$R$^{31}$)$_v$C(=O)OH, —(CR$^{30}$R$^{31}$)$_v$C(=O)OR$^{34}$, —(CR$^{30}$R$^{31}$)$_v$C(=O)NR$^{32}$(CR$^{30}$R$^{31}$)$_w$NR$^{32}$R$^{33}$, —(CR$^{30}$R$^{31}$)$_v$C(=O)NR$^{32}$(CR$^{30}$R$^{31}$)$_w$OR$^{34}$, —(CR$^{30}$R$^{31}$)$_v$N(R$^{32}$)$_v$C(=O)R$^{34}$, —(CR$^{30}$R$^{31}$)N(R$^{32}$)$_v$C(=O)OR$^{34}$, —(CR$^{30}$R$^{31}$)N(R$^{32}$)$_v$C(=O)NR$^{32}$R$^{33}$, —(CR$^{30}$R$^{31}$)$_w$N(R$^{32}$)$_v$C(=O)(CR$^{30}$R$^{31}$)$_w$NR$^{32}$R$^{33}$, —(CR$^{30}$R$^{31}$)$_w$NR$^{32}$(CR$^{30}$R$^{31}$)$_w$NR$^{32}$R$^{33}$, —(CR$^{30}$R$^{31}$)$_v$N(R$^{32}$)CH(=NR$^{36}$), —(CR$^{30}$R$^{31}$)$_v$N(R$^{32}$)C(=NR$^{36}$)R$^{34}$, —(CR$^{30}$R$^{31}$)$_v$C(=NR$^{36}$)NR$^{32}$R$^{33}$, —(CR$^{30}$R$^{31}$)$_v$N(R$^{32}$)C(=NR$^{36}$)NR$^{32}$R$^{33}$, —(CR$^{30}$R$^{31}$)$_v$C(=NR$^{36}$)NR$^{32}$C(=NR$^{36}$)NR$^{32}$R$^{33}$, —(CR$^{30}$R$^{31}$)$_v$heteroaryl-NR$^{32}$R$^{33}$, —C(=O)OH, —C(=O)OR$^{34}$, —C(=O)NR$^{32}$R$^{33}$, —C(=O)NR$^{32}$(CR$^{30}$R$^{31}$)$_w$NR$^{32}$R$^{33}$, —C(=O)NR$^{32}$(CR$^{30}$R$^{31}$)$_w$OH, —C(=O)NR$^{32}$(CR$^{30}$R$^{31}$)$_w$OR$^{34}$, —C(=NR$^{36}$)NR$^{32}$R$^{33}$, —C(=NR$^{36}$)NR$^{32}$C(=O)R$^{34}$, or SR$^{35}$.

In some embodiments of a compound of Formula (Ia), (IIa), (IIa-1), (Ib), (IIb), or (IIb-1), each Y is independently halogen, optionally substituted heteroaryl, —NR$^{32}$R$^{33}$, —OH, —OR$^{34}$, —NR$^{32}$(CR$^{30}$R$^{31}$)$_w$NR$^{32}$R$^{33}$, —NR$^{32}$C(=NR$^{36}$)NR$^{32}$R$^{33}$, —(CR$^{30}$R$^{31}$)$_w$NR$^{32}$R$^{33}$, —SR$^{35}$, —NR$^{32}$(CR$^{30}$R$^{31}$)$_v$CO$_2$H, —NR$^{32}$(CR$^{30}$R$^{31}$)$_v$C(=O)NR$^{32}$R$^{33}$, or —NR$^{32}$(CR$^{30}$R$^{31}$)$_v$heteroaryl; or two Ys are taken together with the atoms to which they are attached to form an optionally substituted heterocycloalkyl. In some embodiments of a compound of Formula (Ia), (IIa), (IIa-1), (Ib), (IIb), or (IIb-1), each Y is independently —NR$^{32}$R$^{33}$. In some embodiments of a compound of Formula (Ia), (IIa), (IIa-1), (Ib), (IIb), or (IIb-1), each Y is independently —(CR$^{30}$R$^{31}$)$_w$NR$^{32}$R$^{33}$. In some embodiments of a compound of Formula (Ia), (IIa), (IIa-1), (Ib), (IIb), or (IIb-1), each Y is independently —NR$^{32}$(CR$^{30}$R$^{31}$)$_w$NR$^{32}$R$^{33}$. In some embodiments of a compound of Formula (Ia), (IIa), (IIa-1), (Ib), (IIb), or (IIb-1), each Y is independently —OH. In some embodiments of a compound of Formula (Ia), (IIa), (IIa-1), (Ib), (IIb), or (IIb-1), each Y is independently halogen, —NR$^{32}$R$^{33}$, —OH, —OR$^{34}$, —NR$^{32}$(CR$^{30}$R$^{31}$)$_w$NR$^{32}$R$^{33}$, —C(=O)OH, or —C(=O)NR$^{32}$R$^{33}$. In some embodiments of a compound of Formula (Ia), (IIa), (IIa-1), (Ib), (IIb), or (IIb-1), each Y is independently halogen, —NR$^{32}$R$^{33}$, —OH, —OR$^{34}$, or —NR$^{32}$(CR$^{30}$R$^{31}$)$_w$NR$^{32}$R$^{33}$. In some embodiments of a compound of Formula (Ia), (IIa), (IIa-1), (Ib), (IIb), or (IIb-1), each Y is independently halogen, —NR$^{32}$R$^{33}$, —OH, —C(=O)OH, or —C(=O)NR$^{32}$R$^{33}$. In some embodiments of a compound of Formula (Ia), (IIa), (IIa-1), (Ib), (IIb), or (IIb-1), each Y is independently —OH or —OR$^{34}$.

In some embodiments of a compound of Formula (Ia), (IIa), (IIa-1), (Ib), (IIb), or (IIb-1), each Y is independently halogen, optionally substituted alkyl, —OH, —OR$^{34}$, —O(CR$^{30}$R$^{31}$)$_w$OH, —O(CR$^{30}$R$^{31}$)$_v$OR$^{34}$, —O(CR$^{30}$R$^{31}$)$_w$NR$^{32}$R$^{33}$, —NR$^{32}$R$^{33}$, —NR$^{32}$(CR$^{30}$R$^{31}$)$_w$NR$^{32}$R$^{33}$, —NR$^{32}$(CR$^{30}$R$^{31}$)$_w$OH, —(CR$^{30}$R$^{31}$)$_w$NR$^{32}$R$^{33}$, —(CR$^{30}$R$^{31}$)$_v$C(=O)NR$^{32}$R$^{33}$, —(CR$^{30}$R$^{31}$)$_v$C(=O)OH, —(CR$^{30}$R$^{31}$)$_v$C(=O)OR$^{34}$, —C(=NR$^{36}$)NR$^{32}$R$^{33}$, —S(=O)$_{1,2}$R$^{34}$, —S(=O)$_{0,1,2}$NR$^{32}$R$^{33}$, —C(=O)NR$^{32}$R$^{33}$, —OC(=O)R$^{34}$, —NR$^{32}$S(=O)$_{0,1,2}$R$^{34}$, —O(CR$^{30}$R$^{31}$)$_w$NR$^{32}$R$^{33}$, —C(=O)OH, —C(=O)OR$^{34}$, —C(=O)NR$^{32}$(CR$^{30}$R$^{31}$)$_w$OH, or —C(=O)NR$^{32}$(CR$^{30}$R$^{31}$)$_v$OR$^{34}$.

In some embodiments of a compound of Formula (Ia), (IIa), (IIa-1), (Ib), (IIb), or (IIb-1), each Y is independently halogen, optionally substituted alkyl, —OH, —OR$^{34}$, —O(CR$^{30}$R$^{31}$)$_w$OH, —O(CR$^{30}$R$^{31}$)$_v$OR$^{34}$, —O(CR$^{30}$R$^{31}$)$_w$NR$^{32}$R$^{33}$, —NR$^{32}$R$^{33}$, —NR$^{32}$(CR$^{30}$R$^{31}$)$_w$NR$^{32}$R$^{33}$, —NR$^{32}$(CR$^{30}$R$^{31}$)$_w$OH, —(CR$^{30}$R$^{31}$)$_w$NR$^{32}$R$^{33}$, —(CR$^{30}$R$^{31}$)$_v$C(=O)NR$^{32}$R$^{33}$, —(CR$^{30}$R$^{31}$)$_v$C(=O)OH, —(CR$^{30}$R$^{31}$)$_v$C(=O)OR$^{34}$, —C(=NR$^{36}$)NR$^{32}$R$^{33}$, —S(=O)$_{1,2}$R$^{34}$, —S(=O)$_{0,1,2}$NR$^{32}$R$^{33}$, —C(=O)NR$^{32}$R$^{33}$, —OC(=O)R$^{34}$, or —NR$^{32}$S(=O)$_{0,1,2}$R$^{34}$.

In some embodiments of a compound of Formula (Ia), (IIa), (IIa-1), (Ib), (IIb), or (IIb-1), each Y is independently halogen, optionally substituted alkyl, —OH, —OR$^{34}$, —O(CR$^{30}$R$^{31}$)$_w$OH, —O(CR$^{30}$R$^{31}$)$_v$OR$^{34}$, —O(CR$^{30}$R$^{31}$)$_w$NR$^{32}$R$^{33}$, —NR$^{32}$R$^{33}$, —NR$^{32}$(CR$^{30}$R$^{31}$)$_w$NR$^{32}$R$^{33}$, —NR$^{32}$(CR$^{30}$R$^{31}$)$_w$OH, —(CR$^{30}$R$^{31}$)$_w$NR$^{32}$R$^{33}$, —(CR$^{30}$R$^{31}$)$_v$C(=O)NR$^{32}$R$^{33}$, —(CR$^{30}$R$^{31}$)$_v$C(=O)OH, —(CR$^{30}$R$^{31}$)$_v$C(=O)OR$^{34}$, —C(=NR$^{36}$)NR$^{32}$R$^{33}$, —S(=O)$_{1,2}$R$^{34}$, —S(=O)$_{0,1,2}$NR$^{32}$R$^{33}$, —O(CR$^{30}$R$^{31}$)$_w$NR$^{32}$R$^{33}$, —C(=O)OH, —C(=O)OR$^{34}$, —C(=O)NR$^{32}$(CR$^{30}$R$^{31}$)$_w$OH, or —C(=O)NR$^{32}$(CR$^{30}$R$^{31}$)$_w$OR$^{34}$.

In some embodiments of a compound of Formula (Ia), (IIa), (IIa-1), (Ib), (IIb), or (IIb-1), each Y is independently halogen, optionally substituted alkyl, —OH, —OR$^{34}$, —O(CR$^{30}$R$^{31}$)$_w$OH, —O(CR$^{30}$R$^{31}$)$_v$OR$^{34}$, —O(CR$^{30}$R$^{31}$)$_w$NR$^{32}$R$^{33}$, —NR$^{32}$R$^{33}$, —NR$^{32}$(CR$^{30}$R$^{31}$)$_w$NR$^{32}$R$^{33}$, —NR$^{32}$(CR$^{30}$R$^{31}$)$_w$OH, —(CR$^{30}$R$^{31}$)$_w$NR$^{32}$R$^{33}$, —(CR$^{30}$R$^{31}$)$_v$C(=O)NR$^{32}$R$^{33}$, —(CR$^{30}$R$^{31}$)$_v$C(=O)OH, —(CR$^{30}$R$^{31}$)$_v$C(=O)OR$^{34}$, —C(=NR$^{36}$)NR$^{32}$R$^{33}$, —S(=O)$_{1,2}$R$^{34}$, or —S(=O)$_{0,1,2}$NR$^{32}$R$^{33}$.

In some embodiments of a compound of Formula (Ia), (IIa), (IIa-1), (Ib), (IIb), or (IIb-1), each Y is independently halogen, —OH, or —OR$^{34}$.

In some embodiments of a compound of Formula (Ia), (IIa), (IIa-1), (Ib), (IIb), or (IIb-1), two Ys are taken together with the atoms to which they are attached to form an optionally substituted cycloalkyl or an optionally substituted heterocycloalkyl. In some embodiments of a compound of Formula (Ia), (IIa), (IIa-1), (Ib), (IIb), or (IIb-1), two Ys are taken together with the atoms to which they are attached to form a heterocycloalkyl optionally substituted with alkyl or halogen.

In some embodiments of a compound of Formula (Ia), (IIa), (IIa-1), (Ib), (IIb), or (IIb-1), each Y is defined by the inclusion of non-hydrogen atoms. In some embodiments, each Y comprises at least 1, 2, 3, 4, 5, 6, 7, 8, 9, 10, 12, 14, 16, 18, 20, 24, 28, 32, 36, 40, 50, or 60 non-hydrogen atoms. In some embodiments of a compound of Formula (Ia), (IIa), (IIa-1), (Ib), (IIb), or (IIb-1), each Y comprises fewer than 50, 40, 36, 32, 28, 24, 20, 18, 16, 14, 12, 10, 9, 8, 7, 6, 5, 4, 3 or 2 non-hydrogen atoms. In some embodiments of a compound of Formula (Ia), (IIa), (IIa-1), (Ib), (IIb), or (IIb-1), each Y is independently a group comprising 1-50 non-hydrogen atoms. In some embodiments of a compound of Formula (Ia), (IIa), (IIa-1), (Ib), (IIb), or (IIb-1), non-hydrogen atoms are atoms generally found in organic molecules. In some embodiments of a compound of Formula (Ia), (IIa), (IIa-1), (Ib), (IIb), or (IIb-1), non-hydrogen atoms are atoms selected from the group consisting of halogen, C, N, O, S, and P. In some embodiments of a compound of Formula (Ia), (IIa), (IIa-1), (Ib), (IIb), or (IIb-1), each Y is independently a group comprising 1-50 non-hydrogen atoms selected from the group consisting of halogen, C, N, O, S, and P. In some embodiments of a compound of Formula (Ia), (IIa), (IIa-1), (Ib), (IIb), or (IIb-1), each Y is independently a group comprising 1-50 non-hydrogen atoms selected from the group consisting of halogen, C, N, and O.

In some embodiments of a compound of Formula (Ia), (IIa), (IIa-1), (Ib), (IIb), or (IIb-1), each Y is defined by its molecular formula. In some embodiments of a compound of Formula (Ia), (IIa), (IIa-1), (Ib), (IIb), or (IIb-1), each Y has the formula $C_aH_bN_cO_d$; wherein each a is independently 0-30; each b is independently 1-69; each c is independently 1-8; and each d is independently 0-10. In some embodiments of a compound of Formula (Ia), (IIa), (IIa-1), (Ib), (IIb), or (IIb-1), each Y has the formula $C_aH_bN_cO_d$; wherein each a is independently 0-10; each b is independently 1-25; each c is independently 1-4; and each d is independently 0-3. In some embodiments of a compound of Formula (Ia), (IIa), (IIa-1), (Ib), (IIb), or (IIb-1), each c is 2. In some embodiments of a compound of Formula (Ia), (IIa), (IIa-1), (Ib), (IIb), or (IIb-1), each c is at least 2.

In some embodiments of a compound of Formula (Ia), (IIa), (IIa-1), (Ib), (IIb), or (IIb-1), each Y is defined by its molecular weight. In some embodiments of a compound of Formula (Ia), (IIa), (IIa-1), (Ib), (IIb), or (IIb-1), each Y has a molecular weight of less than 500, 450, 400, 350, 300, 250, 200, 190, 180, 170, 160, 150, 140, 130, 120, 110, 100, 90, 80, 75, 70, or 50 daltons. In some embodiments of a compound of Formula (Ia), (IIa), (IIa-1), (Ib), (IIb), or (IIb-1), each Y has a molecular weight of less than 200 daltons. In some embodiments of a compound of Formula (Ia), (IIa), (IIa-1), (Ib), (IIb), or (IIb-1), each Y has a molecular weight of less than 150 daltons. In some embodiments of a compound of Formula (Ia), (IIa), (IIa-1), (Ib), (IIb), or (IIb-1), each Y has a molecular weight between 30 and 280 daltons.

In some embodiments of a compound of Formula (Ia), (IIa), (IIa-1), (Ib), (IIb), or (IIb-1),

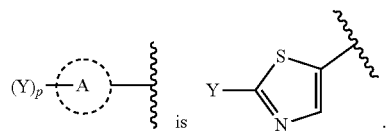

In some embodiments of a compound of Formula (Ia), (IIa), (IIa-1), (Ib), (IIb), or (IIb-1), p is 0-2. In some embodiments of a compound of Formula (Ia), (IIa), (IIa-1), (Ib), (IIb), or (IIb-1), p is 1-3. In some embodiments of a compound of Formula (Ia), (IIa), (IIa-1), (Ib), (IIb), or (IIb-1), p is 1-4. In some embodiments of a compound of Formula (Ia), (IIa), (IIa-1), (Ib), (IIb), or (IIb-1), p is 2 or 3. In some embodiments of a compound of Formula (Ia), (IIa), (IIa-1), (Ib), (IIb), or (IIb-1), p is not 0. In some embodiments of a compound of Formula (Ia), (IIa), (IIa-1), (Ib), (IIb), or (IIb-1), p is 0. In some embodiments of a compound of Formula (Ia), (IIa), (IIa-1), (Ib), (IIb), or (IIb-1), p is 1. In some embodiments of a compound of Formula (Ia), (IIa), (IIa-1), (Ib), (IIb), or (IIb-1), p is 2. In some embodiments of a compound of Formula (Ia), (IIa), (IIa-1), (Ib), (IIb), or (IIb-1), p is 3.

In some embodiments of a compound of Formula (Ia), (IIa), (IIa-1), (Ib), (IIb), or (IIb-1), $A^1$ is hydrogen.

In some embodiments of a compound of Formula (Ia), (IIa), (IIa-1), (Ib), (IIb), or (IIb-1), $A^1$ is Y.

In some embodiments of a compound of Formula (Ia), (IIa), (IIa-1), (Ib), (IIb), or (IIb-1), $A^1$ is Y; and Y is halogen, alkyl, —OH, —$OR^{34}$, —$O(CR^{30}R^{31})_v$OH, —$O(CR^{30}R^{31})_v$$OR^{34}$, —$O(CR^{30}R^{31})_w NR^{32}R^{33}$, —$O(CR^{30}R^{31})_w NR^{32}C(=O)R^{34}$, —$O(CR^{30}R^{31})_w NR^{32}C(=O)OR^{34}$, —$O(CR^{30}R^{31})_w NR^{32}C(=O)NR^{32}R^{33}$, —$O(CR^{30}R^{31})_v C(=O)NR^{32}R^{33}$, —$O(CR^{30}R^{31})_v C(=NR^{36})NR^{32}R^{33}$, —$O(CR^{30}R^{31})_w N(R^{32})C(=NR^{36})R^{34}$, —$O(CR^{30}R^{31})C(=NR^{36})NR^{32}C(=NR^{36})NR^{32}R^{33}$, —$O(CR^{30}R^{31})_w N(R^{32})C(=NR^{36})NR^{32}R^{33}$, —$NR^{32}R^{33}$, —$NR^{32}(CR^{30}R^{31})_w NR^{32}R^{33}$, —$NR^{32}(CR^{30}R^{31})_w OH$, —$NR^{32}(CR^{30}R^{31})_w OR^{34}$, —$NR^{32}C(=O)R^{34}$, —$NR^{32}C(=O)OR^{34}$, —$N(R^{32})_v C(=O)(CR^{30}R^{31})_w NR^{32}R^{33}$, —$NR^{32}C(=O)NR^{32}R^{33}$, —$NR^{32}C(=O)NR^{32}(CR^{30}R^{31})_w NR^{32}R^{33}$, —$NR^{32}C(=NR^{36})NR^{32}R^{33}$, —$N(R^{32})C(=NR^{36})R^{34}$, —$NR^{32}(CR^{30}R^{31})_w N(R^{32})C(=NR^{36})R^{34}$, —$NR^{32}(CR^{30}R^{31})_v C(=NR^{36})NR^{32}R^{33}$, —$NR^{32}(CR^{30}R^{31})_w N(R^{32})C(=NR^{36})NR^{32}R^{33}$, —$NR^{32}(CR^{30}R^{31})_w NR^{32}C(=O)NR^{32}R^{33}$, —$NR^{32}(CR^{30}R^{31})_w NR^{32}C(=O)OR^{34}$, —$NR^{32}(CR^{30}R^{31})_v CO_2H$, —$NR^{32}(CR^{30}R^{31})_v CO_2R^{34}$, —$NR^{32}(CR^{30}R^{31})_v C(=O)NR^{32}R^{33}$, —$N(R^{32})$-heteroaryl-$NR^{32}R^{33}$, —$N(R^{32})$-heterocycloalkyl-$NR^{32}R^{33}$, —$NR^{32}(CR^{30}R^{31})$ heteroaryl, —$NR^{32}(CR^{30}R^{31})$ heterocycloalkyl, —CN, —$(CR^{30}R^{31})_v CN$, —$(CR^{30}R^{31})_w NR^{32}R^{33}$, —C(=O)OH, —$C(=O)OR^{34}$, —$C(=O)NR^{32}R^{33}$, —$C(=O)NR^{32}(CR^{30}R^{31})NR^{32}R^{33}$, —$C(=O)NR^{32}(CR^{30}R^{31})_w OH$, —$C(=O)NR^{32}(CR^{30}R^{31})_w OR^{34}$, —$C(=NR^{36})NR^{32}R^{33}$, —$C(=NR^{36})NR^{32}C(=O)R^{34}$, or $SR^{35}$.

In some embodiments of a compound of Formula (Ia), (IIa), (IIa-1), (Ib), (IIb), or (IIb-1), $A^1$ is Y; and Y is halogen, alkyl, —OH, —$OR^{34}$, —$NR^{32}R^{33}$, —$NR^{32}(CR^{30}R^{31})_w NR^{32}R^{33}$, —$NR^{32}(CR^{30}R^{31})_w OH$, —$NR^{32}(CR^{30}R^{31})_w OR^{34}$, —$NR^{32}C(=O)R^{34}$, —$NR^{32}C(=O)OR^{34}$, —$N(R^{32})_v C(=O)(CR^{30}R^{31})_w NR^{32}R^{33}$, —$NR^{32}C(=O)NR^{32}R^{33}$, —$NR^{32}C(=O)NR^{32}(CR^{30}R^{31})_w NR^{32}R^{33}$, —$NR^{32}C(=NR^{36})NR^{32}R^{33}$, —$N(R^{32})C(=NR^{36})R^{34}$, —$NR^{32}(CR^{30}R^{31})_w N(R^{32})C(=NR^{36})R^{34}$, —$NR^{32}(CR^{30}R^{31})C(=NR^{36})NR^{32}R^{33}$, —$NR^{32}(CR^{30}R^{31})_w N(R^{32})C(=NR^{36})NR^{32}R^{33}$, —$NR^{32}(CR^{30}R^{31})_w NR^{32}C(=O)NR^{32}R^{33}$, —$NR^{32}(CR^{30}R^{31})_w NR^{32}C(=O)OR^{34}$, —$NR^{32}(CR^{30}R^{31})_v CO_2H$, —$NR^{32}(CR^{30}R^{31})_v CO_2R^{34}$, —$NR^{32}(CR^{30}R^{31})_v C(=O)NR^{32}R^{33}$, —$NR^{32}(CR^{30}R^{31})_v$heteroaryl, —$NR^{32}(CR^{30}R^{31})_v$heterocycloalkyl, —C(=O)OH, —$C(=O)OR^{34}$, —$C(=O)NR^{32}R^{33}$, —$C(=O)NR^{32}(CR^{30}R^{31})_w NR^{32}R^{33}$, —$C(=O)NR^{32}(CR^{30}R^{31})_w OH$, —$C(=O)NR^{32}(CR^{30}R^{31})_v OR^{34}$, —$C(=NR^{36})NR^{32}R^{33}$, —$C(=NR^{36})NR^{32}C(=O)R^{34}$, or $SR^{35}$.

In some embodiments of a compound of Formula (Ia), (IIa), (IIa-1), (Ib), (IIb), or (IIb-1), $A^1$ is Y; and Y is halogen, —$NR^{32}R^{33}$, —OH, —$OR^{34}$, —$NR^{32}(CR^{30}R^{31})_w NR^{32}R^{33}$, —$NR^{32}C(=NR^{36})NR^{32}R^{33}$, —$SR^{35}$, —$NR^{32}(CR^{30}R^{31})_v CO_2H$, —$NR^{32}(CR^{30}R^{31})_v C(=O)NR^{32}R^{33}$, —C(=O)OH, —$C(=O)OR^{34}$, or —$C(=O)NR^{32}R^{33}$.

In some embodiments of a compound of Formula (Ia), (IIa), (IIa-1), (Ib), (IIb), or (IIb-1), $A^1$ is Y; and Y is —$NR^{32}R^{33}$, —OH, —$NR^{32}C(=NR^{36})NR^{32}R^{33}$, —C(=O)OH, or —$C(=O)NR^{32}R^{33}$.

In some embodiments of a compound of Formula (Ia), (IIa), (IIa-1), (Ib), (IIb), or (IIb-1), $A^1$ is Y; and Y—$NR^{32}R^{33}$, —OH, —C(=O)OH, or —$C(=O)NR^{32}R^{33}$.

In some embodiments of a compound of Formula (Ia), (IIa), (IIa-1), (Ib), (IIb), or (IIb-1), $A^1$ is Y; and Y is —OH, —$OR^{34}$, —$NR^{32}R^{33}$, —$NR^{32}C(=O)R^{34}$, —$NR^{32}S(=O)_{0,1,2}NR^{32}R^{33}$, —$NR^{32}S(=O)_{0,1,2}R^{34}$, —C(=O)OH, or —$C(=O)OR^{34}$.

In some embodiments of a compound of Formula (Ia), (IIa), (IIa-1), (Ib), (IIb), or (IIb-1), $A^1$ is Y; and Y is —$OR^{34}$, —$NR^{32}R^{33}$, —$NR^{32}C(=O)R^{34}$, —$NR^{32}S(=O)_{0,1,2}NR^{32}R^{33}$, —$NR^{32}S(=O)_{0,1,2}R^{34}$, —C(=O)OH, or —$C(=O)OR^{34}$.

In some embodiments of a compound of Formula (Ia), (IIa), (IIa-1), (Ib), (IIb), or (IIb-1), $A^1$ is Y; and Y is —$NR^{32}C(=O)R^{34}$.

In some embodiments of a compound of Formula (Ia), (IIa), (IIa-1), (Ib), (IIb), or (IIb-1), $A^1$ is Y; and Y is —$NR^{32}S(=O)_{0,1,2}NR^{32}R^{33}$.

In some embodiments of a compound of Formula (Ia), (IIa), (IIa-1), (Ib), (IIb), or (IIb-1), $A^1$ is Y; and Y is —C(=O)OH.

In some embodiments of a compound of Formula (Ia), (IIa), (IIa-1), (Ib), (IIb), or (IIb-1), $A^1$ is Y; and Y is —OH.

In some embodiments of a compound of Formula (Ia), (IIa), (IIa-1), (Ib), (IIb), or (IIb-1), $A^1$ is Y; and Y is —$NR^{32}R^{33}$.

In some embodiments of a compound of Formula (Ia), (IIa), (IIa-1), (Ib), (IIb), or (IIb-1), $A^1$ is Y; and Y is —$OR^{34}$.

In some embodiments of a compound of Formula (Ia), (IIa), (IIa-1), (Ib), (IIb), or (IIb-1), Y is defined as above and $R^{30}$ and $R^{31}$ are independently hydrogen or optionally substituted alkyl; or two $R^{30}$ on adjacent carbon form an alkenyl.

In some embodiments of a compound of Formula (Ia), (IIa), (IIa-1), (Ib), (IIb), or (IIb-1), Y is defined as above and $R^{32}$ and $R^{33}$ are independently hydrogen or optionally substituted alkyl; or $R^{32}$ and $R^{33}$ are taken together with the nitrogen to which they are attached to form an optionally substituted heterocycloalkyl.

In some embodiments of a compound of Formula (Ia), (IIa), (IIa-1), (Ib), (IIb), or (IIb-1), Y is defined as above and $R^{34}$ is optionally substituted alkyl. In some embodiments of a compound of Formula (Ia), (IIa), (IIa-1), (Ib), (IIb), or (IIb-1), Y is defined as above and $R^{34}$ is substituted alkyl.

In some embodiments of a compound of Formula (Ia), (IIa), (IIa-1), (Ib), (IIb), or (IIb-1), Y is defined as above and $R^{35}$ is hydrogen or optionally substituted alkyl.

In some embodiments of a compound of Formula (Ia), (IIa), (IIa-1), (Ib), (IIb), or (IIb-1), Y is defined as above and $R^{36}$ is hydrogen or optionally substituted alkyl.

In some embodiments of a compound of Formula (Ia), (IIa), (IIa-1), (Ib), (IIb), or (IIb-1), Y is defined as above, $R^{30}$ and $R^{31}$ are independently hydrogen or optionally substituted alkyl; or two $R^{30}$ on adjacent carbon form an alkenyl; $R^{32}$ and $R^{33}$ are independently hydrogen or optionally substituted alkyl; or $R^{32}$ and $R^{33}$ are taken together with the nitrogen to which they are attached to form an optionally substituted heterocycloalkyl; $R^{34}$ is optionally substituted alkyl; $R^{35}$ is hydrogen or optionally substituted alkyl; $R^{36}$ is hydrogen or optionally substituted alkyl; v is 1 or 2; and w is 2 or 3.

In some embodiments of a compound of Formula (Ia), (IIa), (IIa-1), (Ib), (IIb), or (IIb-1), Y is defined as above and v is 1 or 2. In some embodiments of a compound of Formula (Ia), (IIa), (IIa-1), (Ib), (IIb), or (IIb-1), v is 1. In some embodiments of a compound of Formula (Ia), (IIa), (IIa-1), (Ib), (IIb), or (IIb-1), v is 2. In some embodiments of a compound of Formula (Ia), (IIa), (IIa-1), (Ib), (IIb), or (IIb-1), v is 3. In some embodiments of a compound of Formula (Ia), (IIa), (IIa-1), (Ib), (IIb), or (IIb-1), v is 4. In some embodiments of a compound of Formula (Ia), (IIa), (IIa-1), (Ib), (IIb), or (IIb-1), v is 5.

In some embodiments of a compound of Formula (Ia), (IIa), (IIa-1), (Ib), (IIb), or (IIb-1), Y is defined as above and w is 2 or 3. In some embodiments of a compound of Formula (Ia), (IIa), (IIa-1), (Ib), (IIb), or (IIb-1), w is 2. In some embodiments of a compound of Formula (Ia), (IIa), (IIa-1), (Ib), (IIb), or (IIb-1), w is 3. In some embodiments of a compound of Formula (Ia), (IIa), (IIa-1), (Ib), (IIb), or (IIb-1), w is 4. In some embodiments of a compound of Formula (Ia), (IIa), (IIa-1), (Ib), (IIb), or (IIb-1), w is 5.

In some embodiments of a compound of Formula (Ia), (IIa), (IIa-1), (Ib), (IIb), or (IIb-1), $R^a$, $R^b$, and $R^c$ are independently hydrogen, optionally substituted alkyl, fluoro, chloro, —OH, —$OR^{54}$, —C(=O)H, —C(=O)OH, —$(CR^{50}R^{51})_vN(R^{52})(CR^{50}R^{51})_vC(=O)OH$, —$(CR^{50}R^{51})_vOH$, —$(CR^{50}R^{51})_vC(=O)OH$, —$(CR^{50}R^{51})_vC(=O)OR^{54}$, or —$(CR^{50}R^{51})_v$heterocycloalkyl. In some embodiments of a compound of Formula (Ia), (IIa), (IIa-1), (Ib), (IIb), or (IIb-1), $R^a$, $R^b$, and $R^c$ are independently hydrogen, fluoro, chloro, optionally substituted alkyl, —$(CR^{50}R^{51})_vC(=O)OH$, or —$(CR^{50}R^{51})_v$heterocycloalkyl. In some embodiments of a compound of Formula (Ia), (IIa), (IIa-1), (Ib), (IIb), or (IIb-1), $R^a$, $R^b$, and $R^c$ are hydrogen.

In some embodiments of a compound of Formula (Ia), (IIa), (IIa-1), (Ib), (IIb), or (IIb-1), $R^a$, $R^b$, and $R^c$ are independently hydrogen, optionally substituted alkyl, fluoro, chloro, —OH, —$OR^{54}$, —C(=O)H, —$SR^{55}$, or —$S(CR^{50}R^{51})_vOH$.

In some embodiments of a compound of Formula (Ia), (IIa), (IIa-1), (Ib), (IIb), or (IIb-1), at least one of $R^a$, $R^b$, and $R^c$ is halogen, cyano, optionally substituted alkyl, optionally substituted cycloalkyl, optionally substituted heterocycloalkyl, optionally substituted aryl, optionally substituted heteroaryl, —OH, —$OR^{54}$, —$O(CR^{50}R^{51})NR^{52}R^{53}$, —$O(CR^{50}R^{51})OH$, —$O(CR^{50}R^{51})_wOR^{54}$, —$O(CR^{50}R^{51})_vC(=O)OH$, —$O(CR^{50}R^{51})_vC(=O)OR^{54}$, —$O(CR^{50}R^{51})_vC(=O)NR^{52}R^{53}$, —$NR^{52}R^{53}$, —$NR^{52}(CR^{50}R^{51})_wNR^{52}R^{53}$, —$NR^{52}(CR^{50}R^{51})_vC(=O)OH$, —$NR^2(CR^{50}R^{51})_vC(=O)OR^{54}$, —$NR^{52}(CR^{50}R^{51})_vC(=O)NR^{52}R^{53}$, —$NR^{52}S(=O)_{1,2}R^{54}$, —$S(=O)_{1,2}R^{54}$, —$SR^{55}$, —$S(CR^{50}R^{51})_vNR^{52}C(=NR^{56})NR^{52}R^{53}$, —$S(CR^{50}R^{51})_vNR^{52}CR^{50}(=NR^{56})$, —$S(CR^{50}R^{51})_vC(=NR^{56})NR^{52}R^{53}$, —$S(CR^{50}R^{51})_vOH$, —$S(CR^{50}R^{51})_wOR^{54}$, —$S(CR^{50}R^{51})_wNR^{52}R^{53}$, —$S(CR^{50}R^{51})_vC(=O)OH$, —$S(CR^{50}R^{51})_vC(=O)OR^{54}$, —$S(CR^{50}R^{51})_vC(=O)NR^{52}R^{53}$, —C(=O)H, —$C(=O)R^{54}$, —C(=O)OH, —$C(=O)OR^{54}$, —$C(=O)NR^{52}R^{53}$, —$(CR^{50}R^{51})_vN(R^{52})(CR^{50}R^{51})_vC(=O)OH$, —$(CR^{50}R^{51})_vOH$, —$(CR^{50}R^{51})_vOR^{54}$, —$(CR^{50}R^{51})_vC(=O)OH$, —$(CR^{50}R^{51})_vC(=O)OR^{54}$, —$(CR^{50}R^{51})_vC(=O)NR^{52}R^{53}$, —$(CR^{50}R^{51})_vOC(=O)R^{54}$, —$(CR^{50}R^{51})_vSR^{55}$, —$(CR^{50}R^{51})_vNR^{52}C(=NR^{56})$, —$(CR^{50}R^{51})_vNR^{52}R^{53}$, —$(CR^{50}R^{51})_vC(=NR^{56})NR^{52}R^{53}$, —$(CR^{50}R^{51})_vC(=O)NR^{52}R^{53}$, —$(CR^{50}R^{51})_v$heterocycloalkyl, or —$(CR^{50}R^{51})_v$heteroaryl.

In some embodiments of a compound of Formula (Ia), (IIa), (IIa-1), (Ib), (IIb), or (IIb-1), at least one of $R^a$, $R^b$, or $R^c$ is optionally substituted alkyl, fluoro, chloro, —OH, —$OR^{54}$, —C(=O)H, —C(=O)OH, —$(CR^{50}R^{51})_vN(R^{52})(CR^{50}R^{51})_vC(=O)OH$, —$(CR^{50}R^{51})_vOH$, —$(CR^{50}R^{51})_vC(=O)OH$, or —$(CR^{50}R^{51})_vC(=O)OR^{54}$, or —$(CR^{50}R^{51})_v$heterocycloalkyl. In some embodiments of a compound of Formula (Ia), (IIa), (IIa-1), (Ib), (IIb), or (IIb-1), at least one of R, $R^b$, or R is alkyl optionally substituted with heterocycloalkyl (optionally substituted with optionally substituted alkyl). In some embodiments of a compound of Formula (Ia), (IIa), (IIa-1), (Ib), (IIb), or (IIb-1), at least one of $R^a$, $R^b$, or R is —$(CR^{50}R^{51})_v$heterocycloalkyl optionally substituted with optionally substituted alkyl.

In some embodiments of a compound of Formula (Ia), (IIa), (IIa-1), (Ib), (IIb), or (IIb-1), R is halogen, cyano, optionally substituted alkyl, optionally substituted cycloalkyl, optionally substituted heterocycloalkyl, optionally substituted aryl, optionally substituted heteroaryl, —OH, —$OR^{54}$, —$O(CR^{50}R^{51})NR^{52}R^{53}$, —$O(CR^{50}R^{51})_vOH$, —$O(CR^{50}R^{51})_wOR^{54}$, —$O(CR^{50}R^{51})_vC(=O)OH$, —$O(CR^{50}R^{51})_vC(=O)OR^{54}$, —$O(CR^{50}R^{51})_vC(=O)NR^{52}R^{53}$, —$NR^{52}R^{53}$, —$NR^{52}(CR^{50}R^{51})_wNR^{52}R^{53}$, —$NR^{52}(CR^{50}R^{51})_vC(=O)OH$, —$NR^2(CR^{50}R^{51})_vC(=O)OR^{54}$, —$NR^{52}(CR^{50}R^{51})_vC(=O)NR^{52}R^{53}$, —$NR^{52}S(=O)_{1,2}R^{54}$, —$S(=O)_{1,2}R^{54}$, —$SR^{55}$, —$S(CR^{50}R^{51})_vNR^{52}C(=NR^{56})NR^{52}R^{53}$, —$S(CR^{50}R^{51})NR^{52}CR^{50}(=NR^{56})$, —$S(CR^{50}R^{51})_vC(=NR^{56})NR^{52}R^{53}$, —$S(CR^{50}R^{51})_vOH$, —$S(CR^{50}R^{51})_wOR^{54}$, —$S(CR^{50}R^{51})_wNR^{52}R^{53}$, —$S(CR^{50}R^{51})_vC(=O)OH$, —$S(CR^{50}R^{51})_vC(=O)OR^{54}$, —$S(CR^{50}R^{51})_vC(=O)NR^{52}R^{53}$, —C(=O)H, —$C(=O)R^{54}$, —C(=O)OH, —$C(=O)OR^{54}$, —$C(=O)NR^{52}R^{53}$, —$(CR^{50}R^{51})_vN(R^{52})(CR^{50}R^{51})_vC(=O)OH$, —$(CR^{50}R^{51})_vOH$, —$(CR^{50}R^{51})_wOR^{54}$, —$(CR^{50}R^{51})_vC(=O)OH$, —$(CR^{50}R^{51})_vC(=O)OR^{54}$, —$(CR^{50}R^{51})_vC(=O)NR^{52}R^{53}$, —$(CR^{50}R^{51})_vOC(=O)R^{54}$, —$(CR^{50}R^{51})_vSR^{55}$, —$(CR^{50}R^{51})_vNR^{52}C(=NR^{56})$, —$(CR^{50}R^{51})_vNR^{52}R^{53}$, —$(CR^{50}R^{51})_vC(=NR^{56})NR^{52}R^{53}$, —$(CR^{50}R^{51})_vC(=O)NR^{52}R^{53}$, —$(CR^{50}R^{51})_v$heterocycloalkyl, or —$(CR^{50}R^{51})_v$heteroaryl.

In some embodiments of a compound of Formula (Ia), (IIa), (IIa-1), (Ib), (IIb), or (IIb-1), $R^c$ is halogen, —OH, —$OR^{54}$, —$S(CR^{50}R^{51})_wOH$, —$S(CR^{50}R^{51})_vC(=O)OH$, or —$S(CR^{50}R^{51})_vC(=O)NR^{52}R^{53}$.

In some embodiments of a compound of Formula (Ia), (IIa), (IIa-1), (Ib), (IIb), or (IIb-1), $R^b$ is halogen, cyano, optionally substituted alkyl, optionally substituted cycloalkyl, optionally substituted heterocycloalkyl, optionally substituted aryl, optionally substituted heteroaryl, —OH, —$OR^{54}$, —$O(CR^{50}R^{51})NR^{52}R^{53}$, —$O(CR^{50}R^{51})_vOH$, —$O(CR^{50}R^{51})_vOR^4$, —$O(CR^{50}R^{51})_vC(=O)OH$, —$O(CR^{50}R^{51})_vC(=O)OR^{54}$, —$O(CR^{50}R^{51})_vC(=O)NR^{52}R^{53}$, —$NR^{52}R^{53}$, —$NR^{52}(CR^{50}R^{51})_vNR^{52}R^{53}$, —$NR^{52}(CR^{50}R^{51})_vC(=O)OH$, —$NR^2(CR^{50}R^{51})_vC(=O)OR^{54}$, —$NR^{52}(CR^{50}R^{51})_vC(=O)NR^{52}R^{53}$, —$NR^{52}S(=O)_{1,2}R^{54}$, —$S(=O)_{1,2}R^{54}$, —$SR^{55}$, —$S(CR^{50}R^{51})NR^{52}C(=NR^{56})NR^{52}R^{53}$, —$S(CR^{50}R^{51})NR^{52}CR^{50}(=NR^{56})$, —$S(CR^{50}R^{50})_vC(=NR^{56})NR^{52}R^{53}$, —$S(CR^{50}R^{51})_vOH$, —$S(CR^{50}R^{51})_wOR^{54}$, —$S(CR^{50}R^{51})_wNR^{52}R^{53}$, —$S(CR^{50}R^{51})_vC(=O)OH$, —$S(CR^{50}R^{51})_vC(=O)OR^{54}$, —$S(CR^{50}R^{51})_vC(=O)NR^{52}R^{53}$, —C(=O)H, —$C(=O)R^{54}$, —C(=O)OH, —$C(=O)OR^{54}$, —$C(=O)NR^{52}R^{53}$, —$(CR^{50}R^{51})_vN(R^{52})(CR^{50}R^{51})_vC(=O)OH$, —$(CR^{50}R^{51})_vOH$, —$(CR^{50}R^{50})_wOR^{54}$, —$(CR^{50}R^{51})_vC(=O)OH$, —$(CR^{50}R^{51})_vC(=O)OR^{54}$, —$(CR^{50}R^{51})_vC(=O)NR^{52}R^{53}$, —$(CR^{50}R^{51})_vOC(=O)R^{54}$, —$(CR^{50}R^{51})_vSR^5$, —$(CR^{50}R^{51})_vNR^{52}C(=NR^{56})$, —$(CR^{50}R^{51})_vNR^{52}R^{53}$, —$(CR^{50}R^{51})_vC(=NR^{56})NR^{52}R^{53}$, —$(CR^{50}R^{51})_vC(=O)NR^{52}R^{53}$, —$(CR^{50}R^{51})_v$heterocycloalkyl, or —$(CR^{50}R^{51})_v$heteroaryl.

In some embodiments of a compound of Formula (Ia), (IIa), (IIa-1), (Ib), (IIb), or (IIb-1), $R^b$ is halogen, —OH, —$OR^{54}$, —$S(CR^{50}R^{51})OH$, —$S(CR^{50}R^{51})_vC(=O)OH$, or —$S(CR^{50}R^{51})_vC(=O)NR^{52}R^{53}$.

In some embodiments of a compound of Formula (Ia), (IIa), (IIa-1), (Ib), (IIb), or (IIb-1), $R^a$, $R^b$, or $R^c$ are defined as above, $R^{50}$ and $R^{51}$ are independently hydrogen or optionally substituted alkyl; or two $R^{50}$ on adjacent carbon form an alkenyl; $R^{52}$ and $R^{53}$ are independently hydrogen or optionally substituted alkyl; or $R^{52}$ and $R^{53}$ are taken together with the nitrogen to which they are attached to form an optionally substituted heterocycloalkyl; $R^{54}$ is optionally substituted alkyl; $R^{55}$ is hydrogen or optionally substituted alkyl; $R^{56}$ is hydrogen or optionally substituted alkyl; each v is independently 1 or 2; and each w is independently 2 or 3.

In some embodiments of a compound of Formula (Ia), (IIa), (IIa-1), (Ib), (IIb), or (IIb-1), $R^a$ is hydrogen. In some embodiments of a compound of Formula (Ia), (IIa), (IIa-1), (Ib), (IIb), or (IIb-1), $R^b$ is hydrogen. In some embodiments of a compound of Formula (Ia), (IIa), (IIa-1), (Ib), (IIb), or (IIb-1), $R^c$ is hydrogen. In some embodiments of a compound of Formula (Ia), (IIa), (IIa-1), (Ib), (IIb), or (IIb-1), $R^a$ is not hydrogen. In some embodiments of a compound of Formula (Ia), (IIa), (IIa-1), (Ib), (IIb), or (IIb-1), $R^b$ is not hydrogen. In some embodiments of a compound of Formula (Ia), (IIa), (IIa-1), (Ib), (IIb), or (IIb-1), $R^c$ is not hydrogen. In some embodiments of a compound of Formula (Ia), (IIa), (IIa-1), (Ib), (IIb), or (IIb-1), $R^a$ and $R^b$ are hydrogen. In some embodiments of a compound of Formula (Ia), (IIa), (IIa-1), (Ib), (IIb), or (IIb-1), $R^a$ and $R^b$ are hydrogen. In some embodiments of a compound of Formula (Ia), (IIa), (IIa-1), (Ib), (IIb), or (IIb-1), $R^b$ and $R^c$ are hydrogen.

In some embodiments of a compound of Formula (Ia), (IIa), (IIa-1), (Ib), (IIb), or (IIb-1), $X^1$ is —OH and $X^2$ is —OH when present. In some embodiments of a compound of Formula (Ia), (IIa), (IIa-1), (Ib), (IIb), or (IIb-1), $X^1$ and $X^2$ are taken together with the boron atom to which they are attached to form a cyclic boronate ester.

In some embodiments of a compound of Formula (Ia), (IIa), (IIa-1), (Ib), (IIb), or (IIb-1), $R^d$ is hydrogen or alkyl. In some embodiments of a compound of Formula (Ia), (IIa), (IIa-1), (Ib), (IIb), or (IIb-1), $R^d$ is hydrogen. In some embodiments of a compound of Formula (Ia), (IIa), (IIa-1), (Ib), (IIb), or (IIb-1), $R^d$ is alkyl.

In some embodiments of a compound of Formula (Ia), (IIa), (IIa-1), (Ib), (IIb), or (IIb-1), each $R^e$ is independently hydrogen or alkyl. In some embodiments of a compound of Formula (Ia), (IIa), (IIa-1), (Ib), (IIb), or (IIb-1), each $R^e$ is hydrogen. In some embodiments of a compound of Formula (Ia), (IIa), (IIa-1), (Ib), (IIb), or (IIb-1), each $R^e$ is independently alkyl. In some embodiments of a compound of Formula (Ia), (IIa), (IIa-1), (Ib), (IIb), or (IIb-1), one $R^e$ is hydrogen and the other $R^e$ is alkyl In some embodiments of a compound of Formula (Ia), (IIa), (IIa-1), (Ib), (IIb), or (IIb-1), n is 1-3. In some embodiments of a compound of Formula (Ia), (IIa), (IIa-1), (Ib), (IIb), or (IIb-1), n is 0-2. In some embodiments of a compound of Formula (Ia), (IIa), (IIa-1), (Ib), (IIb), or (IIb-1), n is 1 or 2. In some embodiments of a compound of Formula (Ia), (IIa), (IIa-1), (Ib), (IIb), or (IIb-1), n is 0 or 1. In some embodiments of a compound of Formula (Ia), (IIa), (IIa-1), (Ib), (IIb), or (IIb-1), n is 2 or 3. In some embodiments of a compound of Formula (Ia), (IIa), (IIa-1), (Ib), (IIb), or (IIb-1), n is 0. In some embodiments of a compound of Formula (Ia), (IIa), (IIa-1), (Ib), (IIb), or (IIb-1), n is 1. In some embodiments of a compound of Formula (Ia), (IIa), (IIa-1), (Ib), (IIb), or (IIb-1), n is 2. In some embodiments of a compound of Formula (Ia), (IIa), (IIa-1), (Ib), (IIb), or (IIb-1), n is 3.

In some embodiments of a compound of Formula (Ia), (IIa), (IIa-1), (Ib), (IIb), or (IIb-1), m is 0-4. In some embodiments of a compound of Formula (Ia), (IIa), (IIa-1), (Ib), (IIb), or (IIb-1), m is 0-3. In some embodiments of a compound of Formula (Ia), (IIa), (IIa-1), (Ib), (IIb), or (IIb-1), m is 1-3. In some embodiments of a compound of Formula (Ia), (IIa), (IIa-1), (Ib), (IIb), or (IIb-1), m is 0-2. In some embodiments of a compound of Formula (Ia), (IIa), (IIa-1), (Ib), (IIb), or (IIb-1), m is 1 or 2. In some embodiments of a compound of Formula (Ia), (IIa), (IIa-1), (Ib), (IIb), or (IIb-1), m is 0 or 1. In some embodiments of a compound of Formula (Ia), (IIa), (IIa-1), (Ib), (IIb), or (IIb-1), m is 2 or 3. In some embodiments of a compound of Formula (Ia), (IIa), (IIa-1), (Ib), (IIb), or (IIb-1), m is 0. In some embodiments of a compound of Formula (Ia), (IIa), (IIa-1), (Ib), (IIb), or (IIb-1), m is 1. In some embodiments of a compound of Formula (Ia), (IIa), (IIa-1), (Ib), (IIb), or (IIb-1), m is 2. In some embodiments of a compound of Formula (Ia), (IIa), (IIa-1), (Ib), (IIb), or (IIb-1), m is 3. In some embodiments of a compound of Formula (Ia), (IIa), (IIa-1), (Ib), (IIb), or (IIb-1), n is 0 or 1 and m is 0 or 1. In some embodiments of a compound of Formula (Ia), (IIa), (IIa-1), (Ib), (IIb), or (IIb-1), n is 0 and m is 0. In some embodiments of a compound of Formula (Ia), (IIa), (IIa-1), (Ib), (IIb), or (IIb-1), n is 0 and m is 1. In some embodiments of a compound of Formula (Ia), (IIa), (IIa-1), (Ib), (IIb), or (IIb-1), n is 1 and m is 0. In some embodiments of a compound of Formula (Ia), (IIa), (IIa-1), (Ib), (IIb), or (IIb-1), n is 2 and m is 0. In some embodiments of a compound of Formula (Ia), (IIa), (IIa-1), (Ib), (IIb), or (IIb-1), n is 0 and m is 2.

In some embodiments of a compound of Formula (Ia), (IIa), (IIa-1), (Ib), (IIb), or (IIb-1), each $R^1$ and $R^2$ is independently hydrogen, —OH, fluoro, chloro, bromo, or optionally substituted alkyl.

In some embodiments of a compound of Formula (Ia), (IIa), (IIa-1), (Ib), (IIb), or (IIb-1), each $R^1$ and $R^2$ is independently hydrogen, fluoro, chloro, bromo, or optionally substituted alkyl. In some embodiments of a compound of Formula (Ia), (IIa), (IIa-1), (Ib), (IIb), or (IIb-1), each $R^1$ and $R^2$ is hydrogen.

In some embodiments of a compound of Formula (Ia), (IIa), (IIa-1), (Ib), (IIb), or (IIb-1), Z is hydrogen. In some embodiments of a compound of Formula (Ia), (IIa), (IIa-1), (Ib), (IIb), or (IIb-1), Z is not hydrogen. In some embodiments of a compound of Formula (Ia), (IIa), (IIa-1), (Ib), (IIb), or (IIb-1), Z is $R^{61}$; and $R^{61}$ is optionally substituted alkyl. In some embodiments of a compound of Formula (Ia), (IIa), (IIa-1), (Ib), (IIb), or (IIb-1), Z is —$R^{60}$OC(=O)$R^{61}$ or —$R^{60}$OC(=O)O$R^{61}$; $R^{60}$ is —$CH_2$— or —CH($CH_3$)—; and $R^{61}$ is optionally substituted alkyl, optionally substituted cycloalkyl, or optionally substituted heterocycloalkyl. In some embodiments of a compound of Formula (Ia), (IIa), (IIa-1), (Ib), (IIb), or (IIb-1), Z is —$R^{60}$OC(=O)$R^{61}$ or —$R^{60}$OC(=O)O$R^{61}$; $R^{60}$ is —$CH_2$— or —CH($CH_3$)—; and $R^{61}$ is optionally substituted alkyl, optionally substituted cycloalkyl, optionally substituted heterocycloalkyl, optionally substituted aryl, or optionally substituted heteroaryl.

In some embodiments of a compound of Formula (Ia), (IIa), (IIa-1), (Ib), (IIb), or (IIb-1), the compound is of formula:
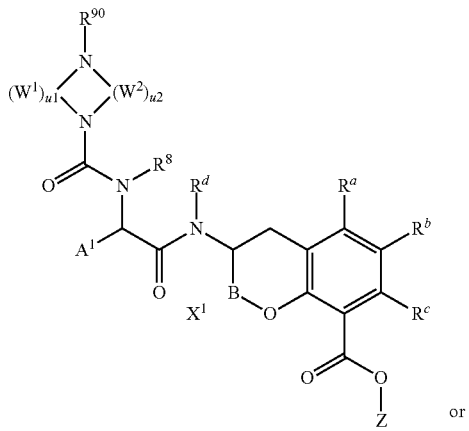
or
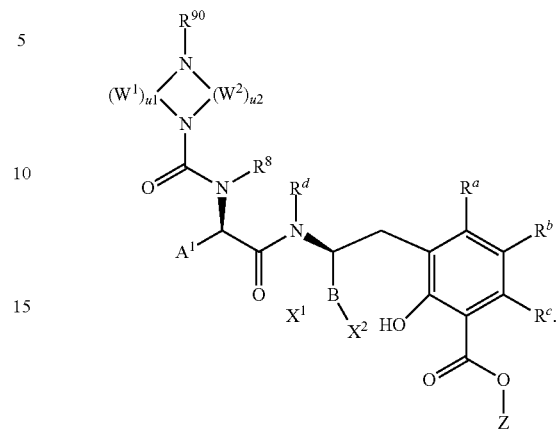
In some embodiments of a compound of Formula (Ia), (IIa), (IIa-1), (Ib), (IIb), or (IIb-1), the compound is of formula:
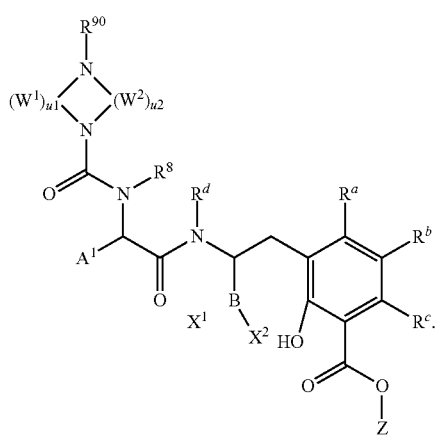
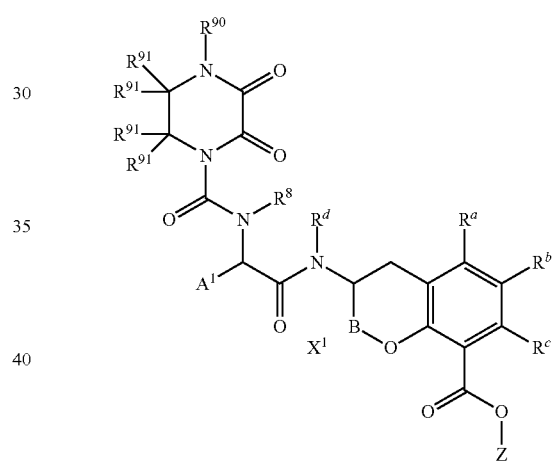
In some embodiments of a compound of Formula (Ia), (IIa), (IIa-1), (Ib), (IIb), or (IIb-1), the compound is of formula:
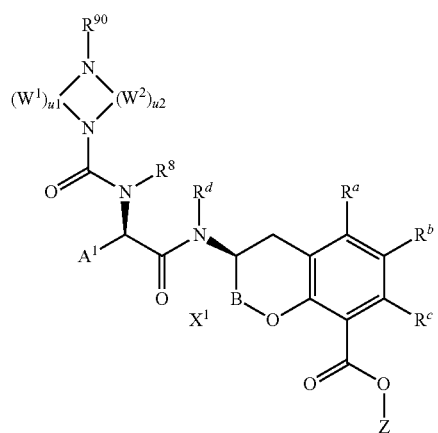
or
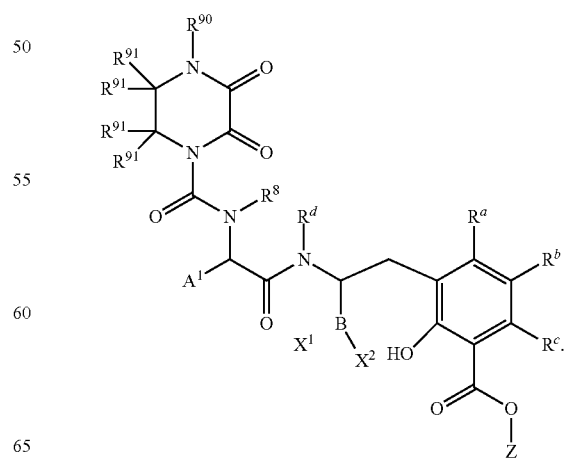

In some embodiments of a compound of Formula (Ia), (IIa), (IIa-1), (Ib), (IIb), or (IIb-1), the compound is of formula:

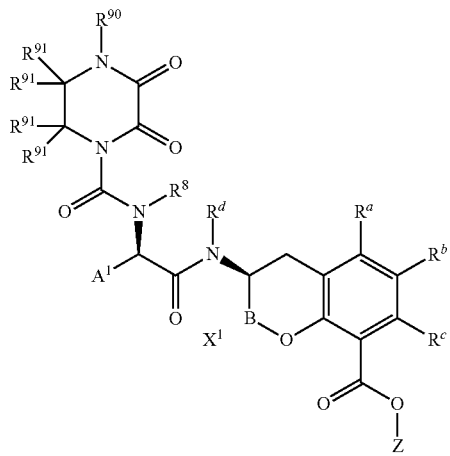

or

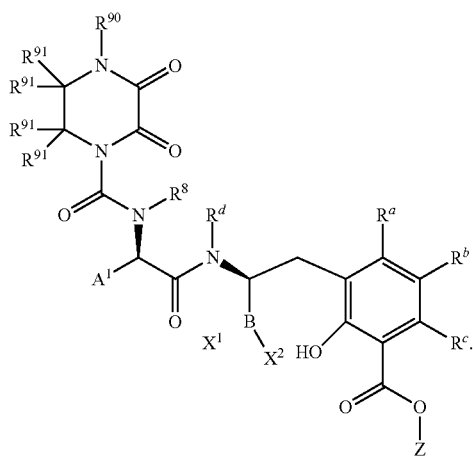

In some embodiments of a compound of Formula (Ia), (IIa), (IIa-1), (Ib), (IIb), or (IIb-1), the compound is of formula:

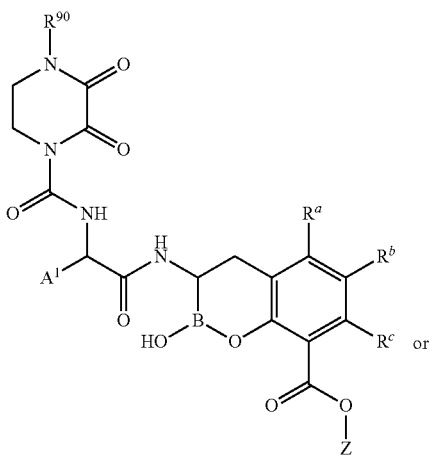

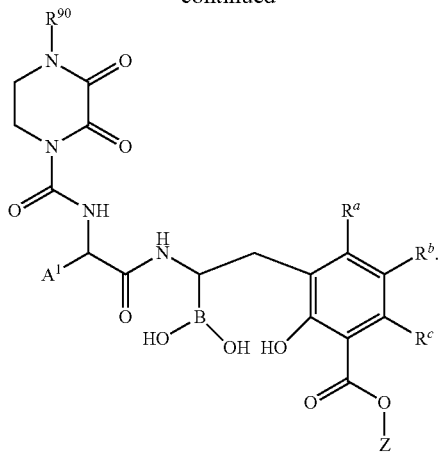

In some embodiments of a compound of Formula (Ia), (IIa), (IIa-1), (Ib), (IIb), or (IIb-1), the compound is of formula:

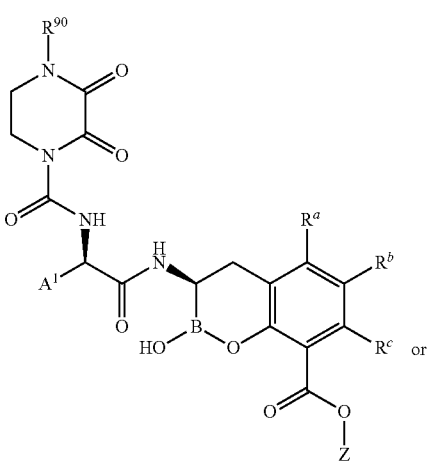

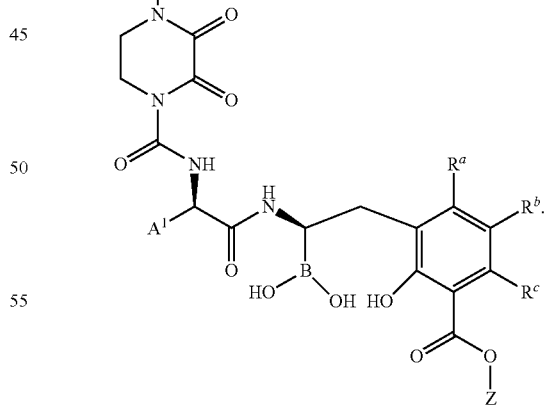

Preparation of Compounds

Described herein are compounds of Formula Formula (Ia), (IIa), (IIa-1), (Ib), (IIb), or (IIb-1) that inhibit the activity of penicillin-binding proteins, and processes for their preparation. Also described herein are pharmaceutically acceptable salt, solvate, stereoisomer, tautomer, N-oxide, dimer, or trimer of compounds of Formula Formula (Ia), (IIa), (IIa-1), (Ib), (IIb), or (IIb-1).

Compounds of Formula Formula (Ia), (IIa), (IIa-1), (Ib), (IIb), or (IIb-1) may be synthesized using standard synthetic reactions known to those of skill in the art or using methods known in the art. The reactions can be employed in a linear sequence to provide the compounds or they may be used to synthesize fragments which are subsequently joined by the methods known in the art.

The starting material used for the synthesis of the compounds described herein may be synthesized or can be obtained from commercial sources. The compounds described herein, and other related compounds having different substituents can be synthesized using techniques and materials known to those of skill in the art, such as described, for example, in March, ADVANCED ORGANIC CHEMISTRY $4^{th}$ Ed., (Wiley 1992); Carey and Sundberg, ADVANCED ORGANIC CHEMISTRY $4^{th}$ Ed., Vols. A and B (Plenum 2000, 2001); Green and Wuts, PROTECTIVE GROUPS IN ORGANIC SYNTHESIS $3^{rd}$ Ed., (Wiley 1999); Fieser and Fieser's Reagents for Organic Synthesis, Volumes 1-17 (John Wiley and Sons, 1991); Rodd's Chemistry of Carbon Compounds, Volumes 1-5 and Supplementals (Elsevier Science Publishers, 1989); Organic Reactions, Volumes 1-40 (John Wiley and Sons, 1991); and Larock's Comprehensive Organic Transformations (VCH Publishers Inc., 1989) (all of which are incorporated by reference in their entirety). General methods for the preparation of compound as disclosed herein may be derived from known reactions in the field, and the reactions may be modified by the use of appropriate reagents and conditions, as would be recognized by the skilled person, for the introduction of the various moieties found in the formulae as provided herein.

The products of the reactions may be isolated and purified, if desired, using conventional techniques, including, but not limited to, filtration, distillation, crystallization, chromatography, and the like. Such materials may be characterized using conventional means, including physical constants and spectral data.

Further Forms of Compounds Disclosed Herein
Isomers Stereoisomers

In some embodiments, due to the oxophilic nature of the boron atom, the compounds described herein may convert to, or exist in equilibrium with, alternate forms, particularly in milieu that contain water (aqueous solution, plasma, etc.). Accordingly, the compounds described herein may exist in an equilibrium between the "closed" cyclic form shown in Formula (Ia), (IIa), or (IIa-1) and the "open" acyclic form shown in Formula (Ib), (IIb), or (IIb-1). In addition the compounds described herein may associate into intramolecular dimers, trimers, and related combinations.

Furthermore, in some embodiments, the compounds described herein exist as geometric isomers. In some embodiments, the compounds described herein possess one or more double bonds. The compounds presented herein include all cis, trans, syn, anti, entgegen (E), and zusammen (Z) isomers as well as the corresponding mixtures thereof. In some situations, the compounds described herein possess one or more chiral centers and each center exists in the R configuration, or S configuration. The compounds described herein include all diastereomeric, enantiomeric, and epimeric forms as well as the corresponding mixtures thereof. In additional embodiments of the compounds and methods provided herein, mixtures of enantiomers and/or diastereoisomers, resulting from a single preparative step, combination, or interconversion are useful for the applications described herein. In some embodiments, the compounds described herein are prepared as their individual stereoisomers by reacting a racemic mixture of the compound with an optically active resolving agent to form a pair of diastereoisomeric compounds, separating the diastereomers and recovering the optically pure enantiomers. In some embodiments, dissociable complexes are preferred (e.g., crystalline diastereomeric salts). In some embodiments, the diastereomers have distinct physical properties (e.g., melting points, boiling points, solubilities, reactivity, etc.) and are separated by taking advantage of these dissimilarities. In some embodiments, the diastereomers are separated by chiral chromatography, or preferably, by separation/resolution techniques based upon differences in solubility. In some embodiments, the optically pure enantiomer is then recovered, along with the resolving agent, by any practical means that would not result in racemization. Compounds described herein may be prepared as a single isomer or a mixture of isomers.

Tautomers

In some situations, compounds described herein exist as tautomers. The compounds described herein include all possible tautomers within the formulas described herein. A "tautomer" refers to a proton shift from one atom of a molecule to another atom of the same molecule. The compounds presented herein may exist as tautomers. Tautomers are compounds that are interconvertible by migration of a hydrogen atom, accompanied by a switch of a single bond and adjacent double bond. In bonding arrangements where tautomerization is possible, a chemical equilibrium of the tautomers will exist. All tautomeric forms of the compounds disclosed herein are contemplated. The exact ratio of the tautomers depends on several factors, including temperature, solvent, and pH.

Labeled Compounds

In some embodiments, the compounds described herein exist in their isotopically-labeled forms. In some embodiments, the methods disclosed herein include methods of treating diseases by administering such isotopically-labeled compounds. In some embodiments, the methods disclosed herein include methods of treating diseases by administering such isotopically-labeled compounds as pharmaceutical compositions. Thus, in some embodiments, the compounds disclosed herein include isotopically-labeled compounds, which are identical to those recited herein, but for the fact that one or more atoms are replaced by an atom having an atomic mass or mass number different from the atomic mass or mass number usually found in nature. Examples of isotopes that can be incorporated into compounds described herein include isotopes of hydrogen, carbon, nitrogen, oxygen, phosphorous, sulfur, fluorine, and chloride, such as $^2H$, $^3H$, $^{13}C$, $^{14}C$, $^{15}N$, $^{18}O$, $^{17}O$, $^{31}P$, $^{32}P$, $^{35}S$, $^{18}F$, and $^{36}Cl$, respectively. Compounds described hereinwhich contain the aforementioned isotopes and/or other isotopes of other atoms are within the scope of this invention. Certain isotopically-labeled compounds, for example those into which radioactive isotopes such as $^3H$ and $^{14}C$ are incorporated, are useful in drug and/or substrate tissue distribution assays. Tritiated, i. e., $^3H$ and carbon-14, i. e., $^{14}C$, isotopes are particularly preferred for their ease of preparation and detectability. Further, substitution with heavy isotopes such as deuterium, i.e., $^3H$, produces certain therapeutic advantages resulting from greater metabolic stability, for example increased in vivo half-life or reduced dosage requirements. In some embodiments, the isotopically labeled compounds, pharmaceutically acceptable salt, ester, prodrug, solvate, hydrate, or derivative thereof is prepared by any suitable method.

In some embodiments, the compounds described herein are labeled by other means, including, but not limited to, the use of chromophores or fluorescent moieties, bioluminescent labels, or chemiluminescent labels.

Pharmaceutically Acceptable Salts

In some embodiments, the compounds described herein exist as their pharmaceutically acceptable salts. In some embodiments, the methods disclosed herein include methods of treating diseases by administering such pharmaceutically acceptable salts. In some embodiments, the methods disclosed herein include methods of treating diseases by administering such pharmaceutically acceptable salts as pharmaceutical compositions.

In some embodiments, the compounds described herein possess acidic or basic groups and therefore react with any of a number of inorganic or organic bases, and inorganic and organic acids, to form a pharmaceutically acceptable salt. In some embodiments, these salts are prepared in situ during the final isolation and purification of the compounds described herein, or by separately reacting a purified compound in its free form with a suitable acid or base, and isolating the salt thus formed.

Examples of pharmaceutically acceptable salts include those salts prepared by reaction of the compounds described herein with a mineral, organic acid or inorganic base, such salts including, acetate, acrylate, adipate, alginate, aspartate, benzoate, benzenesulfonate, bisulfate, bisulfite, bromide, butyrate, butyn-1,4-dioate, camphorate, camphorsulfonate, caproate, caprylate, chlorobenzoate, chloride, citrate, cyclopentanepropionate, decanoate, digluconate, dihydrogenphosphate, dinitrobenzoate, dodecylsulfate, ethanesulfonate, formate, fumarate, glucoheptanoate, glycerophosphate, glycolate, hemisulfate, heptanoate, hexanoate, hexyne-1,6-dioate, hydroxybenzoate, γ-hydroxybutyrate, hydrochloride, hydrobromide, hydroiodide, 2-hydroxyethanesulfonate, iodide, isobutyrate, lactate, maleate, malonate, methanesulfonate, mandelate metaphosphate, methanesulfonate, methoxybenzoate, methylbenzoate, monohydrogenphosphate, 1-napthalenesulfonate, 2-napthalenesulfonate, nicotinate, nitrate, palmoate, pectinate, persulfate, 3-phenylpropionate, phosphate, picrate, pivalate, propionate, pyrosulfate, pyrophosphate, propiolate, phthalate, phenylacetate, phenylbutyrate, propanesulfonate, salicylate, succinate, sulfate, sulfite, succinate, suberate, sebacate, sulfonate, tartrate, thiocyanate, tosylateundeconate, and xylenesulfonate.

Further, the compounds described herein can be prepared as pharmaceutically acceptable salts formed by reacting the free base form of the compound with a pharmaceutically acceptable inorganic or organic acid, including, but not limited to, inorganic acids such as hydrochloric acid, hydrobromic acid, sulfuric acid, nitric acid, phosphoric acid metaphosphoric acid, and the like; and organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, p-toluenesulfonic acid, tartaric acid, trifluoroacetic acid, citric acid, benzoic acid, 3-(4-hydroxybenzoyl)benzoic acid, cinnamic acid, mandelic acid, arylsulfonic acid, methanesulfonic acid, ethanesulfonic acid, 1,2-ethanedisulfonic acid, 2-hydroxyethanesulfonic acid, benzenesulfonic acid, 2-naphthalenesulfonic acid, 4-methylbicyclo-[2.2.2]oct-2-ene-1-carboxylic acid, glucoheptonic acid, 4,4'-methylenebis-(3-hydroxy-2-ene-1-carboxylic acid), 3-phenylpropionic acid, trimethylacetic acid, tertiary butylacetic acid, lauryl sulfuric acid, gluconic acid, glutamic acid, hydroxynaphthoic acid, salicylic acid, stearic acid, and muconic acid. In some embodiments, other acids, such as oxalic, while not in themselves pharmaceutically acceptable, are employed in the preparation of salts useful as intermediates in obtaining the compounds described herein and their pharmaceutically acceptable acid addition salts.

In some embodiments, those compounds described herein which comprise a free acid group react with a suitable base, such as the hydroxide, carbonate, bicarbonate, sulfate, of a pharmaceutically acceptable metal cation, with ammonia, or with a pharmaceutically acceptable organic primary, secondary, tertiary, or quaternary amine. Representative salts include the alkali or alkaline earth salts, like lithium, sodium, potassium, calcium, and magnesium, and aluminum salts and the like. Illustrative examples of bases include sodium hydroxide, potassium hydroxide, choline hydroxide, sodium carbonate, $N^+(C_{1-4} \text{ alkyl})_4$, and the like.

Representative organic amines useful for the formation of base addition salts include ethylamine, diethylamine, ethylenediamine, ethanolamine, diethanolamine, piperazine, and the like. It should be understood that the compounds described herein also include the quaternization of any basic nitrogen-containing groups they contain. In some embodiments, water or oil-soluble or dispersible products are obtained by such quaternization.

Solvates

In some embodiments, the compounds described herein exist as solvates. The invention provides for methods of treating diseases by administering such solvates. The invention further provides for methods of treating diseases by administering such solvates as pharmaceutical compositions.

Solvates contain either stoichiometric or non-stoichiometric amounts of a solvent, and, in some embodiments, are formed during the process of crystallization with pharmaceutically acceptable solvents such as water, ethanol, and the like. Hydrates are formed when the solvent is water, or alcoholates are formed when the solvent is alcohol. Solvates of the compounds described herein can be conveniently prepared or formed during the processes described herein. By way of example only, hydrates of the compounds described herein can be conveniently prepared by recrystallization from an aqueous/organic solvent mixture, using organic solvents including, but not limited to, dioxane, tetrahydrofuran, or methanol. In addition, the compounds provided herein can exist in unsolvated as well as solvated forms. In general, the solvated forms are considered equivalent to the unsolvated forms for the purposes of the compounds and methods provided herein.

Pharmaceutical Compositions/Formulations

In another aspect, provided herein are pharmaceutical compositions comprising a compound described herein, or a pharmaceutically acceptable salt, solvate, stereoisomer, tautomer, N-oxide, dimer, or trimer thereof, and a pharmaceutically acceptable excipient. In some embodiments, the pharmaceutical composition further comprises a beta-lactam antibiotic. In certain embodiments, the beta-lactam antibiotic is a penicillin, cephalosporin, carbapenem, monobactam, bridged monobactam, or a combination thereof.

In some embodiments, the compounds described herein are formulated into pharmaceutical compositions. Pharmaceutical compositions are formulated in a conventional manner using one or more pharmaceutically acceptable inactive ingredients that facilitate processing of the active compounds into preparations that can be used pharmaceutically. Proper formulation is dependent upon the route of administration chosen. A summary of pharmaceutical compositions described herein can be found, for example, in Remington: The Science and Practice of Pharmacy, Nineteenth Ed (Easton, Pa.: Mack Publishing Company, 1995); Hoover, John E., Remington's Pharmaceutical Sciences, Mack Publishing Co., Easton, Pennsylvania 1975; Liberman, H. A. and Lachman, L., Eds., Pharmaceutical Dosage Forms, Marcel Decker, New York, N.Y., 1980; and Pharmaceutical Dosage Forms and Drug Delivery Systems, Seventh Ed. (Lippincott Williams & Wilkins 1999), herein incorporated by reference for such disclosure.

A pharmaceutical composition, as used herein, refers to a mixture of a compound described herein with other chemical components (i.e. pharmaceutically acceptable inactive ingredients), such as carriers, excipients, binders, filling agents, suspending agents, flavoring agents, sweetening agents, disintegrating agents, dispersing agents, surfactants, lubricants, colorants, diluents, solubilizers, moistening agents, plasticizers, stabilizers, penetration enhancers, wetting agents, anti-foaming agents, antioxidants, preservatives, or one or more combination thereof. The pharmaceutical composition facilitates administration of the compound to an organism. In practicing the methods of treatment or use provided herein, therapeutically effective amounts of compounds described herein are administered in a pharmaceutical composition to a mammal having a disease, disorder, or condition to be treated. In some embodiments, the mammal is a human. A therapeutically effective amount can vary widely depending on the severity of the disease, the age and relative health of the subject, the potency of the compound used and other factors. The compounds can be used singly or in combination with one or more therapeutic agents as components of mixtures.

The pharmaceutical formulations described herein are administered to a subject by appropriate administration routes, including, but not limited to, oral, parenteral (e.g., intravenous, subcutaneous, intramuscular), intranasal, buccal, topical, rectal, or transdermal administration routes. The pharmaceutical formulations described herein include, but are not limited to, aqueous liquid dispersions, liquids, gels, syrups, elixirs, slurries, suspensions, self-emulsifying dispersions, solid solutions, liposomal dispersions, aerosols, solid oral dosage forms, powders, immediate release formulations, controlled release formulations, fast melt formulations, tablets, capsules, pills, powders, dragees, effervescent formulations, lyophilized formulations, delayed release formulations, extended release formulations, pulsatile release formulations, multiparticulate formulations, and mixed immediate and controlled release formulations.

Combination Treatment

The compounds described herein may be used in combination with one or more antibiotics in the treatment of bacterial infections. Such antibiotics may be administered, by a route and in an amount commonly used therefore, contemporaneously or sequentially with a compound described herein. When a compound described herein is used contemporaneously with one or more antibiotic, a pharmaceutical composition in unit dosage form containing such other drugs and the compound of the present invention is preferred. However, the combination therapy may also include therapies in which the compound described herein and one or more antibiotic are administered on different overlapping schedules. It is also contemplated that when used in combination with one or more antibiotics, the antibiotics may be used in lower doses than when each is used singly.

Accordingly, the pharmaceutical compositions of the present invention also include those that contain one or more antibiotics, in addition to a compound described herein. In some embodiments, a pharmaceutical composition comprising a compound described herein further comprises a beta-lactam antibiotic. In certain embodiments, the beta-lactam antibiotic is a penicillin, cephalosporin, carbapenem, monobactam, bridged monobactam, or a combination thereof.

In some embodiments, the compounds described herein are used in combination with one or more antibiotics in the treatment of bacterial infections. In certain embodiments, the bacterial infection is a upper or lower respiratory tract infection, a urinary tract infection, a intra-abdominal infection, or a skin infection. In some embodiments, the bacterial infection is an upper or lower respiratory tract infection, a urinary tract infection, an intra-abdominal infection, or a skin infection. In some embodiments, the bacterial infection is uncomplicated or complicated urinary tract infections, uncomplicated or complicated gonorrhea, upper or lower respiratory tract infections, skin or skin structure infections, intra-abdominal infections, central nervous system infections, blood stream infections, or systemic infections.

In some embodiments, the one or more antibiotics are selected from β-lactam antibiotics. β-Lactam antibiotics include, but are not limited to, penicillins, penems, carbapenems, cephalosporins, cephamycins, monobactams, or combinations thereof. Penicillins include, but are not limited to, amoxicillin, ampicillin, azidocillin, azlocillin, bacampicillin, benzathinebenzylpenicillin, benzathinephenoxymethylpenicillin, benzylpenicillin (G), carbenicillin, carindacillin, clometocillin, cloxacillin, dicloxacillin, epicillin, flucloxacillin, hetacillin, mecillinam, metampicillin, meticillin, mezlocillin, nafcillin, oxacillin, penamecillin, pheneticillin, phenoxymethylpenicillin (V), piperacillin, pivampicillin, pivmecillinam, procaine benzylpenicillin, propicillin, sulbenicillin, talampicillin, temocillin, and ticarcillin. Penems include, but are not limited to, faropenem. Carbapenems include, but are not limited to, biapenem, ertapenem, doripenem, imipenem, meropenem, and panipenem. Cephalosporins/Cephamycins include, but are not limited to, cefacetrile, cefaclor, cefadroxil, cefalexin, cefaloglycin, cefalonium, cefaloridine, cefalotin, cefamandole, cefapirin, cefatrizine, cefazaflur, cefazedone, cefazolin, cefbuperazone, cefcapene, cefdaloxime, cefdinir, cefditoren, cefepime, cefetamet, cefixime, cefmenoxime, cefmetazole, cefminox, cefodizime, cefonicid, cefoperazone, ceforanide, cefotaxime, cefotetan, cefotiam, cefovecin, cefoxitin, cefozopran, cefpimizole, cefpiramide, cefpirome, cefpodoxime, cefprozil, cefquinome, cefquinome, cefradine, cefroxadine, cefsulodin, ceftarolinefosamil, ceftazidime, cefteram, ceftezole, ceftibuten, ceftiofur, ceftiolene, ceftizoxime, ceftobiprole, ceftriaxone, cefuroxime, cefuzonam, flomoxef, latamoxef, and loracarbef Monobactams include, but are not limited to, aztreonam, carumonam, nocardicinA, and tigemonam.

Methods

The present disclosure also provides methods for inhibiting bacterial growth, such methods comprising contacting a bacterial cell culture, or a bacterially infected cell culture, tissue, or organism, with a penicillin-binding protein inhibitor described herein. Preferably, the bacteria to be inhibited by administration of a penicillin-binding protein inhibitor described herein are bacteria that are resistant to beta-lactam antibiotics. The term "resistant" is well-understood by those of ordinary skill in the art (see, e g Payne et al., *Antimicrobial Agents and Chemotherapy* 38 767-772 (1994), Hanaki et al., *Antimicrobial Agents and Chemotherapy* 30 1120-1126 (1995)). In some embodiments, the penicillin-binding protein inhibitor described herein is used to treat a bacterial infection that is resistant to beta-lactam antibiotic. In some embodiments, the penicillin-binding protein inhibitor described herein is used to treat a bacterial infection that has developed beta-lactamase enzymes.

These methods are useful for inhibiting bacterial growth in a variety of contexts. In certain embodiments, a compound described herein is administered to an experimental cell culture in vitro to prevent the growth of beta-lactam resistant bacteria. In some embodiments, a compound described herein is administered to a mammal, including a human, to prevent the growth of beta-lactam resistant bacteria in vivo. The method according to this embodiment comprises administering a therapeutically effective amount of a penicillin-binding protein inhibitor described herein for a therapeutically effective period of time to a mammal, including a human. Preferably, the penicillin-binding protein inhibitor described herein is administered in the form of a pharmaceutical composition as described above.

In another aspect provided herein are methods of treating a bacterial infection, which method comprises administering to a subject a pharmaceutical composition comprising a compound described herein, or a pharmaceutically acceptable salt, solvate, stereoisomer, tautomer, N-oxide, dimer, or trimer thereof, and a pharmaceutically acceptable excipient. In some embodiments, the methods of treating a bacterial infection in a subject comprises administering to the subject a pharmaceutical composition as described herein. In some embodiments, the bacterial infection is an upper or lower respiratory tract infection, a urinary tract infection, an intra-abdominal infection, or a skin infection. In some embodiments, the bacterial infection is an upper or lower respiratory tract infection, a urinary tract infection, an intra-abdominal infection, or a skin infection. In some embodiments, the bacterial infection is uncomplicated or complicated urinary tract infections, uncomplicated or complicated gonorrhea, upper or lower respiratory tract infections, skin or skin structure infections, intra-abdominal infections, central nervous system infections, blood stream infections, or systemic infections.

In some embodiments, the infection that is treated or prevented is cause by a bacteria that includes *Pseudomonas aeruginosa, Pseudomonas luorescens, Pseudomonas acidovorans, Pseudomonas alcaligenes, Pseudomonas putida, Stenotrophomonas maltophilia, Burkholderia cepacia, Aeromonas hydrophilia, Escherichia coli, Citrobacter freundii, Salmonella typhimurium, Salmonella typhi, Salmonella paratyphi, Salmonella enteritidis, Shigella dysenteriae, Shigella fexneri, Shigella sonnei, Enterobacter cloacae, Enterobacter aerogenes, Klebsiella pneumoniae, Klebsiella oxytoca, Serratia marcescens, Francisella tularensis, Morganella morganii, Proteus mirabilis, Proteus vulgaris, Providencia alcalifaciens, Providencia rettgeri, Providencia stuartii, Acinetobacter baumannii, Acinetobacter calcoaceticus, Acinetobacter haemolyticus, Yersinia enterocolitica, Yersinia pestis, Yersinia pseudotuberculosis, Yersinia intermedia, Bordetella pertussis, Bordetella parapertussis, Bordetella bronchiseptica, Haemophilus influenzae, Haemophilus parainiuenzae, Haemophilus haemolyticus, Haemophilus parahaemolyticus, Haemophilus ducreyi, Pasteurella multocida, Pasteurella haemolytica, Branhamella catarrhalis, Helicobacter pylori, Campylobacter fetus, Campylobacter jejuni, Campylobacter coli, Borrelia burgdorferi, Vibrio cholerae, Vibrio parahaemolyticus, Legionella pneumophila, Listeria monocytogenes, Neisseria gonorrhoeae, Neisseria meningitidis, Kingella kingae, Moraxella catarrhalis, Gardnerella vaginalis, Bacteroides fragilis, Bacteroides distasonis, Bacteroides 3452A homology group, Bacteroides vulgatus, Bacteroides ovalus, Bacteroides thetaiotaomicron, Bacteroides uniformis, Bacteroides eggerthii, Bacteroides splanchnicus, Clostridium difficile, Mycobacterium tuberculosis, Mycobacterium avium, Mycobacterium intracellulare, Mycobacterium leprae, Corynebacterium diphtheriae, Corynebacterium ulcerans, Streptococcus pneumoniae, Streptococcus agalactiae, Streptococcus pyogenes, Enterococcus faecalis, Enterococcus faecium, Staphylococcus aureus, Staphylococcus epidermidis, Staphylococcus saprophyticus, Staphylococcus intermedius, Staphylococcus hyicus* subsp. *hyicus, Staphylococcus haemolyticus, Staphylococcus hominis*, or *Staphylococcus saccharolyticus*.

In some embodiments, the infection that is treated or prevented is caused by a bacteria that includes *Pseudomonas aeruginosa, Pseudomonas fuorescens, Stenotrophomonas maltophilia, Escherichia coli, Citrobacter freundii, Salmonella typhimurium, Salmonella typhi, Salmonella paratyphi, Salmonella enteritidis, Shigella dysenteriae, Shigella fexneri, Shigella sonnei, Enterobacter cloacae, Enterobacter aerogenes, Klebsiella pneumoniae, Klebsiella oxytoca, Serratia marcescens, Acinetobacter calcoaceticus, Acinetobacter haemolyticus, Yersinia enterocolitica, Yersinia pestis, Yersinia pseudotuberculosis, Yersinia intermedia, Haemophilus infuenzae, Haemophilus parainfuenzae, Haemophilus haemolyticus, Haemophilus parahaemolyticus, Helicobacter pylori, Campylobacter fetus, Campylobacter jejuni, Campylobacter coli, Vibrio cholerae, Vibrio parahaemolyticus, Legionella pneumophila, Listeria monocytogenes, Neisseria gonorrhoeae, Neisseria meningitidis, Moraxella catarrhalis, Bacteroides fragilis, Bacteroides vulgatus, Bacteroides ovalus, Bacteroides thetaiotaomicron, Bacteroides uniformis, Bacteroides eggerthii*, or *Bacteroides splanchnicus*.

In some embodiments, the infection that is treated or prevented is caused by a enterobacteriaceae bacteria. In some embodiments, the infection that is treated or prevented is caused by a bacteria that includes *Escherichia* spp, *Klebsiella* spp., *Enterobacter* spp., *Citrobacter* spp., *Morganella* spp., *Proteus* spp., *Salmonella* spp., *Serratia* spp., *Shigella* spp., or *Yersinia* spp.

In some embodiments, the compounds disclosed herein are useful in the treatment or prevention of infection associated with non-fermenting bacteria. In some embodiments, the compounds disclosed herein are useful in the treatment or prevention of infection associated with non-fermenting gram-negative bacteria. In some embodiments, the non-fermenting gram-negative bacteria is *Pseudomonas aeruginosa, Acinetobacter* spp. (*A. baumannii A. calcoaceticus*), *Stenotrophomonas maltophilia, Elizabethkingia* spp (*E. meningoseptica/E. anophelis, Burkholderia cepacia* complex, *Burkholderia pseudomallei*, or *Burkholderia mallei*.

In some embodiments, the infection that is treated or prevented is turberculosis. In some embodiments, the infection that is treated or prevented is caused by *Mycobacterium tuberculosis*. In some embodiments, the infection that is treated or prevented is caused by a bacteria that is a non-TB mycobacterial species. In some embodiments, the non-TB mycobacterial species is *M. abscessus, M. canum, M. bovis, M. africanum*, or *M. caprae*.

In some embodiments, the infection that is treated or prevented is gonorrhea. In some embodiments, the infection that is treated or prevented is caused by *Neisseria gonorrhoeae*.

In some embodiments, the infection that is treated or prevented is meningitis and other forms of meningococcal disease such as meningococcemia. In some embodiments, the infection that is treated or prevented is caused by *Neisseria meningitidis*.

In some embodiments of the methods described herein, the compound described herein is not administered with a β-lactam antibiotic. In some embodiments of the methods described herein, the compound described herein is not administered with a β-lactamase inhibitor. In some embodiments of the methods described herein, the compound described herein is not administered with a combination of a β-lactam antibiotic and a β-lactamase inhibitor.

EXAMPLES

General Examples for the Preparation of Compounds of Formula Formula (Ia), (IIa), (IIa-1), (Ib), (IIb), or (IIb-1)

The starting materials and intermediates for the compounds of this invention may be prepared by the application or adaptation of the methods described below, their obvious chemical equivalents, or, for example, as described in literature such as The Science of Synthesis, Volumes 1-8. Editors E. M. Carreira et al. Thieme publishers (2001-2008). The use of protective groups may be as described in methodology compendia such as *Greene's Protective Groups in Organic Synthesis,* Fourth Edition. John Wiley & Sons, Inc. 2006.

Certain compounds of Formula I (Scheme 1) are prepared from the corresponding functional-group-protected boronic acid esters A by treatment with a Lewis acid in a solvent such as dichloromethane, at a temperature between −78° C. and 0° C. followed by an aqueous quench

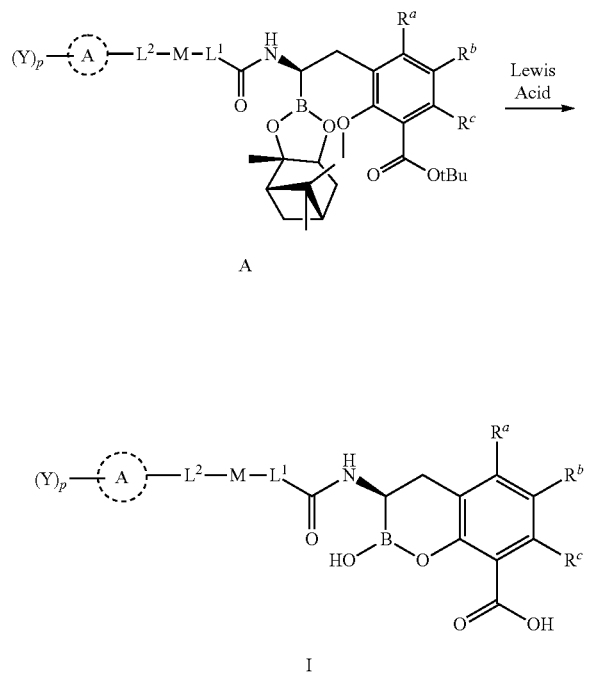

with acid chlorides to provide A. Carboxylic acids (C) or acid chlorides (D) may be obtained from commercial sources, prepared according to known methods in the literature, or prepared by a number of different reaction sequences. Formation of the acid chloride (D) involves treatment of (C) with a chlorinating agent such as thionyl chloride, phosphorous pentachloride or oxalyl chloride, in a solvent such as dichloromethane, in the presence of a catalyst such as DMF, at around room temperature. In certain cases, DMF is also used as a co-solvent. Formation of the anhydride (E) involves treatment of (C) with a sterically hindered acid chloride or chloroformate, such as trimethylacetyl chloride or isopropylchloroformate, in an inert solvent such as dichloromethane, in the presence of a non-nucleophilic base, such as triethyl amine or diisopropylamine at room temperature or below. Formation of the activated ester (F) involves treatment of (C) with an activating reagent system such as EDCI, DCC/HOBt, HATU, BOP reagents or TBTU, in a solvent such as DMF, DMA, NMP or dichloromethane at room temperature or below (*International Journal of Pharmaceutical Sciences Review and Research* (2011), 8(1), 108-119)

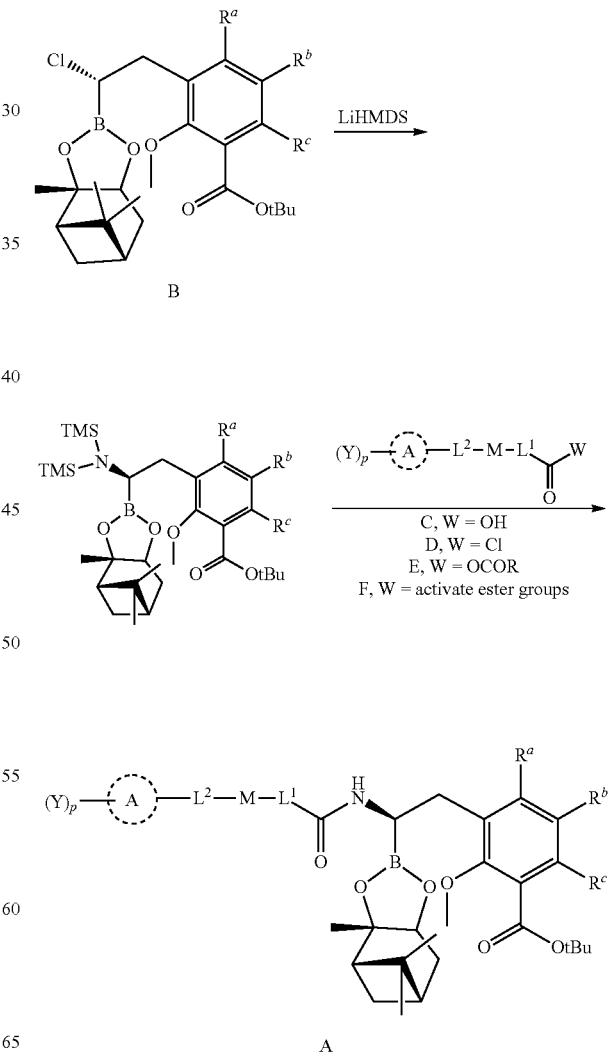

Amide intermediates A may be prepared according to the route outlined in Scheme 2. Chloro-boronates B, prepared by methods described previously (e.g. see WO2014089365), is reacted with silylamine bases such as lithium hexamethyldisilazide, and the intermediate silylamine is treated with carboxylic acids C under amide coupling conditions (such as with carbodiimide dehydrating reagents, HATU, or other coupling reagents) to provide protected amides A. Alternatively, the above silyamine intermediate is allowed to react

SCHEME 3

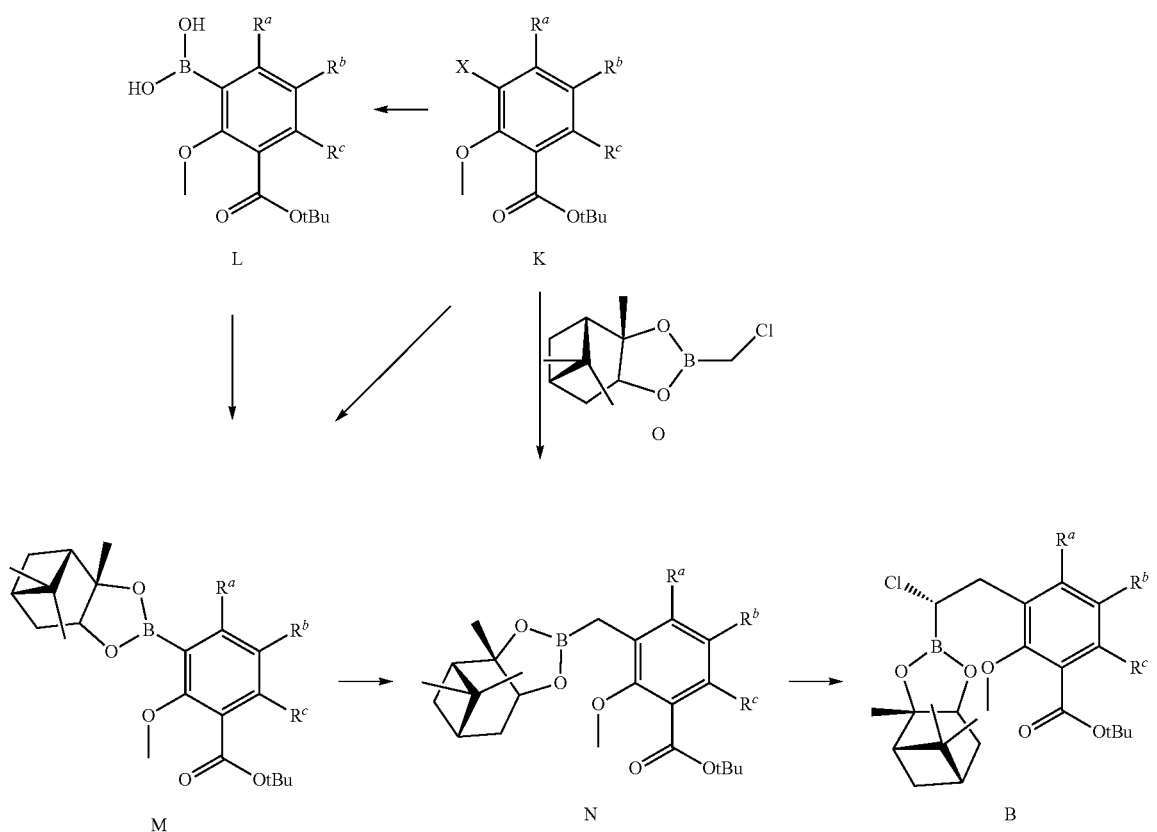

Chloroboronates B may be prepared from aryl halides or aryl triflates K (X=Br, I or OTf) in the manner described in Scheme 3. Compounds K (X=Br, I or OTf) may be converted into boronic acids L by treatment with alkyl lithium reagents, for example n-butyllithium, and then quenching the intermediate aryllithium species with trialkylboronates, followed by aqueous work-up. The boronic acids L may be converted into protected boronate esters M by treatment with 1,2-diols, such as (+)-pinanediol or pinacol. Alternatively, aryl halides K may be converted to boronate esters M by transition-metal-catalyzed reaction with diboron compounds, for example bis[(+)-pinanediolato]diboron and palladium catalysts. Two sequential Matteson reactions, as described previously, provide chloroboronates B bearing a wide range of substituents $R^a$, $R^b$, and $R^c$. Another variant consists of reaction of K with chloromethyl boronate J and isopropylmagnesium chloride to provide desired intermediate N directly.

While there are common themes and strategies among the illustrative examples cited below, the selection of an appropriate reaction sequence (including protecting group requirements) is dictated by the nature and arrangement of the functionality present in the target molecule and, therefore, may involve obvious adaptations of the illustrated methods in order to be applied in a particular case.

General Method A: Deprotection with Boron Trichloride or Boron Tribromide

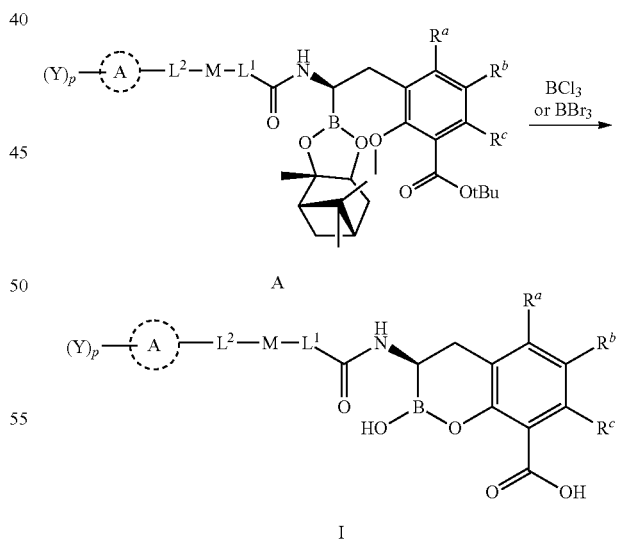

To a solution of the protected precursor A (0.4 mmol) in anhydrous DCM (15 mL) at −78° C. under argon was added dropwise $BCl_3$ or $BBr_3$ (1.0 M in DCM, 2.4-4 mL, 2.4-4 mmol, 6-10 equiv). The reaction mixture was allowed to slowly warmed to 0° C. over 1 h, and stirred between 0-5° C. for an additional 1-2 h, then quenched with water (2 mL)

and methanol (20 mL), evaporated to remove DCM, washed with hexane, and concentrated to a volume of ~4-5 mL. The crude product was purified by reverse phase preparative HPLC and dried using lyophilization to afford the product I.

General Method B: Deprotection with Aluminum Chloride

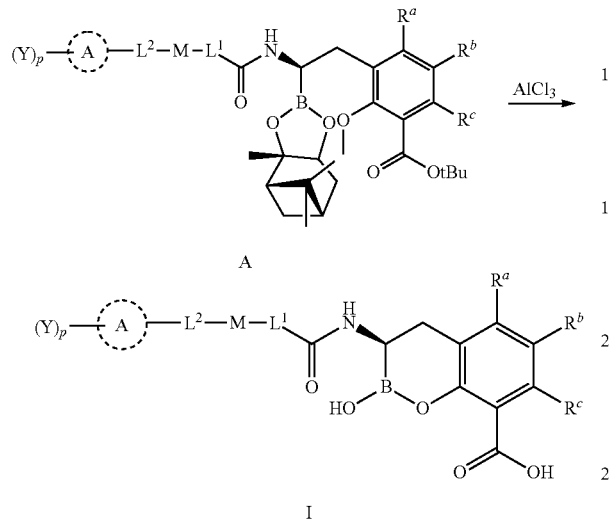

To a solution of the protected precursor A (0.4 mmol) in anhydrous DCM (15 mL) was added AlCl₃ (535 mg, 4 mmol, 10 equiv) in one portion at RT. The reaction mixture was stirred at RT for 24 h, then quenched with water (2 mL) and methanol (20 mL), evaporated to remove DCM, and washed with hexane, and concentrated to a volume of ~4-5 mL. The crude product was purified by reverse phase preparative HPLC and dried using lyophilization to afford the product I.

General Method C: Conversion of Chloro-Boronates to Amides

To a solution of the chloride B (4 mmol) in anhydrous THF (16 mL) was added dropwise LiHMDS (1.0 M in THF, 4.5 mL, 4.5 mmol) at −60° C. under argon. The reaction mixture was allowed to slowly warmed to 0° C. over 45 min, and stirred at RT for an additional 2 h.

In a separate flask was charged the carboxylic acid C (4.2 mmol) and anhydrous DMA (20 mL), to this mixture was added HATU (1.68 g, 4.4 mmol) followed by NMM (0.49 mL, 4.4 mmol). The reaction mixture was stirred at RT for 2 h, at which time the solution from the above reaction was added to the flask, and the reaction mixture was stirred at RT overnight, then diluted with EtOAc, washed with water, brine, and dried over Na₂SO₄, concentrated in vacuo to afford the crude product, which was purified by flash chromatography on silica gel (hexane-EtOAc, 20:1-1:1, or hexane-acetone, 10:1-1:1, or DCM-MeOH, 30:1-10:1) to afford the product A.

SYNTHETIC EXAMPLES

Example 1: (R)-3-((R)-2-amino-2-phenylacetamido)-2-hydroxy-3,4-dihydro-2H-benzo[e][1,2]oxaborinine-8-carboxylic acid

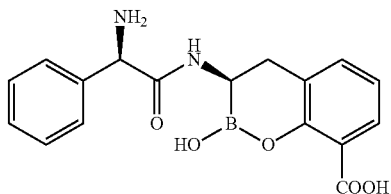 [SMILES: N[C@@H](C(=O)N[C@H]1Cc2cccc(C(=O)O)c2OB1O)c1ccccc1]

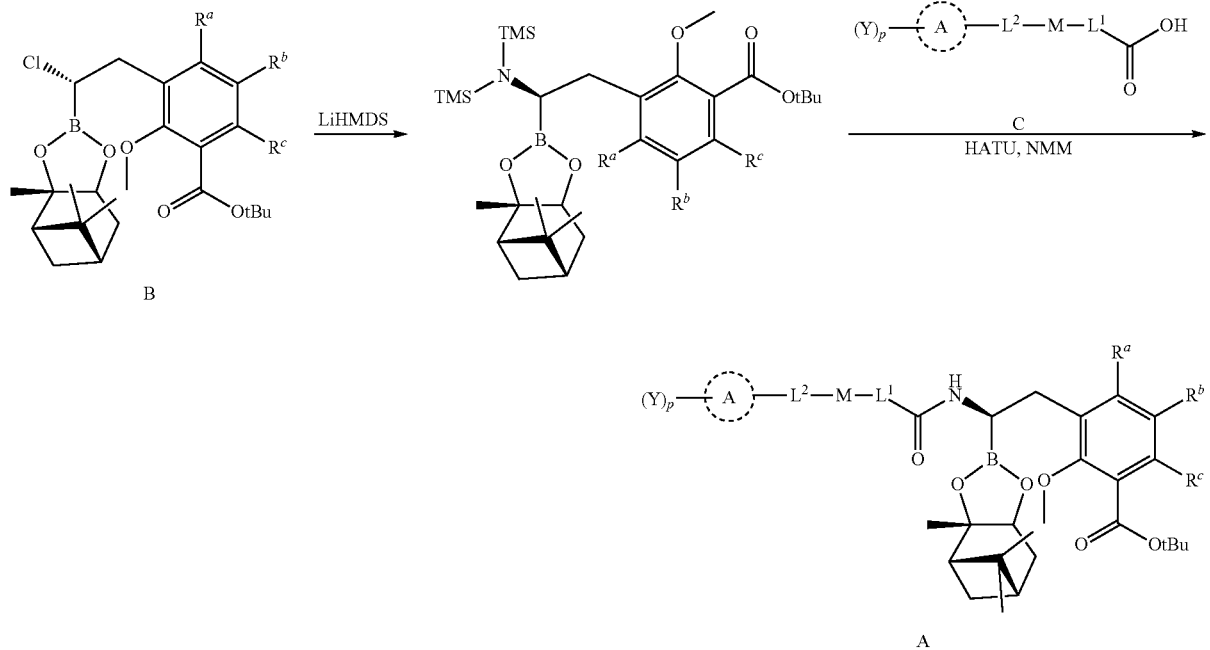

Example 2: (R)-3-((S)-2-amino-2-phenylacetamido)-2-hydroxy-3,4-dihydro-2H-benzo[e][1,2]oxaborinine-8-carboxylic acid

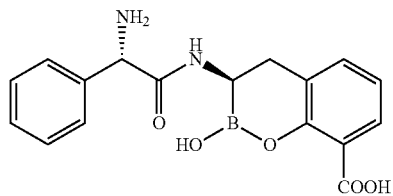 [SMILES: N[C@H](C(=O)N[C@H]1Cc2cccc(C(=O)O)c2OB1O)c1ccccc1]

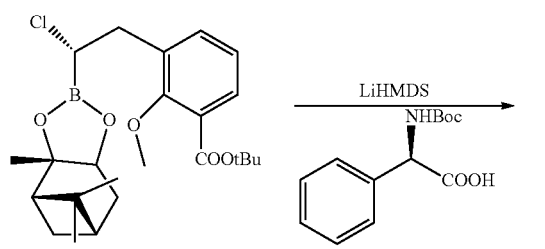

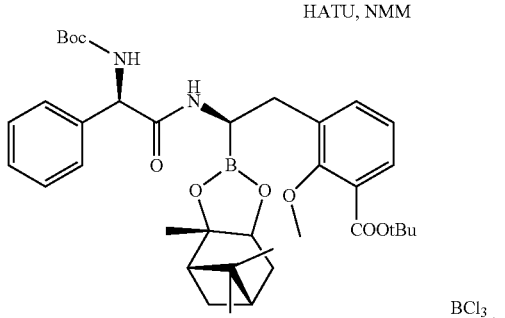

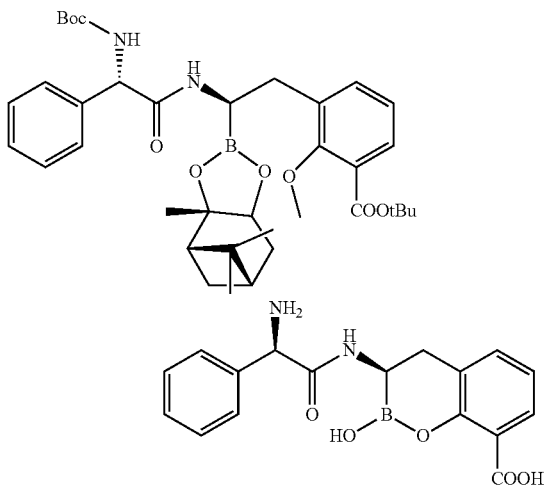

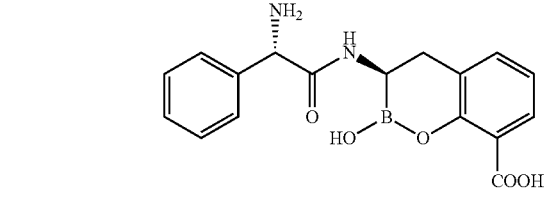

By following General Method C, the chloride was treated with LiHMDS, and then coupled with Boc-D-α-phenylglycine in the presence of HATU and NMM to yield two products after purification by flash chromatography on silica gel (hexane-Et$_2$O, 4:1-1:2), which were tentatively assigned as the two diasteromers (Boc-D-α-phenylglycine racemized during the reaction). ESI-MS m/z 663 (MH)+.

These two products were treated with BCl$_3$ to afford the two title compounds (1 and 2). ESI-MS m/z 341 (MH)$^+$.

Example 3: (R)-3-((R)-2-amino-2-(2-aminothiazol-4-yl)acetamido)-2-hydroxy-3,4-dihydro-2H-benzo[e][1,2]oxaborinine-8-carboxylic acid

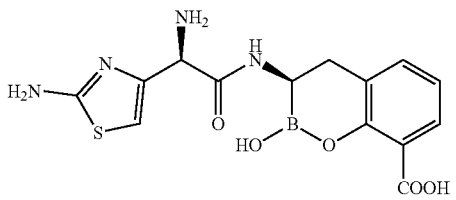 [SMILES: Nc1nc([C@@H](N)C(=O)N[C@H]2Cc3cccc(C(=O)O)c3OB2O)cs1]

Example 4: (R)-3-((S)-2-amino-2-(2-aminothiazol-4-yl)acetamido)-2-hydroxy-3,4-dihydro-2H-benzo[e][1,2]oxaborinine-8-carboxylic acid

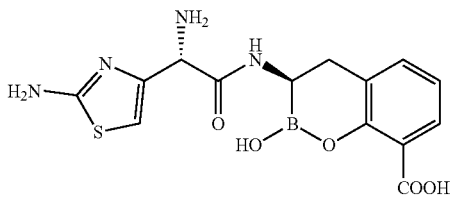 [SMILES: Nc1nc([C@H](N)C(=O)N[C@H]2Cc3cccc(C(=O)O)c3OB2O)cs1]

Step 1. Synthesis of ethyl 2-(2-aminothiazol-4-yl)-2-((tert-butoxycarbonyl)amino)acetate

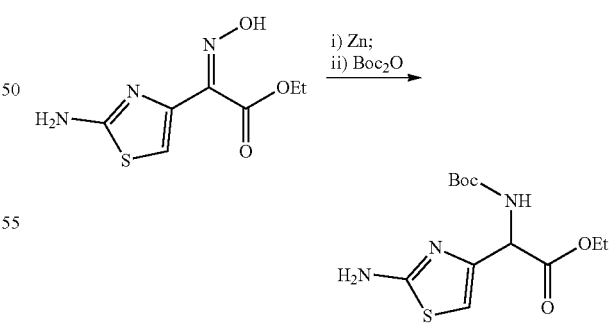

To ethyl 2-amino-α-(hydroxyimino)-4-thiazoleacetate (4.4 g, 20 mmol) in 50% HCOOH (40 mL) and MeOH (20 mL) was added zinc dust (3 g, 46 mmol) at 0° C. The reaction mixture was stirred 0° C. for 3 h, filtered through a pad of Celite, the filtrate was concentrated. To this concentrated mixture was added water (80 mL), basified with K$_2$CO$_3$ to pH ~8-9, then THF (100 mL) was added to the resulting solution followed by Boc₂O (5.24 g, 24 mmol). The reaction was stirred at 0° C. for 1 h, then warmed to RT, added more Boc₂O (1.9 g, 8.7 mmol), stirred for an additional 1 h 40 min, extracted with EtOAc. The organic extracts were dried over Na₂SO₄, and concentrated. The crude product was purified by flash chromatography on silica gel (hexane-EtOAc, 10:1-1:3) to afford the title compound, 4.5 g. ESI-MS m/z 302 (MH)⁺.

Step 2. Synthesis of ethyl 2-((tert-butoxycarbonyl)amino)-2-(2-((tert-butoxycarbonyl)amino)thiazol-4-yl)acetate

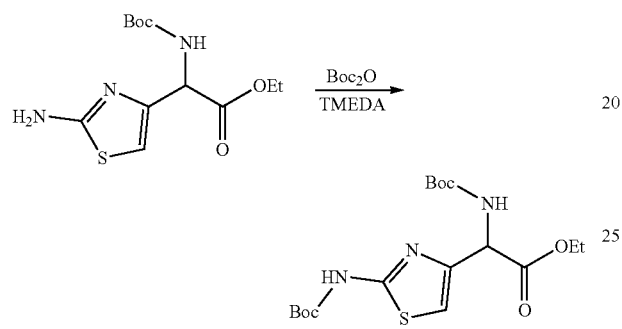

The above product (2.3 g, 7.64 mmol) was dissolved in CH₃CN (50 mL), reacted with Boc₂O (1.9 g, 8.7 mmol) in the presence of TMEDA (3.6 mL, 24 mmol) at RT overnight, then concentrated, and purified by flash chromatography on silica gel (hexane-EtOAc, 10:1-3:2) to afford the title compound, 1.46 g. ESI-MS m/z 402 (MH)⁺.

Step 3. Synthesis of 2-((tert-butoxycarbonyl)amino)-2-(2-((tert-butoxycarbonyl)amino)thiazol-4-yl)acetic acid

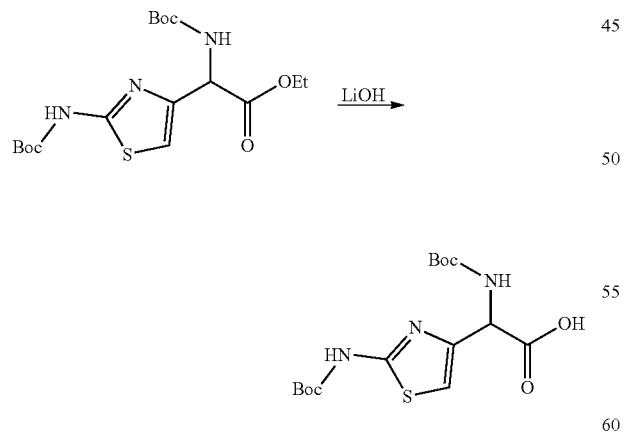

The above product (1.43 g, 3.57 mmol) was dissolved in THF (20 mL) and water (20 mL), treated with LiOH·H₂O (420 mg, 10 mmol) at RT for 2 h, concentrated, acidified with 1 N HCl to pH ~3-4, the solid was collected by filtration, dried in vacuo to afford the title compound, 1.3 g. ESI-MS m/z 374 (MH)⁺.

Step 4. Synthesis of (R)-3-((R)-2-amino-2-(2-aminothiazol-4-yl)acetamido)-2-hydroxy-3,4-dihydro-2H-benzo[e][1,2]oxaborinine-8-carboxylic acid and (R)-3-((S)-2-amino-2-(2-aminothiazol-4-yl)acetamido)-2-hydroxy-3,4-dihydro-2H-benzo[e][1,2]oxaborinine-8-carboxylic acid In a similar manner to the synthesis of Example 1 and Example 2, Example 3 and Example 4 were prepared from the above acid. MS m/z 363 (MH)⁺.

Example 5: (3R)-3-(2-(2-aminothiazol-4-yl)-2-(4-ethyl-2,3-dioxopiperazine-1-carboxamido)acetamido)-2-hydroxy-3,4-dihydro-2H-benzo[e][1,2]oxaborinine-8-carboxylic acid

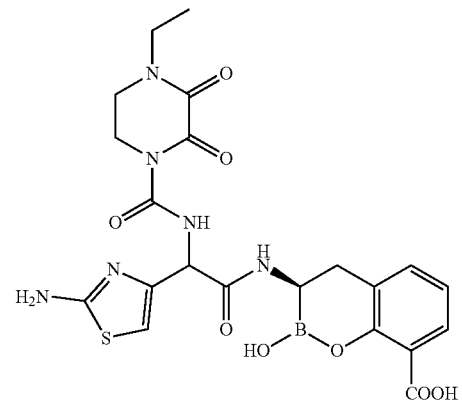

Step 1. Synthesis of ethyl 2-(2-(((benzyloxy)carbonyl)amino)thiazol-4-yl)-2-((tert-butoxycarbonyl)amino)acetate

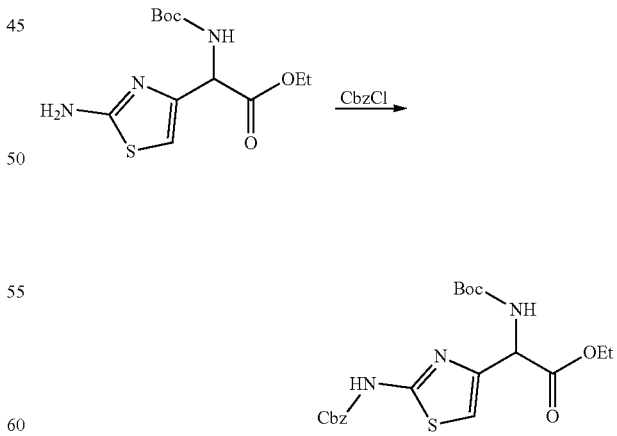

By following standard procedures for CBZ protection of an amine, the title compound was prepared from ethyl 2-(2-aminothiazol-4-yl)-2-((tert-butoxycarbonyl)amino)acetate (from Step 1 of Example 3, Example 4). ESI-MS m/z 436 (MH)⁺.

Step 2. Synthesis of 2-(2-(((benzyloxy)carbonyl)amino)thiazol-4-yl)-2-((tert-butoxycarbonyl)amino)acetic acid

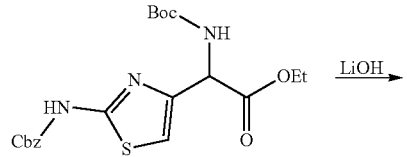

The above product (6.53 g, 15 mmol) in THF (100 mL) and water (100 mL) was treated with lithium hydroxide monohydrate (1.89 g, 45 mmol) at RT for 2 h, then concentrated in vacuo, acidified with 1 N HCl to pH ~3-4. The precipitated solid was collected by filtration, washed with water, and dried in vacuo to afford the title compound, 5.8 g. ESI-MS m/z 408 (MH)$^+$.

Step 3. Synthesis of 2-amino-2-(2-(((benzyloxy)carbonyl)amino)thiazol-4-yl)acetic acid

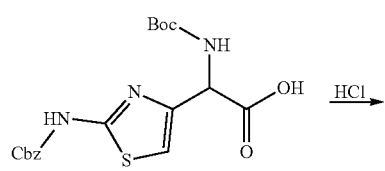

To a solution of the above product (5.8 g, 14.25 mmol) in DCM (120 mL was added 4.0 M HCl in dioxane solution (60 mL, 240 mmol). The reaction mixture was stirred at RT overnight, diluted with diethyl ether. The precipitated solid was collected by filtration, washed with diethyl ether, and dried in vacuo to afford the title compound as the HCl salt, 4.86 g. ESI-MS m/z 308 (MH)$^+$.

Step 4. Synthesis of 2-(2-(((benzyloxy)carbonyl)amino)thiazol-4-yl)-2-(4-ethyl-2,3-dioxopiperazine-1-carboxamido)acetic acid

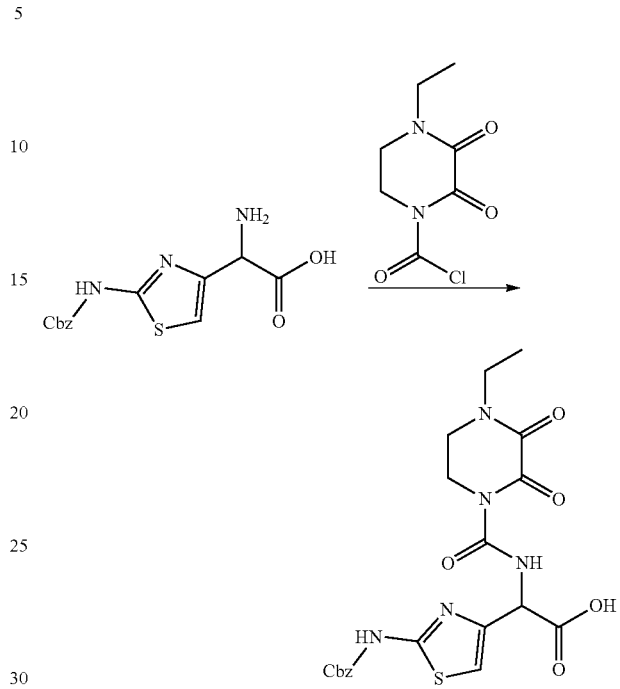

To a solution of the above amino acid (2.06 g, 6 mmol) in THF (60 mL) and water (60 mL) was added a solution of NaOH (480 mg, 12 mmol) in water (5 mL) at 0° C., followed by aqueous saturated NaHCO$_3$ (20 mL), a solution of 4-ethyl-2,3-dioxopiperazine-1-carbonyl chloride (1.54 g, 7.5 mmol) in THF (8 mL), and MeOH (160 mL). The reaction mixture was stirred between 0-10° C. for 1.5 h, then concentrated in vacuo, acidified with 1 N HCl to pH ~2, extracted with EtOAc. The organic extracts were combined, dried over Na$_2$SO$_4$, concentrated in vacuo to afford the crude product, 2.3 g, which was used directly for the next Step without further purification. ESI-MS m/z 476 (MH)$^+$.

Step 5. Synthesis of (3R)-3-(2-(2-aminothiazol-4-yl)-2-(4-ethyl-2,3-dioxopiperazine-1-carboxamido)acetamido)-2-hydroxy-3,4-dihydro-2H-benzo[e][1,2]oxaborinine-8-carboxylic acid

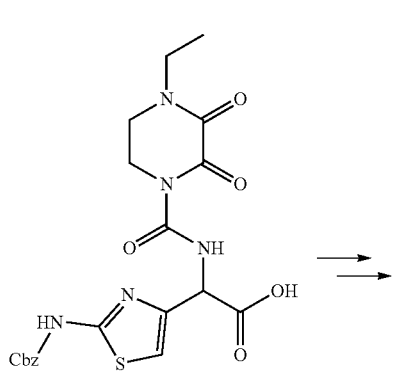

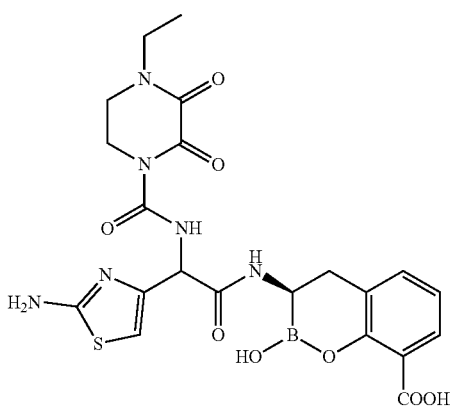 [SMILES: CCN1CCN(C(=O)NC(C(=O)N[C@H]2Cc3cccc(C(=O)O)c3OB2O)c2csc(N)n2)C(=O)C1=O]

The title compound was prepared from the above acid by following the General Method C and General Method A. ESI-MS m/z 531 (MH)+.

Example 6: (3R)-3-(2-(2-aminothiazol-4-yl)-2-(3-ethylureido)acetamido)-2-hydroxy-3,4-dihydro-2H-benzo[e][1,2]oxaborinine-8-carboxylic acid

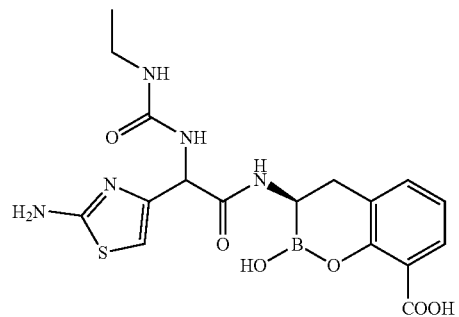 [SMILES: CCNC(=O)NC(C(=O)N[C@H]1Cc2cccc(C(=O)O)c2OB1O)c1csc(N)n1]

Step 1. Synthesis of tert-butyl 3-((2R)-2-(2-(2-(((benzyloxy)carbonyl)amino)thiazol-4-yl)-2-((tert-butoxycarbonyl)amino)acetamido)-2-((3aS,4S,6R)-3a,5,5-trimethylhexahydro-4,6-methanobenzo[d][1,3,2]dioxaborol-2-yl)ethyl)-2-methoxybenzoate

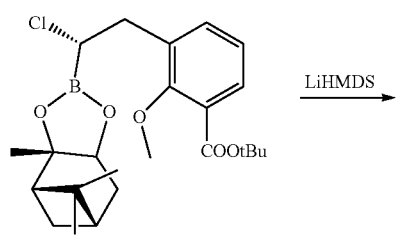

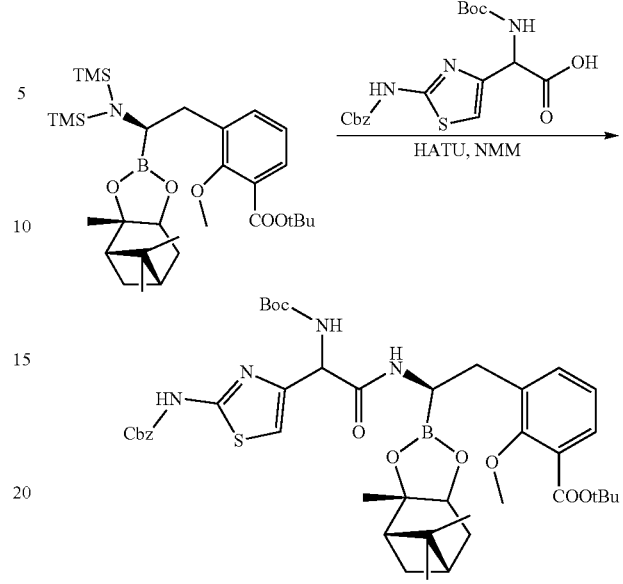

By following the general procedure C, the chloride (prepared as previous reported, WO 2014/089365) was treated with LiHMDS, and then coupled with 2-(2-(((benzyloxy)carbonyl)amino)thiazol-4-yl)-2-((tert-butoxycarbonyl)amino)acetic acid (from step 2 of Example 5) in the presence of HATU and NMM, yielding the title compound. ESI-MS m/z 819 (MH)+.

Step 2. Synthesis of tert-butyl 3-((2R)-2-(2-amino-2-(2-(((benzyloxy)carbonyl)amino)thiazol-4-yl)acetamido)-2-((3aS,4S,6R)-3a,5,5-trimethylhexahydro-4,6-methanobenzo[d][1,3,2]dioxaborol-2-yl)ethyl)-2-methoxybenzoate

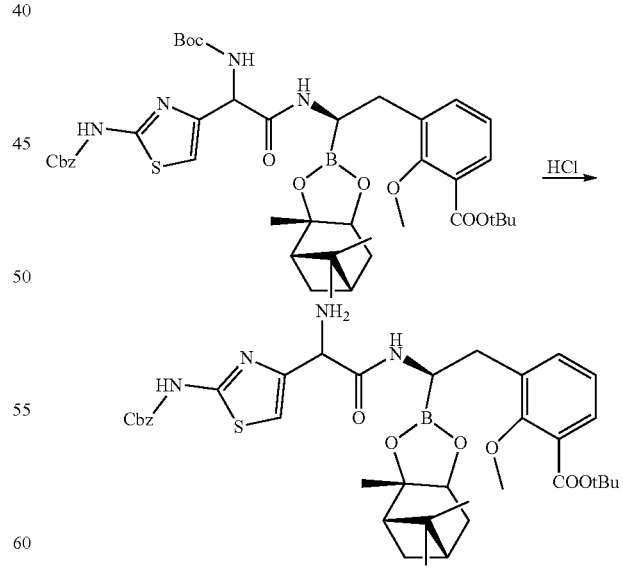

To above product (3 g, 3.66 mmol) was added cold solution of 1.0 M HCl in diethyl ether (100 mL, 100 mmol). The reaction mixture was stirred at RT overnight, and concentrated in vacuo, the residue was washed with hexane, dried in vacuo to afford the title compound as the HCl salt, Step 3. Synthesis of tert-butyl 3-((2R)-2-(2-(2-
(((benzyloxy)carbonyl)amino)thiazol-4-yl)-2-(3-
ethylureido)acetamido)-2-((3aS,4S,6R)-3a,5,5-trim-
ethylhexahydro-4,6-methanobenzo[d][1,3,2]
dioxaborol-2-yl)ethyl)-2-methoxybenzoate

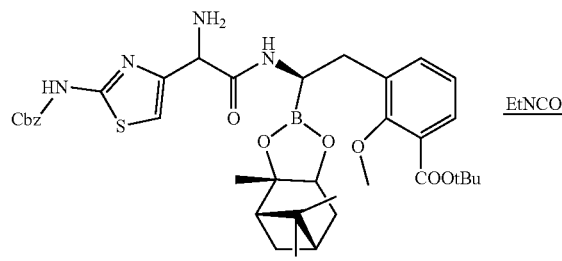

To above product (604 mg, 0.8 mmol) at 0° C. was added diisopropylethylamine (0.21 mL, 1.2 mmol) followed by a DCM (1 mL) solution of ethyl isocyanate (71 mg, 1 mmol). The reaction mixture was allowed to warm up to RT over 1.5 h, washed with water and brine, dried over Na$_2$SO$_4$, concentrated, and purified by flash chromatography on silica gel (hexane-acetone, 2:1-1:3) to yield the product, 270 mg. ESI-MS m/z 790 (MH)$^+$.

Step 4. Synthesis of (3R)-3-(2-(2-aminothiazol-4-
yl)-2-(3-ethylureido)acetamido)-2-hydroxy-3,4-di-
hydro-2H-benzo[e][1,2]oxaborinine-8-carboxylic
acid

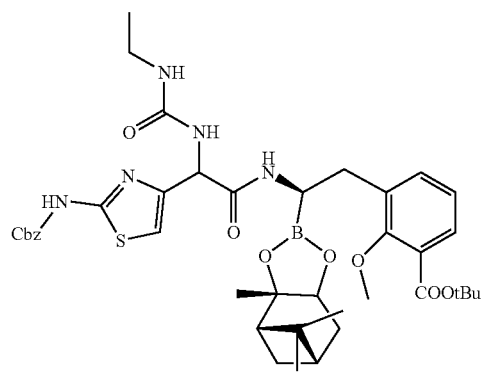

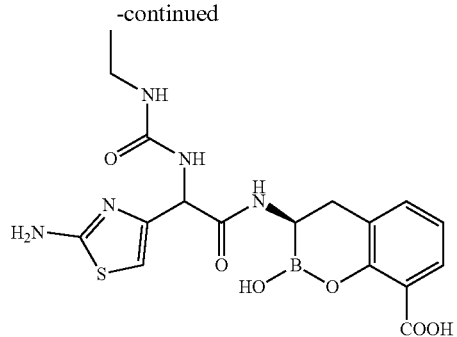

By following the General Method A, the above product was treated with BCl$_3$ to afford the title compound. ESI-MS m/z 434 (MH)$^+$.

Example 7: (3R)-3-(2-(2-aminothiazol-4-yl)-2-(3-
ethylureido)acetamido)-2-hydroxy-3,4-dihydro-2H-
benzo[e][1,2]oxaborinine-8-carboxylic acid

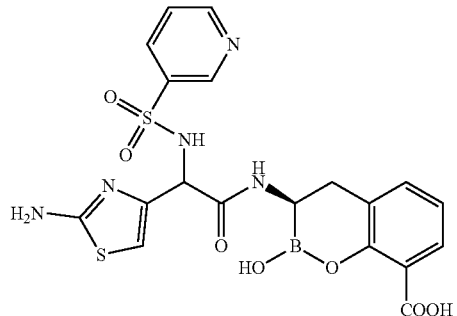 [SMILES: Nc1nc(C(NS(=O)(=O)c2cccnc2)C(=O)N[C@H]2Cc3cccc(C(=O)O)c3OB2O)cs1]

Step 1. Synthesis of tert-butyl 3-((2R)-2-(2-(2-
(((benzyloxy)carbonyl)amino)thiazol-4-yl)-2-(pyri-
dine-3-sulfonamido)acetamido)-2-((3aS,4S,6R)-3a,5,
5-trimethylhexahydro-4,6-methanobenzo[d][1,3,2]
dioxaborol-2-yl)ethyl)-2-methoxybenzoate

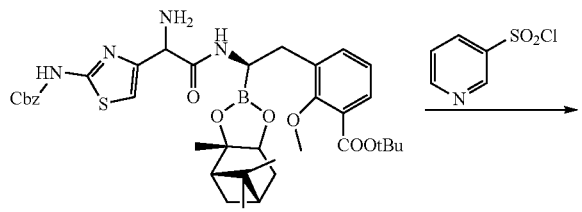

83
-continued

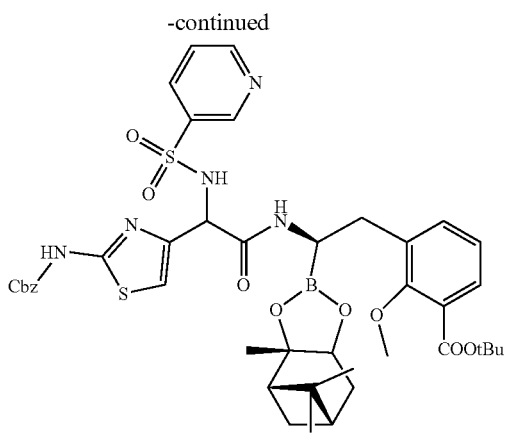

To the amine intermediate (product from step 2 of Example 6) (604 mg, 0.8 mmol) at 0° C. was added diisopropylethylamine (0.37 mL, 2.1 mmol) followed by a DCM (1 mL) solution of pyridine-3-sulfonyl chloride (178 mg, 1 mmol). The reaction mixture was allowed to warm up to RT over 1.5 h, washed with water and brine, dried over $Na_2SO_4$, concentrated, and purified by flash chromatography on silica gel (hexane-acetone, 4:1-2:3) to yield the product, 260 mg. ESI-MS m/z 860 (MH)+.

Step 2. Synthesis of (3R)-3-(2-(2-aminothiazol-4-yl)-2-(pyridine-3-sulfonamido)acetamido)-2-hydroxy-3,4-dihydro-2H-benzo[e][1,2]oxaborinine-8-carboxylic acid

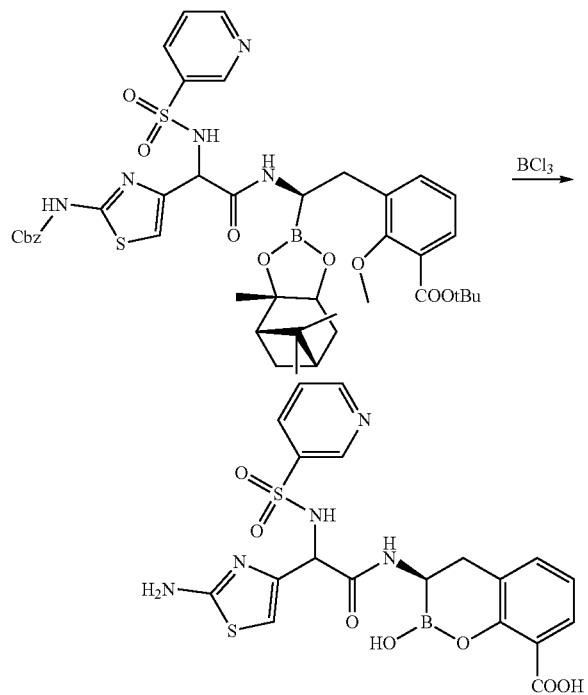

By following the General Method A, the above product was treated with $BCl_3$ to afford the title compound. ESI-MS m/z 504 (MH)+.

84
Example 8: (R)-3-((S)-2-(4-Ethyl-2,3-dioxopiperazine-1-carboxamido)propanamido)-2-hydroxy-3,4-dihydro-2H-benzo[e][1,2]oxaborinine-8-carboxylic acid

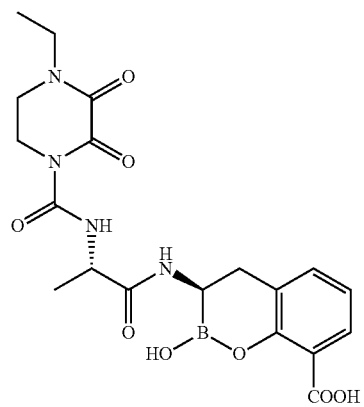 [SMILES: CCN1CCN(C(=O)N[C@@H](C)C(=O)N[C@H]2Cc3cccc(C(=O)O)c3OB2O)C(=O)C1=O]

Step 1. Synthesis of (4-Ethyl-2,3-dioxopiperazine-1-carbonyl)-L-alanine

To a stirred solution of L-alanine (178 mg, 2.0 mmol) in a mixture (40 mL) of tetrahydrofuran (THF) and water (1:1, v/v) was added a saturated solution of sodium bicarbonate in water (6 mL) at 0° C. 4-Ethyl-2,3-dioxopiperazine-1-carbonyl chloride (512 mg, 2.5 mmol, 1.25 eq.) in THF (3 mL) was added dropwise, and the reaction was stirred at 0° C. for 2 h. The volatiles were evaporated under reduced pressure and the resulting aqueous solution was neutralized at 0° C. with 2N HCl to pH 2, and extracted 3 times with ethyl acetate (50 mL each). The combined organic extracts were dried on $Na_2SO_4$, then filtered, and the solvent was evaporated under reduced pressure to generate (4-ethyl-2,3-dioxopiperazine-1-carbonyl)-L-alanine (380 mg), which was used in the next step without further purification.

Step 2. Synthesis of tert-Butyl 3-((2R)-2-((S)-2-(4-Ethyl-2,3-dioxopiperazine-1-carboxamido)-propanamido)-2-((3aS,4S,6S)-3a,5,5-trimethylhexahydro-4,6-methanobenzo[d][1,3,2]dioxaborol-2-yl)ethyl)-2-methoxybenzoate Step 2a A solution of tert-butyl 3-((2S)-2-chloro-2-((3aS,4S,6S)-3a,5,5-trimethylhexahydro-4,6-methanobenzo[d][1,3,2]dioxaborol-2-yl)ethyl)-2-methoxybenzoate (450 mg, 1.0 mmol) in THF (5 mL), stirred at -40° C. under an atmosphere of argon, was treated dropwise with a 1M solution of lithium bis(trimethylsilyl)amide (LHMDS) in THF (1 mL, 1 mmol, 1 eq.). After 5 min the reaction was allowed to warm to room temperature and was stirred for 1 h.

Step 2b

In a separate flask, (4-ethyl-2,3-dioxopiperazine-1-carbonyl)-L-alanine (283 mg, 1.1 mmol, 1.1 eq.), prepared as described in Step 1, in N,N-dimethylacetamide (DMA) (3 mL) was treated with 1-[bis(dimethylamino)methylene]-1H-1,2,3-triazolo[4,5-b]pyridinium 3-oxid hexafluorophosphate (HATU; 456.5 mg, 1.2 mmol, 1.2 eq) and 4-methylmorpholine (NMM; 0.15 mL, 1.3 mmol, 1.3 eq). The reaction mixture generated in Step 2(a) was added and stirring was continued for 12 h. The reaction mixture was diluted with water (20 mL) and extracted three times with diethyl ether (30 ml each). The combined organic extracts were dried on $Na_2SO_4$, then filtered, and the solvent was evaporated under reduced pressure. The product was isolated by flash-chromatography (Silica gel, ethyl acetate-hexanes, 0-100%): tert-butyl 3-((2R)-2-((S)-2-(4-ethyl-2,3-dioxopiperazine-1-carboxamido)propanamido)-2-((3aS,4S,6S)-3a,5,5-trimethylhexahydro-4,6-methanobenzo[d][1,3,2]dioxaborol-2-yl)ethyl)-2-methoxybenzoate (322 mg).

Step 3. (R)-3-((S)-2-(4-Ethyl-2,3-dioxopiperazine-1-carboxamido)propanamido)-2-hydroxy-3,4-dihydro-2H-benzo[e][1,2]oxaborinine-8-carboxylic acid To a stirred solution of tert-butyl 3-((2R)-2-((S)-2-(4-ethyl-2,3-dioxopiperazine-1-carboxamido)propanamido)-2-((3aS,4S,6S)-3a,5,5-trimethylhexahydro-4,6-methanobenzo[d][1,3,2]dioxaborol-2-yl)ethyl)-2-methoxybenzoate (321 mg, 0.5 mmol) in dichloromethane (5 mL) was added dropwise a 1 M solution of boron trichloride (2.5 mL, 2.5 mmol, 5 eq.) at –78° C. The reaction mixture was allowed to warm to 0° C. and was stirred at this temperature for 1 h. The reaction was quenched by addition of water (1.5 mL) and the resulting mixture was stirred for another 20 min. Dichloromethane was evaporated under reduced pressure. The remaining aqueous residue was washed with diethyl ether, then homogenized by addition of acetonitrile and submitted to preparative reverse phase high performance liquid chromatography (Gilson, C18 stationary phase, acetonitrile/water 0-60% mobile phase modified with 0.1% TFA). Fractions containing the desired product were combined and freeze-dried to afford the title compound (38 mg). ESI-MS m/z 447.2 (M+H)$^+$.

Example 9: (R)-3-((2R,4S)-1-(4-ethyl-2,3-dioxopiperazine-1-carbonyl)-4-hydroxypyrrolidine-2-carboxamido)-2-hydroxy-3,4-dihydro-2H-benzo[e][1,2]oxaborinine-8-carboxylic acid

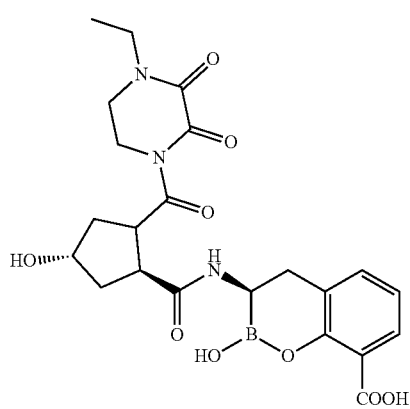 [SMILES: CCN1CCN(C(=O)C2C[C@@H](O)C[C@@H]2C(=O)N[C@H]2Cc3cccc(C(=O)O)c3OB2O)C(=O)C1=O]

The title compound was prepared from trans-4-hydroxy-D-proline and 3-((2S)-2-chloro-2-((3aS,4S,6S)-3a,5,5-trimethylhexahydro-4,6-methanobenzo[d][1,3,2]dioxaborol-2-yl)ethyl)-2-methoxybenzoate, by a procedure similar to Example 8. ESI-MS m/z 489.2 (M+H)$^+$.

Example 10: (3R)-3-(2-(5-amino-1,2,4-thiadiazol-3-yl)-2-(4-ethyl-2,3-dioxopiperazine-1-carboxamido)acetamido)-2-hydroxy-3,4-dihydro-2H-benzo[e][1,2]oxaborinine-8-carboxylic acid

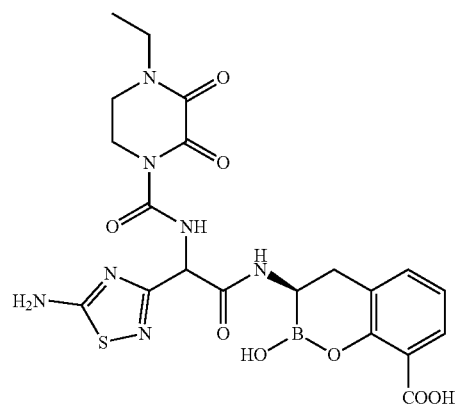 [SMILES: CCN1CCN(C(=O)NC(C(=O)N[C@H]2Cc3cccc(C(=O)O)c3OB2O)c2nsc(N)n2)C(=O)C1=O]

Step 1. Synthesis of methyl 2-(5-amino-1,2,4-thiadiazol-3-yl)-2-(methoxyimino)acetate

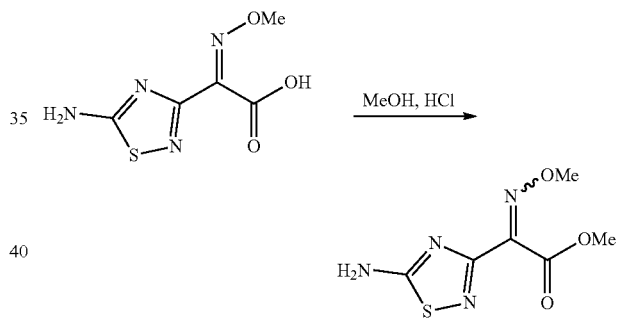

(Z)-2-(5-Amino-1,2,4-thiadiazol-3-yl)-2-(methoxyimino)acetic acid (9.1 g, 45 mmol) was dissolved in 3 M HCl in methanol (150 mL), heated at 60° C. for 8 h, then at 45-50° C. overnight. The reaction mixture was concentrated in vacuo, dissolved in DCM, washed with aqueous saturated $NaHCO_3$, dried over $Na_2SO_4$, and concentrated in vacuo to afford the product as a mixture of E and Z isomers, 8.5 g. ESI-MS m/z 217 (MH)$^+$.

Step 2. Synthesis of 2-(5-(((benzyloxy)carbonyl)amino)-1,2,4-thiadiazol-3-yl)-2-((tert-butoxycarbonyl)amino)acetic acid

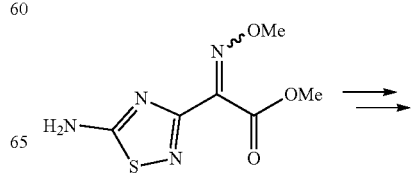

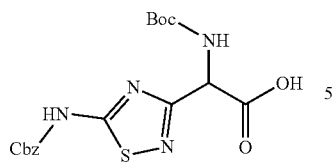

By following the same experimental procedures of Step 1 of Example 3, Example 4, and Step 1, Step 2 of Example 5, the title compound was prepared from the above product. ESI-MS m/z 409 (MH)$^+$.

Step 3. Synthesis of tert-butyl 3-((2R)-2-(2-amino-2-(5-(((benzyloxy)carbonyl)amino)-1,2,4-thiadiazol-3-yl)acetamido)-2-((3aS,4S,6S,7aR)-3a,5,5-trimethylhexahydro-4,6-methanobenzo[d][1,3,2]dioxaborol-2-yl)ethyl)-2-methoxybenzoate

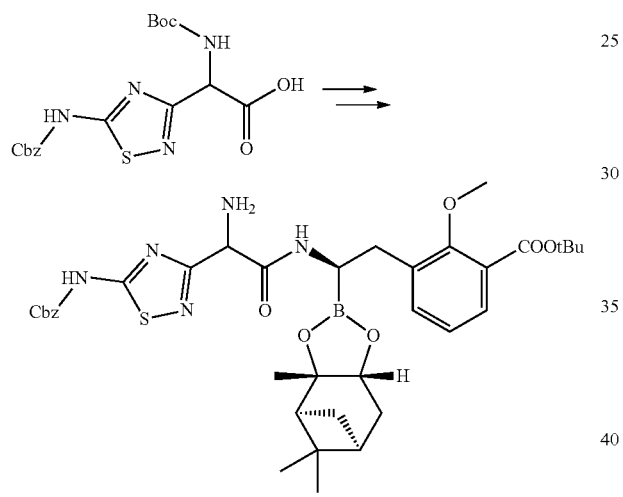

By following the same experimental procedures of Step 1, Step 2 of Example 6, the title compound was prepared from the above product as HCl salt. ESI-MS m/z 719 (MH)$^+$.

Step 4. Synthesis of (3R)-3-(2-(5-amino-1,2,4-thiadiazol-3-yl)-2-(4-ethyl-2,3-dioxopiperazine-1-carboxamido)acetamido)-2-hydroxy-3,4-dihydro-2H-benzo[e][1,2]oxaborinine-8-carboxylic acid

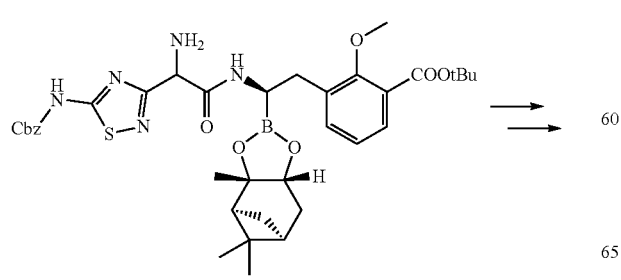

In a similar manner to the synthesis of Example 7, utilizing 4-ethyl-2,3-dioxopiperazine-1-carbonyl chloride in place of pyridine-3-sulfonyl chloride in Step 1, the title compound was prepared from the above amine intermediate. ESI-MS m/z 532 (MH)$^+$.

Example 11: (R)-3-((R)-3-amino-2-(4-ethyl-2,3-dioxopiperazine-1-carboxamido)propanamido)-2-hydroxy-3,4-dihydro-2H-benzo[e][1,2]oxaborinine-8-carboxylic acid, trifluoroacetic acid salt The title compound was prepared from (R)-2-amino-3-((tert-butoxycarbonyl)amino)propanoic acid and 3-((2S)-2-chloro-2-((3aS,4S,6S)-3a,5,5-trimethylhexahydro-4,6-methanobenzo[d][1,3,2]dioxaborol-2-yl)ethyl)-2-methoxybenzoate, by a procedure similar to Example 8. ESI-MS m/z 462.2 (M+H)$^+$.

Example 12: (3R)-3-(2-(4-ethyl-2,3-dioxopiperazine-1-carboxamido)-4-hydroxy-2-methylbutanamido)-2-hydroxy-3,4-dihydro-2H-benzo[e][1,2]oxaborinine-8-carboxylic acid

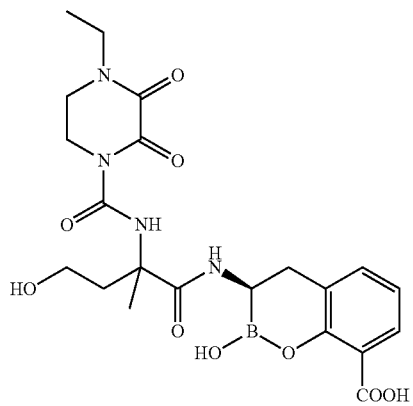 [SMILES: CCN1CCN(C(=O)NC(C)(CCO)C(=O)N[C@H]2Cc3cccc(C(=O)O)c3OB2O)C(=O)C1=O]

Step 1. Synthesis of 4-(benzyloxy)-2-(4-ethyl-2,3-dioxopiperazine-1-carboxamido)-2-methylbutanoic acid

Step 1a. Synthesis of methyl 4-(benzyloxy)-2-(4-ethyl-2,3-dioxopiperazine-1-carboxamido)-2-methylbutanoate To neat methyl 2-amino-4-(benzyloxy)-2-methylbutanoate (1 g, 4 mmol) stirred at 0° C. was added dropwise trimethylamine (3 mL, 21 mmol). To the resulting mixture was added dropwise a solution of 4-ethyl-2,3-dioxopiperazine-1-carbonyl chloride (1 g, 5 mmol) in minimum volume of dichloromethane and stirring was continued at room temperature overnight. The reaction mixture was partitioned between water and dichloromethane and the organic layer was separated, washed twice with water, twice with 0.5 N HCl, and then with brine, dried over sodium sulfate and filtered. The volatiles were evaporated under reduced pressure to afford methyl 4-(benzyloxy)-2-(4-ethyl-2,3-dioxopiperazine-1-carboxamido)-2-methylbutanoate as a viscous oil, which was used in the next step without further purification.

Step 1b. Synthesis of 4-(benzyloxy)-2-(4-ethyl-2,3-dioxopiperazine-1-carboxamido)-2-methylbutanoic acid Methyl 4-(benzyloxy)-2-(4-ethyl-2,3-dioxopiperazine-1-carboxamido)-2-methylbutanoate (405.2 mg, 1 mmol) in a 1:1 (v/v) tetrahydrofuran/water mixture (10 mL) was stirred at room temperature with LiOH (72 mg, 3 mmol) for 30 min. Volatiles were evaporated under reduced pressure, pH was adjusted to 2-3 with HCl 2N, and the product was extracted with ethyl acetate, and further purified by flash chromatography (Silicagel, methanol/dichloromethane 0-20% gradient) to provide 4-(benzyloxy)-2-(4-ethyl-2,3-dioxopiperazine-1-carboxamido)-2-methylbutanoic acid (249.2 mg: 64% vied: ESI-MS m/z 392.2 (M+H)$^+$/414.2 (M+Na)$^+$

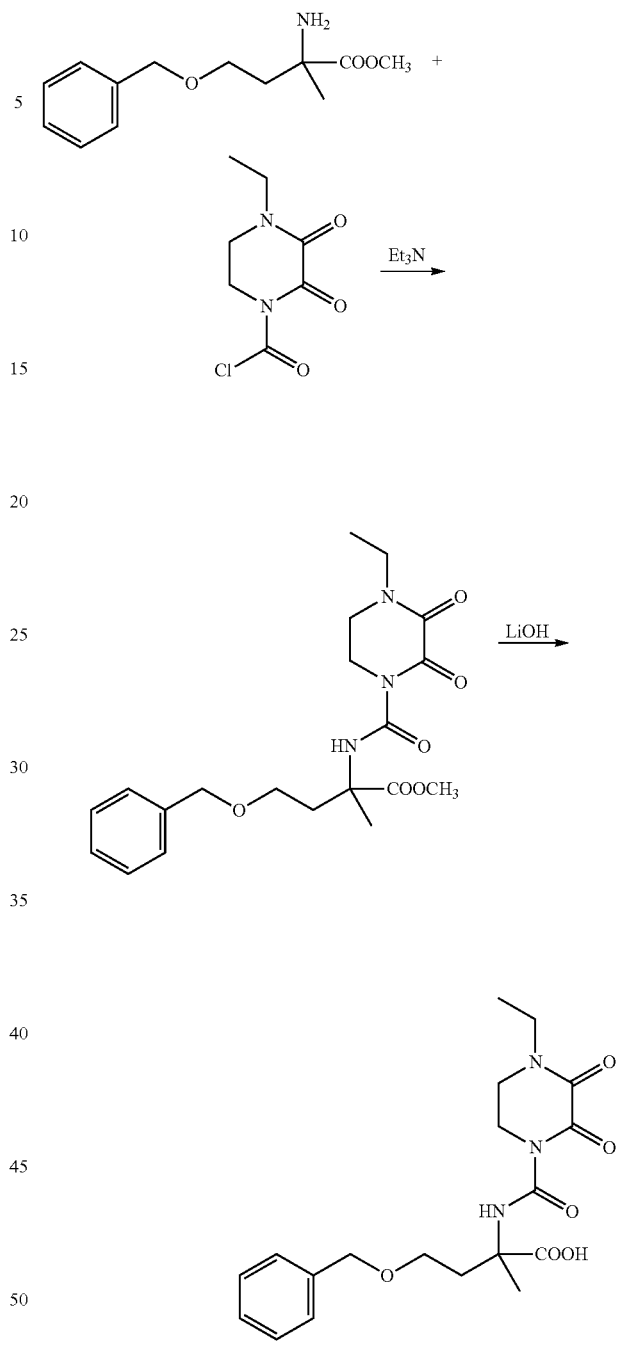

Step 2. Synthesis of (3R)-3-(2-(4-ethyl-2,3-dioxopiperazine-1-carboxamido)-4-hydroxy-2-methylbutanamido)-2-hydroxy-3,4-dihydro-2H-benzo[e][1,2]oxaborinine-8-carboxylic acid The title compound was prepared from 4-(benzyloxy)-2-(4-ethyl-2,3-dioxopiperazine-1-carboxamido)-2-methylbutanoic acid from Example 61, Step 1, and 3-((2S)-2-chloro-2-((3aS,4S,6S)-3a,5,5-trimethylhexahydro-4,6-methanobenzo[d][1,3,2]dioxaborol-2-yl)ethyl)-2-methoxybenzoate, by a procedure similar to Example 8. ESI-MS m/z 491.2 (M+H)$^+$.

Example 13: (3R)-3-(2-(2-amino-5-chlorothiazol-4-yl)-2-(4-(2-fluoroethyl)-2,3-dioxopiperazine-1-carboxamido)acetamido)-2-hydroxy-3,4-dihydro-2H-benzo[e][1,2]oxaborinine-8-carboxylic acid

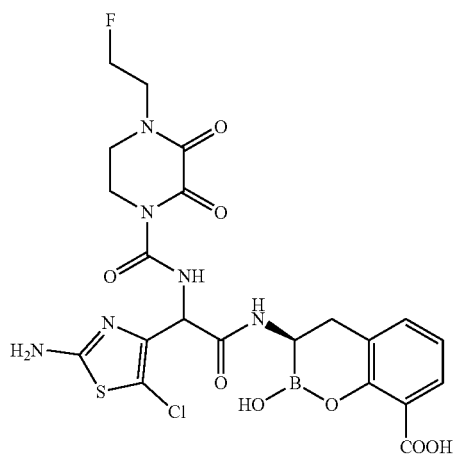 [SMILES: Nc1nc(C(NC(=O)N2CCN(CCF)C(=O)C2=O)C(=O)N[C@H]2Cc3cccc(C(=O)O)c3OB2O)c(Cl)s1]

Step 1. Synthesis of 1-(2-fluoroethyl)piperazine-2,3-dione

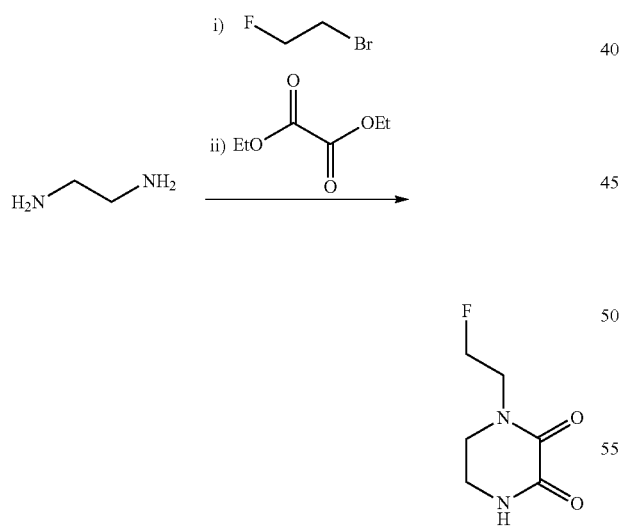

To ethylenediamine (22.5 g, 375 mmol) was added 1-bromo-2-fluoroethane (6.86 g, 54 mmol) in portions over 20 min, stirred for an additional 3.5 h. To the reaction mixture was added diethyl ether (40 mL), the ether layer was separated, and the residue was extracted one more time with diethyl ether (40 mL). The ether extracts were combined, concentrated and dried in vacuo. To the EtOH (35 mL) solution of this crude product (3.0 g, 28.3 mmol) was added diethyl oxalate (3.94 mL, 29 mmol). The reaction mixture was stirred at reflux for 18 h, then concentrated in vacuo, the residue was purified by flash chromatography on silica gel (DCM-MeOH, 30:1-10:1) to afford the product, 3.1 g. ESI-MS m/z 161 (M+H)+.

Step 2. Synthesis of 2,3-dioxo-4-fluoroethylpiperazine-1-carbonyl chloride

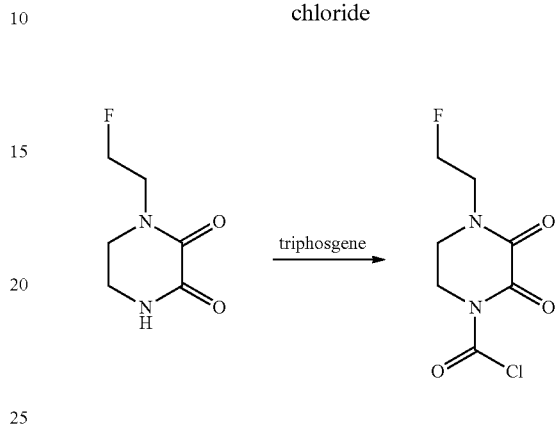

To the above product (1.6 g, 10 mmol) in THF (25 mL) and DCM (10 mL) at −15° C. was added chlorotrimethylsilane (1.4 mL, 11 mmol), followed by triethylamine (1.67 mL, 12 mmol). The reaction mixture was stirred between −15° C.-0° C. for 1 h, then triphosgene (1.2 g, 4 mmol) in THF (6 mL) was added dropwise to the reaction mixture. After addition was complete, the reaction mixture was warmed up to RT over 30 min, stirred for an additional 1 h, and the solid was filtered off and washed with THF. The filtrate was concentrated, triturated with diethyl ether and hexane. The solid was collected by filtration, dried in vacuo to give the title compound, 2.77 g.

Step 3. Synthesis of tert-butyl 3-((2R)-2-(2-(2-(((benzyloxy)carbonyl)amino)thiazol-4-yl)-2-(4-(2-fluoroethyl)-2,3-dioxopiperazine-1-carboxamido)acetamido)-2-((3aS,4S,6S)-3a,5,5-trimethylhexahydro-4,6-methanobenzo[d][1,3,2]dioxaborol-2-yl)ethyl)-2-methoxybenzoate

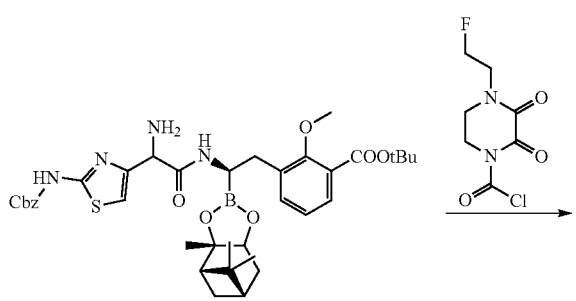

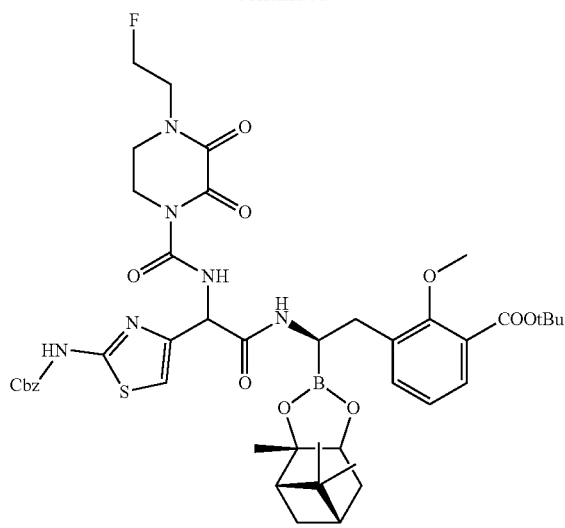

To the amine intermediate (product from Step 2 of Example 6) (1.36 g, 1.8 mmol) at 0° C. was added diisopropylethylamine (1.12 mL, 6.6 mmol) followed by the carbonyl chloride from Step 2 (748 mg, 2.7 mmol). The reaction mixture was allowed to warm up to RT over 2.5 h, washed with water and brine, dried over $Na_2SO_4$, concentrated, and purified by flash chromatography on silica gel (hexane-acetone, 4:1-1:4) to yield the product, 700 mg. ESI-MS m/z 905 (M+H)+.

The product from Step 3 (460 mg, 0.51 mmol) in DMF (3 mL) was treated with NCS (88 mg, 0.66 mmol) at RT for 2 h, diluted with EtOAc, washed with water, brine, dried over $Na_2SO_4$, concentrated, and purified by flash chromatography on silica gel (hexane-acetone, 4:1-1:1) to afford the title compound, 330 mg. ESI-MS m/z 939/941 (MH/MH+2)+.

Step 4. Synthesis of tert-butyl 3-((2R)-2-(2-(2-(((benzyloxy)carbonyl)amino)-5-chlorothiazol-4-yl)-2-(4-(2-fluoroethyl)-2,3-dioxopiperazine-1-carboxamido)acetamido)-2-((3aS,4S,6S,7aR)-3a,5,5-trimethylhexahydro-4,6-methanobenzo[d][1,3,2]dioxaborol-2-yl)ethyl)-2-methoxybenzoate Step 5. Synthesis of (3R)-3-(2-(2-amino-5-chlorothiazol-4-yl)-2-(4-(2-fluoroethyl)-2,3-dioxopiperazine-1-carboxamido)acetamido)-2-hydroxy-3,4-dihydro-2H-benzo[e][1,2]oxaborinine-8-carboxylic acid

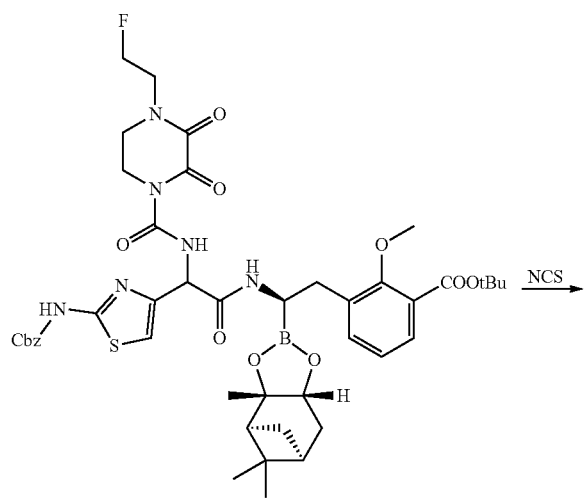

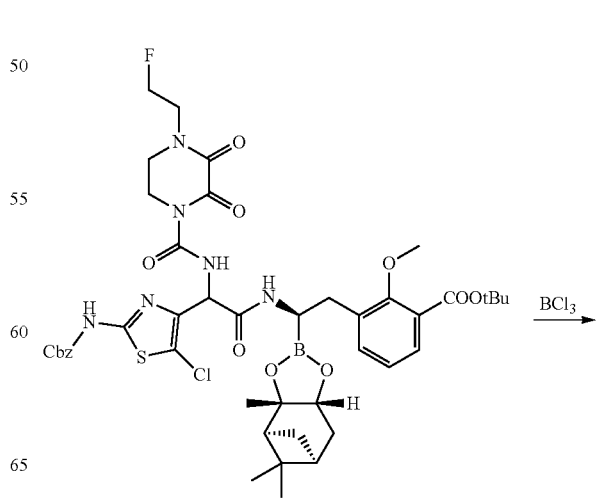

-continued

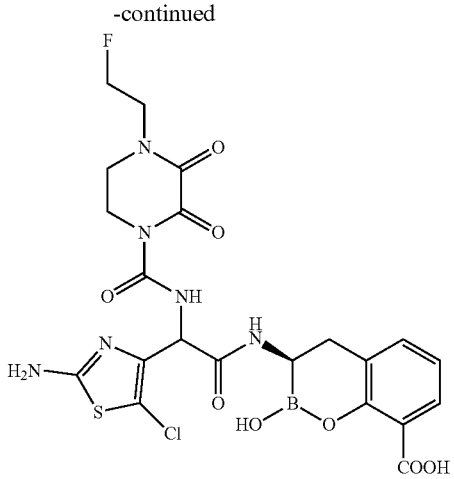

The title compound was prepared by treatment of the above product with BCl₃ by following General Method A. ESI-MS m/z 583/585 (MH/MH+2)⁺.

Example 14: (R)-3-(3-(aminomethyl)-1-(4-ethyl-2,3-dioxopiperazine-1-carbonyl)azetidine-3-carboxamido)-2-hydroxy-3,4-dihydro-2H-benzo[e][1,2]oxaborinine-8-carboxylic acid, trifluoroacetic acid salt

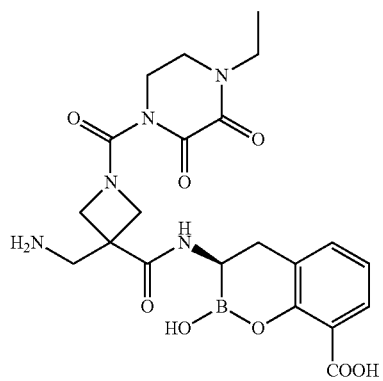 [SMILES: CCN1CCN(C(=O)N2CC(CN)(C(=O)N[C@H]3Cc4cccc(C(=O)O)c4OB3O)C2)C(=O)C1=O]

The title compound was prepared from 3-(((tert-butoxycarbonyl)amino)methyl)azetidine-3-carboxylic acid and 3-((2S)-2-chloro-2-((3aS,4S,6S)-3a,5,5-trimethylhexahydro-4,6-methanobenzo-[d][1,3,2]dioxaborol-2-yl)ethyl)-2-methoxybenzoate, by a procedure similar to Example 8. ESI-MS m/z 488.2 (M+H)⁺.

Example 15: (3R)-3-(3-amino-2-((4-ethyl-2,3-dioxopiperazine-1-carboxamido)methyl)-2-(hydroxymethyl)propanamido)-2-hydroxy-3,4-dihydro-2H-benzo[e][1,2]oxaborinine-8-carboxylic acid, trifluoroacetic acid salt

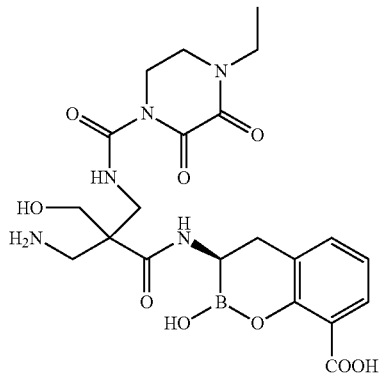 [SMILES: CCN1CCN(C(=O)NCC(CN)(CO)C(=O)N[C@H]2Cc3cccc(C(=O)O)c3OB2O)C(=O)C1=O]

The title compound was isolated as a side product from Example 14, Step 3. ESI-MS m/z 506.2 (M+H)⁺.

Example 16: (3R)-3-(2-(2-aminothiazol-4-yl)-2-(4-ethyl-2,3-dioxopiperazine-1-carboxamido)acetamido)-6-fluoro-2-hydroxy-3,4-dihydro-2H-benzo[e][1,2]oxaborinine-8-carboxylic acid

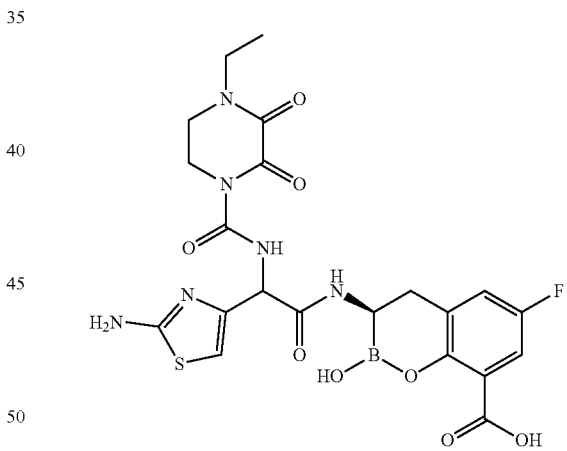

Step 1. Synthesis of tert-butyl 5-fluoro-2-hydroxybenzoate

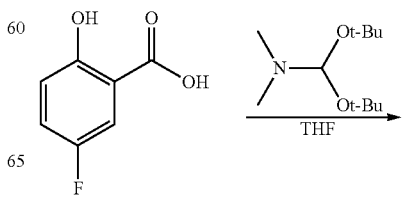

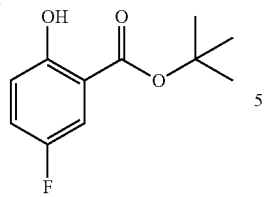

5-Fluorosalicylic acid (10.5 g, 66.9 mmol) in THF (110 mL) under Ar was heated to reflux. N,N-Dimethylformamide di-tert-butyl acetal (50.0 mL, 208 mmol) was added through the condenser in three portions every 30 min. The reaction mixture was stirred at reflux for an additional 23 h. The reaction was diluted with water and extracted two times with DCM. The combined organic layers were washed with water and brine, dried over $Na_2SO_4$, filtered, and concentrated. Column chromatography (0-70% DCM/Hexane) afforded the title compound (10.1 g, 71%). ESI-MS m/z 213 $(MH)^+$.

Step 2. Synthesis of tert-butyl 5-fluoro-2-hydroxy-3-iodobenzoate

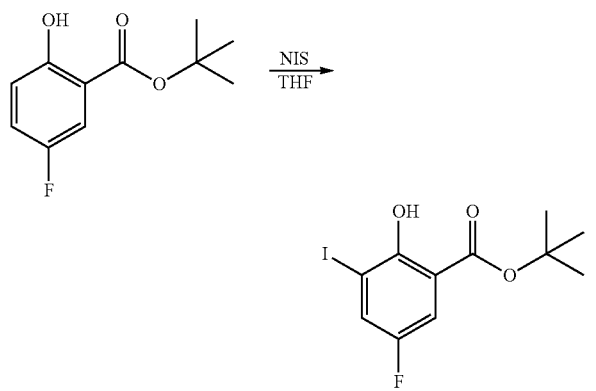

To a solution of tert-butyl 5-fluoro-2-hydroxybenzoate (10.1 g, 47.6 mmol) in DMF (86 mL) under Ar was added N-iodosuccinimide (13.4 g, 59.5 mmol). The reaction was stirred at room temperature for 5 days. The reaction was quenched with water and extracted two times with diethyl ether. The combined organic layers were washed with water and brine, dried over $MgSO_4$, filtered, and concentrated. Column chromatography (0-70% DCM/Hexane) afforded the title compound (7.15 g, 44%). ESI-MS m/z 339 $(MH)^+$.

Step 3. Synthesis of tert-butyl 5-fluoro-3-iodo-2-methoxybenzoate

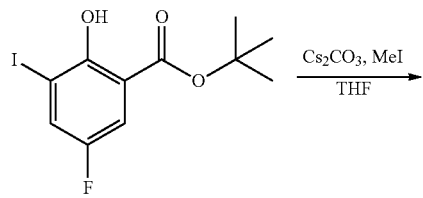

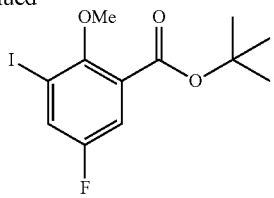

To a solution of tert-butyl 5-fluoro-2-hydroxy-3-iodobenzoate (7.15 g, 21.1 mmol) in DMF (57 mL) under Ar was added cesium carbonate (15.1 g, 46.4 mmol) and the reaction was stirred for 20 min. Iodomethane (3.2 mL, 51.4 mmol) was added and the reaction was stirred at room temperature for 18 h. The reaction was quenched with water and extracted two times with diethyl ether. The combined organic layers were washed with water and brine, dried over $MgSO_4$, filtered, and concentrated. Column chromatography (0-100% DCM/Hexane) afforded the title compound (4.44 g, 60%). ESI-MS m/z 353 $(MH)^+$.

Step 4. Synthesis of tert-butyl 5-fluoro-2-methoxy-3-((3aS)-3a,5,5-trimethylhexahydro-4,6-methanobenzo[d][1,3,2]dioxaborol-2-yl)benzoate

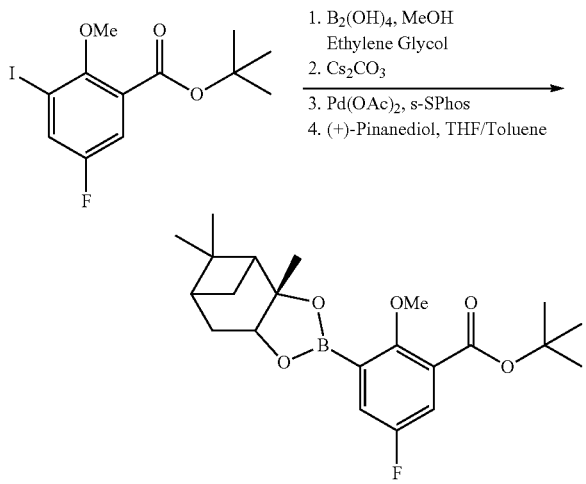

To a solution of tert-butyl 5-fluoro-3-iodo-2-methoxybenzoate (4.44 g, 12.6 mmol) in methanol (64 mL) and ethylene glycol (6.5 mL) under Ar was added tetrahydroxydiboron (1.36 g, 15.2 mmol). The reaction was evacuated and purged with Ar three times and stirred for 15 min. Cesium carbonate (5.94 g, 18.2 mmol) was added in two portions one minute apart and the reaction was stirred at room temperature for 5 min. Palladium acetate (0.059 g, 0.26 mmol) and s-Sphos (0.23 g, 0.45 mmol) were added and reaction was again evacuated and purged with Ar four times and stirred for 3.5 h. The reaction was concentrated, diluted with ethyl acetate, and washed with 1N HCl and brine. The aqueous layers were back extracted and the combined organic layers were dried over $MgSO_4$, filtered, and concentrated. Column chromatography (0-100% Ethyl Acetate/Hexane) afforded the boronic acid which was dissolved in THF (10 mL) and toluene (5 mL) under Ar. (+)-Pinanediol was added and the reaction was stirred at room temperature for 16 h. The reaction was concentrated and azeotroped with toluene to produce the title compound (3.38 g, 66%). ESI-MS m/z 405 (MH)+.

Step 5. Synthesis of tert-butyl 5-fluoro-2-methoxy-3-(((3aS)-3a,5,5-trimethylhexahydro-4,6-methanobenzo[d][1,3,2]dioxaborol-2-yl)methyl)benzoate

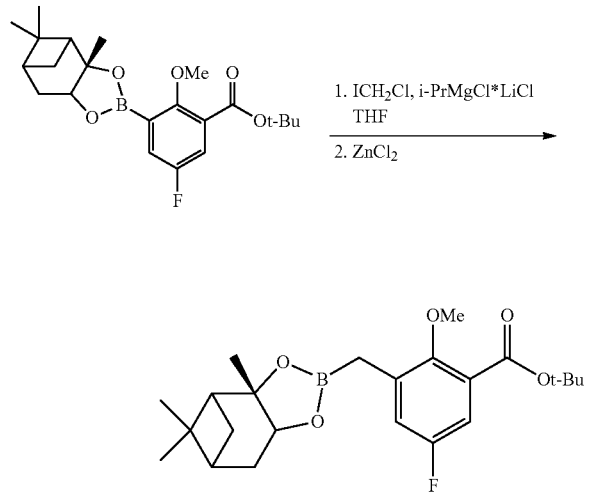

A solution of chloroiodomethane (3.1 mL, 42.6 mmol) in THF (28 mL) under Ar was cooled to −78° C. Isopropylmagnesium chloride lithium chloride complex (1.3 M in THF, 16 mL, 12.3 mmol) was added dropwise over 35 min. The reaction mixture was stirred at −78° C. for 50 min. tert-Butyl 5-fluoro-2-methoxy-3-((3aS)-3a,5,5-trimethylhexahydro-4,6-methanobenzo[d][1,3,2]dioxaborol-2-yl)benzoate (3.38 g, 8.36 mmol) in THF (6 mL) was added dropwise over 30 min and the reaction was stirred at −78° C. for 2 h. Zinc chloride (1.0 M in Et₂O, 14 mL, 14.0 mmol) was added dropwise over 30 min. The reaction was stirred at −78° C. for 20 min then warmed to room temperature for 18 h. The reaction was diluted with diethyl ether and washed with cold 0.1 N HCl. The aqueous layer was back extracted and the combined organic layers were washed with water and brine, dried over MgSO₄, filtered, and concentrated. Column chromatography (0-20% Ethyl Acetate/Hexane) afforded the title compound (1.34 g, 38%). ESI-MS m/z 419 (MH)+.

Step 6. Synthesis of tert-butyl 3-((2S)-2-chloro-2-((3aS)-3a,5,5-trimethylhexahydro-4,6-methanobenzo[d][1,3,2]dioxaborol-2-yl)ethyl)-5-fluoro-2-methoxybenzoate

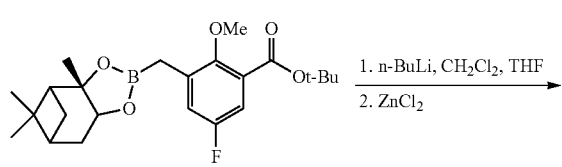

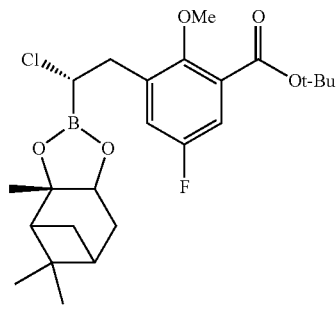

A solution of DCM (0.52 mL, 8.12 mmol) in THF (5.8 mL) under Ar was cooled to −100° C. n-Butyllithium (2.5 M in hexane, 2.5 mL, 6.25 mmol) was added dropwise down the side of the flask over 14 min. The milky white reaction mixture was stirred at −100° C. for 30 min. tert-Butyl 5-fluoro-2-methoxy-3-(((3aS)-3a,5,5-trimethylhexahydro-4,6-methanobenzo[d][1,3,2]dioxaborol-2-yl)methyl)benzoate (1.34 g, 3.2 mmol) in THF (2.5 mL) was added dropwise down the side of the flask over 10 min and the reaction was stirred for 60 min at −100° C. Zinc chloride (1.0 M in Et₂O, 14 mL, 14.0 mmol) was added dropwise down the side of the flask over 11 min. The reaction was stirred at −100° C. for 5 min then warmed to −10° C. for 80 min. The reaction was diluted with diethyl ether and washed with cold 0.05 N HCl and brine, dried over MgSO₄, filtered, and concentrated. Column chromatography (0-20% Ethyl Acetate/Hexane) afforded the title compound (0.74 g, 49%). ESI-MS m/z 467 (MH)+.

Step 7. Synthesis of tert-butyl 3-((2R)-2-(2-(2-(((benzyloxy)carbonyl)amino)thiazol-4-yl)-2-(4-ethyl-2,3-dioxopiperazine-1-carboxamido)acetamido)-2-((3aS)-3a,5,5-trimethylhexahydro-4,6-methanobenzo[d][1,3,2]dioxaborol-2-yl)ethyl)-5-fluoro-2-methoxybenzoate

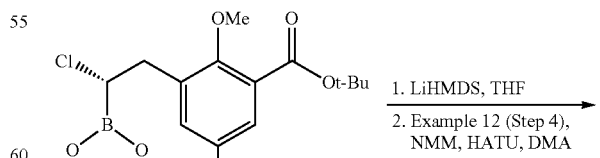

-continued

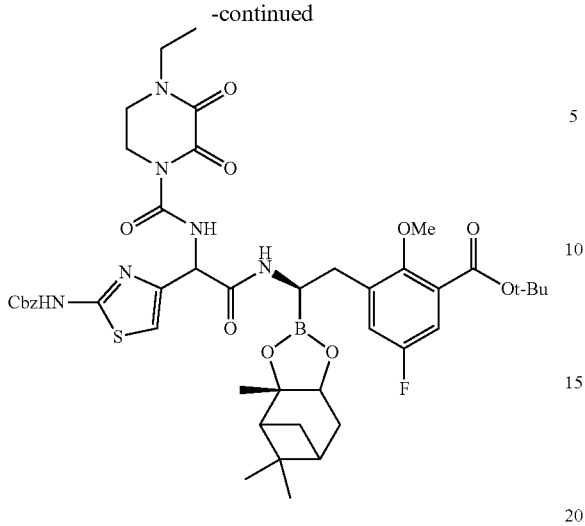

A solution of tert-butyl 3-((2S)-2-chloro-2-((3aS)-3a,5,5-trimethylhexahydro-4,6-methanobenzo[d][1,3,2]dioxaborol-2-yl)ethyl)-5-fluoro-2-methoxybenzoate (0.74 g, 1.57 mmol) in THF (4.0 mL) under Ar was cooled to −25° C. Lithium bis(trimethylsilyl)amide (1.0 M in THF, 1.7 mL, 1.70 mmol) was added dropwise and upon complete addition, the reaction was warmed to room temperature and stirred for 1 h. In a separate flask, HATU (0.63 g, 1.66 mmol) and N-methylmorpholine (0.20 mL, 1.82 mmol) were added to a solution of 2-(2-(((benzyloxy)carbonyl)amino)thiazol-4-yl)-2-(4-ethyl-2,3-dioxopiperazine-1-carboxamido)acetic acid (Example 5, Steps 1-4) (0.72 g, 1.51 mmol) in N,N-dimethylacetamide (4.0 mL) and the reaction stirred at room temperature for 85 min. To this solution was added the original reaction mixture and the resulting reaction mixture was stirred at room temperature for 17.5 h. The reaction was quenched with water and extracted two times with ethyl ether. The combined organic layers were washed with brine, dried over MgSO$_4$, filtered, and concentrated. Column chromatography (5-100% Ethyl Acetate/Hexane) afforded the title compound (0.26 g, 19%). ESI-MS m/z 905 (MH)$^+$.

Step 8. Synthesis of (3R)-3-(2-(2-aminothiazol-4-yl)-2-(4-ethyl-2,3-dioxopiperazine-1-carboxamido)acetamido)-6-fluoro-2-hydroxy-3,4-dihydro-2H-benzo[e][1,2]oxaborinine-8-carboxylic acid

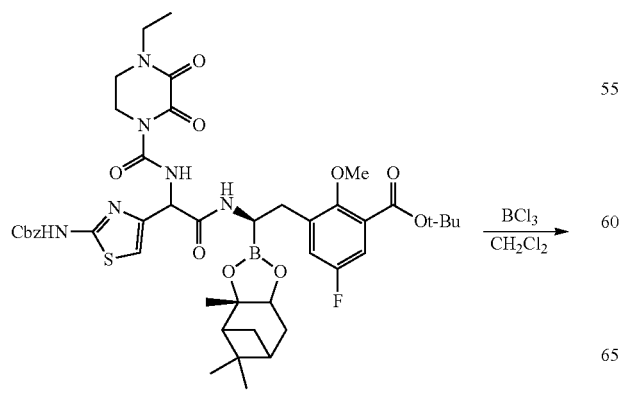

-continued

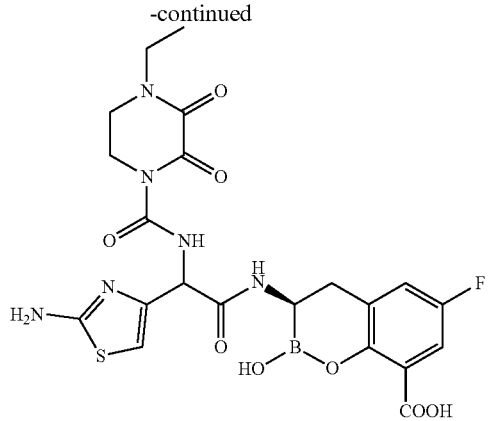

The title compound was prepared by treatment of the above product with BCl$_3$ by following General Method A. ESI-MS m/z 549 (MH)$^+$.

Example 17: (R)-3-((R)-4-amino-2-(4-ethyl-2,3-dioxopiperazine-1-carboxamido)butanamido)-2-hydroxy-3,4-dihydro-2H-benzo[e][1,2]oxaborinine-8-carboxylic acid, trifluoroacetic acid salt

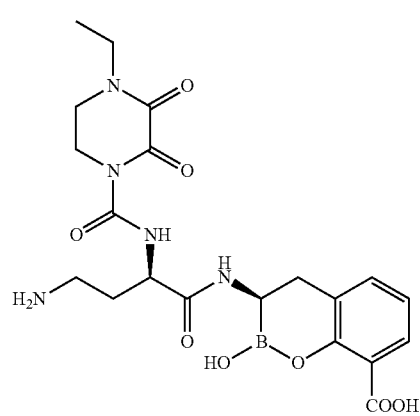 [SMILES: CCN1CCN(C(=O)N[C@H](CCN)C(=O)N[C@H]2Cc3cccc(C(=O)O)c3OB2O)C(=O)C1=O]

The title compound was prepared from (R)-2-amino-4-((tert-butoxycarbonyl)amino)butanoic acid and 3-((2S)-2-chloro-2-((3aS,4S,6S)-3a,5,5-trimethylhexahydro-4,6-methanobenzo[d][1,3,2]dioxaborol-2-yl)ethyl)-2-methoxybenzoate, by a procedure similar to Example 8. ESI-MS m/z 476.2 (M+H)$^+$.

Example 18: (3R)-3-(2-(2-aminothiazol-4-yl)-2-(4-ethyl-3-oxopiperazine-1-carboxamido)acetamido)-2-hydroxy-3,4-dihydro-2H-benzo[e][1,2]oxaborinine-8-carboxylic acid

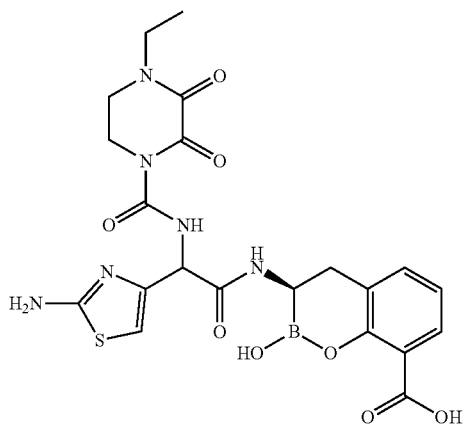 [SMILES: CCN1CCN(C(=O)NC(C(=O)N[C@H]2Cc3cccc(C(=O)O)c3OB2O)c2csc(N)n2)C(=O)C1=O]

Step 1. Synthesis of 4-ethyl-3-oxopiperazine-1-carboxylic acid

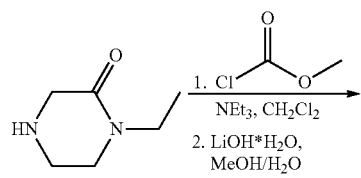

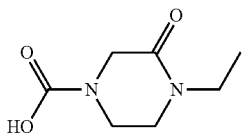

To a solution of 1-ethylpiperazin-2-one (1.08 g, 8.43 mmol) in DCM (38 mL) under Ar was added triethylamine (5.9 mL, 42.3 mmol) and methyl chloroformate (2.0 mL, 25.9 mmol). The reaction mixture was stirred at room temperature for 18 h. The reaction mixture was concentrated then redissolved in methanol (20 mL) and water (20 mL). Lithium hydroxide (1.33 g, 31.6 mmol) was added and the reaction was stirred at room temperature for 43 h. The reaction was concentrated and extracted one time with hexane. The aqueous layer was acidified to pH ~2-3 with 1N HCl and extracted three times with ethyl acetate. Combined organic layers were dried over MgSO$_4$, filtered, and concentrated to afford the title compound (0.22 g, 15%).

Step 2. Synthesis of tert-butyl 3-((2R)-2-(2-(((benzyloxy)carbonyl)amino)thiazol-4-yl)-2-(4-ethyl-3-oxopiperazine-1-carboxamido)acetamido)-2-((3aS)-3a,5,5-trimethylhexahydro-4,6-methanobenzo[d][1,3,2]dioxaborol-2-yl)ethyl)-2-methoxybenzoate

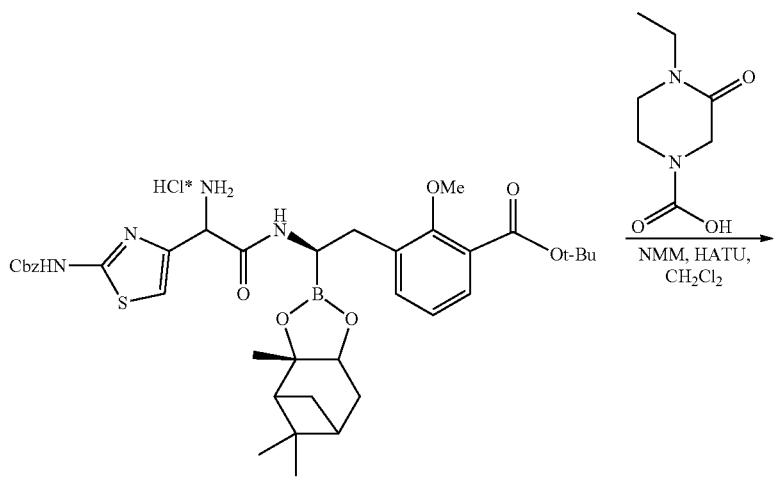

-continued

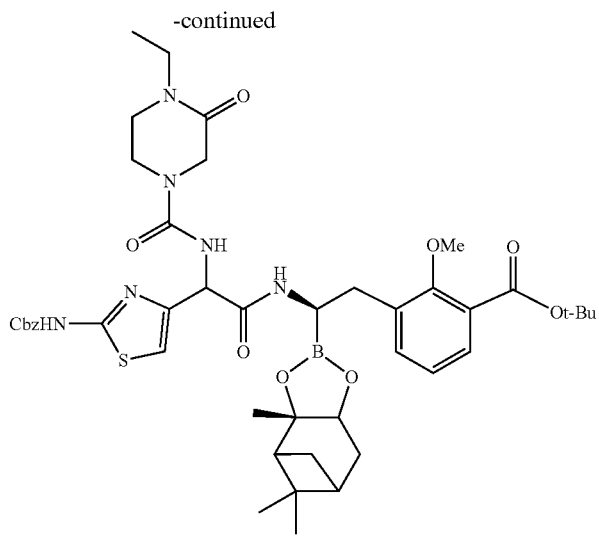

To a suspension of 4-ethyl-3-oxopiperazine-1-carboxylic acid (0.10 g, 0.60 mmol) in DCM (4 mL) under Ar was added HATU (0.25 g, 0.67 mmol) and N-Methylmorpholine (0.07 mL, 0.64 mmol) and the reaction mixture was stirred at room temperature for 75 min. A solution of tert-butyl 3-((2R)-2-(2-amino-2-(2-(((benzyloxy)carbonyl)amino)thiazol-4-yl)acetamido)-2-((3aS,4S,6R)-3a,5,5-trimethylhexahydro-4,6-methanobenzo[d][1,3,2]dioxaborol-2-yl)ethyl)-2-methoxybenzoate (Example 6, Steps 1-2) (0.20 g, 0.27 mmol), N-methylmorpholine (0.10 mL, 0.91 mmol), and DCM (2 mL) was added and the reaction stirred at room temperature for 21 h. The reaction was diluted with water and extracted three times with ethyl acetate. The combined organic layers were washed with brine, dried over MgSO$_4$, filtered, and concentrated. Column chromatography (5-100% Ethyl Acetate/Hexane) afforded the title compound (0.081 g, 35%). ESI-MS m/z 874 (MH)$^+$.

Step 3. Synthesis of (3R)-3-(2-(2-aminothiazol-4-yl)-2-(4-ethyl-3-oxopiperazine-1-carboxamido)acetamido)-2-hydroxy-3,4-dihydro-2H-benzo[e][1,2]oxaborinine-8-carboxylic acid

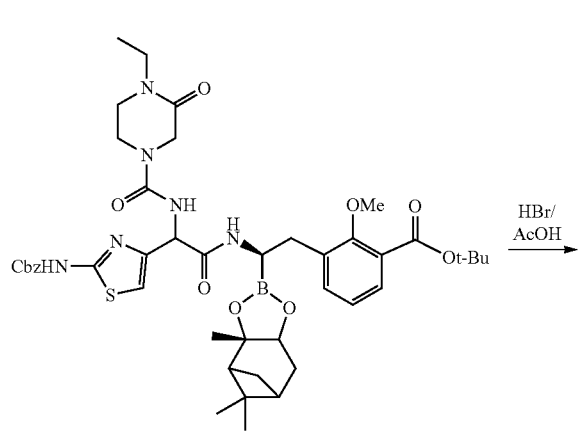

HBr/
AcOH
→

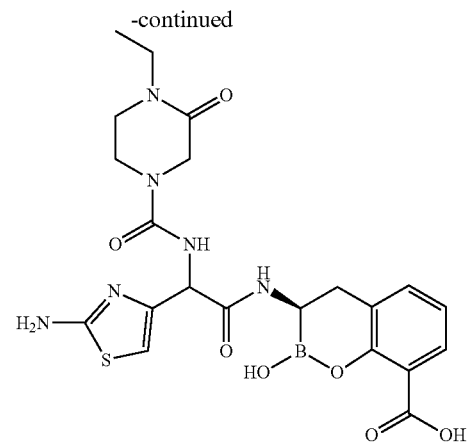

tert-Butyl 3-((2R)-2-(2-(2-(((benzyloxy)carbonyl)amino)thiazol-4-yl)-2-(4-ethyl-3-oxopiperazine-1-carboxamido)acetamido)-2-((3aS)-3a,5,5-trimethylhexahydro-4,6-methanobenzo[d][1,3,2]dioxaborol-2-yl)ethyl)-2-methoxybenzoate (0.081 g, 0.093 mmol) was dissolved in hydrobromic acid (33% in acetic acid, 1.5 mL) under Ar and stirred at room temperature for 21 h. The reaction was diluted with water and purified by preparative HPLC followed by lyophilization to provide the title compound (0.030 g, 62%). ESI-MS m/z 517 (MH)$^+$.

Example 19: (R)-3-((S)-2-amino-4-(4-ethyl-2,3-dioxopiperazin-1-yl)-4-oxobutanamido)-2-hydroxy-3,4-dihydro-2H-benzo[e][1,2]oxaborinine-8-carboxylic acid

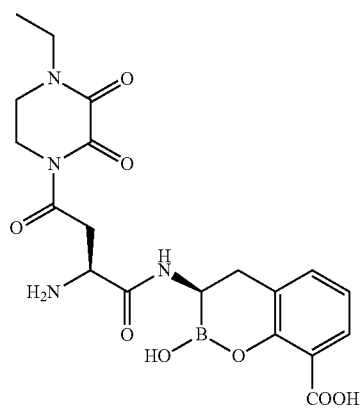 [SMILES: CCN1CCN(C(=O)C[C@H](N)C(=O)N[C@H]2Cc3cccc(C(=O)O)c3OB2O)C(=O)C1=O]

Step 1: Synthesis of benzyl (S)-2-((tert-butoxycarbonyl)amino)-4-(ethyl-2,3-dioxopiperazin-1-yl)-4-oxobutanoate

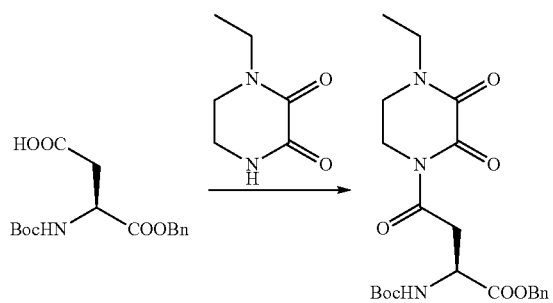

To Boc-Asp-OBzl 5 g (15.5 mmol) in dichloromethane (50 mL) was added triethylamine 6.43 mL (46.4 mmol), followed by HATU 7 g (18.6 mmol) and the mixture was stirred at RT for 30 min. 1-Ethylpiperazine-2,3-dione 2.6 g (18.6 mmol) was added to the reaction in one portion, stirred at RT for 1 h and diluted with dichloromethane. The solution was washed with water/brine, dried over sodium sulfate, concentrated and purified using silica gel chromatography (70-80% ethyl acetate/hexanes) to give the desired compound, 5.64 g. ESI-MS m/z 448 (MH)+.

Step 2: Synthesis of (S)-2-((tert-butoxycarbonyl)amino)-4-(4-ethyl-2,3-dioxopiperzin-1-yl)-4-oxobutanoic acid

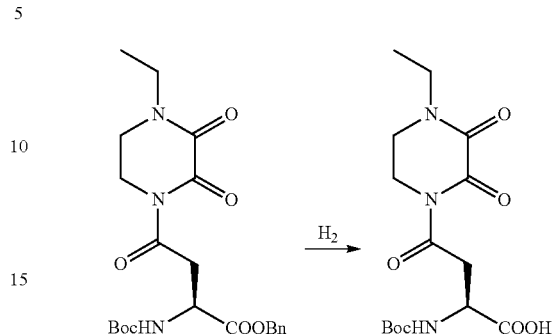

To benzyl (S)-2-((tert-butoxycarbonyl)amino)-4-(ethyl-2,3-dioxopiperazin-1-yl)-4-oxobutanoate 2.8 g (6.26 mmol) in ethyl acetate (20 mL) was added 10% palladium on carbon under an atmosphere of argon and the reaction was stirred under hydrogen at RT for 18 h. The mixture was filtered through celite, washed with ethyl acetate/methanol, concentrated and dried under high vacuum to give the desired compound, 2.24 g. ESI-MS m/z 358 (MH)+.

Step 3: Synthesis of tert-butyl 3-((2R)-2-((S)-2-((tert-butoxycarbonylamino)-4-(4-ethyl-2,3-dioxopiperazin-1-yl)-4-oxobutanamido)-2-((3aS,4S,6R)-3a,5,5-trimethylhexahydro-4,6-methanobenzo[d][1,3,2]dioxaborol-2-yl)ethyl)-2-methoxybenzoate

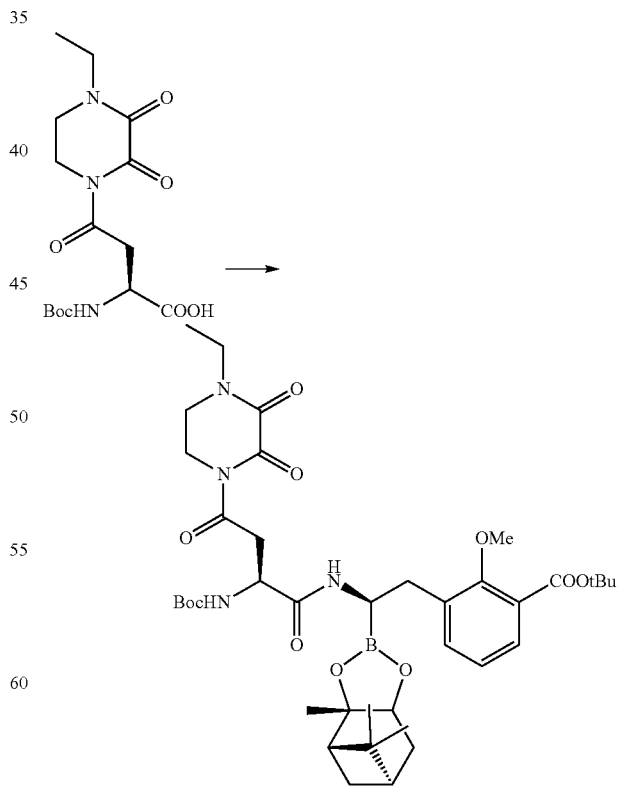

tert-Butyl 3-((2R)-2-((S)-2-((tert-butoxycarbonylamino)-4-(4-ethyl-2,3-dioxopiperazin-1-yl)-4-oxobutanamido)-2-

((3aS,4S,6R)-3a,5,5-trimethylhexahydro-4,6-methanobenzo[d][1,3,2]dioxaborol-2-yl)ethyl)-2-methoxybenzoate was prepared from the above acid by following the General Method C. ESI-MS m/z 769 (MH)⁺.

Step 4: Synthesis of (R)-3-((S)-2-amino-4-(4-ethyl-2,3-dioxopiperazin-1-yl)-4-oxobutanamido)-2-hydroxy-3,4-dihydro-2H-benzo[e][1,2]oxaborinine-8-carboxylic acid

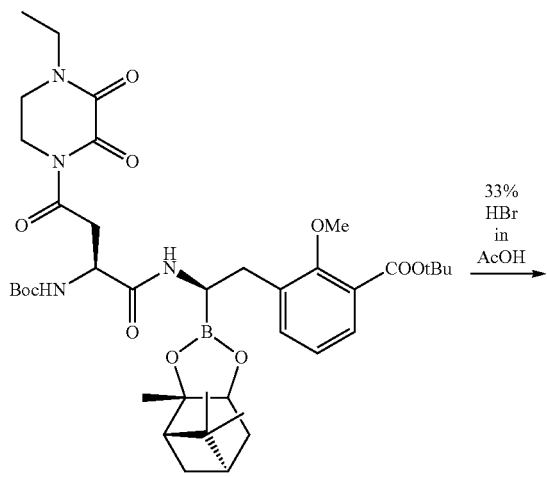

To tert-butyl 3-((2R)-2-((S)-2-((tert-butoxycarbonylamino)-4-(4-ethyl-2,3-dioxopiperazin-1-yl)-4-oxobutanamido)-2-((3aS,4S,6R)-3a,5,5-trimethylhexahydro-4,6-methanobenzo[d][1,3,2]dioxaborol-2-yl)ethyl)-2-methoxybenzoate 0.397 g (0.52 mmol) was added 33% hydrobromic acid in acetic acid (4 mL) and stirred at RT for 18 h. The reaction was quenched with water and methanol, concentrated to remove organics, purified using reverse phase chromatography and stirred with water to give the title compound. ESI-MS m/z 447 (MH)⁺.

Example 20: (3R)-3-(2-(2-aminothiazol-4-yl)-2-(4-ethyl-2,3-dioxopiperazine-1-carboxamido)acetamido)-2-hydroxy-6-methyl-3,4-dihydro-2H-benzo[e][1,2]oxaborinine-8-carboxylic acid

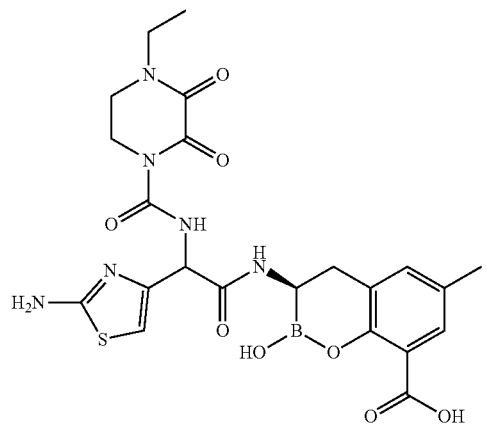 [SMILES: CCN1CCN(C(=O)NC(C(=O)N[C@H]2Cc3cc(C)cc(C(=O)O)c3OB2O)c2csc(N)n2)C(=O)C1=O]

The title compound was synthesized following the procedures in Example 16, Steps 1-7 and Example 18, Step 3. ESI-MS m/z 545 (MH)⁺.

Example 21: (3R)-3-(2-(3,4-dimethoxyphenyl)-2-(4-ethyl-2,3-dioxopiperazine-1-carboxamido)acetamido)-2-hydroxy-3,4-dihydro-2H-benzo[e][1,2]oxaborinine-8-carboxylic acid

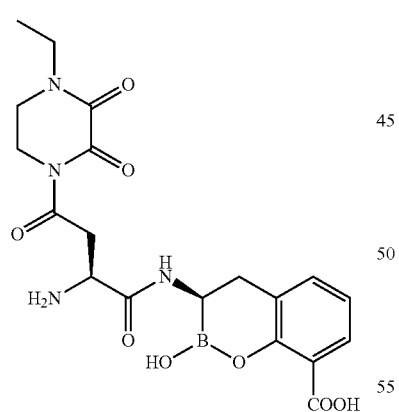

In a similar manner to the synthesis of Example 5, utilizing 2-amino-2-(3,4-dimethoxyphenyl)acetic acid in place of 2-amino-2-(2-(((benzyloxy)carbonyl)amino)thiazol-4-yl)acetic acid in Step 4, and utilizing BCl₃ in the final deprotection reaction, the title compound was prepared. ESI-MS m/z 569 (MH)⁺.

Example 22: (3R)-3-(2-(3,4-dihydroxyphenyl)-2-(4-ethyl-2,3-dioxopiperazine-1-carboxamido)acetamido)-2-hydroxy-3,4-dihydro-2H-benzo[e][1,2]oxaborinine-8-carboxylic acid

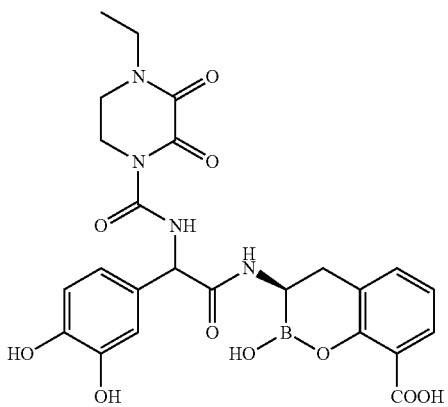

In a similar manner to the synthesis of Example 21, utilizing BBr$_3$ in the final deprotection reaction in place of BCl$_3$, the title compound was prepared. ESI-MS m/z 541 (MH)$^+$.

Example 23: (R)-3-((R)-3-carboxy-2-(4-ethyl-2,3-dioxopiperazine-1-carboxamido)propanamido)-2-hydroxy-3,4-dihydro-2H-benzo[e][1,2]oxaborinine-8-carboxylic acid

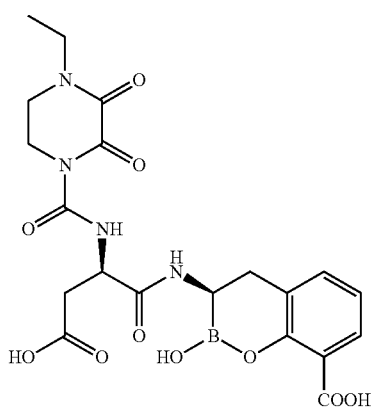 [SMILES: CCN1CCN(C(=O)N[C@H](CC(=O)O)C(=O)N[C@H]2Cc3cccc(C(=O)O)c3OB2O)C(=O)C1=O]

The title compound was prepared from (R)-2-amino-4-(tert-butoxy)-4-oxobutanoic acid and 3-((2S)-2-chloro-2-((3aS,4S,6S)-3a,5,5-trimethylhexahydro-4,6-methanobenzo[d][1,3,2]dioxaborol-2-yl)ethyl)-2-methoxybenzoate, by a procedure similar to Example 8. ESI-MS m/z 491.2 (M+H)$^+$.

Example 24: (R)-3-((S)-3-carboxy-2-(4-ethyl-2,3-dioxopiperazine-1-carboxamido)propanamido)-2-hydroxy-3,4-dihydro-2H-benzo[e][1,2]oxaborinine-8-carboxylic acid

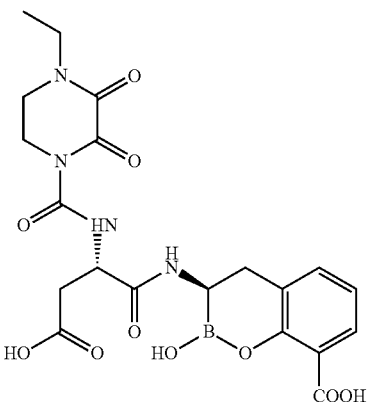 [SMILES: CCN1CCN(C(=O)N[C@@H](CC(=O)O)C(=O)N[C@H]2Cc3cccc(C(=O)O)c3OB2O)C(=O)C1=O]

The title compound was isolated from the procedure for Example 23, as the later eluting epimer in reverse phase HPLC. ESI-MS m/z 491.2 (M+H)$^+$.

Example 25: (3R)-3-(2-(2-aminothiazol-4-yl)-2-(2,3-dihydroxybenzamido)acetamido)-2-hydroxy-3,4-dihydro-2H-benzo[e][1,2]oxaborinine-8-carboxylic acid

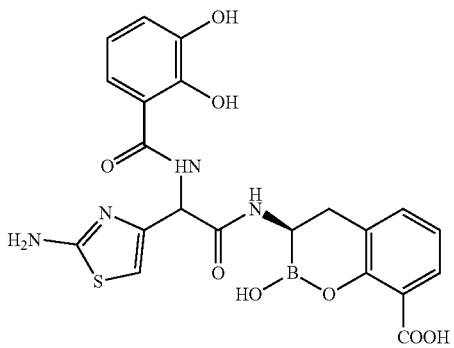 [SMILES: Nc1nc(C(NC(=O)c2cccc(O)c2O)C(=O)N[C@H]2Cc3cccc(C(=O)O)c3OB2O)cs1]

In a similar manner to previously described, utilizing 2,3-dimethoxybenzoic acid in place of 2-methoxyisonicotinic acid in Step 1, the title compound was prepared. ESI-MS m/z 499 (MH)$^+$.

Example 26: (3R)-3-(2-(4-ethyl-2,3-dioxopiperazine-1-carboxamido)-2-(4-methoxyphenyl)acetamido)-2-hydroxy-3,4-dihydro-2H-benzo[e][1,2]oxaborinine-8-carboxylic acid

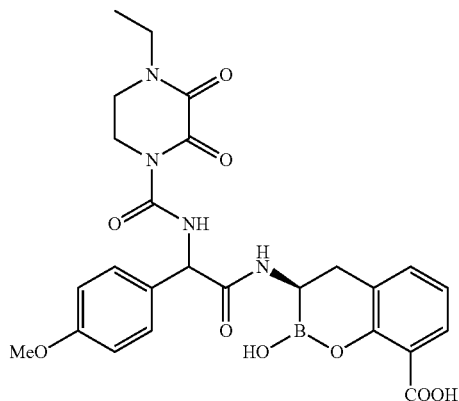 [SMILES: CCN1CCN(C(=O)NC(C(=O)N[C@H]2Cc3cccc(C(=O)O)c3OB2O)c2ccc(OC)cc2)C(=O)C1=O]

In a similar manner to the synthesis of Example 5, utilizing 2-amino-2-(4-methoxyphenyl)acetic acid in place of 2-amino-2-(2-(((benzyloxy)carbonyl)amino)thiazol-4-yl) acetic acid in Step 4, and utilizing BCl₃ in the final deprotection reaction, the title compound was prepared. ESI-MS m/z 539 (MH)⁺.

Example 27: (3R)-3-(2-(4-ethyl-2,3-dioxopiperazine-1-carboxamido)-2-(4-hydroxyphenyl)acetamido)-2-hydroxy-3,4-dihydro-2H-benzo[e][1,2]oxaborinine-8-carboxylic acid

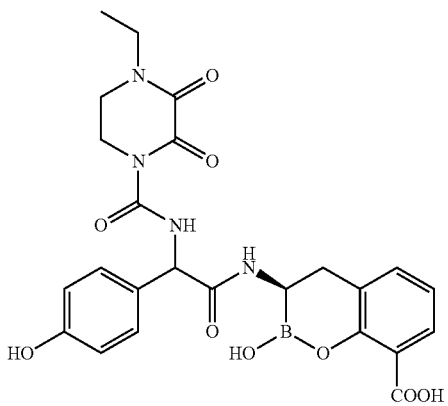 [SMILES: CCN1CCN(C(=O)NC(C(=O)N[C@H]2Cc3cccc(C(=O)O)c3OB2O)c2ccc(O)cc2)C(=O)C1=O]

In a similar manner to the synthesis of Example 26, utilizing BBr₃ in the final deprotection reaction in place of BCl₃, the title compound was prepared. ESI-MS m/z 525 (MH)⁺.

Example 28: (R)-3-((2R,4R)-1-(4-ethyl-2,3-dioxopiperazine-1-carbonyl)-4-hydroxypyrrolidine-2-carboxamido)-2-hydroxy-3,4-dihydro-2H-benzo[e][1,2]oxaborinine-8-carboxylic acid

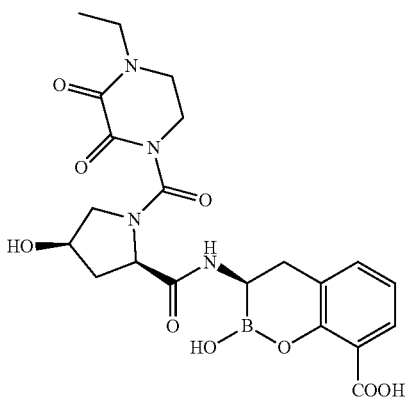 [SMILES: CCN1CCN(C(=O)N2C[C@H](O)C[C@@H]2C(=O)N[C@H]2Cc3cccc(C(=O)O)c3OB2O)C(=O)C1=O]

The title compound was prepared from cis-4-hydroxy-D-proline and 3-((2S)-2-chloro-2-((3aS,4S,6S)-3a,5,5-trimethylhexahydro-4,6-methanobenzo[d][1,3,2]dioxaborol-2-yl) ethyl)-2-methoxybenzoate, by a procedure similar to Example 8. ESI-MS m/z 489.2 (M+H)⁺.

Example 29: (3R)-3-(2-(4-ethyl-2,3-dioxopiperazine-1-carboxamido)-2-(4-hydroxy-3,5-dimethoxyphenyl)acetamido)-2-hydroxy-3,4-dihydro-2H-benzo[e][1,2]oxaborinine-8-carboxylic acid

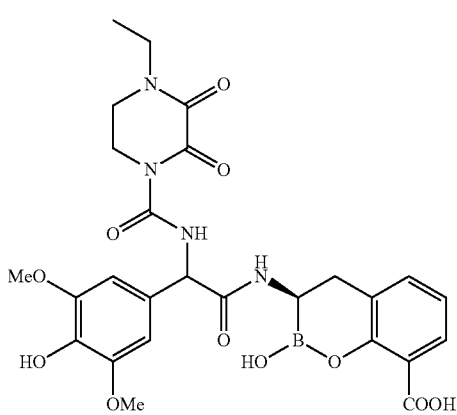

Example 30: (3R)-3-(2-(4-ethyl-2,3-dioxopiperazine-1-carboxamido)-2-(3,4,5-trimethoxyphenyl)acetamido)-2-hydroxy-3,4-dihydro-2H-benzo[e][1,2]oxaborinine-8-carboxylic acid

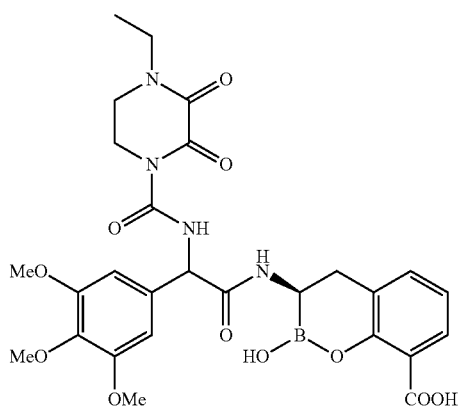 [SMILES: CCN1CCN(C(=O)NC(C(=O)N[C@H]2Cc3cccc(C(=O)O)c3OB2O)c2cc(OC)c(OC)c(OC)c2)C(=O)C1=O]

In a similar manner to the synthesis of Example 5, utilizing 2-amino-2-(3,4,5-trimethoxyphenyl)acetic acid in place of 2-amino-2-(2-(((benzyloxy)carbonyl)amino)thiazol-4-yl)acetic acid in Step 4, and utilizing $BCl_3$ in the final deprotection reaction, the Example 29 and Example 30 were prepared. Example 29: ESI-MS m/z 585 (MH)$^+$, Example 30: ESI-MS m/z 599 (MH)$^+$.

Example 31: (3R)-3-(2-(4-ethyl-2,3-dioxopiperazine-1-carboxamido)-2-(3,4,5-trihydroxyphenyl)acetamido)-2-hydroxy-3,4-dihydro-2H-benzo[e][1,2]oxaborinine-8-carboxylic acid

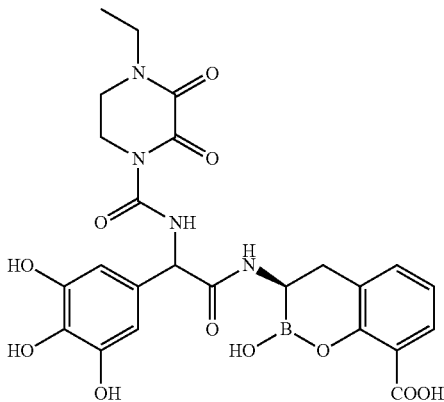 [SMILES: CCN1CCN(C(=O)NC(C(=O)N[C@H]2Cc3cccc(C(=O)O)c3OB2O)c2cc(O)c(O)c(O)c2)C(=O)C1=O]

In a similar manner to the synthesis of Example 29, Example 30, utilizing $BBr_3$ in the final deprotection reaction in place of $BCl_3$, the title compound was prepared. ESI-MS m/z 557 (MH)$^+$.

Example 32: (R)-3-((R)-2-amino-4-(4-ethyl-2,3-dioxopiperazin-1-yl)-4-oxobutanamido)-2-hydroxy-3,4-dihydro-2H-benzo[e][1,2]oxaborinine-8-carboxylic acid

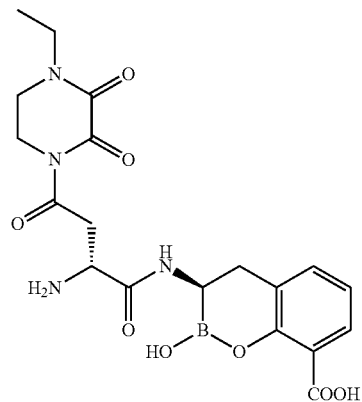 [SMILES: CCN1CCN(C(=O)C[C@@H](N)C(=O)N[C@H]2Cc3cccc(C(=O)O)c3OB2O)C(=O)C1=O]

The title compound was prepared according to the method of Example 19, utilizing (R)-4-(benzyloxy)-3-((tert-butoxycarbonyl)amino)-4-oxobutanoic acid in place of Boc-Asp-OBzl in Step 1. ESI-MS m/z 447 (MH)$^+$.

Example 33: (3R)-3-(2,3-bis(4-ethyl-2,3-dioxopiperazine-1-carboxamido)propanamido)-2-hydroxy-3,4-dihydro-2H-benzo[e][1,2]oxaborinine-8-carboxylic acid

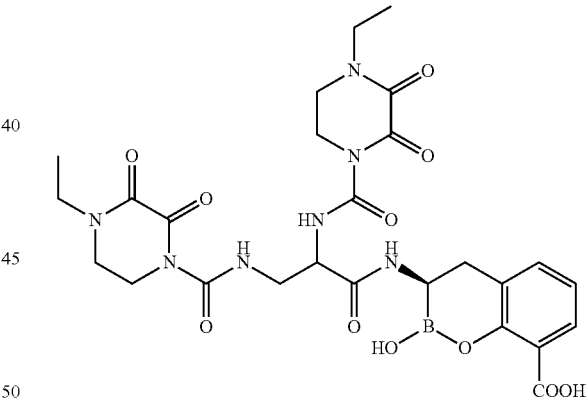

Step 1. Synthesis of tert-butyl 3-((R)-2-((R)-3-((tert-butoxycarbonyl)amino)-2-(4-ethyl-2,3-dioxopiperazine-1-carboxamido)propanamido)-2-((3aS,4S,6S,7aR)-3a,5,5-trimethylhexahydro-4,6-methanobenzo[d][1,3,2]dioxaborol-2-yl)ethyl)-2-methoxybenzoate

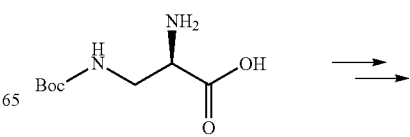

117

-continued

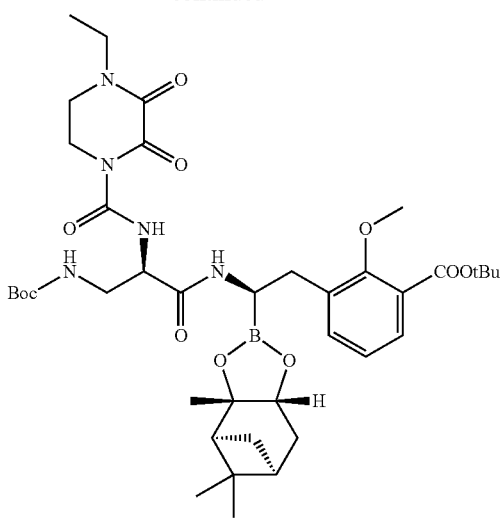

The title compound was prepared from (R)-2-amino-3-((tert-butoxycarbonyl)amino)propanoic acid by following Step 4 of Example 5 and the General Method C. ESI-MS m/z 784 (MH)+.

Step 2. Synthesis of tert-butyl 3-((R)-2-((R)-3-amino-2-(4-ethyl-2,3-dioxopiperazine-1-carboxamido)propanamido)-2-((3aS,4S,6S,7aR)-3a,5,5-trimethylhexahydro-4,6-methanobenzo[d][1,3,2]dioxaborol-2-yl)ethyl)-2-methoxybenzoate

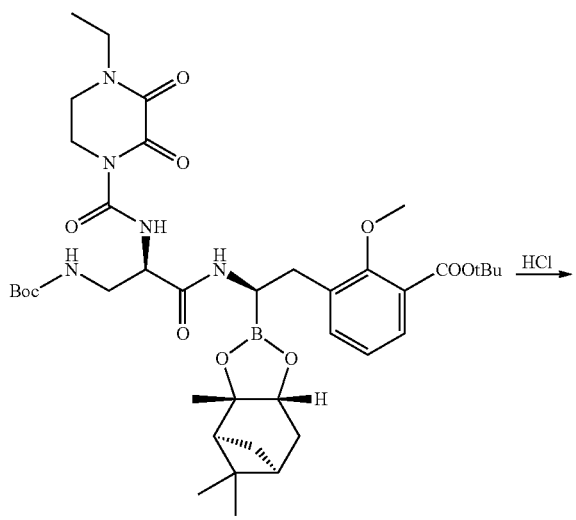

118

-continued

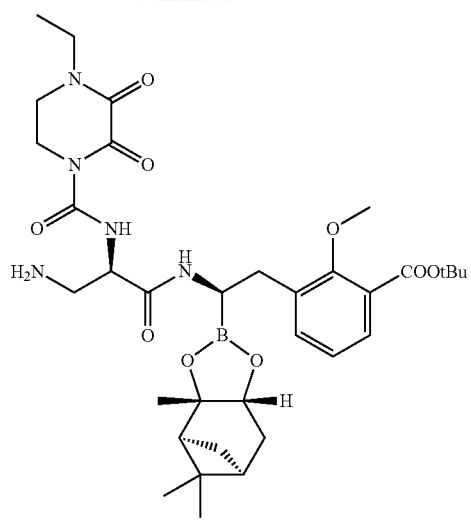

The above product (7.83 g, 10 mmol) was treated with 1.0 M HCl in diethyl ether (200 mL, 200 mmol) at RT overnight, and concentrated in vacuo, the residue was washed with hexane, dried in vacuo to afford the title compound as the HCl salt, which was used directly for the next step without further purification. ESI-MS m/z 684 (MH)+.

Step 3. Synthesis of (3R)-3-(2,3-bis(4-ethyl-2,3-dioxopiperazine-1-carboxamido)propanamido)-2-hydroxy-3,4-dihydro-2H-benzo[e][1,2]oxaborinine-8-carboxylic acid

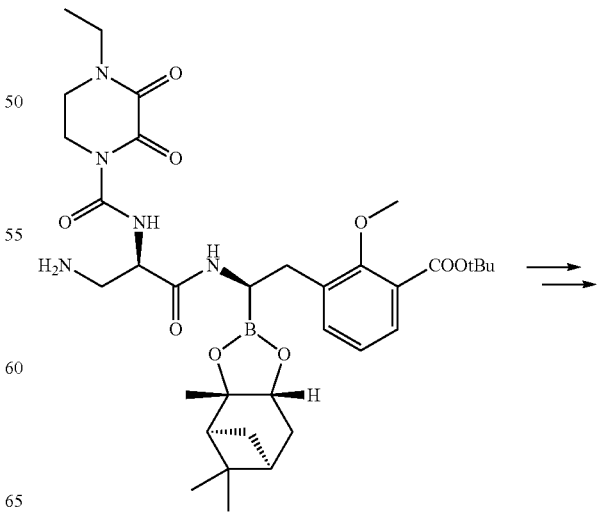

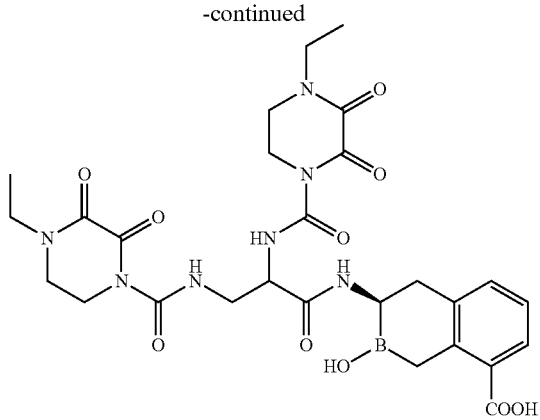

In a similar manner to the synthesis of Example 7, utilizing 4-ethyl-2,3-dioxopiperazine-1-carbonyl chloride in place of pyridine-3-sulfonyl chloride, the title compound was prepared. ESI-MS m/z 630 (MH)+.

Example 34: (3R)-3-(2-(4-ethyl-2,3-dioxopiperazine-1-carboxamido)-2-(6-methoxypyridin-3-yl) acetamido)-2-hydroxy-3,4-dihydro-2H-benzo[e][1,2] oxaborinine-8-carboxylic acid

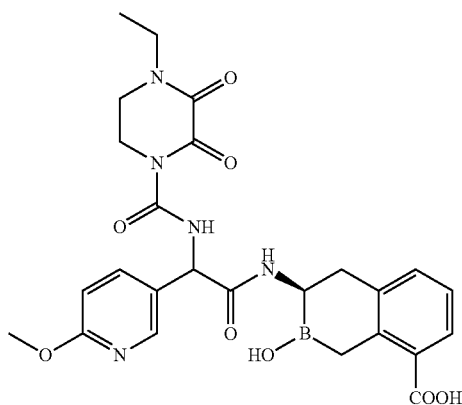 [SMILES: CCN1CCN(C(=O)NC(C(=O)N[C@H]2Cc3cccc(C(=O)O)c3CB2O)c2ccc(OC)nc2)C(=O)C1=O]

Step 1: Synthesis of ethyl 2-((tert-butoxycarbonyl) amino)-2-(6-methoxypyridin-3-yl)acetate

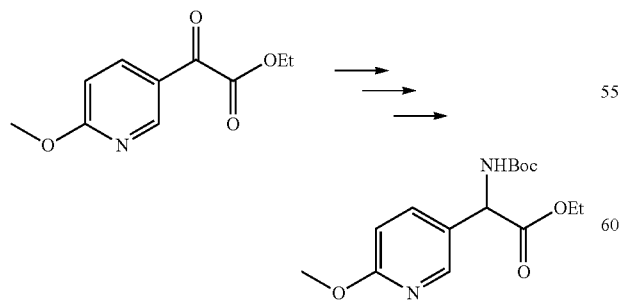

To ethyl 2-(6-methoxypyridin-3-yl)-2-oxoacetate 2 g (9.56 mmol) in methanol (24 mL) at 0° C. was added hydroxylamine hydrochloride 0.86 g (12.4 mmol), followed by pyridine 0.85 mL (10.5 mmol) and the mixture was warmed at RT for 18 h. The reaction was diluted with dichloromethane, washed with 0.5 N HCl, water/brine, dried over sodium sulfate, concentrated and dried under high vacuum to give ethyl-2-(hydroxyimino)-2-(6-methoxypyridin-3-yl)acetate, 1.71 g. ESI-MS m/z 225 (MH)+.

To ethyl-2-(hydroxyimino)-2-(6-methoxypyridin-3-yl)acetate 1.71 g (7.63 mmol) was added 50% formic acid (15 mL) and methanol (8 mL), followed by zinc 1.15 g (17.6 mmol) at 0° C. and the mixture was stirred at this temperature for 3 h. The reaction was filtered through celite and concentrated to dryness to give ethyl 2-amino-2-(6-methoxypyridin-3-yl)acetate. ESI-MS m/z 211 (MH)+.

To ethyl 2-amino-2-(6-methoxypyridin-3-yl)acetate 1.6 g (7.62 mmol) was added water (27 mL) and basified with $K_2CO_3$ to pH 8-9. Tetrahydrofuran (33 mL) was added to the mixture, followed by di-tert-butyl dicarbonate 2 g (9.14 mmol, 1.2 eq) at 0° C. and was warmed at RT for 2 h. The reaction was diluted with ethyl acetate, washed with water/brine, dried over sodium sulfate and concentrated. The product was purified on silica gel (30% ethyl acetate/hexanes) to give the desired compound, 1.87 g. ESI-MS m/z 311 (MH)+.

Step 2: Synthesis of (3R)-3-(2-(4-ethyl-2,3-dioxopiperazine-1-carboxamido)-2-(6-methoxypyridin-3-yl)acetamido)-2-hydroxy-3,4-dihydro-2H-benzo[e][1,2]oxaborinine-8-carboxylic acid

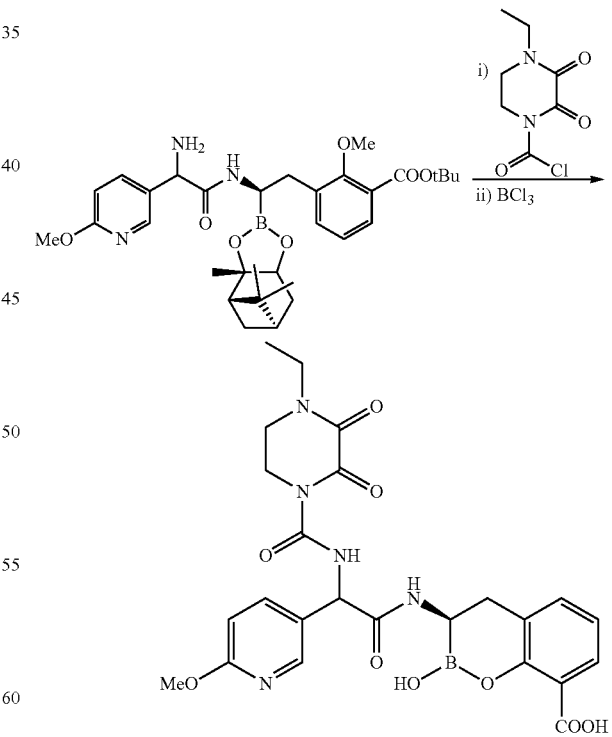

In a similar manner to the synthesis of Example 7 utilizing 4-ethyl-2,3-dioxopiperazine-1-carbonyl chloride in place of pyridine-3-sulfonyl chloride, the title compound was prepared. ESI-MS m/z 540 (MH)+.

Example 35: (3R)-3-(3-(3,4-dihydroxybenzamido)-2-(4-ethyl-2,3-dioxopiperazine-1-carboxamido)propanamido)-2-hydroxy-3,4-dihydro-2H-benzo[e][1,2]oxaborinine-8-carboxylic acid

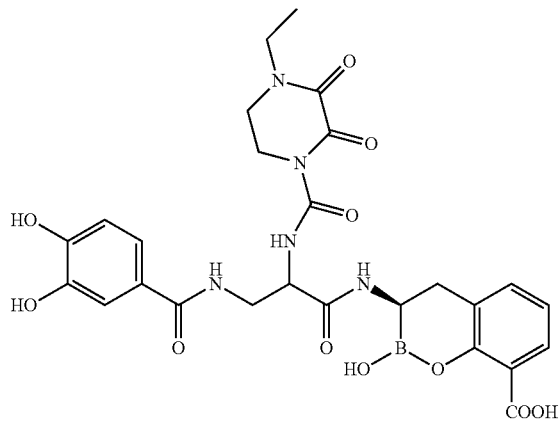 [SMILES: CCN1CCN(C(=O)NC(CNC(=O)c2ccc(O)c(O)c2)C(=O)N[C@H]2Cc3cccc(C(=O)O)c3OB2O)C(=O)C1=O]

In a similar manner to the synthesis of Example 33, utilizing 3,4-dimethoxybenzoyl chloride in place of 4-ethyl-2,3-dioxopiperazine-1-carbonyl chloride, the title compound was prepared. ESI-MS m/z 598 (MH)$^+$.

Example 36: (3R)-3-(3-(2,3-dihydroxybenzamido)-2-(4-ethyl-2,3-dioxopiperazine-1-carboxamido)propanamido)-2-hydroxy-3,4-dihydro-2H-benzo[e][1,2]oxaborinine-8-carboxylic acid

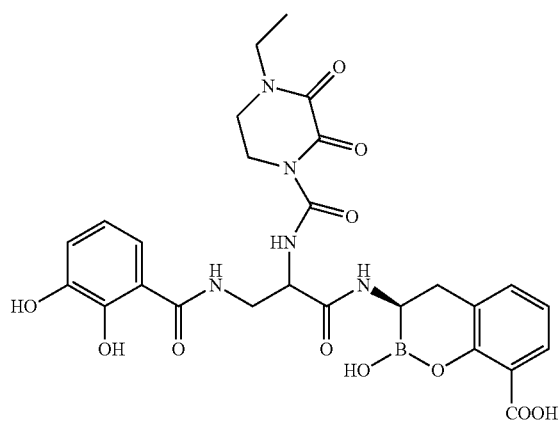 [SMILES: CCN1CCN(C(=O)NC(CNC(=O)c2cccc(O)c2O)C(=O)N[C@H]2Cc3cccc(C(=O)O)c3OB2O)C(=O)C1=O]

In a similar manner to the synthesis of Example 33, utilizing 2,3-dimethoxybenzoyl chloride in place of 4-ethyl-2,3-dioxopiperazine-1-carbonyl chloride, the title compound was prepared. ESI-MS m/z 598 (MH)$^+$.

Example 37: (3R)-3-(2-(2-chloro-3,4-dihydroxyphenyl)-2-(4-ethyl-2,3-dioxopiperazine-1-carboxamido)acetamido)-2-hydroxy-3,4-dihydro-2H-benzo[e][1,2]oxaborinine-8-carboxylic acid

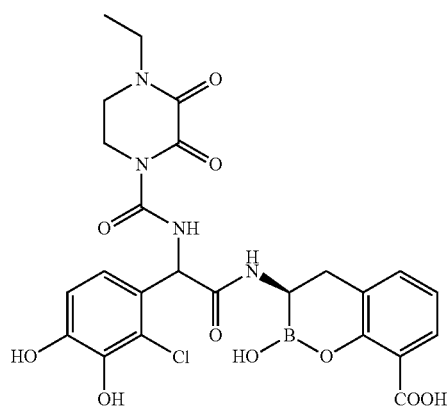 [SMILES: CCN1CCN(C(=O)NC(C(=O)N[C@H]2Cc3cccc(C(=O)O)c3OB2O)c2ccc(O)c(O)c2Cl)C(=O)C1=O]

Step 1. Synthesis of 2-((tert-butoxycarbonyl)amino)-2-(2-chloro-3,4-dimethoxyphenyl)acetic acid

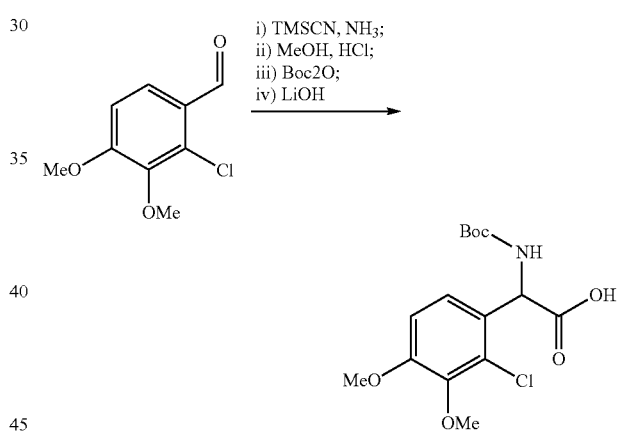

Step 1a

To 2-chloro-3,4-dimethoxybenzaldehyde (6.4 g, 32 mmol) was added 7 N NH$_3$ in methanol (200 mL) at 0° C. followed by TMSCN (5.8 mL, 45.6 mmol). The reaction mixture was stirred at 0° C. for 15 min, then heated at 45° C. for 6.5 h, then concentrated in vacuo.

Step 1b

The crude product was dissolved in methanol (150 mL) and 4 N HCl in dioxane (150 mL), heated at 50° C. for 3 days, then concentrated. The residue was dissolved in DCM, washed with aqueous saturated NaHCO$_3$, dried over Na$_2$SO$_4$, and concentrated in vacuo.

Step 1c

This crude product was dissolved in THF (80 mL), added TEA (5.76 mL, 41 mmol) followed by Boc$_2$O (11.2 g, 51.2 mmol). The reaction mixture was stirred at RT for 2 h, concentrated, and purified by flash chromatography on silica gel (hexane-EtOAc, 10:1-1:1) to afford the title compound, 10.9 g. ESI-MS m/z 382 (M+Na)⁺.

Step 1d

This product (10.9 g, 30.4 mmol) in THF (100 mL), MeOH (100 mL) and water (100 mL) was treated with LiOH·H₂O (6.39 g, 152 mmol) at RT for 1 h, then concentrated, extracted with Et₂O. The aqueous was acidified with 1 N HCl to pH=2-3, extracted with DCM. The organic extracts were combined, dried over Na₂SO₄, and concentrated in vacuo, yielding the title compound, 10.3 g. ESI-MS m/z 368 (M+Na)⁺.

Step 2. Synthesis of tert-butyl 3-((2R)-2-(2-amino-2-(2-chloro-3,4-dimethoxyphenyl)acetamido)-2-((3aS,4S,6S,7aR)-3a,5,5-trimethylhexahydro-4,6-methanobenzo[d][1,3,2]dioxaborol-2-yl)ethyl)-2-methoxybenzoate

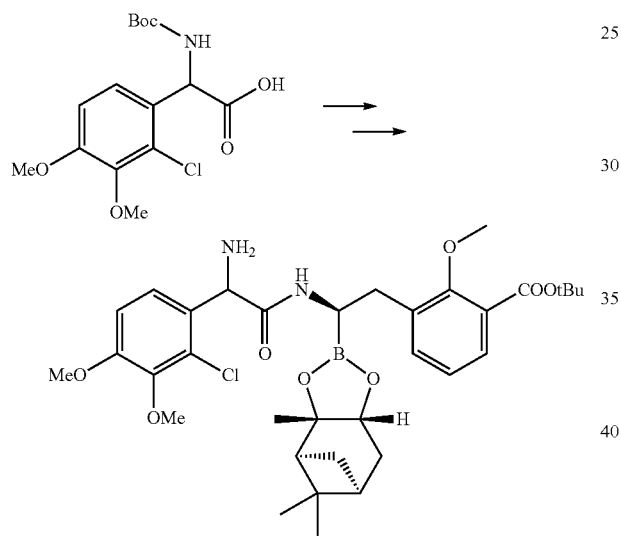

By following the same experimental procedures of Step 1, Step 2 of Example 6, the title compound was prepared from the above product as HCl salt. ESI-MS m/z 657/659 (MH/MH+2)⁺.

Step 3. Synthesis of (3R)-3-(2-(2-chloro-3,4-dihydroxyphenyl)-2-(4-ethyl-2,3-dioxopiperazine-1-carboxamido)acetamido)-2-hydroxy-3,4-dihydro-2H-benzo[e][1,2]oxaborinine-8-carboxylic acid

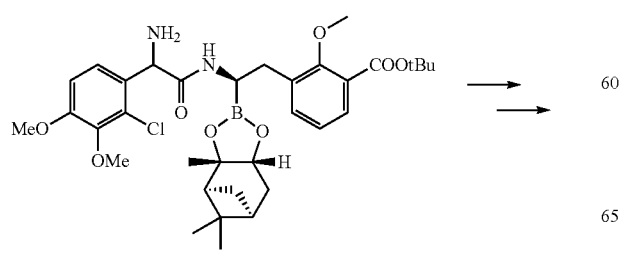

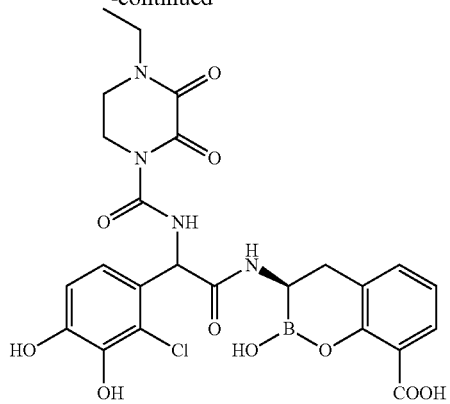

In a similar manner to the synthesis of Example 7, utilizing 4-ethyl-2,3-dioxopiperazine-1-carbonyl chloride in place of pyridine-3-sulfonyl chloride in Step 1, the title compound was prepared from the above amine intermediate. ESI-MS m/z 575/577 (MH/MH+2)⁺.

Example 38: (R)-3-((S)-2-(3,4-dihydroxyphenyl)-2-(4-ethyl-2,3-dioxopiperazine-1-carboxamido)acetamido)-2-hydroxy-3,4-dihydro-2H-benzo[e][1,2]oxaborinine-8-carboxylic acid

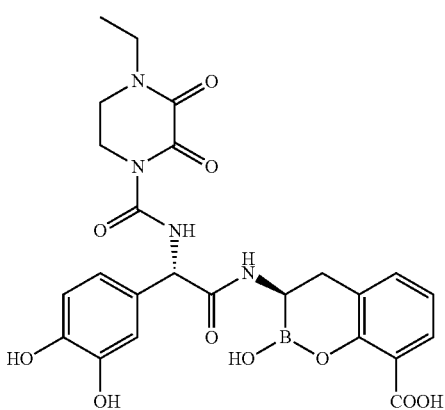 [SMILES: CCN1CCN(C(=O)N[C@H](C(=O)N[C@H]2Cc3cccc(C(=O)O)c3OB2O)c2ccc(O)c(O)c2)C(=O)C1=O]

Example 39: (R)-3-((R)-2-(3,4-dihydroxyphenyl)-2-(4-ethyl-2,3-dioxopiperazine-1-carboxamido)acetamido)-2-hydroxy-3,4-dihydro-2H-benzo[e][1,2]oxaborinine-8-carboxylic acid

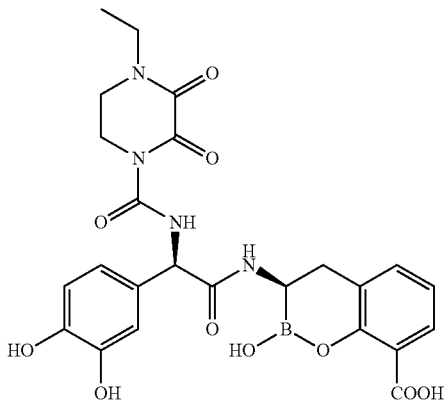 [SMILES: CCN1CCN(C(=O)N[C@@H](C(=O)N[C@H]2Cc3cccc(C(=O)O)c3OB2O)c2ccc(O)c(O)c2)C(=O)C1=O]

The title compounds, Example 38 and Example 39, were prepared by separation of diastereomeric mixture of Example 22 using a Zorbax column from Agilent Technologies (SB-C18 Prep HT column 30×150 mm 5-micron), mobile phase: 10%-30% $CH_3CN$—$H_2O$, flow rate: 45 mL/min, gradient time: 15 min, Example 38 was isolated as the first eluting peak, Example 39 isolated as the second eluting peak. ESI-MS m/z 541 $(M+H)^+$.

Example 40: (R)-3-((R)-3-(3,4-dihydroxyphenyl)-2-(4-ethyl-2,3-dioxopiperazine-1-carboxamido)propanamido)-2-hydroxy-3,4-dihydro-2H-benzo[e][1,2]oxaborinine-8-carboxylic acid

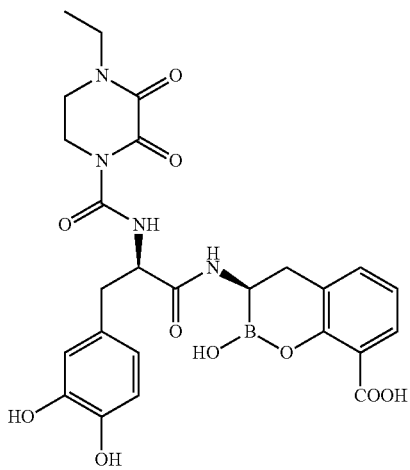 [SMILES: CCN1CCN(C(=O)N[C@H](Cc2ccc(O)c(O)c2)C(=O)N[C@H]2Cc3cccc(C(=O)O)c3OB2O)C(=O)C1=O]

In a similar manner to the synthesis of Example 5 utilizing (R)-2-amino-3-(3,4-dimethoxyphenyl)propanoic acid in place of 2-amino-2-(2-(((benzyloxy)carbonyl)amino)thiazol-4-yl)acetic acid, and utilizing boron tribromide in the final deprotection reaction, the title compound was prepared. ESI-MS m/z 555 $(MH)^+$.

Example 41: (3R)-3-(2-(4-ethyl-2,3-dioxopiperazine-1-carboxamido)-2-(6-hydroxypyridin-3-yl)acetamido)-2-hydroxy-3,4-dihydro-2H-benzo[e][1,2]oxaborinine-8-carboxylic acid

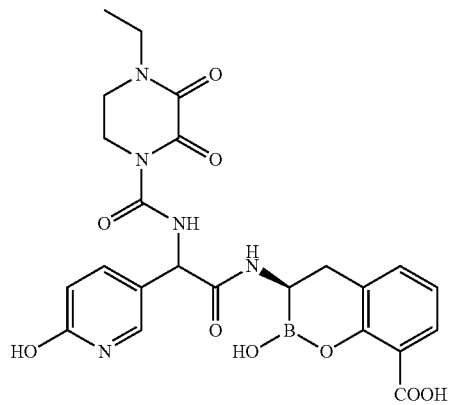 [SMILES: CCN1CCN(C(=O)NC(C(=O)N[C@H]2Cc3cccc(C(=O)O)c3OB2O)c2ccc(O)nc2)C(=O)C1=O]

Step 1: (3R)-3-(2-(4-ethyl-2,3-dioxopiperazine-1-carboxamido)-2-(6-methoxypyridin-3-yl)acetamido)-2-hydroxy-3,4-dihydro-2H-benzo[e][1,2]oxaborinine-8-carboxylic acid

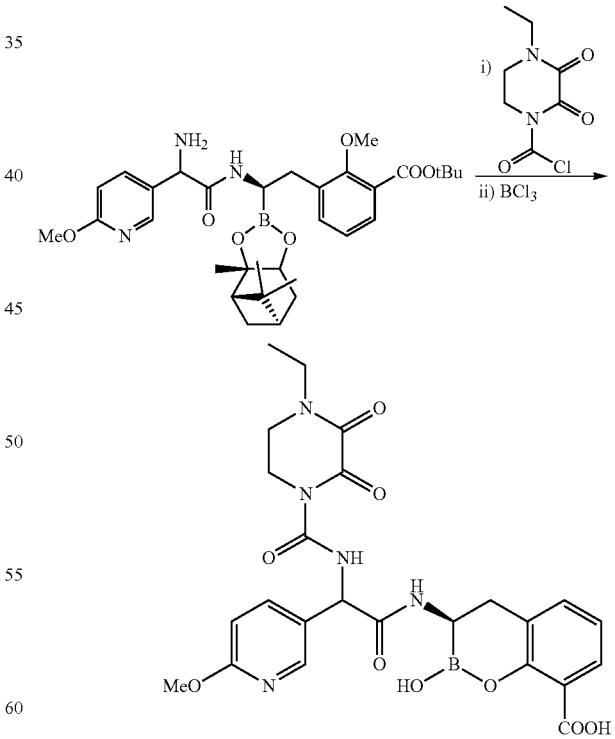

In a similar manner to the synthesis of Example 7 utilizing 4-ethyl-2,3-dioxopiperazine-1-carbonyl chloride in place of pyridine-3-sulfonyl chloride, the desired compound was prepared. ESI-MS m/z 540 $(MH)^+$.

Step 2: (3R)-3-(2-(4-ethyl-2,3-dioxopiperazine-1-carboxamido)-2-(6-hydroxypyridin-3-yl)acetamido)-2-hydroxy-3,4-dihydro-2H-benzo[e][1,2]oxaborinine-8-carboxylic acid Example 42: (3R)-3-(3-(3-bromo-4,5-dihydroxyphenyl)-3-(4-ethyl-2,3-dioxopiperazine-1-carboxamido)propanamido)-2-hydroxy-3,4-dihydro-2H-benzo[e][1,2]oxaborinine-8-carboxylic acid

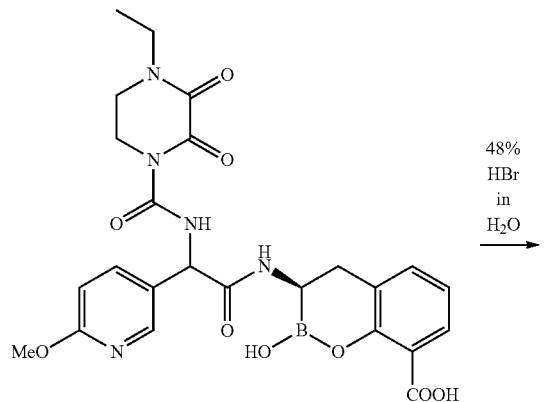

48% HBr in H₂O

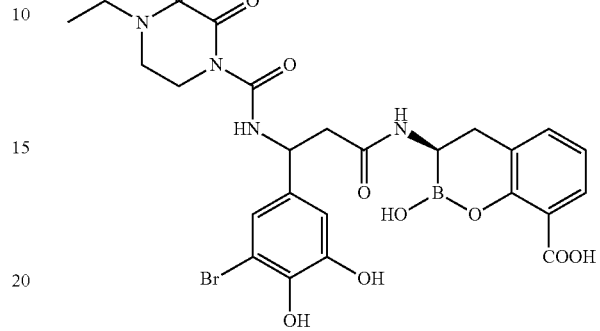

By sequentially following the experimental procedures described in Step 4 of Example 5 utilizing 3-(3,4-dimethoxyphenyl)-DL-beta-alanine in place of 2-amino-2-(2-(((benzyloxy)carbonyl)amino)thiazol-4-yl)acetic acid, the General Method C, and General Method A utilizing BBr₃ for the final deprotection reaction, the title compound was prepared. ESI-MS m/z 633/635 (MH/MH+2)⁺.

Example 43: (3R)-3-(3-(3-chloro-4,5-dihydroxyphenyl)-3-(4-ethyl-2,3-dioxopiperazine-1-carboxamido)propanamido)-2-hydroxy-3,4-dihydro-2H-benzo[e][1,2]oxaborinine-8-carboxylic acid

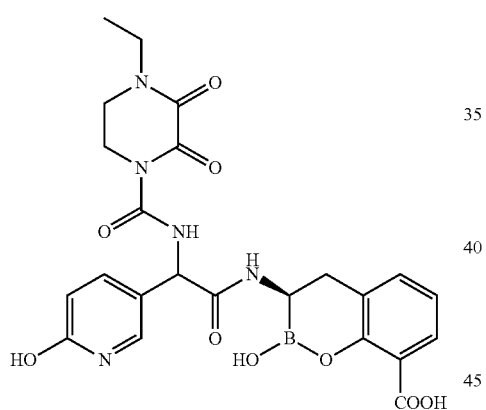

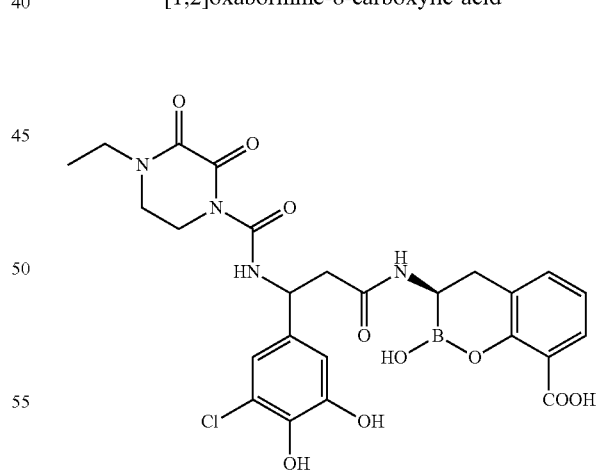

To (3R)-3-(2-(4-ethyl-2,3-dioxopiperazine-1-carboxamido)-2-(6-methoxypyridin-3-yl)acetamido)-2-hydroxy-3,4-dihydro-2H-benzo[e][1,2]oxaborinine-8-carboxylic acid 0.05 g (0.1 mmol) was added 48% hydrogen bromide in water (0.5 mL), followed by ethanol (0.15 mL) and the mixture was heated at 80° C. for 18 h. The reaction was quenched with water and purified using reverse phase chromatography to give the title compound. ESI-MS m/z 526 (MH)⁺.

By sequentially following the experimental procedures described in Step 4 of Example 5 utilizing 3-(3,4-dimethoxyphenyl)-DL-beta-alanine in place of 2-amino-2-(2-(((benzyloxy)carbonyl)amino)thiazol-4-yl)acetic acid, the General Method C, the NCS chlorination reaction as described in Step 1 of Example 13, and deprotection with BBr₃, the title compound was prepared. ESI-MS m/z 589/591 (MH/MH+2)⁺.

Example 44: (3R)-3-(2-(2,3-dihydroxyphenyl)-2-(4-ethyl-2,3-dioxopiperazine-1-carboxamido)acetamido)-2-hydroxy-3,4-dihydro-2H-benzo[e][1,2]oxaborinine-8-carboxylic acid

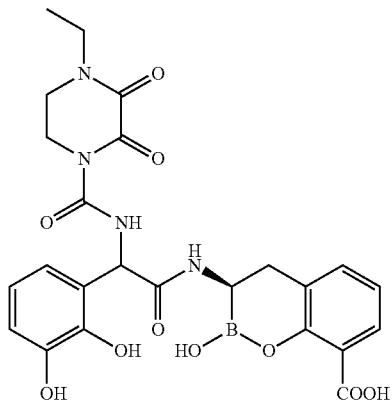 [SMILES: CCN1CCN(C(=O)NC(C(=O)N[C@H]2Cc3cccc(C(=O)O)c3OB2O)c2cccc(O)c2O)C(=O)C1=O]

In a similar manner to the synthesis of Example 5, utilizing 2-amino-2-(2,3-dimethoxyphenyl)acetic acid in place of 2-amino-2-(2-(((benzyloxy)carbonyl)amino)thiazol-4-yl)acetic acid in Step 4, and utilizing BBr$_3$ in the final deprotection reaction, the title compound was prepared. ESI-MS m/z 541 (MH)$^+$.

Example 45: (3R)-3-(2-(3-chloro-4,5-dihydroxyphenyl)-2-(4-ethyl-2,3-dioxopiperazine-1-carboxamido)acetamido)-2-hydroxy-3,4-dihydro-2H-benzo[e][1,2]oxaborinine-8-carboxylic acid

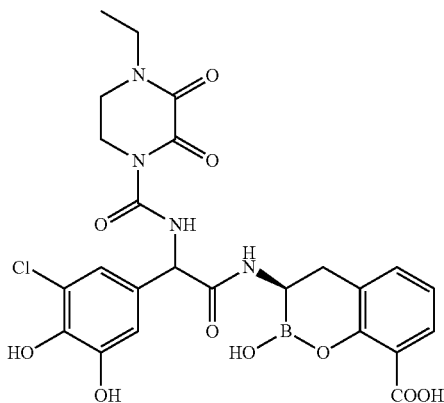 [SMILES: CCN1CCN(C(=O)NC(C(=O)N[C@H]2Cc3cccc(C(=O)O)c3OB2O)c2cc(O)c(O)c(Cl)c2)C(=O)C1=O]

In a similar manner to the synthesis of Example 62, the fully protected precursor of Example 81 and Example 82 was converted to the title compound by treatment with NCS followed by BBr$_3$. ESI-MS m/z 575/577 (MH/MH+2)$^+$.

Example 46: (3R)-3-(3-(3,4-dihydroxyphenyl)-2-(4-ethyl-2,3-dioxopiperazine-1-carboxamido)-3-hydroxypropanamido)-2-hydroxy-3,4-dihydro-2H-benzo[e][1,2]oxaborinine-8-carboxylic acid

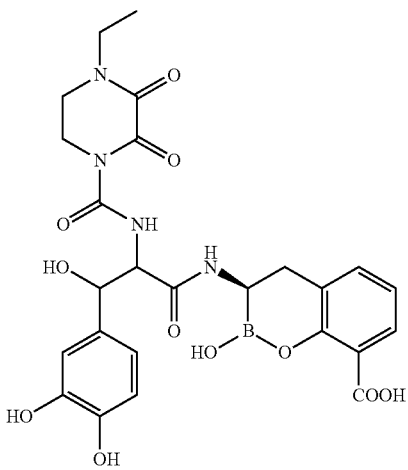 [SMILES: CCN1CCN(C(=O)NC(C(=O)N[C@H]2Cc3cccc(C(=O)O)c3OB2O)C(O)c2ccc(O)c(O)c2)C(=O)C1=O]

The title compound was prepared from 2-amino-3-(3,4-bis(benzyloxy)phenyl)-3-hydroxypropanoic acid and 3-((2S)-2-chloro-2-((3aS,4S,6S)-3a,5,5-trimethylhexahydro-4,6-methanobenzo[d]-[1,3,2]dioxaborol-2-yl)ethyl)-2-methoxybenzoate, by a procedure similar to Example 8. ESI-MS m/z 571.2 (M+H)$^+$.

Example 47: (3R)-3-(3-(2-chloro-3,4-dihydroxyphenyl)-2-(4-ethyl-2,3-dioxopiperazine-1-carboxamido)-3-hydroxypropanamido)-2-hydroxy-3,4-dihydro-2H-benzo[e][1,2]oxaborinine-8-carboxylic acid

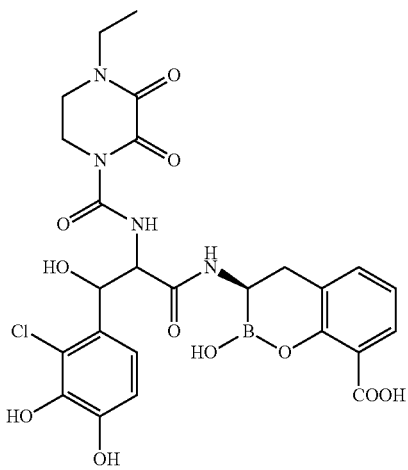 [SMILES: CCN1CCN(C(=O)NC(C(=O)N[C@H]2Cc3cccc(C(=O)O)c3OB2O)C(O)c2ccc(O)c(O)c2Cl)C(=O)C1=O]

The title compound was prepared from 2-amino-3-(2-chloro-3,4-dimethoxyphenyl)-3-hydroxypropanoic acid and 3-((2S)-2-chloro-2-((3aS,4S,6S)-3a,5,5-trimethylhexahydro-4,6-methanobenzo[d]-[1,3,2]dioxaborol-2-yl)ethyl)-2-methoxybenzoate, by a procedure similar to Example 8. ESI-MS m/z 605.1 (M+H)$^+$.

Example 48: (3R)-3-(3-(2,3-dihydroxyphenyl)-2-(4-ethyl-2,3-dioxopiperazine-1-carboxamido)-3-hydroxypropanamido)-2-hydroxy-3,4-dihydro-2H-benzo[e][1,2]oxaborinine-8-carboxylic acid

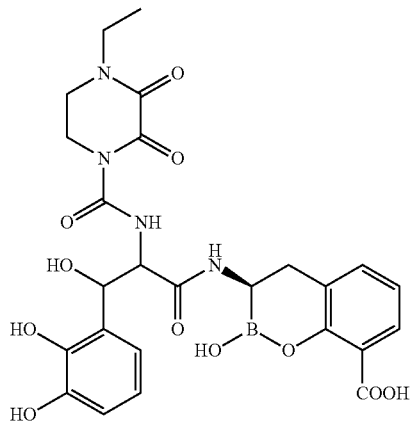 [SMILES: CCN1CCN(C(=O)NC(C(=O)N[C@H]2Cc3cccc(C(=O)O)c3OB2O)C(O)c2cccc(O)c2O)C(=O)C1=O]

The title compound was prepared from 2-amino-3-(2,3-dimethoxyphenyl)-3-hydroxypropanoic acid and 3-((2S)-2-chloro-2-((3aS,4S,6S)-3a,5,5-trimethylhexahydro-4,6-methanobenzo[d]-[1,3,2]dioxaborol-2-yl)ethyl)-2-methoxybenzoate, by a procedure similar to Example 8. ESI-MS m/z 571.2 (M+H)$^+$.

Example 49: (3R)-3-(2-(3-(2-aminoethoxy)-4-hydroxyphenyl)-2-(4-ethyl-2,3-dioxopiperazine-1-carboxamido)acetamido)-2-hydroxy-3,4-dihydro-2H-benzo[e][1,2]oxaborinine-8-carboxylic acid

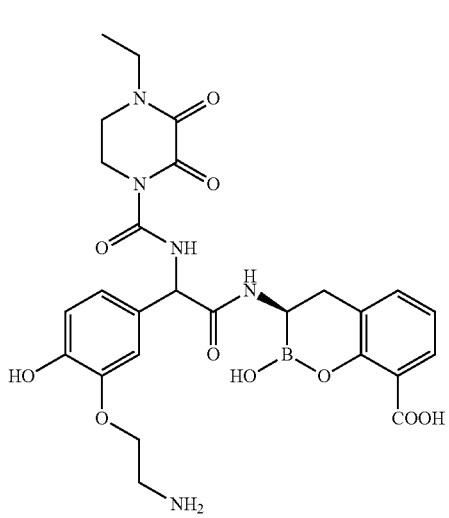 [SMILES: CCN1CCN(C(=O)NC(C(=O)N[C@H]2Cc3cccc(C(=O)O)c3OB2O)c2ccc(O)c(OCCN)c2)C(=O)C1=O]

Example 50: (3R)-3-(2-(3-(2-(((benzyloxy)carbonyl)amino)ethoxy)-4-hydroxyphenyl)-2-(4-ethyl-2,3-dioxopiperazine-1-carboxamido)acetamido)-2-hydroxy-3,4-dihydro-2H-benzo[e][1,2]oxaborinine-8-carboxylic acid

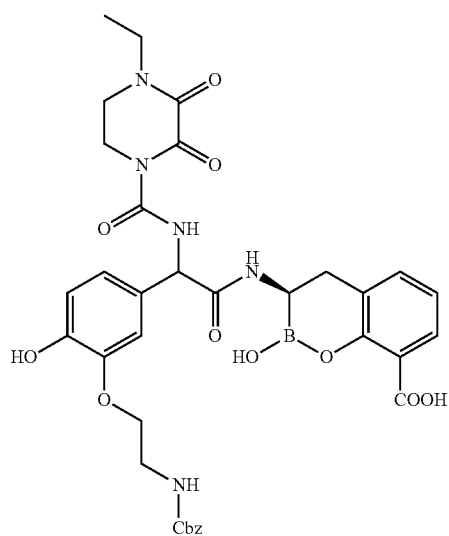 [SMILES: CCN1CCN(C(=O)NC(C(=O)N[C@H]2Cc3cccc(C(=O)O)c3OB2O)c2ccc(O)c(OCCNC(=O)OCc3ccccc3)c2)C(=O)C1=O]

Step 1. Synthesis of benzyl (2-(2-(benzyloxy)-5-formylphenoxy)ethyl)carbamate

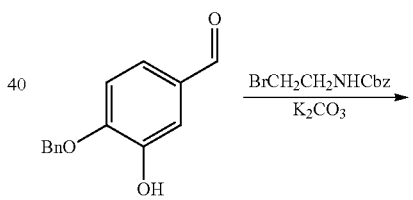

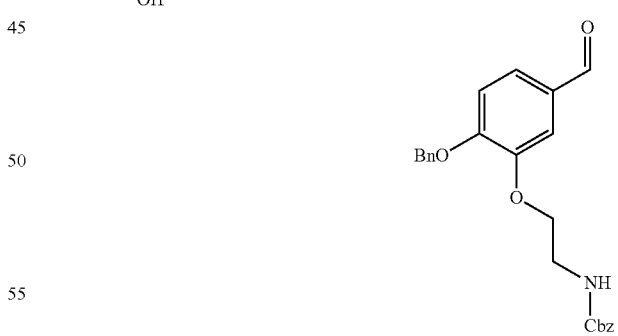

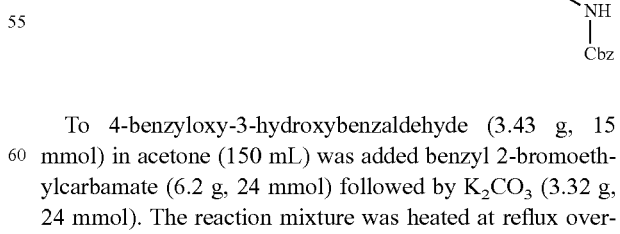

To 4-benzyloxy-3-hydroxybenzaldehyde (3.43 g, 15 mmol) in acetone (150 mL) was added benzyl 2-bromoethylcarbamate (6.2 g, 24 mmol) followed by K$_2$CO$_3$ (3.32 g, 24 mmol). The reaction mixture was heated at reflux overnight, cooled to RT, filtered, the filtrate was concentrated in vacuo. To the residue was added hexane, the solid was collected by filtration, washed with hexane, dried in vacuo to afford the title compound, 5 g. ESI-MS m/z 406 (MH)$^+$.

Step 2. Synthesis of (3R)-3-(2-(3-(2-aminoethoxy)-4-hydroxyphenyl)-2-(4-ethyl-2,3-dioxopiperazine-1-carboxamido)acetamido)-2-hydroxy-3,4-dihydro-2H-benzo[e][1,2]oxaborinine-8-carboxylic acid, and (3R)-3-(2-(3-(2-(((benzyloxy)carbonyl)amino)ethoxy)-4-hydroxyphenyl)-2-(4-ethyl-2,3-dioxoperazine-1-carboxamido)acetamido)-2-hydroxy-3,4-dihydro-2H-benzo[e][1,2]oxaborinine-8-carboxylic acid

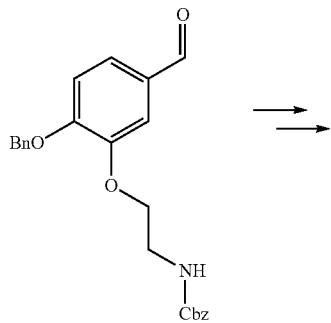

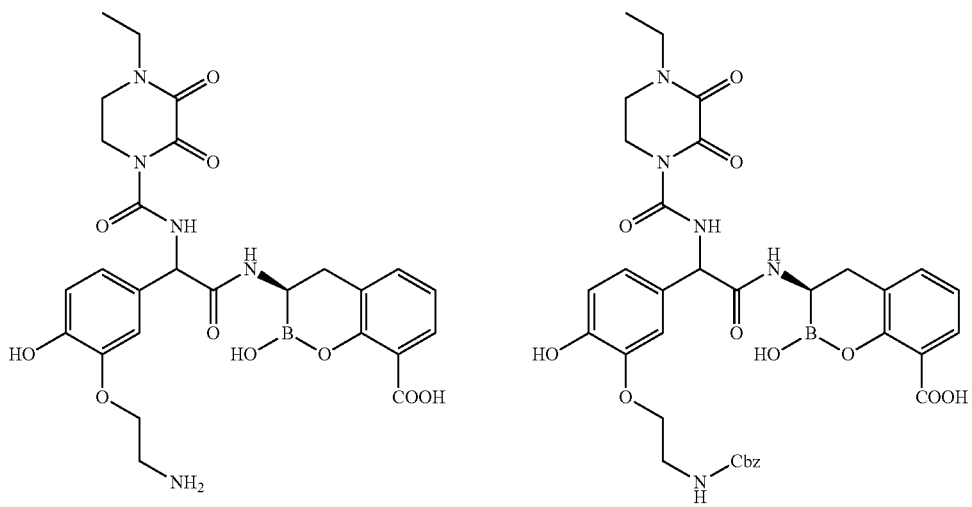

In a similar manner to the synthesis of Example 37, the above aldehyde was converted to the title compounds, Example 49 and Example 50 utilizing $BCl_3$ for the final deprotection reaction.

Example 49: ESI-MS m/z 584 (MH)$^+$; Example 50: ESI-MS m/z 718 (MH)$^+$.

Example 51: (3R)-3-(2-(2-aminothiazol-5-yl)-2-(4-ethyl-2,3-dioxopiperazine-1-carboxamido)acetamido)-2-hydroxy-3,4-dihydro-2H-benzo[e][1,2]oxaborinine-8-carboxylic acid

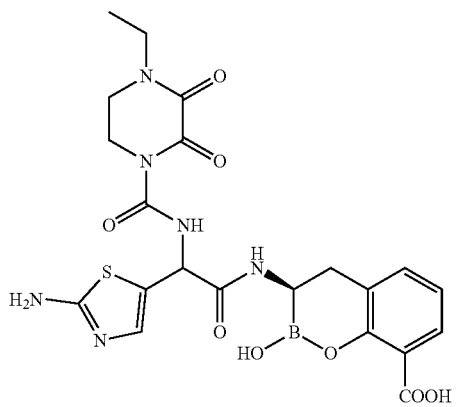 [SMILES: CCN1CCN(C(=O)NC(C(=O)N[C@H]2Cc3cccc(C(=O)O)c3OB2O)c2cnc(N)s2)C(=O)C1=O]

In a similar manner to the synthesis of Example 37, utilizing tert-butyl (5-formylthiazol-2-yl)carbamate in place of 2-chloro-3,4-dimethoxybenzaldehyde in Step 1, the title compound was prepared. ESI-MS m/z 531 (M+H)$^+$.

Example 52: (3R)-3-(2-(2-chloro-3,4-dihydroxyphenyl)-2-(2-oxoimidazolidine-1-carboxamido)acetamido)-2-hydroxy-3,4-dihydro-2H-benzo[e][1,2]oxaborinine-8-carboxylic acid

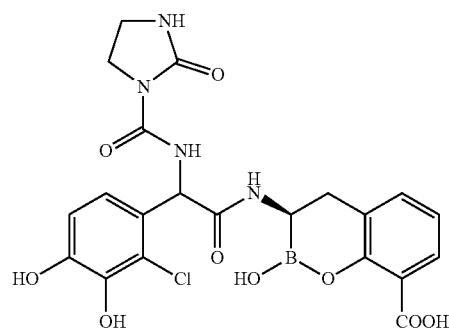 [SMILES: O=C(O)c1cccc2c1OB(O)[C@@H](NC(=O)C(NC(=O)N1CCNC1=O)c1ccc(O)c(O)c1Cl)C2]

In a similar manner to the synthesis of Example 37, utilizing 2-oxoimidazolidine-1-carbonyl chloride in place of 4-ethyl-2,3-dioxopiperazine-1-carbonyl chloride in Step 3, the title compound was prepared. ESI-MS m/z 519/521 (MH/MH+2)$^+$.

Example 53: (R)-3-(3-((4-ethyl-2,3-dioxopiperazine-1-carboxamido)methyl)azetidine-3-carboxamido)-2-hydroxy-3,4-dihydro-2H-benzo[e][1,2]oxaborinine-8-carboxylic acid, trifluoroacetic acid salt

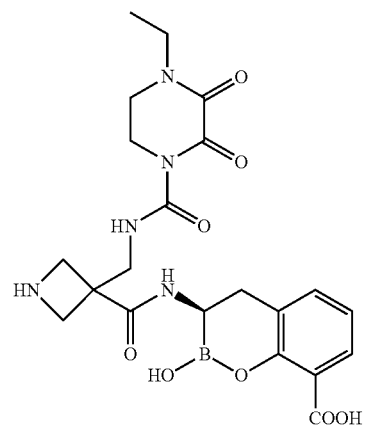 [SMILES: CCN1CCN(C(=O)NCC2(C(=O)N[C@H]3Cc4cccc(C(=O)O)c4OB3O)CNC2)C(=O)C1=O]

The title compound was prepared from 3-(aminomethyl)-1-(tert-butoxycarbonyl)azetidine-3-carboxylic acid hydrochloride salt and 3-((2S)-2-chloro-2-((3aS,4S,6S)-3a,5,5-trimethylhexahydro-4,6-methanobenzo-[d][1,3,2]dioxaborol-2-yl)ethyl)-2-methoxybenzoate, by a procedure similar to Example 8. ESI-MS m/z 488.2 (M+H)$^+$.

Example 54: (3R)-3-(2-(3,5-dimethyl-1H-pyrazol-4-yl)-2-(4-ethyl-2,3-dioxopiperazine-1-carboxamido)acetamido)-2-hydroxy-3,4-dihydro-2H-benzo[e][1,2]oxaborinine-8-carboxylic acid, trifluoroacetic acid salt

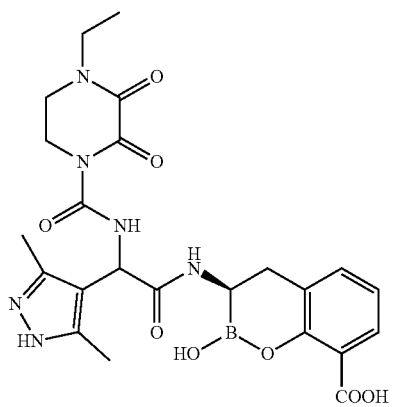 [SMILES: CCN1CCN(C(=O)NC(C(=O)N[C@H]2Cc3cccc(C(=O)O)c3OB2O)c2c(C)n[nH]c2C)C(=O)C1=O]

The title compound was prepared from 2-amino-2-(3,5-dimethyl-1H-pyrazol-4-yl)acetic acid and 3-((2S)-2-chloro-2-((3aS,4S,6S)-3a,5,5-trimethylhexahydro-4,6-methano-benzo-[d][1,3,2]dioxaborol-2-yl)ethyl)-2-methoxybenzoate, by a procedure similar to Example 8. ESI-MS m/z 527.2 (M+H)$^+$.

Example 55: (3R)-3-(2-(4-ethyl-2,3-dioxopiperazine-1-carboxamido)-2-(pyrrolidin-3-yl)acetamido)-2-hydroxy-3,4-dihydro-2H-benzo[e][1,2]oxaborinine-8-carboxylic acid, trifluoroacetic acid salt

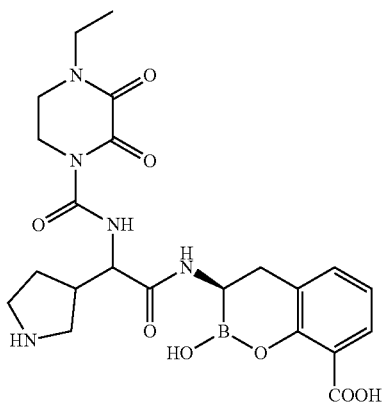 [SMILES: CCN1CCN(C(=O)NC(C(=O)N[C@H]2Cc3cccc(C(=O)O)c3OB2O)C2CCNC2)C(=O)C1=O]

The title compound was prepared from 2-amino-2-(1-(tert-butoxycarbonyl)pyrrolidin-3-yl)acetic acid and 3-((2S)-2-chloro-2-((3aS,4S,6S)-3a,5,5-trimethylhexahydro-4,6-methanobenzo-[d][1,3,2]dioxaborol-2-yl)ethyl)-2-methoxybenzoate, by a procedure similar to Example 8. ESI-MS m/z 502.2 (M+H)⁺.

Example 56: (3R)-3-(2-(4-ethyl-2,3-dioxopiperazine-1-carboxamido)-2-(pyridin-2-yl)acetamido)-2-hydroxy-3,4-dihydro-2H-benzo[e][1,2]oxaborinine-8-carboxylic acid

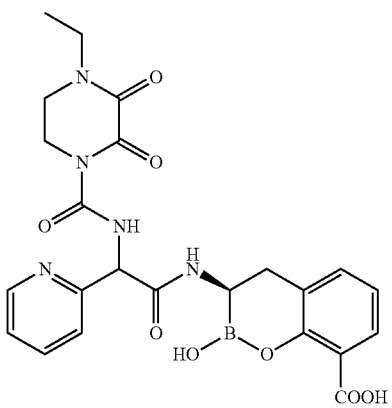

Step 1: Synthesis of lithium 2-((tert-butoxycarbonyl)amino)-2-(pyridin-2-yl)acetate

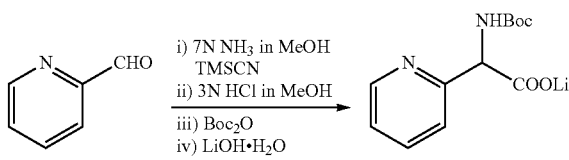

To picolinaldehyde 2.00 g (18.7 mmol) at 0° C. was added 7 N ammonia in methanol (59 mL), followed by trimethylsilyl cyanide 3.51 mL (28 mmol, 1.5 eq), stirred at 45° C. for 7 h and concentrated in vacuo. The crude product was dissolved in 3N hydrochloric acid in methanol (54 mL), stirred at 50° C. for 18 h and concentrated in vacuo to give the HCl salt. The reaction was slurried in tetrahydrofuran (40 mL) and cooled at 0° C. Triethylamine 8 mL (56 mmol, 3 eq) was added, followed by di-tert-butyl dicarbonate 6.11 g (28 mmol, 1.5 eq), warmed at RT for 1 h and concentrated in vacuo. The product was purified by flash chromatography on silica gel (20-30% ethyl acetate/hexanes) to give the desired product, 3.64 g. Methyl 2-((tert-butoxycarbonyl)amino)-2-(pyridin-2-yl)acetate 3.64 g (13.7 mmol) was dissolved in tetrahydrofuran (30 mL)/H₂O (30 mL), followed by lithium hydroxide monohydrate 0.689 g (16.4 mmol, 1.5 eq) and was stirred at RT for 2 h and concentrated. The product was azeotroped with toluene and dried under high vacuum for 18 h to give the title compound, 3.53 g. ESI-MS m/z 253 (M+H)⁺.

Step 2: Synthesis of (3R)-3-(2-(4-ethyl-2,3-dioxopiperazine-1-carboxamido)-2-(pyridin-2-yl)acetamido)-2-hydroxy-3,4-dihydro-2H-benzo[e][1,2]oxaborinine-8-carboxylic acid

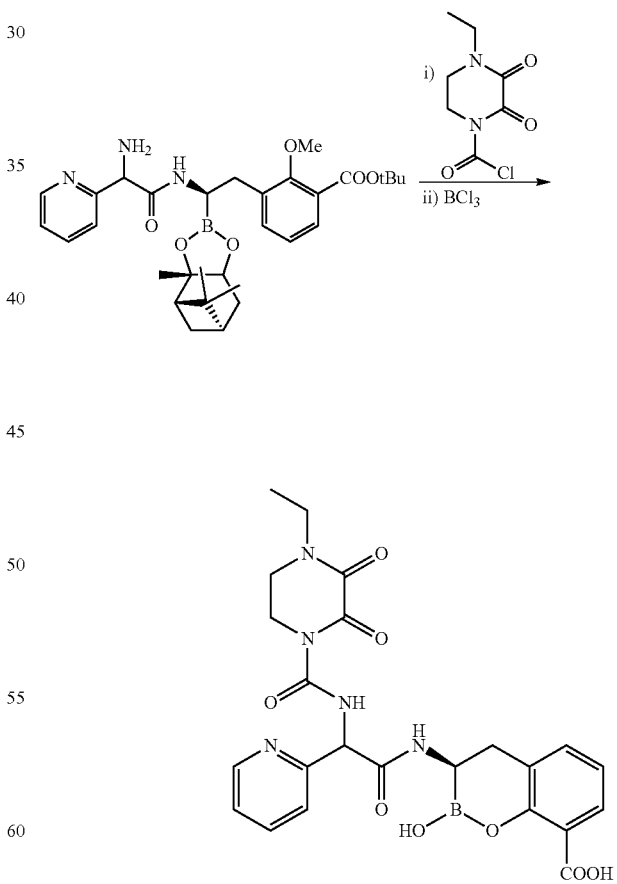

In a similar manner to the synthesis of Example 7 utilizing 4-ethyl-2,3-dioxopiperazine-1-carbonylchloride in place of pyridine-3-sulfonyl chloride, the title compound was prepared. ESI-MS m/z 510 (M+H)⁺.

Example 57: (3R)-3-(2-(1-(2-amino-2-oxoethyl)pyrrolidin-3-yl)-2-(4-ethyl-2,3-dioxopiperazine-1-carboxamido)acetamido)-2-hydroxy-3,4-dihydro-2H-benzo[e][1,2]oxaborinine-8-carboxylic acid, trifluoroacetic acid salt

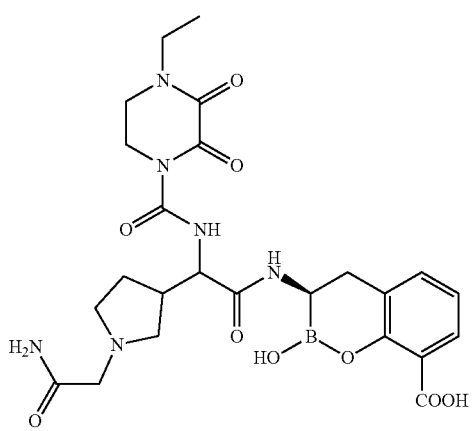 [SMILES: CCN1CCN(C(=O)NC(C(=O)N[C@H]2Cc3cccc(C(=O)O)c3OB2O)C2CCN(CC(N)=O)C2)C(=O)C1=O]

The title compound was prepared using an adaption of a literature procedure (Li, Z., et al., Proc. Nat. Acad. Sci. 2013, 100, 414-419). To a stirred solution of the title compound of Example 55 (26.4 mg. 0.043 mmol) and 2-bromoacetamide (7.1 mg, 0.051 mmol) in 0.25 mL acetonitrile, was added a saturated aqueous solution of $NaHCO_3$ (0.05 mL) at 0° C. The reaction mixture was allowed to warm to room temperature and stirred for 5 h. The desired product was isolated by submitting the reaction mixture directly to reverse-phase flash chromatography (C18-Silica gel, water-acetonitrile 0-50% gradient, modified with 0.1% TFA) followed by lyophilization. ESI-MS m/z 559.2 (M+H)$^+$.

Example 58: (3R)-3-(2-(2-chloro-3,4-dihydroxyphenyl)-2-(3-(methylsulfonyl)-2-oxoimidazolidine-1-carboxamido)acetamido)-2-hydroxy-3,4-dihydro-2H-benzo[e][1,2]oxaborinine-8-carboxylic acid

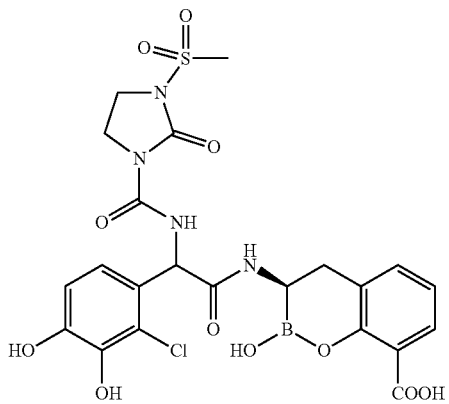 [SMILES: CS(=O)(=O)N1CCN(C(=O)NC(C(=O)N[C@H]2Cc3cccc(C(=O)O)c3OB2O)c2ccc(O)c(O)c2Cl)C1=O]

In a similar manner to the synthesis of Example 37, utilizing 3-(methylsulfonyl)-2-oxoimidazolidine-1-carbonyl chloride in place of 4-ethyl-2,3-dioxopiperazine-1-carbonyl chloride in Step 3, the title compound was prepared. ESI-MS m/z 597/599 (MH/MH+2)$^+$.

Example 59: (3R)-3-(2-(2-chloro-3,4-dihydroxyphenyl)-2-(4-oxo-1,4-dihydro-1,5-naphthyridine-3-carboxamido)acetamido)-2-hydroxy-3,4-dihydro-2H-benzo[e][1,2]oxaborinine-8-carboxylic acid

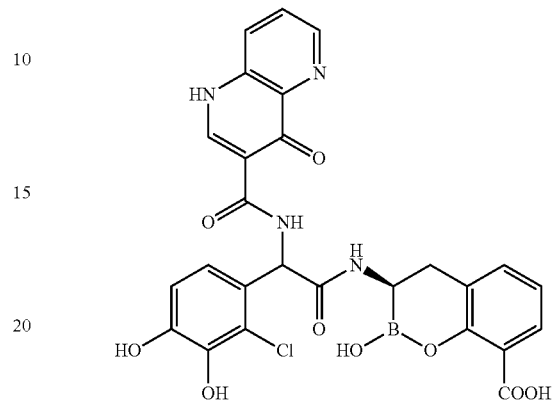

In a similar manner to the synthesis of Example 37, utilizing 4-oxo-1,4-dihydro-1,5-naphthyridine-3-carbonyl chloride in place of 4-ethyl-2,3-dioxopiperazine-1-carbonyl chloride in Step 3, the title compound was prepared. ESI-MS m/z 579/580 (MH/MH+2)$^+$.

Example 60: (3R)-3-(2-(4-ethyl-2,3-dioxopiperazine-1-carboxamido)-2-(1-methyl-1H-pyrazol-4-yl)acetamido)-2-hydroxy-3,4-dihydro-2H-benzo[e][1,2]oxaborinine-8-carboxylic acid

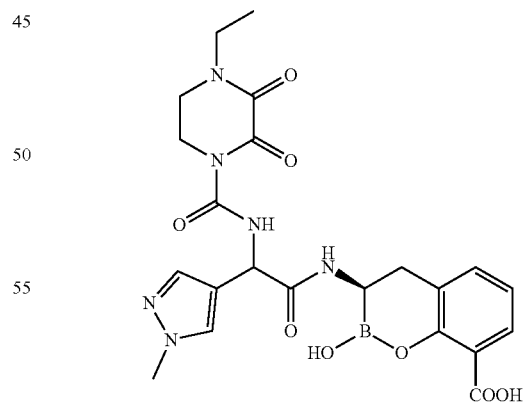

The title compound was prepared from 2-amino-2-(1-methyl-1H-pyrazol-4-yl)acetic acid and 3-((2S)-2-chloro-2-((3aS,4S,6S)-3a,5,5-trimethylhexahydro-4,6-methanobenzo-[d][1,3,2]dioxaborol-2-yl)ethyl)-2-methoxybenzoate, by a procedure similar to Example 8. ESI-MS m/z 513.1 (M+H)$^+$.

Example 61: (3R)-3-(2-(4-ethyl-2,3-dioxopiperazine-1-carboxamido)-2-(4-morpholinophenyl)acetamido)-2-hydroxy-3,4-dihydro-2H-benzo[e][1,2]oxaborinine-8-carboxylic acid

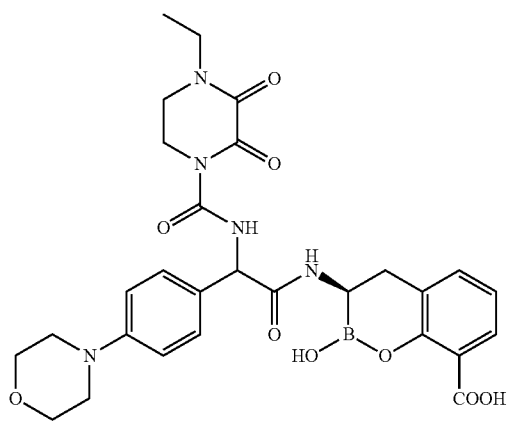 [SMILES: CCN1CCN(C(=O)NC(C(=O)N[C@H]2Cc3cccc(C(=O)O)c3OB2O)c2ccc(N3CCOCC3)cc2)C(=O)C1=O]

Step 1: Synthesis of methyl 2-(tert-butoxycarbonyl)amino-2-(4-morpholinophenyl)acetate

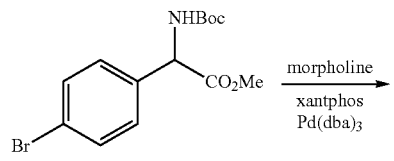

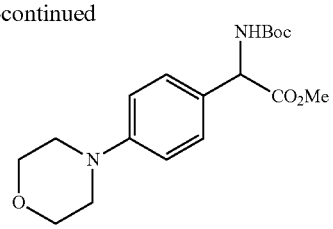

To a dried Schlenk flask was added 2-((tert-butoxycarbonyl)amino)-2-(4-bromophenyl)acetate 0.76 g (2.21 mmol), Xantphos 0.256 g (0.44 mmol, 0.2 eq), Pd(dba)$_3$ 0.2 g (0.22 mmol, 0.1 eq), cesium carbonate 2.16 g (6.6 mmol, 3 eq) and morpholine 0.39 mL (4.42 mmol, 2 eq) under an atmosphere of argon. Dioxane (22 mL) was added to the mixture, degassed 3× and heated at 100° C. for 18 h. The reaction was filtered through Celite, diluted with dichloromethane, washed with water/brine, dried over sodium sulfate and concentrated. The crude product was purified by flash chromatography on silica gel (30-40% ethyl acetate/hexanes) to afford the title compound, 0.42 g. ESI-MS m/z 351 (M+H)$^+$.

Step 2: Synthesis of (3R)-3-(2-(4-ethyl-2,3-dioxopiperazine-1-carboxamido)-2-(4-morpholinophenyl)acetamido)-2-hydroxy-3,4-dihydro-2H-benzo[e][1,2]oxaborinine-8-carboxylic acid

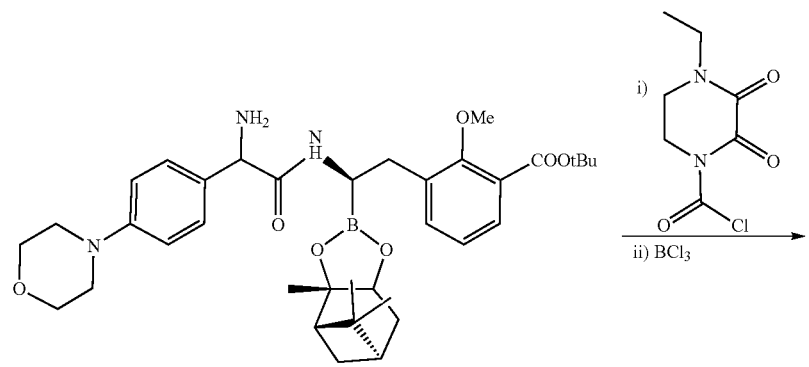

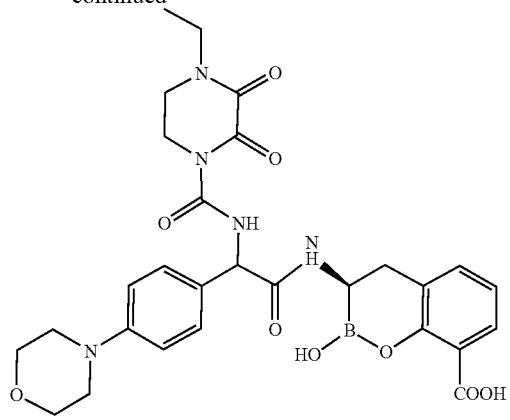

In a similar manner to the synthesis of Example 7 utilizing 4-ethyl-2,3-dioxopiperazine-1-carbonyl chloride in place of pyridine-3-sulfonyl chloride, the title compound was prepared. ESI-MS m/z 594 (M+H)+.

Example 62: (R)-3-((R)-2-(4-ethyl-2,3-dioxopiperazine-1-carboxamido)-2-(1-(hydroxymethyl) cyclopropyl)acetamido)-2-hydroxy-3,4-dihydro-2H-benzo[e][1,2]oxaborinine-8-carboxylic acid

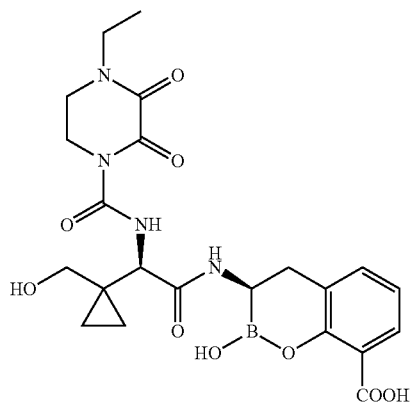 [SMILES: CCN1CCN(C(=O)N[C@@H](C(=O)N[C@H]2Cc3cccc(C(=O)O)c3OB2O)C2(CO)CC2)C(=O)C1=O]

Step 1a. Synthesis of 2-amino-2-(1-((benzyloxy)methyl)cyclopropyl)acetonitrile

1-[(Phenylmethoxy)methyl]cyclopropanecarboxaldehyde (3.91 g, 20.6 mmol) in ethanol (80 mL) was treated at room temperature with ammonium acetate (16 g, 206 mmol, 10 eq) for 2 hours under argon. Neat TMSCN (5 mL, 41.1 mmol, 2 eq) was added dropwise and the reaction mixture was stirred overnight. The reaction was quenched with saturated aqueous NaHCO₃ and extracted with ethyl acetate. The combined organic extracts were dried over Na₂SO₄, filtered and the solvent was evaporated under reduced pressure. The desired product was isolated by flash chromatography (ethyl acetate/hexanes gradient, Silica gel): 1.8 g (40% yield).

Step 1b. Synthesis of methyl 2-amino-2-(1-((benzyloxy)methyl)cyclopropyl)acetate 2-Amino-2-(1-((benzyloxy)methyl)cyclopropyl)acetonitrile (1.8 g, 8.3 mmol) in anhydrous methanol (40 mL) was treated with a 3M solution of hydrochloric acid in methanol (40 mL) at 0° C. and the resulting reaction mixture was further saturated with gas HCl for 15 min at the same temperature. The flask was next equipped with a condenser and the reaction mixture was stirred at 60° C. overnight, under argon. The volatiles were evaporated under reduced pressure and the residue was suspended in ethyl acetate and neutralized at 0° C. with saturated aqueous NaHCO₃ and further extracted with ethyl acetate. The combined organic extracts were washed with brine, dried over Na₂SO₄, filtered and the solvent was evaporated under reduced pressure. The desired product was isolated by flash chromatography (ethyl acetate/hexanes gradient, Silica gel): 1.55 g (75% yield).

Step 1c. Synthesis of 2-(1-((benzyloxy)methyl)cyclopropyl)-2-(4-ethyl-2,3-dioxopiperazine-1-carboxamido) acetic acid Methyl 2-amino-2-(1-((benzyloxy)methyl)cyclopropyl)acetate (1.5 g, 6 mmol) in a 1:1 (v/v) tetrahydrofuran/water mixture (100 mL) was treated at 0° C. with LiOH (217 mg, 9 mmol, 1.5 eq) in water (10 mL), and the resulting reaction mixture was stirred for 2 hours. The pH was adjusted to 8.5-9 with dilute hydrochloric acid; the reaction mixture was treated with 4-ethyl-2,3-dioxopiperazine-1-carbonyl chloride (1.54 g, 7.53 mmol, 1.25 eq.) in THF (15 mL), and the stirring was continued at 0° C. for 30 min. The volatiles were evaporated under reduced pressure and the resulting aqueous solution was neutralized at 0° C. with 2 N HCl to pH 2, and extracted 3 times with ethyl acetate (100 mL each). The combined organic extracts were dried over Na₂SO₄, then filtered, and the solvent was evaporated under reduced pressure to generate 2-(1-((benzyloxy)methyl)cyclopropyl)-2-(4-ethyl-2,3-dioxopiperazine-1-carboxy-amido) acetic acid (2.2 g, 90% yield), which was used in the next step without further purification

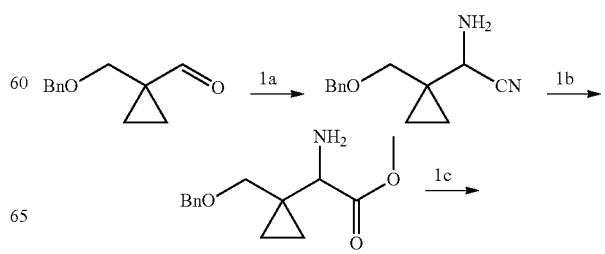

-continued

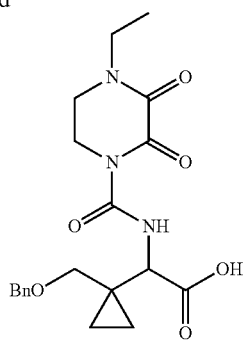

Step 2. Synthesis of (R)-3-((R)-2-(4-ethyl-2,3-dioxopiperazine-1-carboxamido)-2-(1-(hydroxymethyl)cyclopropyl)acetamido)-2-hydroxy-3,4-dihydro-2H-benzo[e][1,2]oxaborinine-8-carboxylic acid The title compound was prepared from 2-(1-((benzyloxy)methyl)cyclopropyl)-2-(4-ethyl-2,3-dioxopiperazine-1-carboxamido)acetic acid and 3-((2S)-2-chloro-2-((3aS,4S,6S)-3a,5,5-trimethyl-hexahydro-4,6-methanobenzo[d][1,3,2]dioxaborol-2-yl)ethyl)-2-methoxybenzoate and isolated by reverse phase HPLC (Gilson) as the more polar isomer, by a procedure similar to Example 8. ESI-MS m/z 503.0 (M+H)⁺.

Example 63: (R)-3-((S)-2-(4-ethyl-2,3-dioxopiperazine-1-carboxamido)-2-(1-(hydroxymethyl)cyclopropyl)acetamido)-2-hydroxy-3,4-dihydro-2H-benzo[e][1,2]oxaborinine-8-carboxylic acid

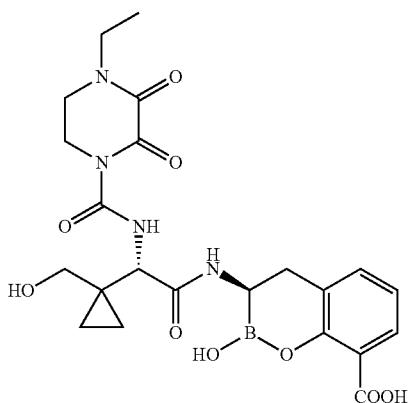 [SMILES: CCN1CCN(C(=O)N[C@H](C(=O)N[C@H]2Cc3cccc(C(=O)O)c3OB2O)C2(CO)CC2)C(=O)C1=O]

The title compound was isolated by reverse phase HPLC (Gilson) as the less polar isomer from the procedure described in Example 62. ESI-MS m/z 503.1 (M+H)⁺.

Example 64: (3R)-3-(2-(4-(2-aminoethyl)phenyl)-2-(4-ethyl-2,3-dioxopiperazine-1-carboxamido)acetamido)-2-hydroxy-3,4-dihydro-2H-benzo[e][1,2]oxaborinine-8-carboxylic acid

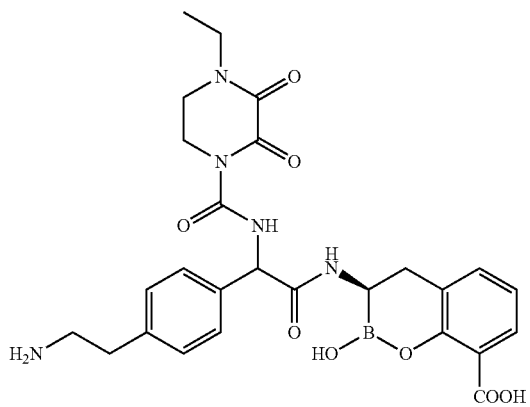 [SMILES: CCN1CCN(C(=O)NC(C(=O)N[C@H]2Cc3cccc(C(=O)O)c3OB2O)c2ccc(CCN)cc2)C(=O)C1=O]

Step 1: Synthesis of methyl 2-(4-(2-(((benzyloxy)carbonyl)amino)ethyl)phenyl)-2-((tert-butoxycarbonyl)amino)acetate

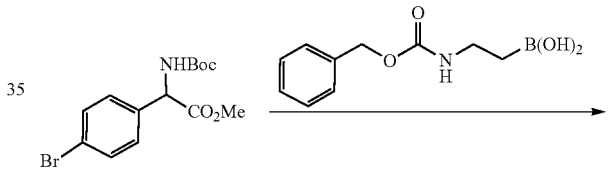

To 2-((tert-butoxycarbonyl)amino)-2-(4-bromophenyl)acetate 1 g (2.91 mmol) was added (2-(((benzyloxy)carbonyl)amino)ethyl)boronic acid 0.97 g (4.36 mmol, 1.5 eq), cesium carbonate 2.84 g (8.72 mmol, 3 eq), Pd(dppf)Cl₂-dichloromethane 0.24 g (0.29 mmol, 0.1 eq), followed by dioxane (19 mL) and degassed 3× under an atmosphere of argon. The reaction mixture was heated at 100° C. for 4 h, cooled at RT, diluted with dichloromethane, filtered through Celite, washed with water/brine, dried over sodium sulfate and concentrated. The crude product was purified by flash chromatography on silica gel (30% ethyl acetate/hexanes) to afford the title compound, 0.75 g. ESI-MS m/z 443 (M+H)⁺.

Step 2: Synthesis of (3R)-3-(2-(4-(2-aminoethyl)phenyl)-2-(4-ethyl-2,3-dioxopiperazine-1-carboxamido)acetamido)-2-hydroxy-3,4-dihydro-2H-benzo[e][1,2]oxaborinine-8-carboxylic acid

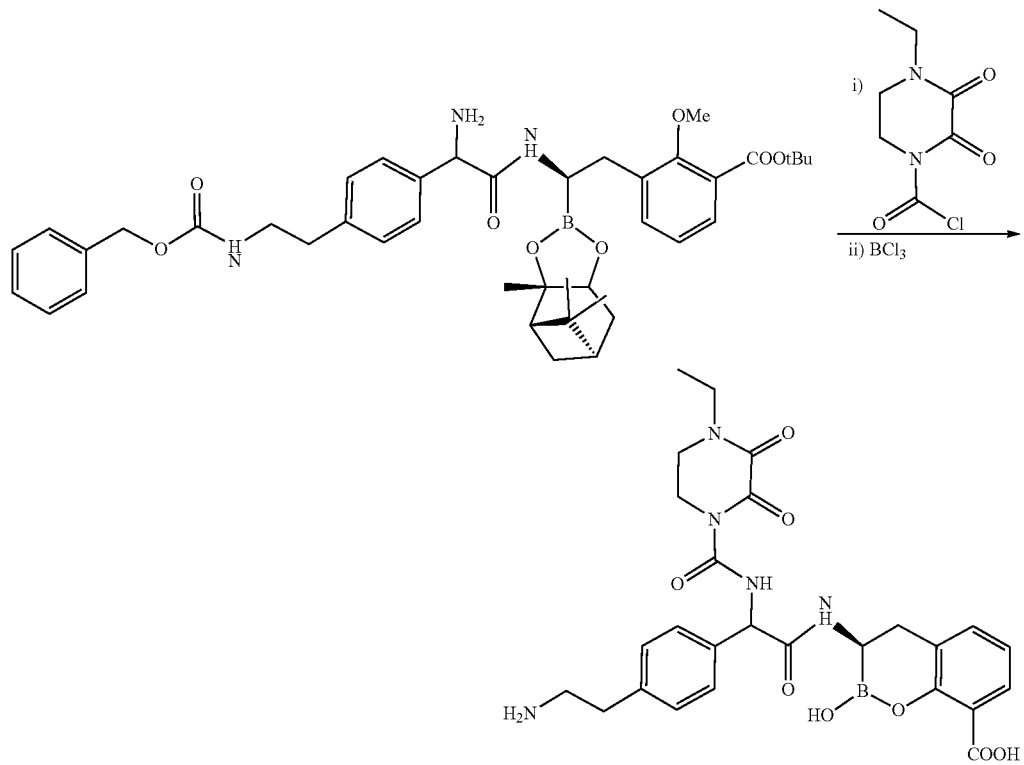

In a similar manner to the synthesis of Example 7 utilizing 4-ethyl-2,3-dioxopiperazine-1-carbonyl chloride in place of pyridine-3-sulfonyl chloride, the title compound was prepared. ESI-MS m/z 552 (M+H)$^+$.

Example 65: (3R)-3-(2-(2-chloro-6-methoxypyridin-3-yl)-2-(4-ethyl-2,3-dioxopiperazine-1-carboxamido)acetamido)-2-hydroxy-3,4-dihydro-2H-benzo[e][1,2]oxaborinine-8-carboxylic acid In a similar manner to the synthesis of Example 34, the title compound was prepared. ESI-MS m/z 574 (M+H)$^+$.

Example 66: (R)-3-((2R,3R)-3-(2-amino-2-oxoethoxy)-2-(4-ethyl-2,3-dioxopiperazine-1-carboxamido)butanamido)-2-hydroxy-3,4-dihydro-2H-benzo[e][1,2]oxaborinine-8-carboxylic acid

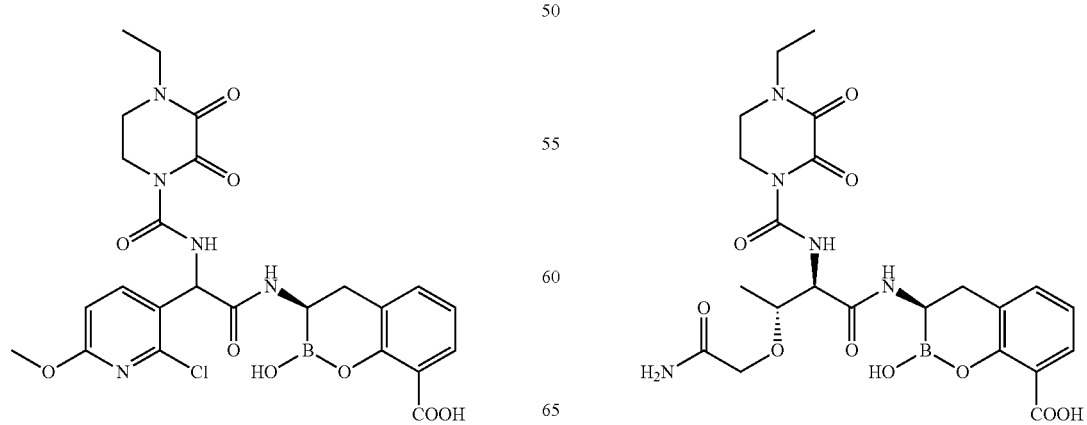

Step 1. Synthesis of O-(2-amino-2-oxoethyl)-N-(tert-butoxycarbonyl)-D-allothreonine (tert-Butoxycarbonyl)-D-allothreonine (1 g, 4.6 mmol) in anhydrous dimethylformamide (5 mL) was treated at 0° C. with sodium hydride (547 mg 60% w/w suspension in oil, 13.8 mmol, 3 eq) for 30 min, under argon. 2-Bromoacetamide (945 mg, 6.9 mmol, 1.5 eq) in in anhydrous dimethylformamide (5 mL) was added dropwise and the reaction mixture was stirred overnight at room temperature. The reaction was quenched with saturated aqueous ammonium chloride and extracted with diethyl ether. The combined organic extracts were dried over $Na_2SO_4$, filtered and the solvent was evaporated under reduced pressure. The desired product was isolated by flash chromatography (methanol/dichloromethane gradient, Silica gel), 476 mg (38% yield)

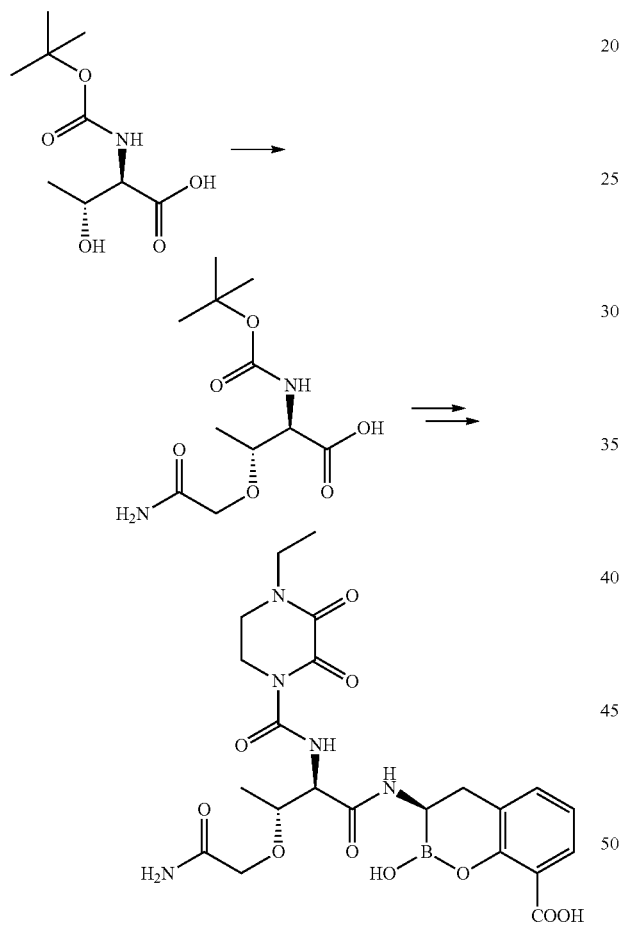

Step 2. Synthesis of (R)-3-((2R,3R)-3-(2-amino-2-oxoethoxy)-2-(4-ethyl-2,3-dioxopiperazine-1-carboxamido)butanamido)-2-hydroxy-3,4-dihydro-2H-benzo[e][1,2]oxaborinine-8-carboxylic acid The title compound was prepared from O-(2-amino-2-oxoethyl)-N-(tert-butoxycarbonyl)-D-allothreonine and 3-((2S)-2-chloro-2-((3aS,4S,6S)-3a,5,5-trimethyl-hexahydro-4,6-methanobenzo[d][1,3,2]dioxaborol-2-yl)ethyl)-2-methoxybenzoate by a procedure similar to Example 6, employing 4-ethyl-2,3-dioxopiperazine-1-carbonyl chloride instead of ethyl isocyanate. ESI-MS m/z 534.2 (M+H)⁺.

Example 67: (3R)-3-(2-(2-chloro-6-hydroxypyridin-3-yl)-2-(4-ethyl-2,3-dioxopiperazine-1-carboxamido)acetamido)-2-hydroxy-3,4-dihydro-2H-benzo[e][1,2]oxaborinine-8-carboxylic acid

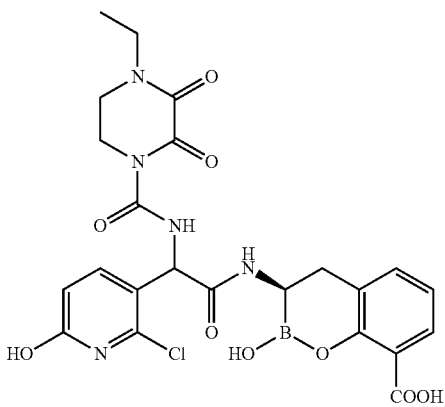 [SMILES: CCN1CCN(C(=O)NC(C(=O)N[C@H]2Cc3cccc(C(=O)O)c3OB2O)c2ccc(O)nc2Cl)C(=O)C1=O]

In a similar manner to the synthesis of Example 41, the title compound was prepared. ESI-MS m/z 560 (M+H).

Example 68: (3R)-3-(2-(4-ethyl-2,3-dioxopiperazine-1-carboxamido)-3-(sulfamoylamino)propanamido)-2-hydroxy-3,4-dihydro-2H-benzo[e][1,2]oxaborinine-8-carboxylic acid

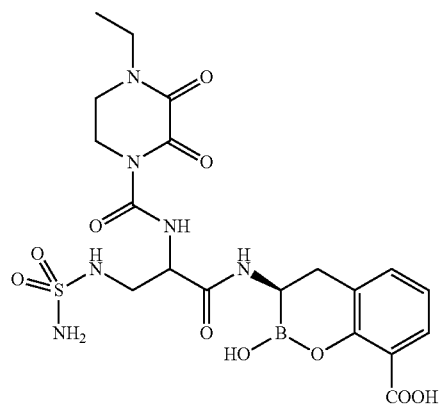 [SMILES: CCN1CCN(C(=O)NC(CNS(N)(=O)=O)C(=O)N[C@H]2Cc3cccc(C(=O)O)c3OB2O)C(=O)C1=O]

In a similar manner to the synthesis of Example 33, utilizing tert-butyl (chlorosulfonyl)carbamate (derived from chlorosulfonyl isocyanate and tert-butanol) in place of 4-ethyl-2,3-dioxopiperazine-1-carbonyl chloride in Step 3, the title compound was prepared. ESI-MS m/z 541 (M+H)⁺.

Example 69: (3R)-3-(3-acetamido-2-(4-ethyl-2,3-dioxopiperazine-1-carboxamido)propanamido)-2-hydroxy-3,4-dihydro-2H-benzo[e][1,2]oxaborinine-8-carboxylic acid

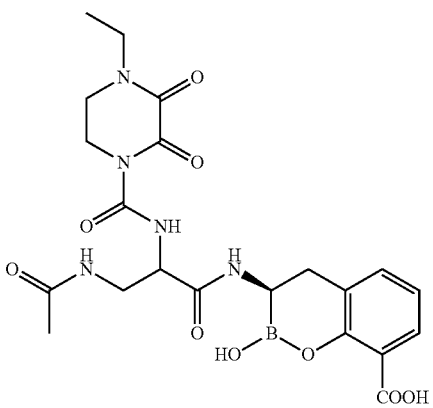 [SMILES: CCN1CCN(C(=O)NC(CNC(C)=O)C(=O)N[C@H]2Cc3cccc(C(=O)O)c3OB2O)C(=O)C1=O]

In a similar manner to the synthesis of Example 33, utilizing acetyl chloride in place of 4-ethyl-2,3-dioxopiperazine-1-carbonyl chloride in Step 3, the title compound was prepared. ESI-MS m/z 504 (M+H)+.

Example 70: (3R)-3-(2-(2-chloro-3,4-dihydroxyphenyl)-2-(4-ethyl-2,3-dioxopiperazine-1-carboxamido)acetamido)-2-hydroxy-3,4-dihydro-2H-benzo[e][1,2]oxaborinine-8-carboxylic acid

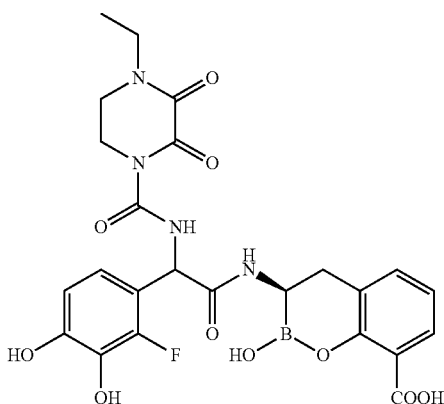 [SMILES: CCN1CCN(C(=O)NC(C(=O)N[C@H]2Cc3cccc(C(=O)O)c3OB2O)c2ccc(O)c(O)c2F)C(=O)C1=O]

In a similar manner to the synthesis of Example 37, utilizing 2-fluoro-3,4-dimethoxybenzaldehyde in place of 2-chloro-3,4-dimethoxybenzaldehyde in Step 1, the title compound was prepared. ESI-MS m/z 559 (M+H)+.

Example 71: (3R)-3-(2-(2-chloro-3,4-dihydroxyphenyl)-2-(4-(2-fluoroethyl)-2,3-dioxopiperazine-1-carboxamido)acetamido)-2-hydroxy-3,4-dihydro-2H-benzo[e][1,2]oxaborinine-8-carboxylic acid

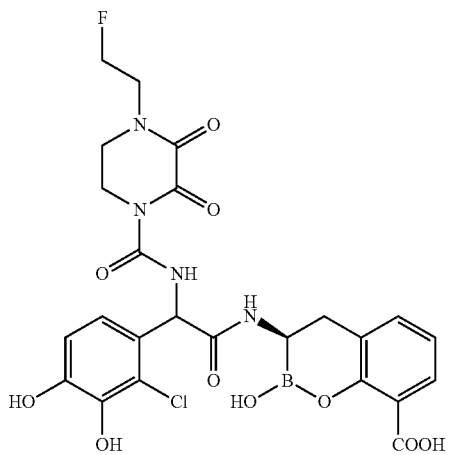 [SMILES: O=C(O)c1cccc2c1OB(O)[C@@H](NC(=O)C(NC(=O)N1CCN(CCF)C(=O)C1=O)c1ccc(O)c(O)c1Cl)C2]

In a similar manner to the synthesis of Example 37, utilizing 4-fluoroethyl-2,3-dioxopiperazine-1-carbonyl chloride (product from Step 2 of Example 13) in place of 4-ethyl-2,3-dioxopiperazine-1-carbonyl chloride in Step 3, the title compound was prepared. ESI-MS m/z 593/595 (MH/MH+2)+.

Example 72: (3R)-3-(2-(1-(carboxymethyl)piperidin-4-yl)-2-(4-ethyl-2,3-dioxopiperazine-1-carboxamido)acetamido)-2-hydroxy-3,4-dihydro-2H-benzo[e][1,2]oxaborinine-8-carboxylic acid, trifluoroacetic acid salt

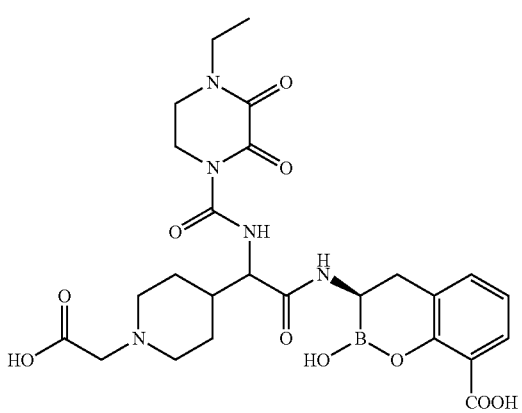 [SMILES: CCN1CCN(C(=O)NC(C(=O)N[C@H]2Cc3cccc(C(=O)O)c3OB2O)C2CCN(CC(=O)O)CC2)C(=O)C1=O]

Step 1. Synthesis of tert-butyl 4-(2-(((R)-2-(3-(tert-butoxycarbonyl)-2-methoxyphenyl)-1-((3aS,4S,6S,7aR)-3a,5,5-trimethylhexahydro-4,6-methanobenzo[d][1,3,2]dioxaborol-2-yl)ethyl)amino)-1-(4-ethyl-2,3-dioxopiperazine-1-carboxamido)-2-oxoethyl)piperidine-1-carboxylate tert-Butyl 4-(2-(((R)-2-(3-(tert-butoxycarbonyl)-2-methoxyphenyl)-1-((3aS,4S,6S,7aR)-3a,5,5-trimethylhexahydro-4,6-methanobenzo[d][1,3,2]dioxaborol-2-yl)ethyl)amino)-1-(4-ethyl-2,3-dioxopiperazine-1-carboxamido)-2-oxoethyl)piperidine-1-carboxylate was prepared from 2-amino-2-(1-(tert-butoxycarbonyl)piperidin-4-yl)acetic acid and 3-((2S)-2-chloro-2-((3aS,4S,6S)-3a,5,5-trimethylhexahydro-4,6-methanobenzo-[d][1,3,2]dioxaborol-2-yl)ethyl)-2-methoxybenzoate by a procedure similar to Example 8, Steps 1 and 2.

Step 2. Synthesis of tert-butyl 3-((2R)-2-(2-(1-(2-(tert-butoxy)-2-oxoethyl)piperidin-4-yl)-2-(4-ethyl-2,3-dioxopiperazine-1-carboxamido)acetamido)-2-((3aS,4S,6S,7aR)-3a,5,5-trimethylhexahydro-4,6-methanobenzo[d][1,3,2]dioxaborol-2-yl)ethyl)-2-methoxybenzoate Step 2a tert-Butyl 4-(2-(((R)-2-(3-(tert-butoxycarbonyl)-2-methoxyphenyl)-1-((3aS,4S,6S,7aR)-3a,5,5-trimethylhexahydro-4,6-methanobenzo[d][1,3,2]dioxaborol-2-yl)ethyl)amino)-1-(4-ethyl-2,3-dioxopip-erazine-1-carboxamido)-2-oxoethyl)piperidine-1-carboxylate was converted to tert-butyl 3-((2R)-2-(2-(4-ethyl-2,3-dioxopiperazine-1-carboxamido)-2-(piperidin-4-yl)acetamido)-2-((3aS,4S,6S,7aR)-3a,5,5-trimethylhexahydro-4,6-methanobenzo[d][1,3,2]dioxaborol-2-yl)ethyl)-2-methoxybenzoate, hydrochloric acid salt by a procedure similar to Example 6, Step 2.

Step 2b tert-Butyl 3-((2R)-2-(2-(4-ethyl-2,3-dioxopiperazine-1-carboxamido)-2-(piperidin-4-yl) acet-amido)-2-((3aS,4S,6S,7aR)-3a,5,5-trimethylhexahydro-4,6-methanobenzo[d][1,3,2]dioxaborol-2-yl) ethyl)-2-methoxybenzoate, hydrochloric acid salt (193.5 mg, 0.25 mmol) in acetonitrile (2 mL) was treated with diisopropylethylamine (0.1 mL, 0.5 mmol, 2 eq) and tert-butyl 2-bromoacetate (0.04 mL, 0.275 mmol, 1.1 eq) overnight, at room temperature. The reaction mixture was partitioned between diethyl ether and water and the aqueous phase was extracted two more times with diethyl ether. The combined organic extracts were dried over $Na_2SO_4$, filtered, and the solvent was evaporated under reduced pressure. The crude product was further dried on high vacuum overnight and used in the next step without purification

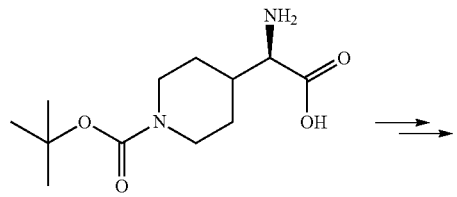

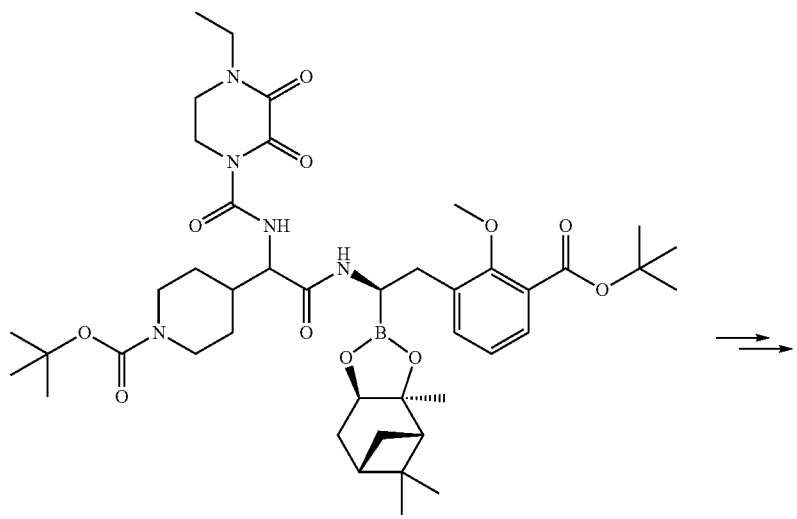

Step 3. Synthesis of (3R)-3-(2-(1-(carboxymethyl)piperidin-4-yl)-2-(4-ethyl-2,3-dioxopiperazine-1-carboxamido)acetamido)-2-hydroxy-3,4-dihydro-2H-benzo[e][1,2]oxaborinine-8-carboxylic acid, trifluoroacetic acid salt The title compound was prepared from the product of Step 2b in this example by a procedure similar to Example 8, Step 3. ESI-MS m/z 574.3 (M+H)⁺.

Example 73: (R)-3-((R)-3-((carboxymethyl)amino)-2-(4-ethyl-2,3-dioxopiperazine-1-carbox-amido)propanamido)-2-hydroxy-3,4-dihydro-2H-benzo[e][1,2]oxaborinine-8-carboxylic acid, trifluoroacetic acid salt

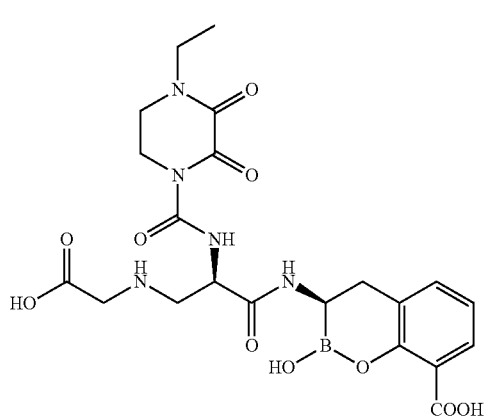 [SMILES: CCN1CCN(C(=O)N[C@H](CNCC(=O)O)C(=O)N[C@H]2Cc3cccc(C(=O)O)c3OB2O)C(=O)C1=O]

The title compound was prepared from (R)-2-amino-3-((tert-butoxycarbonyl)amino)propanoic acid and 3-((2S)-2-chloro-2-((3aS,4S,6S)-3a,5,5-trimethylhexahydro-4,6-methanobenzo-[d][1,3,2]dioxa-borol-2-yl)ethyl)-2-methoxybenzoate, by a procedure similar to Example 72. ESI-MS m/z 520.2 (M+H)⁺.

Example 74: (3R)-3-(2-(4-ethyl-2,3-dioxopiperazine-1-carboxamido)-2-(4-(2-hydroxyethoxy)phenyl)acetamido)-2-hydroxy-3,4-dihydro-2H-benzo[e][1,2]oxaborinine-8-carboxylic acid

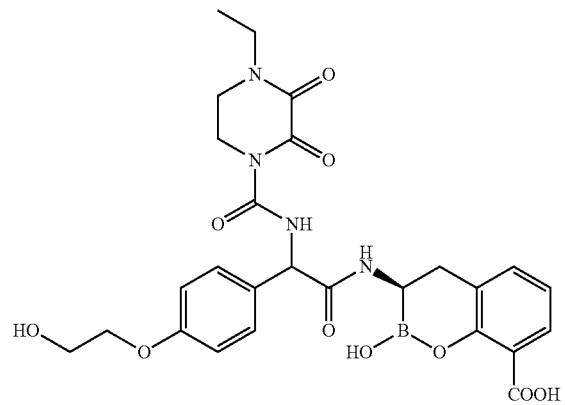 [SMILES: CCN1CCN(C(=O)NC(C(=O)N[C@H]2Cc3cccc(C(=O)O)c3OB2O)c2ccc(OCCO)cc2)C(=O)C1=O]

Step 1: Synthesis of methyl 2-(4-(2-(benzyloxy)ethoxy)phenyl)-2-((tert-butoxycarbonyl)amino)acetate

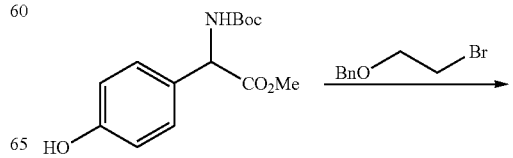

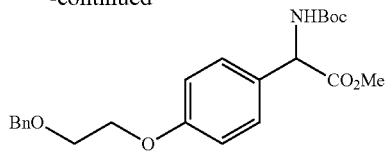

To methyl 2-(4-hydroxyphenyl)-2-((tert-butoxycarbonyl)amino)acetate 1 g (3.56 mmol) in N,N-dimethylformamide (10 mL) was added cesium carbonate 3.5 g (10.7 mmol, 3 eq), followed by ((2-bromoethoxy)methyl)benzene 0.84 mL (5.34 mmol, 1.5 eq) and the mixture was heated at 80° C. for 1.5 h. The reaction was cooled at RT, diluted with ethyl acetate, washed with water/brine, dried over sodium sulfate, and concentrated. The crude product was purified by flash chromatography on silica gel (30% ethyl acetate/hexanes) to afford the title compound, 1.4 g. ESI-MS m/z 416 (M+H)$^+$.

Step 2: Synthesis of (3R)-3-(2-(4-ethyl-2,3-dioxopiperazine-1-carboxamido)-2-(4-(2-hydroxyethoxy)phenyl)acetamido)-2-hydroxy-3,4-dihydro-2H-benzo[e][1,2]oxaborinine-8-carboxylic acid

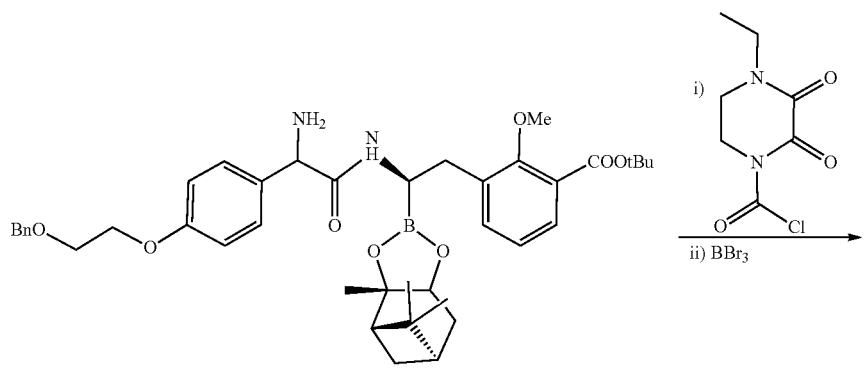

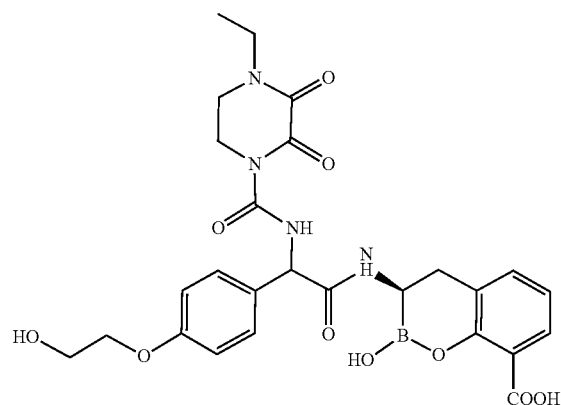

In a similar manner to the synthesis of Example 7 utilizing 4-ethyl-2,3-dioxopiperazine-1-carbonyl chloride in place of pyridine-3-sulfonyl chloride, the title compound was prepared. ESI-MS m/z 569 (M+H)+.

Example 75: (R)-3-((R)-2-(4-ethyl-2,3-dioxopiperazine-1-carboxamido)-3-((trifluoromethyl) sulfonamido)propanamido)-2-hydroxy-3,4-dihydro-2H-benzo[e][1,2]oxaborinine-8-carboxylic acid

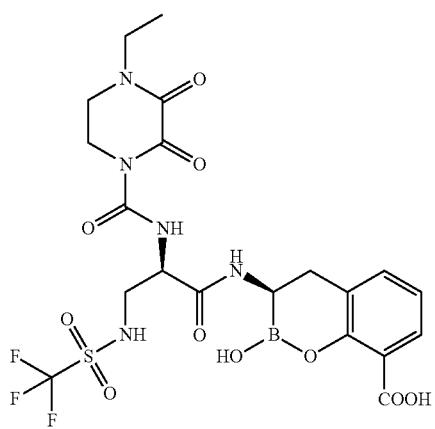 [SMILES: CCN1CCN(C(=O)N[C@H](CNS(=O)(=O)C(F)(F)F)C(=O)N[C@H]2Cc3cccc(C(=O)O)c3OB2O)C(=O)C1=O]

The title compound was prepared by a procedure similar to Examples 72 and 73, except for employing trifluoromethanesulfonyl chloride instead of tert-butyl 2-bromoacetate and dichloromethane as a solvent in Step 2b. ESI-MS m/z 594.1 (M+H)+.

Example 76: (3R)-3-(2-(4-ethyl-2,3-dioxopiperazine-1-carboxamido)-2-(4-(2-fluoroethoxy)phenyl)acetamido)-2-hydroxy-3,4-dihydro-2H-benzo[e][1,2]oxaborinine-8-carboxylic acid

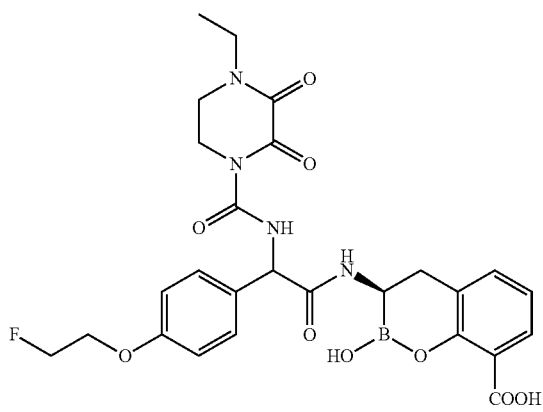 [SMILES: CCN1CCN(C(=O)NC(C(=O)N[C@H]2Cc3cccc(C(=O)O)c3OB2O)c2ccc(OCCF)cc2)C(=O)C1=O]

In a similar manner to the synthesis of Example 74 utilizing boron trichloride in place of boron tribromide, the title compound was prepared. ESI-MS m/z 571 (M+H)+.

Example 77: (3R)-3-(2-(4-ethyl-2,3-dioxopiperazine-1-carboxamido)-2-(1-sulfamoylpiperidin-4-yl)acetamido)-2-hydroxy-3,4-dihydro-2H-benzo[e][1,2]oxaborinine-8-carboxylic acid

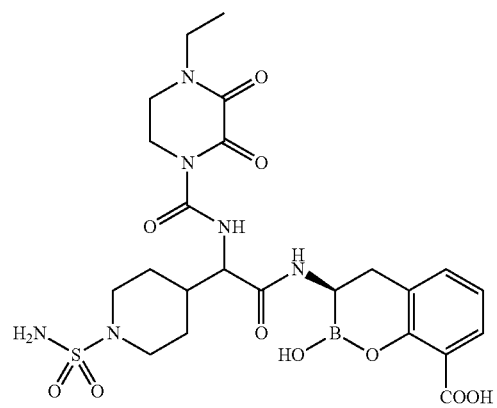 [SMILES: CCN1CCN(C(=O)NC(C(=O)N[C@H]2Cc3cccc(C(=O)O)c3OB2O)C2CCN(S(N)(=O)=O)CC2)C(=O)C1=O]

Step 1. Synthesis of tert-butyl 3-((2R)-2-(2-(1-(N-(tert-butoxycarbonyl)sulfamoyl)piperidin-4-yl)-2-(4-ethyl-2,3-dioxopiperazine-1-carboxamido)acetamido)-2-((3aS,4S,6S,7aR)-3a,5,5-trimethylhexahydro-4,6-methanobenzo[d][1,3,2]dioxaborol-2-yl)ethyl)-2-methoxybenzoate tert-Butyl 3-((2R)-2-(2-(4-ethyl-2,3-dioxopiperazine-1-carboxamido)-2-(piperidin-4-yl) acetamido)-2-((3aS,4S,6S,7aR)-3a,5,5-trimethylhexahydro-4,6-methanobenzo[d][1,3,2]dioxaborol-2-yl)ethyl)-2-methoxybenzoate, hydrochloric acid salt (from Example 72 Step 2a; 193.5 mg, 0.25 mmol) in dichloromethane (3 mL) was treated at 0° C. with diisopropylethylamine (0.07 mL, 0.4 mmol, 1.6 eq) and a solution of tert-butyl (chlorosulfonyl)carbamate in dichloromethane (2 mL), freshly prepared separately from isocyanate sulfuryl chloride (40 mg, 0.275 mmol, 1.1 eq) and tert-butanol (20.5 mg, 0.275 mmol, 1.1 eq). The reaction mixture was stirred at room temperature for 2 hours and next it was partitioned between diethyl ether and water. The aqueous phase was extracted two more times with diethyl ether. The combined organic extracts were dried over Na2SO4, filtered, and the solvent was evaporated under reduced pressure. The crude product was further dried on high vacuum overnight and used in the next step without purification

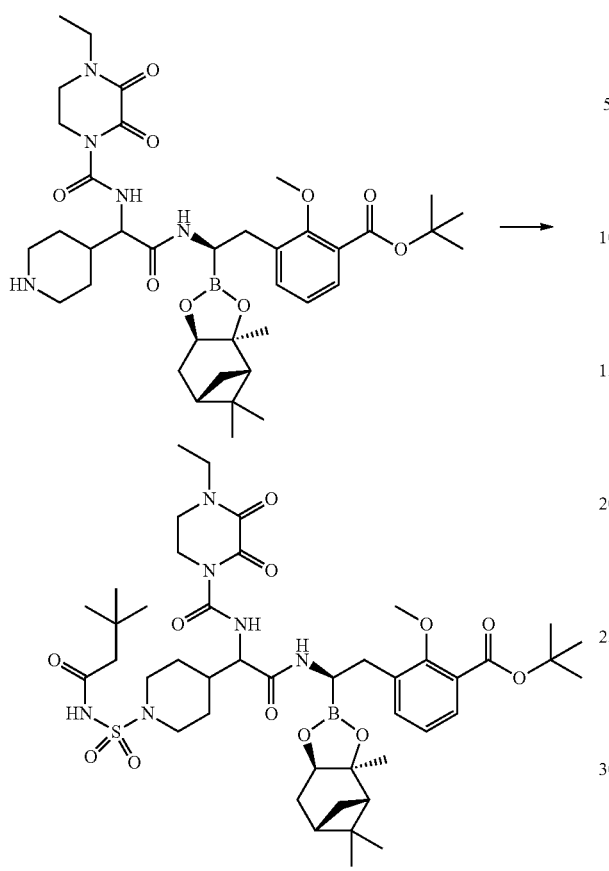

Step 2. Synthesis of (3R)-3-(2-(4-ethyl-2,3-di-oxopiperazine-1-carboxamido)-2-(1-sulfamoyl-piperidin-4-yl)acetamido)-2-hydroxy-3,4-dihydro-2H-benzo[e][1,2]oxaborinine-8-carboxylic acid The title compound was prepared from the product of Step 1 in this example by a procedure similar to Example 8, Step 3. ESI-MS m/z 595.2 (M+H)⁺.

Example 78: (3R)-3-(2-(4-ethyl-2,3-dioxopiperazine-1-carboxamido)-2-(1-sulfamoylazetidin-3-yl)acetamido)-2-hydroxy-3,4-dihydro-2H-benzo[e][1,2]oxaborinine-8-carboxylic acid

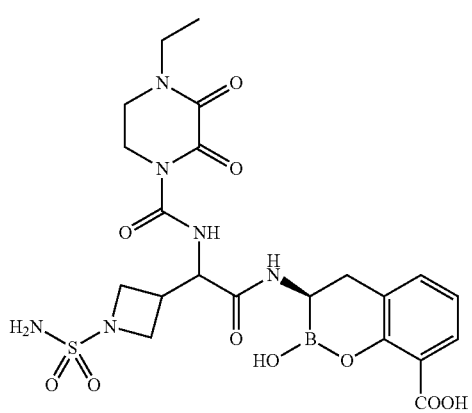 [SMILES: CCN1CCN(C(=O)NC(C(=O)N[C@H]2Cc3cccc(C(=O)O)c3OB2O)C2CN(S(N)(=O)=O)C2)C(=O)C1=O]

The title compound was prepared from tert-butyl 3-(1-amino-2-methoxy-2-oxoethyl)azetidine-1-carboxylate and 3-((2S)-2-chloro-2-((3aS,4S,6S)-3a,5,5-trimethylhexahydro-4,6-methanobenzo-[d][1,3,2]dioxaborol-2-yl)ethyl)-2-methoxybenzoate by a procedure similar to Example 62, Step 1c, and Example 77. ESI-MS m/z 567.1 (M+H)⁺.

Example 79: (3R)-3-(2-(4-ethyl-2,3-dioxopiperazine-1-carboxamido)-4-hydroxy-3-((sulfamoylamino)methyl)butanamido)-2-hydroxy-3,4-dihydro-2H-benzo[e][1,2]oxaborinine-8-carboxylic acid

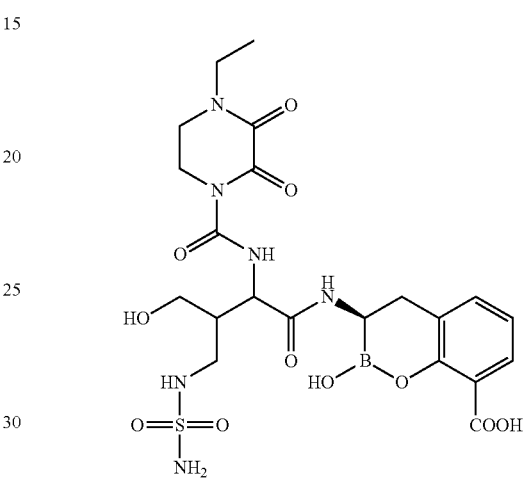

The title compound was isolated by reverse phase HPLC (Gilson) as a byproduct of the final step in Example 78. ESI-MS m/z 585.1 (M+H)⁺.

Example 80: (3R)-3-(4-chloro-2-(4-ethyl-2,3-dioxopiperazine-1-carboxamido)-3-((sulfamoylamino)methyl)butanamido)-2-hydroxy-3,4-dihydro-2H-benzo[e][1,2]oxaborinine-8-carboxylic acid

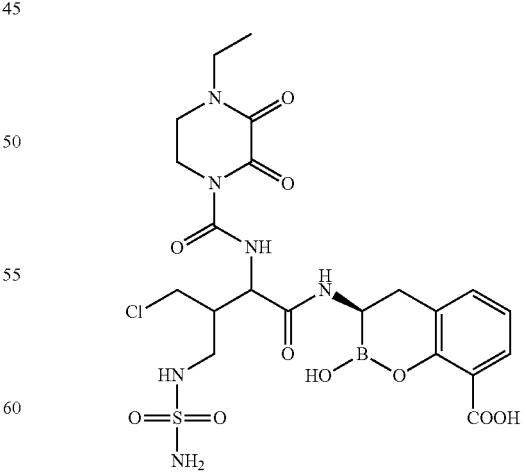

The title compound was isolated by reverse phase HPLC (Gilson) as a byproduct of the final step in Example 78. ESI-MS m/z 603.1 (M+H)⁺.

Example 81: (3R)-3-(2-(4-ethyl-2,3-dioxopiperazine-1-carboxamido)-2-(5-methoxypyridin-2-yl)acetamido)-2-hydroxy-3,4-dihydro-2H-benzo[e][1,2]oxaborinine-8-carboxylic acid

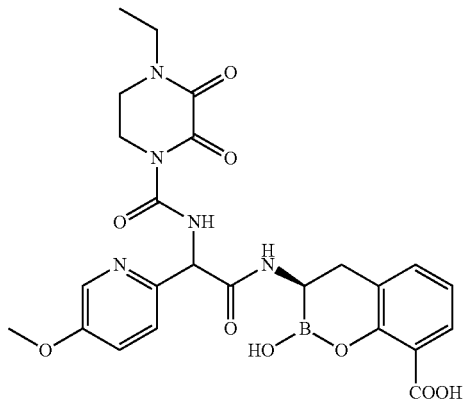 [SMILES: CCN1CCN(C(=O)NC(C(=O)N[C@H]2Cc3cccc(C(=O)O)c3OB2O)c2ccc(OC)cn2)C(=O)C1=O]

In a similar manner to the synthesis of Example 56 utilizing lithium 2-((tert-butoxycarbonyl)amino)-2-(5-methoxypyridin-2-yl)acetate in place of lithium 2-((tert-butoxycarbonyl)amino)-2-(pyridin-2-yl)acetate, the title compound was prepared. ESI-MS m/z 540 (M+H)$^+$.

Example 82: (3R)-3-(2-(2-chloro-3,4-dihydroxyphenyl)-2-(2,3-dioxo-4-propylpiperazine-1-carboxamido)acetamido)-2-hydroxy-3,4-dihydro-2H-benzo[e][1,2]oxaborinine-8-carboxylic acid

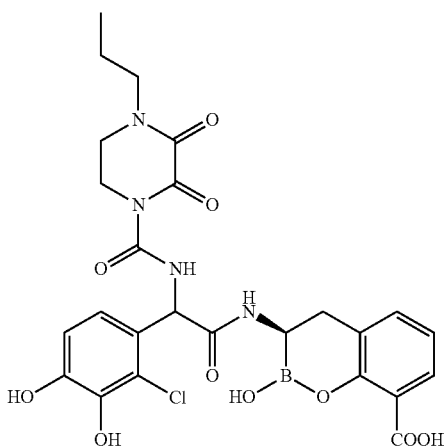 [SMILES: CCCN1CCN(C(=O)NC(C(=O)N[C@H]2Cc3cccc(C(=O)O)c3OB2O)c2ccc(O)c(O)c2Cl)C(=O)C1=O]

Step 1. Synthesis of 2,3-dioxo-4-propylpiperazine-1-carbonyl chloride

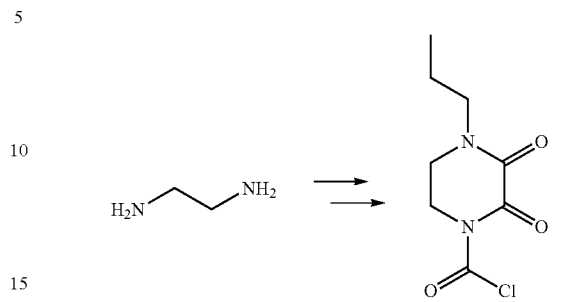

In a similar manner to the synthesis of 2,3-dioxo-4-fluoroethylpiperazine-1-carbonyl chloride described in Step 1 and Step 2 of Example 13, utilizing the commercially available N-propylethylenediamine in Step 1, the title compound was prepared.

Step 2. Synthesis of (3R)-3-(2-(2-chloro-3,4-dihydroxyphenyl)-2-(2,3-dioxo-4-propylpiperazine-1-carboxamido)acetamido)-2-hydroxy-3,4-dihydro-2H-benzo[e][1,2]oxaborinine-8-carboxylic acid

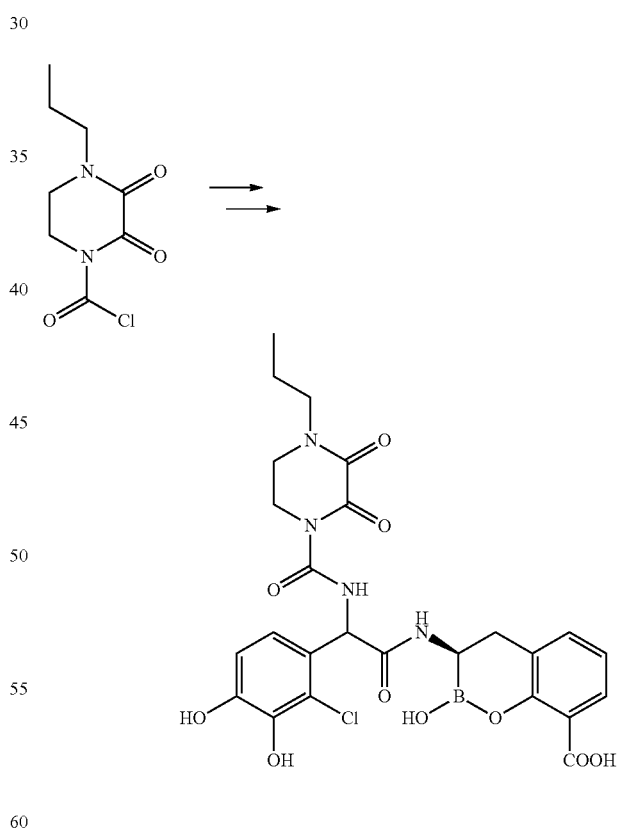

In a similar manner to the synthesis of Example 37, utilizing 4-propyl-2,3-dioxopiperazine-1-carbonyl chloride (product from Step 1) in place of 4-ethyl-2,3-dioxopiperazine-1-carbonyl chloride in Step 3, the title compound was prepared. ESI-MS m/z 589/591 (MH/MH+2)$^+$.

Example 83: (R)-3-((R)-2-(4-ethyl-2,3-dioxopiperazine-1-carboxamido)-3-(methylsulfonamido)propanamido)-2-hydroxy-3,4-dihydro-2H-benzo[e][1,2]oxaborinine-8-carboxylic acid

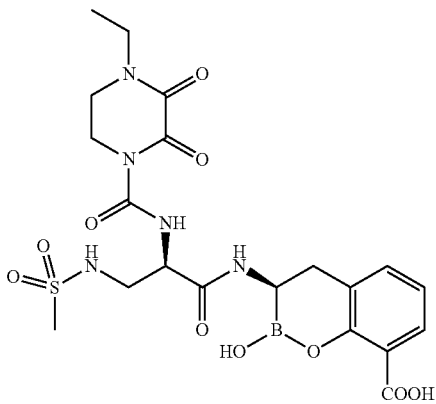 [SMILES: CCN1CCN(C(=O)N[C@H](CNS(C)(=O)=O)C(=O)N[C@H]2Cc3cccc(C(=O)O)c3OB2O)C(=O)C1=O]

Example 84: (R)-3-((S)-2-(4-ethyl-2,3-dioxopiperazine-1-carboxamido)-3-(methylsulfonamido)propanamido)-2-hydroxy-3,4-dihydro-2H-benzo[e][1,2]oxaborinine-8-carboxylic acid

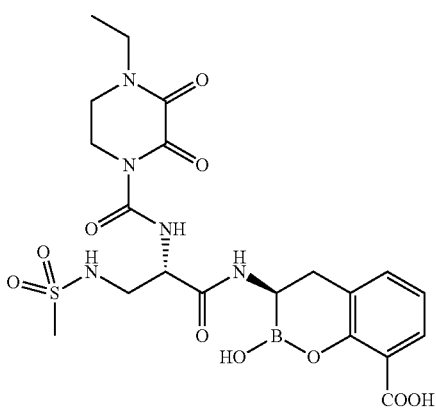 [SMILES: CCN1CCN(C(=O)N[C@@H](CNS(C)(=O)=O)C(=O)N[C@H]2Cc3cccc(C(=O)O)c3OB2O)C(=O)C1=O]

In a similar manner to the synthesis of Example 33, utilizing methanesulfonyl chloride in place of 4-ethyl-2,3-dioxopiperazine-1-carbonyl chloride in Step 3, the title compounds, Example 83 and Example 84 were separated by reverse phase HPLC. ESI-MS m/z 540 (M+H)$^+$.

Example 85: (3R)-3-(2-(2-chloro-4,5-dihydroxyphenyl)-2-(4-ethyl-2,3-dioxopiperazine-1-carboxamido)acetamido)-2-hydroxy-3,4-dihydro-2H-benzo[e][1,2]oxaborinine-8-carboxylic acid

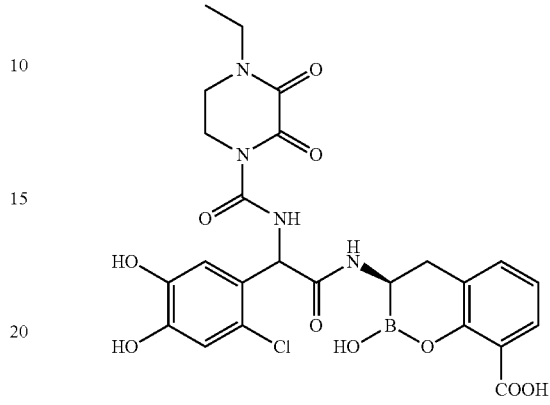

In a similar manner to the synthesis of Example 37, utilizing 2-chloro-4,5-dimethoxybenzaldehyde in place of 2-chloro-3,4-dimethoxybenzaldehyde in Step 1, the title compound was prepared. ESI-MS m/z 575 (M+H)$^+$.

Example 86: (3R)-3-(2-(4-ethyl-2,3-dioxopiperazine-1-carboxamido)-2-(2-fluoro-6-hydroxypyridin-3-yl)acetamido)-2-hydroxy-3,4-dihydro-2H-benzo[e][1,2]oxaborinine-8-carboxylic acid

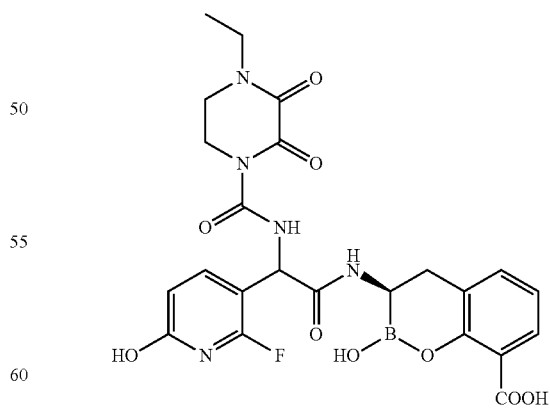

In a similar manner to the synthesis of Example 41, the title compound was prepared. ESI-MS m/z 544 (M+H)$^+$.

Example 87: (3R)-3-(2-(4-ethyl-2,3-dioxopiperazine-1-carboxamido)-2-(2-fluoro-4-hydroxyphenyl)acetamido)-2-hydroxy-3,4-dihydro-2H-benzo[e][1,2]oxaborinine-8-carboxylic acid

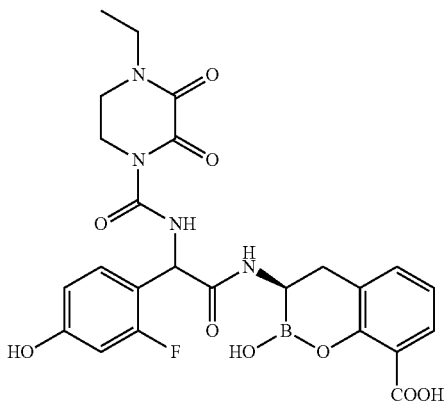

In a similar manner to the synthesis of Example 37, utilizing 2-fluoro-4-methoxybenzaldehyde in place of 2-chloro-3,4-dimethoxybenzaldehyde in Step 1, the title compound was prepared. ESI-MS m/z 543 (M+H)⁺.

Example 88: (3R)-3-(2-(2-chloro-4-hydroxyphenyl)-2-(4-ethyl-2,3-dioxopiperazine-1-carboxamido)acetamido)-2-hydroxy-3,4-dihydro-2H-benzo[e][1,2]oxaborinine-8-carboxylic acid

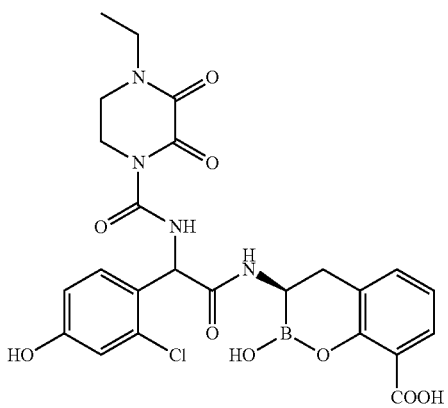

In a similar manner to the synthesis of Example 37, utilizing 2-chloro-4-methoxybenzaldehyde in place of 2-chloro-3,4-dimethoxybenzaldehyde in Step 1, the title compound was prepared. ESI-MS m/z 559/561 (MH/MH+2)⁺.

Example 89: (3R)-3-(2-(4-ethyl-2,3-dioxopiperazine-1-carboxamido)-2-(5-hydroxypyridin-2-yl)acetamido)-2-hydroxy-3,4-dihydro-2H-benzo[e][1,2]oxaborinine-8-carboxylic acid

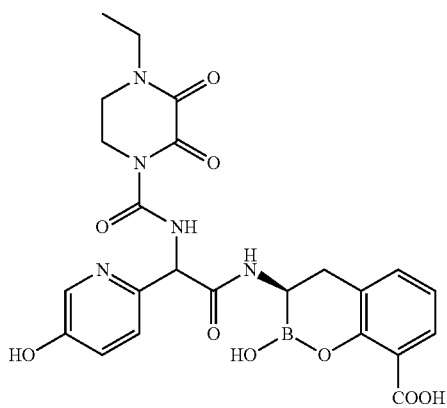 [SMILES: CCN1CCN(C(=O)NC(C(=O)N[C@H]2Cc3cccc(C(=O)O)c3OB2O)c2ccc(O)cn2)C(=O)C1=O]

Step 1: Synthesis of 5-(benzyloxy)picolinaldehyde

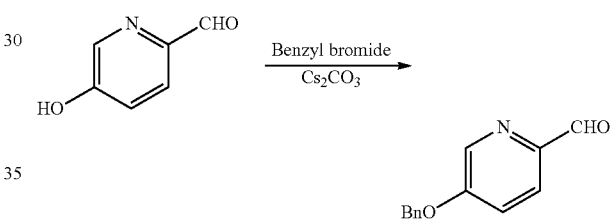

To 5-hydroxypicolinaldehyde 1.1 g (8.94 mmol) in N,N-dimethylformamide (10 mL) was added cesium carbonate 8.7 g (26.8 mmol, 3 eq), followed by benzyl bromide 1.32 mL (13.4 mmol, 1.5 eq) and heated at 80° C. for 2 h. The reaction was diluted with ethyl acetate, washed with water/brine, dried over sodium sulfate and concentrated. The product was purified by flash chromatography on silica gel (3% methanol/dichloromethane) using preparatory TLC plates to give the desired product, 1.12 g.
ESI-MS m/z 214 (M+H)⁺.

Step 2: Synthesis of lithium 2-(5-(benzyloxy)pyridin-2-yl)-2-((tert-butoxycarbonyl)amino)acetate

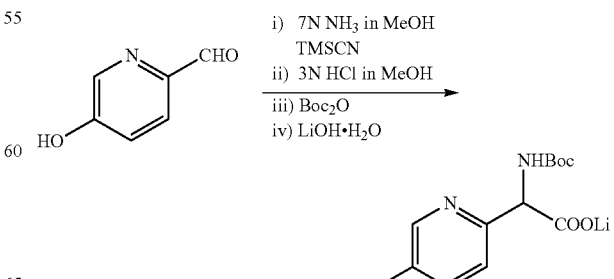

In a similar manner to the synthesis of Example 56 utilizing 5-(benzyloxy)picolinaldehyde in place of picolinaldehyde to give the title compound. ESI-MS m/z 359 (M+H)⁺.

Step 3: Synthesis of (3R)-3-(2-(4-ethyl-2,3-dioxopiperazine-1-carboxamido)-2-(5-hydroxypyridin-2-yl)acetamido)-2-hydroxy-3,4-dihydro-2H-benzo[e][1,2]oxaborinine-8-carboxylic acid

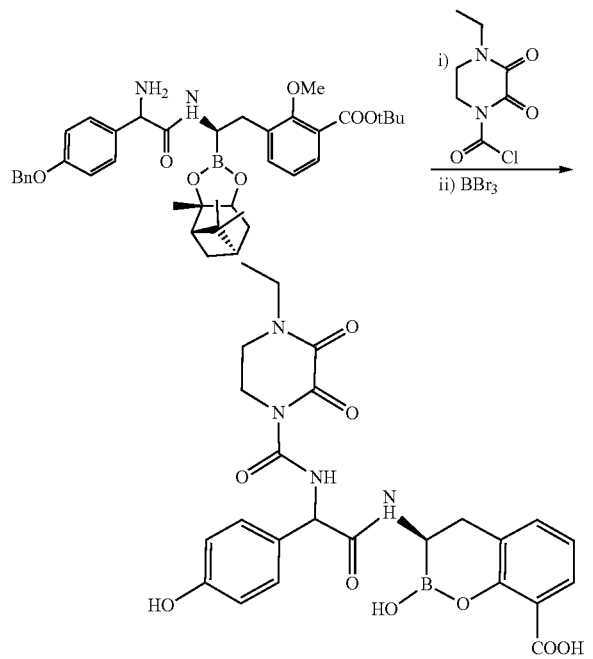

In a similar manner to the synthesis of Example 7 utilizing 4-ethyl-2,3-dioxopiperazine-1-carbonyl chloride in place of pyridine-3-sulfonyl chloride, the title compound was prepared. ESI-MS m/z 526 (M+H)⁺.

Example 90: (3R)-3-(2-(4-ethyl-2,3-dioxopiperazine-1-carboxamido)-2-(2-fluoro-4,5-dihydroxyphenyl)acetamido)-2-hydroxy-3,4-dihydro-2H-benzo[e][1,2]oxaborinine-8-carboxylic acid

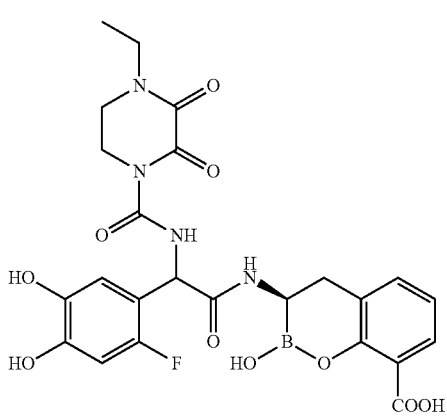 [SMILES: CCN1CCN(C(=O)NC(C(=O)N[C@H]2Cc3cccc(C(=O)O)c3OB2O)c2cc(O)c(O)cc2F)C(=O)C1=O]

In a similar manner to the synthesis of Example 37, utilizing 2-fluoro-4,5-dimethoxybenzaldehyde in place of 2-chloro-3,4-dimethoxybenzaldehyde in Step 1, the title compound was prepared. ESI-MS m/z 575 (M+H)⁺.

Example 91: (R)-3-((R)-2-(1-carbamimidoylpiperidin-4-yl)-2-(4-ethyl-2,3-dioxopiperazine-1-carboxamido)acetamido)-2-hydroxy-3,4-dihydro-2H-benzo[e][1,2]oxaborinine-8-carboxylic acid

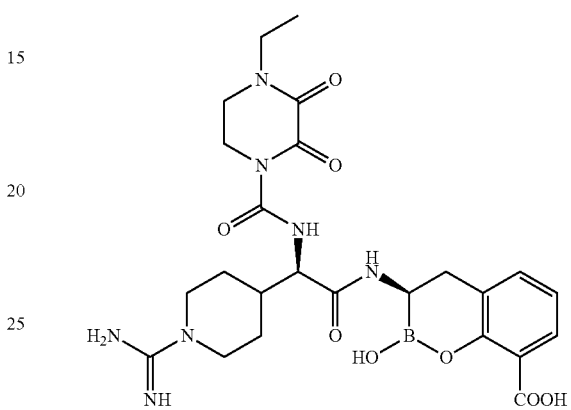

The title compound was prepared from tert-butyl 3-((2R)-2-(2-(4-ethyl-2,3-dioxopiperazine-1-carboxamido)-2-(piperidin-4-yl)acetamido)-2-((3aS,4S,6S,7aR)-3a,5,5-trimethylhexahydro-4,6-methanobenzo[d][1,3,2]dioxaborol-2-yl)ethyl)-2-methoxybenzoate, hydrochloric acid salt (from Example 72, Step 2a) and tert-butyl (Z)-(((tert-butoxycarbonyl)amino)(1H-pyrazol-1-yl)methylene)carbamate by a procedure similar to Example 72. ESI-MS m/z 558.2 (M+H)⁺.

Example 92: (R)-3-((S)-2-(1-carbamimidoylpiperidin-4-yl)-2-(4-ethyl-2,3-dioxopiperazine-1-carboxamido)acetamido)-2-hydroxy-3,4-dihydro-2H-benzo[e][1,2]oxaborinine-8-carboxylic acid

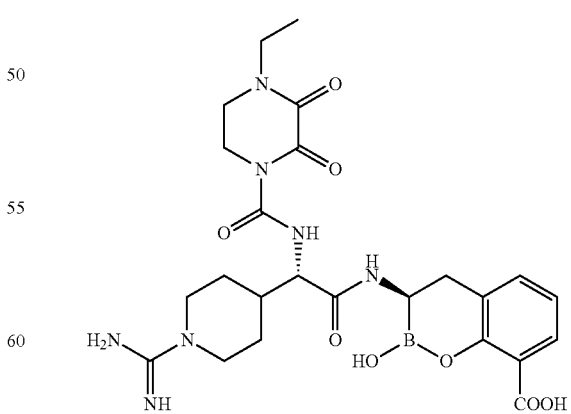

The title compound was isolated by reverse phase HPLC (Gilson) as the more polar isomer in Example 91. ESI-MS m/z 558.1 (M+H)⁺.

Example 93: (3R)-3-(2-(4-ethyl-2,3-dioxopiperazine-1-carboxamido)-2-(2-fluoro-4,5-dihydroxyphenyl)acetamido)-2-hydroxy-3,4-dihydro-2H-benzo[e][1,2]oxaborinine-8-carboxylic acid

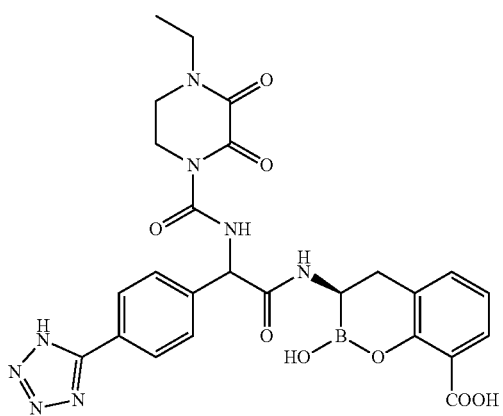 [SMILES: CCN1CCN(C(=O)NC(C(=O)N[C@H]2Cc3cccc(C(=O)O)c3OB2O)c2ccc(-c3nnn[nH]3)cc2)C(=O)C1=O]

In a similar manner to the synthesis of Example 37, utilizing 4-(1H-tetrazol-5-yl)benzaldehyde in place of 2-chloro-3,4-dimethoxybenzaldehyde in Step 1, the title compound was prepared. ESI-MS m/z 577 (M+H)$^+$.

Example 94: (R)-3-((2R,3R)-2-(4-(2-fluoroethyl)-2,3-dioxopiperazine-1-carboxamido)-3-hydroxybutanamido)-2,6,7-trihydroxy-3,4-dihydro-2H-benzo[e][1,2]oxaborinine-8-carboxylic acid

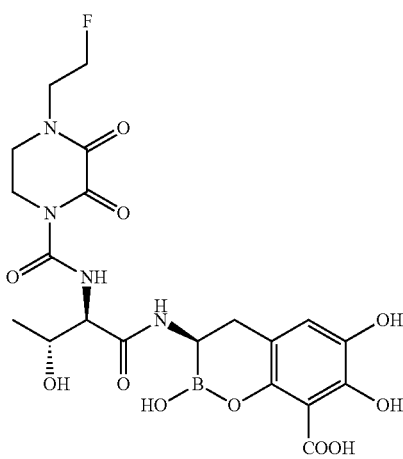 [SMILES: C[C@@H](O)[C@@H](NC(=O)N1CCN(CCF)C(=O)C1=O)C(=O)N[C@H]1Cc2cc(O)c(O)c(C(=O)O)c2OB1O]

Step 1. Synthesis of tert-butyl 3-bromo-2,5,6-trimethoxybenzoate

Step 1a 2,3,6-Trimethoxybenzoic acid (10.6 g, 50 mmol) in dioxane (100 mL) was treated dropwise with a solution of bromine (8 g, 2.6 mL) in dioxane (50 mL) at room temperature. The reaction mixture was stirred for an additional 2 hours and next it was partitioned between water and diethyl ether. The organic extracts were dried over Na$_2$SO$_4$, filtered, and the solvent was evaporated under reduced pressure. The crude product was further dried on high vacuum and used in the next step without purification.

Step 1b

The product of Step 1a in dichloromethane (100 mL) was treated with tert-butyl 2,2,2-trichloroacetimidate (18 mL, 100 mmol) at room temperature, overnight. The reaction mixture was diluted with hexanes and filtered. The solvent in the filtrate was evaporated and the resulting product was purified by flash chromatography (ethyl acetate/hexane 0 to 10% gradient, Silica gel) to afford tert-butyl 3-bromo-2,5,6-trimethoxybenzoate (16 g, 92% yield) Step 2. Synthesis of tert-butyl 2,3,6-trimethoxy-5-((3aS,4S,6S,7aR)-3a,5,5-trimethylhexahydro-4,6-methanobenzo[d][1,3,2]dioxaborol-2-yl)benzoate.

A mixture of tert-butyl 3-bromo-2,5,6-trimethoxybenzoate (4.64 g, 13.4 mmol), bis[(+)-pinanediolato]diboron (7.2 g, 20 mmol), [1,1'-bis(diphenylphosphino)ferrocene]dichloropalladium(II), complex with dichloromethane (570 mg, 0.7 mmol), and potassium acetate (4.1 g, 42 mmol) in dimethylformamide (50 mL) was stirred at 80° C. overnight, under argon. The cooled reaction mixture was diluted with ethyl acetate and filtered through Celite. The solvent in the filtrate was evaporated under reduced pressure and the residue was partitioned between diethyl ether and water. The aqueous phase was extracted two more times with diethyl ether. The organic extracts were dried over Na$_2$SO$_4$, filtered, and the solvent was evaporated under reduced pressure. The product was isolated by flash chromatography (ethyl acetate/hexane 0 to 10% gradient, Silica gel): 5.1 g (86% yield).

Step 3. Synthesis of tert-butyl 3-((S)-2-chloro-2-((3aS,4S,6S,7aR)-3a,5,5-trimethylhexahydro-4,6-methanobenzo[d][1,3,2]dioxaborol-2-yl)ethyl)-2,5,6-trimethoxybenzoate tert-Butyl 2,3,6-trimethoxy-5-((3aS,4S,6S,7aR)-3a,5,5-trimethylhexahydro-4,6-methanobenzo[d][1,3,2]dioxaborol-2-yl)benzoate was converted to tert-butyl 3-((S)-2-chloro-2-((3aS,4S,6S,7aR)-3a,5,5-trimethylhexahydro-4,6-methanobenzo[d][1,3,2]dioxaborol-2-yl)ethyl)-2,5,6-trimethoxybenzoate by a two-step procedure similar to Example 16, Steps 5 and 6

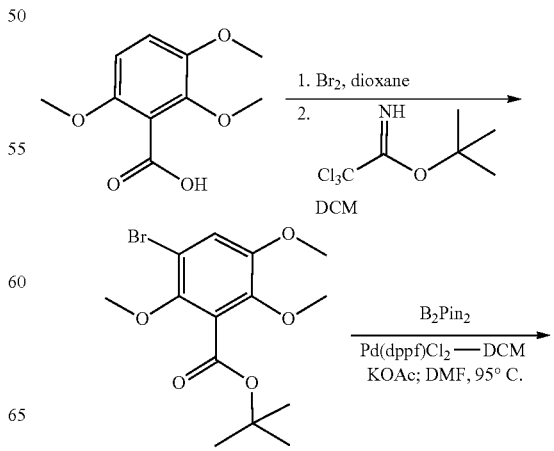

-continued

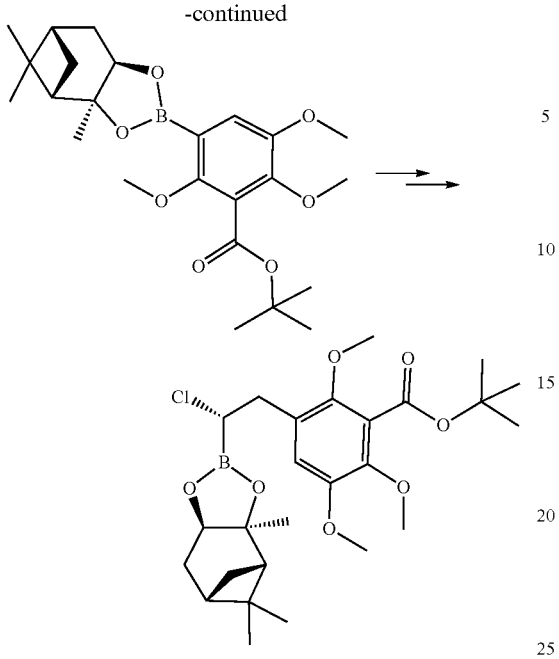

Step 4. Synthesis of (R)-3-((2R,3R)-2-(4-(2-fluoro-ethyl)-2,3-dioxopiperazine-1-carboxamido)-3-hydroxybutanamido)-2,6,7-trihydroxy-3,4-dihydro-2H-benzo[e][1,2]oxaborinine-8-carboxylic acid The title compound was prepared from D-allothreonine, 4-(2-fluoroethyl)-2,3-dioxopiperazine-1-carbonyl chloride (prepared as in Example 13), and tert-butyl 3-((S)-2-chloro-2-((3aS,4S,6S,7aR)-3a,5,5-trimethylhexahydro-4,6-methanobenzo[d][1,3,2]dioxaborol-2-yl)ethyl)-2,5,6-trimethoxybenzoate by a procedure similar to Example 8, employing boron tribromide instead of boron trichloride. ESI-MS m/z 527.1 (M+H)⁺.

Example 95: (R)-3-((2R,3R)-2-(4-ethyl-2,3-dioxopiperazine-1-carboxamido)-3-hydroxybutanamido)-2,6,7-trihydroxy-3,4-dihydro-2H-benzo[e][1,2]oxaborinine-8-carboxylic acid

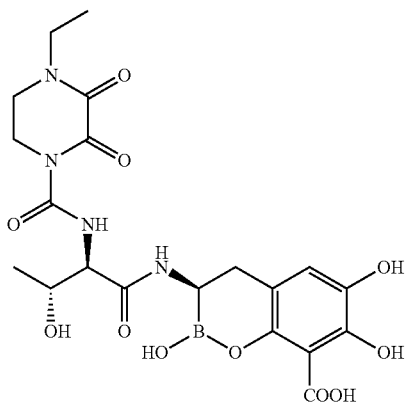 [SMILES: CCN1CCN(C(=O)N[C@@H](C(=O)N[C@H]2Cc3cc(O)c(O)c(C(=O)O)c3OB2O)[C@@H](C)O)C(=O)C1=O]

The title compound was prepared from D-allo-threonine and tert-butyl 3-((S)-2-chloro-2-((3aS,4S,6S,7aR)-3a,5,5-trimethylhexahydro-4,6-methanobenzo[d][1,3,2]dioxaborol-2-yl)ethyl)-2,5,6-trimethoxybenzoate by a procedure similar to Example 94. ESI-MS m/z 509.2 (M+H)⁺.

Example 96: (R)-3-((2R,3S)-2-(4-ethyl-2,3-dioxopiperazine-1-carboxamido)-3-hydroxybutanamido)-2,6,7-trihydroxy-3,4-dihydro-2H-benzo[e][1,2]oxaborinine-8-carboxylic acid

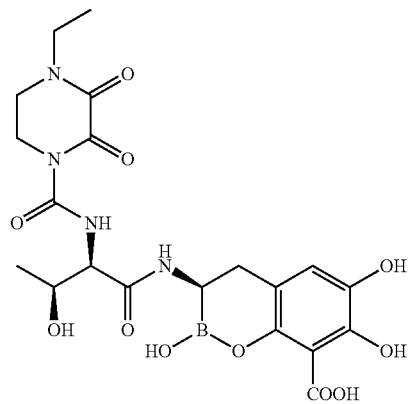 [SMILES: CCN1CCN(C(=O)N[C@@H](C(=O)N[C@H]2Cc3cc(O)c(O)c(C(=O)O)c3OB2O)[C@H](C)O)C(=O)C1=O]

The title compound was prepared from D-threonine and tert-butyl 3-((S)-2-chloro-2-((3aS,4S,6S,7aR)-3a,5,5-trimethylhexahydro-4,6-methanobenzo[d][1,3,2]dioxaborol-2-yl)ethyl)-2,5,6-trimethoxybenzoate by a procedure similar to Example 94. ESI-MS m/z 509.1 (M+H)⁺.

Example 97: (R)-3-((R)-2-(2-aminothiazol-4-yl)-2-(4-ethyl-2,3-dioxopiperazine-1-carboxamido)propanamido)-2-hydroxy-3,4-dihydro-2H-benzo[e][1,2]oxaborinine-8-carboxylic acid

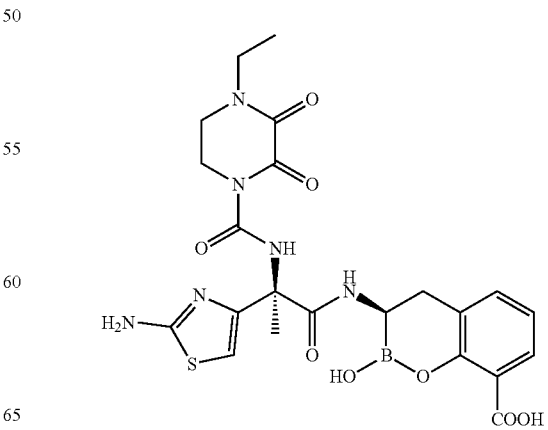

Example 98: (R)-3-((S)-2-(2-aminothiazol-4-yl)-2-(4-ethyl-2,3-dioxopiperazine-1-carboxamido)propanamido)-2-hydroxy-3,4-dihydro-2H-benzo[e][1,2]oxaborinine-8-carboxylic acid

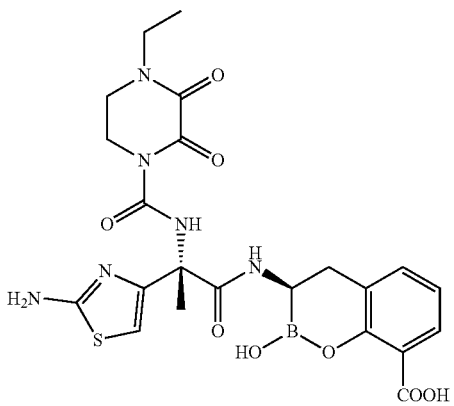

In a similar manner to the synthesis of Example 37, utilizing 1-(2-aminothiazol-4-yl)ethanone in place of 2-chloro-3,4-dimethoxybenzaldehyde in Step 1, the title compounds, Example 97 and Example 98 were separated by reversed phase HPLC. ESI-MS m/z 545 (M+H)$^+$.

Example 99: (3R)-3-(2-(4-(2-fluoroethyl)-2,3-dioxopiperazine-1-carboxamido)-2-(5-hydroxypyridin-2-yl)acetamido)-2-hydroxy-3,4-dihydro-2H-benzo[e][1,2]oxaborinine-8-carboxylic acid In a similar manner to the synthesis of Example 89 utilizing 4-(2-fluoroethyl)-2,3-dioxopiperazine-1-carbonyl chloride in place of 4-ethyl-2,3-dioxopiperazine-1-carbonyl chloride, the title compound was prepared. ESI-MS m/z 544 (M+H)$^+$.

Example 100: (3R)-3-(2-(2-aminothiazol-5-yl)-2-(4-(2-fluoroethyl)-2,3-dioxopiperazine-1-carboxamido)acetamido)-2-hydroxy-3,4-dihydro-2H-benzo[e][1,2]oxaborinine-8-carboxylic acid

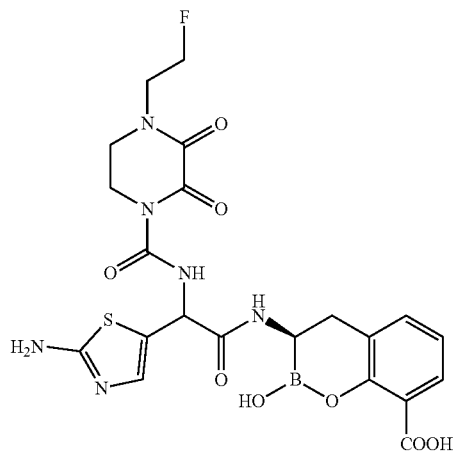 [SMILES: Nc1ncc(C(NC(=O)N2CCN(CCF)C(=O)C2=O)C(=O)N[C@H]2Cc3cccc(C(=O)O)c3OB2O)s1]

In a similar manner to the synthesis of Example 37, utilizing tert-butyl (5-formylthiazol-2-yl)carbamate in place of 2-chloro-3,4-dimethoxybenzaldehyde in Step 1, and utilizing 4-fluoroethyl-2,3-dioxopiperazine-1-carbonyl chloride (product from Step 2 of Example 13) in place of 4-ethyl-2,3-dioxopiperazine-1-carbonyl chloride in Step 3, the title compound was prepared. ESI-MS m/z 549 (M+H)$^+$.

Example 101: (3R)-3-(2-(2-aminothiazol-5-yl)-2-(2,3-dioxo-4-propylpiperazine-1-carboxamido)acetamido)-2-hydroxy-3,4-dihydro-2H-benzo[e][1,2]oxaborinine-8-carboxylic acid

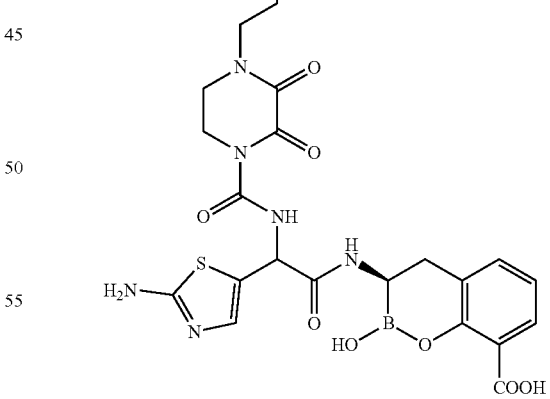

In a similar manner to the synthesis of Example 37, utilizing tert-butyl (5-formylthiazol-2-yl)carbamate in place of 2-chloro-3,4-dimethoxybenzaldehyde in Step 1, and utilizing 4-propyl-2,3-dioxopiperazine-1-carbonyl chloride (product from Step 1 of Example 82) in place of 4-ethyl-2,3-dioxopiperazine-1-carbonyl chloride in Step 3, the title compound was prepared. ESI-MS m/z 545 (M+H)$^+$.

Example 102: (3R)-3-(2-(4-ethyl-2,3-dioxopiperazine-1-carboxamido)-2-(4-sulfamoylphenyl)acetamido)-2-hydroxy-3,4-dihydro-2H-benzo[e][1,2]oxaborinine-8-carboxylic acid

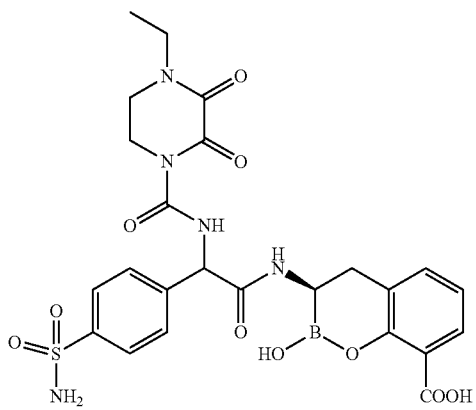 [SMILES: CCN1CCN(C(=O)NC(C(=O)N[C@H]2Cc3cccc(C(=O)O)c3OB2O)c2ccc(S(N)(=O)=O)cc2)C(=O)C1=O]

In a similar manner to the synthesis of Example 37, utilizing 4-formylbenzenesulfonamide in place of 2-chloro-3,4-dimethoxybenzaldehyde in Step 1, the title compounds was prepared. ESI-MS m/z 588 (M+H)$^+$.

Example 103: (3R)-3-(2-(4-(2-fluoroethyl)-2,3-dioxopiperazine-1-carboxamido)-2-(4-sulfamoylphenyl)acetamido)-2-hydroxy-3,4-dihydro-2H-benzo[e][1,2]oxaborinine-8-carboxylic acid

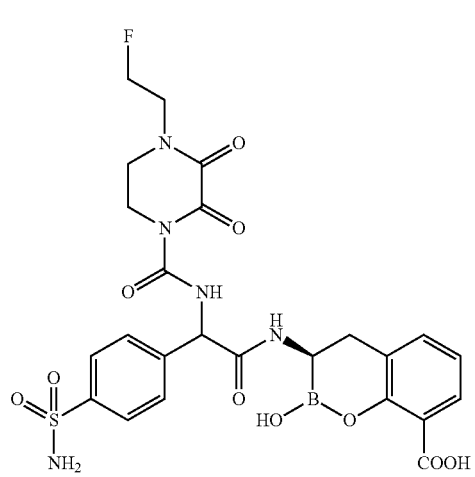 [SMILES: NS(=O)(=O)c1ccc(C(NC(=O)N2CCN(CCF)C(=O)C2=O)C(=O)N[C@H]2Cc3cccc(C(=O)O)c3OB2O)cc1]

In a similar manner to the synthesis of Example 37, utilizing 4-formylbenzenesulfonamide in place of 2-chloro-3,4-dimethoxybenzaldehyde in Step 1, and utilizing 4-fluoroethyl-2,3-dioxopiperazine-1-carbonyl chloride (product from Step 2 of Example 13) in place of 4-ethyl-2,3-dioxopiperazine-1-carbonyl chloride in Step 3, the title compound was prepared. ESI-MS m/z 549 (M+H)$^+$.

Example 104: (3R)-3-(2-(6-aminopyridin-2-yl)-2-(4-ethyl-2,3-dioxopiperazine-1-carboxamido)acetamido)-2-hydroxy-3,4-dihydro-2H-benzo[e][1,2]oxaborinine-8-carboxylic acid

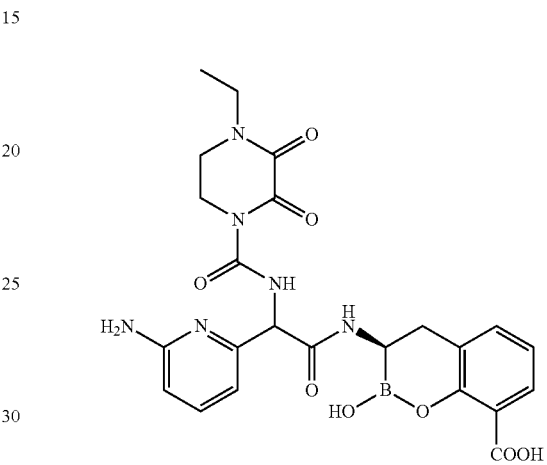

Step 1: Synthesis of benzyl (6-formylpyridin-2-yl)carbamate

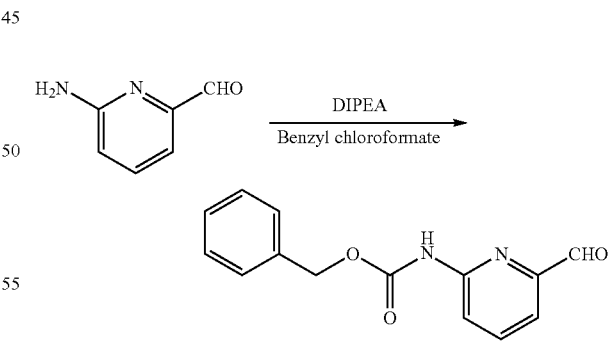

To 6-aminopicolinaldehyde 1.5 g (12.3 mmol) in tetrahydrofuran (45 mL) at 0° C. was added diisopropylethylamine 3.2 mL (17.2 mmol, 1.4 eq), followed by benzyl chloroformate 2.41 mL (17.2 mmol, 1.4 eq) and the reaction was stirred at RT for 18 h. The solvent was concentrated off and purified by flash chromatography on silica gel (20% ethyl acetate/hexanes) to afford the title compound, 1.97 g. ESI-MS m/z 257 (M+H)$^+$.

Step 2: Synthesis of (3R)-3-(2-(6-aminopyridin-2-yl)-2-(4-ethyl-2,3-dioxopiperazine-1-carboxamido)acetamido)-2-hydroxy-3,4-dihydro-2H-benzo[e][1,2]oxaborinine-8-carboxylic acid

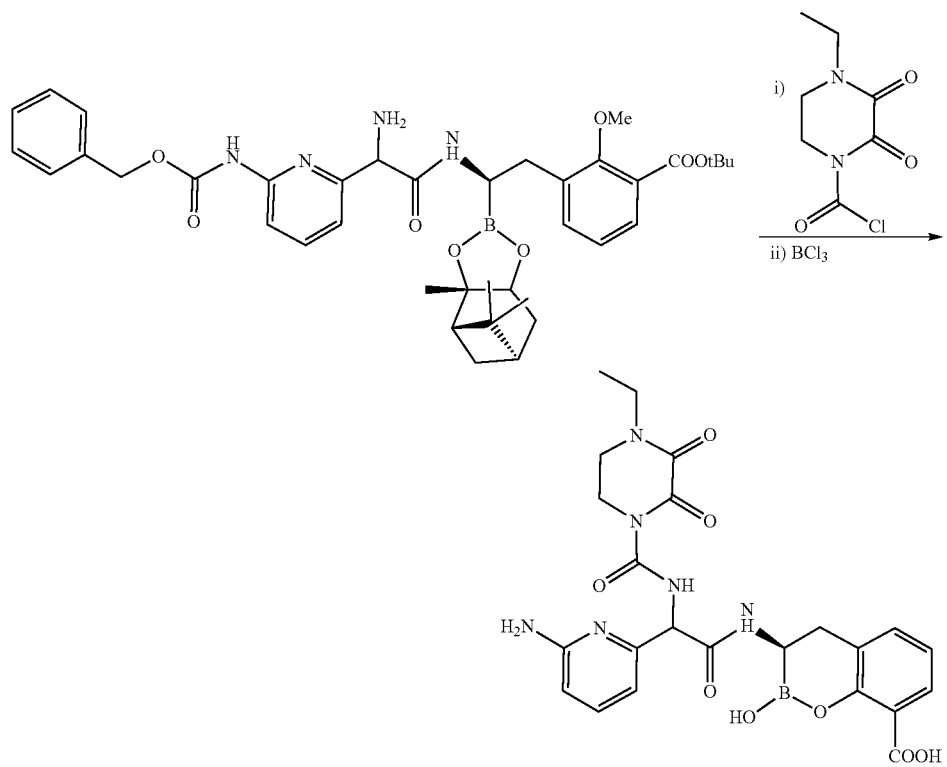

In a similar manner to the synthesis of Example 56, the title compound was prepared. ESI-MS m/z 525 (M+H)$^+$.

Example 105: (3R)-3-(2-(4-ethyl-2,3-dioxopiperazine-1-carboxamido)-2-(pyridin-3-yl)acetamido)-2-hydroxy-3,4-dihydro-2H-benzo[e][1,2]oxaborinine-8-carboxylic acid Step 1. Synthesis of tert-butyl 3-((2R)-2-(2-amino-2-(pyridin-3-yl)acetamido)-2-((3aS,4S,6S,7aR)-3a,5,5-trimethylhexahydro-4,6-methanobenzo[d][1,3,2]dioxaborol-2-yl)ethyl)-2-methoxybenzoate

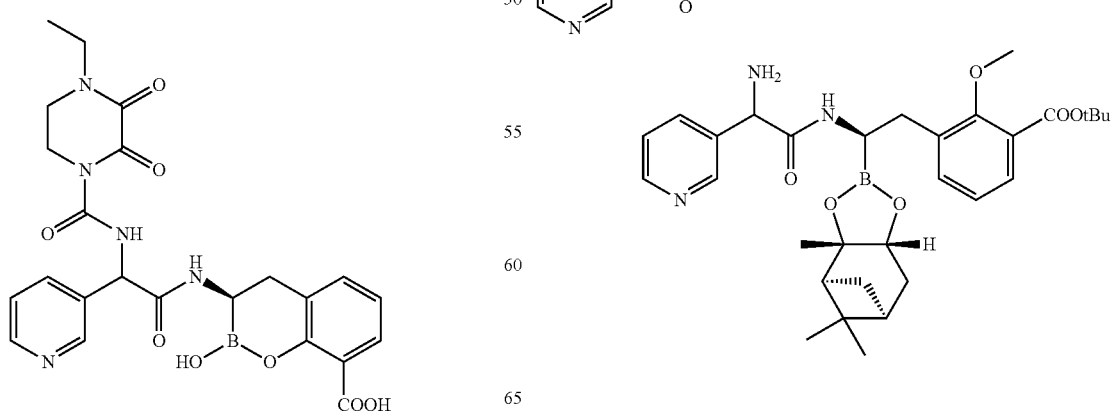

By following the same experimental procedures of Step 1 and Step 1 of Example 6, the title compound was prepared from 2-((tert-butoxycarbonyl)amino)-2-(pyridin-3-yl)acetic acid as an HCl salt. ESI-MS m/z 564 (M+H)⁺.

Step 2. Synthesis of tert-butyl 3-((2R)-2-(2-(4-ethyl-2,3-dioxopiperazine-1-carboxamido)-2-(pyridin-3-yl)acetamido)-2-((3aS,4S,6S,7aR)-3a,5,5-trimethylhexahydro-4,6-methanobenzo[d][1,3,2]dioxaborol-2-yl)ethyl)-2-methoxybenzoate Step 3. Synthesis of (3R)-3-(2-(4-ethyl-2,3-dioxopiperazine-1-carboxamido)-2-(pyridin-3-yl)acetamido)-2-hydroxy-3,4-dihydro-2H-benzo[e][1,2]oxaborinine-8-carboxylic acid

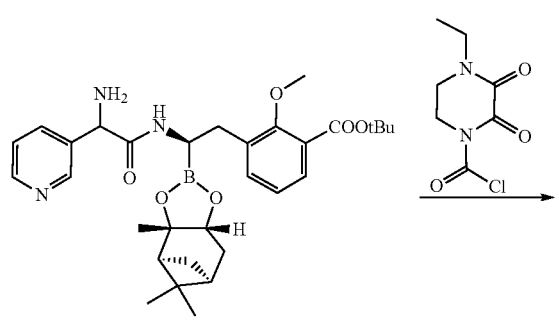

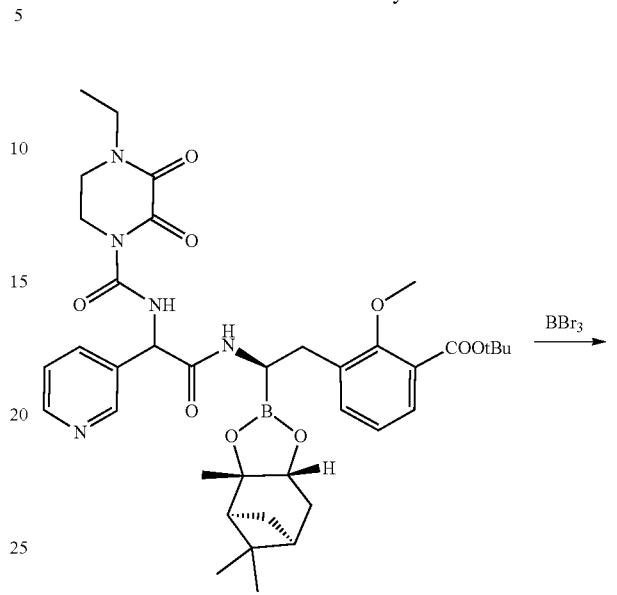

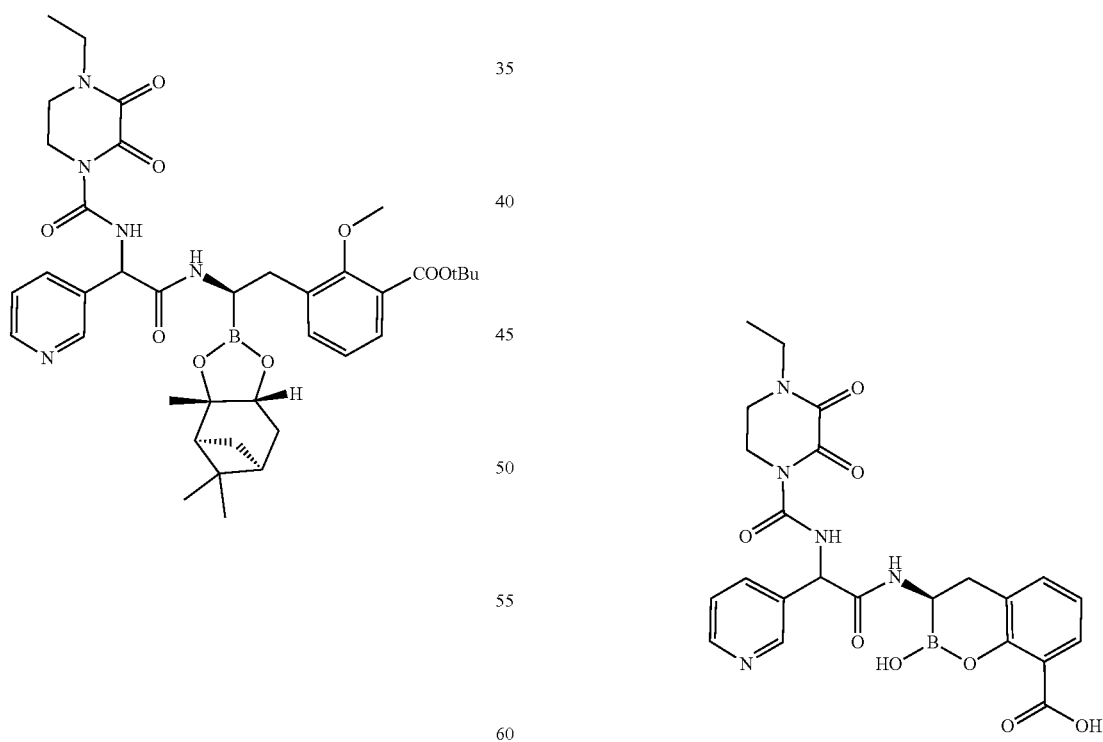

In a similar manner to the synthesis of Example 7, utilizing 4-ethyl-2,3-dioxopiperazine-1-carbonyl chloride in place of pyridine-3-sulfonyl chloride in Step 1, the title compound was prepared from the above amine intermediate. ESI-MS m/z 732 (M+H)⁺.

By following the General Method A, the above product was treated with BBr₃ to afford the title compound. ESI-MS m/z 510 (M+H)⁺.

Example 106: (3R)-3-(2-(4-ethyl-2,3-dioxopiperazine-1-carboxamido)-2-(1-methylpyridin-1-ium-3-yl)acetamido)-2-hydroxy-3,4-dihydro-2H-benzo[e][1,2]oxaborinine-8-carboxylate

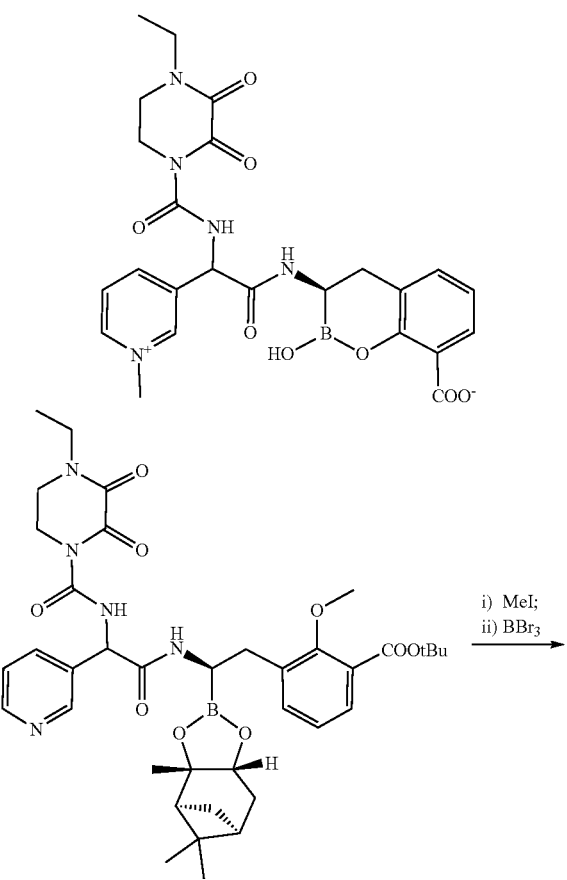

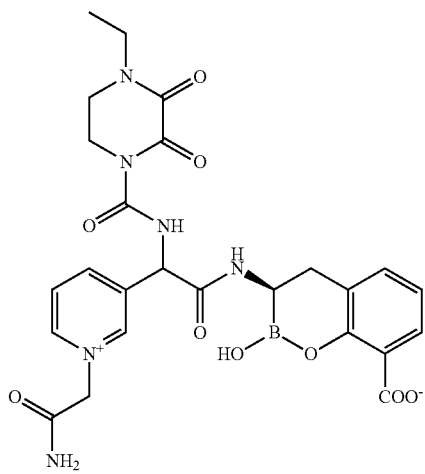

Example 107: (3R)-3-(2-(1-(2-amino-2-oxoethyl)pyridin-1-ium-3-yl)-2-(4-ethyl-2,3-dioxopiperazine-1-carboxamido)acetamido)-2-hydroxy-3,4-dihydro-2H-benzo[e][1,2]oxaborinine-8-carboxylate In a similar manner to the synthesis of Example 106, utilizing 2-bromoacetamide in place of methyl iodide, the title compound was prepared. ESI-MS m/z 567 (M+H)$^+$.

Example 108: 2-(3-(2-(((R)-8-carboxy-2-hydroxy-3,4-dihydro-2H-benzo[e][1,2]oxaborinin-3-yl)amino)-1-(4-ethyl-2,3-dioxopiperazine-1-carboxamido)-2-oxoethyl)pyridin-1-ium-1-yl)acetate

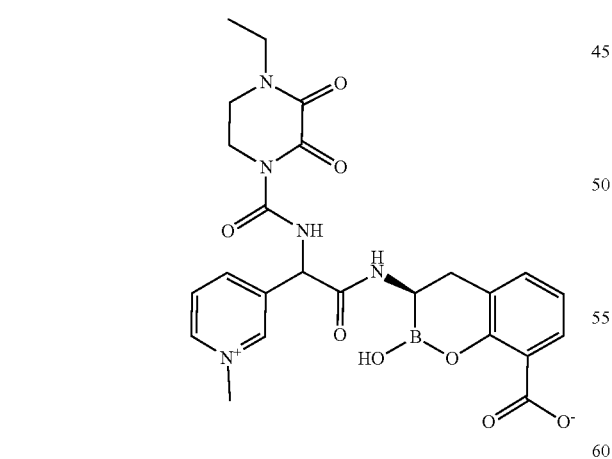

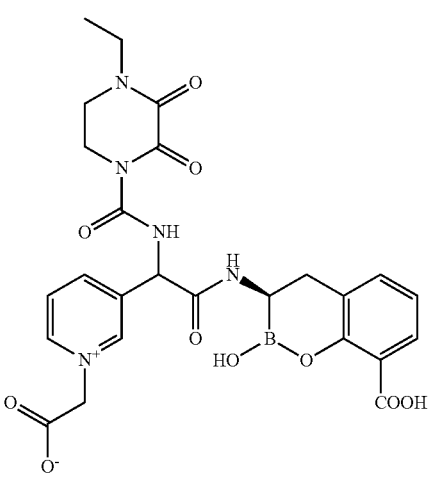 [SMILES: CCN1CCN(C(=O)NC(C(=O)N[C@H]2Cc3cccc(C(=O)O)c3OB2O)c2ccc[n+](CC(=O)[O-])c2)C(=O)C1=O]

The product from Step 2 of Example 105 (183 mg, 0.25 mmol) was dissolved in acetone (5 mL), reacted with methyl iodide (0.19 mL, 3 mmol) at RT overnight, and then concentrated. By following the General Method A, this crude product was treated with BBr$_3$ to afford the title compound. ESI-MS m/z 524 (M+H)$^+$.

In a similar manner to the synthesis of Example 106, utilizing tert-butyl 2-bromoacetate in place of methyl iodide, the title compound was prepared. ESI-MS m/z 568 (M+H)$^+$.

Example 109: (3R)-3-(2-(2-aminothiazol-4-yl)-2-(4-ethyl-2,3-dioxopiperazine-1-carboxamido)acetamido)-7-fluoro-2-hydroxy-3,4-dihydro-2H-benzo[e][1,2]oxaborinine-8-carboxylic acid

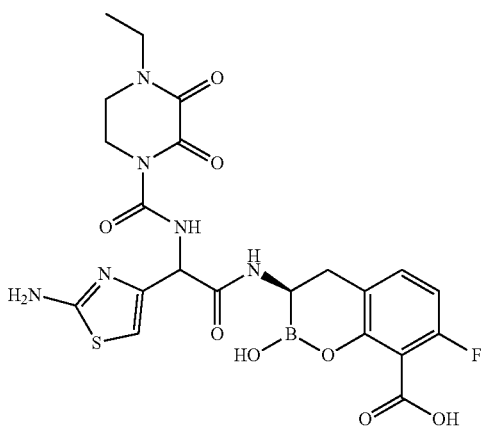 [SMILES: CCN1CCN(C(=O)NC(C(=O)N[C@H]2Cc3ccc(F)c(C(=O)O)c3OB2O)c2csc(N)n2)C(=O)C1=O]

Step 1. Synthesis of tert-butyl(4-fluoro-2-methoxyphenoxy)dimethylsilane

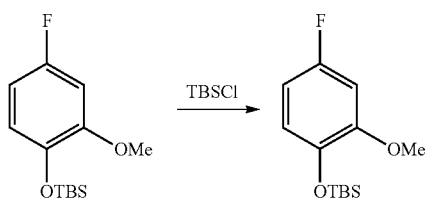 [SMILES: COc1cc(F)ccc1O[Si](C)(C)C(C)(C)C ; "TBSCl" ; COc1cc(F)ccc1O[Si](C)(C)C(C)(C)C]

To a solution of 4-fluoro-2-methoxyphenol (5.68 g, 40 mmol) in DCM (100 mL) was added TEA (11.2 mL, 80 mmol), 4-DMAP (488 mg, 4 mmol) followed by TBSCl (7.5 g, 49.8 mmol). The reaction mixture was stirred at RT for overnight, then re-cooled to 0° C., Boc₂O (36.7 g, 168 mmol) was added. The reaction mixture was stirred at RT overnight, washed with aqueous NaHCO₃, dried over Na₂SO₄, and concentrated. The crude product was purified by flash chromatography on silica gel (hexane-EtOAc, 50:1-10:1) to afford the title compound, 10 g. ESI-MS m/z 257 (M+H)⁺.

Step 2. Synthesis of tert-butyl 3-((tert-butyldimethylsilyl)oxy)-6-fluoro-2-methoxybenzoate

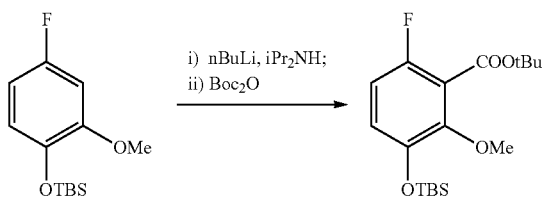

To a solution of diisopropylamine (6.6 mL, 46.8 mmol) in anhydrous THF (120 mL) at −65° C. was added nBuLi (2.5 M, 18.72 mL, 46.8 mmol) dropwise under argon. The reaction mixture was stirred between −60° C.--55° C. for 20 min. To this reaction mixture was added the above product (10 g, 39 mmol) in THF (15 mL) dropwise, stirred for 1 h, then Boc₂O (28.19 g, 129 mmol) was added. The reaction mixture was slowly warmed up to RT, and stirred at RT overnight, quenched with water, extracted with ethyl acetate. The organic extracts were washed with brine, dried over Na₂SO₄, and concentrated. The crude product was purified by flash chromatography on silica gel (DCM-hexane, 1:20-1:1) to afford the title compound (8 g), which was contaminated with some by product and Boc₂O. ESI-MS m/z 357 (M+H)⁺.

Step 3. Synthesis of tert-butyl 6-fluoro-3-hydroxy-2-methoxybenzoate

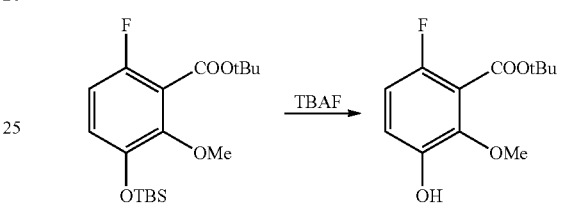

To a solution of the above product (8 g, 22.5 mmol) in THF (150 mL) was added TBAF (1.0 M, 50 mL, 50 mmol), the reaction was stirred at RT for 1.5 h, diluted with EtOAc, washed with saturated aqueous NaHCO₃, brine, dried over Na₂SO₄, and concentrated. The crude product was purified by flash chromatography on silica gel (hexane-EtOAc, 40:1-2:1) to afford the title compound, 1.4 g, ESI-MS m/z 243 (M+H)⁺, and O-Boc product, 2.6 g, ESI-MS m/z 343 (M+H)⁺. The O-Boc product (2.6 g) was treated with excess piperidine in DCM at RT overnight to afford additional 1.4 g of the title compound after purification by flash chromatography.

Step 4. Synthesis of tert-butyl 6-fluoro-2-methoxy-3-(((trifluoromethyl)sulfonyl)oxy)benzoate

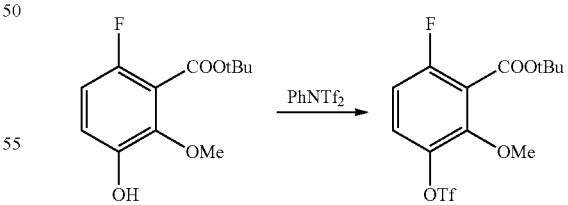

To a solution of the above product (1.4 g, 5.8 mmol) in DCM (50 mL) was added PhNTf₂ (2.9 g, 8.12 mmol), TEA (2.03 mL, 14.5 mmol) and 4-DMAP (71 mg, 0.58 mmol). The reaction mixture was stirred at RT overnight, washed with saturated aqueous NaHCO₃, dried over Na₂SO₄, and concentrated. The crude product was purified by flash chromatography on silica gel (hexane-DCM, 10:1-1:4) to afford the title compound, 1.9 g. ESI-MS m/z 375 (M+Na)⁺.

Step 5. Synthesis of tert-butyl 6-fluoro-2-methoxy-3-((3aS,4S,6S)-3a,5,5-trimethylhexahydro-4,6-methanobenzo[d][1,3,2]dioxaborol-2-yl)benzoate

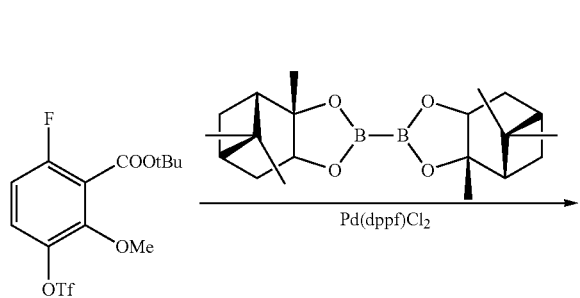

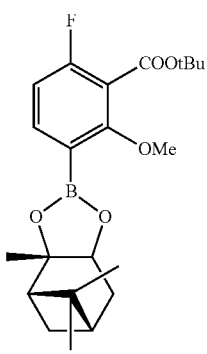

To the above product (3.85 g, 10.3 mmol) in dry DMF (35 mL) was added bis[(+)-pinanediolato]diboron (5.7 g, 15.9 mmol), KOAc (3.1 g, 31.6 mmol) and Pd(dppf)Cl₂-DCM (430 mg, 0.53 mmol). The reaction mixture was stirred at 90-100° C. overnight, added water, and extracted with diethyl ether. The ether extracts were washed with water, brine, dried over Na₂SO₄, and concentrated. The crude product was purified by flash chromatography on silica gel (hexane-DCM, 10:1-1:10) to afford the title compound, 2.4 g. ESI-MS m/z 831 (2M+Na)⁺.

Step 6. Synthesis of tert-butyl 6-fluoro-2-methoxy-3-(((3aS,4S,6S)-3a,5,5-trimethylhexahydro-4,6-methanobenzo[d][1,3,2]dioxaborol-2-yl)methyl)benzoate

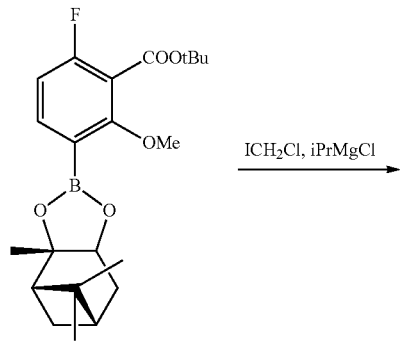

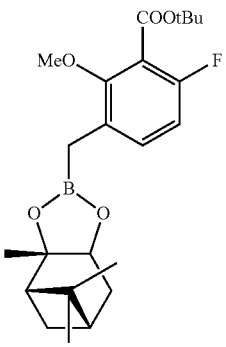

To a solution of chloroiodomethane (3.2 mL, 43.9 mmol) in THF (70 mL) at −78° C. was added dropwise under Argon isopropyl magnesium chloride lithium chloride complex solution (1.3 M in THF, 16.8 mL, 21.8 mmol) over 20 min. The resulting solution was stirred at −78° C. for 45 min, then a solution of the above product (2.38 g, 5.89 mmol) in THF (9 mL) was added slowly over 20 min. After the addition was completed, the reaction mixture was stirred for 1.5 h. To this solution was added ZnCl₂ solution (1.0 M in ether, 6.4 mL, 6.4 mmol) dropwise, and stirring continued for 15 min after the addition was completed. The cold bath was removed, the reaction mixture was stirred at RT overnight, cooled to −30° C., diluted with diethyl ether, washed with aqueous NH₄Cl, water and brine, dried over Na₂SO₄, and concentrated, purified by flash chromatography on silica gel (hexane-EtOAc, 20:1-5:1) to give the title compound, 2.24 g. ESI-MS m/z 441 (M+Na)⁺.

Step 7. Synthesis of tert-butyl 3-((2S)-2-chloro-2-((3aS,4S,6S)-3a,5,5-trimethylhexahydro-4,6-methanobenzo[d][1,3,2]dioxaborol-2-yl)ethyl)-6-fluoro-2-methoxybenzoate

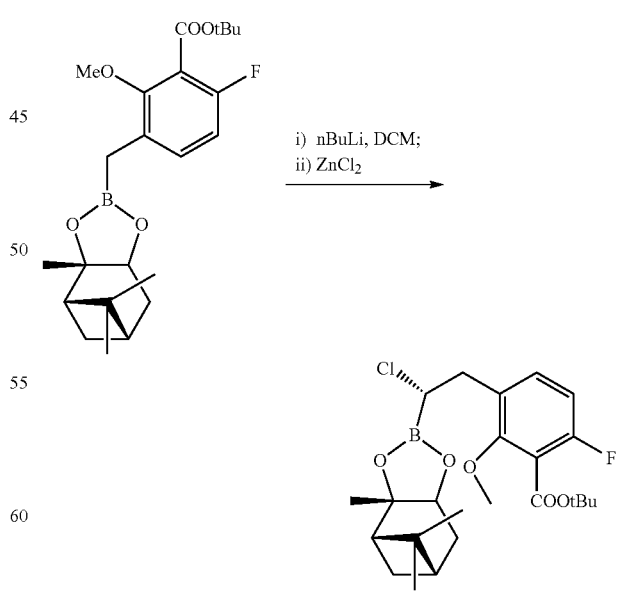

To a cooled (−100° C. MeOH/N₂) solution of DCM (0.82 mL, 12.8 mmol) in THF (15 mL) was added dropwise, down the side of the flask nBuLi (2.5 M in hexane, 3.06 mL, 7.65 mmol) over 20 min. The resulting mixture was stirred for 45 min, then a solution of the above product (2.24 g, 5.36 mmol) in THF (8 mL) was added slowly down the side of the flask over 20 min, and stirring continued for 45 min after the addition was completed. To the resulting mixture was added dropwise a solution of ZnCl$_2$ (1.0 M in ether, 7.3 mL, 7.3 mmol) over 5 min. After 15 min, the methanol/N$_2$ bath was replaced with a dry ice/acetone bath (−10° C.), and stirring continued for 1.5 h. The reaction mixture was diluted with diethyl ether and washed with aqueous NH$_4$Cl, water and brine, dried over Na$_2$SO$_4$, and concentrated. The crude product was purified by flash chromatography on silica gel (hexane-EtOAc, 20:1-4:1) to afford the title compound, 2.1 g. ESI-MS m/z 489 (M+Na)$^+$.

Step 8. Synthesis of (3R)-3-(2-(2-aminothiazol-4-yl)-2-(4-ethyl-2,3-dioxopiperazine-1-carboxamido)acetamido)-7-fluoro-2-hydroxy-3,4-dihydro-2H-benzo[e][1,2]oxaborinine-8-carboxylic acid

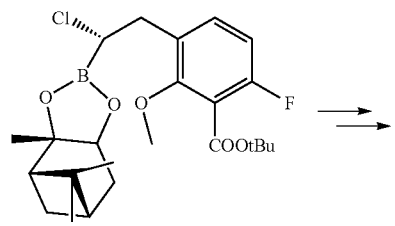

Example 110: (R)-3-((2R,3R)-2-(4-ethyl-2,3-dioxopiperazine-1-carboxamido)-3-hydroxybutanamido)-7-fluoro-2-hydroxy-3,4-dihydro-2H-benzo[e][1,2]oxaborinine-8-carboxylic acid

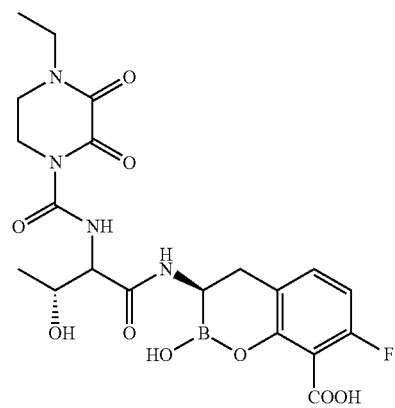 [SMILES: CCN1CCN(C(=O)NC(C(=O)N[C@H]2Cc3ccc(F)c(C(=O)O)c3OB2O)[C@@H](C)O)C(=O)C1=O]

The title compound was prepared from D-allothreonine and tert-butyl 3-((S)-2-chloro-2-((3aS,4S,6S,7aR)-3a,5,5-trimethylhexahydro-4,6-methanobenzo[d][1,3,2]dioxaborol-2-yl)ethyl)-6-fluoro-2-methoxybenzoate (from Example 109) by a procedure similar to Example 8. ESI-MS m/z 495.2 (M+H)$^+$.

Example 111: (3R)-3-(2-(4-ethyl-2,3-dioxopiperazine-1-carboxamido)-2-(pyrimidin-2-yl)acetamido)-2-hydroxy-3,4-dihydro-2H-benzo[e][1,2]oxaborinine-8-carboxylic acid

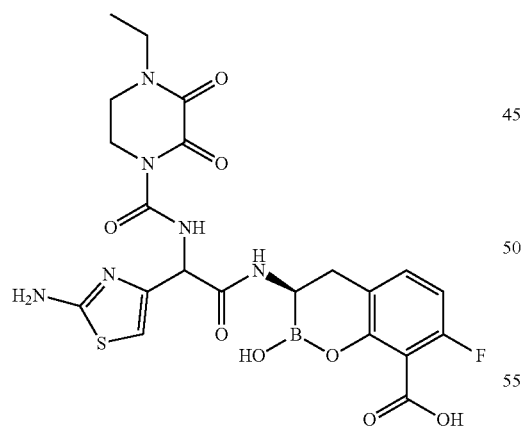

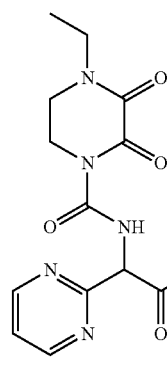

In a similar manner to the synthesis of Example 5, the title compound was prepared from the above chloride by following the General Method C and General Method A. ESI-MS m/z 549 (M+H)$^+$.

In a similar manner to the synthesis of Example 56 utilizing lithium 2-((tert-butoxycarbonyl)amino)-2-(pyrimidin-2-yl)acetate in place of lithium 2-((tert-butoxycarbonyl)amino)-2-(pyridin-2-yl)acetate, the title compound was prepared. ESI-MS m/z 511 (M+H)$^+$.

Example 112: (3R)-3-(2-(4-ethyl-2,3-dioxopiperazine-1-carboxamido)-2-(4-sulfamoylphenyl)acetamido)-2-hydroxy-3,4-dihydro-2H-benzo[e][1,2]oxaborinine-8-carboxylic acid

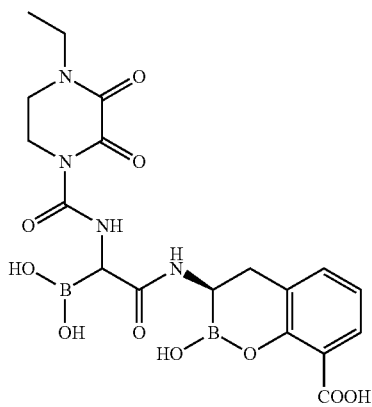 [SMILES: CCN1CCN(C(=O)NC(B(O)O)C(=O)N[C@H]2Cc3cccc(C(=O)O)c3OB2O)C(=O)C1=O]

Step 1. Synthesis of benzyl 2-(4-bromophenyl)-2-((tert-butoxycarbonyl)amino)acetate

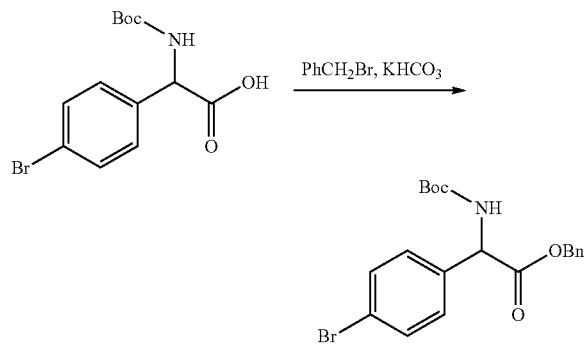

To a solution of 2-(4-bromophenyl)-2-((tert-butoxycarbonyl)amino)acetic acid (4.95 g, 15 mmol) in DMF (100 mL) was added KHCO$_3$ (2.25 g, 22.5 mmol), followed by benzyl bromide (3.08 g, 18 mmol). The reaction mixture was stirred at RT for 5 h, diluted with ethyl acetate, washed with water, brine, dried over Na$_2$SO$_4$, concentrated in vacuo to afford the crude product, which was used directly for the next step without further purification. ESI-MS m/z 420/422 (MH/MH+2)$^+$.

Step 2. Synthesis of benzyl 2-((tert-butoxycarbonyl)amino)-2-(4-((3aS,4S,6S)-3a,5,5-trimethylhexahydro-4,6-methanobenzo[d][1,3,2]dioxaborol-2-yl)phenyl)acetate

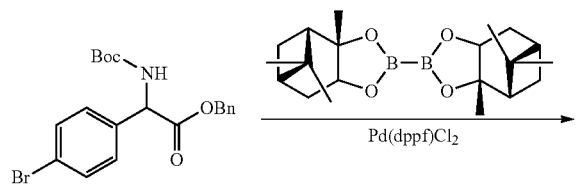

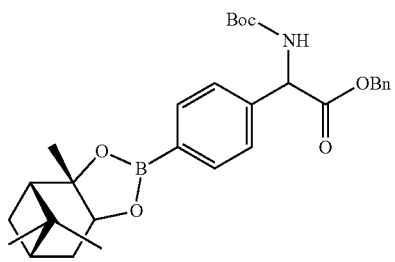

To the above product (2.94 g, 7 mmol) in dry dioxane (50 mL) was added bis[(+)-pinanediolato]diboron (3.4 g, 9.5 mmol), KOAc (2.2 g, 22.4 mmol) and Pd(dppf)Cl$_2$·DCM (300 mg, 0.37 mmol). The reaction mixture was stirred at 90-100° C. overnight, filtered through a pad of Celite, and concentrated. The crude product was purified by flash chromatography on silica gel (hexane-EtOAc, 20:1-4:1) to afford the title compound, 3.6 g. ESI-MS m/z 542 (M+Na)$^+$.

Step 3. Synthesis of 2-((tert-butoxycarbonyl)amino)-2-(4-((3aS,4S,6S)-3a,5,5-trimethylhexahydro-4,6-methanobenzo[d][1,3,2]dioxaborol-2-yl)phenyl)acetic acid

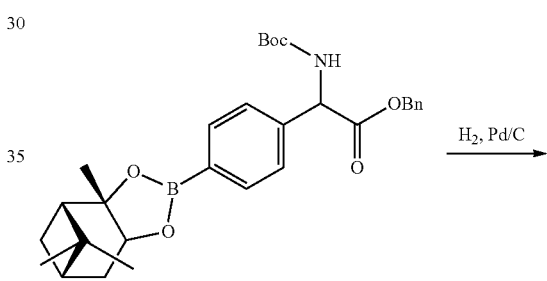

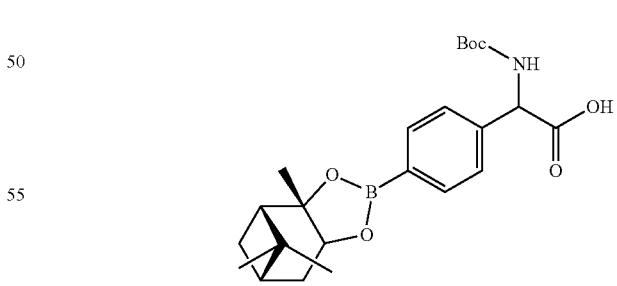

The above product (3.6 g, 6.94 mmol) in EtOAc (150 mL) was hydrogenated using a hydrogen balloon in the presence of 10% Pd/C (600 mg) at RT for 2 h. The reaction mixture was filtered through a pad of Celite, and concentrated in vacuo to afford the crude product, which was used directly for the next step without further purification. ESI-MS m/z 452 (M+Na)$^+$.

Step 4. Synthesis of (3R)-3-(2-(4-boronophenyl)-2-(4-ethyl-2,3-dioxopiperazine-1-carboxamido)acetamido)-2-hydroxy-3,4-dihydro-2H-benzo[e][1,2]oxaborinine-8-carboxylic acid

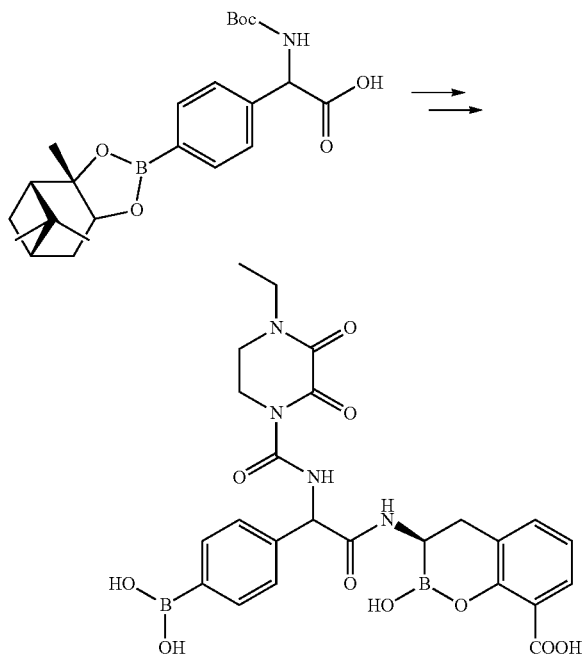

In a similar manner to the synthesis of Example 6, utilizing 4-ethyl-2,3-dioxopiperazine-1-carbonyl chloride in place of ethyl isocyanate in Step 3, the title compound was prepared from the above acid. ESI-MS m/z 553 (M+H)+.

Example 113: (3R)-3-(2-(4-boronophenyl)-2-(4-(2-fluoroethyl)-2,3-dioxopiperazine-1-carboxamido)acetamido)-2-hydroxy-3,4-dihydro-2H-benzo[e][1,2]oxaborinine-8-carboxylic acid

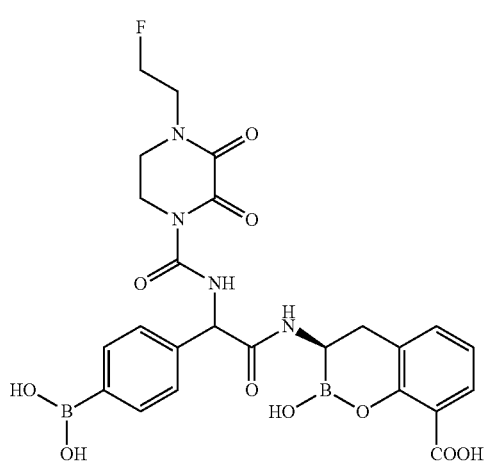 [SMILES: O=C(O)c1cccc2c1OB(O)[C@@H](NC(=O)C(NC(=O)N1CCN(CCF)C(=O)C1=O)c1ccc(B(O)O)cc1)C2]

In a similar manner to the synthesis of Example 112, utilizing 4-fluoroethyl-2,3-dioxopiperazine-1-carbonyl chloride (product from Step 2 of Example 13) in place of 4-ethyl-2,3-dioxopiperazine-1-carbonyl chloride in Step 4, the title compound was prepared. ESI-MS m/z 571 (M+H)+.

Example 114: (3R)-3-(2-(4-ethyl-2,3-dioxopiperazine-1-carboxamido)-2-(5-fluoropyridin-2-yl)acetamido)-2-hydroxy-3,4-dihydro-2H-benzo[e][1,2]oxaborinine-8-carboxylic acid

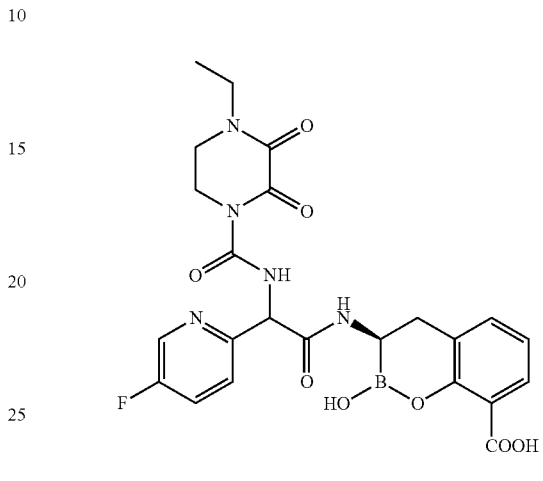

In a similar manner to the synthesis of Example 56 utilizing lithium 2-((tert-butoxycarbonyl)amino)-2-(5-fluoropyridin-2-yl)acetate in place of lithium 2-((tert-butoxycarbonyl)amino)-2-(pyridin-2-yl)acetate, the title compound was prepared. ESI-MS m/z 528 (M+H)+.

Example 115: (3R)-3-(2-(4-ethyl-2,3-dioxopiperazine-1-carboxamido)-2-(thiophen-2-yl)acetamido)-2-hydroxy-3,4-dihydro-2H-benzo[e][1,2]oxaborinine-8-carboxylic acid

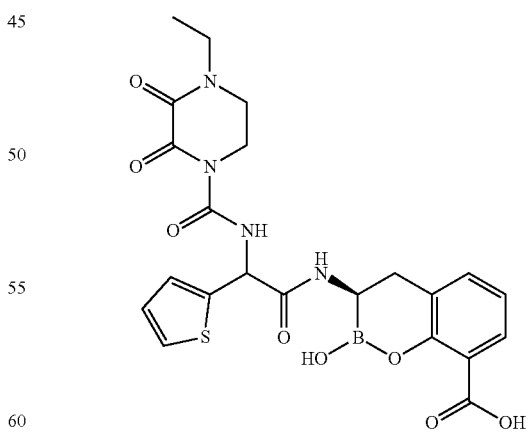

The title compound was prepared from 2-amino-2-(thiophen-2-yl)acetic acid and 3-((2S)-2-chloro-2-((3aS,4S,6S)-3a,5,5-trimethylhexahydro-4,6-methanobenzo-[d][1,3,2]dioxaborol-2-yl)ethyl)-2-methoxybenzoate, by a procedure similar to Example 8. ESI-MS m/z 515.2 (M+H)+.

Example 116: (3R)-3-(2-cyclopentyl-2-(4-ethyl-2,3-dioxopiperazine-1-carboxamido)acetamido)-2-hydroxy-3,4-dihydro-2H-benzo[e][1,2]oxaborinine-8-carboxylic acid

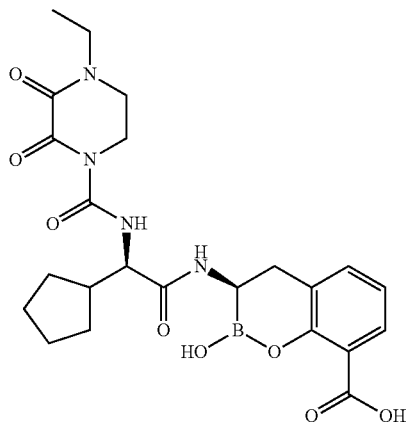 [SMILES: CCN1CCN(C(=O)N[C@@H](C(=O)N[C@H]2Cc3cccc(C(=O)O)c3OB2O)C2CCCC2)C(=O)C1=O]

The title compound was prepared from (R)-2-amino-2-cyclopentylacetic acid and 3-((2S)-2-chloro-2-((3aS,4S,6S)-3a,5,5-trimethylhexahydro-4,6-methanobenzo-[d][1,3,2]dioxaborol-2-yl)ethyl)-2-methoxybenzoate, by a procedure similar to Example 8. ESI-MS m/z 501.2 (M+H)$^+$.

Example 117: (3R)-3-(2-(4-ethyl-2,3-dioxopiperazine-1-carboxamido)-2-(6-hydroxypyridin-2-yl)acetamido)-2-hydroxy-3,4-dihydro-2H-benzo[e][1,2]oxaborinine-8-carboxylic acid

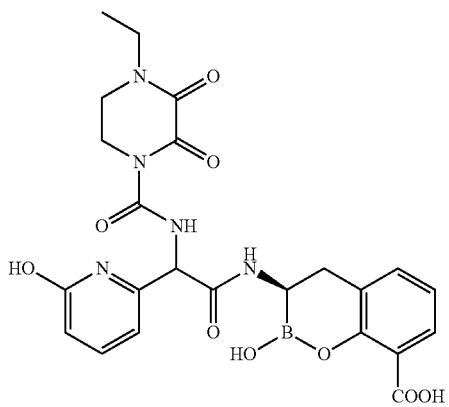 [SMILES: CCN1CCN(C(=O)NC(C(=O)N[C@H]2Cc3cccc(C(=O)O)c3OB2O)c2cccc(O)n2)C(=O)C1=O]

In a similar manner to the synthesis of Example 41, the title compound was prepared. ESI-MS m/z 526 (M+H)$^+$.

Example 118: (3R)-3-(2-(4-ethyl-2,3-dioxopiperazine-1-carboxamido)-2-(4-(methylsulfonyl)phenyl)acetamido)-2-hydroxy-3,4-dihydro-2H-benzo[e][1,2]oxaborinine-8-carboxylic acid

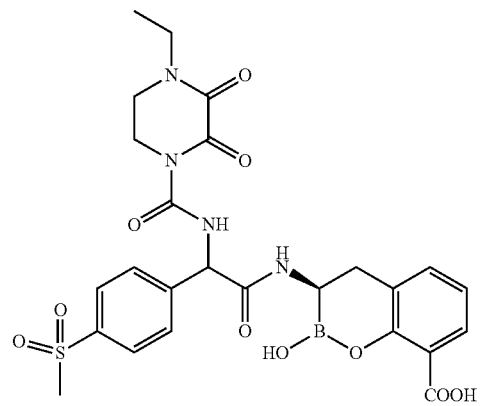 [SMILES: CCN1CCN(C(=O)NC(C(=O)N[C@H]2Cc3cccc(C(=O)O)c3OB2O)c2ccc(S(C)(=O)=O)cc2)C(=O)C1=O]

In a similar manner to the synthesis of Example 37, utilizing 4-(methylsulfonyl)benzaldehyde in place of 2-chloro-3,4-dimethoxybenzaldehyde in Step 1, the title compounds was prepared. ESI-MS m/z 587 (M+H)$^+$.

Example 119: (3R)-3-(2-(4-(2-fluoroethyl)-2,3-dioxopiperazine-1-carboxamido)-2-(4-(methylsulfonyl)phenyl)acetamido)-2-hydroxy-3,4-dihydro-2H-benzo[e][1,2]oxaborinine-8-carboxylic acid

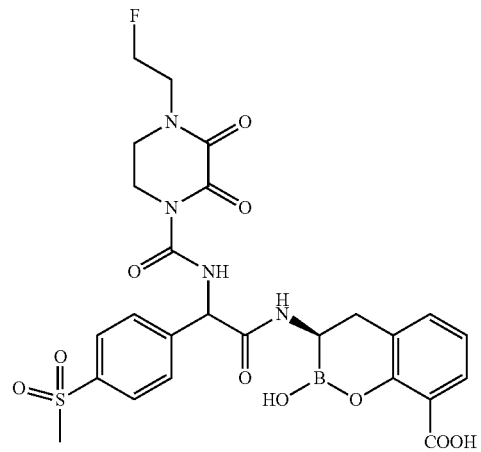 [SMILES: CS(=O)(=O)c1ccc(C(NC(=O)N2CCN(CCF)C(=O)C2=O)C(=O)N[C@H]2Cc3cccc(C(=O)O)c3OB2O)cc1]

In a similar manner to the synthesis of Example 37, utilizing 4-(methylsulfonyl)benzaldehyde in place of 2-chloro-3,4-dimethoxybenzaldehyde in Step 1, and utilizing 4-fluoroethyl-2,3-dioxopiperazine-1-carbonyl chloride (product from Step 2 of Example 13) in place of 4-ethyl-2,3-dioxopiperazine-1-carbonyl chloride in Step 3, the title compound was prepared. ESI-MS m/z 605 (M+H)$^+$.

Example 120: (3R)-3-(2-(4-ethyl-2,3-dioxopiperazine-1-carboxamido)-2-(6-methoxypyridin-2-yl)acetamido)-2-hydroxy-3,4-dihydro-2H-benzo[e][1,2]oxaborinine-8-carboxylic acid

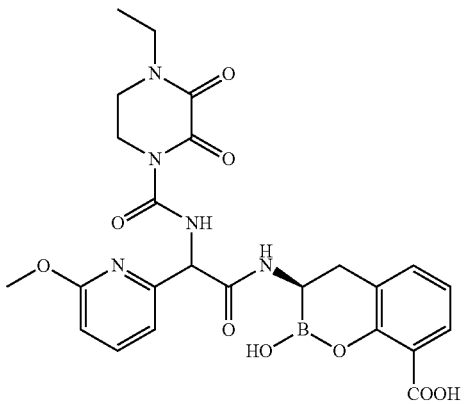 [SMILES: CCN1CCN(C(=O)NC(C(=O)N[C@H]2Cc3cccc(C(=O)O)c3OB2O)c2cccc(OC)n2)C(=O)C1=O]

In a similar manner to the synthesis of Example 56 utilizing lithium 2-((tert-butoxycarbonyl)amino)-2-(6-methoxypyridin-2-yl)acetate in place of lithium 2-((tert-butoxycarbonyl)amino)-2-(pyridin-2-yl)acetate, the title compound was prepared. ESI-MS m/z 540 (M+H)+.

Example 121: (3R)-3-(2-(4-ethyl-2,3-dioxopiperazine-1-carboxamido)-2-(5-hydroxypyrazin-2-yl)acetamido)-2-hydroxy-3,4-dihydro-2H-benzo[e][1,2]oxaborinine-8-carboxylic acid

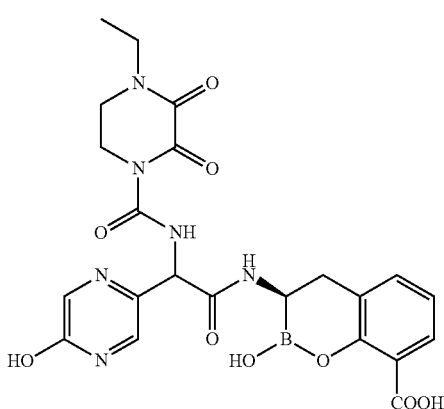 [SMILES: CCN1CCN(C(=O)NC(C(=O)N[C@H]2Cc3cccc(C(=O)O)c3OB2O)c2cnc(O)cn2)C(=O)C1=O]

In a similar manner to the synthesis of Example 41, the title compound was prepared. ESI-MS m/z 527 (M+H)+.

Example 122: (3R)-3-(2-(4-ethyl-2,3-dioxopiperazine-1-carboxamido)-2-(tetrahydrofuran-2-yl)acetamido)-2-hydroxy-3,4-dihydro-2H-benzo[e][1,2]oxaborinine-8-carboxylic acid

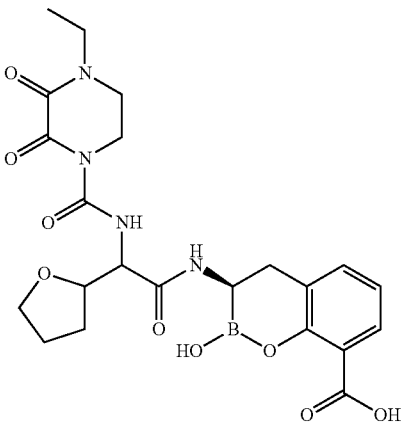 [SMILES: CCN1CCN(C(=O)NC(C(=O)N[C@H]2Cc3cccc(C(=O)O)c3OB2O)C2CCCO2)C(=O)C1=O]

The title compound was prepared from 2-amino-2-(tetrahydrofuran-2-yl)acetic acid and 3-((2S)-2-chloro-2-((3aS,4S,6S)-3a,5,5-trimethylhexahydro-4,6-methanobenzo-[d][1,3,2]dioxaborol-2-yl)ethyl)-2-methoxybenzoate, by a procedure similar to Example 8. ESI-MS m/z 503.2 (M+H)+.

Example 123: (3R)-3-(2-(1,1-dioxidotetrahydrothiophen-3-yl)-2-(4-ethyl-2,3-dioxopiperazine-1-carboxamido)acetamido)-2-hydroxy-3,4-dihydro-2H-benzo[e][1,2]oxaborinine-8-carboxylic acid

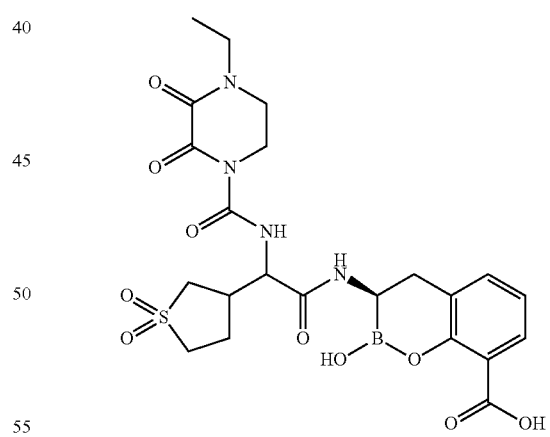

The title compound was prepared from 1-thiopheneacetic acid, α-aminotetrahydro-, 1,1-dioxide and 3-((2S)-2-chloro-2-((3aS,4S,6S)-3a,5,5-trimethylhexahydro-4,6-methanobenzo-[d][1,3,2]dioxaborol-2-yl)ethyl)-2-methoxybenzoate, by a procedure similar to Example 8. ESI-MS m/z 551.1 (M+H)+.

Example 124: (3R)-3-(2-(2-chloro-3,4-dihydroxyphenyl)-2-(4-ethyl-2,3-dioxopiperazine-1-carboxamido)acetamido)-7-fluoro-2-hydroxy-3,4-dihydro-2H-benzo[e][1,2]oxaborinine-8-carboxylic acid

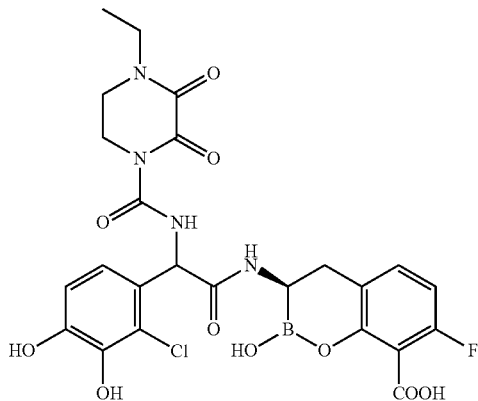 [SMILES: CCN1CCN(C(=O)NC(C(=O)N[C@H]2Cc3ccc(F)c(C(=O)O)c3OB2O)c2ccc(O)c(O)c2Cl)C(=O)C1=O]

In a similar manner to the synthesis of Example 37, utilizing the chloride intermediate from Step 7 of Example 109 in Step 2, the title compound was prepared. ESI-MS m/z 593/595 (MH/MH+2)+.

Example 125: (3R)-3-(2-(2-chloro-3,4-dihydroxyphenyl)-2-(4-(2-fluoroethyl)-2,3-dioxopiperazine-1-carboxamido)acetamido)-2-hydroxy-3,4-dihydro-2H-benzo[e][1,2]oxaborinine-8-carboxylic acid

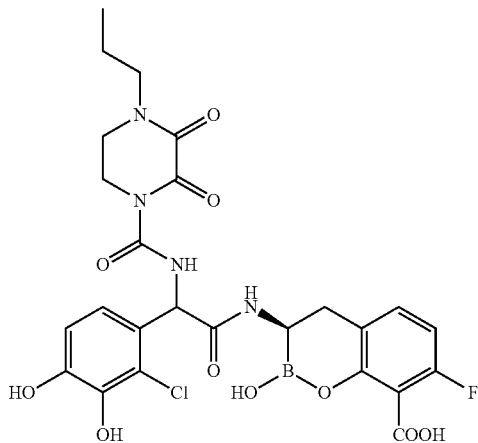 [SMILES: CCCN1CCN(C(=O)NC(C(=O)N[C@H]2Cc3ccc(F)c(C(=O)O)c3OB2O)c2ccc(O)c(O)c2Cl)C(=O)C1=O]

In a similar manner to the synthesis of Example 124, utilizing 4-propyl-2,3-dioxopiperazine-1-carbonyl chloride (product from Step 1 of Example 82) in place of 4-ethyl-2,3-dioxopiperazine-1-carbonyl chloride in Step 3, the title compound was prepared. ESI-MS m/z 607/609 (MH/MH+2)+.

Example 126: (R)-7-fluoro-3-((2R,3R)-2-(4-(2-fluoroethyl)-2,3-dioxopiperazine-1-carboxamido)-3-hydroxybutanamido)-2-hydroxy-3,4-dihydro-2H-benzo[e][1,2]oxaborinine-8-carboxylic acid

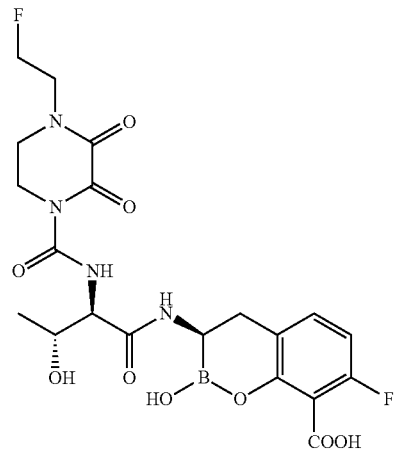 [SMILES: C[C@@H](O)[C@@H](NC(=O)N1CCN(CCF)C(=O)C1=O)C(=O)N[C@H]1Cc2ccc(F)c(C(=O)O)c2OB1O]

The title compound was prepared from D-allothreonine and tert-butyl 3-((S)-2-chloro-2-((3aS,4S,6S,7aR)-3a,5,5-trimethylhexahydro-4,6-methanobenzo[d][1,3,2]dioxaborol-2-yl)ethyl)-6-fluoro-2-methoxybenzoate (from Example 109), by a procedure similar to Example 8. ESI-MS m/z 513.1 (M+H)+.

Example 127: (3R)-3-(2-(4-ethyl-2,3-dioxopiperazine-1-carboxamido)-2-(5-methylpyridin-2-yl)acetamido)-2-hydroxy-3,4-dihydro-2H-benzo[e][1,2]oxaborinine-8-carboxylic acid

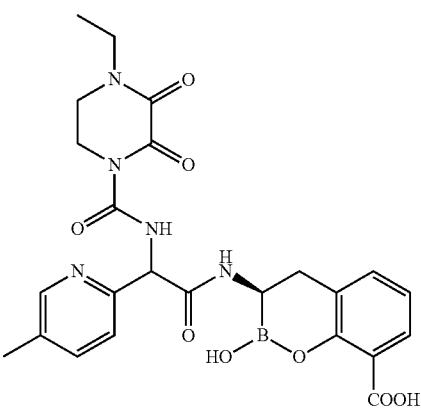 [SMILES: CCN1CCN(C(=O)NC(C(=O)N[C@H]2Cc3cccc(C(=O)O)c3OB2O)c2ccc(C)cn2)C(=O)C1=O]

The title compound was prepared according to the method of Example 56 utilizing lithium 2-((tert-butoxycarbonyl)amino)-2-(5-methylpyridin-2-yl)acetate in place of lithium 2-((tert-butoxycarbonyl)amino)-2-(pyridin-2-yl)acetate. ESI-MS m/z 524 (M+H)+.

Example 128: (3R)-3-(2-(4-ethyl-2,3-dioxopiperazine-1-carboxamido)-2-(5-hydroxypyridin-2-yl)acetamido)-7-fluoro-2-hydroxy-3,4-dihydro-2H-benzo[e][1,2]oxaborinine-8-carboxylic acid

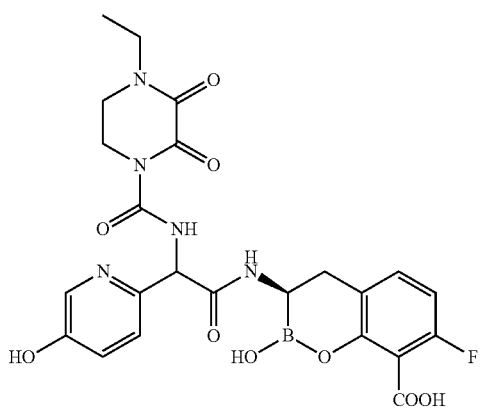 [SMILES: CCN1CCN(C(=O)NC(C(=O)N[C@H]2Cc3ccc(F)c(C(=O)O)c3OB2O)c2ccc(O)cn2)C(=O)C1=O]

Step 1: Synthesis of 5-(benzyloxy)picolinaldehyde

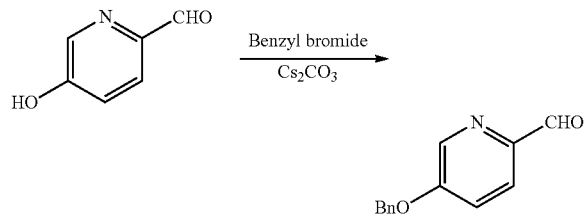

To 5-hydroxypicolinaldehyde 1.1 g (8.94 mmol) in N,N-dimethylformamide (10 mL) was added cesium carbonate 8.7 g (26.8 mmol, 3 eq), followed by benzyl bromide 1.32 mL (13.4 mmol, 1.5 eq) and heated at 80° C. for 2 h. The reaction was diluted with ethyl acetate, washed with water/brine, and dried over sodium sulfate and concentrated. The product was purified by flash chromatography on silica gel (3% methanol/dichloromethane) using preparatory TLC plates to give the desired product, 1.12 g.
ESI-MS m/z 214 (M+H)$^+$.

Step 2: Synthesis of lithium 2-(5-(benzyloxy)pyridin-2-yl)-2-((tert-butoxycarbonyl)amino)acetate

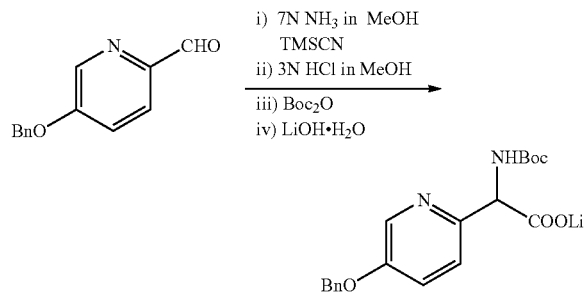

In a similar manner to the synthesis of Example 56 utilizing 5-(benzyloxy)picolinaldehyde in place of picolinaldehyde to give the title compound. ESI-MS m/z 359 (M+H)$^+$.

Step 3: Synthesis of tert-butyl 3-((2R)-2-(2-(5-(benzyloxy)pyridin-2-yl)-2-((tert-butoxycarbonyl)amino)acetamido)-2-((3aS,4S,6S)-3a,5,5-trimethylhexahydro-4,6-methanobenzo[d][1,3,2] dioxaborol-2-yl)ethyl)-6-fluoro-2-methoxybenzoate

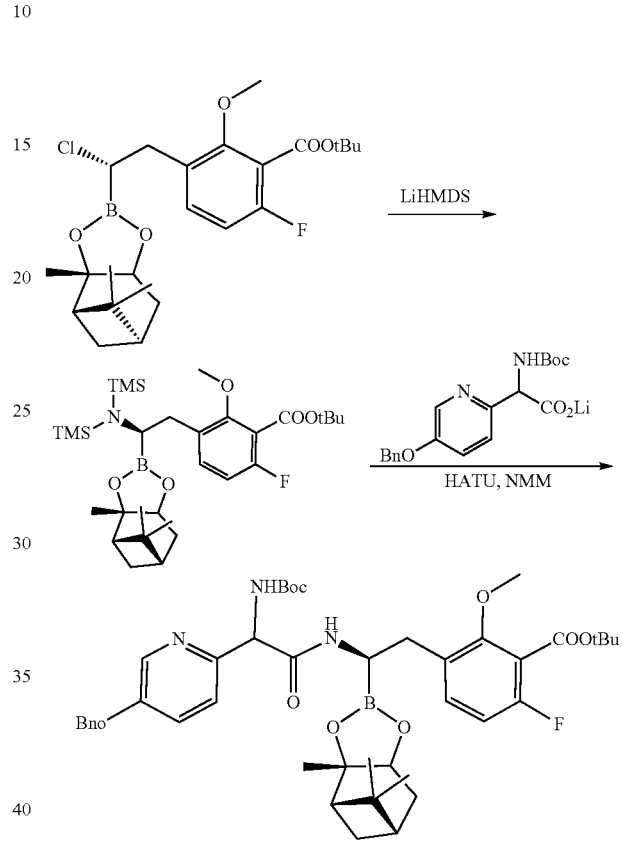

By following General Method C, tert-butyl 3-((2S)-2-chloro-2-((3aS,4S,6R)-3a,5,5-trimethylhexahydro-4,6-methanobenzo[d][1,3,2]dioxaborol-2-yl)ethyl)-6-fluoro-2-methoxybenzoate was treated with LiHMDS, and then coupled with lithium 2-(5-(benzyloxy)pyridin-2-yl)-2-((tert-butoxycarbonyl)amino)acetate from the above reaction in the presence of HATU and NMM, yielding the title compound. ESI-MS m/z 788 (M+H)$^+$.

Step 4: Synthesis of (3R)-3-(2-(4-ethyl-2,3-dioxopiperazine-1-carboxamido)-2-(5-hydroxypyridin-2-yl)acetamido)-7-fluoro-2-hydroxy-3,4-dihydro-2H-benzo[e][1,2]oxaborinine-8-carboxylic acid

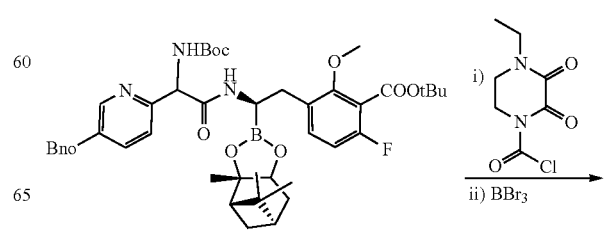

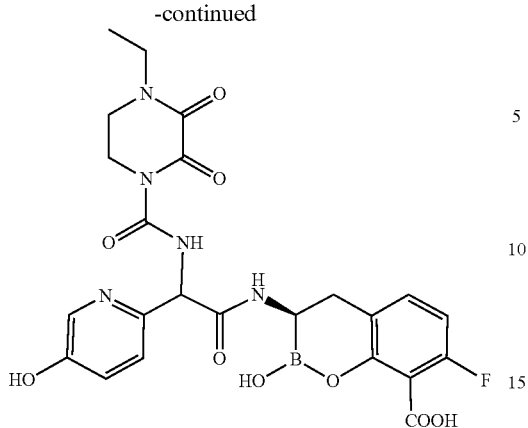

In a similar manner to the synthesis of Example 7 utilizing 4-ethyl-2,3-dioxopiperazine-1-carbonylchloride in place of pyridine-3-sulfonyl chloride, the title compound was prepared. ESI-MS m/z 544 (M+H)⁺.

Example 129: (3R)-3-(3-chloro-2-(4-ethyl-2,3-dioxopiperazine-1-carboxamido)-6-hydroxyhexanamido)-2-hydroxy-3,4-dihydro-2H-benzo[e][1,2]oxaborinine-8-carboxylic acid

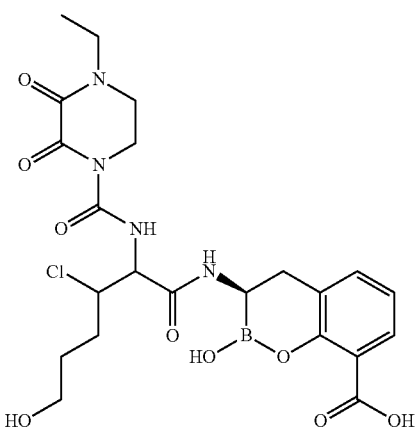 [SMILES: CCN1CCN(C(=O)NC(C(=O)N[C@H]2Cc3cccc(C(=O)O)c3OB2O)C(Cl)CCCO)C(=O)C1=O]

The title compound was a byproduct isolated as a mixture of isomers (more polar) by reverse phase HPLC (Gilson), from the final Step in Example 122. ESI-MS m/z 539.2 (M+H)⁺.

Example 130: (3R)-3-(3-chloro-2-(4-ethyl-2,3-dioxopiperazine-1-carboxamido)-6-hydroxyhexanamido)-2-hydroxy-3,4-dihydro-2H-benzo[e][1,2]oxaborinine-8-carboxylic acid

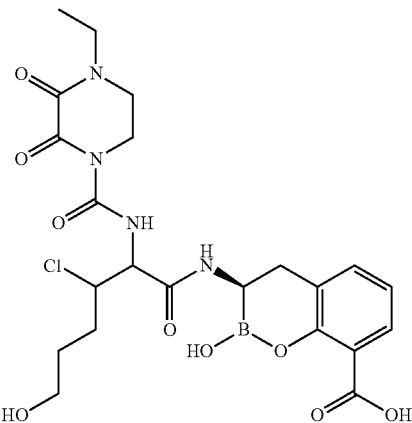 [SMILES: CCN1CCN(C(=O)NC(C(=O)N[C@H]2Cc3cccc(C(=O)O)c3OB2O)C(Cl)CCCO)C(=O)C1=O]

The title compound was a byproduct isolated as a single isomer (less polar) by reverse phase HPLC (Gilson), from the final step in Example 122. ESI-MS m/z 539.2 (M+H)⁺.

Example 131: (3R)-3-(2-(2-chloro-3,4-dihydroxyphenyl)-2-(4-(2-fluoroethyl)-2,3-dioxopiperazine-1-carboxamido)acetamido)-2-hydroxy-3,4-dihydro-2H-benzo[e][1,2]oxaborinine-8-carboxylic acid

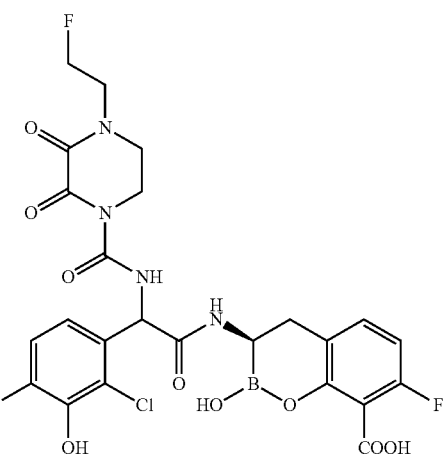

In a similar manner to the synthesis of Example 124, utilizing 4-fluoroethyl-2,3-dioxopiperazine-1-carbonyl chloride (product from Step 2 of Example 13) in place of 4-ethyl-2,3-dioxopiperazine-1-carbonyl chloride in Step 3, the title compound was prepared. ESI-MS m/z 611/613 (MH/MH+2)⁺.

Example 132: (3R)-3-(2-(5-aminopyridin-2-yl)-2-(4-ethyl-2,3-dioxopiperazine-1-carboxamido)acetamido)-2-hydroxy-3,4-dihydro-2H-benzo[e][1,2]oxaborinine-8-carboxylic acid

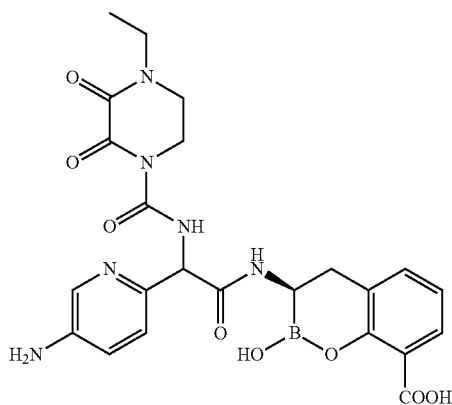 [SMILES: CCN1CCN(C(=O)NC(C(=O)N[C@H]2Cc3cccc(C(=O)O)c3OB2O)c2ccc(N)cn2)C(=O)C1=O]

Step 1. Synthesis of 6-(1,3-dioxolan-2-yl)pyridin-3-amine

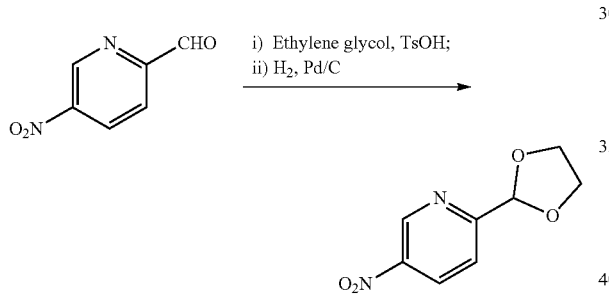

5-Nitropicolinaldehyde (9.13 g, 60 mmol) in toluene (400 mL) was reacted with ethylene glycol (22.5 mL, 400 mmol) in the presence of toluenesulfonic acid monohydrate (570 mg, 3 mmol) at reflux for 5 h. The reaction mixture was cooled to RT, washed with aqueous $NaHCO_3$, water, brine, dried over $Na_2SO_4$, concentrated in vacuo to afford the crude product, which was dissolved in EtOH (420 mL), hydrogenated in the presence of 10% Pd/C (1.5 g) at RT overnight. The reaction mixture was filtered through a pad of Celite, the filtrate was concentrated in vacuo to afford the title compound, 9.6 g. ESI-MS m/z 167 (M+H)+.

Step 2. Synthesis of benzyl (6-formylpyridin-3-yl)carbamate

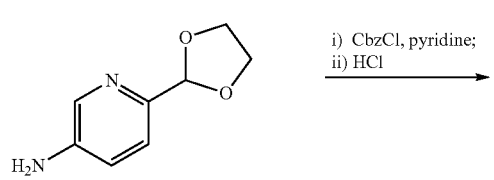

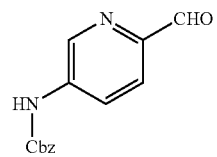

To the product from Step 1 (4.32 g, 26 mmol) in THF (120 mL) at 0° C. was added pyridine (9.7 mL, 120 mmol), followed by dropwise addition of benzyl chloroformate (4.9 mL, 33.8 mmol), after 1 h at RT, added more benzyl chloroformate (1.4 mL). The reaction mixture was stirred at RT overnight, diluted with EtOAc, washed with water, brine, dried over $Na_2SO_4$, concentrated to afford a solid product, which was washed with hexane, dried in vacuo to give 7.7 g of product. This product (4.61 g, 15.4 mmol) was dissolved in THF (80 mL), treated with 1 N HCl (80 mL) at 60° C. overnight, cooled to RT, basified with solid $Na_2CO_3$ to pH ~10, extracted with EtOAc. The combined organic extracts were dried over $Na_2SO_4$, concentrated in vacuo to afford the crude product, which was used directly for the next step without further purification. ESI-MS m/z 257 (M+H)+.

Step 3. Synthesis of lithium 2-(5-(((benzyloxy)carbonyl)amino)pyridin-2-yl)-2-((tert-butoxycarbonyl)amino)acetate

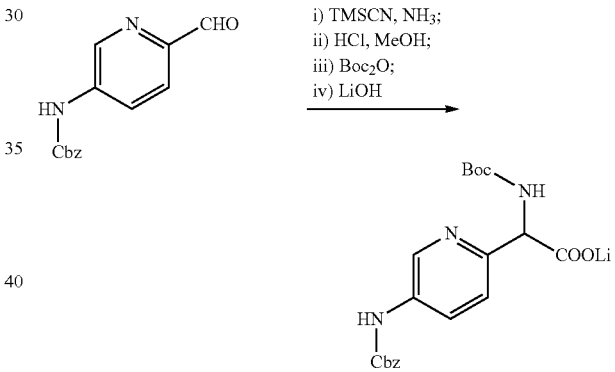

By following the same procedures as described in Step 1 of Example 37, except in Step 1d, after hydrolysis with LiOH, the reaction mixture was concentrated in vacuo without acidification to yield the crude lithium salt of the amino acid, which was used directly for the next step without further purification.

Step 4. Synthesis of (3R)-3-(2-(4-boronophenyl)-2-(4-ethyl-2,3-dioxopiperazine-1-carboxamido)acetamido)-2-hydroxy-3,4-dihydro-2H-benzo[e][1,2]oxaborinine-8-carboxylic acid

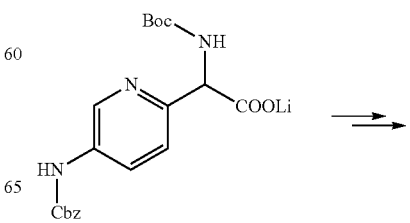

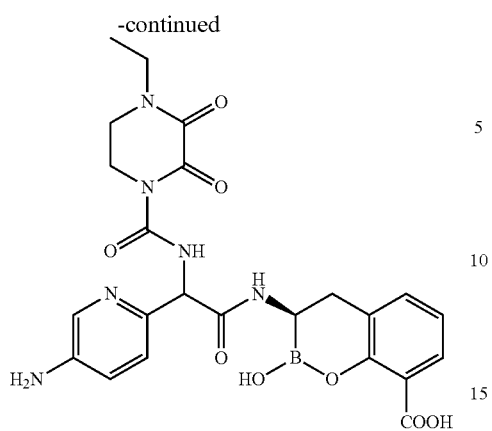

In a similar manner to the synthesis of Example 37, the title compound was prepared from the above product of Step 3. ESI-MS m/z 525 (M+H)⁺.

Example 133: (R)-3-((2R,3R)-2-(2,3-dioxo-4-propylpiperazine-1-carboxamido)-3-hydroxybutanamido)-7-fluoro-2-hydroxy-3,4-dihydro-2H-benzo[e][1,2]oxaborinine-8-carboxylic acid

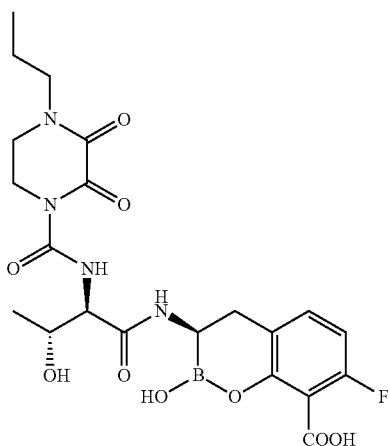 [SMILES: CCCN1CCN(C(=O)N[C@@H](C(=O)N[C@H]2Cc3ccc(F)c(C(=O)O)c3OB2O)[C@@H](C)O)C(=O)C1=O]

The title compound was prepared from D-allothreonine, 2,3-dioxo-4-propyl-1-piperazinecarbonyl chloride, and tert-butyl 3-((S)-2-chloro-2-((3aS,4S,6S,7aR)-3a,5,5-trimethylhexahydro-4,6-methanobenzo[d][1,3,2]dioxaborol-2-yl)ethyl)-6-fluoro-2-methoxybenzoate (from Example 109), by a procedure similar to Example 8. ESI-MS m/z 509.1 (M+H)⁺.

Example 134: (3R)-3-(2-(2,3-dioxo-4-propylpiperazine-1-carboxamido)-2-(5-hydroxypyridin-2-yl)acetamido)-2-hydroxy-3,4-dihydro-2H-benzo[e][1,2]oxaborinine-8-carboxylic acid

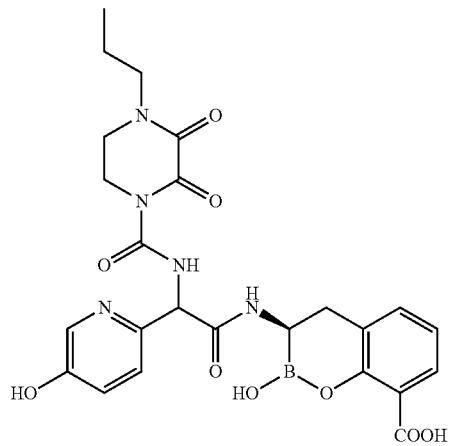 [SMILES: CCCN1CCN(C(=O)NC(C(=O)N[C@H]2Cc3cccc(C(=O)O)c3OB2O)c2ccc(O)cn2)C(=O)C1=O]

In a similar manner to the synthesis of Example 128 utilizing 4-propyl-2,3-dioxopiperazine-1-carbonyl chloride in place of 4-ethyl-2,3-dioxopiperazine-1-carbonyl chloride, the title compound was prepared. ESI-MS m/z 540 (M+H)⁺.

Example 135: (3R)-3-(2-(4-ethyl-2,3-dioxopiperazine-1-carboxamido)-2-(3-fluoro-5-hydroxypyridin-2-yl)acetamido)-2-hydroxy-3,4-dihydro-2H-benzo[e][1,2]oxaborinine-8-carboxylic acid

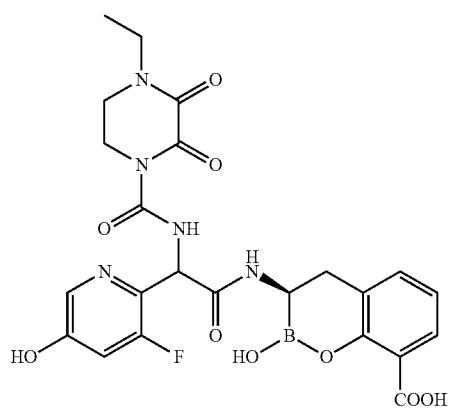 [SMILES: CCN1CCN(C(=O)NC(C(=O)N[C@H]2Cc3cccc(C(=O)O)c3OB2O)c2ncc(O)cc2F)C(=O)C1=O]

In a similar manner to the synthesis of Example 128, the title compound was prepared. ESI-MS m/z 544 (M+H)⁺.

Example 136: (3R)-3-(2-(4-ethyl-2,3-dioxopiperazine-1-carboxamido)-2-(2-fluoro-4,5-dihydroxyphenyl)acetamido)-7-fluoro-2-hydroxy-3,4-dihydro-2H-benzo[e][1,2]oxaborinine-8-carboxylic acid

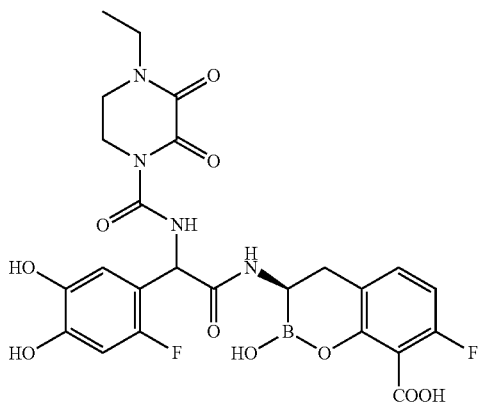 [SMILES: CCN1CCN(C(=O)NC(C(=O)N[C@H]2Cc3ccc(F)c(C(=O)O)c3OB2O)c2cc(O)c(O)cc2F)C(=O)C1=O]

In a similar manner to the synthesis of Example 90, utilizing the chloride intermediate from Step 7 of Example 109 in Step 2, the title compound was prepared. ESI-MS m/z 577 (M+H)+.

Example 137: (3R)-3-(2-(4-ethyl-2,3-dioxopiperazine-1-carboxamido)-2-(thiophen-3-yl)acetamido)-2-hydroxy-3,4-dihydro-2H-benzo[e][1,2]oxaborinine-8-carboxylic acid

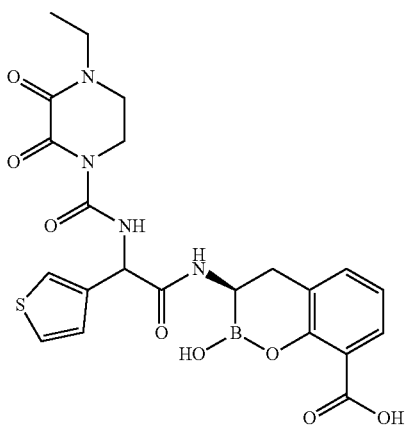 [SMILES: CCN1CCN(C(=O)NC(C(=O)N[C@H]2Cc3cccc(C(=O)O)c3OB2O)c2ccsc2)C(=O)C1=O]

The title compound was prepared from (R)-3-thienylglycine and 3-((2S)-2-chloro-2-((3aS,4S,6S)-3a,5,5-trimethylhexahydro-4,6-methanobenzo-[d][1,3,2]dioxaborol-2-yl)ethyl)-2-methoxybenzoate, by a procedure similar to Example 8. ESI-MS m/z 515.1 (M+H)+.

Example 138: (R)-3-((R)-2-(4-ethyl-2,3-dioxopiperazine-1-carboxamido)-2-(thiophen-3-yl)acetamido)-7-fluoro-2-hydroxy-3,4-dihydro-2H-benzo[e][1,2]oxaborinine-8-carboxylic acid

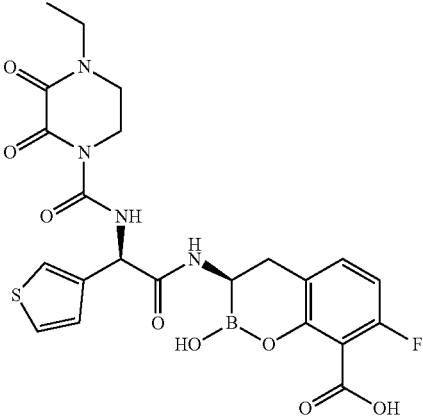

The title compound was prepared from (R)-3-thienylglycine and tert-butyl 3-((S)-2-chloro-2-((3aS,4S,6S,7aR)-3a,5,5-trimethyl-hexahydro-4,6-methanobenzo[d][1,3,2]dioxaborol-2-yl)ethyl)-6-fluoro-2-methoxybenzoate (from Example 109), by a procedure similar to Example 8. ESI-MS m/z 533.1 (M+H)+.

Example 139: (R)-3-((S)-2-(4-ethyl-2,3-dioxopiperazine-1-carboxamido)-2-(thiophen-3-yl)acetamido)-7-fluoro-2-hydroxy-3,4-dihydro-2H-benzo[e][1,2]oxaborinine-8-carboxylic acid

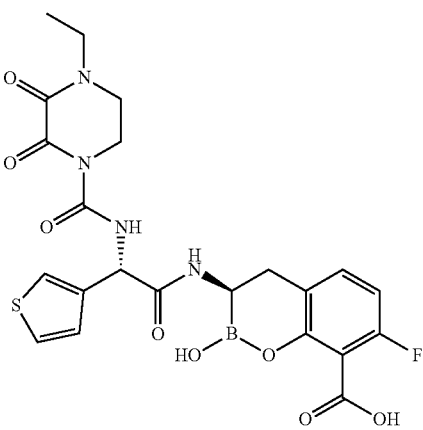

The title compound was isolated by reverse phase HPLC (Gilson) as the less polar isomer in Example 140. ESI-MS m/z 533.1 (M+H)+.

Example 140: (3R)-3-(2-(5,6-dihydroxypyridin-2-yl)-2-(4-ethyl-2,3-dioxopiperazine-1-carboxamido)acetamido)-2-hydroxy-3,4-dihydro-2H-benzo[e][1,2]oxaborinine-8-carboxylic acid

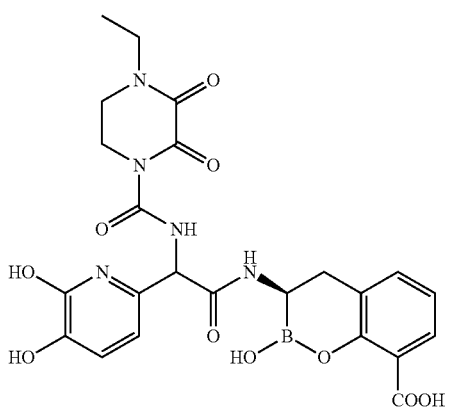 [SMILES: CCN1CCN(C(=O)NC(C(=O)N[C@H]2Cc3cccc(C(=O)O)c3OB2O)c2ccc(O)c(O)n2)C(=O)C1=O]

Step 1: Synthesis of lithium 2-((tert-butoxycarbonyl)amino)-2-(5,6-dimethoxypyridin-2-yl)acetate

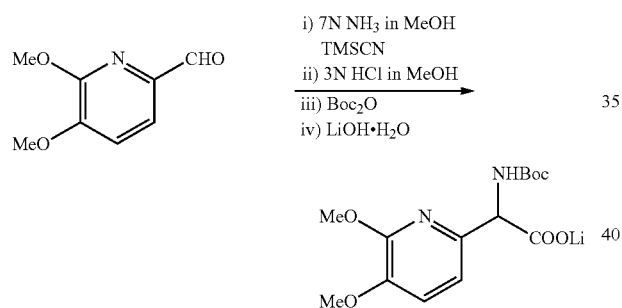

In a similar manner to the synthesis of Example 56, utilizing 5,6-dimethoxypicolinaldehyde in place of picolinaldehyde, the title compound was prepared. ESI-MS m/z 313 (M+H)+.

Step 2: Synthesis of (3R)-3-(2-(5,6-dihydroxypyridin-2-yl)-2-(4-ethyl-2,3-dioxopiperazine-1-carboxamido)acetamido)-2-hydroxy-3,4-dihydro-2H-benzo[e][1,2]oxaborinine-8-carboxylic acid

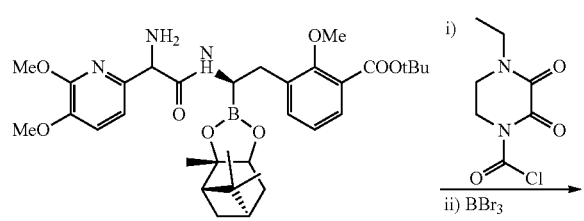

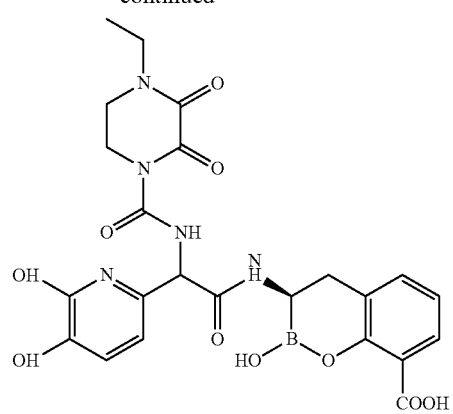

In a similar manner to the synthesis of Example 128, utilizing 4-ethyl-2,3-dioxopiperazine-1-carbonyl chloride in place of 4-propyl-2,3-dioxopiperazine-1-carbonyl chloride, the title compound was prepared. ESI-MS m/z 542 (M+H)+.

Example 141: (3R)-3-(2-(4-ethyl-2,3-dioxopiperazine-1-carboxamido)-2-(pyridin-3-yl)acetamido)-7-fluoro-2-hydroxy-3,4-dihydro-2H-benzo[e][1,2]oxaborinine-8-carboxylic acid

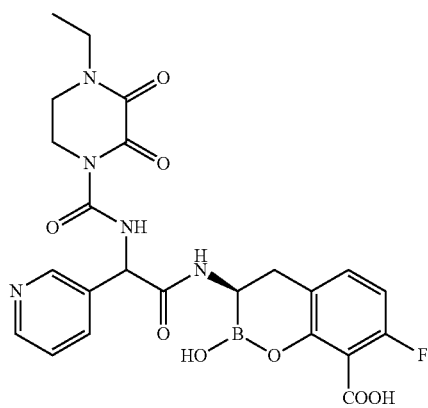 [SMILES: CCN1CCN(C(=O)NC(C(=O)N[C@H]2Cc3ccc(F)c(C(=O)O)c3OB2O)c2cccnc2)C(=O)C1=O]

In a similar manner to the synthesis of Example 56 utilizing tert-butyl 3-((2S)-2-chloro-2-((3aS,4S,6R)-3a,5,5-trimethylhexahydro-4,6-methanobenzo[d][1,3,2]dioxaborol-2-yl)ethyl)-6-fluoro-2-methoxybenzoate in place of tert-butyl 3-((2S)-2-chloro-2-((3aS,4S,6R)-3a,5,5-trimethylhexahydro-4,6-methanobenzo[d][1,3,2]dioxaborol-2-yl)ethyl)-2-methoxybenzoate, the title compound was prepared. ESI-MS m/z 528 (M+H)+.

Example 142: (3R)-3-(2-(4-ethyl-2,3-dioxopiperazine-1-carboxamido)-2-(thiophen-2-yl)acetamido)-7-fluoro-2-hydroxy-3,4-dihydro-2H-benzo[e][1,2]oxaborinine-8-carboxylic acid

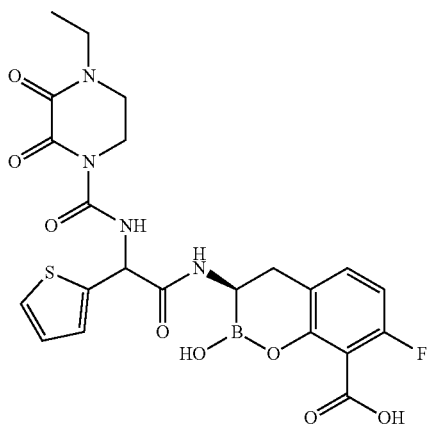 [SMILES: CCN1CCN(C(=O)NC(C(=O)N[C@H]2Cc3ccc(F)c(C(=O)O)c3OB2O)c2cccs2)C(=O)C1=O]

The title compound was prepared from 2-thienylglycine and tert-butyl 3-((S)-2-chloro-2-((3aS,4S,6S,7aR)-3a,5,5-trimethyl-hexahydro-4,6-methanobenzo[d][1,3,2]dioxaborol-2-yl)ethyl)-6-fluoro-2-methoxybenzoate (from Example 109), by a procedure similar to Example 8. ESI-MS m/z 533.2 (M+H)+.

Example 143: (3R)-3-(2-(4-ethyl-2,3-dioxopiperazine-1-carboxamido)-2-(4-hydroxy-3-sulfamoylphenyl)acetamido)-2-hydroxy-3,4-dihydro-2H-benzo[e][1,2]oxaborinine-8-carboxylic acid

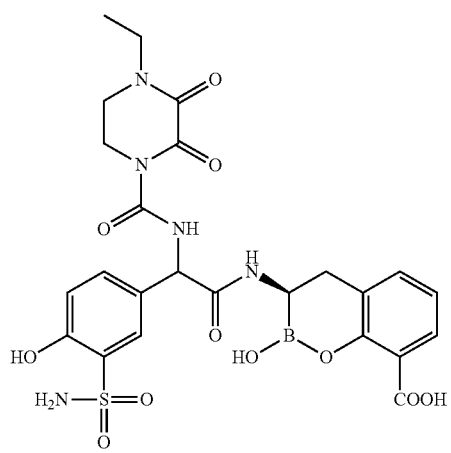 [SMILES: CCN1CCN(C(=O)NC(C(=O)N[C@H]2Cc3cccc(C(=O)O)c3OB2O)c2ccc(O)c(S(N)(=O)=O)c2)C(=O)C1=O]

Example 144: (3R)-3-(2-(4-ethyl-2,3-dioxopiperazine-1-carboxamido)-2-(4-methoxy-3-sulfamoylphenyl)acetamido)-2-hydroxy-3,4-dihydro-2H-benzo[e][1,2]oxaborinine-8-carboxylic acid

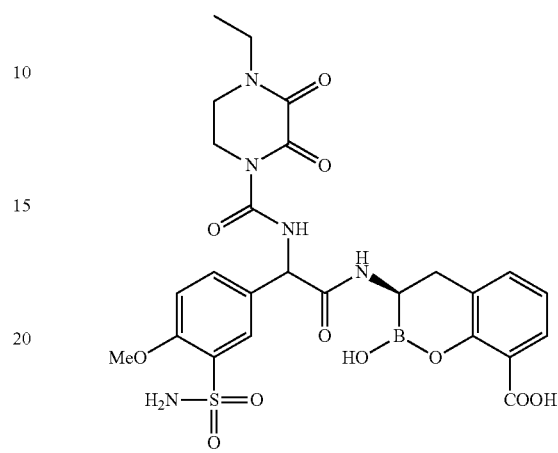

In a similar manner to the synthesis of Example 37, utilizing 5-formyl-2-methoxybenzenesulfonamide in place of 2-chloro-3,4-dimethoxybenzaldehyde in Step 1, Example 143 was isolated as the first eluting peak, and Example 144 was isolated as the second eluting peak by reversed phase HPLC. ESI-MS m/z 587 (M+H)+.

Example 145: (3R)-3-(2-(4-ethyl-2,3-dioxopiperazine-1-carboxamido)-2-(3-fluoro-5-hydroxypyridin-2-yl)acetamido)-7-fluoro-2-hydroxy-3,4-dihydro-2H-benzo[e][1,2]oxaborinine-8-carboxylic acid

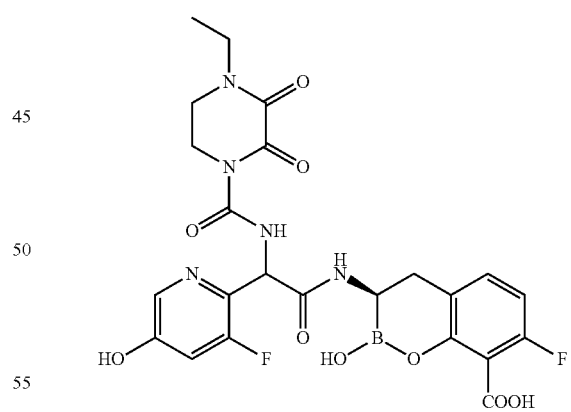

In a similar manner to the synthesis of Example 135 utilizing tert-butyl 3-((2S)-2-chloro-2-((3aS,4S,6R)-3a,5,5-trimethylhexahydro-4,6-methanobenzo[d][1,3,2]dioxaborol-2-yl)ethyl)-6-fluoro-2-methoxybenzoate in place of tert-butyl 3-((2S)-2-chloro-2-((3aS,4S,6R)-3a,5,5-trimethylhexahydro-4,6-methanobenzo[d][1,3,2]dioxaborol-2-yl)ethyl)-2-methoxybenzoate, the title compound was prepared. ESI-MS m/z 562 (M+H)+.

Example 146: (R)-3-((2R,3S)-2-(4-ethyl-2,3-dioxopiperazine-1-carboxamido)-3-methoxybutanamido)-2-hydroxy-3,4-dihydro-2H-benzo[e][1,2]oxaborinine-8-carboxylic acid

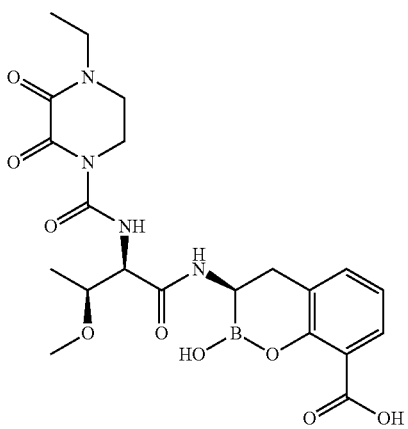 [SMILES: CCN1CCN(C(=O)N[C@@H](C(=O)N[C@H]2Cc3cccc(C(=O)O)c3OB2O)[C@H](C)OC)C(=O)C1=O]

The title compound was prepared from O-methyl-D-threonine and 3-((2S)-2-chloro-2-((3aS,4S,6S)-3a,5,5-trimethylhexahydro-4,6-methanobenzo-[d][1,3,2]dioxaborol-2-yl)ethyl)-2-methoxybenzoate, by a procedure similar to Example 8. ESI-MS m/z 491.2 (M+H)+.

Example 147: (R)-3-((2S,3S)-2-(4-ethyl-2,3-dioxopiperazine-1-carboxamido)-3-methoxybutanamido)-2-hydroxy-3,4-dihydro-2H-benzo[e][1,2]oxaborinine-8-carboxylic acid

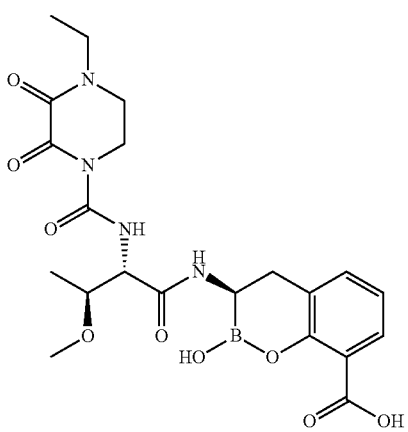 [SMILES: CCN1CCN(C(=O)N[C@H](C(=O)N[C@H]2Cc3cccc(C(=O)O)c3OB2O)[C@H](C)OC)C(=O)C1=O]

The title compound was isolated by reverse phase HPLC (Gilson) as the more polar isomer from the last Step of Example 146. ESI-MS m/z 491.1 (M+H)+.

Example 148: (3R)-3-(2-(6-aminopyridin-3-yl)-2-(4-ethyl-2,3-dioxopiperazine-1-carboxamido)acetamido)-2-hydroxy-3,4-dihydro-2H-benzo[e][1,2]oxaborinine-8-carboxylic acid

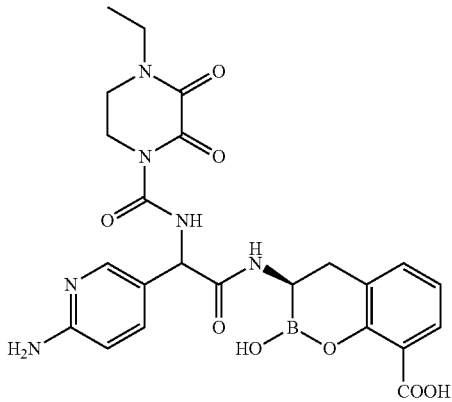 [SMILES: CCN1CCN(C(=O)NC(C(=O)N[C@H]2Cc3cccc(C(=O)O)c3OB2O)c2ccc(N)nc2)C(=O)C1=O]

Step 1: Synthesis of benzyl (5-formylpyridin-2-yl)carbamate

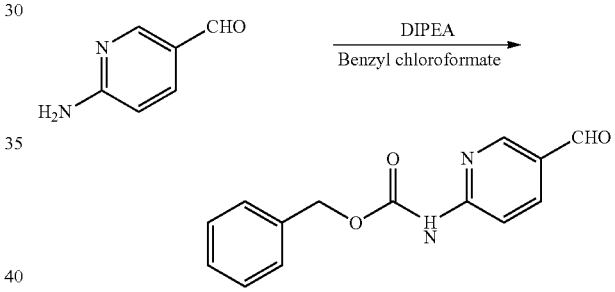

To 6-aminonicotinaldehyde (2.0 g, 16.4 mmol) in tetrahydrofuran (60 mL) at 0° C. was added diisopropylethylamine (3.43 mL, 19.6 mmol, 1.2 eq), followed by benzyl chloroformate (2.76 mL, 19.6 mmol, 1.2 eq) and the reaction was stirred at RT for 18 h. The solution was concentrated and the residue purified by flash chromatography on silica gel (30% ethyl acetate/hexanes) to afford the title compound, 1.04 g. ESI-MS m/z 257 (M+H)+.

Step 2: Synthesis of (3R)-3-(2-(6-aminopyridin-3-yl)-2-(4-ethyl-2,3-dioxopiperazine-1-carboxamido)acetamido)-2-hydroxy-3,4-dihydro-2H-benzo[e][1,2]oxaborinine-8-carboxylic acid

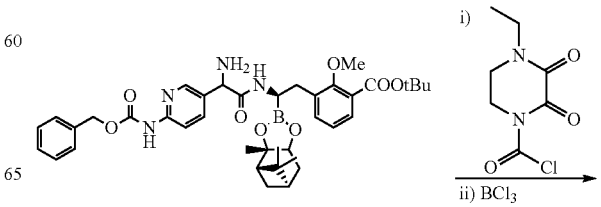

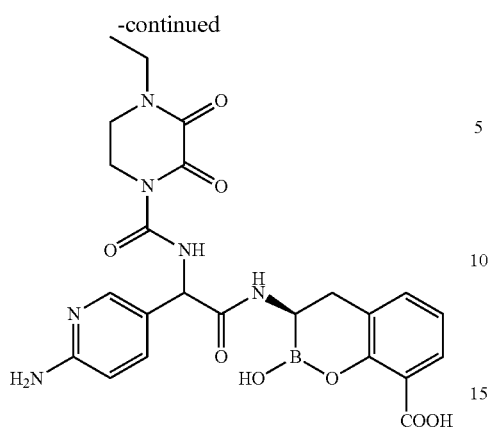

In a similar manner to the synthesis of Example 134, utilizing 4-ethyl-2,3-dioxopiperazine-1-carbonyl chloride in place of 4-propyl-2,3-dioxopiperazine-1-carbonyl chloride, the title compound was prepared. ESI-MS m/z 525 (MH)⁺.

Example 149: (3R)-3-(2-(4-ethyl-2,3-dioxopiperazine-1-carboxamido)-2-(2-fluoro-3,4-dihydroxyphenyl)acetamido)-7-fluoro-2-hydroxy-3,4-dihydro-2H-benzo[e][1,2]oxaborinine-8-carboxylic acid

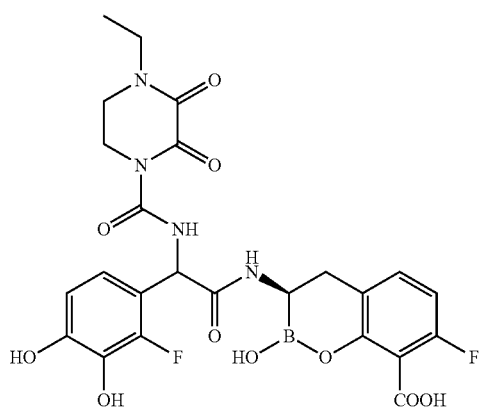 [SMILES: CCN1CCN(C(=O)NC(C(=O)N[C@H]2Cc3ccc(F)c(C(=O)O)c3OB2O)c2ccc(O)c(O)c2F)C(=O)C1=O]

In a similar manner to the synthesis of Example 70, utilizing the chloride intermediate from Step 7 of Example 109 in Step 2, the title compound was prepared. ESI-MS m/z 577 (M+H)⁺.

Example 150: (3R)-3-(2-(4-ethyl-2,3-dioxopiperazine-1-carboxamido)-2-(3-chloro-5-hydroxypyridin-2-yl)acetamido)-2-hydroxy-3,4-dihydro-2H-benzo[e][1,2]oxaborinine-8-carboxylic acid

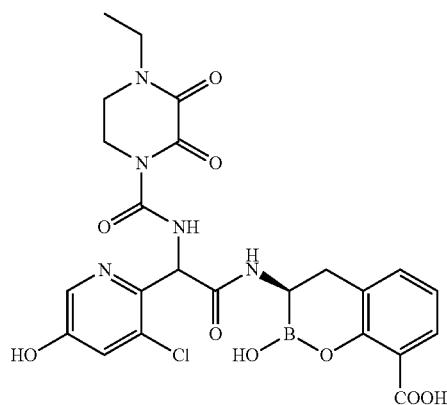

In a similar manner to the synthesis of Example 134 utilizing 4-ethyl-2,3-dioxopiperazine-1-carbonyl chloride in place of 4-propyl-2,3-dioxopiperazine-1-carbonyl chloride, the title compound was prepared. ESI-MS m/z 560 (M+H)⁺.

Example 151: (3R)-3-(2-(3-chloro-5-hydroxypyridin-2-yl)-2-(4-ethyl-2,3-dioxopiperazine-1-carboxamido)acetamido)-7-fluoro-2-hydroxy-3,4-dihydro-2H-benzo[e][1,2]oxaborinine-8-carboxylic acid In a similar manner to the synthesis of Example 135 utilizing tert-butyl 3-((2S)-2-chloro-2-((3aS,4S,6R)-3a,5,5-trimethylhexahydro-4,6-methanobenzo[d][1,3,2]dioxaborol-2-yl)ethyl)-6-fluoro-2-methoxybenzoate in place of tert-butyl 3-((2S)-2-chloro-2-((3aS,4S,6R)-3a,5,5-trimethylhexahydro-4,6-methanobenzo[d][1,3,2]dioxaborol-2-yl)ethyl)-2-methoxybenzoate, the title compound was prepared. ESI-MS m/z 578 (M+H)⁺.

Example 152: (3R)-3-(2-(2-aminothiazol-5-yl)-2-(4-ethyl-2,3-dioxopiperazine-1-carboxamido)acetamido)-7-fluoro-2-hydroxy-3,4-dihydro-2H-benzo[e][1,2]oxaborinine-8-carboxylic acid

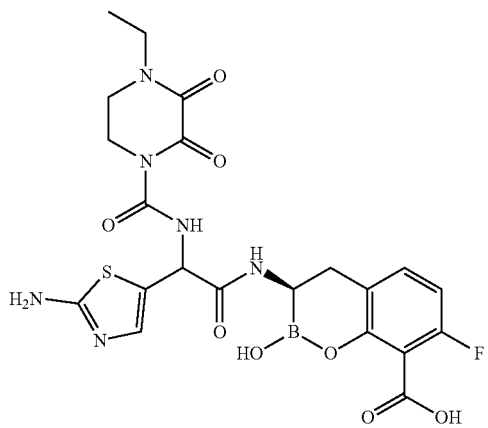 [SMILES: CCN1CCN(C(=O)NC(C(=O)N[C@H]2Cc3ccc(F)c(C(=O)O)c3OB2O)c2cnc(N)s2)C(=O)C1=O]

In a similar manner to the synthesis of Example 51, utilizing the chloride intermediate from Step 7 of Example 109 in Step 2, the title compound was prepared. ESI-MS m/z 549 (M+H)⁺.

Example 153: (3R)-3-(2-(2-aminothiazol-5-yl)-2-(4-(2-fluoroethyl)-2,3-dioxopiperazine-1-carboxamido)acetamido)-7-fluoro-2-hydroxy-3,4-dihydro-2H-benzo[e][1,2]oxaborinine-8-carboxylic acid

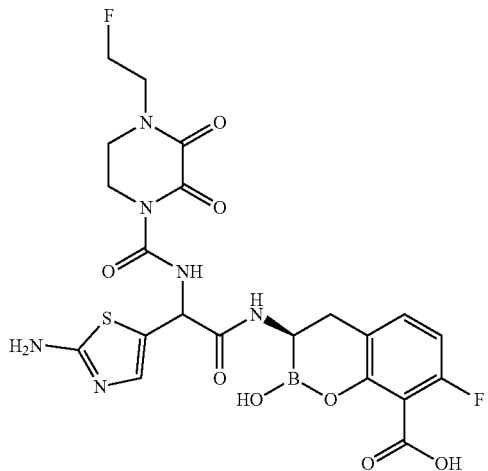 [SMILES: Nc1ncc(C(NC(=O)N2CCN(CCF)C(=O)C2=O)C(=O)N[C@H]2Cc3ccc(F)c(C(=O)O)c3OB2O)s1]

In a similar manner to the synthesis of Example 152, utilizing 4-fluoroethyl-2,3-dioxopiperazine-1-carbonyl chloride (product from Step 2 of Example 13) in place of 4-ethyl-2,3-dioxopiperazine-1-carbonyl chloride in Step 3, the title compound was prepared. ESI-MS m/z 567 (M+H)⁺.

Example 154: (3R)-3-(2-(4-ethyl-2,3-dioxopiperazine-1-carboxamido)-2-(5-(methylsulfonamido)pyridin-2-yl)acetamido)-2-hydroxy-3,4-dihydro-2H-benzo[e][1,2]oxaborinine-8-carboxylic acid

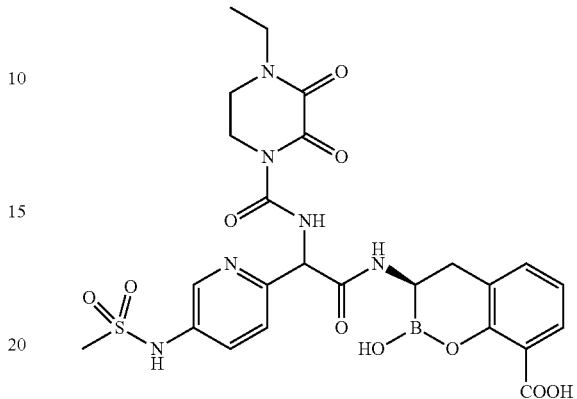

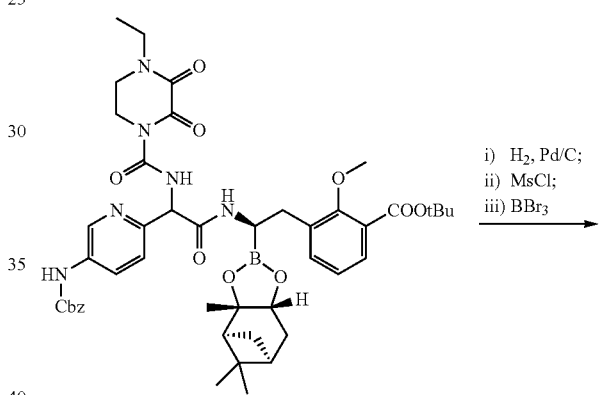

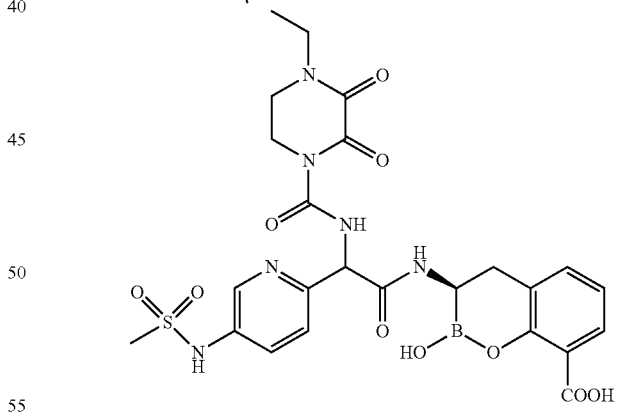

The intermediate from Step 4 of Example 132 (528 mg, 0.6 mmol) in MeOH (30 mL) was hydrogenated in the presence of 10% Pd/C (106 mg) and 0.2 mL of dioxane solution of 4 M HCl at RT for 3 h. The reaction mixture was filtered, the filtrate was concentrated in vacuo. The crude product was dissolved in DCM (20 mL). To this solution was added at 0° C. iPr₂NEt (0.32 mL, 1.8 mmol), followed by methanesulfonyl chloride (0.055 mL, 0.72 mmol). The reaction mixture was stirred at RT for 1 h, added more methanesulfonyl chloride (0.15 mL) and a catalytic amount of 4-DMAP. After additional 2 h at RT, the reaction mixture was washed with water, brine, dried over Na$_2$SO$_4$, concentrated in vacuo to afford the crude product, which was subjected to the General Method A by treatment with BBr$_3$ to afford the title compound. ESI-MS m/z 603 (M+H)$^+$.

Example 155: (R)-3-((S)-2-(4-ethyl-2,3-dioxopiperazine-1-carboxamido)-2-(3-fluoro-4-hydroxyphenyl)acetamido)-2-hydroxy-3,4-dihydro-2H-benzo[e][1,2]oxaborinine-8-carboxylic acid

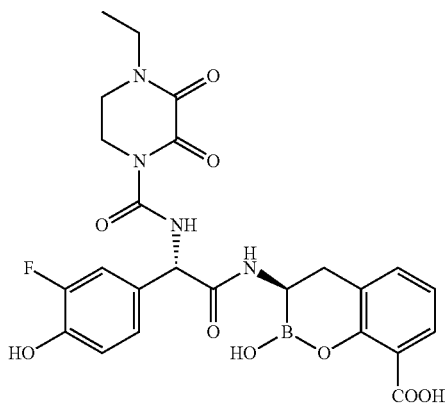 [SMILES: CCN1CCN(C(=O)N[C@H](C(=O)N[C@H]2Cc3cccc(C(=O)O)c3OB2O)c2ccc(O)c(F)c2)C(=O)C1=O]

Example 156: (R)-3-((R)-2-(4-ethyl-2,3-dioxopiperazine-1-carboxamido)-2-(3-fluoro-4-hydroxyphenyl)acetamido)-2-hydroxy-3,4-dihydro-2H-benzo[e][1,2]oxaborinine-8-carboxylic acid

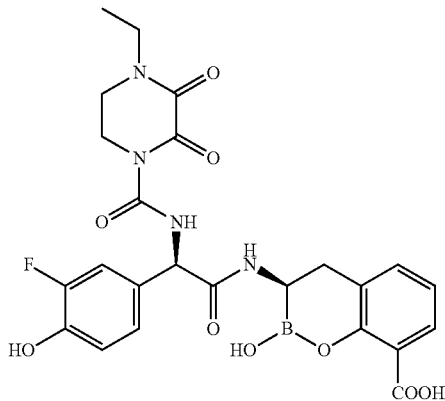 [SMILES: CCN1CCN(C(=O)N[C@@H](C(=O)N[C@H]2Cc3cccc(C(=O)O)c3OB2O)c2ccc(O)c(F)c2)C(=O)C1=O]

In a similar manner to the synthesis of Example 5, utilizing 2-amino-2-(3-fluoro-4-methoxyphenyl)acetic acid in place of 2-amino-2-(2-(((benzyloxy)carbonyl)amino)thiazol-4-yl)acetic acid in Step 4, and utilizing BBr$_3$ in the final deprotection reaction, the title compounds, Example 155 and Example 156 were separated by reversed phase HPLC as the first eluting peak and the second eluting peak respectively. ESI-MS m/z 543 (M+H)$^+$.

Example 157: (3R)-3-((3S)-2-(4-ethyl-2,3-dioxopiperazine-1-carboxamido)-4,4,4-trifluoro-3-hydroxybutanamido)-2-hydroxy-3,4-dihydro-2H-benzo[e][1,2]oxaborinine-8-carboxylic acid

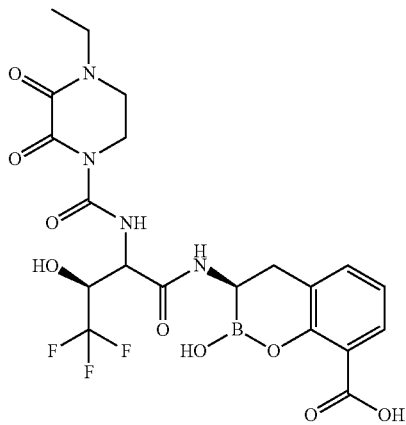

The title compound was prepared as a mixture of epimers from (2R,3S)-2-amino-4,4,4-trifluoro-3-hydroxybutanoic acid (Cho, J. et al. Tetrahedron Lett. 2015, 56, 127-131) and 3-((2S)-2-chloro-2-((3aS,4S,6S)-3a,5,5-trimethylhexahydro-4,6-methanobenzo-[d][1,3,2]dioxaborol-2-yl)ethyl)-2-methoxybenzoate, by a procedure similar to Example 8. ESI-MS m/z 531.1 (M+H)$^+$.

Example 158: (R)-3-((2R,3S)-2-(4-ethyl-2,3-dioxopiperazine-1-carboxamido)-4,4,4-trifluoro-3-hydroxybutanamido)-7-fluoro-2-hydroxy-3,4-dihydro-2H-benzo[e][1,2]oxaborinine-8-carboxylic acid

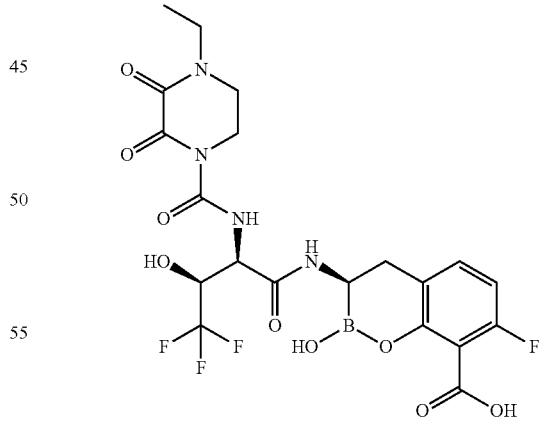

The title compound was prepared from (2R,3S)-2-amino-4,4,4-trifluoro-3-hydroxybutanoic acid (Cho, J. et al. Tetrahedron Lett. 2015, 56, 127-131) and tert-butyl 3-((S)-2-chloro-2-((3aS,4S,6S,7aR)-3a,5,5-trimethyl-hexahydro-4,6-methanobenzo[d][1,3,2]dioxa-borol-2-yl)ethyl)-6-fluoro-2-methoxybenzoate (from Example 109), by a procedure similar to Example 8. ESI-MS m/z 549.1 (M+H)$^+$.

Example 159: (R)-3-((2S,3S)-2-(4-ethyl-2,3-dioxopiperazine-1-carboxamido)-4,4,4-trifluoro-3-hydroxybutanamido)-7-fluoro-2-hydroxy-3,4-dihydro-2H-benzo[e][1,2]oxaborinine-8-carboxylic acid

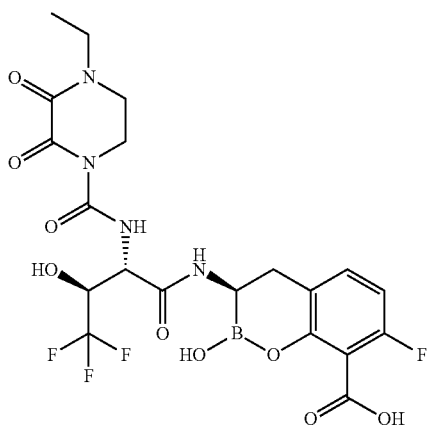 [SMILES: CCN1CCN(C(=O)N[C@H](C(=O)N[C@H]2Cc3ccc(F)c(C(=O)O)c3OB2O)[C@H](O)C(F)(F)F)C(=O)C1=O]

The title compound was isolated by reverse phase HPLC (Gilson) as the less polar isomer in the last step of Example 158. ESI-MS m/z 549.1 (M+H)$^+$.

Example 160: (R)-3-((S)-2-(4-ethyl-2,3-dioxopiperazine-1-carboxamido)-2-(3-fluoro-4-hydroxyphenyl)acetamido)-7-fluoro-2-hydroxy-3,4-dihydro-2H-benzo[e][1,2]oxaborinine-8-carboxylic acid

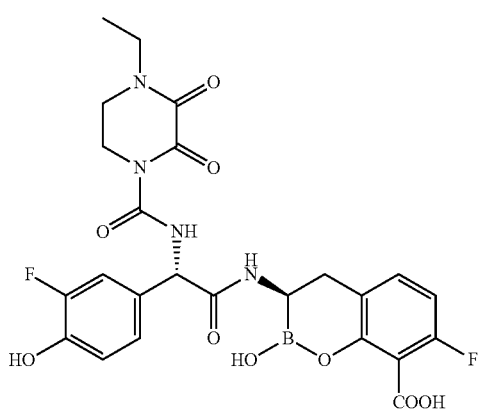 [SMILES: CCN1CCN(C(=O)N[C@H](C(=O)N[C@H]2Cc3ccc(F)c(C(=O)O)c3OB2O)c2ccc(O)c(F)c2)C(=O)C1=O]

Example 161: (R)-3-((R)-2-(4-ethyl-2,3-dioxopiperazine-1-carboxamido)-2-(3-fluoro-4-hydroxyphenyl)acetamido)-7-fluoro-2-hydroxy-3,4-dihydro-2H-benzo[e][1,2]oxaborinine-8-carboxylic acid

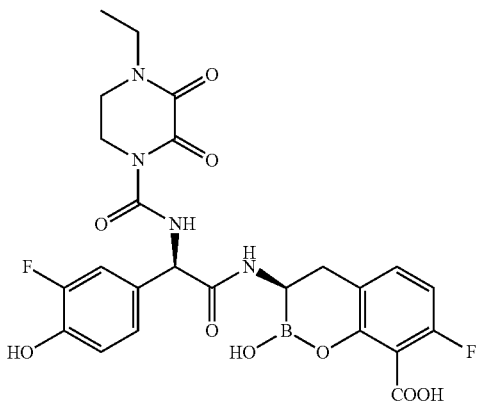

In a similar manner to the synthesis of Example 155 and Example 156, utilizing the chloride intermediate from Step 7 of Example 109, Example 160 and Example 161 were separated by reversed phase HPLC as the first eluting peak and the second eluting peak respectively. ESI-MS m/z 561 (M+H)$^+$.

Example 162: (3R)-3-(2-(4-ethyl-2,3-dioxopiperazine-1-carboxamido)-2-(3-fluoropyridin-2-yl)acetamido)-2-hydroxy-3,4-dihydro-2H-benzo[e][1,2]oxaborinine-8-carboxylic acid

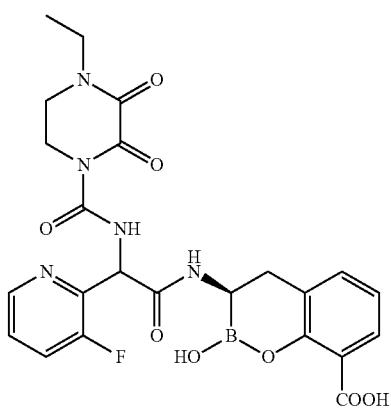 [SMILES: CCN1CCN(C(=O)NC(C(=O)N[C@H]2Cc3cccc(C(=O)O)c3OB2O)c2ncccc2F)C(=O)C1=O]

In a similar manner to the synthesis of Example 56 utilizing lithium 2-((tert-butoxycarbonyl)amino)-2-(3-fluoropyridin-2-yl)acetate in place of lithium 2-((tert-butoxycarbonyl)amino)-2-(pyridin-2-yl)acetate, the title compound was prepared. ESI-MS m/z 528 (M+H)$^+$.

Example 163: (R)-3-((2R,3S)-2-(4-ethyl-2,3-dioxopiperazine-1-carboxamido)-4,4-difluoro-3-hydroxybutanamido)-7-fluoro-2-hydroxy-3,4-dihydro-2H-benzo[e][1,2]oxaborinine-8-carboxylic acid

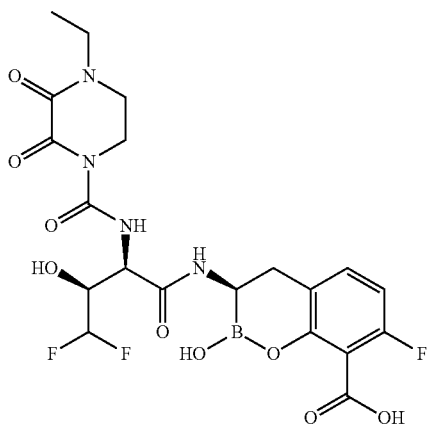 [SMILES: CCN1CCN(C(=O)N[C@@H](C(=O)N[C@H]2Cc3ccc(F)c(C(=O)O)c3OB2O)[C@H](O)C(F)F)C(=O)C1=O]

The title compound was prepared from (2R,3S)-2-amino-4,4-difluoro-3-hydroxybutanoic acid (Cho, J. et al. Tetrahedron Lett. 2015, 56, 127-131) and tert-butyl 3-((S)-2-chloro-2-((3aS,4S,6S,7aR)-3a,5,5-trimethyl-hexahydro-4,6-methanobenzo[d][1,3,2]dioxa-borol-2-yl)ethyl)-6-fluoro-2-methoxybenzoate (from Example 109), by a procedure similar to Example 8. ESI-MS m/z 531.1 (M+H)$^+$.

Example 164: (R)-3-((2S,3S)-2-(4-ethyl-2,3-dioxopiperazine-1-carboxamido)-4,4-difluoro-3-hydroxybutanamido)-7-fluoro-2-hydroxy-3,4-dihydro-2H-benzo[e][1,2]oxaborinine-8-carboxylic acid

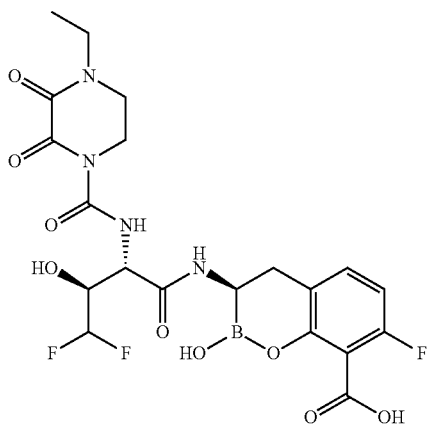 [SMILES: CCN1CCN(C(=O)N[C@H](C(=O)N[C@H]2Cc3ccc(F)c(C(=O)O)c3OB2O)[C@H](O)C(F)F)C(=O)C1=O]

The title compound was isolated by reverse phase HPLC (Gilson) as the less polar isomer in the last step of Example 163. ESI-MS m/z 531.1 (M+H)$^+$.

Example 165: (3R)-3-(2-(4-ethyl-2,3-dioxopiperazine-1-carboxamido)-2-(thiazol-4-yl)acetamido)-7-fluoro-2-hydroxy-3,4-dihydro-2H-benzo[e][1,2]oxaborinine-8-carboxylic acid

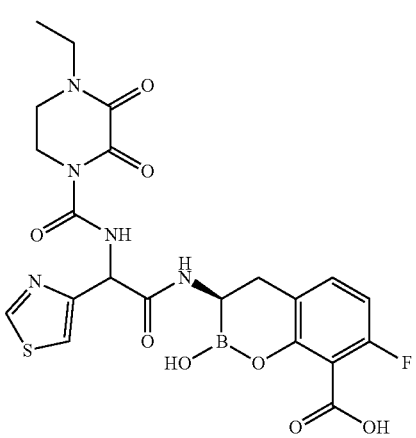 [SMILES: CCN1CCN(C(=O)NC(C(=O)N[C@H]2Cc3ccc(F)c(C(=O)O)c3OB2O)c2cscn2)C(=O)C1=O]

In a similar manner to the synthesis of Example 152, the title compound was prepared from 2-((tert-butoxycarbonyl)amino)-2-(thiazol-4-yl)acetic acid. ESI-MS m/z 534 (M+H)$^+$.

Example 166: (R)-3-((S)-2-(4-ethyl-2,3-dioxopiperazine-1-carboxamido)-2-(3-hydroxy-4-sulfamoylphenyl)acetamido)-2-hydroxy-3,4-dihydro-2H-benzo[e][1,2]oxaborinine-8-carboxylic acid

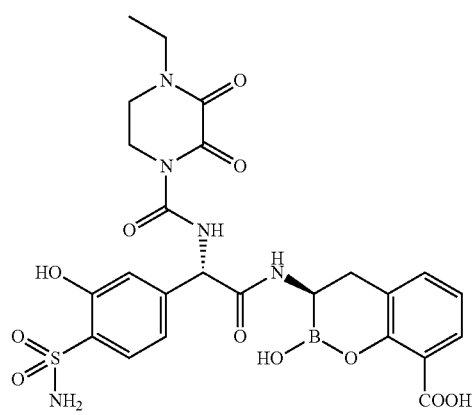 [SMILES: CCN1CCN(C(=O)N[C@H](C(=O)N[C@H]2Cc3cccc(C(=O)O)c3OB2O)c2ccc(S(N)(=O)=O)c(O)c2)C(=O)C1=O]

Example 167: (R)-3-((R)-2-(4-ethyl-2,3-dioxopiperazine-1-carboxamido)-2-(3-hydroxy-4-sulfamoylphenyl)acetamido)-2-hydroxy-3,4-dihydro-2H-benzo[e][1,2]oxaborinine-8-carboxylic acid

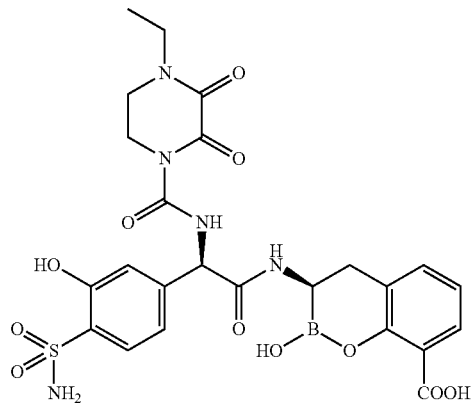 [SMILES: CCN1CCN(C(=O)N[C@@H](C(=O)N[C@H]2Cc3cccc(C(=O)O)c3OB2O)c2ccc(S(N)(=O)=O)c(O)c2)C(=O)C1=O]

In a similar manner to the synthesis of Example 37, utilizing 4-formyl-2-methoxybenzenesulfonamide in place of 2-chloro-3,4-dimethoxybenzaldehyde in Step 1, the title compounds, Example 166 and Example 167 were separated by reversed phase HPLC as the first eluting peak and the second eluting peak, respectively. ESI-MS m/z 604 (M+H)+.

Example 169: (R)-3-((R)-2-(4-ethyl-2,3-dioxopiperazine-1-carboxamido)-2-(3-methoxy-4-sulfamoylphenyl)acetamido)-2-hydroxy-3,4-dihydro-2H-benzo[e][1,2]oxaborinine-8-carboxylic acid

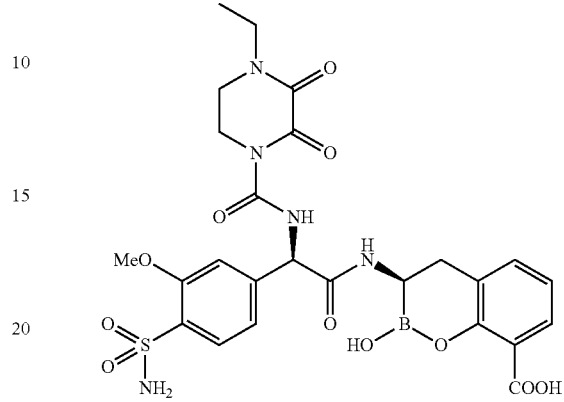

In a similar manner to the synthesis of Example 166 and Example 167, utilizing BCl₃ in the final deprotection reaction in place of BBr₃, the title compounds, Example 168 and Example 169 were separated by reversed phase HPLC as the first eluting peak and the second eluting peak respectively. ESI-MS m/z 618 (M+H)+.

Example 168: (R)-3-((S)-2-(4-ethyl-2,3-dioxopiperazine-1-carboxamido)-2-(3-methoxy-4-sulfamoylphenyl)acetamido)-2-hydroxy-3,4-dihydro-2H-benzo[e][1,2]oxaborinine-8-carboxylic acid

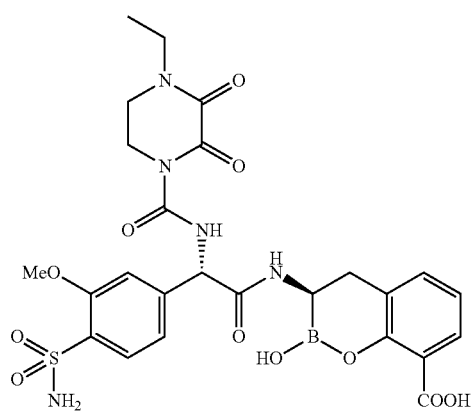 [SMILES: CCN1CCN(C(=O)N[C@H](C(=O)N[C@H]2Cc3cccc(C(=O)O)c3OB2O)c2ccc(S(N)(=O)=O)c(OC)c2)C(=O)C1=O]

Example 170: (R)-3-((R)-2-(4-(2-fluoroethyl)-2,3-dioxopiperazine-1-carboxamido)-2-(3-hydroxy-4-sulfamoylphenyl)acetamido)-2-hydroxy-3,4-dihydro-2H-benzo[e][1,2]oxaborinine-8-carboxylic acid

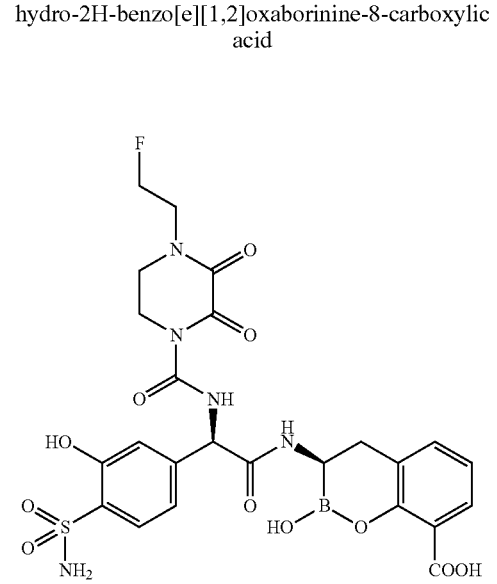

Example 171: (R)-3-((S)-2-(4-(2-bromoethyl)-2,3-dioxopiperazine-1-carboxamido)-2-(3-hydroxy-4-sulfamoylphenyl)acetamido)-2-hydroxy-3,4-dihydro-2H-benzo[e][1,2]oxaborinine-8-carboxylic acid

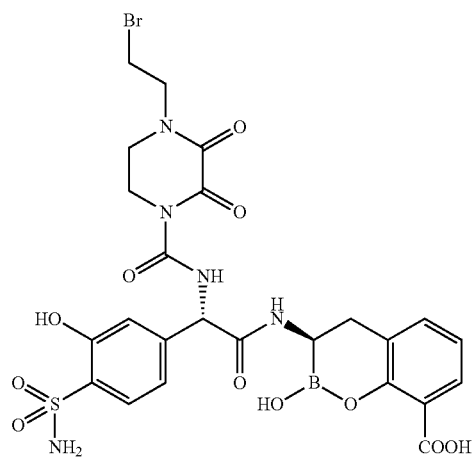 [SMILES: NS(=O)(=O)c1ccc([C@H](NC(=O)N2CCN(CCBr)C(=O)C2=O)C(=O)N[C@H]2Cc3cccc(C(=O)O)c3OB2O)cc1O]

Example 172: (R)-3-((R)-2-(4-(2-bromoethyl)-2,3-dioxopiperazine-1-carboxamido)-2-(3-hydroxy-4-sulfamoylphenyl)acetamido)-2-hydroxy-3,4-dihydro-2H-benzo[e][1,2]oxaborinine-8-carboxylic acid

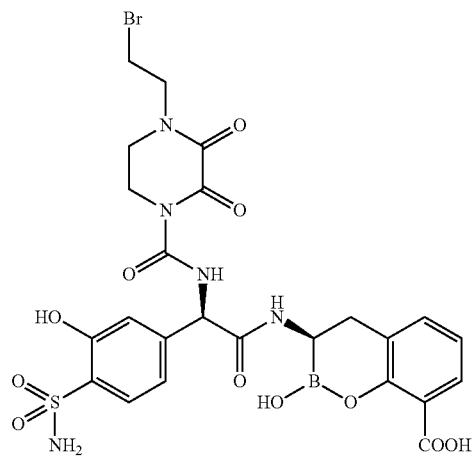 [SMILES: NS(=O)(=O)c1ccc([C@@H](NC(=O)N2CCN(CCBr)C(=O)C2=O)C(=O)N[C@H]2Cc3cccc(C(=O)O)c3OB2O)cc1O]

In a similar manner to the synthesis of Example 166 and Example 167, utilizing 4-fluoroethyl-2,3-dioxopiperazine-1-carbonyl chloride (product from Step 2 of Example 13) in place of 4-ethyl-2,3-dioxopiperazine-1-carbonyl chloride, Example 170, Example 171, and Example 172 were separated by reversed phase HPLC. Example 170, ESI-MS m/z 622 (M+H)+; Example 171, Example 172, ESI-MS m/z 682/684 (MH/MH+2)+.

Example 173: (R)-3-((2R,3S)-2-(4-ethyl-2,3-dioxopiperazine-1-carboxamido)-4,4-difluoro-3-hydroxybutanamido)-2-hydroxy-3,4-dihydro-2H-benzo[e][1,2]oxaborinine-8-carboxylic acid

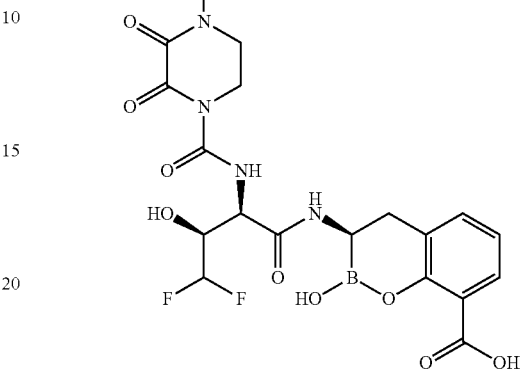

The title compound was prepared from (2R,3S)-2-amino-4,4-difluoro-3-hydroxybutanoic acid (Cho, J. et al. Tetrahedron Lett. 2015, 56, 127-131) and 3-((2S)-2-chloro-2-((3aS,4S,6S)-3a,5,5-trimethylhexahydro-4,6-methanobenzo-[d][1,3,2]dioxaborol-2-yl)ethyl)-2-methoxybenzoate, by a procedure similar to Example 8. ESI-MS m/z 513.1 (M+H)+.

Example 174: (R)-3-((2S,3S)-2-(4-ethyl-2,3-dioxopiperazine-1-carboxamido)-4,4-difluoro-3-hydroxybutanamido)-2-hydroxy-3,4-dihydro-2H-benzo[e][1,2]oxaborinine-8-carboxylic acid

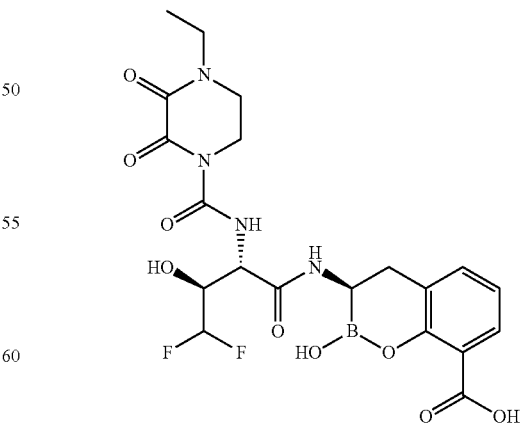

The title compound was isolated by reverse phase HPLC (Gilson) as the less polar isomer in the last step of Example 173. ESI-MS m/z 513.1 (M+H)+.

Example 175: (3R)-3-(2-(2-aminothiazol-4-yl)-2-(4-ethyl-2,3-dioxopiperazine-1-carboxamido)acetamido)-6,7-difluoro-2-hydroxy-3,4-dihydro-2H-benzo[e][1,2]oxaborinine-8-carboxylic acid

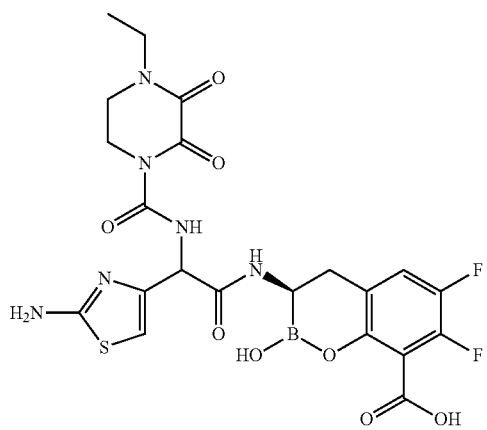 [SMILES: CCN1CCN(C(=O)NC(C(=O)N[C@H]2Cc3cc(F)c(F)c(C(=O)O)c3OB2O)c2csc(N)n2)C(=O)C1=O]

Step 1. Synthesis of tert-butyl 3-bromo-5,6-difluoro-2-hydroxybenzoate

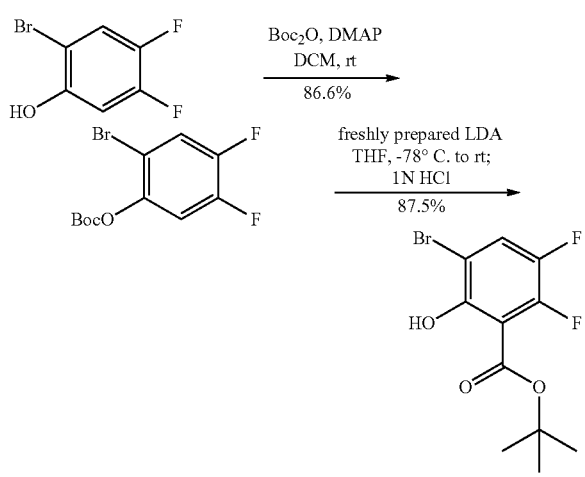

To a mixture of 2-bromo-4,5-difluorophenol (19.82 g, 94.8 mmol) and Boc₂O (25.34 g, 116 mmol) in DCM (300 mL) was added DMAP (0.636 g, 5.2 mmol) at room temperature. The reaction mixture was stirred at room temperature for 15 h. After the solvent was evaporated under reduced pressure, the residue was purified by flash chromatography on silica gel (340 g column) eluted with 0 to 20% ethyl acetate/hexanes to afford 25.40 g (86.6%) of 2-bromo-4,5-difluorophenyl tert-butyl carbonate.

To a solution of 2-bromo-4,5-difluorophenyl tert-butyl carbonate (25.40 g, 82.2 mmol) in THF (100 mL) at −78° C. under argon was added freshly prepared LDA, n-BuLi (2.5 M in hexane, 40 mL, 100 mmol) was added dropwise to a solution of DIPA (14 mL, 99.9 mmol) in THF (100 mL) at −78° C. under argon and the resulting solution was stirred at −78° C. for 1 h, via cannula. The reaction mixture was allowed to slowly warm to room temperature overnight and then quenched with 1 N HCl (200 mL), extracted with ethyl acetate (3×). The combined organic phase was dried over Na₂SO₄. After the solvent was evaporated under reduced pressure, the residue was purified by flash chromatography on silica gel (340 g column) eluted with 0 to 20% ethyl acetate/hexanes to afford 22.23 g (87.5%) of tert-butyl 3-bromo-5,6-difluoro-2-hydroxybenzoate.

Step 2. Synthesis of tert-butyl 3-bromo-5,6-difluoro-2-methoxybenzoate

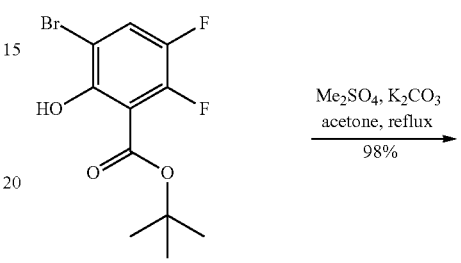

A mixture of tert-butyl 3-bromo-5,6-difluoro-2-hydroxybenzoate (18.63 g, 60.3 mmol), dimethyl sulfate (11 mL, 116 mmol), and K₂CO₃ (17.05 g, 123 mmol) in acetone (150 mL) was stirred at 80° C. for 62 h. After cooling to room temperature, the reaction mixture was filtered, washed with ethyl acetate. After the filtrate was evaporated under reduced pressure, the residue was purified by flash chromatography on silica gel (340 g column) eluted with 0 to 20% ethyl acetate/hexanes to afford 19.11 g (98%) of tert-butyl 3-bromo-5,6-difluoro-2-methoxybenzoate. ESI-MS m/z 266.9, 268.9 (M−56)⁺.

Step 3. Synthesis of tert-butyl 2,3-difluoro-6-methoxy-5-(((3aS,4S,6S,7aR)-3a,5,5-trimethylhexahydro-4,6-methanobenzo[d][1,3,2]dioxaborol-2-yl)methyl)benzoate

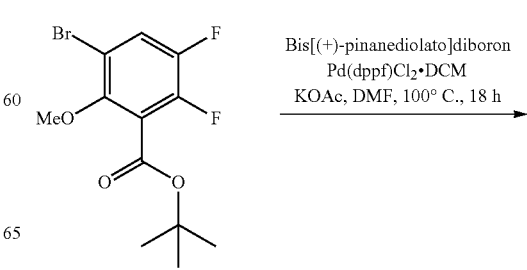

233
-continued

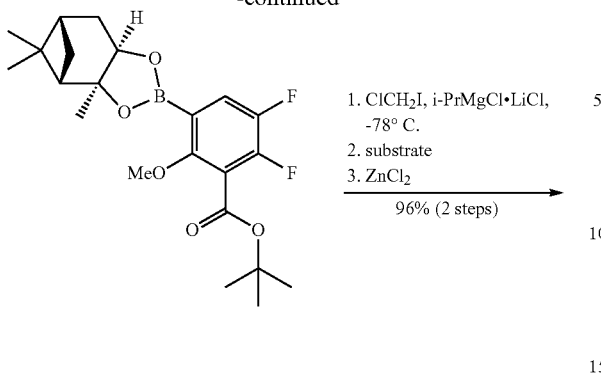

1. ClCH₂I, i-PrMgCl·LiCl, −78° C.
2. substrate
3. ZnCl₂

96% (2 steps)

234

Step 4. Synthesis of tert-butyl 3-((S)-2-chloro-2-((3aS,4S,6S,7aR)-3a,5,5-trimethylhexahydro-4,6-methanobenzo[d][1,3,2]dioxaborol-2-yl)ethyl)-5,6-difluoro-2-methoxybenzoate

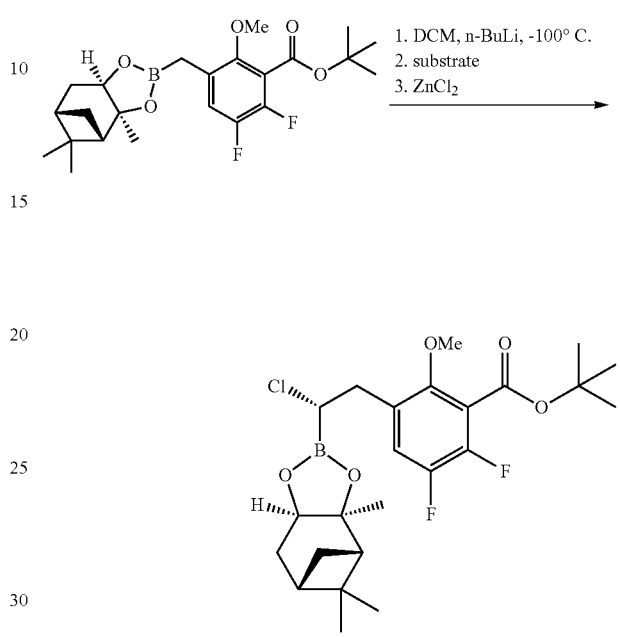

1. DCM, n-BuLi, −100° C.
2. substrate
3. ZnCl₂

A mixture of tert-butyl 3-bromo-5,6-difluoro-2-methoxybenzoate (19.05 g, 58.95 mmol), bis[(+)-pinanediolato]diboron (28.04 g, 78.30 mmol), KOAc (18.46 g, 188 mmol), and Pd(dppf)Cl₂·DCM (2.36 g, 2.89 mmol) in DMF (130 mL) was stirred at 100° C. under argon for 18 h. After cooling to room temperature, the reaction mixture was quenched with water, filtered through Celite, extracted with ethyl acetate (3×). The combined organic phase was dried over Na₂SO₄. After the solvent was evaporated under reduced pressure, the residue was purified by flash chromatography on silica gel (340 g column) eluted with 0 to 20% ethyl acetate/hexanes to afford 25.10 g of tert-butyl 2,3-difluoro-6-methoxy-5-((3aS,4S,6S,7aR)-3a,5,5-trimethylhexahydro-4,6-methanobenzo[d][1,3,2]dioxaborol-2-yl)benzoate. ESI-MS m/z 867.4 (2M+Na)⁺.

To a solution of chloroiodomethane (21 mL, 288 mmol) in THF (200 mL) at −78° C. under argon was added i-PrMgCl·LiCl (1.3 M in THF, 100 mL, 130 mmol) dropwise over 40 min. The resulting mixture was stirred at −78° C. for an additional hour and then a solution of tert-butyl 2,3-difluoro-6-methoxy-5-((3aS,4S,6S,7aR)-3a,5,5-trimethylhexahydro-4,6-methanobenzo[d][1,3,2]dioxaborol-2-yl)benzoate (25.10 g) in THF (60 mL) was added dropwise over 25 min. After the reaction mixture was stirred at −78° C. for 2 h, ZnCl₂ (1.0 M in diethyl ether, 90 mL, 90 mmol) was added dropwise over 20 min. The reaction mixture was then allowed to slowly warm to room temperature overnight. The mixture was cooled to −30° C. and quenched with aqueous NH₄Cl (200 mL), extracted with ethyl acetate (3×). The combined organic phase was dried over Na₂SO₄. After the solvent was evaporated under reduced pressure, the residue was purified by flash chromatography on silica gel (340 g column) eluted with 0 to 20% ethyl acetate/hexanes to afford 24.88 g (96%) of tert-butyl 2,3-difluoro-6-methoxy-5-(((3aS,4S,6S,7aR)-3a,5,5-trimethylhexahydro-4,6-methanobenzo[d][1,3,2]dioxaborol-2-yl)methyl)benzoate. ESI-MS m/z 459.2 (M+Na)⁺.

The Matteson reaction was carried out as described in Example 16 Step 6 by using tert-butyl 2,3-difluoro-6-methoxy-5-(((3aS,4S,6S,7aR)-3a,5,5-trimethylhexahydro-4,6-methanobenzo[d][1,3,2]dioxaborol-2-yl)methyl)benzoate as the substrate to afford tert-butyl 3-((S)-2-chloro-2-((3aS,4S,6S,7aR)-3a,5,5-trimethylhexahydro-4,6-methanobenzo[d][1,3,2]dioxaborol-2-yl)ethyl)-5,6-difluoro-2-methoxybenzoate. ESI-MS m/z 507.1 (M+Na)⁺.

Step 5. Synthesis of tert-butyl 3-((2R)-2-(2-(2-(((benzyloxy)carbonyl)amino)thiazol-4-yl)-2-(4-ethyl-2,3-dioxopiperazine-1-carboxamido)acetamido)-2-((3aS,4S,6S,7aR)-3a,5,5-trimethylhexahydro-4,6-methanobenzo[d][1,3,2]dioxaborol-2-yl)ethyl)-5,6-difluoro-2-methoxybenzoate

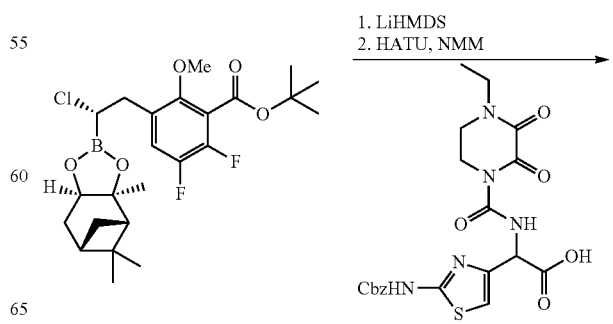

1. LiHMDS
2. HATU, NMM

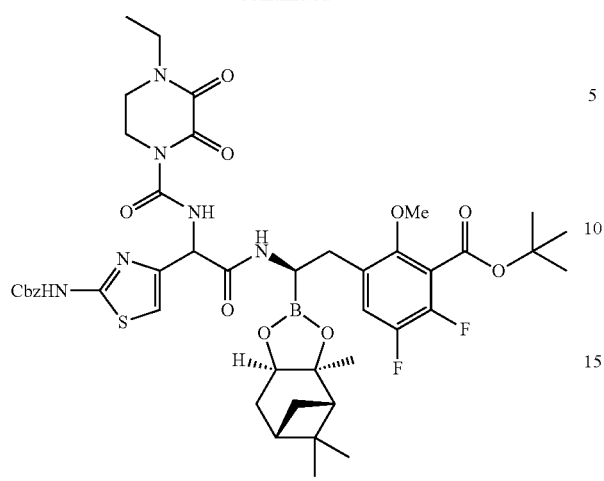

The amide formation was carried out as described in Example 16 Step 7, by using tert-butyl 3-((S)-2-chloro-2-((3aS,4S,6S,7aR)-3a,5,5-trimethylhexahydro-4,6-methanobenzo[d][1,3,2]dioxaborol-2-yl)ethyl)-5,6-difluoro-2-methoxybenzoate as the substrate to afford tert-butyl 3-((2R)-2-(2-(2-(((benzyloxy)carbonyl)amino)thiazol-4-yl)-2-(4-ethyl-2,3-dioxopiperazine-1-carboxamido)acetamido)-2-((3aS,4S,6S,7aR)-3a,5,5-trimethylhexahydro-4,6-methanobenzo[d][1,3,2]dioxaborol-2-yl)ethyl)-5,6-difluoro-2-methoxybenzoate. ESI-MS m/z 923.3 (M+H)$^+$.

Step 6. Synthesis of (3R)-3-(2-(2-aminothiazol-4-yl)-2-(4-ethyl-2,3-dioxopiperazine-1-carboxamido)acetamido)-6,7-difluoro-2-hydroxy-3,4-dihydro-2H-benzo[e][1,2]oxaborinine-8-carboxylic acid

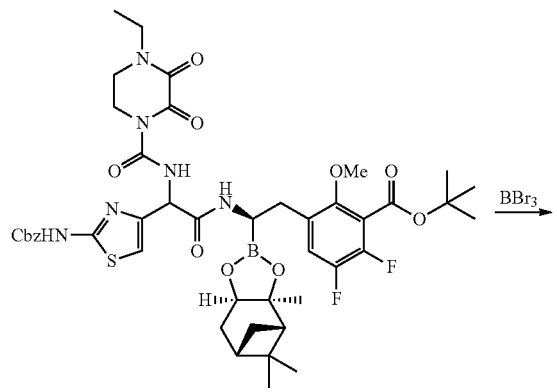

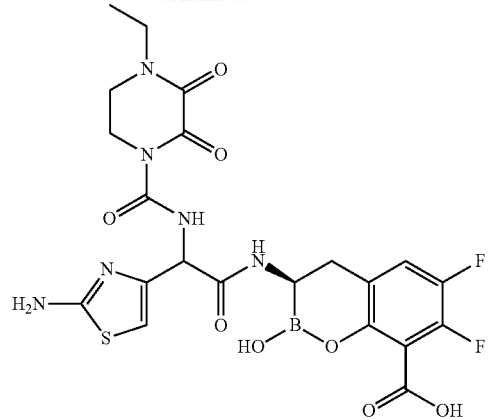

The full deprotection of tert-butyl 3-((2R)-2-(2-(2-(((benzyloxy)carbonyl)amino)thiazol-4-yl)-2-(4-ethyl-2,3-dioxopiperazine-1-carboxamido)acetamido)-2-((3aS,4S,6S,7aR)-3a,5,5-trimethylhexahydro-4,6-methanobenzo[d][1,3,2]dioxaborol-2-yl)ethyl)-5,6-difluoro-2-methoxybenzoate was carried out as described in General Method A with BBr$_3$ to afford (3R)-3-(2-(2-aminothiazol-4-yl)-2-(4-ethyl-2,3-dioxopiperazine-1-carboxamido)acetamido)-6,7-difluoro-2-hydroxy-3,4-dihydro-2H-benzo[e][1,2]oxaborinine-8-carboxylic acid. ESI-MS m/z 567.1 (M+H)$^+$.

Example 176: (R)-3-((S)-2-(4-ethyl-2,3-dioxopiperazine-1-carboxamido)-2-(3-fluoro-5-hydroxypyridin-2-yl)acetamido)-2-hydroxy-3,4-dihydro-2H-benzo[e][1,2]oxaborinine-8-carboxylic acid

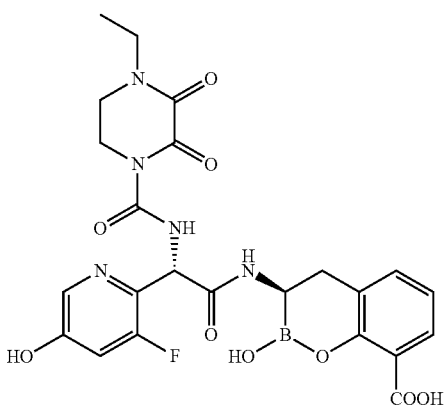

The title compound was prepared according to the method of Example 135 and isolated as the first eluting peak using a Zorbax column from Agilent Technologies (SB-C18 Prep HT column 30×150 mm 5-micron) 10%-30% CH$_3$CN—H$_2$O+0.1% trifluoroacetic acid, flow rate: 45 mL/min, gradient time: 12 min. ESI-MS m/z 544 (M+H)$^+$.

Example 177: (R)-3-((R)-2-(4-ethyl-2,3-dioxopiperazine-1-carboxamido)-2-(3-fluoro-5-hydroxypyridin-2-yl)acetamido)-2-hydroxy-3,4-dihydro-2H-benzo[e][1,2]oxaborinine-8-carboxylic acid

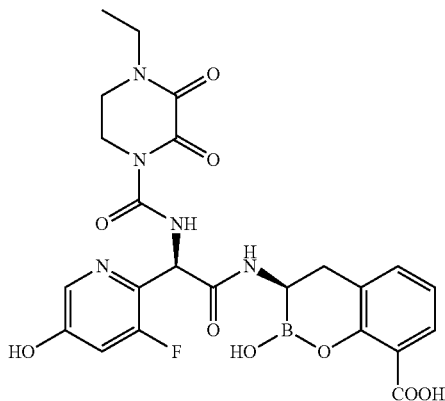 [SMILES: CCN1CCN(C(=O)N[C@@H](C(=O)N[C@H]2Cc3cccc(C(=O)O)c3OB2O)c2ncc(O)cc2F)C(=O)C1=O]

The title compound was prepared according to the method of Example 135 and isolated as the second eluting peak using a Zorbax column from Agilent Technologies (SB-C18 Prep HT column 30×150 mm 5-micron) 10%-25% CH$_3$CN—H$_2$O+0.1% trifluoroacetic acid, flow rate: 45 mL/min, gradient time: 15 min. ESI-MS m/z 544 (M+H)$^+$.

Example 178: (3R)-3-(2-(4-ethyl-2,3-dioxopiperazine-1-carboxamido)-2-(5-hydroxy-3-methylpyridin-2-yl)acetamido)-2-hydroxy-3,4-dihydro-2H-benzo[e][1,2]oxaborinine-8-carboxylic acid

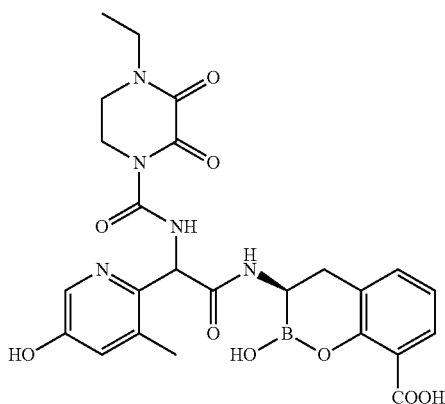

In a similar manner to the synthesis of Example 134 utilizing 4-ethyl-2,3-dioxopiperazine-1-carbonyl chloride in place of 4-propyl-2,3-dioxopiperazine-1-carbonyl chloride, the title compound was prepared. ESI-MS m/z 540 (M+H)$^+$.

Example 179: (3R)-3-(2-(3-fluoro-5-hydroxypyridin-2-yl)-2-(4-(2-fluoroethyl)-2,3-dioxopiperazine-1-carboxamido)acetamido)-2-hydroxy-3,4-dihydro-2H-benzo[e][1,2]oxaborinine-8-carboxylic acid In a similar manner to the synthesis of Example 134 utilizing 4-(2-fluoroethyl)-2,3-dioxopiperazine-1-carbonyl chloride in place of 4-propyl-2,3-dioxopiperazine-1-carbonyl chloride, the title compound was prepared. ESI-MS m/z 562 (M+H)$^+$.

Example 180: (3R)-3-(2-(2-chloro-3,4-dihydroxyphenyl)-2-(4-ethyl-2,3-dioxopiperazine-1-carboxamido)acetamido)-6,7-difluoro-2-hydroxy-3,4-dihydro-2H-benzo[e][1,2]oxaborinine-8-carboxylic acid

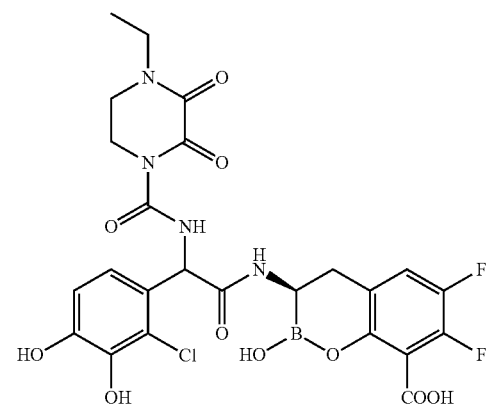

In a similar manner to the synthesis of Example 37, utilizing the chloride intermediate from Step 4 of Example 175 in Step 2, the title compound was prepared. ESI-MS m/z 611/613 (MH/MH+2)$^+$.

Example 181: (3R)-3-(2-(4-ethyl-2,3-dioxopiperazine-1-carboxamido)-2-(4-sulfamoylphenyl)acetamido)-7-fluoro-2-hydroxy-3,4-dihydro-2H-benzo[e][1,2]oxaborinine-8-carboxylic acid

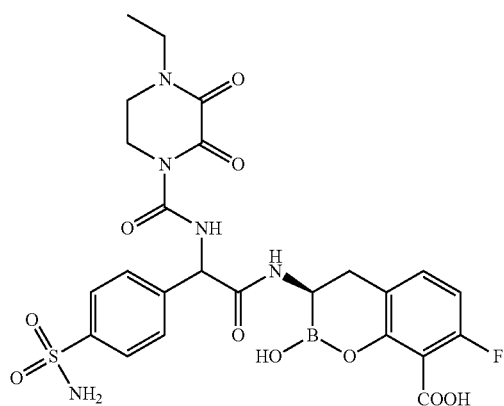 [SMILES: CCN1CCN(C(=O)NC(C(=O)N[C@H]2Cc3ccc(F)c(C(=O)O)c3OB2O)c2ccc(S(N)(=O)=O)cc2)C(=O)C1=O]

In a similar manner to the synthesis of Example 102, utilizing the chloride intermediate from Step 7 of Example 109 in Step 2, the title compound was prepared. ESI-MS m/z 606 (M+H)+.

Example 182: (3R)-7-fluoro-3-(2-(4-(2-fluoroethyl)-2,3-dioxopiperazine-1-carboxamido)-2-(4-sulfamoylphenyl)acetamido)-2-hydroxy-3,4-dihydro-2H-benzo[e][1,2]oxaborinine-8-carboxylic acid

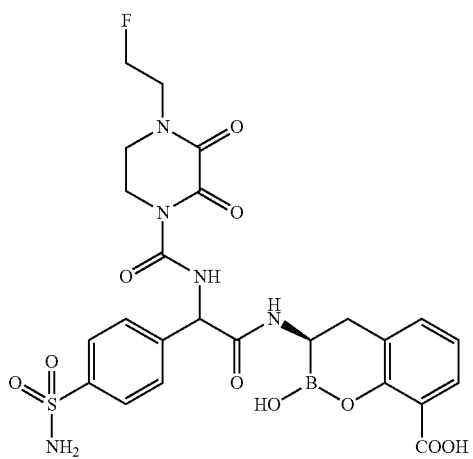 [SMILES: NS(=O)(=O)c1ccc(C(NC(=O)N2CCN(CCF)C(=O)C2=O)C(=O)N[C@H]2Cc3cccc(C(=O)O)c3OB2O)cc1]

In a similar manner to the synthesis of Example 103, utilizing the chloride intermediate from Step 7 of Example 109 in Step 2, the title compound was prepared. ESI-MS m/z 624 (M+H)+.

Example 183: (3R)-7-fluoro-3-(2-(3-fluoro-5-hydroxypyridin-2-yl)-2-(4-(2-fluoroethyl)-2,3-dioxopiperazine-1-carboxamido)acetamido)-2-hydroxy-3,4-dihydro-2H-benzo[e][1,2]oxaborinine-8-carboxylic acid

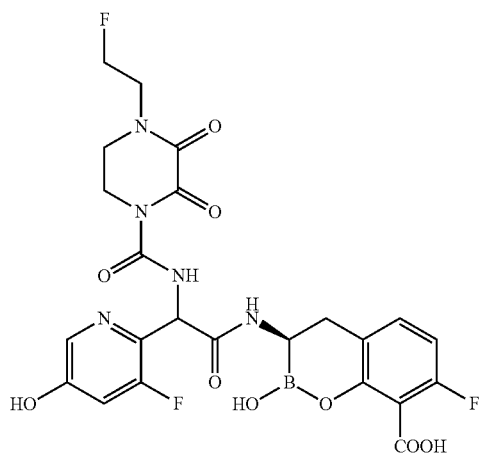 [SMILES: O=C(O)c1c(F)ccc2c1OB(O)[C@@H](NC(=O)C(NC(=O)N1CCN(CCF)C(=O)C1=O)c1ncc(O)cc1F)C2]

In a similar manner to the synthesis of Example 179, utilizing tert-butyl 3-((2S)-2-chloro-2-((3aS,4S,6R)-3a,5,5-trimethylhexahydro-4,6-methanobenzo[d][1,3,2]dioxaborol-2-yl)ethyl)-6-fluoro-2-methoxybenzoate in place of tert-butyl 3-((2S)-2-chloro-2-((3aS,4S,6R)-3a,5,5-trimethylhexahydro-4,6-methanobenzo[d][1,3,2]dioxaborol-2-yl)ethyl)-2-methoxybenzoate, the title compound was prepared. ESI-MS m/z 580 (M+H)+.

Example 184: (3R)-3-(2-(2-aminothiazol-4-yl)-2-(4-ethyl-2,3-dioxopiperazine-1-carboxamido)acetamido)-5,7-difluoro-2-hydroxy-3,4-dihydro-2H-benzo[e][1,2]oxaborinine-8-carboxylic acid

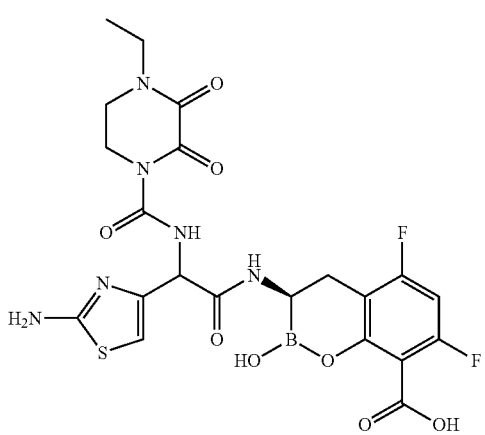

241

-continued

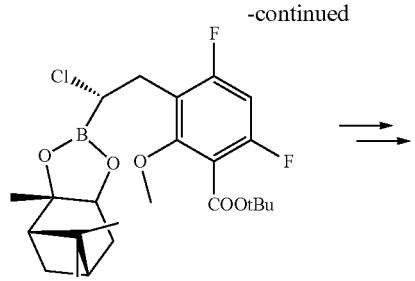

In a similar manner to the synthesis of Example 5, the title compound was prepared from the difluoro-substituted chloride intermediate (which was prepared according to the reported procedures, WO2015/179308) by following the General Method C and General Method A. ESI-MS m/z 567 (M+H)⁺.

Example 185: (3R)-3-(2-(2-chloro-3,4-dihydroxyphenyl)-2-(4-ethyl-2,3-dioxopiperazine-1-carboxamido)acetamido)-5,7-difluoro-2-hydroxy-3,4-dihydro-2H-benzo[e][1,2]oxaborinine-8-carboxylic acid

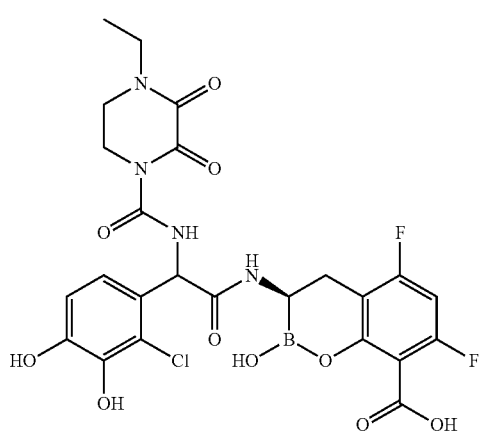

242

-continued

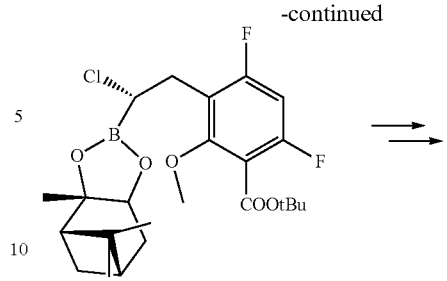

In a similar manner to the synthesis of Example 37, the title compound was prepared from the difluoro-substituted chloride intermediate (which was prepared according to the reported procedures, WO2015/179308) by following the General Method C and General Method A. ESI-MS m/z 611/613 (MH/MH+2)⁺.

Example 186: (3R)-3-(2-(4-carbamoylphenyl)-2-(4-ethyl-2,3-dioxopiperazine-1-carboxamido)acetamido)-2-hydroxy-3,4-dihydro-2H-benzo[e][1,2]oxaborinine-8-carboxylic acid

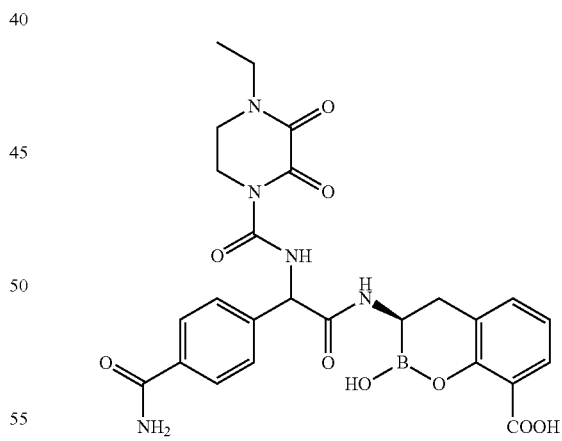

Step 1. Synthesis of tert-butyl (tert-butoxycarbonyl)(4-cyanobenzyl) carbamate

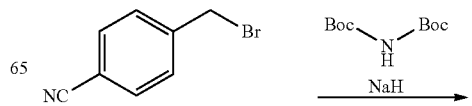

243
-continued

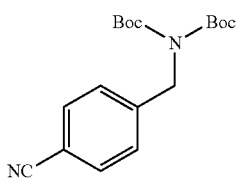

To a suspension of NaH (60%, 2.5 g, 61.6 mmol (in THF (100 mL) was added at −5° C. to −10° C. 4-cyanobenzyl bromide (10 g, 51 mmol), followed by di-tert-butyl iminocarbonate (12.82 g, 59 mmol) in THF (30 mL) dropwise over 15 min. The reaction mixture was stirred at RT overnight, quenched with ice-water, extracted with EtOAc. The combined organic extracts were washed with water, brine, dried over $Na_2SO_4$, concentrated in vacuo to afford the crude product, which was washed with hexane, and dried in vacuo, 15.7 g. ESI-MS m/z 333 (M+H)$^+$.

Step 2. Synthesis of tert-butyl 2-((tert-butoxycarbonyl)amino)-2-(4-cyanophenyl)acetate

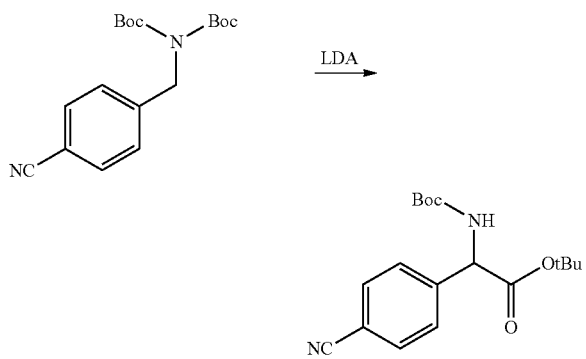

To the above product (6.8 g, 20.5 mmol) in THF (160 mL) was added at −78° C. LDA (2.0 M, 15 mL, 30 mmol) dropwise under Argon. After the addition was complete, The reaction mixture was stirred at −78° C. for 1 h 45 min, quenched with 1 N HCl, extracted with EtOAc. The combined organic extracts were washed with brine, dried over $Na_2SO_4$, concentrated in vacuo to afford the crude product. The crude product was purified by flash chromatography on silica gel (hexane-EtOAc, 20:1-1:1) to afford the title compound, 4.9 g. ESI-MS m/z 333 (M+H)$^+$.

Step 3. Synthesis of 2-((tert-butoxycarbonyl)amino)-2-(4-carbamoylphenyl)acetic acid

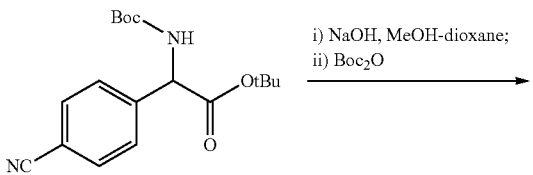

244
-continued

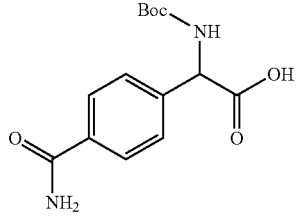

The above product (2 g, 6 mmol) in dioxane (54 mL) was treated with 4 N NaOH in MeOH (6 mL, 24 mmol) at reflux for 3.5 h. The reaction mixture was cooled to 0° C., water was added, and the resulting mixture was acidified with 1 N HCl to pH ~9, then added a THF (8 mL) solution of $Boc_2O$ (2.18 g, 10 mmol). The reaction mixture was stirred at RT for 1.5 h, concentrated, extracted with diethyl ether. The aqueous was acidified with 1 N HCl to pH ~2, extracted with EtOAc. The organic extracts were combined, dried over $Na_2SO_4$, concentrated in vacuo to afford the title compound, 1.6 g. ESI-MS m/z 295 (M+H)$^+$.

Step 4. Synthesis of (3R)-3-(2-(4-boronophenyl)-2-(4-ethyl-2,3-dioxopiperazine-1-carboxamido)acetamido)-2-hydroxy-3,4-dihydro-2H-benzo[e][1,2]oxaborinine-8-carboxylic acid

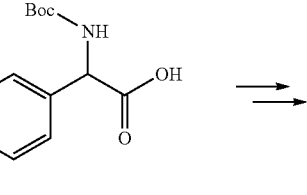

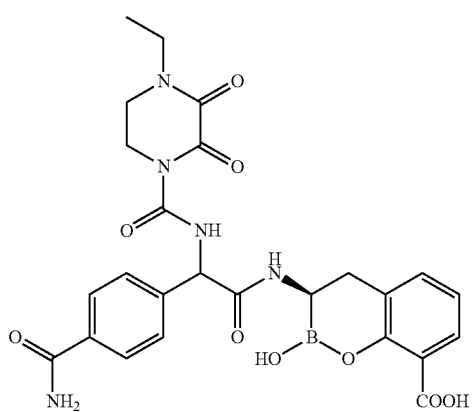 [SMILES: CCN1CCN(C(=O)NC(C(=O)N[C@H]2Cc3cccc(C(=O)O)c3OB2O)c2ccc(C(N)=O)cc2)C(=O)C1=O]

In a similar manner to the synthesis of Example 6, utilizing 4-ethyl-2,3-dioxopiperazine-1-carbonyl chloride in place of of ethyl isocyanate in Step 3, the title compound was prepared from the above acid. ESI-MS m/z 552 (M+H)$^+$.

Example 187: (3R)-3-(2-(4-carbamoylphenyl)-2-(4-(2-fluoroethyl)-2,3-dioxopiperazine-1-carboxamido)acetamido)-2-hydroxy-3,4-dihydro-2H-benzo[e][1,2]oxaborinine-8-carboxylic acid

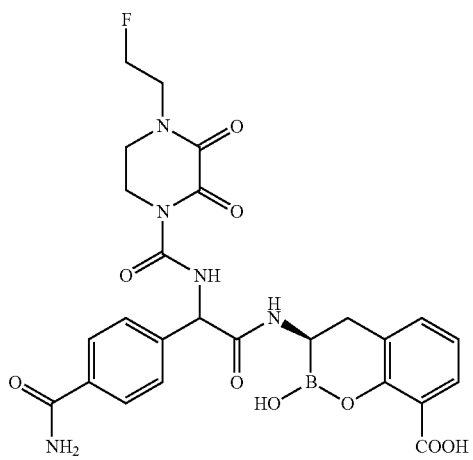 [SMILES: NC(=O)c1ccc(C(NC(=O)N2CCN(CCF)C(=O)C2=O)C(=O)N[C@H]2Cc3cccc(C(=O)O)c3OB2O)cc1]

In a similar manner to the synthesis of Example 186, utilizing 4-fluoroethyl-2,3-dioxopiperazine-1-carbonyl chloride (product from Step 2 of Example 13) in place of 4-ethyl-2,3-dioxopiperazine-1-carbonyl chloride in Step 4, the title compound was prepared. ESI-MS m/z 570 (M+H)+.

Example 188: (R)-3-((S)-2-(2-chloro-3,4-dihydroxyphenyl)-2-(4-ethyl-2,3-dioxopiperazine-1-carboxamido)acetamido)-7-fluoro-2-hydroxy-3,4-dihydro-2H-benzo[e][1,2]oxaborinine-8-carboxylic acid

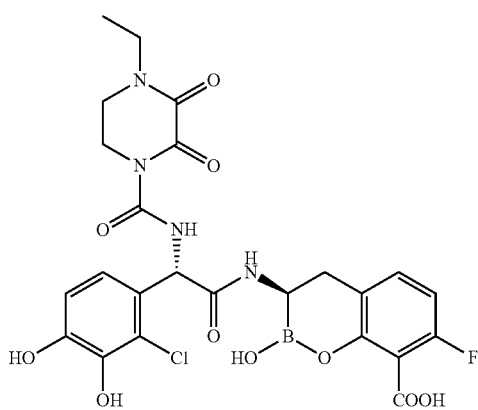 [SMILES: CCN1CCN(C(=O)N[C@H](C(=O)N[C@H]2Cc3ccc(F)c(C(=O)O)c3OB2O)c2ccc(O)c(O)c2Cl)C(=O)C1=O]

Example 189: (R)-3-((R)-2-(2-chloro-3,4-dihydroxyphenyl)-2-(4-ethyl-2,3-dioxopiperazine-1-carboxamido)acetamido)-7-fluoro-2-hydroxy-3,4-dihydro-2H-benzo[e][1,2]oxaborinine-8-carboxylic acid

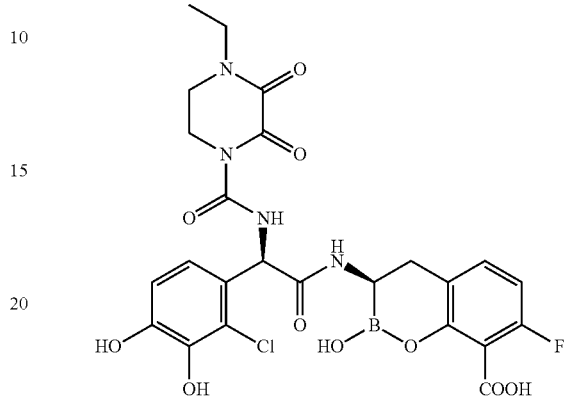

In a similar manner to the synthesis of Example 38 and Example 39, the title compounds, Example 188 and Example 189, were prepared by separation of diastereomeric mixture of Example 124 using a Zorbax column, Example 188 was isolated as the first eluting peak, Example 189 isolated as the second eluting peak. ESI-MS m/z 593/595 (MH/MH+2)+.

Example 190: (R)-3-((R)-2-(2-chloro-3,4-dihydroxyphenyl)-2-(4-ethyl-2,3-dioxopiperazine-1-carboxamido)acetamido)-2-hydroxy-3,4-dihydro-2H-benzo[e][1,2]oxaborinine-8-carboxylic acid

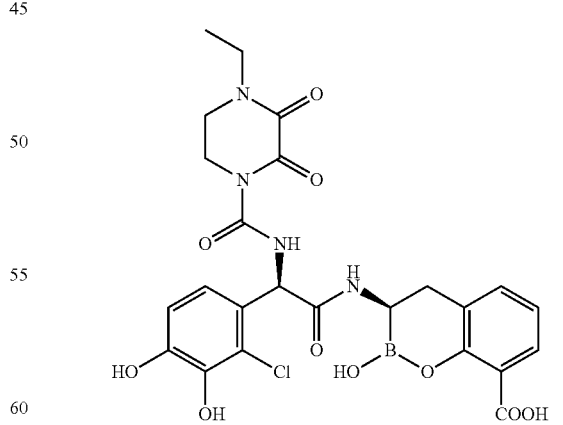

In a similar manner to the preparation of Example 39 and Example 189, the title compound was isolated from the diastereomeric mixture of Example 37 using a Zorbax column, as the second eluting peak. ESI-MS m/z 575/577 (MH/MH+2)+.

Example 191: (3R)-3-(2-((R)-4-ethyl-6-methyl-2,3-dioxopiperazine-1-carboxamido)-2-(3-fluoro-5-hydroxypyridin-2-yl)acetamido)-2-hydroxy-3,4-dihydro-2H-benzo[e][1,2]oxaborinine-8-carboxylic acid

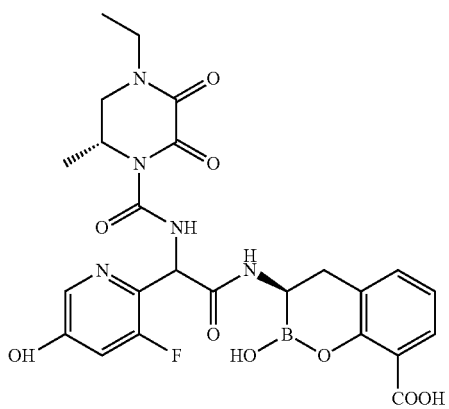 [SMILES: CCN1C[C@@H](C)N(C(=O)NC(C(=O)N[C@H]2Cc3cccc(C(=O)O)c3OB2O)c2ncc(O)cc2F)C(=O)C1=O]

In a similar manner to the synthesis of Example 134 utilizing (R)-4-ethyl-6-methyl-2,3-dioxopiperazine-1-carbonyl chloride in place of 4-propyl-2,3-dioxopiperazine-1-carbonyl chloride, the title compound was prepared. ESI-MS m/z 558 (M+H)$^+$.

Example 192: (3R)-3-(2-((S)-4-ethyl-6-methyl-2,3-dioxopiperazine-1-carboxamido)-2-(3-fluoro-5-hydroxypyridin-2-yl)acetamido)-2-hydroxy-3,4-dihydro-2H-benzo[e][1,2]oxaborinine-8-carboxylic acid

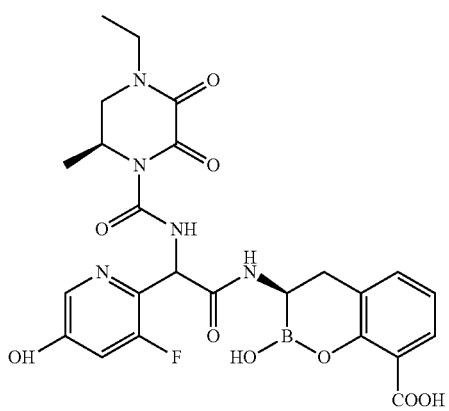 [SMILES: CCN1C[C@H](C)N(C(=O)NC(C(=O)N[C@H]2Cc3cccc(C(=O)O)c3OB2O)c2ncc(O)cc2F)C(=O)C1=O]

In a similar manner to the synthesis of Example 134 utilizing (S)-4-ethyl-6-methyl-2,3-dioxopiperazine-1-carbonyl chloride in place of 4-propyl-2,3-dioxopiperazine-1-carbonyl chloride, the title compound was prepared. ESI-MS m/z 558 (M+H)$^+$.

Example 193: (3R)-3-(2-(2-aminothiazol-4-yl)-2-(4-ethyl-2-hydroxy-3-oxopiperazine-1-carboxamido)acetamido)-2-hydroxy-3,4-dihydro-2H-benzo[e][1,2]oxaborinine-8-carboxylic acid

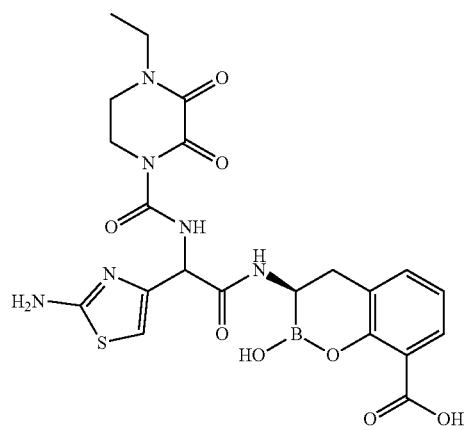 [SMILES: CCN1CCN(C(=O)NC(C(=O)N[C@H]2Cc3cccc(C(=O)O)c3OB2O)c2csc(N)n2)C(=O)C1=O]

In a similar manner to the synthesis of Example 194, Example 5 was reduced with NaBH$_4$ to yield the title compound. ESI-MS m/z 533 (M+H)$^+$.

Example 194: (3R)-3-(2-(2-chloro-3,4-dihydroxyphenyl)-2-(4-ethyl-2-hydroxy-3-oxopiperazine-1-carboxamido)acetamido)-7-fluoro-2-hydroxy-3,4-dihydro-2H-benzo[e][1,2]oxaborinine-8-carboxylic acid

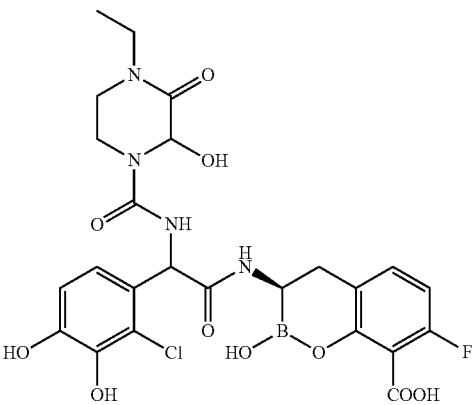

To a solution of Example 124 (19 mg, 0.034 mmol) in MeOH (1 mL) was added NaBH$_4$ (3 mg, 0.079 mmol). After 5 min, the reaction mixture was diluted with 0.5 mL of water, and subjected to reversed phase HPLC purification to yield the title compound after lyopholization. ESI-MS m/z 617 (M+Na)$^+$.

Example 195: Ethyl (3R)-3-(2-(4-ethyl-2,3-di-oxopiperazine-1-carboxamido)-2-(3-fluoro-5-hydroxypyridin-2-yl)acetamido)-2-hydroxy-3,4-dihydro-2H-benzo[e][1,2]oxaborinine-8-carboxylate

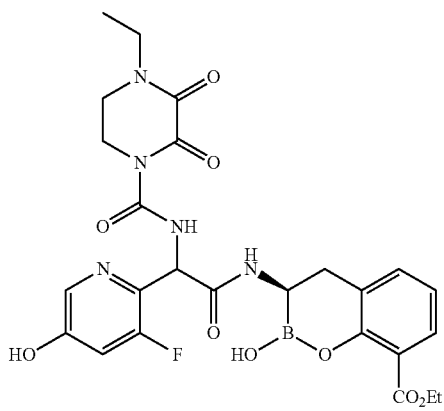 [SMILES: CCOC(=O)c1cccc2c1OB(O)[C@@H](NC(=O)C(NC(=O)N1CCN(CC)C(=O)C1=O)c1ncc(O)cc1F)C2]

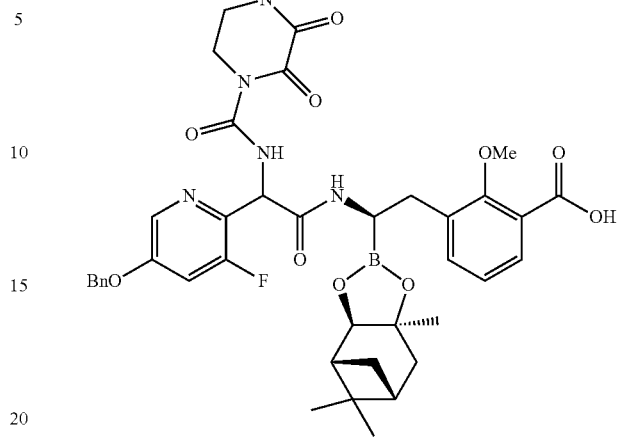

To tert-butyl 3-((2R)-2-(2-(5-(benzyloxy)-3-fluoropyridin-2-yl)-2-(4-ethyl-2,3-dioxopiperazine-1-carboxamido)acetamido)-2-((3aR,4R,6R,7aS)-5,5,7α-trimethylhexahydro-4,6-methanobenzo[d][1,3,2]dioxaborol-2-yl)ethyl)-2-methoxybenzoate 0.698 g (0.82 mmol) in dichloromethane (9 mL) at 0° C. was added trifluoroacetic acid (0.9 mL) and warmed at RT for 2 h. The reaction was concentrated, azeotroped with toluene and concentrated in vacuo to give the title compound, 0.652 g. ESI-MS m/z 800 (M+H)⁺.

Step 1: Synthesis of 3-((2R)-2-(2-(5-(benzyloxy)-3-fluoropyridin-2-yl)-2-(4-ethyl-2,3-dioxopiperazine-1-carboxamido)acetamido)-2-((3aR,4R,6R,7aS)-5,5,7α-trimethylhexahydro-4,6-methanobenzo[d][1,3,2]dioxaborol-2-yl)ethyl)-2-methoxybenzoic acid Step 2: Synthesis of ethyl 3-((2R)-2-(2-(5-(benzyloxy)-3-fluoropyridin-2-yl)-2-(4-ethyl-2,3-dioxopiperazine-1-carboxamido)acetamido)-2-((3aR,4R,6R,7aS)-5,5,7α-trimethylhexahydro-4,6-methanobenzo[d][1,3,2]dioxaborol-2-yl)ethyl)-2-methoxybenzoate

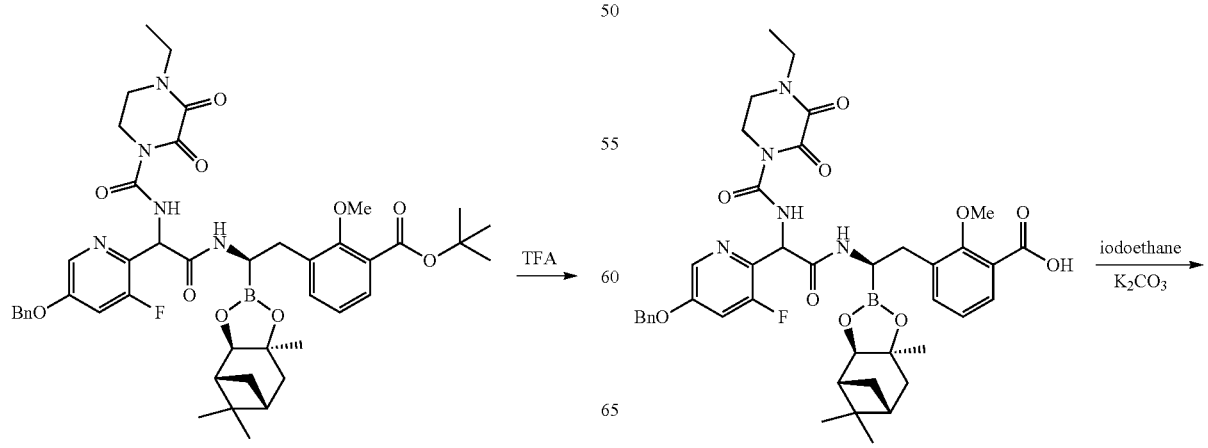

-continued

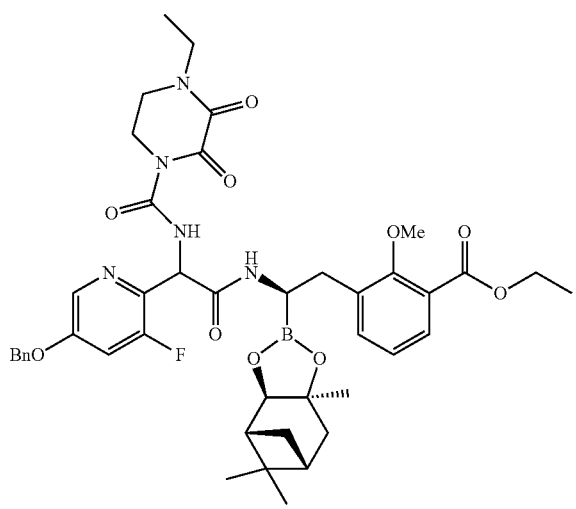

To 3-((2R)-2-(2-(5-(benzyloxy)-3-fluoropyridin-2-yl)-2-(4-ethyl-2,3-dioxopiperazine-1-carboxamido)acetamido)-2-((3aR,4R,6R,7aS)-5,5,7a-trimethylhexahydro-4,6-methanobenzo[d][1,3,2]dioxaborol-2-yl)ethyl)-2-methoxybenzoic acid 0.632 g (0.8 mmol) in N,N-dimethylformamide (6 mL) was added potassium carbonate 0.164 g (1.19 mmol, 1.5 eq), followed by iodoethane 0.127 mL (1.58 mmol, 2 eq) and stirred at RT for 5 h. The reaction was diluted with ethyl acetate, washed with water/brine, dried over sodium sulfate and concentrated. The product was purified by flash chromatography on silica gel (5% methanol/dichloromethane) using preparatory TLC plates to give the desired product, 0.201 g. ESI-MS m/z 828 (M+H)⁺.

Step 3: Synthesis of ethyl (3R)-3-(2-(4-ethyl-2,3-dioxopiperazine-1-carboxamido)-2-(3-fluoro-5-hydroxypyridin-2-yl)acetamido)-2-hydroxy-3,4-dihydro-2H-benzo[e][1,2]oxaborinine-8-carboxylate

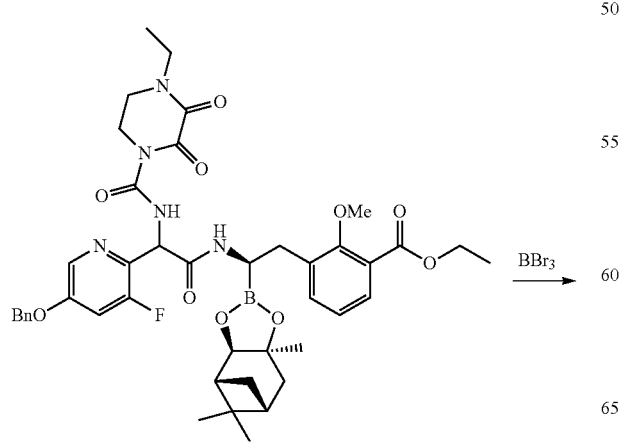

-continued

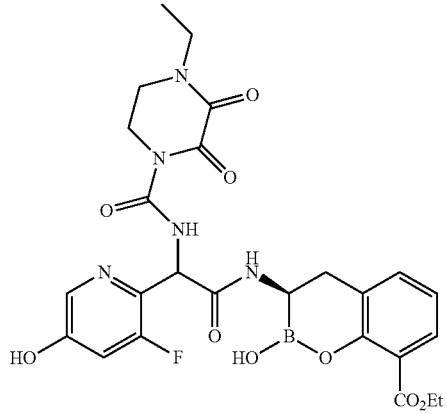

To ethyl 3-((2R)-2-(2-(5-(benzyloxy)-3-fluoropyridin-2-yl)-2-(4-ethyl-2,3-dioxopiperazine-1-carboxamido)acetamido)-2-((3aR,4R,6R,7aS)-5,5,7a-trimethylhexahydro-4,6-methanobenzo[d][1,3,2]dioxaborol-2-yl)ethyl)-2-methoxybenzoate 0.201 g (0.24 mmol) in dichloromethane (7 mL) at −78° C. was added 1M boron tribromide in dichloromethane 2.2 mL (2.2 mmol, 9 eq) and warmed at 0° C. for 30 min. The reaction was quenched with water/methanol and purified using reverse phase chromatography to give the title compound. ESI-MS m/z 572 (M+H)⁺.

Example 196: Ethyl (R)-3-((2R,3R)-2-(4-ethyl-2,3-dioxopiperazine-1-carboxamido)-3-hydroxybutanamido)-2-hydroxy-3,4-dihydro-2H-benzo[e][1,2]oxaborinine-8-carboxylate

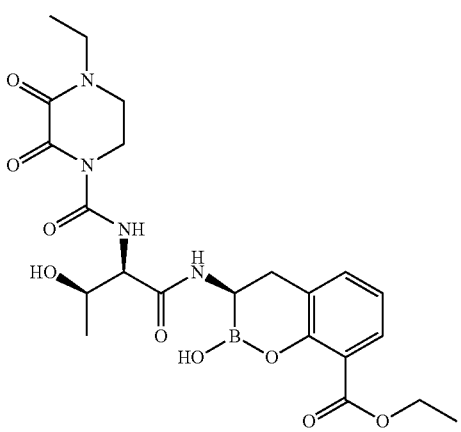 [SMILES: CCOC(=O)c1cccc2c1OB(O)[C@@H](NC(=O)[C@H](NC(=O)N1CCN(CC)C(=O)C1=O)[C@@H](C)O)C2]

Step 1. Synthesis of tert-butyl 3-((2R)-2-((2R,3R)-2-(4-ethyl-2,3-dioxopiperazine-1-carboxamido)-3-hydroxybutanamido)-2-((3aS,4S,6S)-3a,5,5-trimethylhexahydro-4,6-methanobenzo[d][1,3,2]dioxaborol-2-yl)ethyl)-2-methoxybenzoate tert-Butyl 3-((2R)-2-((2R,3R)-2-(4-ethyl-2,3-dioxopiperazine-1-carboxamido)-3-hydroxybutan-amido)-2-((3aS,4S,6S)-3a,5,5-trimethylhexahydro-4,6-methanobenzo[d][1,3,2]dioxaborol-2-yl)ethyl)-2-methoxybenzoate was prepared from D-allothreonine and 3-((2S)-2-chloro-2-((3aS,4S,6S)-3a,5,5-trimethylhexahydro-4,6-methanobenzo-[d][1,3,2]dioxaborol-2-yl)ethyl)-2-methoxybenzoate, by a procedure similar to Example 8. Steps 1 and 2.

Step 2. Synthesis of ethyl 3-((2R)-2-((2R,3R)-2-(4-ethyl-2,3-dioxopiperazine-1-carboxamido)-3-hydroxybutanamido)-2-((3aS,4S,6S)-3a,5,5-trimethylhexahydro-4,6-methanobenzo[d][1,3,2]dioxaborol-2-yl)ethyl)-2-methoxybenzoate Step 2a tert-Butyl 3-((2R)-2-((2R,3R)-2-(4-ethyl-2,3-dioxopiperazine-1-carboxamido)-3-hydroxybutan-amido)-2-((3aS,4S,6S)-3a,5,5-trimethylhexahydro-4,6-methanobenzo[d][1,3,2]dioxaborol-2-yl)ethyl)-2-methoxybenzoate (700 mg, 1 mmol) in dichloromethane (8 mL) was treated with trifluoroacetic acid (1 mL) at room temperature for 3 hours. The volatiles were evaporated under reduced pressure, and the residue was further dried on high vacuum overnight and used in the next step without purification.

Step 2b

The product of Step 2a (321 mg, 0.5 mmol) in N-Methyl-2-pyrrolidone (2 mL) was treated with triethylamine (0.15 mL) and iodoethane (0.05 mL, 1.25 eq) at 50° C., overnight, under argon. The reaction mixture was partitioned between water and diethyl ether and the aqueous phase was extracted two more times with diethyl ether. The combined organic extracts were dried over $Na_2SO_4$, filtered, and the solvent was evaporated under reduced pressure. The product was further dried on high vacuum overnight and used in the next step without purification

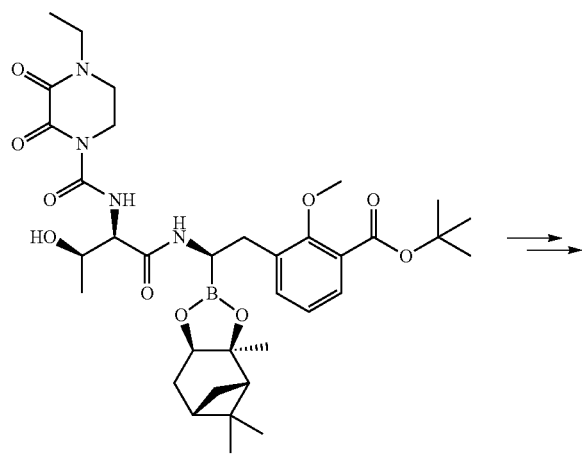

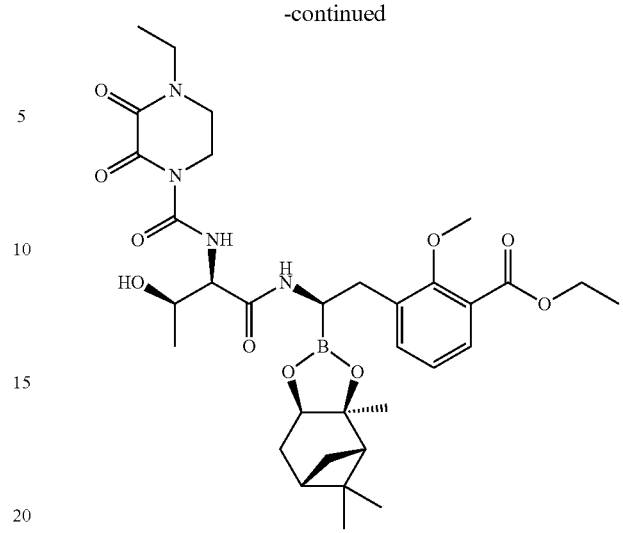

Step 3. Synthesis of ethyl (R)-3-((2R,3R)-2-(4-ethyl-2,3-dioxopiperazine-1-carboxamido)-3-hydroxybutanamido)-2-hydroxy-3,4-dihydro-2H-benzo[e][1,2]oxaborinine-8-carboxylate Ethyl 3-((2R)-2-((2R,3R)-2-(4-ethyl-2,3-dioxopiperazine-1-carboxamido)-3-hydroxybutan-amido)-2-((3aS,4S,6S)-3a,5,5-trimethylhexahydro-4,6-methanobenzo[d][1,3,2]dioxaborol-2-yl)ethyl)-2-methoxybenzoate was converted to the title compound by a procedure similar to Example 8, Step 3. ESI-MS m/z 505.2 (M+H)$^+$.

Example 197: Ethyl (3R)-3-(2-(4-ethyl-2,3-dioxopiperazine-1-carboxamido)-2-phenylacetamido)-2-hydroxy-3,4-dihydro-2H-benzo[e][1,2]oxaborinine-8-carboxylate

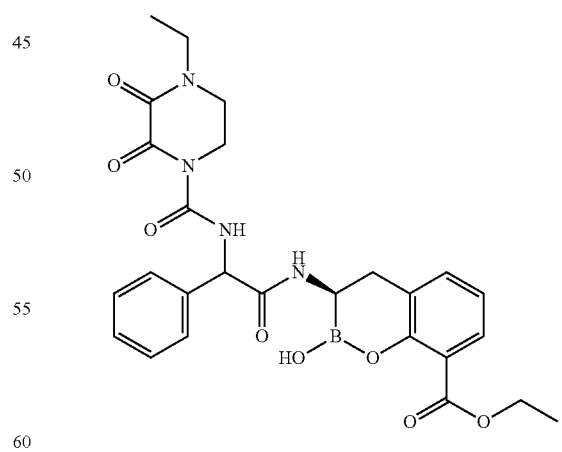

The title compound was prepared from (R)-2-(4-ethyl-2,3-dioxopiperazine-1-carboxamido)-2-phenylacetic acid and 3-((2S)-2-chloro-2-((3aS,4S,6S)-3a,5,5-trimethylhexahydro-4,6-methanobenzo-[d][1,3,2]dioxaborol-2-yl)ethyl)-2-methoxybenzoate by a procedure similar to Example 196. ESI-MS m/z 537.2 (M+H)$^+$.

Example 198: (Pivaloyloxy)methyl (3R)-3-(2-(4-ethyl-2,3-dioxopiperazine-1-carboxamido)-3-hydroxybutanamido)-2-hydroxy-3,4-dihydro-2H-benzo[e][1,2]oxaborinine-8-carboxylate

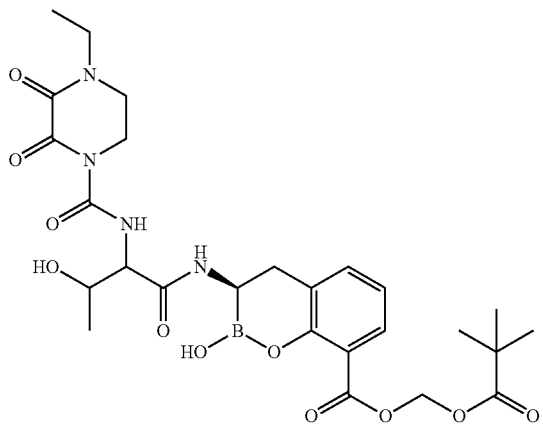 [SMILES: CCN1CCN(C(=O)NC(C(=O)N[C@H]2Cc3cccc(C(=O)OCOC(=O)C(C)(C)C)c3OB2O)C(C)O)C(=O)C1=O]

Step 1. Synthesis of (3R)-3-(2-(4-ethyl-2,3-dioxopiperazine-1-carboxamido)-3-hydroxybutanamido)-2-hydroxy-3,4-dihydro-2H-benzo[e][1,2]oxaborinine-8-carboxylic acid (3R)-3-(2-(4-ethyl-2,3-dioxopiperazine-1-carboxamido)-3-hydroxybutanamido)-2-hydroxy-3,4-dihydro-2H-benzo[e][1,2]oxaborinine-8-carboxylic acid was prepared from D-allothreonine and 3-((2S)-2-chloro-2-((3aS,4S,6S)-3a,5,5-trimethylhexahydro-4,6-methanobenzo-[d][1,3,2]dioxaborol-2-yl)ethyl)-2-methoxybenzoate, by a procedure similar to Example 8.

Step 2. Synthesis of (pivaloyloxy)methyl (3R)-3-(2-(4-ethyl-2,3-dioxopiperazine-1-carboxamido)-3-hydroxybutanamido)-2-hydroxy-3,4-dihydro-2H-benzo[e][1,2]oxaborinine-8-carboxylate (3R)-3-(2-(4-ethyl-2,3-dioxopiperazine-1-carboxamido)-3-hydroxybutanamido)-2-hydroxy-3,4-dihydro-2H-benzo[e][1,2]oxaborinine-8-carboxylic acid (210 mg, 0.44 mmol) in N-Methyl-2-pyrrolidone (2 mL) was treated with sodium carbonate (106 mg, 1 mmol, 2.3 eq), sodium bromide (103 mg, 1 mmol, 2.3 eq), and chloromethyl pivalate (0.1 mL, 0.66 mmol, 1.5 eq) overnight at room temperature. The reaction mixture was cooled to 0° C., acidified to pH 4 with 2N hydrochloric acid, and extracted with ethyl acetate. The combined organic extracts were dried over $Na_2SO_4$, filtered, and the solvent was evaporated under reduced pressure. The product was isolated by reverse phase preparative HPLC (Gilson). ESI-MS m/z 591.3 $(M+H)^+$.

Example 199: (Pivaloyloxy)methyl (3R)-3-(2-(4-ethyl-2,3-dioxopiperazine-1-carboxamido)-2-phenylacetamido)-2-hydroxy-3,4-dihydro-2H-benzo[e][1,2]oxaborinine-8-carboxylate

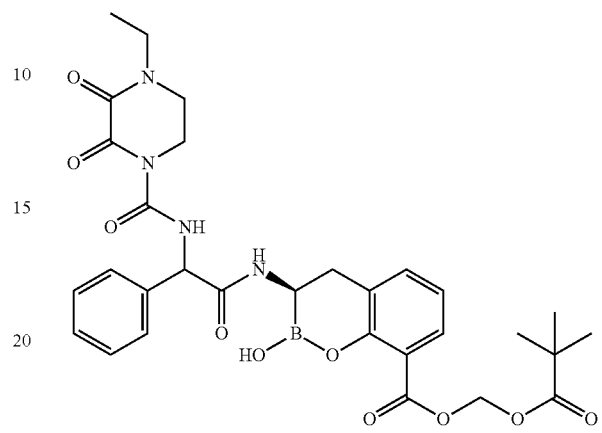

The title compound was prepared from (R)-2-(4-ethyl-2,3-dioxopiperazine-1-carboxamido)-2-phenylacetic acid and 3-((2S)-2-chloro-2-((3aS,4S,6S)-3a,5,5-trimethylhexahydro-4,6-methanobenzo-[d][1,3,2]dioxaborol-2-yl)ethyl)-2-methoxybenzoate, by a procedure similar to Example 198. ESI-MS m/z 539.2 [M−(Piv)+H]+.

Example 200: (Pivaloyloxy)methyl (3R)-3-(2-(4-ethyl-2,3-dioxopiperazine-1-carboxamido)-2-(3-fluoro-5-hydroxypyridin-2-yl)acetamido)-2-hydroxy-3,4-dihydro-2H-benzo[e][1,2]oxaborinine-8-carboxylate

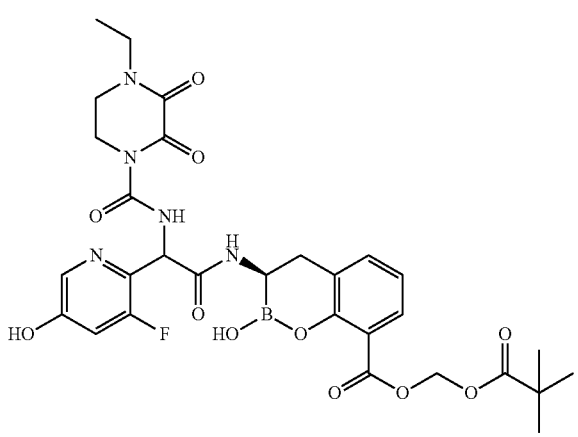 [SMILES: CCN1CCN(C(=O)NC(C(=O)N[C@H]2Cc3cccc(C(=O)OCOC(=O)C(C)(C)C)c3OB2O)c2ncc(O)cc2F)C(=O)C1=O]

Step 1: Synthesis of (3R)-3-(2-(5-(benzyloxy)-3-fluoropyridin-2-yl)-2-(4-ethyl-2,3-dioxopiperazine-1-carboxamido)acetamido)-2-hydroxy-3,4-dihydro-2H-benzo[e][1,2]oxaborinine-8-carboxylic acid trifluoroacetic acid
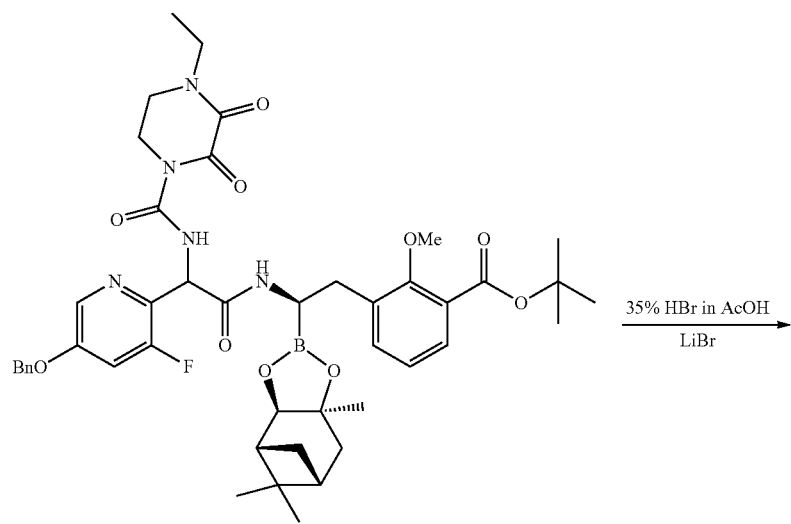
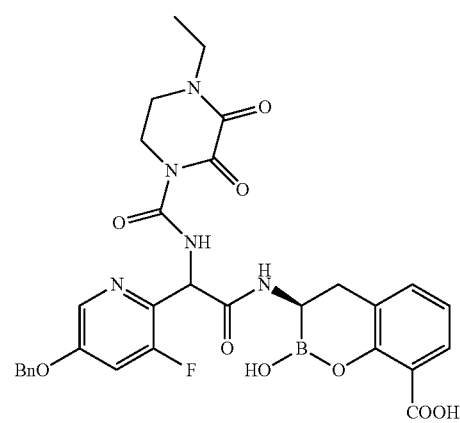

To tert-butyl 3-((2R)-2-(2-(5-(benzyloxy)-3-fluoropyridin-2-yl)-2-(4-ethyl-2,3-dioxopiperazine-1-carboxamido)acetamido)-2-((3aR,4R,6R,7aS)-5,5,7a-trimethylhexahydro-4,6-methanobenzo[d][1,3,2]dioxaborol-2-yl)ethyl)-2-methoxybenzoate 0.71 g (0.83 mmol) in acetonitrile (20 mL) was added lithium bromide 0.216 g (2.5 mmol, 3 eq), followed by 33% hydrogen bromide in acetic acid (8 mL) and the mixture was heated at 50° C. for 30 min. The reaction was quenched with water/methanol, concentrated and purified using reverse phase chromatography to give the title compound, 0.23 g. ESI-MS m/z 634 (M+H)+.

Step 2: Synthesis of (pivaloyloxy)methyl (3R)-3-(2-(5-(benzyloxy)-3-fluoropyridin-2-yl)-2-(4-ethyl-2,3-dioxopiperazine-1-carboxamido)acetamido)-2-hydroxy-3,4-dihydro-2H-benzo[e][1,2]oxaborinine-8-carboxylate

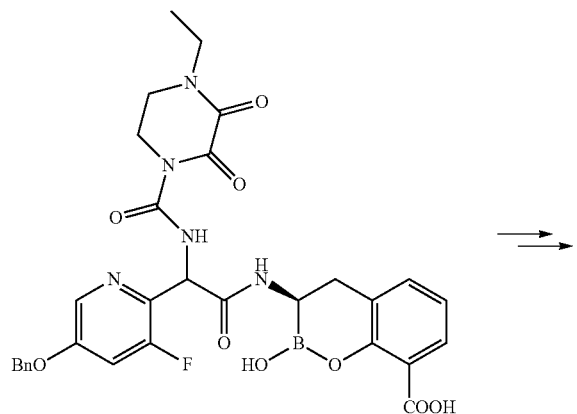

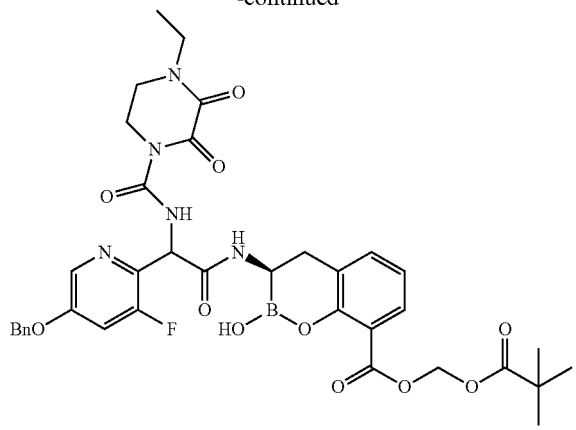

To (3R)-3-(2-(5-(benzyloxy)-3-fluoropyridin-2-yl)-2-(4-ethyl-2,3-dioxopiperazine-1-carboxamido)acetamido)-2-hydroxy-3,4-dihydro-2H-benzo[e][1,2]oxaborinine-8-carboxylic acid trifluoroacetic acid 0.23 g (0.31 mmol) in acetonitrile (2.3 mL) was added a solution of sodium carbonate 0.098 g (0.92 mmol, 3 eq) and sodium bromide 0.095 g (0.92 mmol, 3 eq) in water (2.3 mL). The mixture was adjusted to pH=8-9 and concentrated in vacuo. To this solid was added 1-methyl-2-pyrrolidinone (2.3 mL), followed by chloromethyl pivalate 0.075 mL (0.52 mmol, 1.7 eq) and stirred at RT for 18 h. Water was added to the reaction, extracted with 10% tert-butyl methyl ether/hexanes and diluted with ethyl acetate. The aqueous layer was adjusted to pH=5.5-6 using 2N hydrochloric acid and extracted. The organic layer was washed with water/brine, dried over sodium sulfate and concentrated to give the title compound. ESI-MS m/z 748 (M+H)+.

Step 3: Synthesis of (pivaloyloxy)methyl (3R)-3-(2-(4-ethyl-2,3-dioxopiperazine-1-carboxamido)-2-(3-fluoro-5-hydroxypyridin-2-yl)acetamido)-2-hydroxy-3,4-dihydro-2H-benzo[e][1,2]oxaborinine-8-carboxylate

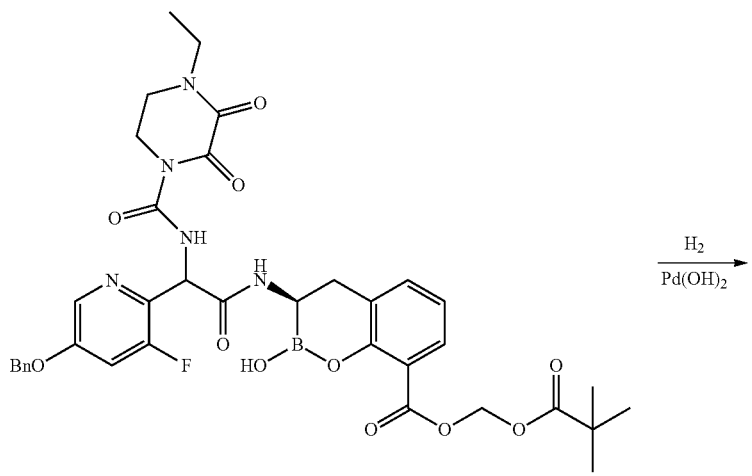

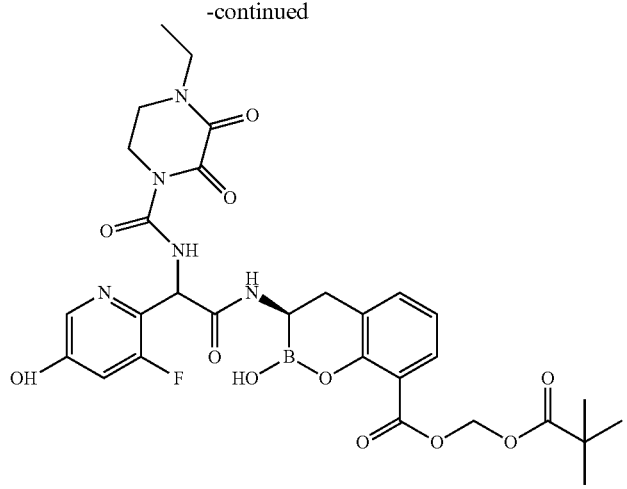

To (pivaloyloxy)methyl (3R)-3-(2-(5-(benzyloxy)-3-fluoropyridin-2-yl)-2-(4-ethyl-2,3-dioxopiperazine-1-carboxamido)acetamido)-2-hydroxy-3,4-dihydro-2H-benzo[e][1,2]oxaborinine-8-carboxylate under an atmosphere of argon was added anhydrous methanol (4 mL), followed by Pd(OH)$_2$ on carbon and the mixture was stirred under 1 atmosphere of hydrogen for 1 h. The reaction was filtered through a pad of Celite, concentrated and purified using reverse phase chromatography to give the title compound. ESI-MS m/z 658 (M+H)$^+$.

Example 201: (Pivaloyloxy)methyl (3R)-3-(2-(5-acetoxy-3-fluoropyridin-2-yl)-2-(4-ethyl-2,3-dioxopiperazine-1-carboxamido)acetamido)-2-hydroxy-3,4-dihydro-2H-benzo[e][1,2]oxaborinine-8-carboxylate

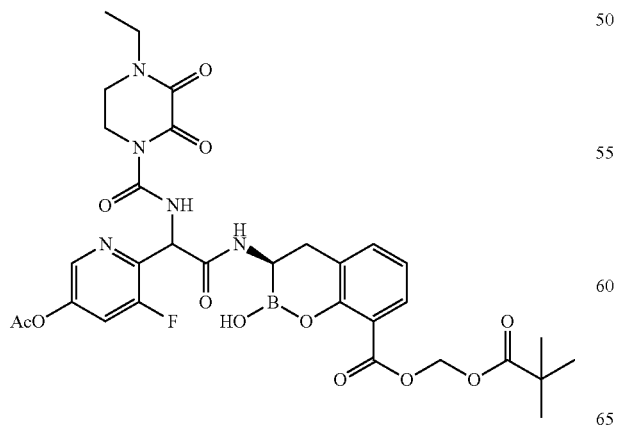

Step 1: Synthesis of (pivaloyloxy)methyl (3R)-3-(2-(4-ethyl-2,3-dioxopiperazine-1-carboxamido)-2-(3-fluoro-5-hydroxypyridin-2-yl)acetamido)-2-hydroxy-3,4-dihydro-2H-benzo[e][1,2]oxaborinine-8-carboxylate

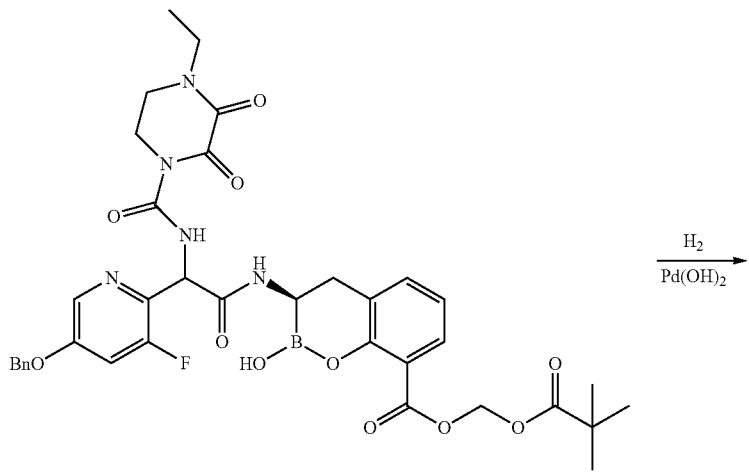

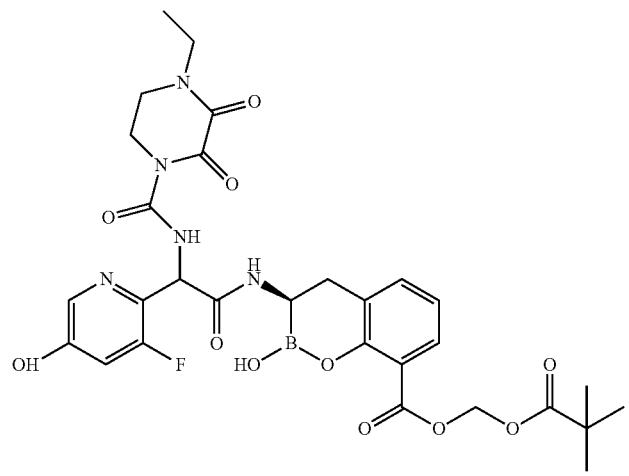

To (pivaloyloxy)methyl (3R)-3-(2-(5-(benzyloxy)-3-fluoropyridin-2-yl)-2-(4-ethyl-2,3-dioxopiperazine-1-carboxamido)acetamido)-2-hydroxy-3,4-dihydro-2H-benzo[e][1,2]oxaborinine-8-carboxylate under an atmosphere of argon was added anhydrous methanol (4 mL), followed by Pd(OH)$_2$ on carbon and the mixture was stirred under 1 atmosphere of hydrogen for 1 h. The reaction was filtered through a pad of Celite and concentrated to give the title compound. ESI-MS m/z 658 (M+H)$^+$.

Step 2: Synthesis of (pivaloyloxy)methyl (3R)-3-(2-(5-acetoxy-3-fluoropyridin-2-yl)-2-(4-ethyl-2,3-dioxopiperazine-1-carboxamido)acetamido)-2-hydroxy-3,4-dihydro-2H-benzo[e][1,2]oxaborinine-8-carboxylate

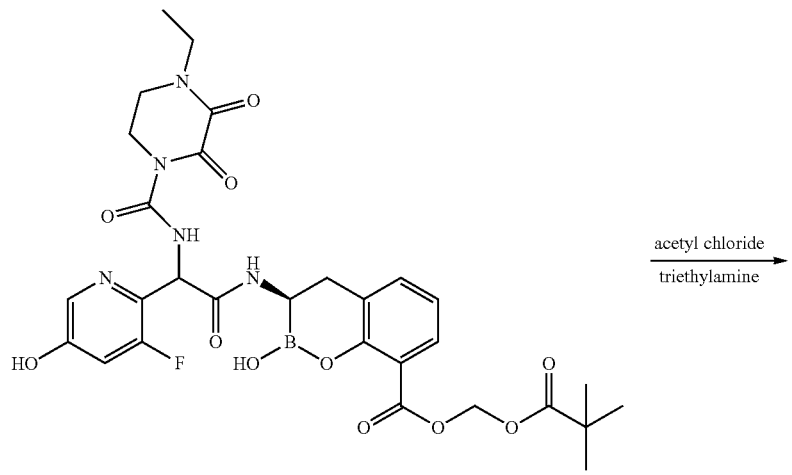

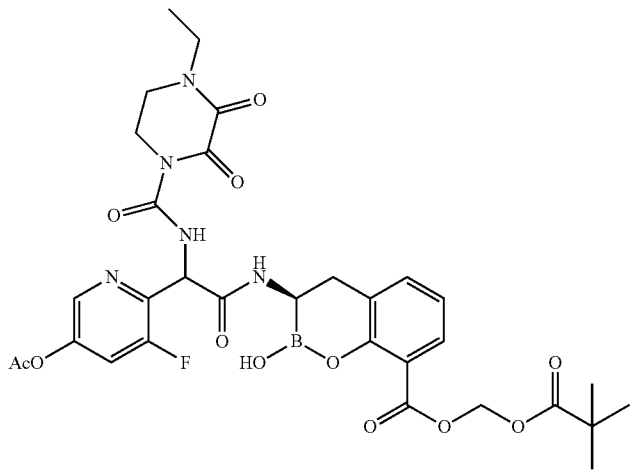

To (pivaloyloxy)methyl (3R)-3-(2-(4-ethyl-2,3-dioxopiperazine-1-carboxamido)-2-(3-fluoro-5-hydroxypyridin-2-yl)acetamido)-2-hydroxy-3,4-dihydro-2H-benzo[e][1,2]oxaborinine-8-carboxylate 0.2 g (0.31 mmol) in dichloromethane (5 mL) at 0° C. was added triethylamine 0.128 mL (0.92 mmol, 3 eq), followed by acetyl chloride 0.033 mL (0.46 mmol, 1.5 eq) and the mixture was warmed at RT for 1 h. The product was quenched with water/methanol, concentrated and purified using reverse phase chromatography to give the title compound. ESI-MS m/z 700 (M+H)$^+$.

Example 202: (3R)-3-(2-(4-ethyl-2,3-dioxopiperazine-1-carboxamido)-2-(5-hydroxypyrimidin-2-yl)acetamido)-2-hydroxy-3,4-dihydro-2H-benzo[e][1,2]oxaborinine-8-carboxylic acid

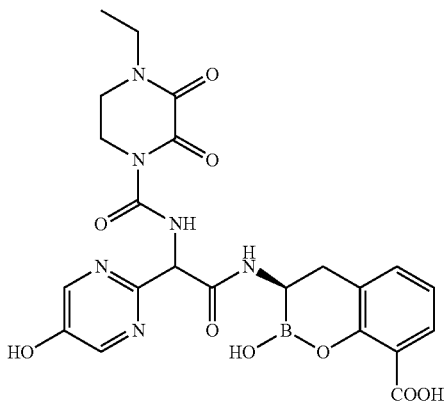

In a similar manner to the synthesis of Example 89, the title compound was prepared. ESI-MS m/z 527 (MH)+.

Example 203: (3R)-3-(2-(4-ethyl-2,3-dioxopiperazine-1-carboxamido)-2-(2-fluoro-4-sulfamoylphenyl)acetamido)-2-hydroxy-3,4-dihydro-2H-benzo[e][1,2]oxaborinine-8-carboxylic acid

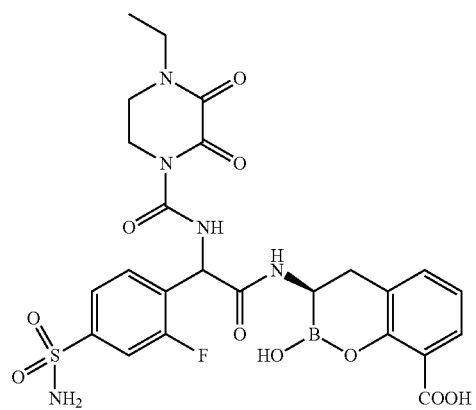 [SMILES: CCN1CCN(C(=O)NC(C(=O)N[C@H]2Cc3cccc(C(=O)O)c3OB2O)c2ccc(S(N)(=O)=O)cc2F)C(=O)C1=O]

In a similar manner to the synthesis of Example 37, utilizing 3-fluoro-4-formylbenzenesulfonamide in place of 2-chloro-3,4-dimethoxybenzaldehyde in Step 1, the title compounds were prepared. ESI-MS m/z 606 (MH)+.

Example 204: (3R)-3-(2-(2-fluoro-4-sulfamoylphenyl)-2-(4-(2-fluoroethyl)-2,3-dioxopiperazine-1-carboxamido)acetamido)-2-hydroxy-3,4-dihydro-2H-benzo[e][1,2]oxaborinine-8-carboxylic acid

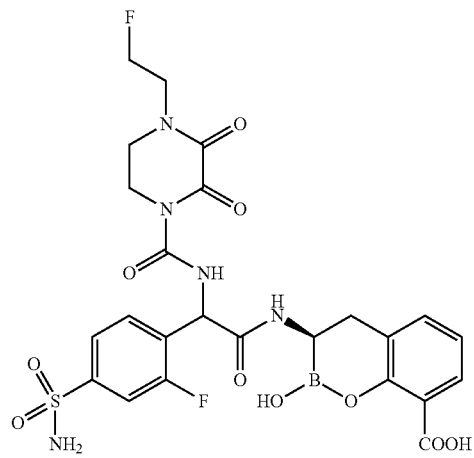 [SMILES: NS(=O)(=O)c1ccc(C(NC(=O)N2CCN(CCF)C(=O)C2=O)C(=O)N[C@H]2Cc3cccc(C(=O)O)c3OB2O)c(F)c1]

In a similar manner to the synthesis of Example 37, utilizing 3-fluoro-4-formylbenzenesulfonamide in place of 2-chloro-3,4-dimethoxybenzaldehyde in Step 1, and utilizing 4-fluoroethyl-2,3-dioxopiperazine-1-carbonyl chloride (product from Step 2 of Example 13) in place of 4-ethyl-2,3-dioxopiperazine-1-carbonyl chloride in Step 3, the title compound was prepared. ESI-MS m/z 624 (MH)+.

Example 205: (3R)-3-(2-(2-amino-5-fluorothiazol-4-yl)-2-(4-ethyl-2,3-dioxopiperazine-1-carboxamido)acetamido)-2-hydroxy-3,4-dihydro-2H-benzo[e][1,2]oxaborinine-8-carboxylic acid

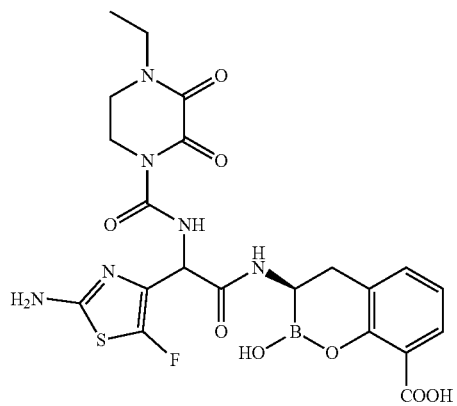 [SMILES: CCN1CCN(C(=O)NC(C(=O)N[C@H]2Cc3cccc(C(=O)O)c3OB2O)c2nc(N)sc2F)C(=O)C1=O]

In a similar manner to the synthesis of Example 5, the title compound was prepared. ESI-MS m/z 549 (MH)+.

Example 206: (3R)-3-(2-(2-chloro-3,4-dihydroxy-phenyl)-2-((S)-4-ethyl-6-methyl-2,3-dioxopiperazine-1-carboxamido)acetamido)-7-fluoro-2-hydroxy-3,4-dihydro-2H-benzo[e][1,2]oxaborinine-8-carboxylic acid

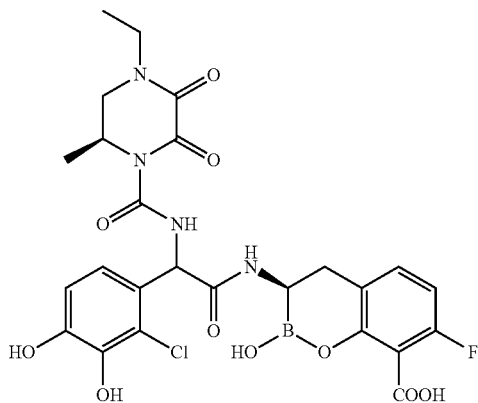 [SMILES: CCN1C[C@H](C)N(C(=O)NC(C(=O)N[C@H]2Cc3ccc(F)c(C(=O)O)c3OB2O)c2ccc(O)c(O)c2Cl)C(=O)C1=O]

In a similar manner to the synthesis of Example 124 utilizing (S)-4-ethyl-6-methyl-2,3-dioxopiperazine-1-carbonyl chloride in place of 4-ethyl-2,3-dioxopiperazine-1-carbonyl chloride in Step 3, the title compound was prepared. ESI-MS m/z 607/609 (MH/MH+2)+.

Example 207: (3R)-3-(2-(5-acetoxy-3-fluoropyridin-2-yl)-2-(4-ethyl-2,3-dioxopiperazine-1-carboxamido)acetamido)-2-hydroxy-3,4-dihydro-2H-benzo[e][1,2]oxaborinine-8-carboxylic acid

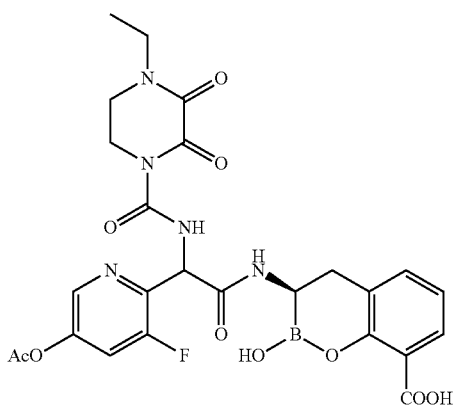 [SMILES: CCN1CCN(C(=O)NC(C(=O)N[C@H]2Cc3cccc(C(=O)O)c3OB2O)c2ncc(OC(C)=O)cc2F)C(=O)C1=O]

Step 1: Synthesis of (3R)-3-(2-(4-ethyl-2,3-dioxopiperazine-1-carboxamido)-2-(3-fluoro-5-hydroxypyridin-2-yl)acetamido)-2-hydroxy-3,4-dihydro-2H-benzo[e][1,2]oxaborinine-8-carboxylic acid

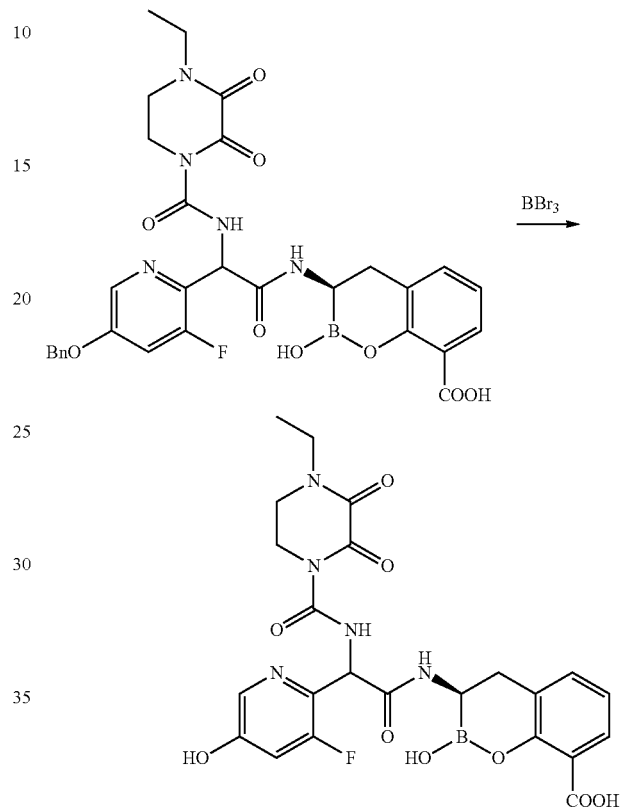

In a similar manner to the synthesis of Example 137, the title compound was prepared. ESI-MS m/z 544 (MH)+.

Step 2: Synthesis of (3R)-3-(2-(5-acetoxy-3-fluoropyridin-2-yl)-2-(4-ethyl-2,3-dioxopiperazine-1-carboxamido)acetamido)-2-hydroxy-3,4-dihydro-2H-benzo[e][1,2]oxaborinine-8-carboxylic acid

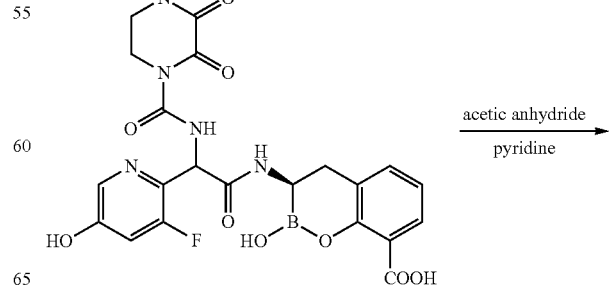

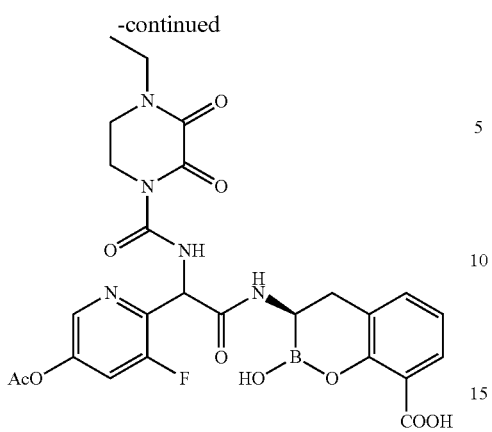

To (3R)-3-(2-(4-ethyl-2,3-dioxopiperazine-1-carboxamido)-2-(3-fluoro-5-hydroxypyridin-2-yl)acetamido)-2-hydroxy-3,4-dihydro-2H-benzo[e][1,2]oxaborinine-8-carboxylic acid 0.07 g (0.13 mmol) in dichloromethane (3 mL) at 0° C. was added 0.021 mL (0.26 mmol, 2 eq) pyridine, followed by 0.016 mL (0.17 mmol, 1.3 eq) acetic anhydride and stirred at this temperature for 1 h. The reaction was warmed at RT for 1 h, quenched with water/methanol and purified using reverse phase chromatography to give the title compound. ESI-MS m/z 586 (MH)+.

Example 208: (3R)-3-(2-((S)-4-ethyl-6-methyl-2,3-dioxopiperazine-1-carboxamido)-2-(3-fluoro-5-hydroxypyridin-2-yl)acetamido)-7-fluoro-2-hydroxy-3,4-dihydro-2H-benzo[e][1,2]oxaborinine-8-carboxylic acid

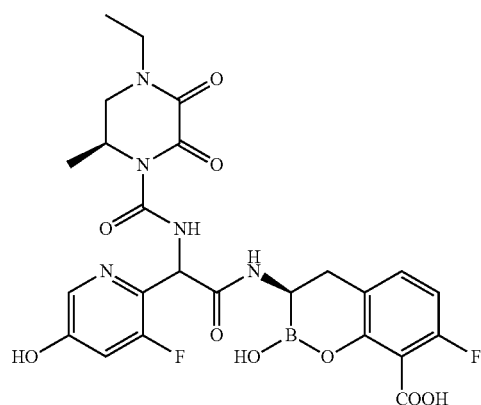 [SMILES: CCN1C[C@H](C)N(C(=O)NC(C(=O)N[C@H]2Cc3ccc(F)c(C(=O)O)c3OB2O)c2ncc(O)cc2F)C(=O)C1=O]

In a similar manner to the synthesis of Example 145, utilizing (S)-4-ethyl-6-methyl-2,3-dioxopiperazine-1-carbonyl chloride in place of 4-ethyl-2,3-dioxopiperazine-1-carbonyl chloride, the title compound was prepared. ESI-MS m/z 576 (MH)+.

Example 209: (3R)-3-(2-(4-(3-aminopropoxy)-2-fluorophenyl)-2-(4-ethyl-2,3-dioxopiperazine-1-carboxamido)acetamido)-2-hydroxy-3,4-dihydro-2H-benzo[e][1,2]oxaborinine-8-carboxylic acid In a similar manner to the synthesis of Example 135, utilizing 2-(4-(3-(((benzyloxy)carbonyl)amino)propoxy)-2-fluorophenyl)-2-((tert-butoxycarbonyl)amino)acetic acid in place of lithium 2-(5-(benzyloxy)-3-fluoropyridin-2-yl)-2-((tert-butoxycarbonyl)amino)acetate, the title compound was prepared. ESI-MS m/z 600 (MH)+.

Example 210: (3R)-3-(2-(4-ethyl-2,3-dioxopiperazine-1-carboxamido)-2-(3-fluoro-4-sulfamoylphenyl)acetamido)-2-hydroxy-3,4-dihydro-2H-benzo[e][1,2]oxaborinine-8-carboxylic acid In a similar manner to the synthesis of Example 37, utilizing 2-fluoro-4-formylbenzenesulfonamide in place of 2-chloro-3,4-dimethoxybenzaldehyde in Step 1, the title compounds was prepared. ESI-MS m/z 606 (MH)+.

Example 211: (3R)-3-(2-(3-fluoro-4-sulfamoylphenyl)-2-(4-(2-fluoroethyl)-2,3-dioxopiperazine-1-carboxamido)acetamido)-2-hydroxy-3,4-dihydro-2H-benzo[e][1,2]oxaborinine-8-carboxylic acid

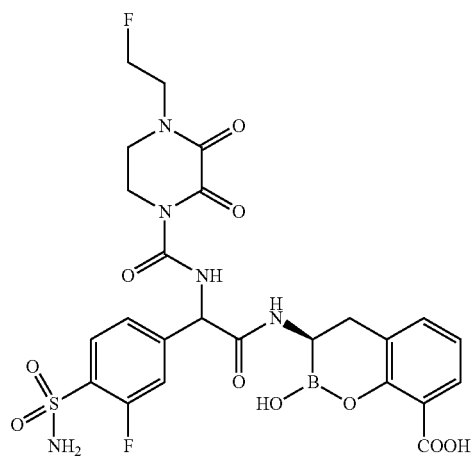 [SMILES: NS(=O)(=O)c1ccc(C(NC(=O)N2CCN(CCF)C(=O)C2=O)C(=O)N[C@H]2Cc3cccc(C(=O)O)c3OB2O)cc1F]

In a similar manner to the synthesis of Example 37, utilizing 2-fluoro-4-formylbenzenesulfonamide in place of 2-chloro-3,4-dimethoxybenzaldehyde in Step 1, and utilizing 4-fluoroethyl-2,3-dioxopiperazine-1-carbonyl chloride (product from Step 2 of Example 13) in place of 4-ethyl-2,3-dioxopiperazine-1-carbonyl chloride in Step 3, the title compound was prepared. ESI-MS m/z 624 (MH)+.

Example 212: (3R)-3-(2-(4-carboxyphenyl)-2-(4-ethyl-2,3-dioxopiperazine-1-carboxamido)acetamido)-2-hydroxy-3,4-dihydro-2H-benzo[e][1,2]oxaborinine-8-carboxylic acid

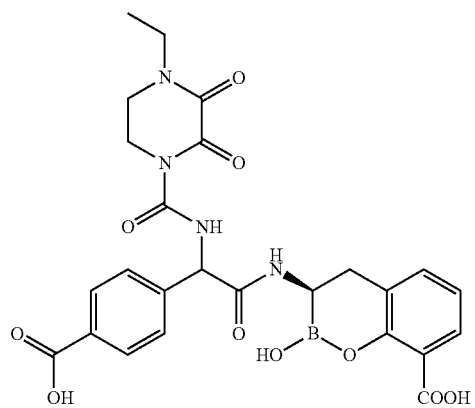 [SMILES: CCN1CCN(C(=O)NC(C(=O)N[C@H]2Cc3cccc(C(=O)O)c3OB2O)c2ccc(C(=O)O)cc2)C(=O)C1=O]

In a similar manner to the synthesis of Example 5, utilizing 2-amino-2-(4-(tert-butoxycarbonyl)phenyl)acetic acid (which was prepared from tert-butyl 4-acetylbenzoate by following the reported procedures: WO2013051597) in place of 2-amino-2-(2-(((benzyloxy)carbonyl)amino)thiazol-4-yl)acetic acid in Step 4, and utilizing TMSI in the final deprotection reaction in DCM at RT for 2 h, the title compound was prepared. ESIMS m/z 553 (MH)+.

Example 213: (3R)-3-(2-(4-(2-fluoroethyl)-2,3-dioxopiperazine-1-carboxamido)-2-(4-(N-(2-hydroxyethyl)sulfamoyl)phenyl)acetamido)-2-hydroxy-3,4-dihydro-2H-benzo[e][1,2]oxaborinine-8-carboxylic acid

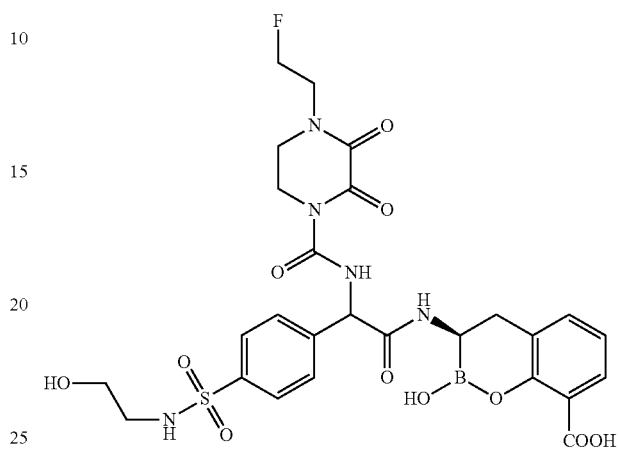

Step 1. Synthesis of tert-butyl 3-((2R)-2-(2-(4-(N-(2-(benzyloxy)ethyl)sulfamoyl)phenyl)-2-((tert-butoxycarbonyl)amino)acetamido)-2-((3aS,4S,6S,7aR)-3a,5,5-trimethylhexahydro-4,6-methanobenzo[d][1,3,2]dioxaborol-2-yl)ethyl)-2-methoxybenzoate The fully protected intermediate from the synthesis of Example 102 and Example 103 (890 mg, 1.2 mmol) was reacted with 2-benzyloxyethyl bromide (301 mg, 1.4 mmol) in the presence of K$_2$CO$_3$ (346 mg, 2.5 mmol) in acetone (8 mL) at 75-80° C. for 20 h, concentrated and purified by flash chromatography on silica gel (hexane-DCM-acetone, 4:1:1-2:1:1) to afford the title compound, 250 mg. ESI-MS m/z 875 (MH)+.

Step 2. Synthesis of (3R)-3-(2-(4-(2-fluoroethyl)-2,3-dioxopiperazine-1-carboxamido)-2-(4-(N-(2-hydroxyethyl)sulfamoyl)phenyl)acetamido)-2-hydroxy-3,4-dihydro-2H-benzo[e][1,2]oxaborinine-8-carboxylic acid

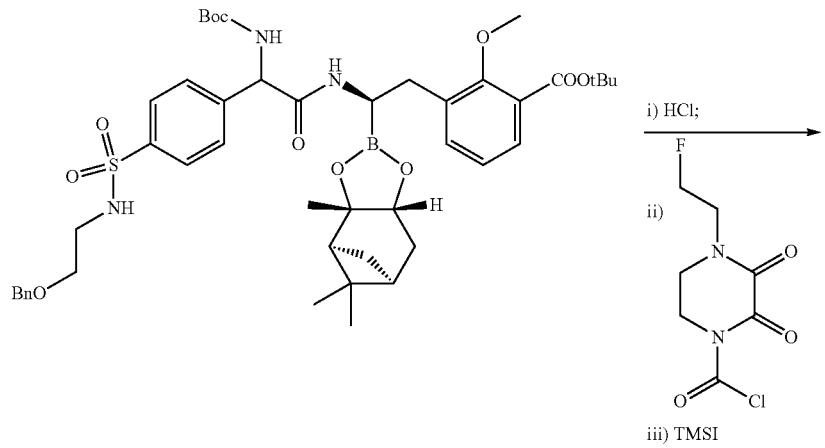

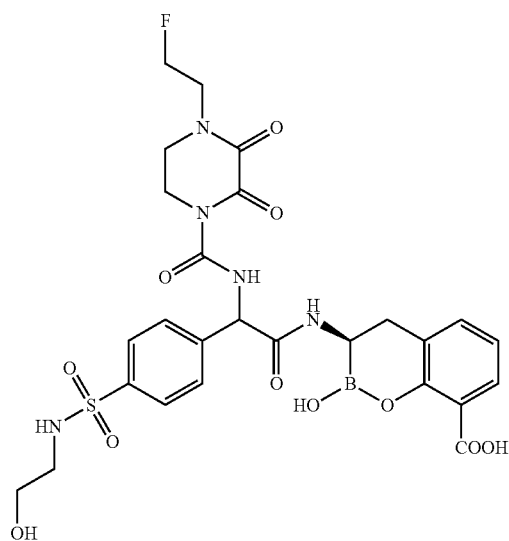

By following the same procedures described in Step 2 of Example 6, and followed by reaction of the amine intermediate with 4-fluoroethyl-2,3-dioxopiperazine-1-carbonyl chloride as described in Step 3 of Example 13, and final deprotection with TMSI in DCM at RT for 2 h, the title compound was prepared from the above amine intermediate. ESI-MS m/z 650 (MH)+.

Example 214: (3R)-3-(2-(5-amino-3-fluoropyridin-2-yl)-2-(4-ethyl-2,3-dioxopiperazine-1-carboxamido)acetamido)-2-hydroxy-3,4-dihydro-2H-benzo[e][1,2]oxaborinine-8-carboxylic acid

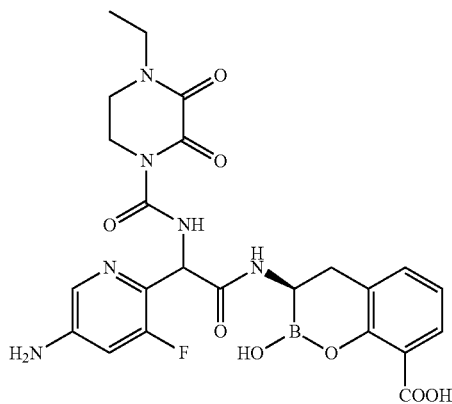 [SMILES: CCN1CCN(C(=O)NC(C(=O)N[C@H]2Cc3cccc(C(=O)O)c3OB2O)c2ncc(N)cc2F)C(=O)C1=O]

In a similar manner to the synthesis of Example 148, the title compound was prepared. ESI-MS m/z 543 (MH)$^+$.

Example 215: (3R)-3-(2-(2-aminothiazol-4-yl)-2-(4-ethyl-2,3-dioxopiperazine-1-carboxamido)acetamido)-7-chloro-2-hydroxy-3,4-dihydro-2H-benzo[e][1,2]oxaborinine-8-carboxylic acid

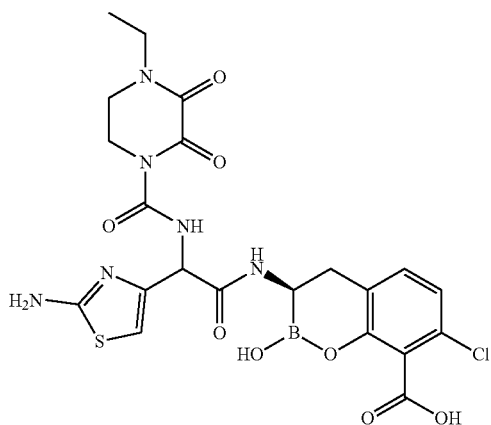 [SMILES: CCN1CCN(C(=O)NC(C(=O)N[C@H]2Cc3ccc(Cl)c(C(=O)O)c3OB2O)c2csc(N)n2)C(=O)C1=O]

Step 1. Synthesis of tert-butyl 3-bromo-6-chloro-2-hydroxybenzoate

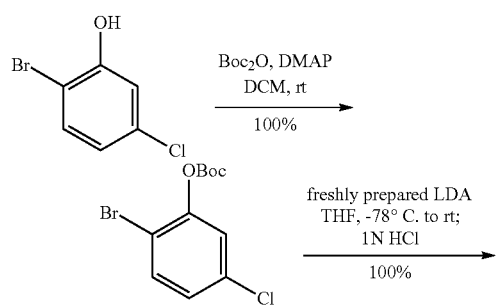

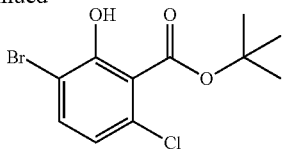

To a mixture of 2-bromo-5-chlorophenol (23.236 g, 121.6 mmol) and Boc$_2$O (33.475 g, 153.4 mmol) in DCM (300 mL) was added DMAP (0.962 g, 7.87 mmol) at room temperature. The reaction mixture was stirred at room temperature for 25 h. After the solvent was evaporated under reduced pressure, the residue was purified by flash chromatography on silica gel (340 g column) eluted with 0 to 20% ethyl acetate/hexanes to afford 37.41 g (100%) of 2-bromo-5-chlorophenyl tert-butyl carbonate. ESI-MS m/z 292.0, 293.9 (M–15)$^+$, 251.0, 253.0 (M–56)$^+$.

To a solution of 2-bromo-5-chlorophenyl tert-butyl carbonate (37.41 g, 121.6 mmol) in THF (250 mL) at –78° C. under argon was added freshly prepared LDA, n-BuLi (2.5 M in hexane, 57 mL, 142.5 mmol) was added dropwise to a solution of DIPA (20.0 mL, 142.7 mmol) in THF (150 mL) at –78° C. under argon and the resulting solution was stirred at –78° C. for 2 h, via cannula. The reaction mixture was allowed to slowly warm to room temperature overnight and then quenched with 2 N HCl (160 mL), extracted with ethyl acetate (3×), dried over Na$_2$SO$_4$, and evaporated under reduced pressure to afford 37.64 g (100%) of tert-butyl 3-bromo-6-chloro-2-hydroxybenzoate. ESI-MS m/z 251.0, 252.9 (M–56)$^+$.

Step 2. Synthesis of tert-butyl 3-bromo-6-chloro-2-methoxybenzoate

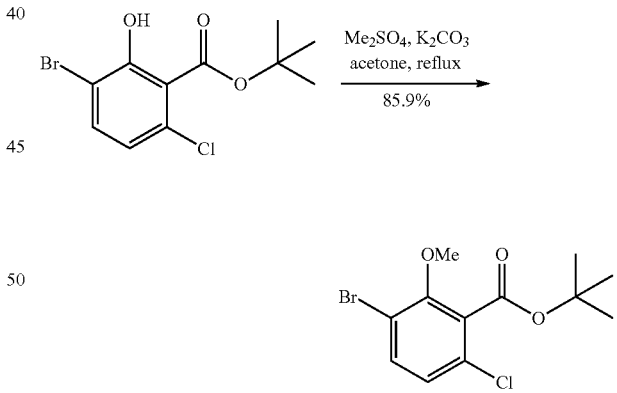

A mixture of tert-butyl 3-bromo-6-chloro-2-hydroxybenzoate (37.64 g, 121.6 mmol), dimethyl sulfate (30.65 g, 243.0 mmol), and K$_2$CO$_3$ (34.40 g, 248.9 mmol) in acetone (250 mL) was stirred at 80° C. for 65 h. After cooling to room temperature, the reaction mixture was filtered, washed with ethyl acetate. After the filtrate was evaporated under reduced pressure, the residue was purified by flash chromatography on silica gel (340 g column) eluted with 0 to 20% ethyl acetate/hexanes to afford 33.61 g (85.9%) of tert-butyl 3-bromo-6-chloro-2-methoxybenzoate. ESI-MS m/z 264.9, 267.0 (M–56)$^+$.

Step 3. Synthesis of tert-butyl 6-chloro-2-methoxy-3-(((3aS,4S,6S,7aR)-3a,5,5-trimethylhexahydro-4,6-methanobenzo[d][1,3,2]dioxaborol-2-yl)methyl)benzoate

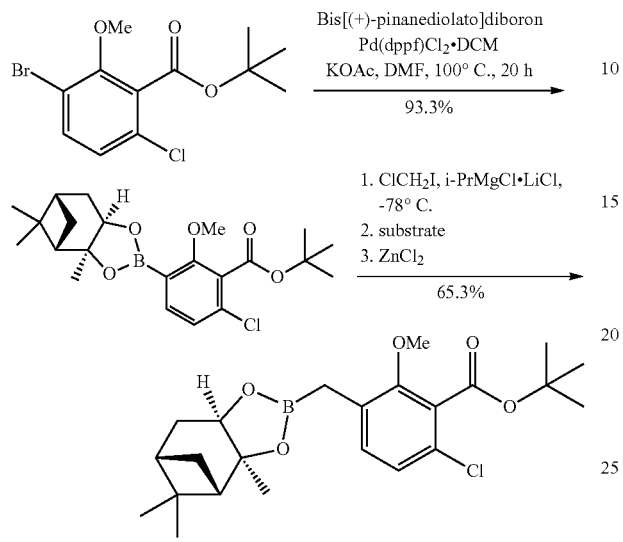

A mixture of tert-butyl 3-bromo-6-chloro-2-methoxybenzoate (27.23 g, 84.67 mmol), Bis[(+)-pinanediolato]diboron (40.50 g, 113.1 mmol), KOAc (27.15 g, 276.6 mmol), and Pd(dppf)Cl$_2$·DCM (3.60 g, 4.40 mmol) in DMF (180 mL) was stirred at 100° C. under argon for 20 h. After cooling to room temperature, the reaction mixture was quenched with water, filtered through Celite, extracted with ethyl acetate (3×). The combined organic phase was dried over Na$_2$SO$_4$. After the solvent was evaporated under reduced pressure, the residue was purified by flash chromatography on silica gel (340 g column) eluted with 0 to 20% ethyl acetate/hexanes to afford 33.24 g (93.3%) of tert-butyl 6-chloro-2-methoxy-3-((3aS,4S,6S,7aR)-3a,5,5-trimethylhexahydro-4,6-methanobenzo[d][1,3,2]dioxaborol-2-yl)benzoate as a solid. ESI-MS m/z 863.4, 865.4 (2M+Na)$^+$.

To a solution of chloroiodomethane (68.40 g, 387.8 mmol) in THF (250 mL) at −78° C. under argon was added i-PrMgCl·LiCl (1.3 M in THF, 164 mL, 213.2 mmol) dropwise over 50 min. The resulting mixture was stirred at −78° C. for an additional hour and then a solution of tert-butyl 6-chloro-2-methoxy-3-((3aS,4S,6S,7aR)-3a,5,5-trimethylhexahydro-4,6-methanobenzo[d][1,3,2]dioxaborol-2-yl)benzoate (33.14 g, 78.8 mmol) in THF (100 mL) was added dropwise over 25 min. After the reaction mixture was stirred at −78° C. for 2.5 h, ZnCl$_2$ (1.0 M in diethyl ether, 154 mL, 154 mmol) was added dropwise over 20 min. The reaction mixture was then allowed to slowly warm to room temperature overnight. The mixture was cooled to −30° C. and quenched with aqueous NH$_4$Cl, extracted with ethyl acetate (3×). The combined organic phase was dried over Na$_2$SO$_4$. After the solvent was evaporated under reduced pressure, the residue was purified by flash chromatography on silica gel (340 g column) eluted with 0 to 20% ethyl acetate/hexanes to afford 22.37 g (65.3%) of tert-butyl 6-chloro-2-methoxy-3-(((3aS,4S,6S,7aR)-3a,5,5-trimethylhexahydro-4,6-methanobenzo[d][1,3,2]dioxaborol-2-yl)methyl)benzoate. ESI-MS m/z 457.2 (M+Na)$^+$.

Step 4. Synthesis of tert-butyl 6-chloro-3-((S)-2-chloro-2-((3aS,4S,6S,7aR)-3a,5,5-trimethylhexahydro-4,6-methanobenzo[d][1,3,2]dioxaborol-2-yl)ethyl)-2-methoxybenzoate

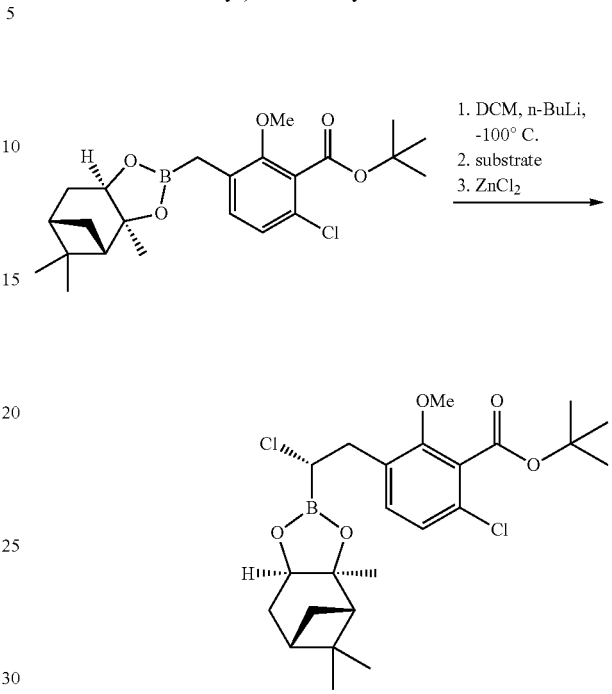

The Matteson reaction was carried out as described in Example 16 Step 6 by using tert-butyl 6-chloro-2-methoxy-3-(((3aS,4S,6S,7aR)-3a,5,5-trimethylhexahydro-4,6-methanobenzo[d][1,3,2]dioxaborol-2-yl)methyl)benzoate as the substrate to afford tert-butyl 6-chloro-3-((S)-2-chloro-2-((3aS,4S,6S,7aR)-3a,5,5-trimethylhexahydro-4,6-methanobenzo[d][1,3,2]dioxaborol-2-yl)ethyl)-2-methoxybenzoate. ESI-MS m/z 505.2, 507.2 (M+Na)$^+$.

Step 5. Synthesis of tert-butyl 3-((2R)-2-(2-(2-((tert-butoxycarbonyl)amino)thiazol-4-yl)-2-(4-ethyl-2,3-dioxopiperazine-1-carboxamido)acetamido)-2-((3aS,4S,6S,7aR)-3a,5,5-trimethylhexahydro-4,6-methanobenzo[d][1,3,2]dioxaborol-2-yl)ethyl)-6-chloro-2-methoxybenzoate

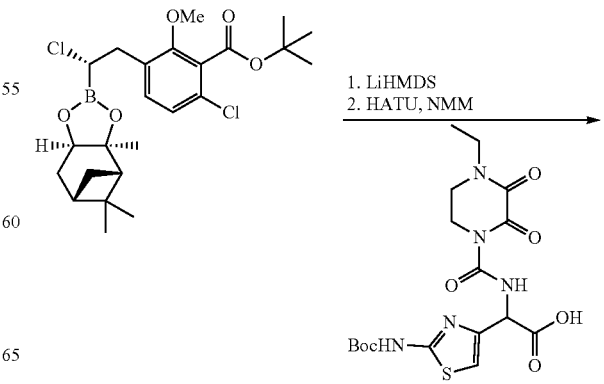

281

-continued

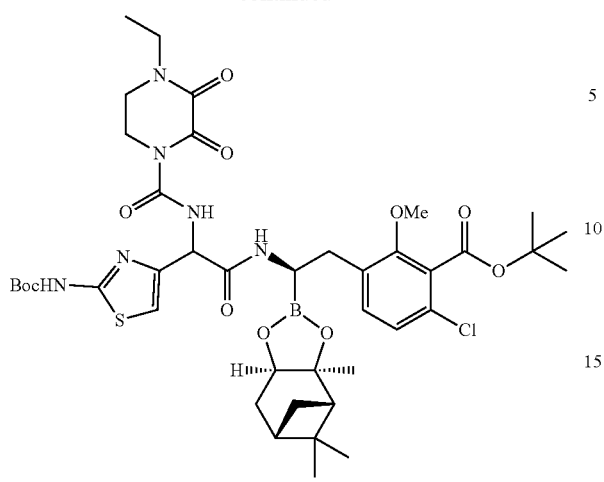

The amide formation was carried out as described in Example 16 Step 7 by using tert-butyl 6-chloro-3-((S)-2-chloro-2-((3aS,4S,6S,7aR)-3a,5,5-trimethylhexahydro-4,6-methanobenzo[d][1,3,2]dioxaborol-2-yl)ethyl)-2-methoxybenzoate as the substrate to afford tert-butyl 3-((2R)-2-(2-(2-((tert-butoxycarbonyl)amino)thiazol-4-yl)-2-(4-ethyl-2,3-dioxopiperazine-1-carboxamido)acetamido)-2-((3aS,4S,6S,7aR)-3a,5,5-trimethylhexahydro-4,6-methanobenzo[d][1,3,2]dioxaborol-2-yl)ethyl)-6-chloro-2-methoxybenzoate. ESI-MS m/z 887.4 (M+H)+.

Step 6. Synthesis of (3R)-3-(2-(2-aminothiazol-4-yl)-2-(4-ethyl-2,3-dioxopiperazine-1-carboxamido)acetamido)-7-chloro-2-hydroxy-3,4-dihydro-2H-benzo[e][1,2]oxaborinine-8-carboxylic acid

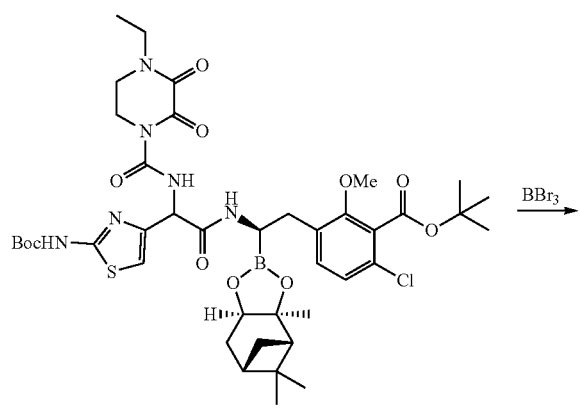

282

-continued

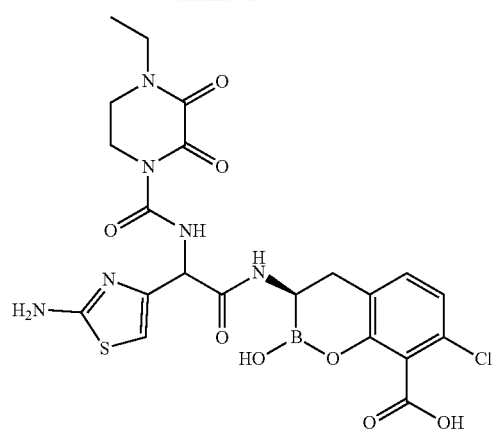

The full deprotection of tert-butyl 3-((2R)-2-(2-(2-((tert-butoxycarbonyl)amino)thiazol-4-yl)-2-(4-ethyl-2,3-dioxopiperazine-1-carboxamido)acetamido)-2-((3aS,4S,6S,7aR)-3a,5,5-trimethylhexahydro-4,6-methanobenzo[d][1,3,2]dioxaborol-2-yl)ethyl)-6-chloro-2-methoxybenzoate was carried out as described in General Method A with BBr3 to afford (3R)-3-(2-(2-aminothiazol-4-yl)-2-(4-ethyl-2,3-dioxopiperazine-1-carboxamido)acetamido)-7-chloro-2-hydroxy-3,4-dihydro-2H-benzo[e][1,2]oxaborinine-8-carboxylic acid. ESI-MS m/z 565.1 (M+H)+.

Example 216: (3R)-7-chloro-3-(2-(4-ethyl-2,3-dioxopiperazine-1-carboxamido)-2-(3-fluoro-5-hydroxypyridin-2-yl)acetamido)-2-hydroxy-3,4-dihydro-2H-benzo[e][1,2]oxaborinine-8-carboxylic acid

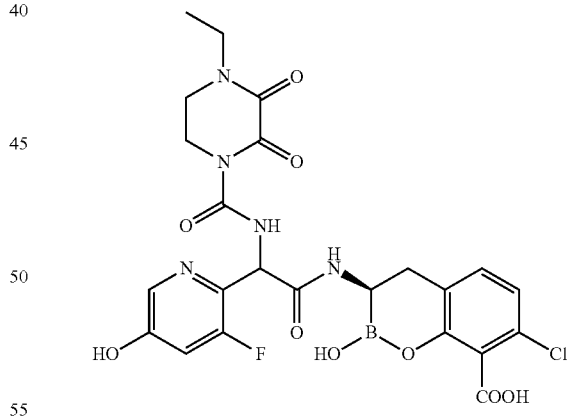

In a similar manner to the synthesis of Example 145, utilizing tert-butyl 6-chloro-3-((2S)-2-chloro-2-((3aS,4S,6R)-3a,5,5-trimethylhexahydro-4,6-methanobenzo[d][1,3,2]dioxaborol-2-yl)ethyl)-2-methoxybenzoate in place of tert-butyl 3-((2S)-2-chloro-2-((3aS,4S,6R)-3a,5,5-trimethylhexahydro-4,6-methanobenzo[d][1,3,2]dioxaborol-2-yl)ethyl)-6-fluoro-2-methoxybenzoate, the title compound was prepared. ESI-MS m/z 578 (MH)+.

Example 217: (3R)-7-chloro-3-(2-(2-chloro-3,4-dihydroxyphenyl)-2-(4-ethyl-2,3-dioxopiperazine-1-carboxamido)acetamido)-2-hydroxy-3,4-dihydro-2H-benzo[e][1,2]oxaborinine-8-carboxylic acid

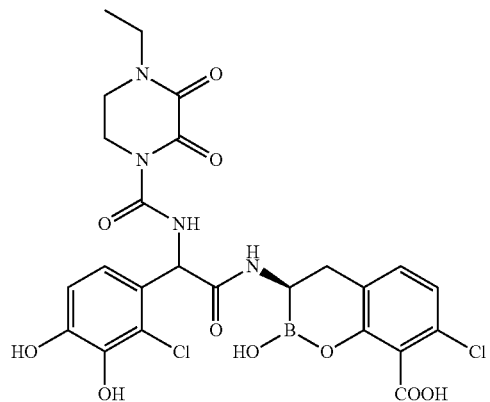 [SMILES: CCN1CCN(C(=O)NC(C(=O)N[C@H]2Cc3ccc(Cl)c(C(=O)O)c3OB2O)c2ccc(O)c(O)c2Cl)C(=O)C1=O]

In a similar manner to the synthesis of Example 37, utilizing tert-butyl 6-chloro-3-((S)-2-chloro-2-((3aS,4S,6S,7aR)-3a,5,5-trimethylhexahydro-4,6-methanobenzo[d][1,3,2]dioxaborol-2-yl)ethyl)-2-methoxybenzoate (synthesis described in Example 215) in Step 2, the title compound was prepared. ESI-MS m/z 609/611/613 (MH/MH+2/MH+4)⁺.

Example 218: (3R)-3-(2-((S)-4,6-diethyl-2,3-dioxopiperazine-1-carboxamido)-2-(3-fluoro-5-hydroxypyridin-2-yl)acetamido)-2-hydroxy-3,4-dihydro-2H-benzo[e][1,2]oxaborinine-8-carboxylic acid

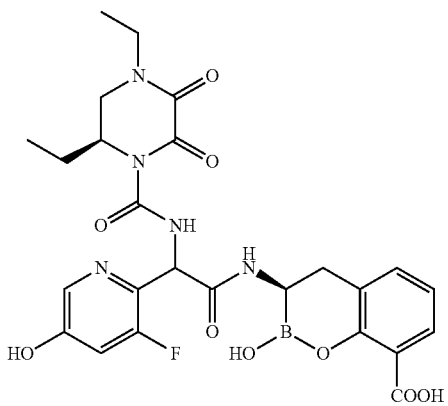

In a similar manner to the synthesis of Example 192, utilizing (S)-4,6-diethyl-2,3-dioxopiperazine-1-carbonyl chloride in place of (S)-4-ethyl-6-methyl-2,3-dioxopiperazine-1-carbonyl chloride, the title compound was prepared. ESI-MS m/z 572 (MH)⁺.

Example 219: (3R)-3-(2-(3-fluoro-5-hydroxypyridin-2-yl)-2-(4-oxo-1,4-dihydropyridine-3-carboxamido)acetamido)-2-hydroxy-3,4-dihydro-2H-benzo[e][1,2]oxaborinine-8-carboxylic acid

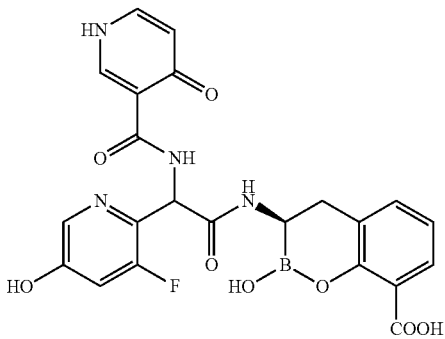 [SMILES: O=C(O)c1cccc2c1OB(O)[C@@H](NC(=O)C(NC(=O)c1c[nH]ccc1=O)c1ncc(O)cc1F)C2]

Step 1: Synthesis of tert-butyl 3-((2R)-2-(2-(5-(benzyloxy)pyridin-2-yl)-2-(4-oxo-1,4-dihydropyridine-3-carboxamido)acetamido)-2-((3aS,4S,6S)-3a,5,5-trimethylhexahydro-4,6-methanobenzo[d][1,3,2]dioxaborol-2-yl)ethyl)-2-methoxybenzoate

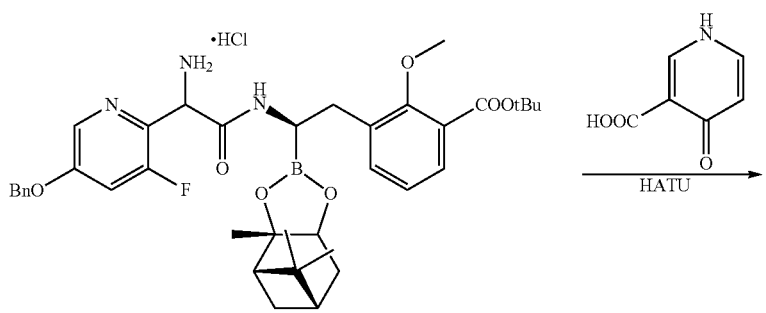

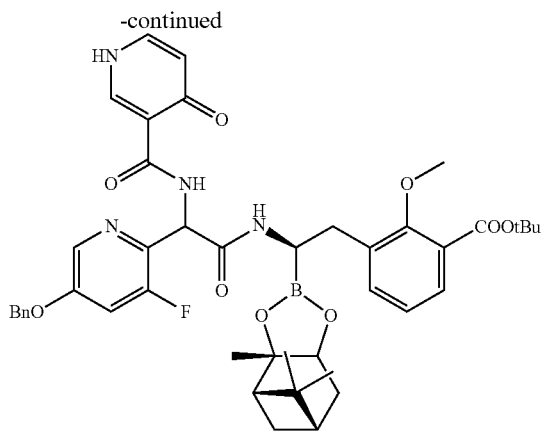

To tert-butyl 3-((2R)-2-(2-amino-2-(5-(benzyloxy)pyridin-2-yl)acetamido)-2-((3aS,4S,6S)-3a,5,5-trimethylhexahydro-4,6-methanobenzo[d][1,3,2]dioxaborol-2-yl)ethyl)-2-methoxybenzoate hydrogen chloride 0.29 g (0.39 mmol) in N,N-dimethylformamide (5 mL) was added triethylamine 0.17 mL (1.18 mmol, 3 eq), HATU 0.17 g (0.43 mmol, 1.1 eq), followed by 4-oxo-1,4-dihydropyridine-3-carboxylic acid 0.07 g (0.47 mmol, 1.2 eq) and was stirred at rt for 18 h. The reaction was diluted with ethyl acetate, washed with 0.5 M aq. hydrogen chloride, water, 0.5 M sodium carbonate, dried over sodium sulfate and concentrated to afford the title compound. ESI-MS m/z 809 (MH)⁺.

Step 2: Synthesis of tert-butyl 3-((2R)-2-(2-(3-fluoro-5-hydroxypyridin-2-yl)-2-(4-oxo-1,4-dihydropyridine-3-carboxamido)acetamido)-2-((3aS,4S,6S)-3a,5,5-trimethylhexahydro-4,6-methanobenzo[d][1,3,2]dioxaborol-2-yl)ethyl)-2-methoxybenzoate

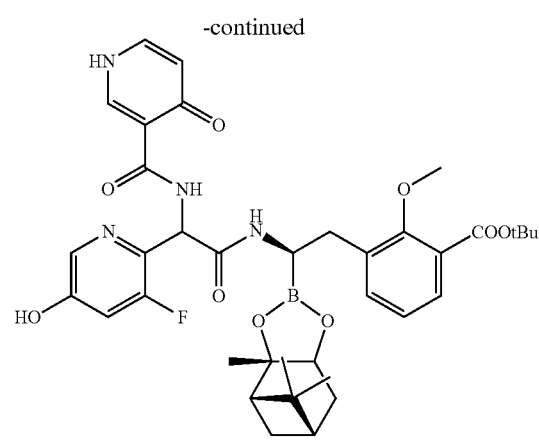

To tert-butyl 3-((2R)-2-(2-(5-(benzyloxy)pyridin-2-yl)-2-(4-oxo-1,4-dihydropyridine-3-carboxamido)acetamido)-2-((3aS,4S,6S)-3a,5,5-trimethylhexahydro-4,6-methanobenzo[d][1,3,2]dioxaborol-2-yl)ethyl)-2-methoxybenzoate 0.25 g (0.31 mmol) in methanol (5 mL) under an atmosphere of argon was added a spatula tip of palladium hydroxide and stirred at RT under a hydrogen balloon for 18 h. The reaction was filtered through a pad of celite and concentrated in vacuo to afford the title compound. ESI-MS m/z 719 (MH)⁺.

Step 3. Synthesis of (3R)-3-(2-(3-fluoro-5-hydroxypyridin-2-yl)-2-(4-oxo-1,4-dihydropyridine-3-carboxamido)acetamido)-2-hydroxy-3,4-dihydro-2H-benzo[e][1,2]oxaborinine-8-carboxylic acid

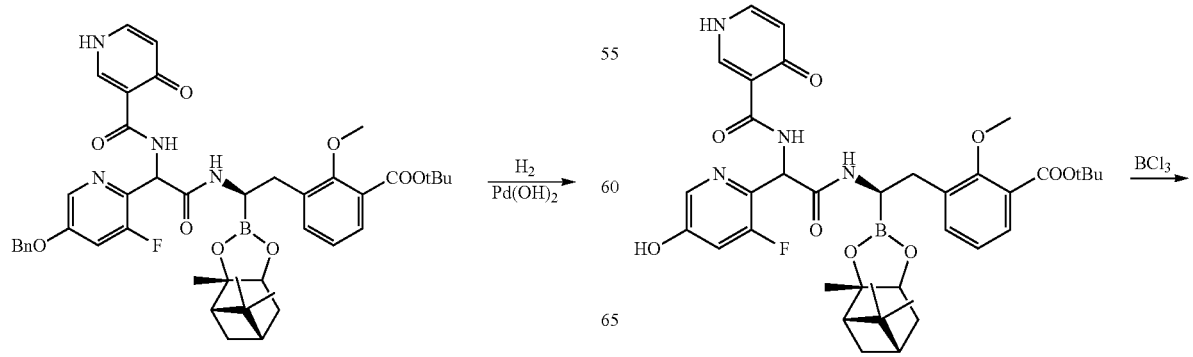

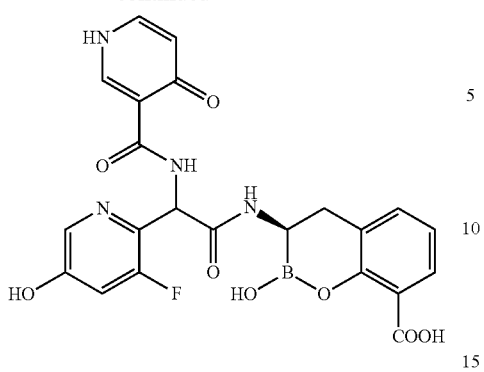

In a similar manner to the synthesis of Example 223, utilizing boron trichloride in place of boron tribromide in Step 1, the title compound was prepared. ESI-MS m/z 497 (MH)$^+$.

Example 220: (R)-3-((R)-2-(4-(2-aminoethyl)-2,3-dioxopiperazine-1-carboxamido)-2-(2-chloro-3,4-dihydroxyphenyl)acetamido)-2-hydroxy-3,4-dihydro-2H-benzo[e][1,2]oxaborinine-8-carboxylic acid

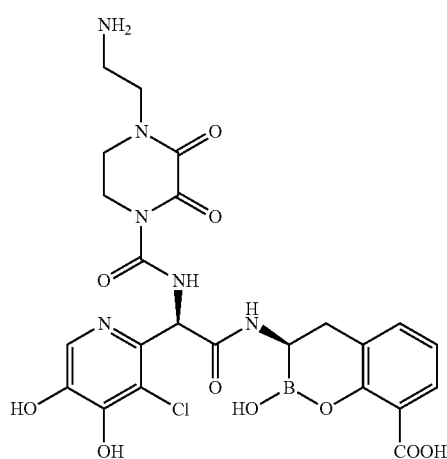 [SMILES: NCCN1CCN(C(=O)N[C@@H](C(=O)N[C@H]2Cc3cccc(C(=O)O)c3OB2O)c2ncc(O)c(O)c2Cl)C(=O)C1=O]

Example 221: (R)-3-((S)-2-(4-(2-aminoethyl)-2,3-dioxopiperazine-1-carboxamido)-2-(2-chloro-3,4-dihydroxyphenyl)acetamido)-2-hydroxy-3,4-dihydro-2H-benzo[e][1,2]oxaborinine-8-carboxylic acid

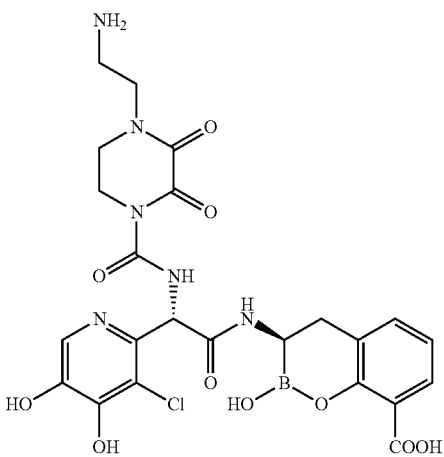 [SMILES: NCCN1CCN(C(=O)N[C@H](C(=O)N[C@H]2Cc3cccc(C(=O)O)c3OB2O)c2ncc(O)c(O)c2Cl)C(=O)C1=O]

Step 1. Synthesis of tert-butyl (2-(4-(chlorocarbonyl)-2,3-dioxopiperazin-1-yl)ethyl)carbamate

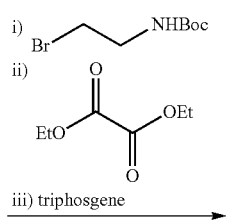

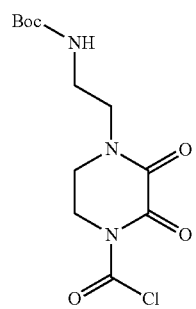

By following the same procedures as described for the synthesis of 4-fluoroethyl-2,3-dioxopiperazine-1-carbonyl chloride in Step 1 and Step 2 of Example 13, the title compound was prepared from tert-butyl (2-bromoethyl) carbamate.

289

Step 2. (R)-3-((S)-2-(4-(2-aminoethyl)-2,3-di-oxopiperazine-1-carboxamido)-2-(2-chloro-3,4-dihydroxyphenyl)acetamido)-2-hydroxy-3,4-dihydro-2H-benzo[e][1,2]oxaborinine-8-carboxylic acid & (R)-3-((S)-2-(4-(2-aminoethyl)-2,3-dioxopiperazine-1-carboxamido)-2-(2-chloro-3,4-dihydroxyphenyl)acetamido)-2-hydroxy-3,4-dihydro-2H-benzo[e][1,2]oxaborinine-8-carboxylic acid In a similar manner to the synthesis of Example 37, utilizing the above carbonyl chloride in place of 4-ethyl-2,3-dioxopiperazine-1-carbonyl chloride, the title compound, Example 238, and Example 239 were prepared by reversed phase HPLC separation using a C-18 column from Waters (XBridge Prep C18 column 30×100 mm 5-micron), mobile phase: 5%-55% CH$_3$CN—H$_2$O containing 0.1% TFA, flow rate: 45 mL/min, gradient time: 12 min, Example 220 was isolated as the first eluting peak, Example 221 isolated as the second eluting peak. ESI-MS m/z 704/706 (MH/MH+2)$^+$.

Example 222: (3R)-3-(2-(2-chloro-3,4-dihydroxyphenyl)-2-((S)-3,4-dioxooctahydropyrrolo[1,2-a]pyrazine-2-carboxamido)acetamido)-2-hydroxy-3,4-dihydro-2H-benzo[e][1,2]oxaborinine-8-carboxylic acid

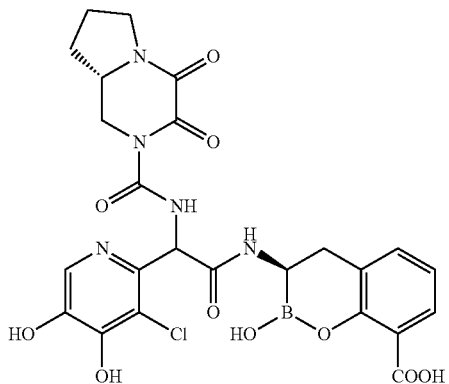 [SMILES: O=C(O)c1cccc2c1OB(O)[C@@H](NC(=O)C(NC(=O)N1C[C@@H]3CCCN3C(=O)C1=O)c1ncc(O)c(O)c1Cl)C2]

In a similar manner to the synthesis of Example 37, utilizing (S)-3,4-dioxohexahydropyrrolo[1,2-a]pyrazine-2(1H)-carbonyl chloride (which was prepared from (S)-pyrrolidin-2-ylmethanamine in a similar manner to 4-fluoroethyl-2,3-dioxopiperazine-1-carbonyl chloride) in place of 4-ethyl-2,3-dioxopiperazine-1-carbonyl chloride, the title compound, was prepared. ESI-MS m/z 587/589 (MH/MH+2)$^+$.

290

Example 223: (3R)-3-(2-((S)-3,4-dioxooctahydropyrrolo[1,2-a]pyrazine-2-carboxamido)-2-(3-fluoro-5-hydroxypyridin-2-yl)acetamido)-2-hydroxy-3,4-dihydro-2H-benzo[e][1,2]oxaborinine-8-carboxylic acid

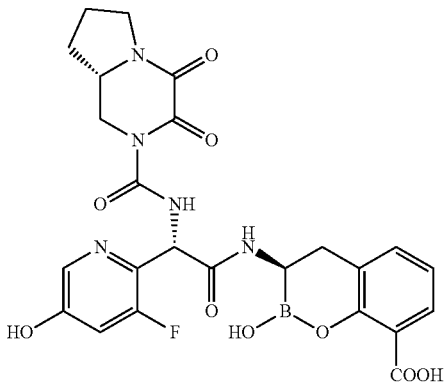 [SMILES: O=C(O)c1cccc2c1OB(O)[C@@H](NC(=O)[C@@H](NC(=O)N1C[C@@H]3CCCN3C(=O)C1=O)c1ncc(O)cc1F)C2]

In a similar manner to the synthesis of Example 135, utilizing (S)-3,4-dioxohexahydropyrrolo[1,2-a]pyrazine-2(1H)-carbonyl chloride in place of 4-ethyl-2,3-dioxopiperazine-1-carbonyl chloride, the title compound was prepared. ESI-MS m/z 556 (MH)$^+$.

Example 224: (3R)-3-(2-(2-chloro-3,4-dihydroxyphenyl)-2-((S)-4-(2-hydroxyethyl)-6-methyl-2,3-dioxopiperazine-1-carboxamido)acetamido)-2-hydroxy-3,4-dihydro-2H-benzo[e][1,2]oxaborinine-8-carboxylic acid

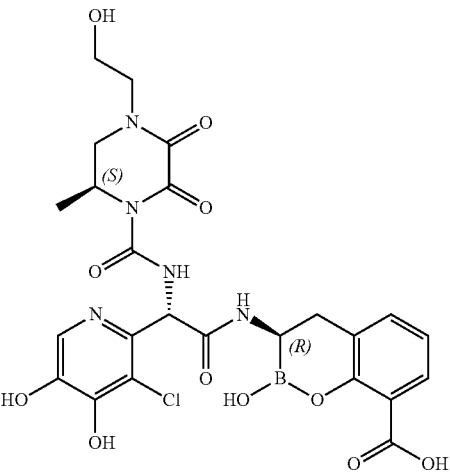

Step 1. Synthesis of (S)-1-(2-(benzyloxy)ethyl)-5-methylpiperazine-2,3-dione

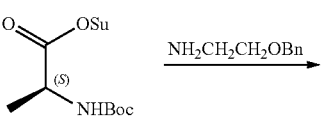

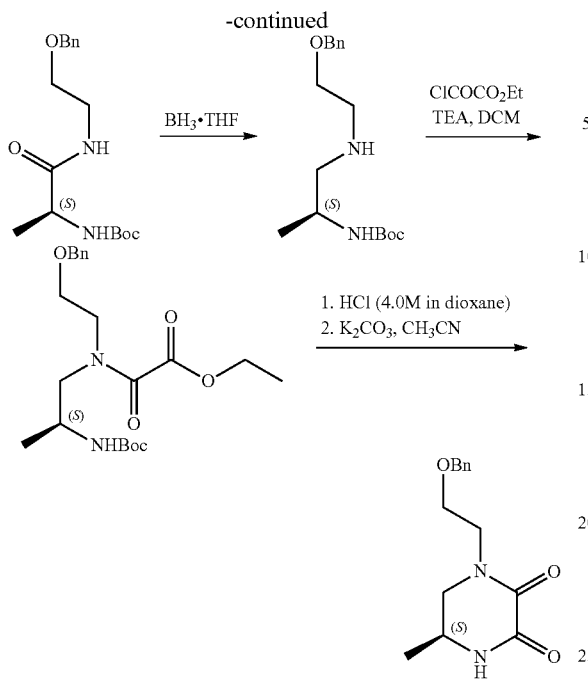

To a mixture of Boc-Ala-OSu (6.08 g, 21.2 mmol) in DCM (40 mL) was added dropwise a solution of 2-(benzyloxy)-1-ethanamine (3.38 g, 22.3 mmol) in DCM (10 mL) at 0° C. The mixture was allowed to slowly warm to room temperature overnight. After 23 h, the reaction mixture was quenched with saturated NaHCO₃, extracted with DCM (3×), dried over Na₂SO₄. After the solvent was evaporated under reduced pressure, the residue was purified by flash chromatography on silica gel (120 g column) eluted with 0 to 50% ethyl acetate/hexanes to afford tert-butyl (S)-(1-((2-(benzyloxy)ethyl)amino)-1-oxopropan-2-yl)carbamate (6.87 g). ESI-MS m/z 345.2 (M+Na)⁺, 267.2 (M+H−56)⁺.

To a solution of tert-butyl (S)-(1-((2-(benzyloxy)ethyl)amino)-1-oxopropan-2-yl)carbamate (6.87 g) in THF (40 mL) was added dropwise a solution of Borane tetrahydrofuran complex solution (1.0 M in THF, 85 mL, 85 mmol) at 0° C. The mixture was allowed to slowly warm to room temperature overnight. After 7 d, the reaction mixture was carefully quenched with MeOH at 0° C. The mixture was then evaporated under reduced pressure to afford tert-butyl (S)-(1-((2-(benzyloxy)ethyl)amino)propan-2-yl)carbamate (6.85 g), which was used in the next step directly. ESI-MS m/z 309.3 (M+H)⁺.

To a solution of tert-butyl (S)-(1-((2-(benzyloxy)ethyl)amino)propan-2-yl)carbamate (6.85 g), obtained as described above, and TEA (3.8 mL, 27 mmol) in DCM (50 mL) was added dropwise ethyl chlorooxoacetate (3.63 g, 26.6 mmol) at 0° C. The reaction mixture was allowed to slowly warm to room temperature overnight and then quenched with saturated NaHCO₃, extracted with DCM (3×), dried over Na₂SO₄, and evaporated under reduced pressure to afford ethyl (S)-2-((2-(benzyloxy)ethyl)(2-((tert-butoxycarbonyl)amino)propyl)amino)-2-oxoacetate (8.66 g), which was used in the next step directly. ESI-MS m/z 409.2 (M+H)⁺, 431.2 (M+Na)⁺.

A mixture of ethyl (S)-2-((2-(benzyloxy)ethyl)(2-((tert-butoxycarbonyl)amino)propyl)amino)-2-oxoacetate (8.66 g), obtained as described above, and 4.0 M HCl in 1,4-dioxane (60 mL) was stirred at room temperature for 3 h. The solvent was then evaporated under reduced pressure to afford ethyl (S)-2-((2-aminopropyl)(2-(benzyloxy)ethyl)amino)-2-oxoacetate. ESI-MS m/z 309.2 (M+H)⁺.

A mixture of ethyl (S)-2-((2-aminopropyl)(2-(benzyloxy)ethyl)amino)-2-oxoacetate, obtained as described above, and K₂CO₃ (6.15 g, 44.5 mmol) in CH₃CN (100 mL) was stirred at room temperature for 16 h. The mixture was then filtered through Celite, washed with DCM. After the solvent was evaporated under reduced pressure, the residue was purified by flash chromatography on silica gel (340 g column) eluted with 0 to 20% MeOH/ethyl acetate to afford 1.63 g (29% in 5 steps) of (S)-1-(2-(benzyloxy)ethyl)-5-methylpiperazine-2,3-dione. ESI-MS m/z 263.2 (M+H)⁺.

Step 2. Synthesis of (S)-4-(2-(benzyloxy)ethyl)-6-methyl-2,3-dioxopiperazine-1-carbonyl chloride

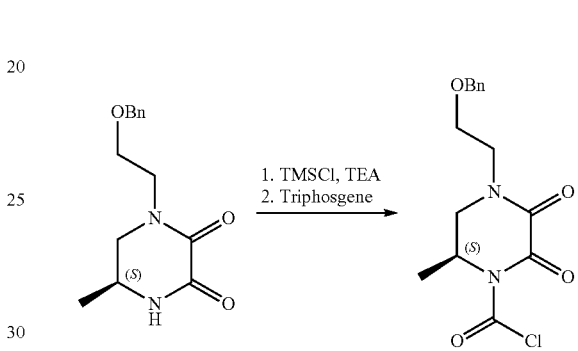

To a solution of (S)-1-(2-(benzyloxy)ethyl)-5-methylpiperazine-2,3-dione (1.63 g, 6.21 mmol) in THF (10 mL) and DCM (10 mL) were added dropwise TMSCI (1.0 mL, 7.88 mmol) and TEA (1.2 mL, 8.61 mmol) at −65° C. under argon. After 3 h, the reaction mixture was then stirred at 0° C. for an additional 1.5 h. A solution of triphosgene (0.834 g, 2.81 mmol) in THF (10 mL) was added at 0° C. The mixture was allowed to slowly warm to room temperature overnight and then filtered, washed with THF. The filtrate was evaporated under reduced pressure to afford (S)-4-(2-(benzyloxy)ethyl)-6-methyl-2,3-dioxopiperazine-1-carbonyl chloride (2.025 g) as a solid, which was used in the next step directly.

Step 3. Synthesis of tert-butyl 3-((2R)-2-(2-((S)-4-(2-(benzyloxy)ethyl)-6-methyl-2,3-dioxopiperazine-1-carboxamido)-2-(2-chloro-3,4-dimethoxyphenyl)acetamido)-2-((3aS,4S,6S,7aR)-3a,5,5-trimethylhexahydro-4,6-methanobenzo[d][1,3,2]dioxaborol-2-yl)ethyl)-2-methoxybenzoate

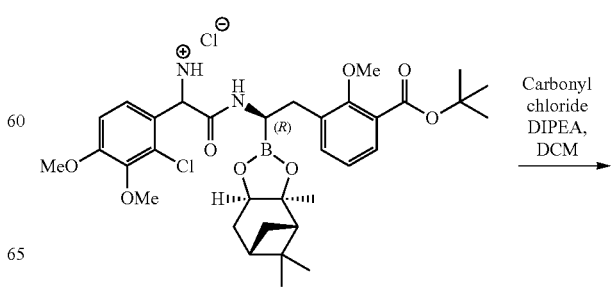

-continued

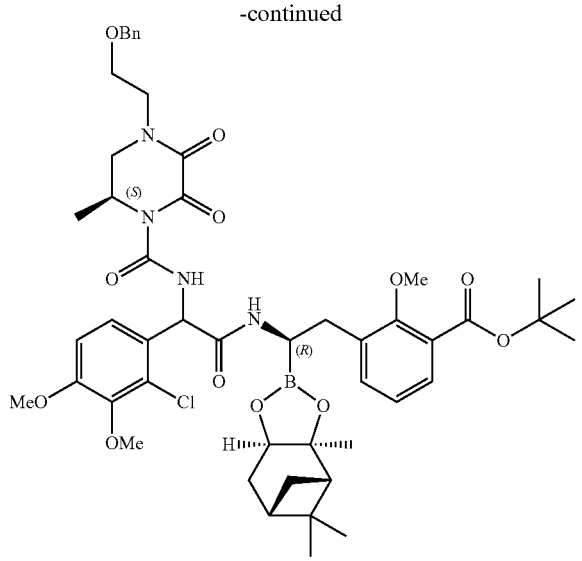

A mixture of 2-(((R)-2-(3-(tert-butoxycarbonyl)-2-methoxyphenyl)-1-((3aS,4S,6S,7aR)-3a,5,5-trimethylhexahydro-4,6-methanobenzo[d][1,3,2]dioxaborol-2-yl)ethyl)amino)-1-(2-chloro-3,4-dimethoxyphenyl)-2-oxoethan-1-aminium chloride (0.215 g, 0.31 mmol), (S)-4-(2-(benzyloxy)ethyl)-6-methyl-2,3-dioxopiperazine-1-carbonyl chloride (0.140 g, 0.43 mmol), and DIPEA (0.2 mL, 1.15 mmol) in DCM (10 mL) was stirred at room temperature for 2.5 h. The mixture was then quenched with brine, extracted with DCM (2×), dried over Na$_2$SO$_4$, and evaporated under reduced pressure to afford tert-butyl 3-((2R)-2-(2-((S)-4-(2-(benzyloxy)ethyl)-6-methyl-2,3-dioxopiperazine-1-carboxamido)-2-(2-chloro-3,4-dimethoxyphenyl)acetamido)-2-((3aS,4S,6S,7aR)-3a,5,5-trimethylhexahydro-4,6-methanobenzo[d][1,3,2]dioxaborol-2-yl)ethyl)-2-methoxybenzoate (0.35 g), which was used in the next step directly. ESI-MS m/z 967.4 (M+Na)$^+$, 889.3 (M+H−56)$^+$.

Step 4. Synthesis of (3R)-3-(2-(2-chloro-3,4-dihydroxyphenyl)-2-((S)-4-(2-hydroxyethyl)-6-methyl-2,3-dioxopiperazine-1-carboxamido)acetamido)-2-hydroxy-3,4-dihydro-2H-benzo[e][1,2]oxaborinine-8-carboxylic acid

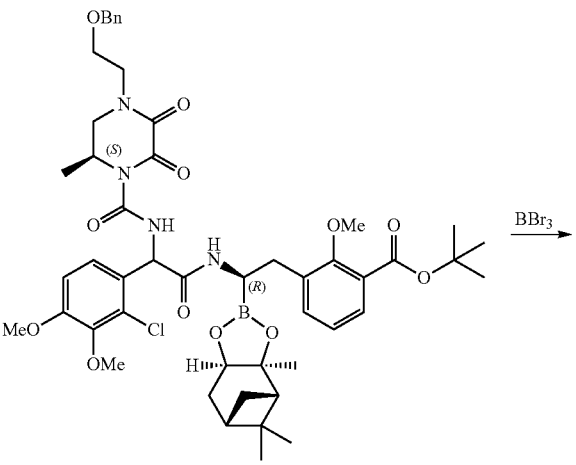

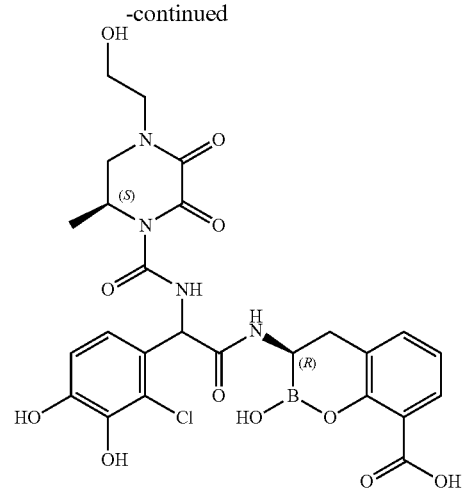

The full deprotection of tert-butyl 3-((2R)-2-(2-((S)-4-(2-(benzyloxy)ethyl)-6-methyl-2,3-dioxopiperazine-1-carboxamido)-2-(2-chloro-3,4-dimethoxyphenyl)acetamido)-2-((3aS,4S,6S,7aR)-3a,5,5-trimethylhexahydro-4,6-methanobenzo[d][1,3,2]dioxaborol-2-yl)ethyl)-2-methoxybenzoate was carried out as described in General Method A with BBr$_3$ to afford (3R)-3-(2-(2-chloro-3,4-dihydroxyphenyl)-2-((S)-4-(2-hydroxyethyl)-6-methyl-2,3-dioxopiperazine-1-carboxamido)acetamido)-2-hydroxy-3,4-dihydro-2H-benzo[e][1,2]oxaborinine-8-carboxylic acid. ESI-MS m/z 605.2 (M+H)$^+$.

Example 225: (R)-3-((R)-2-(4-(2-aminoethyl)-2,3-dioxopiperazine-1-carboxamido)-2-(3-fluoro-5-hydroxypyridin-2-yl)acetamido)-2-hydroxy-3,4-dihydro-2H-benzo[e][1,2]oxaborinine-8-carboxylic acid

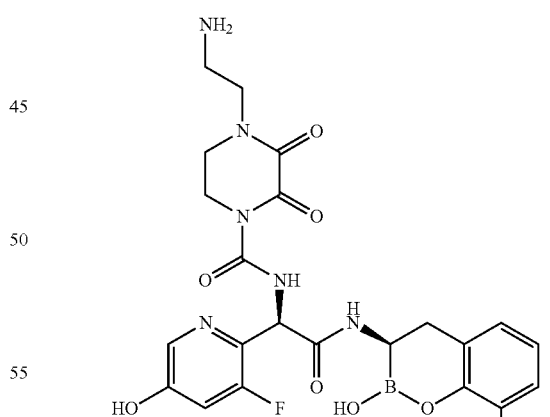

In a similar manner to the synthesis of Example 223, utilizing tert-butyl (2-(4-(chlorocarbonyl)-2,3-dioxopiperazin-1-yl)ethyl)carbamate in place of (S)-3,4-dioxohexahydropyrrolo[1,2-a]pyrazine-2(1H)-carbonyl, the title compound was prepared. ESI-MS m/z 559 (MH)$^+$.

Example 226: (R)-3-((S)-2-(4-(2-aminoethyl)-2,3-dioxopiperazine-1-carboxamido)-2-(3-fluoro-5-hydroxypyridin-2-yl)acetamido)-2-hydroxy-3,4-dihydro-2H-benzo[e][1,2]oxaborinine-8-carboxylic acid

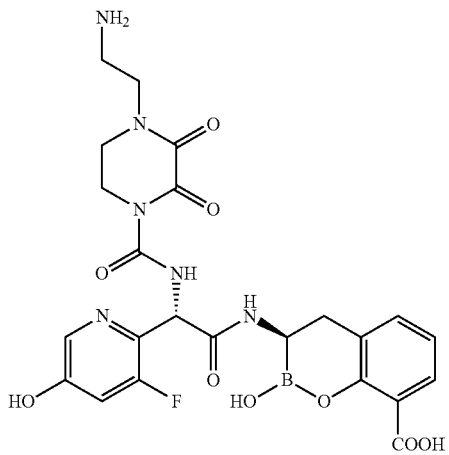 [SMILES: NCCN1CCN(C(=O)N[C@H](C(=O)N[C@H]2Cc3cccc(C(=O)O)c3OB2O)c2ncc(O)cc2F)C(=O)C1=O]

In a similar manner to the synthesis of Example 223, utilizing tert-butyl (2-(4-(chlorocarbonyl)-2,3-dioxopiperazin-1-yl)ethyl)carbamate in place of (S)-3,4-dioxohexahydropyrrolo[1,2-a]pyrazine-2(1H)-carbonyl, the title compound was prepared. ESI-MS m/z 559 (MH)⁺.

Example 227: (R)-3-((R)-2-(4-(2-aminoethyl)-2,3-dioxopiperazine-1-carboxamido)-2-(2-chloro-3,4-dihydroxyphenyl)acetamido)-7-fluoro-2-hydroxy-3,4-dihydro-2H-benzo[e][1,2]oxaborinine-8-carboxylic acid

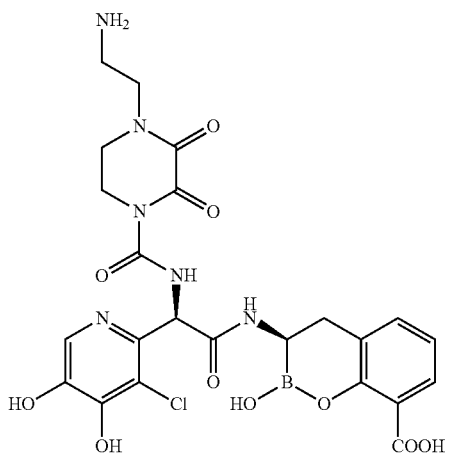 [SMILES: NCCN1CCN(C(=O)N[C@@H](C(=O)N[C@H]2Cc3cccc(C(=O)O)c3OB2O)c2ncc(O)c(O)c2Cl)C(=O)C1=O]

In a similar manner to the synthesis of Example 124, utilizing the above carbonyl chloride described in Step 1 of Example 221 in place of 4-ethyl-2,3-dioxopiperazine-1-carbonyl chloride, the title compound was prepared after reversed phase HPLC purification, isolated as the first eluting peak. ESI-MS m/z 608/610 (MH/MH+2)⁺.

Example 228: (3R)-3-(2-(4-(2-acetamidoethyl)-2,3-dioxopiperazine-1-carboxamido)-2-(2-chloro-3,4-dihydroxyphenyl)acetamido)-2-hydroxy-3,4-dihydro-2H-benzo[e][1,2]oxaborinine-8-carboxylic acid

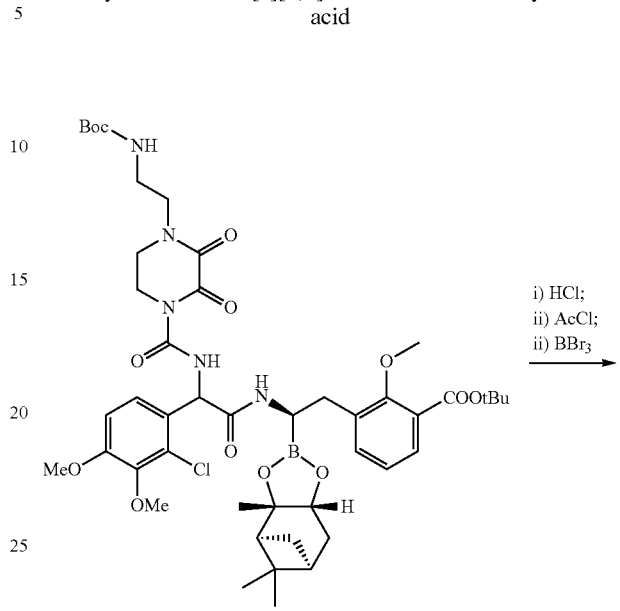

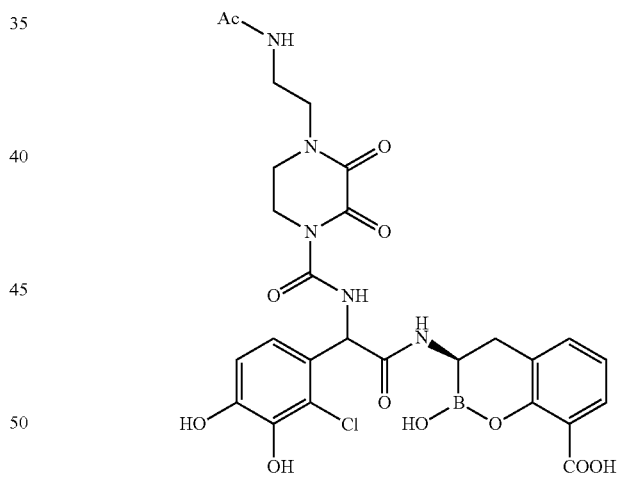

The fully protected intermediate from the synthesis of Example 220 and Example 221 (1.6 g, 1.7 mmol) was treated with 2.0 M hydrogen chloride in diethylether (22 mL, 44 mmol) and 4.0 M hydrogen chloride in dioxane (11 mL, 44 mmol) at RT overnight, then concentrated in vacuo. To this crude amine intermediate (289 mg, 0.35 mmol) in DCM (8 mL) was added diisopropylethylamine (0.28 mL, 1.6 mmol) followed by acetyl chloride (56 mg, 0.71 mmol). The reaction mixture was stirred at RT for 1 h, washed with water, brine, dried and concentrated in vacuo. This crude product was subjected to deprotection with BBr₃ by following the General Method A to afford the title compound. ESI-MS m/z 632/634 (MH/MH+2)⁺.

Example 229: (3R)-3-(2-(2-chloro-3,4-dihydroxyphenyl)-2-(4-(2-(methylsulfonamido)ethyl)-2,3-dioxopiperazine-1-carboxamido)acetamido)-2-hydroxy-3,4-dihydro-2H-benzo[e][1,2]oxaborinine-8-carboxylic acid

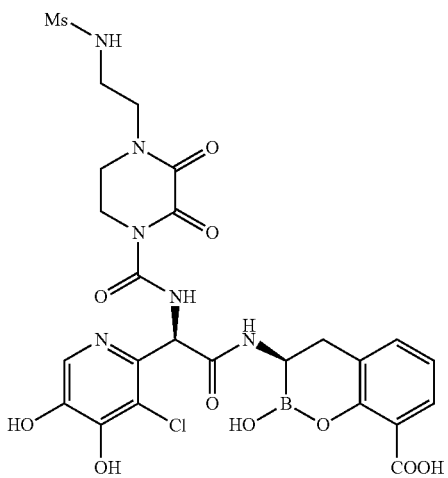 [SMILES: CS(=O)(=O)NCCN1CCN(C(=O)N[C@@H](C(=O)N[C@H]2Cc3cccc(C(=O)O)c3OB2O)c2ncc(O)c(O)c2Cl)C(=O)C1=O]

In a similar manner to the synthesis of Example 228, utilizing methanesulfonyl chloride in place of acetyl chloride, the title compound was prepared. ESI-MS m/z 668/670 (MH/MH+2)⁺.

Example 230: (R)-3-((R)-2-(4-(2-aminoethyl)-2,3-dioxopiperazine-1-carboxamido)-2-(3-fluoro-5-hydroxypyridin-2-yl)acetamido)-7-fluoro-2-hydroxy-3,4-dihydro-2H-benzo[e][1,2]oxaborinine-8-carboxylic acid

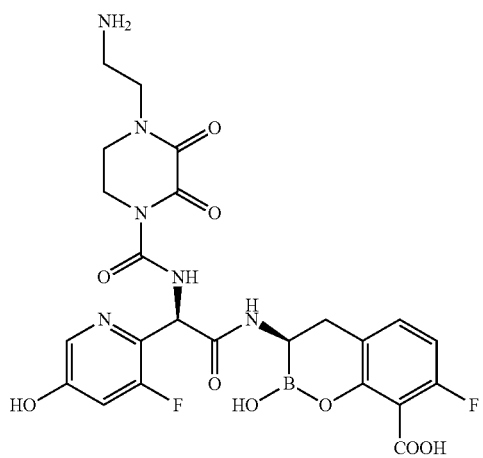 [SMILES: NCCN1CCN(C(=O)N[C@@H](C(=O)N[C@H]2Cc3ccc(F)c(C(=O)O)c3OB2O)c2ncc(O)cc2F)C(=O)C1=O]

In a similar manner to the synthesis of Example 223, utilizing tert-butyl 3-((2S)-2-chloro-2-((3aS,4S,6R)-3a,5,5-trimethylhexahydro-4,6-methanobenzo[d][1,3,2]dioxaborol-2-yl)ethyl)-6-fluoro-2-methoxybenzoate in place of tert-butyl 3-((2S)-2-chloro-2-((3aS,4S,6R)-3a,5,5-trimethylhexahydro-4,6-methanobenzo[d][1,3,2]dioxaborol-2-yl)ethyl)-2-methoxybenzoate, the title compound was prepared. ESI-MS m/z 577 (MH)⁺.

Example 231: (R)-3-((S)-2-(4-(2-aminoethyl)-2,3-dioxopiperazine-1-carboxamido)-2-(3-fluoro-5-hydroxypyridin-2-yl)acetamido)-7-fluoro-2-hydroxy-3,4-dihydro-2H-benzo[e][1,2]oxaborinine-8-carboxylic acid

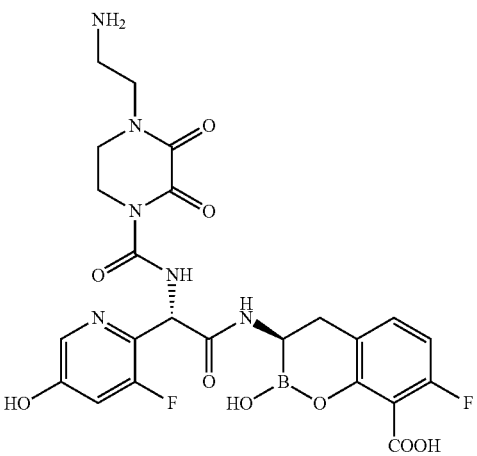 [SMILES: NCCN1CCN(C(=O)N[C@H](C(=O)N[C@H]2Cc3ccc(F)c(C(=O)O)c3OB2O)c2ncc(O)cc2F)C(=O)C1=O]

In a similar manner to the synthesis of Example 223, utilizing tert-butyl 3-((2S)-2-chloro-2-((3aS,4S,6R)-3a,5,5-trimethylhexahydro-4,6-methanobenzo[d][1,3,2]dioxaborol-2-yl)ethyl)-6-fluoro-2-methoxybenzoate in place of tert-butyl 3-((2S)-2-chloro-2-((3aS,4S,6R)-3a,5,5-trimethylhexahydro-4,6-methanobenzo[d][1,3,2]dioxaborol-2-yl)ethyl)-2-methoxybenzoate, the title compound was prepared. ESI-MS m/z 577 (MH)⁺

Example 232: (3R)-3-(2-(2-chloro-3,4-dihydroxyphenyl)-2-((R)-3,4-dioxooctahydropyrrolo[1,2-a]pyrazine-2-carboxamido)acetamido)-2-hydroxy-3,4-dihydro-2H-benzo[e][1,2]oxaborinine-8-carboxylic acid

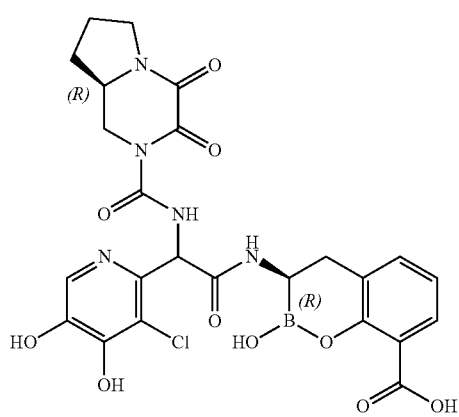

Step 1. Synthesis of (R)-hexahydropyrrolo[1,2-a]pyrazine-3,4-dione

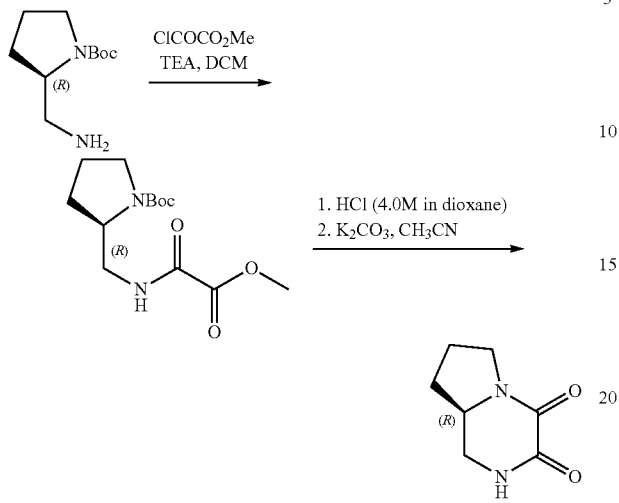

To a solution of (R)-1-Boc-2-(aminomethyl)pyrrolidine (5.77 g, 28.8 mmol) and TEA (4.5 mL, 32.3 mmol) in DCM (80 mL) was added dropwise methyl chlorooxoacetate (3.79 g, 30.9 mmol) at 0° C. The reaction mixture was allowed to slowly warm to room temperature overnight and then quenched with saturated NaHCO₃, extracted with DCM (3×), dried over Na₂SO₄, and evaporated under reduced pressure to afford tert-butyl (R)-2-((2-methoxy-2-oxoacetamido)methyl)pyrrolidine-1-carboxylate (10.35 g), which was used in the next step directly. ESI-MS m/z 309.2 (M+Na)⁺.

A mixture of tert-butyl (R)-2-((2-methoxy-2-oxoacetamido)methyl)pyrrolidine-1-carboxylate (10.35 g), obtained as described above, and 4.0 M HCl in 1,4-dioxane (40 mL) was stirred at room temperature for 3 h. The solvent was then evaporated under reduced pressure to afford methyl (R)-2-oxo-2-((pyrrolidin-2-ylmethyl)amino)acetate. ESI-MS m/z 187.1 (M+H)⁺.

A mixture of methyl (R)-2-oxo-2-((pyrrolidin-2-ylmethyl)amino)acetate, obtained as described above, and K₂CO₃ (12.90 g, 93.3 mmol) in CH₃CN (100 mL) was stirred at room temperature for 21 h. The mixture was then filtered through Celite, washed with DCM. After the solvent was evaporated under reduced pressure, the residue was purified by flash chromatography on silica gel (120 g column) eluted with 0 to 15% MeOH/DCM to afford 0.91 g (21% in 3 steps) of (R)-hexahydropyrrolo[1,2-a]pyrazine-3,4-dione. ESI-MS m/z 155.1 (M+H)⁺.

Step 2. Synthesis of (R)-3,4-dioxohexahydropyrrolo[1,2-a]pyrazine-2(1H)-carbonyl chloride

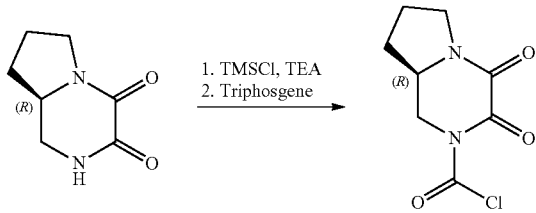

To a solution of (R)-hexahydropyrrolo[1,2-a]pyrazine-3,4-dione (0.90 g, 5.8 mmol) in THF (10 mL) and DCM (10 mL) were added dropwise TMSCl (0.9 mL, 7.1 mmol) and TEA (1.0 mL, 7.2 mmol) at −65° C. under argon. After 3 h, the reaction mixture was then stirred at 0° C. for an additional 1 h. A solution of triphosgene (0.800 g, 2.7 mmol) in THF (10 mL) was added at 0° C. The mixture was allowed to slowly warm to room temperature overnight and then filtered, washed with THF. The filtrate was evaporated under reduced pressure to afford (R)-3,4-dioxohexahydropyrrolo[1,2-a]pyrazine-2(1H)-carbonyl chloride (1.16 g), which was used in the next step directly.

Step 3. Synthesis of tert-butyl 3-((2R)-2-(2-(2-chloro-3,4-dimethoxyphenyl)-2-((R)-3,4-dioxooctahydropyrrolo[1,2-a]pyrazine-2-carboxamido)acetamido)-2-((3aS,4S,6S,7aR)-3a,5,5-trimethylhexahydro-4,6-methanobenzo[d][1,3,2]dioxaborol-2-yl)ethyl)-2-methoxybenzoate

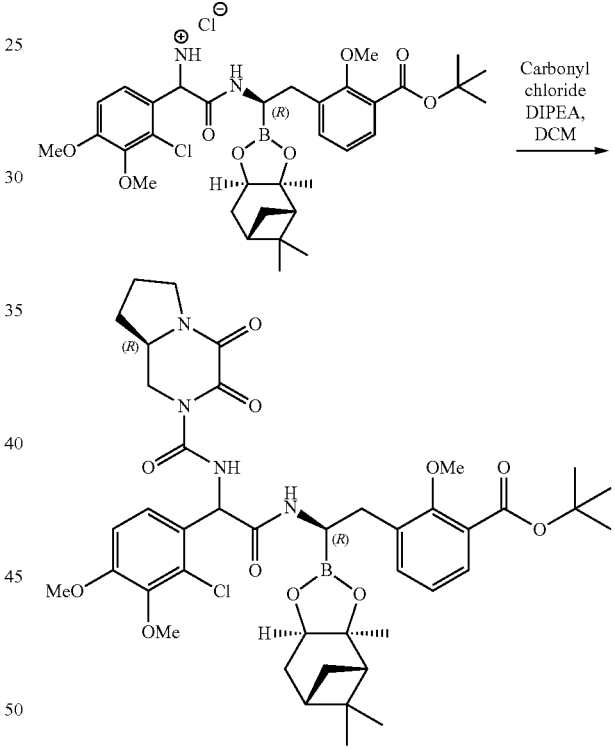

A mixture of 2-(((R)-2-(3-(tert-butoxycarbonyl)-2-methoxyphenyl)-1-((3aS,4S,6S,7aR)-3a,5,5-trimethylhexahydro-4,6-methanobenzo[d][1,3,2]dioxaborol-2-yl)ethyl)amino)-1-(2-chloro-3,4-dimethoxyphenyl)-2-oxoethan-1-aminium chloride (0.247 g, 0.356 mmol), (R)-3,4-dioxohexahydropyrrolo[1,2-a]pyrazine-2(1H)-carbonyl chloride (0.09 g, 0.415 mmol), and DIPEA (0.2 mL, 1.15 mmol) in DCM (10 mL) was stirred at room temperature for 3 h. The mixture was then quenched with brine, extracted with DCM (2×), dried over Na₂SO₄, and evaporated under reduced pressure to afford tert-butyl 3-((2R)-2-(2-(2-chloro-3,4-dimethoxyphenyl)-2-((R)-3,4-dioxooctahydropyrrolo[1,2-a]pyrazine-2-carboxamido)acetamido)-2-((3aS,4S,6S,7aR)-3a,5,5-trimethylhexahydro-4,6-methanobenzo[d][1,3, 2]dioxaborol-2-yl)ethyl)-2-methoxybenzoate (0.30 g), which was used in the next step directly. ESI-MS m/z 859.4 (M+Na)⁺, 781.3 (M+H−56)⁺.

Step 4. Synthesis of (3R)-3-(2-(2-chloro-3,4-dihydroxyphenyl)-2-((R)-3,4-dioxooctahydropyrrolo[1,2-a]pyrazine-2-carboxamido)acetamido)-2-hydroxy-3,4-dihydro-2H-benzo[e][1,2]oxaborinine-8-carboxylic acid amido)-2-hydroxy-3,4-dihydro-2H-benzo[e][1,2]oxaborinine-8-carboxylic acid. ESI-MS m/z 587.1 (M+H)⁺.

Example 233: (3R)-3-(2-(4-(3-aminopropyl)-2,3-dioxopiperazine-1-carboxamido)-2-(2-chloro-3,4-dihydroxyphenyl)acetamido)-2-hydroxy-3,4-dihydro-2H-benzo[e][1,2]oxaborinine-8-carboxylic acid

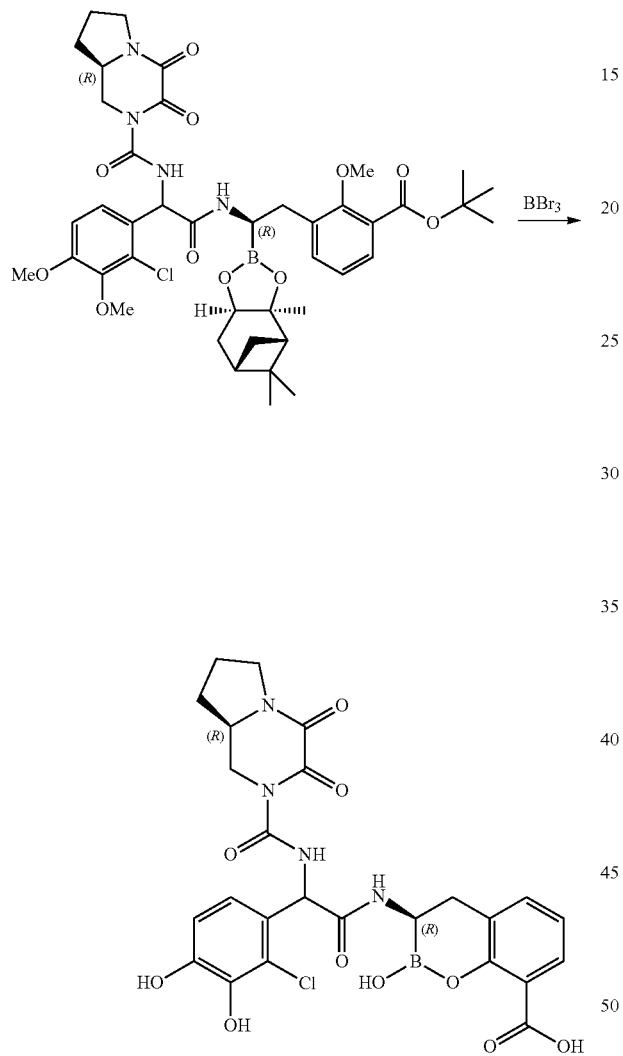

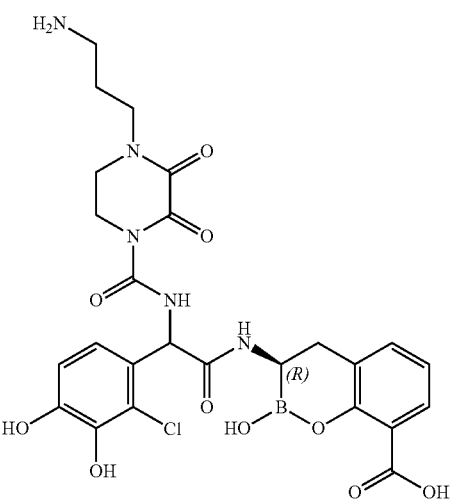

Step 1. Synthesis of tert-butyl 3-((2R)-2-(2-(4-(3-((tert-butoxycarbonyl)amino)propyl)-2,3-dioxopiperazine-1-carboxamido)-2-(2-chloro-3,4-dimethoxyphenyl)acetamido)-2-((3aS,4S,6S,7aR)-3a,5,5-trimethylhexahydro-4,6-methanobenzo[d][1,3,2]dioxaborol-2-yl)ethyl)-2-methoxybenzoate The full deprotection of tert-butyl 3-((2R)-2-(2-(2-chloro-3,4-dimethoxyphenyl)-2-((R)-3,4-dioxooctahydropyrrolo[1,2-a]pyrazine-2-carboxamido)acetamido)-2-((3aS,4S,6S,7aR)-3a,5,5-trimethylhexahydro-4,6-methanobenzo[d][1,3,2]dioxaborol-2-yl)ethyl)-2-methoxybenzoate was carried out as described in General Method A with BBr₃ to afford (3R)-3-(2-(2-chloro-3,4-dihydroxyphenyl)-2-((R)-3,4-dioxooctahydropyrrolo[1,2-a]pyrazine-2-carboxamido)acet-

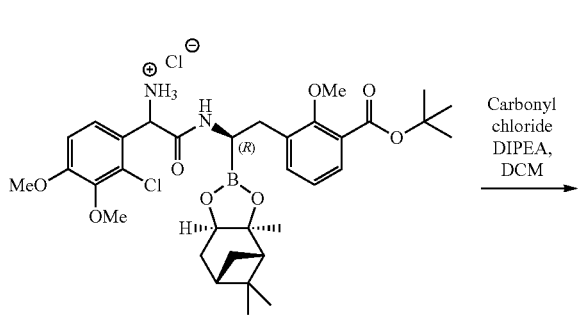

303
-continued

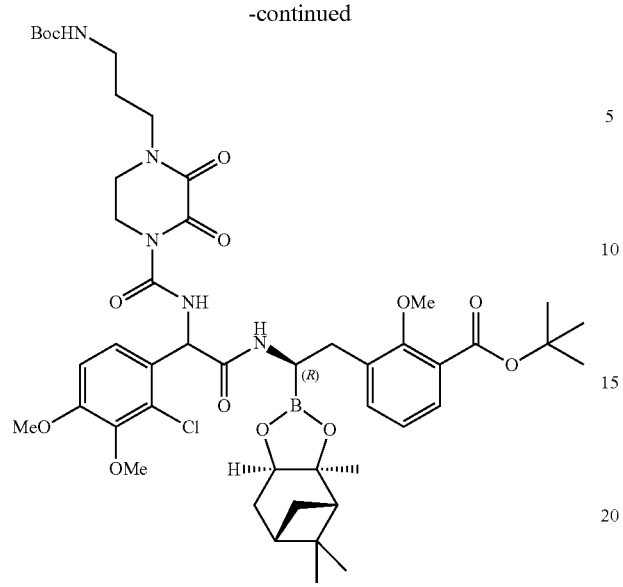

A mixture of 2-(((R)-2-(3-(tert-butoxycarbonyl)-2-methoxyphenyl)-1-((3aS,4S,6S,7aR)-3a,5,5-trimethylhexahydro-4,6-methanobenzo[d][1,3,2]dioxaborol-2-yl)ethyl)amino)-1-(2-chloro-3,4-dimethoxyphenyl)-2-oxoethan-1-aminium chloride (0.326 g, 0.47 mmol), tert-butyl (3-(4-(chlorocarbonyl)-2,3-dioxopiperazin-1-yl)propyl)carbamate (0.20 g, 0.60 mmol), prepared as described in the Step 1 of Example 236, and DIPEA (0.3 mL, 1.72 mmol) in DCM (15 mL) was stirred at room temperature for 3 h. The mixture was then quenched with brine, extracted with DCM (2×), dried over $Na_2SO_4$, and evaporated under reduced pressure to afford tert-butyl 3-((2R)-2-(2-(4-(3-((tert-butoxycarbonyl)amino)propyl)-2,3-dioxopiperazine-1-carboxamido)-2-(2-chloro-3,4-dimethoxyphenyl)acetamido)-2-((3aS,4S,6S,7aR)-3a,5,5-trimethylhexahydro-4,6-methanobenzo[d][1,3,2]dioxaborol-2-yl)ethyl)-2-methoxybenzoate (0.60 g), which was used in the next step directly. ESI-MS m/z 976.4 (M+Na)$^+$, 854.4 (M+H-Boc)$^+$, 798.3 (M+H-Boc-56)$^+$.

304

Step 2. Synthesis of (3R)-3-(2-(4-(3-aminopropyl)-2,3-dioxopiperazine-1-carboxamido)-2-(2-chloro-3,4-dihydroxyphenyl)acetamido)-2-hydroxy-3,4-dihydro-2H-benzo[e][1,2]oxaborinine-8-carboxylic acid The full deprotection of tert-butyl 3-((2R)-2-(2-(4-(3-((tert-butoxycarbonyl)amino)propyl)-2,3-dioxopiperazine-1-carboxamido)-2-(2-chloro-3,4-dimethoxyphenyl)acetamido)-2-((3aS,4S,6S,7aR)-3a,5,5-trimethylhexahydro-4,6-methanobenzo[d][1,3,2]dioxaborol-2-yl)ethyl)-2-methoxybenzoate was carried out as described in General Method A with $BBr_3$ to afford (3R)-3-(2-(4-(3-aminopropyl)-2,3-dioxopiperazine-1-carboxamido)-2-(2-chloro-3,4-dihydroxyphenyl)acetamido)-2-hydroxy-3,4-dihydro-2H-benzo[e][1,2]oxaborinine-8-carboxylic acid. ESI-MS m/z 604.2 (M+H)$^+$.

Example 234: (3R)-3-(2-((R)-4-ethyl-6-(hydroxymethyl)-2,3-dioxopiperazine-1-carboxamido)-2-(3-fluoro-5-hydroxypyridin-2-yl)acetamido)-2-hydroxy-3,4-dihydro-2H-benzo[e][1,2]oxaborinine-8-carboxylic acid

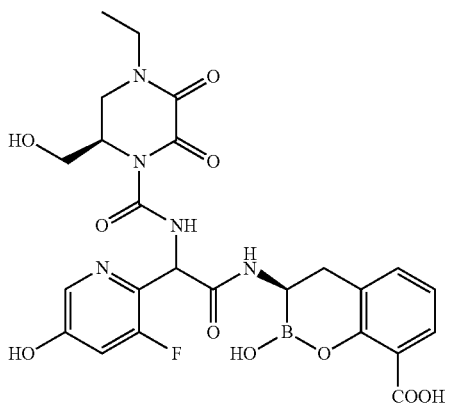 [SMILES: CCN1C[C@H](CO)N(C(=O)NC(C(=O)N[C@H]2Cc3cccc(C(=O)O)c3OB2O)c2ncc(O)cc2F)C(=O)C1=O]

Step 1: Synthesis of (R)-3-(benzyloxy)-2-((tert-butoxycarbonyl)amino)propyl methanesulfonate

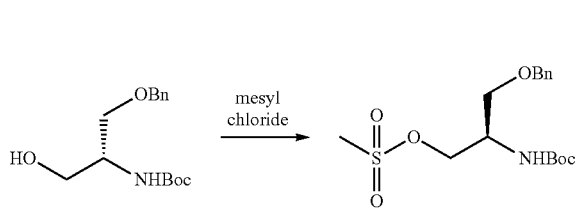 [SMILES: CC(C)(C)OC(=O)N[C@H](CO)COCc1ccccc1 ; CC(C)(C)OC(=O)N[C@H](COCc1ccccc1)COS(C)(=O)=O]

To tert-butyl (R)-(1-(benzyloxy)-3-hydroxypropan-2-yl)carbamate 0.9 g (3.21 mmol) in dichloromethane (8 mL) at 0° C. was added triethylamine 0.49 mL (3.53 mmol, 1.1 eq), followed by mesyl chloride 0.27 mL (3.53 mmol, 1.1 eq) and was warmed at RT for 1 h. The reaction was washed with water/brine, dried over sodium sulfate, and concentrated to afford the title compound. ESI-MS m/z 360 (MH)+.

Step 2: Synthesis of tert-butyl (R)-(1-(benzyloxy)-3-(ethylamino)propan-2-yl)carbamate

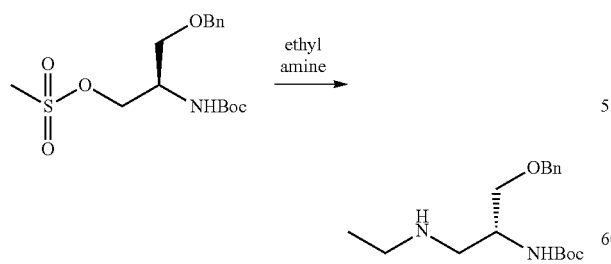

To (R)-3-(benzyloxy)-2-((tert-butoxycarbonyl)amino)propyl methanesulfonate 1.21 g (3.37 mmol) in tetrahydrofuran (15 mL) was added 2M ethyl amine in tetrahydrofuran (25.3 mL) (50.6 mmol, 15 eq) and the solution was stirred at RT for 7 days. The reaction was diluted with dichloromethane, washed with water/brine, dried over sodium sulfate and concentrated to afford the title compound. ESI-MS m/z 309 (MH)+.

Step 3: Synthesis of (R)-3-(benzyloxy)-N1-ethylpropane-1,2-diamine dihydrochloride

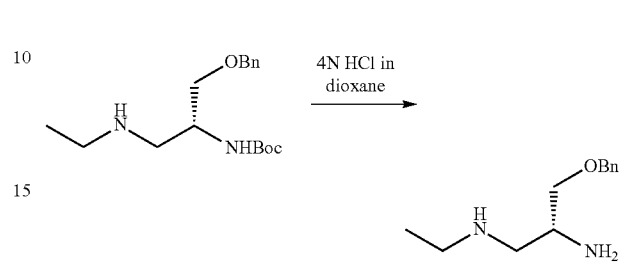

To tert-butyl (R)-(1-(benzyloxy)-3-(ethylamino)propan-2-yl)carbamate 1.1 g (3.51 mmol) was added 4N HCl in dioxane (12 mL), stirred at RT for 2 h and concentrated in vacuo to afford the title compound. ESI-MS m/z 209 (MH)+.

Step 4: Synthesis of (R)-5-((benzyloxy)methyl)-1-ethylpiperazine-2,3-dione

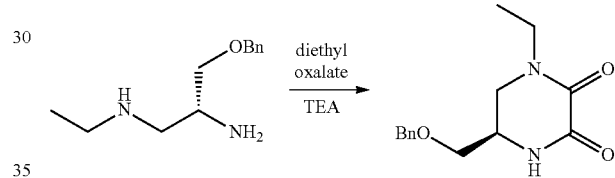

To (R)-3-(benzyloxy)-N1-ethylpropane-1,2-diamine dihydrochloride 0.98 g (3.51 mmol) in ethanol (19 mL) was added triethylamine 0.97 mL (7.01 mmol, 2 eq), followed by 0.51 mL (3.79 mmol, 1.08 eq) diethyl oxalate and the solution was heated at reflux for 18 h and concentrated. The product was purified by flash chromatography on silica gel (4% methanol/dichloromethane) to afford the title compound. ESI-MS m/z 263 (MH)+.

Step 4: Synthesis of (R)-6-((benzyloxy)methyl)-4-ethyl-2,3-dioxopiperazine-1-carbonyl chloride

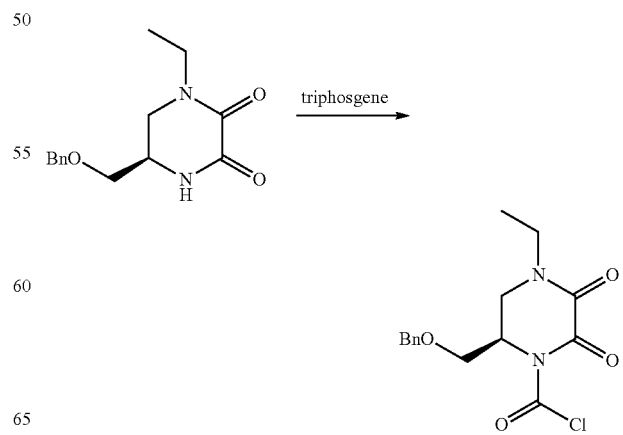

To (R)-5-((benzyloxy)methyl)-1-ethylpiperazine-2,3-dione 0.15 g (0.58 mmol) in tetrahydrofuran (1 mL)/dichloromethane (1 mL) at −20° C. was added chloro trimethylsilane 0.08 mL (0.64 mmol, 1.1 eq), followed by triethylamine 0.09 mL (0.7 mmol, 1.2 eq) and the mixture was warmed at 0° C. for 1 h. Triphosgene 0.07 g (0.23 mmol, 0.4 eq) in tetrahydrofuran (1 mL) was added, warmed at RT for 1 h and filtered. The filtrate was concentrated, triturated with ether, filtered and dried under vacuum to afford the title compound. ESI-MS m/z 325 (MH)⁺.

Step 5: Synthesis of (3R)-3-(2-((R)-4-ethyl-6-(hydroxymethyl)-2,3-dioxopiperazine-1-carboxamido)-2-(3-fluoro-5-hydroxypyridin-2-yl)acetamido)-2-hydroxy-3,4-dihydro-2H-benzo[e][1,2]oxaborinine-8-carboxylic acid

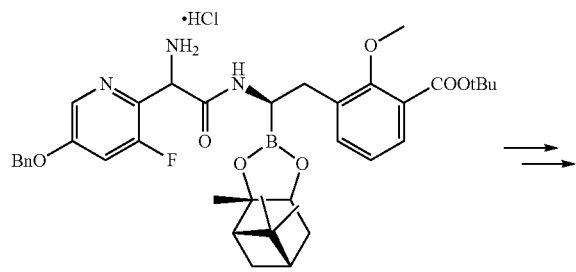

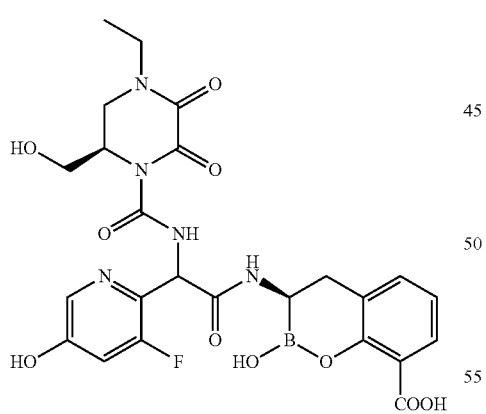

In a similar manner to the synthesis of Example 135, utilizing (R)-6-((benzyloxy)methyl)-4-ethyl-2,3-dioxopiperazine-1-carbonyl chloride in place of 4-ethyl-2,3-dioxopiperazine-1-carbonyl chloride, the title compound was prepared. ESI-MS m/z 574 (MH)⁺.

Example 235: (3R)-3-(2-(2-chloro-3,4-dihydroxyphenyl)-2-(4-(2-(3-ethylureido)ethyl)-2,3-dioxopiperazine-1-carboxamido)acetamido)-2-hydroxy-3,4-dihydro-2H-benzo[e][1,2]oxaborinine-8-carboxylic acid

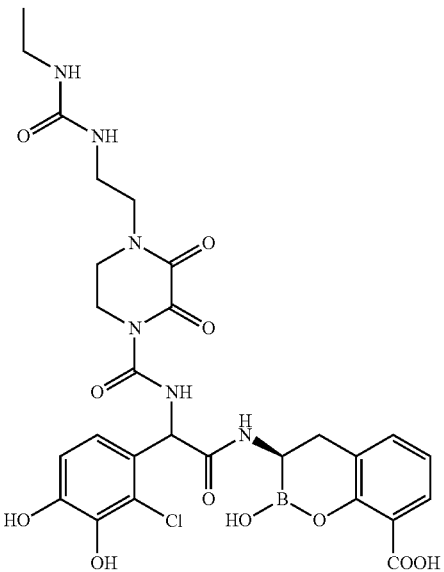 [SMILES: CCNC(=O)NCCN1CCN(C(=O)NC(C(=O)N[C@H]2Cc3cccc(C(=O)O)c3OB2O)c2ccc(O)c(O)c2Cl)C(=O)C1=O]

In a similar manner to the synthesis of Example 228, utilizing ethyl isocyanate in place of acetyl chloride, the title compound was prepared. ESI-MS m/z 661/663 (MH/MH+2)⁺.

Example 236: (R)-3-((R)-2-(4-(3-aminopropyl)-2,3-dioxopiperazine-1-carboxamido)-2-(2-chloro-3,4-dihydroxyphenyl)acetamido)-7-fluoro-2-hydroxy-3,4-dihydro-2H-benzo[e][1,2]oxaborinine-8-carboxylic acid

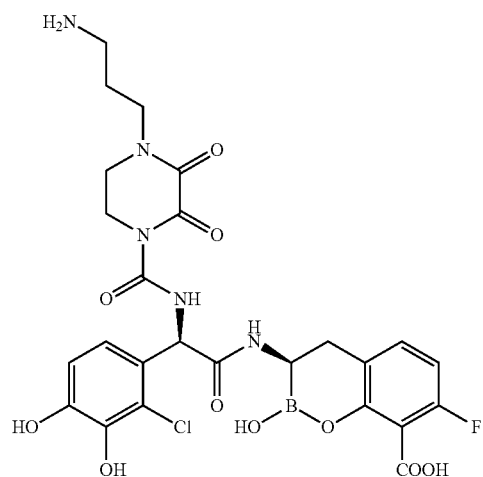 [SMILES: NCCCN1CCN(C(=O)N[C@@H](C(=O)N[C@H]2Cc3ccc(F)c(C(=O)O)c3OB2O)c2ccc(O)c(O)c2Cl)C(=O)C1=O]

Step 1. Synthesis of tert-butyl (3-(4-(chlorocarbonyl)-2,3-dioxopiperazin-1-yl)propyl)carbamate

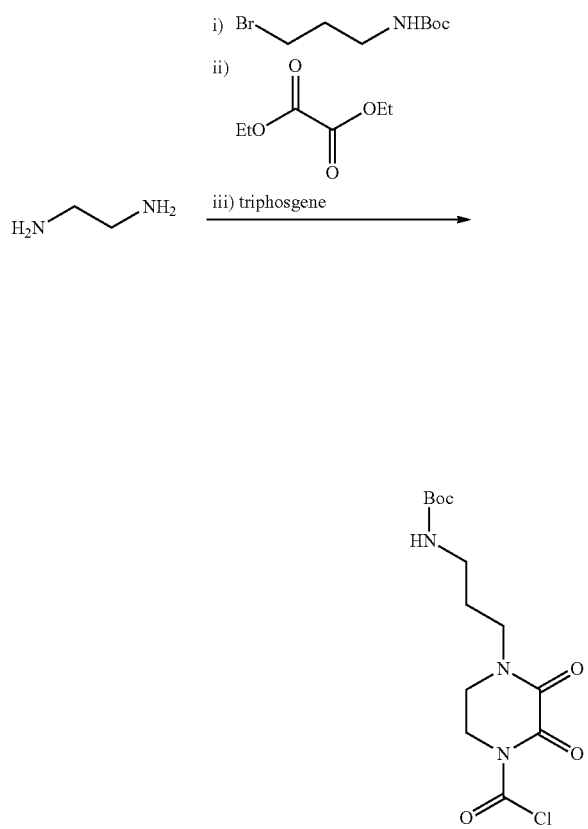

By following the same procedures as described for the synthesis of 4-fluoroethyl-2,3-dioxopiperazine-1-carbonyl chloride in Step 1 and Step 2 of Example 13, the title compound was prepared from tert-butyl (3-bromopropyl) carbamate.

Step 2. (R)-3-((S)-2-(4-(2-aminoethyl)-2,3-dioxopiperazine-1-carboxamido)-2-(2-chloro-3,4-dihydroxyphenyl)acetamido)-2-hydroxy-3,4-dihydro-2H-benzo[e][1,2]oxaborinine-8-carboxylic acid & (R)-3-((S)-2-(4-(2-aminoethyl)-2,3-dioxopiperazine-1-carboxamido)-2-(2-chloro-3,4-dihydroxyphenyl)acetamido)-2-hydroxy-3,4-dihydro-2H-benzo[e][1,2]oxaborinine-8-carboxylic acid In a similar manner to the synthesis of Example 124, utilizing the above carbonyl chloride in place of 4-ethyl-2,3-dioxopiperazine-1-carbonyl chloride, the title compound was prepared after reversed phase HPLC purification, isolated as the first eluting peak. ESI-MS m/z 622/624 (MH/MH+2)⁺.

Example 237: (3R)-3-(2-(2-chloro-3,4-dihydroxyphenyl)-2-((R)-4-ethyl-6-(hydroxymethyl)-2,3-dioxopiperazine-1-carboxamido)acetamido)-7-fluoro-2-hydroxy-3,4-dihydro-2H-benzo[e][1,2]oxaborinine-8-carboxylic acid

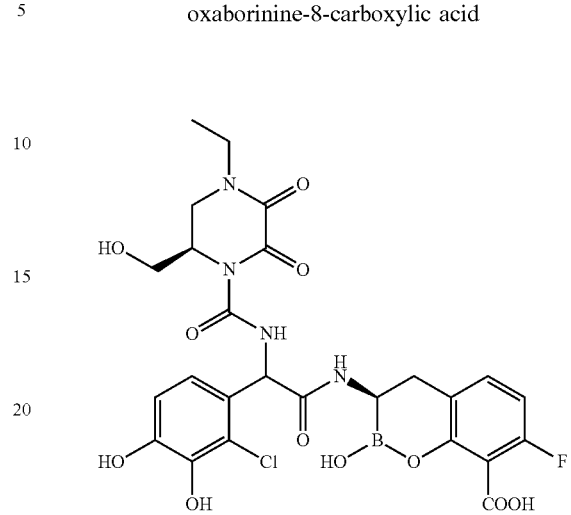

In a similar manner to the synthesis of Example 124 utilizing (R)-6-((benzyloxy)methyl)-4-ethyl-2,3-dioxopiperazine-1-carbonyl chloride (synthesis described in Example 234) in place of 4-ethyl-2,3-dioxopiperazine-1-carbonyl chloride in Step 3, the title compound was prepared. ESI-MS m/z 623/625 (MH/MH+2)⁺.

Example 238: (3R)-3-(2-((S)-6-(2-aminoethyl)-4-ethyl-2,3-dioxopiperazine-1-carboxamido)-2-(2-chloro-3,4-dihydroxyphenyl)acetamido)-7-fluoro-2-hydroxy-3,4-dihydro-2H-benzo[e][1,2]oxaborinine-8-carboxylic acid

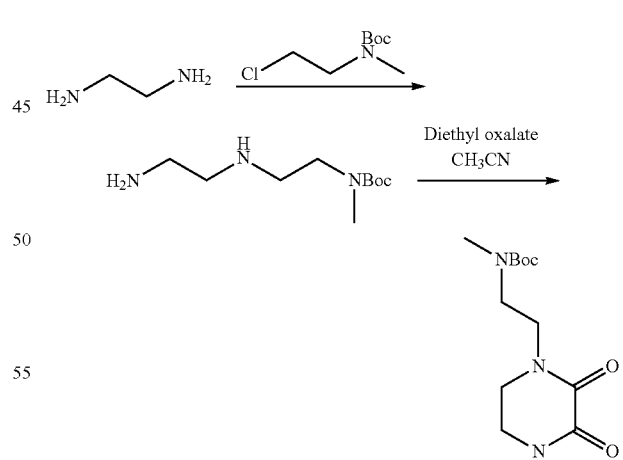

In a similar manner to the synthesis of Example 124 utilizing benzyl (S)-(2-(1-(chlorocarbonyl)-4-ethyl-5,6-dioxopiperazin-2-yl)ethyl)carbamate (synthesis described in Example 240) in place of 4-ethyl-2,3-dioxopiperazine-1-carbonyl chloride in Step 3, the title compound was prepared. ESI-MS m/z 636/638 (MH/MH+2)⁺.

Example 239: (3R)-3-(2-(2-chloro-3,4-dihydroxy-phenyl)-2-(4-(2-(methylamino)ethyl)-2,3-dioxopip-erazine-1-carboxamido)acetamido)-2-hydroxy-3,4-dihydro-2H-benzo[e][1,2]oxaborinine-8-carboxylic acid

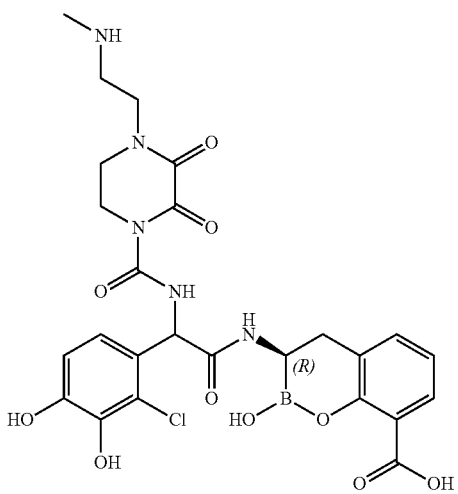

Step 1. Synthesis of tert-butyl (2-(2,3-dioxopiper-azin-1-yl)ethyl)(methyl)carbamate

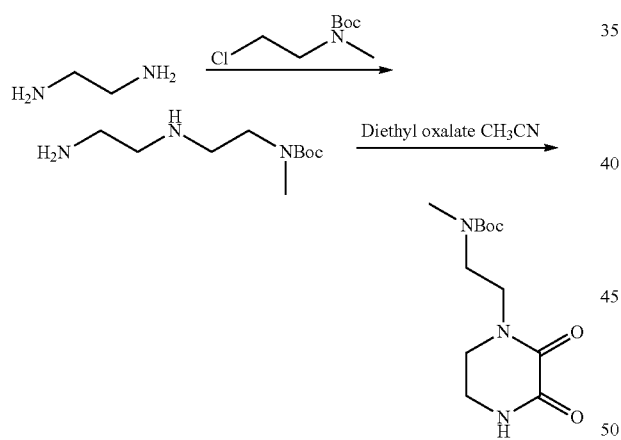

To ethylenediamine (21.88 g, 364 mmol) was added dropwise tert-butyl N-(2-chloroethyl)-N-methylcarbamate (6.984 g, 36 mmol) under argon. The mixture was stirred at room temperature for 27 h and then quenched with brine, extracted with Et$_2$O (2×), dried over Na$_2$SO$_4$, and evaporated under reduced pressure to afford 6.95 g (88.7%) of tert-butyl (2-((2-aminoethyl)amino)ethyl)(methyl)carbamate. ESI-MS m/z 218.2 (M+H)$^+$.

A mixture of tert-butyl (2-((2-aminoethyl)amino)ethyl)(methyl)carbamate (6.95 g, 32 mmol) and diethyl oxalate (5.785 g, 39.6 mmol) in CH$_3$CN (50 mL) was heated at 100° C. for 22 h. After the solvent was evaporated under reduced pressure, the residue was purified by flash chromatography on silica gel (340 g column) eluted with 0 to 15% MeOH/DCM to afford 5.82 g (67%) of tert-butyl (2-(2,3-dioxopip-erazin-1-yl)ethyl)(methyl)carbamate. ESI-MS m/z 294.2 (M+Na)$^+$, 172.2 (M+H-Boc)$^+$.

Step 2. Synthesis of tert-butyl (2-(4-(chlorocarbo-nyl)-2,3-dioxopiperazin-1-yl)ethyl)(methyl)carbamate

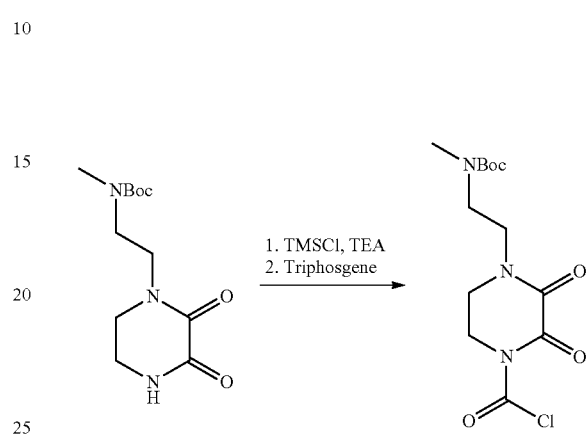

To a solution of tert-butyl (2-(2,3-dioxopiperazin-1-yl)ethyl)(methyl)carbamate (1.58 g, 5.82 mmol) in THF (10 mL) and DCM (10 mL) were added dropwise TMSCl (0.9 mL, 7.1 mmol) and TEA (1.0 mL, 7.2 mmol) at −65° C. under argon. After 3 h, the reaction mixture was then stirred at 0° C. for an additional 1 h. A solution of triphosgene (0.828 g, 2.79 mmol) in THF (10 mL) was added at 0° C. The mixture was allowed to slowly warm to room temperature overnight and then filtered, washed with THF. The filtrate was evaporated under reduced pressure to afford tert-butyl (2-(4-(chlorocarbonyl)-2,3-dioxopiperazin-1-yl)ethyl)(methyl)carbamate (2.03 g) as a solid, which was used in the next step directly.

Step 3. Synthesis of tert-butyl 3-((2R)-2-(2-(4-(2-((tert-butoxycarbonyl)(methyl)amino)ethyl)-2,3-dioxopiperazine-1-carboxamido)-2-(2-chloro-3,4-dimethoxyphenyl)acetamido)-2-((3aS,4S,6S,7aR)-3a,5,5-trimethylhexahydro-4,6-methanobenzo[d][1,3,2]dioxaborol-2-yl)ethyl)-2-methoxybenzoate

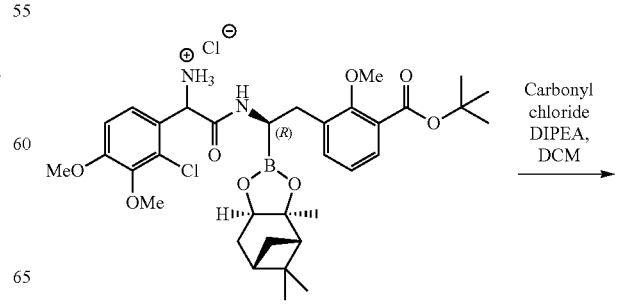

313
-continued

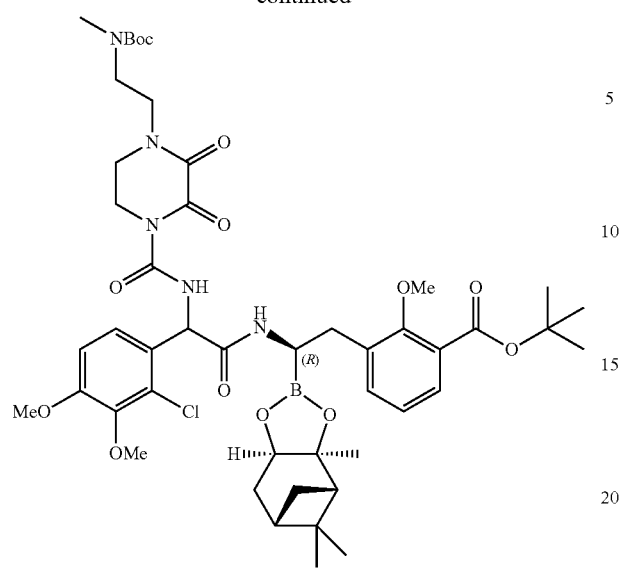

A mixture of 2-(((R)-2-(3-(tert-butoxycarbonyl)-2-methoxyphenyl)-1-((3aS,4S,6S,7aR)-3a,5,5-trimethylhexahydro-4,6-methanobenzo[d][1,3,2]dioxaborol-2-yl)ethyl)amino)-1-(2-chloro-3,4-dimethoxyphenyl)-2-oxoethan-1-aminium chloride (0.305 g, 0.44 mmol), tert-butyl (2-(4-(chlorocarbonyl)-2,3-dioxopiperazin-1-yl)ethyl)(methyl)carbamate (0.196 g, 0.587 mmol), and DIPEA (0.3 mL, 1.72 mmol) in DCM (15 mL) was stirred at room temperature for 3 h. The mixture was then quenched with brine, extracted with DCM (2×), dried over $Na_2SO_4$, and evaporated under reduced pressure to afford tert-butyl 3-((2R)-2-(2-(4-(2-((tert-butoxycarbonyl)(methyl)amino)ethyl)-2,3-dioxopiperazine-1-carboxamido)-2-(2-chloro-3,4-dimethoxyphenyl)acetamido)-2-((3aS,4S,6S,7aR)-3a,5,5-trimethylhexahydro-4,6-methanobenzo[d][1,3,2]dioxaborol-2-yl)ethyl)-2-methoxybenzoate (0.50 g), which was used in the next step directly. ESI-MS m/z 976.3 (M+Na)$^+$, 798.3 (M+H-Boc-56)$^+$.

314

Step 4. Synthesis of (3R)-3-(2-(2-chloro-3,4-dihydroxyphenyl)-2-(4-(2-(methylamino)ethyl)-2,3-dioxopiperazine-1-carboxamido)acetamido)-2-hydroxy-3,4-dihydro-2H-benzo[e][1,2]oxaborinine-8-carboxylic acid

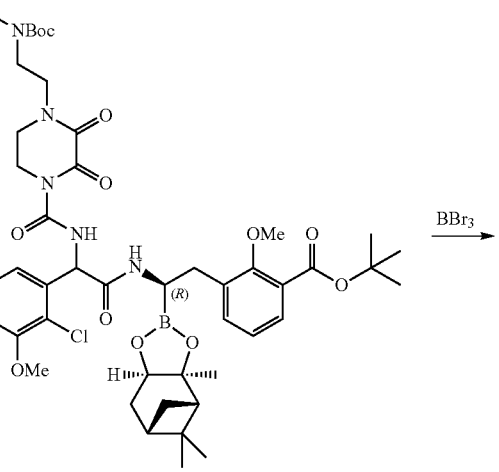

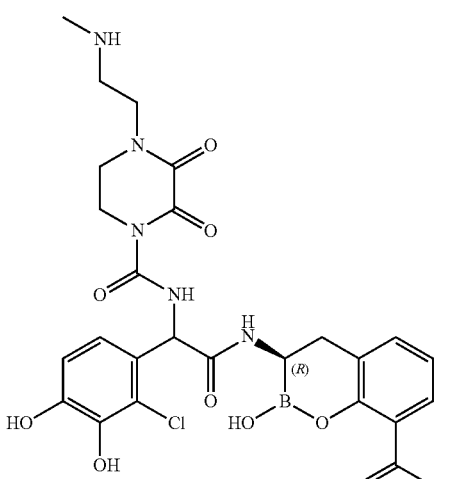

The full deprotection of tert-butyl 3-((2R)-2-(2-(4-(2-((tert-butoxycarbonyl)(methyl)amino)ethyl)-2,3-dioxopiperazine-1-carboxamido)-2-(2-chloro-3,4-dimethoxyphenyl)acetamido)-2-((3aS,4S,6S,7aR)-3a,5,5-trimethylhexahydro-4,6-methanobenzo[d][1,3,2]dioxaborol-2-yl)ethyl)-2-methoxybenzoate was carried out as described in General Method A with $BBr_3$ to afford (3R)-3-(2-(2-chloro-3,4-dihydroxyphenyl)-2-(4-(2-(methylamino)ethyl)-2,3-dioxopiperazine-1-carboxamido)acetamido)-2-hydroxy-3,4-dihydro-2H-benzo[e][1,2]oxaborinine-8-carboxylic acid. ESI-MS m/z 604.2 (M+H)$^+$.

Example 240: (3R)-3-(2-((S)-6-(2-aminoethyl)-4-ethyl-2,3-dioxopiperazine-1-carboxamido)-2-(3-fluoro-5-hydroxypyridin-2-yl)acetamido)-2-hydroxy-3,4-dihydro-2H-benzo[e][1,2]oxaborinine-8-carboxylic acid

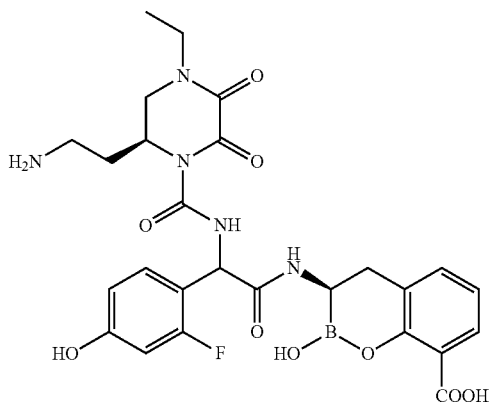 [SMILES: CCN1C[C@H](CCN)N(C(=O)NC(C(=O)N[C@H]2Cc3cccc(C(=O)O)c3OB2O)c2ccc(O)cc2F)C(=O)C1=O]

In a similar manner to the synthesis of Example 234, utilizing benzyl tert-butyl (4-hydroxybutane-1,3-diyl)(S)-dicarbamate in place of tert-butyl (R)-(1-(benzyloxy)-3-hydroxypropan-2-yl)carbamate in Step 1, the title compound was prepared. ESI-MS m/z 587 (MH)+.

Example 241: (3R)-3-(2-(4-ethyl-2,3-dioxopiperazine-1-carboxamido)-2-(3-fluoro-5-((2-hydroxyethyl)carbamoyl)pyridin-2-yl)acetamido)-2-hydroxy-3,4-dihydro-2H-benzo[e][1,2]oxaborinine-8-carboxylic acid

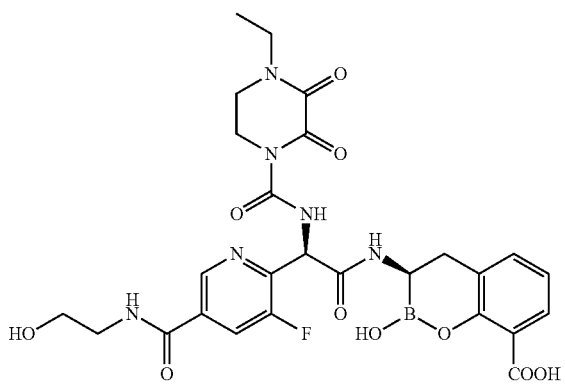 [SMILES: CCN1CCN(C(=O)N[C@@H](C(=O)N[C@H]2Cc3cccc(C(=O)O)c3OB2O)c2ncc(C(=O)NCCO)cc2F)C(=O)C1=O]

Step 1: Synthesis of 6-(1-((tert-butoxycarbonyl)amino)-2-ethoxy-2-oxoethyl)-5-fluoronicotinic acid

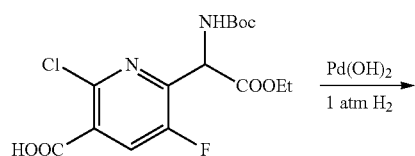

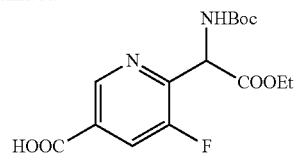

To 6-(1-((tert-butoxycarbonyl)amino)-2-ethoxy-2-oxoethyl)-2-chloro-5-fluoronicotinic acid 2 g (5.32 mmol) in methanol (20 mL) under an atmosphere of argon was added a spatula tip of palladium hydroxide and stirred at RT under a hydrogen balloon for 18 h. The reaction was filtered through a pad of celite and concentrated in vacuo to afford the title compound. ESI-MS m/z 343 (MH)+.

Step 2: Synthesis of ethyl 2-(5-((2-(benzyloxy)ethyl)carbamoyl)-3-fluoropyridin-2-yl)-2-((tert-butoxycarbonyl)amino)acetate

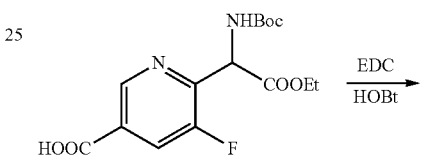

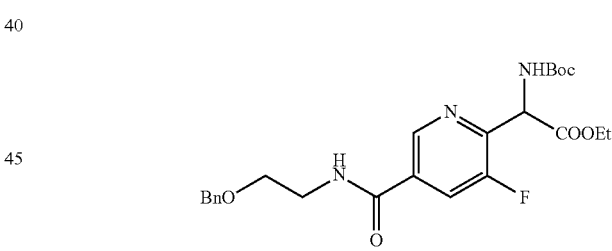

To 6-(1-((tert-butoxycarbonyl)amino)-2-ethoxy-2-oxoethyl)-5-fluoronicotinic acid 0.95 g (2.78 mmol) in dichloromethane (13 mL) was added triethylamine 1.15 mL (8.33 mmol, 3 eq), N-(3-dimethylaminopropyl)-N-ethylcarbodiimide hydrochloride 0.59 g (3.05 mmol, 1.1 eq), 1-hydroxybenzotriazole hydrate 0.41 g (3.06 mmol, 1.1 eq), followed by 2-(benzyloxy)ethan-1-amine) 0.5 mL (3.33 mmol, 1.2 eq) and the reaction was stirred at RT for 18 h. The mixture was diluted with dichloromethane, washed with water/brine, dried over sodium sulfate and concentrated. The product was purified by flash chromatography on silica gel (30% ethyl acetate/hexanes) to afford the title compound. ESI-MS m/z 476 (MH)+.

Step 3: Synthesis of (3R)-3-(2-(4-ethyl-2,3-di-oxopiperazine-1-carboxamido)-2-(3-fluoro-5-((2-hydroxyethyl)carbamoyl)pyridin-2-yl)acetamido)-2-hydroxy-3,4-dihydro-2H-benzo[e][1,2]oxaborinine-8-carboxylic acid
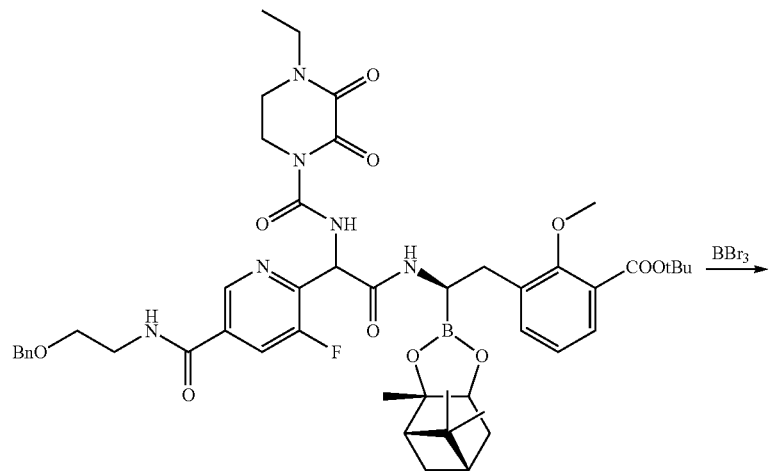
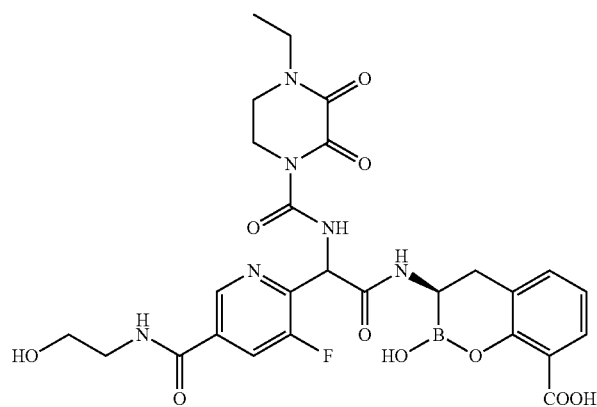

In a similar manner to the synthesis of Example 135, the title compound was prepared. ESI-MS m/z 615 (MH)⁺.

Example 242: (R)-3-((R)-2-(2-chloro-3,4-dihydroxyphenyl)-2-(4-(2-(methylamino)ethyl)-2,3-dioxopiperazine-1-carboxamido)acetamido)-7-fluoro-2-hydroxy-3,4-dihydro-2H-benzo[e][1,2]oxaborinine-8-carboxylic acid

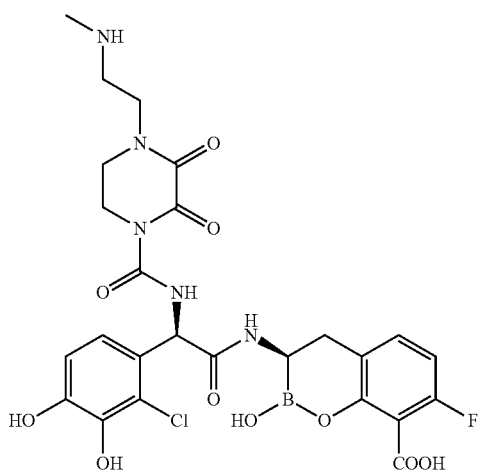 [SMILES: CNCCN1CCN(C(=O)N[C@@H](C(=O)N[C@H]2Cc3ccc(F)c(C(=O)O)c3OB2O)c2ccc(O)c(O)c2Cl)C(=O)C1=O]

In a similar manner to the synthesis of Example 124, utilizing tert-butyl (2-(4-(chlorocarbonyl)-2,3-dioxopiperazin-1-yl)ethyl)(methyl)carbamate (synthesis described in Example 239) in place of 4-ethyl-2,3-dioxopiperazine-1-carbonyl chloride, the title compound was prepared after reversed phase HPLC purification, isolated as the first eluting peak. ESI-MS m/z 622/624 (MH/MH+2)⁺.

Example 243: (3R)-3-(2-(4-(2-acetamidoethyl)-2,3-dioxopiperazine-1-carboxamido)-2-(2-chloro-3,4-dihydroxyphenyl)acetamido)-7-fluoro-2-hydroxy-3,4-dihydro-2H-benzo[e][1,2]oxaborinine-8-carboxylic acid

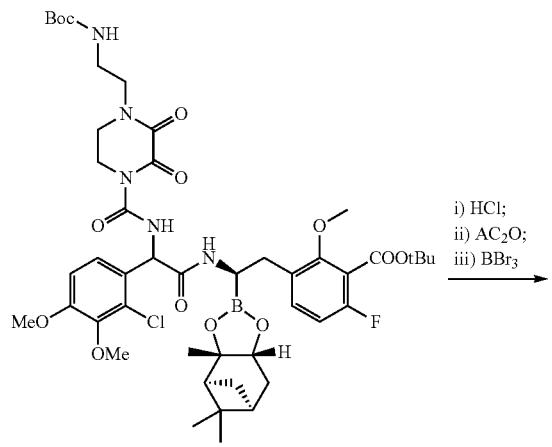

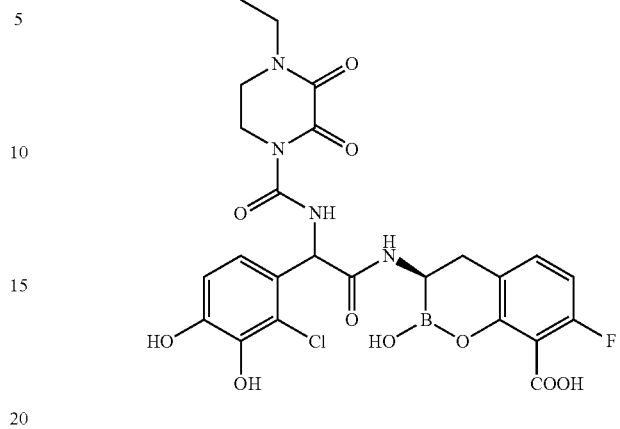

The fully protected intermediate from the synthesis of Example 227 (1.5 g, 1.57 mmol) was treated with 2.0 M hydrogen chloride in diethylether (20 mL, 40 mmol) and 4.0 M hydrogen chloride in dioxane (10 mL, 40 mmol) at RT overnight, then concentrated in vacuo. To this crude amine intermediate (252 mg, 0.3 mmol) in DCM (12 mL) was added diisopropylethylamine (0.18 mL, 1 mmol) followed by acetic anhydride (61 mg, 0.6 mmol). The reaction mixture was stirred at RT for 1 h, washed with water, brine, dried and concentrated in vacuo. This crude product was subjected to deprotection with BBr₃ by following the General Method A to afford the title compound. ESI-MS m/z 650/652 (MH/MH+2)⁺.

Example 244: (3R)-3-(2-(2-chloro-3,4-dihydroxyphenyl)-2-(2,3-dioxo-4-(2-(sulfamoylamino)ethyl)piperazine-1-carboxamido)acetamido)-7-fluoro-2-hydroxy-3,4-dihydro-2H-benzo[e][1,2]oxaborinine-8-carboxylic acid

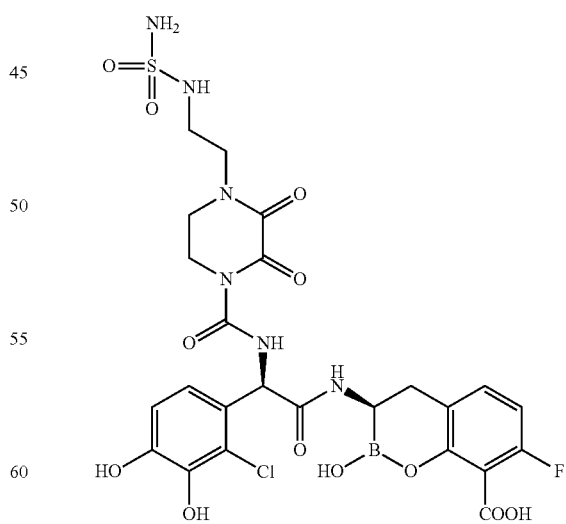

In a similar manner to the synthesis of Example 243, utilizing tert-butyl (chlorosulfonyl)carbamate in place of acetic anhydride, the title compound was prepared. ESI-MS m/z 687/689 (MH/MH+2)⁺.

Example 245: (3R)-3-(2-(4-ethyl-2,2-dimethyl-5,6-dioxopiperazine-1-carboxamido)-2-(3-fluoro-5-hydroxypyridin-2-yl)acetamido)-2-hydroxy-3,4-dihydro-2H-benzo[e][1,2]oxaborinine-8-carboxylic acid

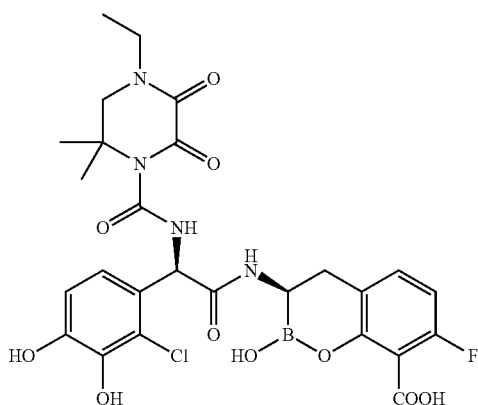 [SMILES: CCN1CC(C)(C)N(C(=O)N[C@@H](C(=O)N[C@H]2Cc3ccc(F)c(C(=O)O)c3OB2O)c2ccc(O)c(O)c2Cl)C(=O)C1=O]

In a similar manner to the synthesis of Example 135, utilizing 4-ethyl-2,2-dimethyl-5,6-dioxopiperazine-1-carbonyl chloride in place of 4-ethyl-2,3-dioxopiperazine-1-carbonyl chloride, the title compound was prepared. ESI-MS m/z 572 (MH)+.

Example 246: (3R)-3-(2-(5-carbamoyl-3-fluoropyridin-2-yl)-2-(4-ethyl-2,3-dioxopiperazine-1-carboxamido)acetamido)-2-hydroxy-3,4-dihydro-2H-benzo[e][1,2]oxaborinine-8-carboxylic acid

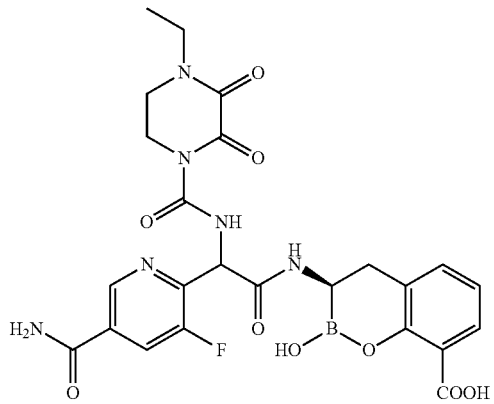 [SMILES: CCN1CCN(C(=O)NC(C(=O)N[C@H]2Cc3cccc(C(=O)O)c3OB2O)c2ncc(C(N)=O)cc2F)C(=O)C1=O]

In a similar manner to the synthesis of Example 241, utilizing (2,4-dimethoxyphenyl)methanamine in place of 2-(benzyloxy)ethan-1-amine in Step 2, the title compound was prepared. ESI-MS m/z 571 (MH)+.

Example 247: (3R)-3-(2-(4-ethyl-2,3-dioxopiperazine-1-carboxamido)-2-(4-hydroxy-3-nitrophenyl)acetamido)-2-hydroxy-3,4-dihydro-2H-benzo[e][1,2]oxaborinine-8-carboxylic acid

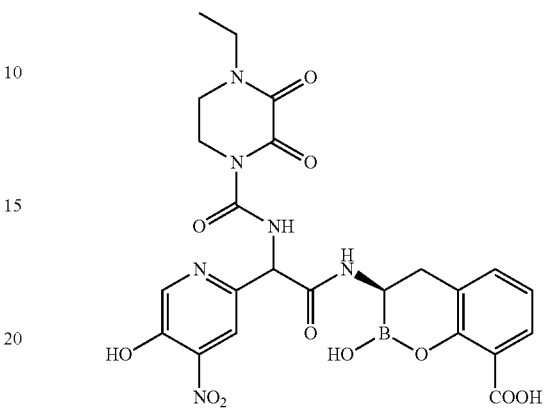

In a similar manner to the synthesis of Example 37, utilizing 4-methoxy-3-nitrobenzaldehyde in place of 2-chloro-3,4-dimethoxybenzaldehyde in Step 1, the title compound was prepared. ESI-MS m/z 570 (M+H)+.

Example 248: (3R)-3-(2-((S)-4-(2-aminoethyl)-6-methyl-2,3-dioxopiperazine-1-carboxamido)-2-(2-chloro-3,4-dihydroxyphenyl)acetamido)-2-hydroxy-3,4-dihydro-2H-benzo[e][1,2]oxaborinine-8-carboxylic acid

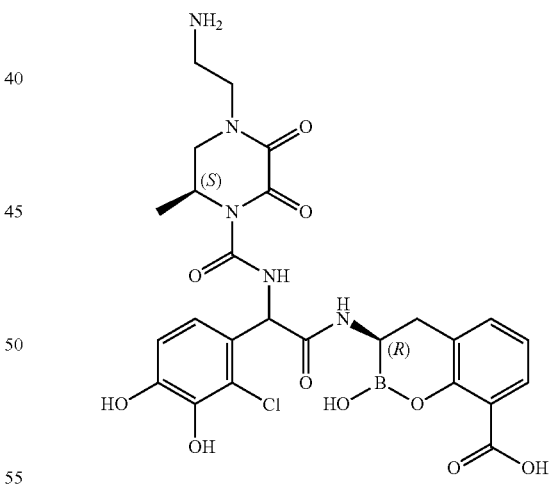

Step 1. Synthesis of tert-butyl (S)-(2-(5-methyl-2,3-dioxopiperazin-1-yl)ethyl)carbamate

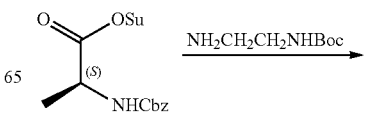

-continued

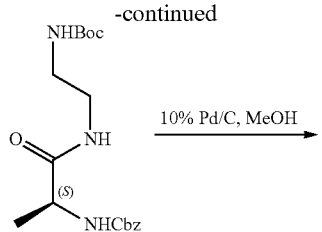

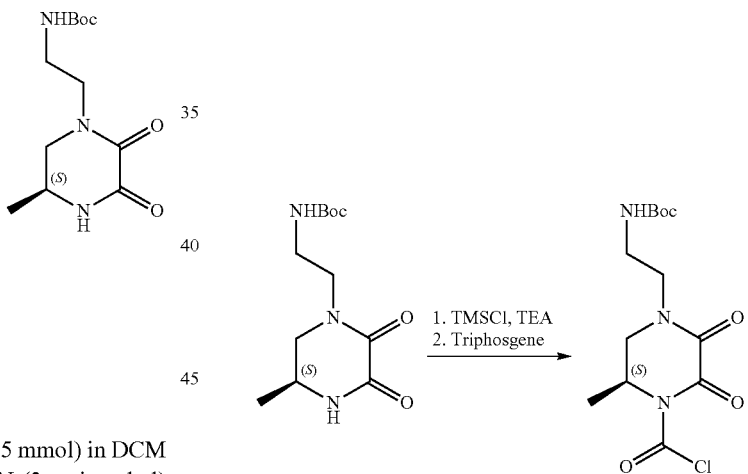

To a mixture of Z-Ala-OSu (16.18 g, 50.5 mmol) in DCM (300 mL) was added dropwise tert-butyl N-(2-aminoethyl)carbamate (8.83 g, 55.1 mmol) at 0° C. The mixture was allowed to slowly warm to room temperature overnight. After 23 h, the reaction mixture was quenched with saturated NaHCO$_3$, extracted with DCM (3×), dried over Na$_2$SO$_4$. After the solvent was evaporated under reduced pressure, the residue was purified by flash chromatography on silica gel (120 g column) eluted with 0 to 10% MeOH/DCM to afford 13.55 (73.4%) of benzyl (S)-(1-((2-((tert-butoxycarbonyl)amino)ethyl)amino)-1-oxopropan-2-yl)carbamate. ESI-MS m/z 388.2 (M+Na)$^+$, 310.1 (M+H−56)$^+$, 266.2 (M+H−Boc)$^+$.

A mixture of benzyl (S)-(1-((2-((tert-butoxycarbonyl)amino)ethyl)amino)-1-oxopropan-2-yl)carbamate (13.55 g, 37.08 mmol) and 10% Pd/C (wet support, 2.08 g, 0.98 mmol) in MeOH (200 mL) was stirred under hydrogen balloon for 2 h. The mixture was then filtered, washed with MeOH. The filtrate was evaporated under reduced pressure to afford tert-butyl (S)-(2-(2-aminopropanamido)ethyl)carbamate (8.93 g), which was used in the next step directly. ESI-MS m/z 232.2 (M+H)$^+$.

To a solution of tert-butyl (S)-(2-(2-aminopropanamido)ethyl)carbamate (4.36 g, 18.8 mmol) in THF (40 mL) was added dropwise a solution of Borane tetrahydrofuran complex solution (1.0 M in THF, 100 mL, 100 mmol) at 0° C. The mixture was allowed to slowly warm to room temperature overnight. After 7 d, the reaction mixture was carefully quenched with MeOH at 0° C. The mixture was then evaporated under reduced pressure to afford tert-butyl (S)-(2-((2-aminopropyl)amino)ethyl)carbamate (3.48 g), which was used in the next step directly. ESI-MS m/z 218.2 (M+H)$^+$.

A mixture of tert-butyl (S)-(2-((2-aminopropyl)amino)ethyl)carbamate (3.48 g), obtained as described above, and diethyl oxalate (2.339 g, 16 mmol) in CH$_3$CN (50 mL) was heated at 90° C. for 18 h. After the solvent was evaporated under reduced pressure, the residue was purified by flash chromatography on silica gel (100 g column) eluted with 0 to 15% MeOH/DCM to afford 0.62 g (14%) of tert-butyl (S)-(2-(5-methyl-2,3-dioxopiperazin-1-yl)ethyl)carbamate. ESI-MS m/z 565.3 (2M+Na)$^+$, 443.2 (2M+H-Boc)$^+$, 216.1 (M+H−56)$^+$.

Step 2. Synthesis of tert-butyl (S)-(2-(4-(chlorocarbonyl)-5-methyl-2,3-dioxopiperazin-1-yl)ethyl)carbamate To a solution of tert-butyl (S)-(2-(5-methyl-2,3-dioxopiperazin-1-yl)ethyl)carbamate (0.51 g, 1.88 mmol) in THF (6 mL) and DCM (6 mL) were added dropwise TMSCl (0.3 mL, 2.36 mmol) and TEA (0.33 mL, 2.37 mmol) at −65° C. under argon. After 3 h, the reaction mixture was then stirred at 0° C. for an additional 2 h. A solution of triphosgene (0.30 g, 1.01 mmol) in THF (10 mL) was added at 0° C. The mixture was allowed to slowly warm to room temperature overnight and then filtered, washed with THF. The filtrate was evaporated under reduced pressure to afford tert-butyl (S)-(2-(4-(chlorocarbonyl)-5-methyl-2,3-dioxopiperazin-1-yl)ethyl)carbamate (0.66 g) as a solid, which was used in the next step directly.

Step 3. Synthesis of tert-butyl 3-((2R)-2-(2-((S)-4-(2-((tert-butoxycarbonyl)amino)ethyl)-6-methyl-2,3-dioxopiperazine-1-carboxamido)-2-(2-chloro-3,4-dimethoxyphenyl)acetamido)-2-((3aS,4S,6S,7aR)-3a,5,5-trimethylhexahydro-4,6-methanobenzo[d][1,3,2]dioxaborol-2-yl)ethyl)-2-methoxybenzoate

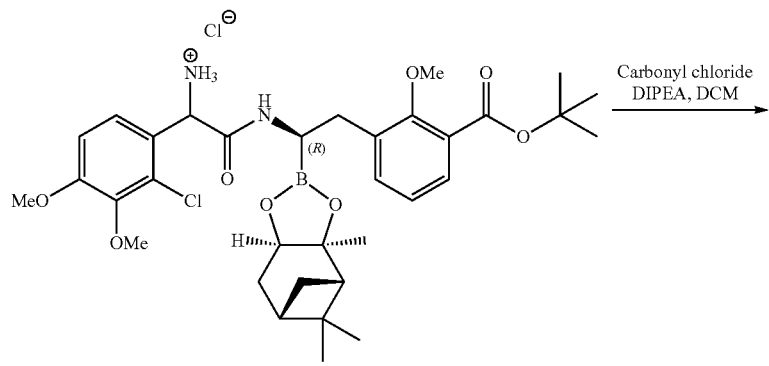

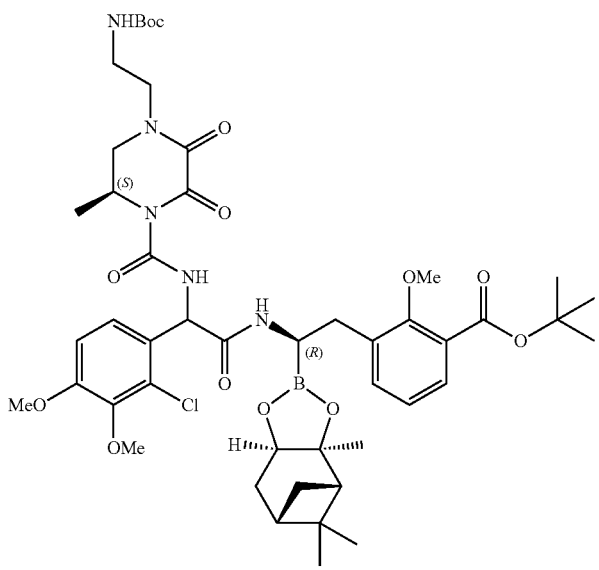

A mixture of 2-(((R)-2-(3-(tert-butoxycarbonyl)-2-methoxyphenyl)-1-((3aS,4S,6S,7aR)-3a,5,5-trimethylhexahydro-4,6-methanobenzo[d][1,3,2]dioxaborol-2-yl)ethyl)amino)-1-(2-chloro-3,4-dimethoxyphenyl)-2-oxoethan-1-aminium chloride (0.316 g, 0.456 mmol), tert-butyl (S)-(2-(4-(chlorocarbonyl)-5-methyl-2,3-dioxopiperazin-1-yl)ethyl)carbamate (0.20 g, 0.60 mmol), and DIPEA (0.3 mL, 1.72 mmol) in DCM (15 mL) was stirred at room temperature for 3 h. The mixture was then quenched with brine, extracted with DCM (2×), dried over $Na_2SO_4$, and evaporated under reduced pressure to afford tert-butyl 3-((2R)-2-(2-((S)-4-(2-((tert-butoxycarbonyl)amino)ethyl)-6-methyl-2,3-dioxopiperazine-1-carboxamido)-2-(2-chloro-3,4-dimethoxyphenyl)acetamido)-2-((3aS,4S,6S,7aR)-3a,5,5-trimethylhexahydro-4,6-methanobenzo[d][1,3,2]dioxaborol-2-yl)ethyl)-2-methoxybenzoate (0.53 g), which was used in the next step directly. ESI-MS m/z 976.4 (M+Na)$^+$, 898.3 (M+H−56)$^+$, 798.3 (M+H-Boc-56)$^+$.

327

Step 4. Synthesis of (3R)-3-(2-((S)-4-(2-amino-ethyl)-6-methyl-2,3-dioxopiperazine-1-carbox-amido)-2-(2-chloro-3,4-dihydroxyphenyl)acet-amido)-2-hydroxy-3,4-dihydro-2H-benzo[e][1,2] oxaborinine-8-carboxylic acid

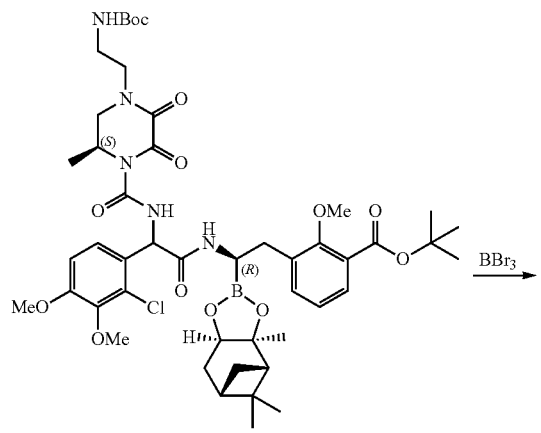

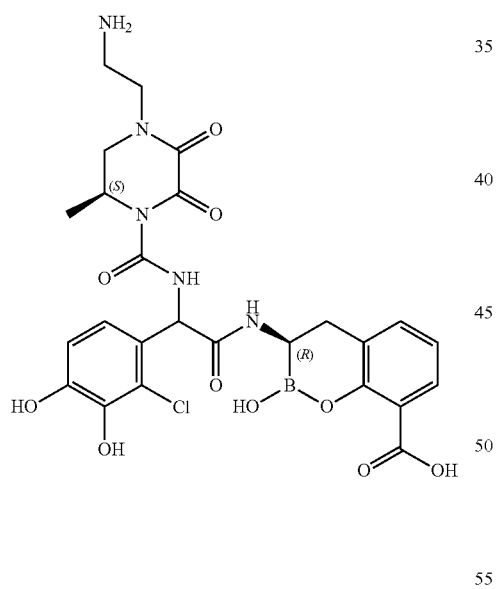

The full deprotection of tert-butyl 3-((2R)-2-(2-((S)-4-(2-((tert-butoxycarbonyl)amino)ethyl)-6-methyl-2,3-dioxopiperazine-1-carboxamido)-2-(2-chloro-3,4-dimethoxyphenyl) acetamido)-2-((3aS,4S,6S,7aR)-3a,5,5-trimethylhexahydro-4,6-methanobenzo[d][1,3,2]dioxaborol-2-yl)ethyl)-2-methoxybenzoate was carried out as described in General Method A with BBr₃ to afford (3R)-3-(2-((S)-4-(2-amino-ethyl)-6-methyl-2,3-dioxopiperazine-1-carboxamido)-2-(2-chloro-3,4-dihydroxyphenyl)acetamido)-2-hydroxy-3,4-dihydro-2H-benzo[e][1,2]oxaborinine-8-carboxylic acid. ESI-MS m/z 604.2 (M+H)⁺.

328

Example 249: (3R)-3-(2-(4-(carboxymethyl)-2,3-dioxopiperazine-1-carboxamido)-2-(2-chloro-3,4-dihydroxyphenyl)acetamido)-2-hydroxy-3,4-di-hydro-2H-benzo[e][1,2]oxaborinine-8-carboxylic acid

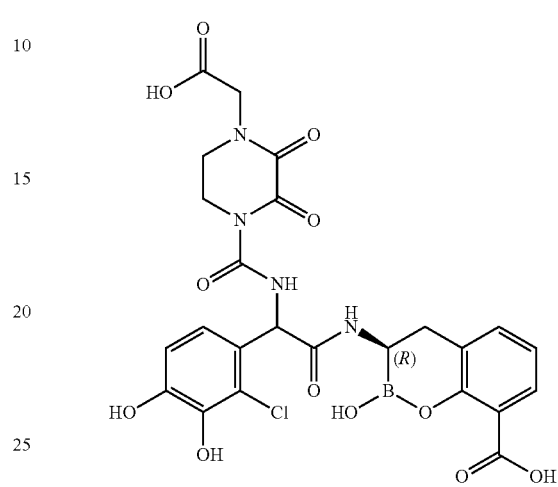

Step 1. Synthesis of ethyl 2-(2,3-dioxopiperazin-1-yl)acetate

A mixture of N-Beta-aminoethyl-gly-OEt 2HCl (5.37 g, 24.5 mmol), K₂CO₃ (12.40 g, 89.7 mmol), and diethyl oxalate (4.076 g, 27.9 mmol) in CH₃CN (100 mL) was heated at 90° C. for 47 h. The mixture was then filtered through Celite, washed with DCM. After the solvent was evaporated under reduced pressure, the residue was purified by flash chromatography on silica gel (100 g column) eluted with 0 to 20% MeOH/DCM to afford 1.54 g (31%) of ethyl 2-(2,3-dioxopiperazin-1-yl)acetate. ESI-MS m/z 423.1 (2M+Na)⁺, 401.2 (2M+H)⁺, 201.1 (M+H)⁺.

Step 2. Synthesis of ethyl 2-(4-(chlorocarbonyl)-2,3-dioxopiperazin-1-yl)acetate

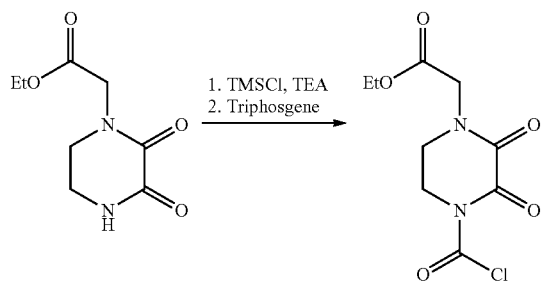 [SMILES: CCOC(=O)CN1CCNC(=O)C1=O ; CCOC(=O)CN1CCN(C(=O)Cl)C(=O)C1=O]

To a solution of ethyl 2-(2,3-dioxopiperazin-1-yl)acetate (1.51 g, 7.54 mmol) in THF (15 mL) and DCM (15 mL) were added dropwise TMSCl (1.2 mL, 9.45 mmol) and TEA (1.5 mL, 10.8 mmol) at −65° C. under argon. After 3 h, the reaction mixture was then stirred at 0° C. for an additional 1 h. A solution of triphosgene (1.174 g, 3.95 mmol) in THF (15 mL) was added at 0° C. The mixture was allowed to slowly warm to room temperature overnight and then filtered, washed with THF. The filtrate was evaporated under reduced pressure to afford ethyl 2-(4-(chlorocarbonyl)-2,3-dioxopiperazin-1-yl)acetate (2.20 g), which was used in the next step directly.

Step 3. Synthesis of tert-butyl 3-((2R)-2-(2-(2-chloro-3,4-dimethoxyphenyl)-2-(4-(2-ethoxy-2-oxoethyl)-2,3-dioxopiperazine-1-carboxamido)acetamido)-2-((3aS,4S,6S,7aR)-3a,5,5-trimethylhexahydro-4,6-methanobenzo[d][1,3,2]dioxaborol-2-yl)ethyl)-2-methoxybenzoate

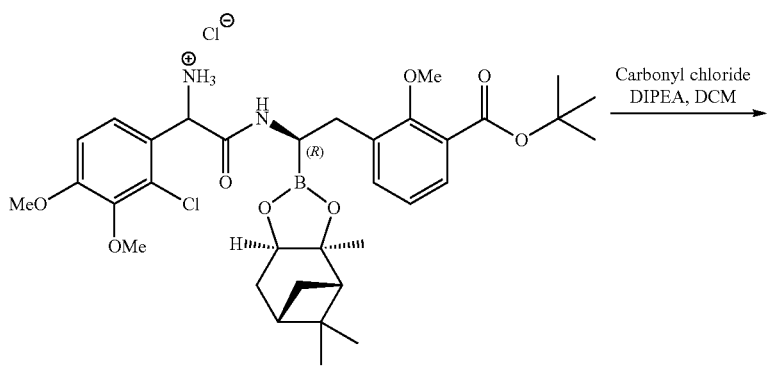

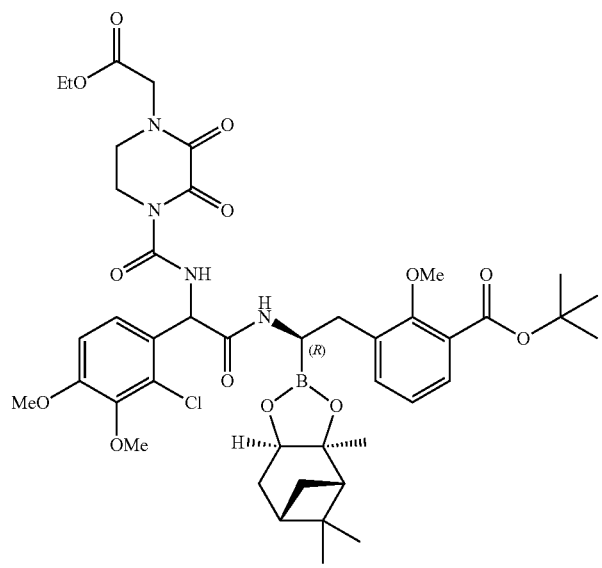

A mixture of 2-(((R)-2-(3-(tert-butoxycarbonyl)-2-methoxyphenyl)-1-((3aS,4S,6S,7aR)-3a,5,5-trimethylhexahydro-4,6-methanobenzo[d][1,3,2]dioxaborol-2-yl)ethyl)amino)-1-(2-chloro-3,4-dimethoxyphenyl)-2-oxoethan-1-aminium chloride (0.909 g, 1.31 mmol), ethyl 2-(4-(chlorocarbonyl)-2,3-dioxopiperazin-1-yl)acetate (0.52 g, 1.98 mmol), and DIPEA (0.9 mL, 5.17 mmol) in DCM (40 mL) was stirred at room temperature for 17 h. The mixture was then quenched with brine, extracted with DCM (2×), dried over $Na_2SO_4$, and evaporated under reduced pressure to afford tert-butyl 3-((2R)-2-(2-(2-chloro-3,4-dimethoxyphenyl)-2-(4-(2-ethoxy-2-oxoethyl)-2,3-dioxopiperazine-1-carboxamido)acetamido)-2-((3aS,4S,6S,7aR)-3a,5,5-trimethylhexahydro-4,6-methanobenzo[d][1,3,2]dioxaborol-2-yl)ethyl)-2-methoxybenzoate (1.82 g), which was used in the next step directly. ESI-MS m/z 827.3 (M+H−56)⁺.

Step 4. Synthesis of (3R)-3-(2-(4-(carboxymethyl)-2,3-dioxopiperazine-1-carboxamido)-2-(2-chloro-3,4-dihydroxyphenyl)acetamido)-2-hydroxy-3,4-dihydro-2H-benzo[e][1,2]oxaborinine-8-carboxylic acid

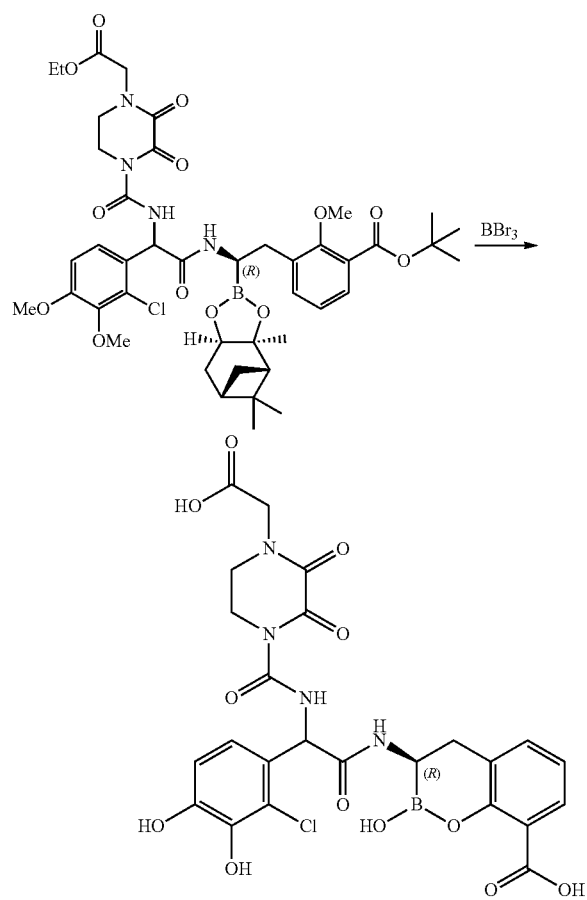

The full deprotection of tert-butyl 3-((2R)-2-(2-(2-chloro-3,4-dimethoxyphenyl)-2-(4-(2-ethoxy-2-oxoethyl)-2,3-dioxopiperazine-1-carboxamido)acetamido)-2-((3aS,4S,6S,7aR)-3a,5,5-trimethylhexahydro-4,6-methanobenzo[d][1,3,2]dioxaborol-2-yl)ethyl)-2-methoxybenzoate was carried out as described in General Method A with $BBr_3$ to afford (3R)-3-(2-(4-(carboxymethyl)-2,3-dioxopiperazine-1-carboxamido)-2-(2-chloro-3,4-dihydroxyphenyl)acetamido)-2-hydroxy-3,4-dihydro-2H-benzo[e][1,2]oxaborinine-8-carboxylic acid. ESI-MS m/z 605.1 (M+H)⁺.

Example 250: (R)-3-((R)-2-((S)-4-(2-aminoethyl)-6-methyl-2,3-dioxopiperazine-1-carboxamido)-2-(2-chloro-3,4-dihydroxyphenyl)acetamido)-7-fluoro-2-hydroxy-3,4-dihydro-2H-benzo[e][1,2]oxaborinine-8-carboxylic acid

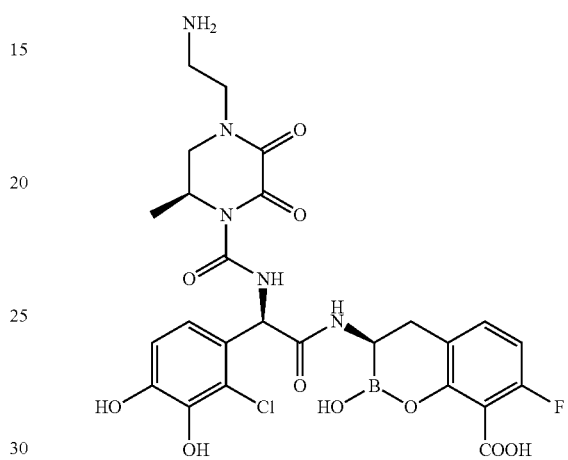

In a similar manner to the synthesis of Example 124, utilizing tert-butyl (S)-(2-(4-(chlorocarbonyl)-5-methyl-2,3-dioxopiperazin-1-yl)ethyl)carbamate (synthesis described in Example 248) in place of 4-ethyl-2,3-dioxopiperazine-1-carbonyl chloride, the title compound was prepared after reversed phase HPLC purification, isolated as the first eluting peak. ESI-MS m/z 608/610 (MH/MH+2)⁺.

Example 251: (R)-3-((R)-2-(2-chloro-6-fluoro-3,4-dihydroxyphenyl)-2-(4-ethyl-2,3-dioxopiperazine-1-carboxamido)acetamido)-7-fluoro-2-hydroxy-3,4-dihydro-2H-benzo[e][1,2]oxaborinine-8-carboxylic acid

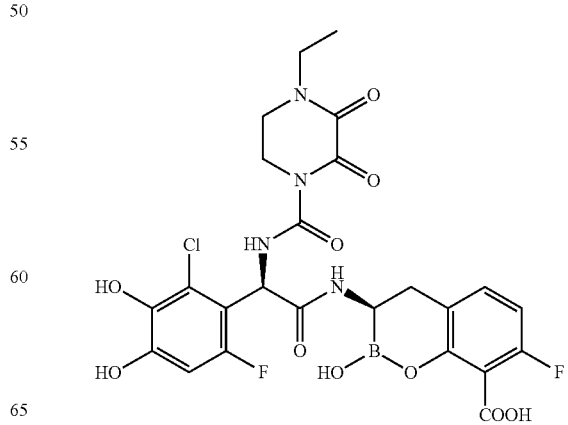

Step 1. Synthesis of 2-fluoro-5-hydroxy-4-methoxybenzaldehyde

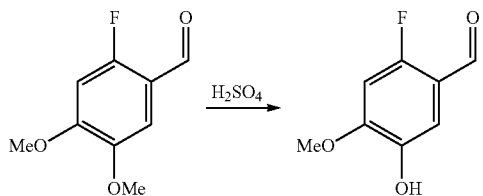

2-Fluoro-4,5-dimethoxybenzaldehyde (7.5 g, 40.8 mmol) in concentrated sulfuric acid (30 mL) was heated at 90° C. for 5 h, then cooled to RT, poured into ice-water, extracted with EtOAc. The organic extracts were combined, washed with brine, dried over $Na_2SO_4$, concentrated in vacuo. To the residue was added a mixed solvent of hexane-EtOAc (1:1, 50 mL). The solid was collected by filtration to afford the title compound, 4.6 g. ESI-MS m/z 171 $(MH)^+$.

Step 2. Synthesis of 2-chloro-6-fluoro-3-hydroxy-4-methoxybenzaldehyde

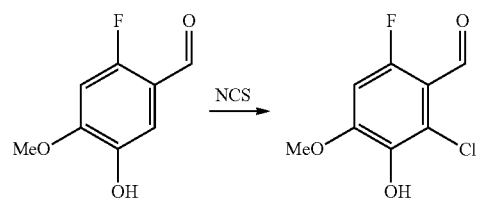

To the above product (4.6 g, 27.1 mmol) in DMF (50 mL) was added NCS (4.81 g, 36 mmol). The reaction mixture was stirred at RT overnight, diluted with diethylether, washed with water, brine, dried over $Na_2SO_4$, concentrated in vacuo to afford the crude product, 5.2 g, which was used directly for the next step without further purification. ESI-MS m/z 205/207 $(MH/MH+2)^+$.

Step 3. Synthesis of 2-chloro-6-fluoro-3,4-dimethoxybenzaldehyde

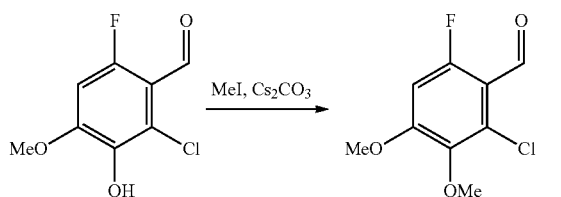 [SMILES: COc1cc(F)c(C=O)c(Cl)c1O ; COc1cc(F)c(C=O)c(Cl)c1OC]

To the above crude product (5.2 g, 25.5 mmol) in DMF (60 mL) was added $Cs_2CO_3$ (20.8 g, 63.8 mmol) followed by iodomethane (5 mL, 80 mmol). The reaction mixture was stirred at RT overnight, diluted with diethylether, washed with water, brine, dried over $Na_2SO_4$, concentrated in vacuo. The residue was purified by flash chromatography on silica gel (hexane-EtOAc, 10:1-2:1) to afford the title compound, 3 g. ESI-MS m/z 219/221 $(MH/MH+2)^+$.

Step 4. Synthesis of (R)-3-((R)-2-(2-chloro-6-fluoro-3,4-dihydroxyphenyl)-2-(4-ethyl-2,3-dioxopiperazine-1-carboxamido)acetamido)-7-fluoro-2-hydroxy-3,4-dihydro-2H-benzo[e][1,2]oxaborinine-8-carboxylic acid

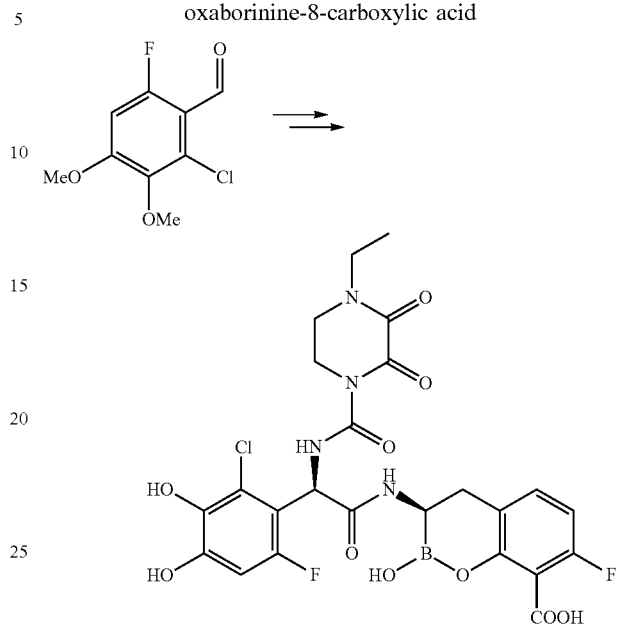

In a similar manner to the synthesis of Example 37, utilizing the above aldehyde in place of 2-chloro-3,4-dimethoxybenzaldehyde in Step 1, the title compound was prepared after reversed phase HPLC purification, isolated as the first eluting peak. ESI-MS m/z 611/613 $(MH/MH+2)^+$.

Example 252: (R)-3-((R)-2-(4-(3-aminopropyl)-2,3-dioxopiperazine-1-carboxamido)-2-(3-fluoro-5-hydroxypyridin-2-yl)acetamido)-2-hydroxy-3,4-dihydro-2H-benzo[e][1,2]oxaborinine-8-carboxylic acid

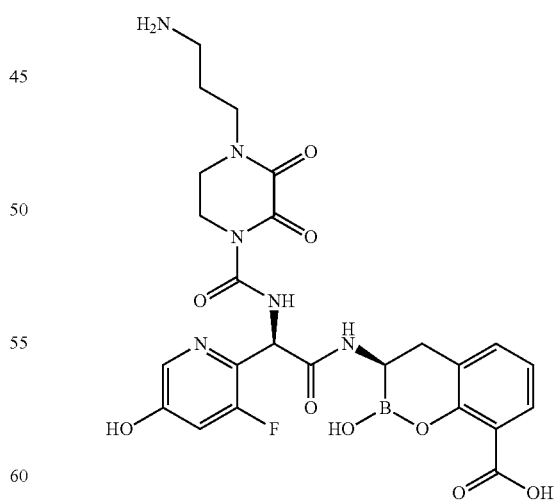

In a similar manner to the synthesis of Example 135, utilizing tert-butyl (3-(4-(chlorocarbonyl)-2,3-dioxopiperazin-1-yl)propyl)carbamate in place of 4-ethyl-2,3-dioxopiperazine-1-carbonyl chloride, the title compound was prepared. ESI-MS m/z 573 $(MH)^+$

TABLE 1

Example compounds.

| Ex. | Structure | MW | ESI-MS (m/z) for [MH]+ |
|---|---|---|---|
| 1 | (structure) | 340.1 | 341 |
| 2 | (structure) | 340.1 | 341 |
| 3 | (structure) | 362.2 | 363 |
| 4 | (structure) | 362.2 | 363 |
| 5 | (structure) | 530.3 | 531 |
| 6 | (structure) | 433.2 | 434 |

TABLE 1-continued
Example compounds.
| Ex. | Structure | MW | ESI-MS (m/z) for [MH]+ |
|---|---|---|---|
| 7 | 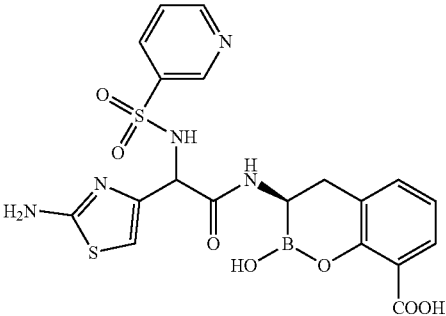 [SMILES: Nc1nc(C(NS(=O)(=O)c2cccnc2)C(=O)N[C@H]2Cc3cccc(C(=O)O)c3OB2O)cs1] | 503.3 | 504 |
| 8 | 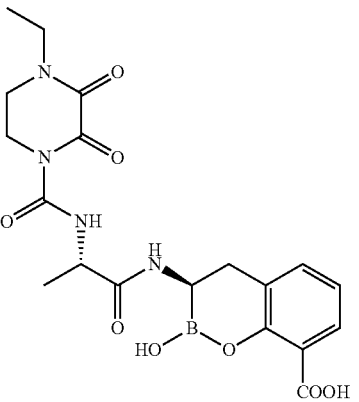 [SMILES: CCN1CCN(C(=O)N[C@@H](C)C(=O)N[C@H]2Cc3cccc(C(=O)O)c3OB2O)C(=O)C1=O] | 446.2 | 447 |
| 9 | 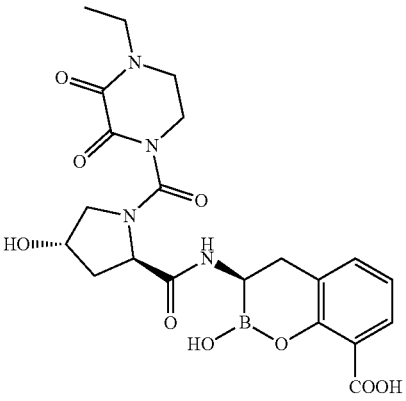 [SMILES: CCN1CCN(C(=O)N2C[C@@H](O)C[C@@H]2C(=O)N[C@H]2Cc3cccc(C(=O)O)c3OB2O)C(=O)C1=O] | 488.3 | 489 |
| 10 | 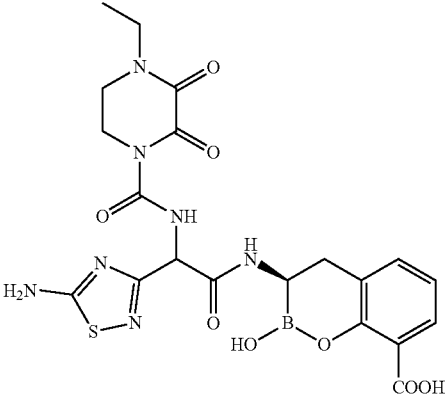 [SMILES: CCN1CCN(C(=O)NC(C(=O)N[C@H]2Cc3cccc(C(=O)O)c3OB2O)c2nsc(N)n2)C(=O)C1=O] | 531.3 | 532 |

TABLE 1-continued

Example compounds.

| Ex. | Structure | MW | ESI-MS (m/z) for [MH]+ |
|-----|-----------|------|------|
| 11  | 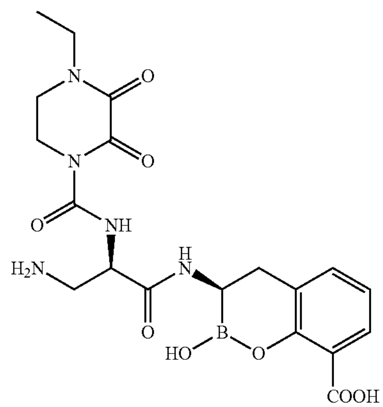 [SMILES: CCN1CCN(C(=O)N[C@H](CN)C(=O)N[C@H]2Cc3cccc(C(=O)O)c3OB2O)C(=O)C1=O]          | 461.3 | 462 |
| 12  | 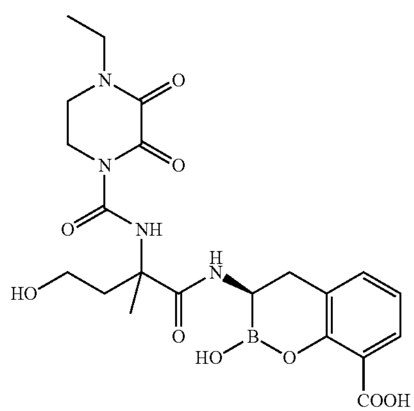 [SMILES: CCN1CCN(C(=O)NC(C)(CCO)C(=O)N[C@H]2Cc3cccc(C(=O)O)c3OB2O)C(=O)C1=O]          | 490.3 | 491 |
| 13  | 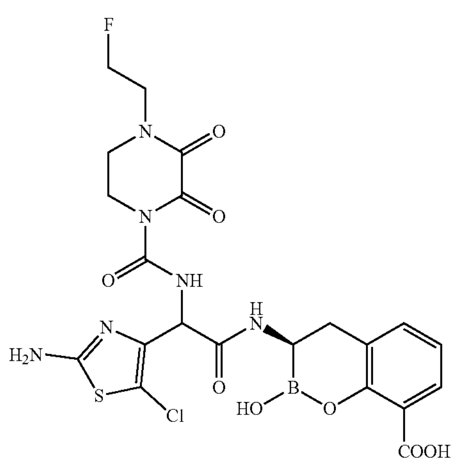 [SMILES: Nc1nc(C(NC(=O)N2CCN(CCF)C(=O)C2=O)C(=O)N[C@H]2Cc3cccc(C(=O)O)c3OB2O)c(Cl)s1]          | 582.7 | 583 |

TABLE 1-continued

Example compounds.

| Ex. | Structure | MW | ESI-MS (m/z) for [MH]$^+$ |
|---|---|---|---|
| 14 | 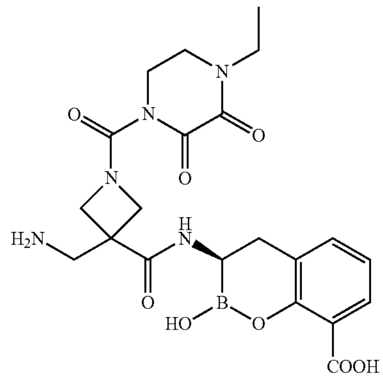 [SMILES: CCN1CCN(C(=O)N2CC(CN)(C(=O)N[C@H]3Cc4cccc(C(=O)O)c4OB3O)C2)C(=O)C1=O] | 487.3 | 488 |
| 15 | 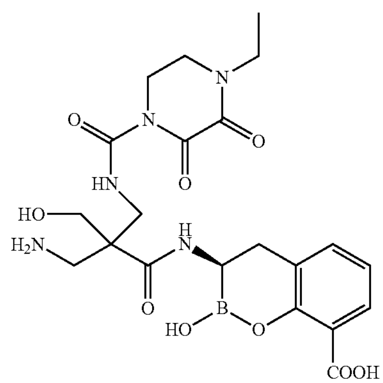 [SMILES: CCN1CCN(C(=O)NCC(CN)(CO)C(=O)N[C@H]2Cc3cccc(C(=O)O)c3OB2O)C(=O)C1=O] | 505.3 | 506 |
| 16 | 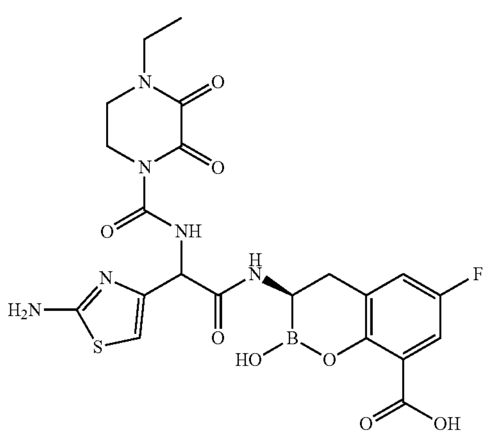 [SMILES: CCN1CCN(C(=O)NC(C(=O)N[C@H]2Cc3cc(F)cc(C(=O)O)c3OB2O)c2csc(N)n2)C(=O)C1=O] | 548.3 | 549 |

TABLE 1-continued

Example compounds.

| Ex. | Structure | MW | ESI-MS (m/z) for [MH]+ |
|---|---|---|---|
| 17 | 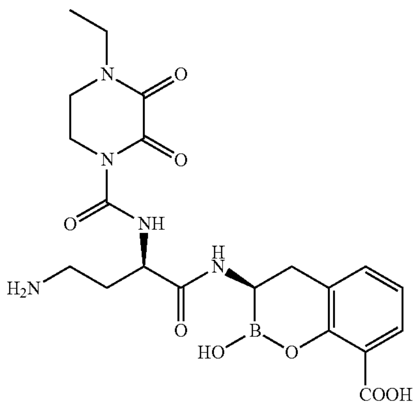 [SMILES: CCN1CCN(C(=O)N[C@H](CCN)C(=O)N[C@H]2Cc3cccc(C(=O)O)c3OB2O)C(=O)C1=O] | 475.3 | 476 |
| 18 | 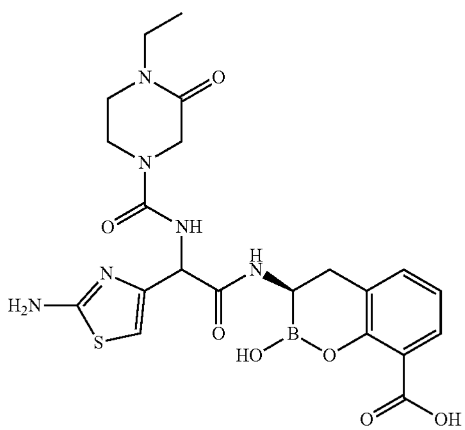 [SMILES: CCN1CCN(C(=O)NC(C(=O)N[C@H]2Cc3cccc(C(=O)O)c3OB2O)c2csc(N)n2)CC1=O] | 516.3 | 517 |
| 19 | 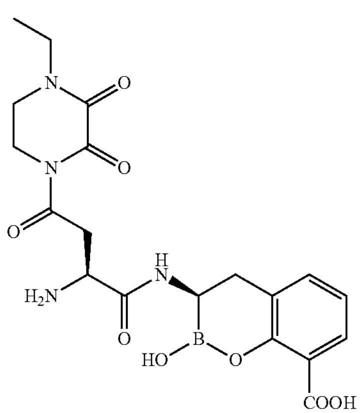 [SMILES: CCN1CCN(C(=O)C[C@H](N)C(=O)N[C@H]2Cc3cccc(C(=O)O)c3OB2O)C(=O)C1=O] | 446.2 | 447.2 |

TABLE 1-continued
Example compounds.
| Ex. | Structure | MW | ESI-MS (m/z) for [MH]+ |
|---|---|---|---|
| 20 | 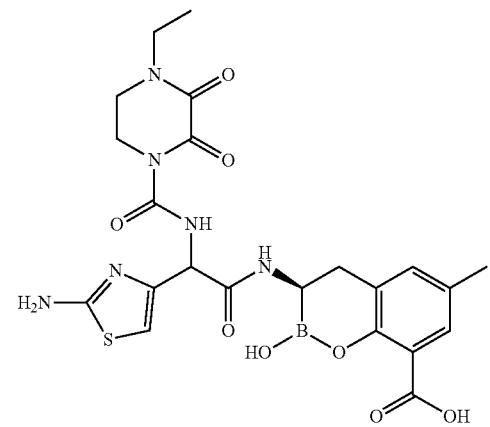 [SMILES: CCN1CCN(C(=O)NC(C(=O)N[C@H]2Cc3cc(C)cc(C(=O)O)c3OB2O)c2csc(N)n2)C(=O)C1=O] | 544.3 | 545 |
| 21 | 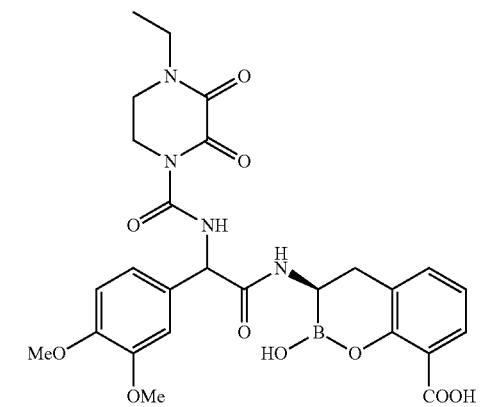 [SMILES: CCN1CCN(C(=O)NC(C(=O)N[C@H]2Cc3cccc(C(=O)O)c3OB2O)c2ccc(OC)c(OC)c2)C(=O)C1=O] | 568.3 | 569 |
| 22 | 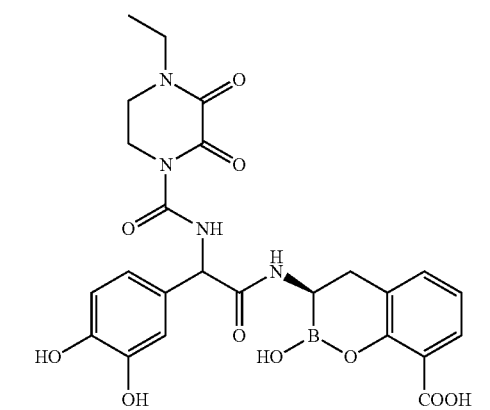 | 540.3 | 541 |

TABLE 1-continued

Example compounds.

| Ex. | Structure | MW | ESI-MS (m/z) for [MH]+ |
|---|---|---|---|
| 23 | 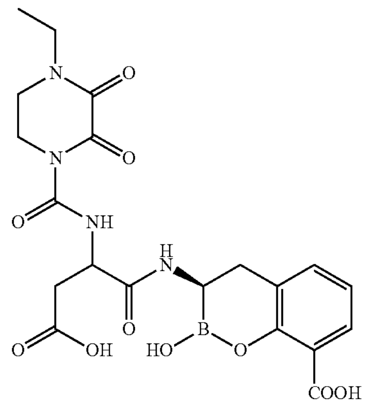 [SMILES: CCN1CCN(C(=O)NC(CC(=O)O)C(=O)N[C@H]2Cc3cccc(C(=O)O)c3OB2O)C(=O)C1=O] | 490.3 | 491 |
| 24 | 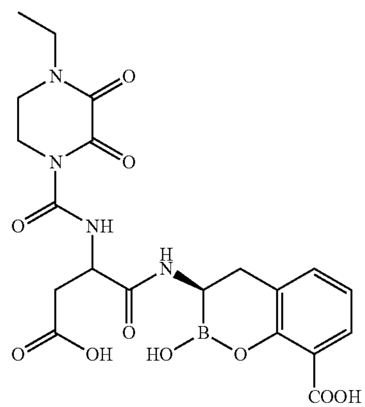 [SMILES: CCN1CCN(C(=O)NC(CC(=O)O)C(=O)N[C@H]2Cc3cccc(C(=O)O)c3OB2O)C(=O)C1=O] | 490.3 | 491 |
| 25 | 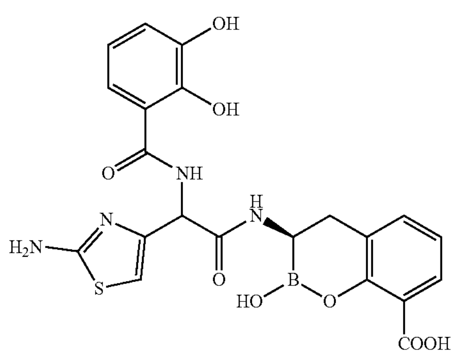 [SMILES: Nc1nc(C(NC(=O)c2cccc(O)c2O)C(=O)N[C@H]2Cc3cccc(C(=O)O)c3OB2O)cs1] | 498.3 | 499 |
| 26 | 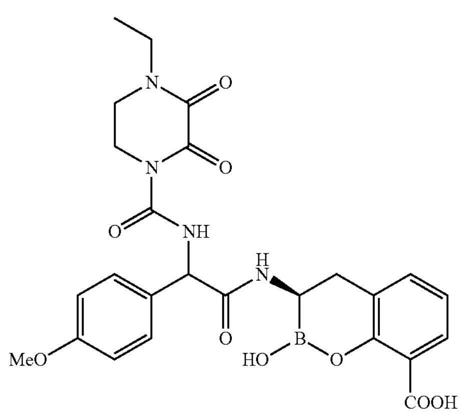 [SMILES: CCN1CCN(C(=O)NC(C(=O)N[C@H]2Cc3cccc(C(=O)O)c3OB2O)c2ccc(OC)cc2)C(=O)C1=O] | 538.3 | 539 |

TABLE 1-continued
Example compounds.
| Ex. | Structure | MW | ESI-MS (m/z) for [MH]+ |
|---|---|---|---|
| 27 | 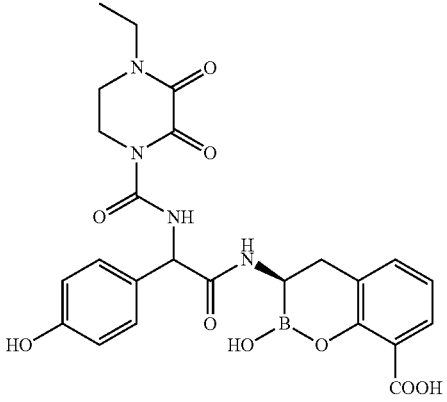 | 524.3 | 525 |
| 28 | 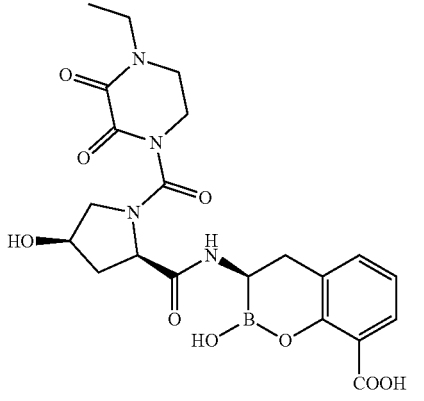 [SMILES: CCN1CCN(C(=O)N2C[C@H](O)C[C@@H]2C(=O)N[C@H]2Cc3cccc(C(=O)O)c3OB2O)C(=O)C1=O] | 488.3 | 489 |
| 29 | 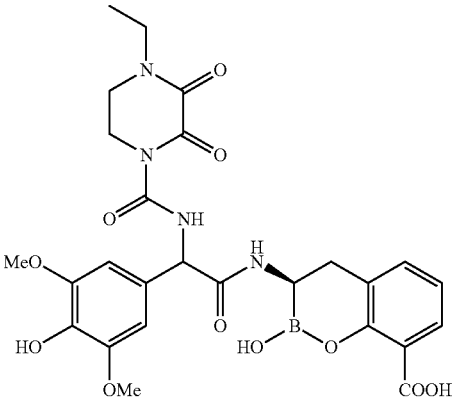 [SMILES: CCN1CCN(C(=O)NC(C(=O)N[C@H]2Cc3cccc(C(=O)O)c3OB2O)c2cc(OC)c(O)c(OC)c2)C(=O)C1=O] | 584.3 | 585 |

TABLE 1-continued

Example compounds.

| Ex. | Structure | MW | ESI-MS (m/z) for [MH]+ |
|---|---|---|---|
| 30 | 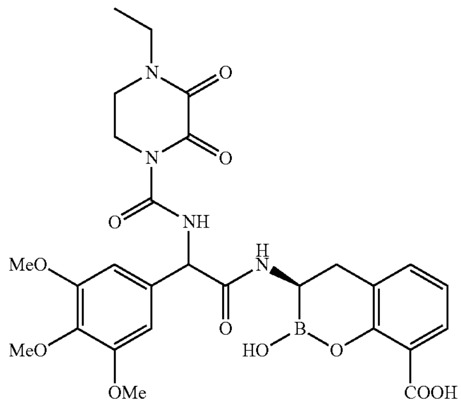 [SMILES: CCN1CCN(C(=O)NC(C(=O)N[C@H]2Cc3cccc(C(=O)O)c3OB2O)c2cc(OC)c(OC)c(OC)c2)C(=O)C1=O] | 598.4 | 599 |
| 31 | 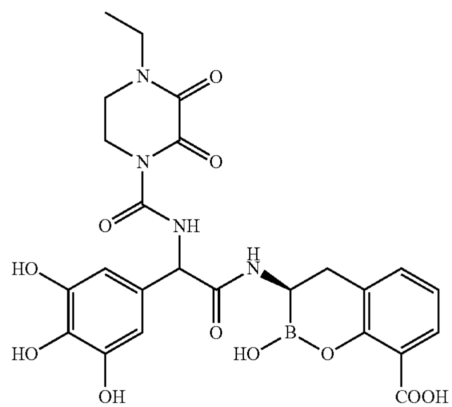 | 556.3 | 557 |
| 32 | 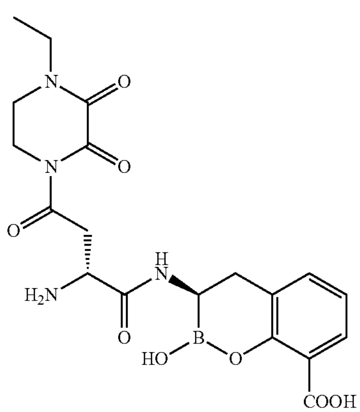 [SMILES: CCN1CCN(C(=O)C[C@@H](N)C(=O)N[C@H]2Cc3cccc(C(=O)O)c3OB2O)C(=O)C1=O] | 446.2 | 447.2 |

TABLE 1-continued

Example compounds.

| Ex. | Structure | MW | ESI-MS (m/z) for [MH]+ |
|---|---|---|---|
| 33 | 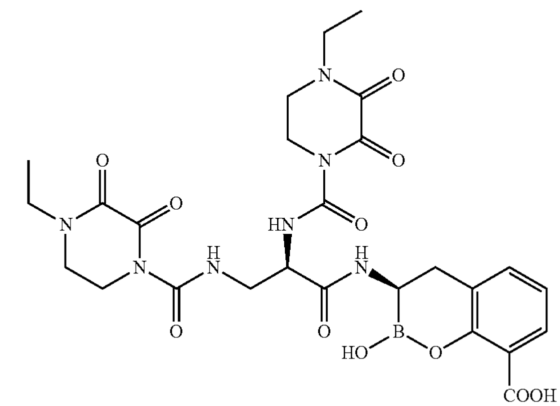 [SMILES: CCN1CCN(C(=O)NC[C@@H](NC(=O)N2CCN(CC)C(=O)C2=O)C(=O)N[C@H]2Cc3cccc(C(=O)O)c3OB2O)C(=O)C1=O] | 629.4 | 630 |
| 34 | 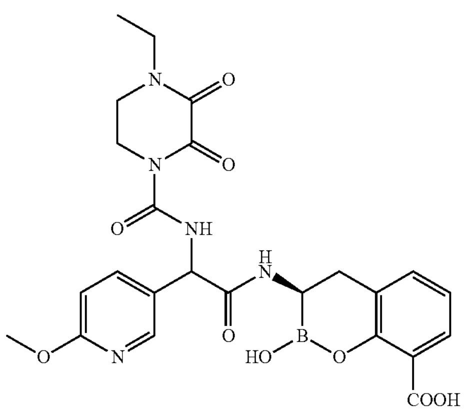 [SMILES: CCN1CCN(C(=O)NC(C(=O)N[C@H]2Cc3cccc(C(=O)O)c3OB2O)c2ccc(OC)nc2)C(=O)C1=O] | 539.3 | 540.2 |
| 35 | 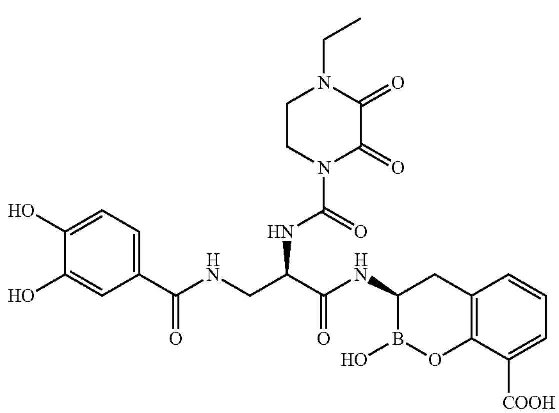 [SMILES: CCN1CCN(C(=O)N[C@H](CNC(=O)c2ccc(O)c(O)c2)C(=O)N[C@H]2Cc3cccc(C(=O)O)c3OB2O)C(=O)C1=O] | 597.3 | 598 |

TABLE 1-continued

Example compounds.

| Ex. | Structure | MW | ESI-MS (m/z) for [MH]+ |
|---|---|---|---|
| 36 | 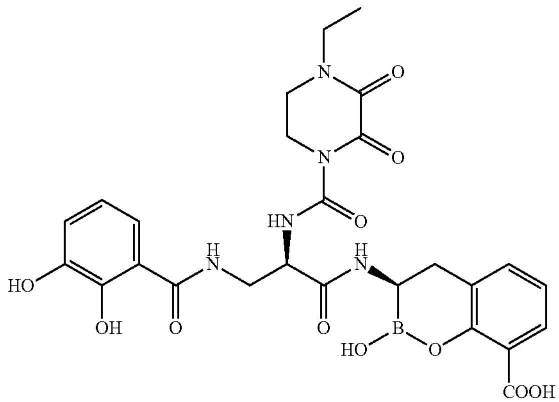 [SMILES: CCN1CCN(C(=O)N[C@H](CNC(=O)c2cccc(O)c2O)C(=O)N[C@H]2Cc3cccc(C(=O)O)c3OB2O)C(=O)C1=O] | 597.3 | 598 |
| 37 | 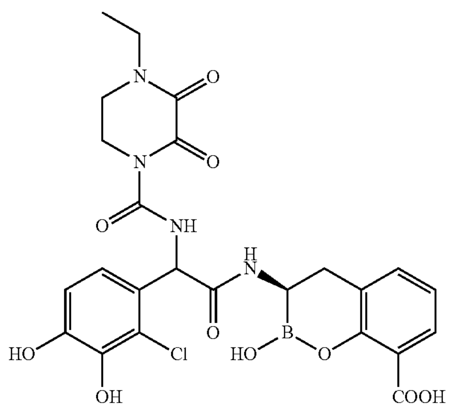 | 574.7 | 575/577 |
| 38 | 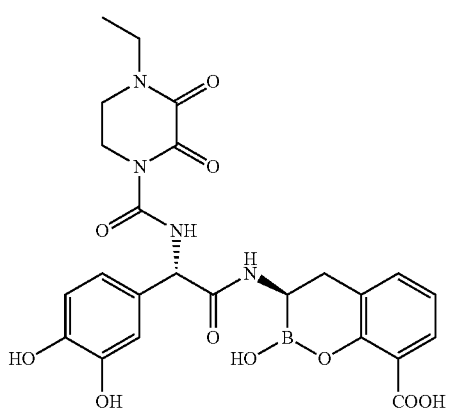 | 540.3 | 541 |

TABLE 1-continued

Example compounds.

| Ex. | Structure | MW | ESI-MS (m/z) for [MH]+ |
|---|---|---|---|
| 39 | 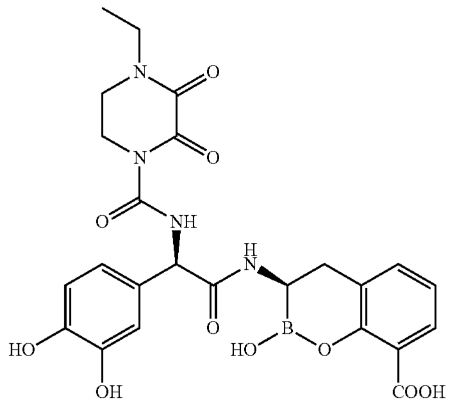 [SMILES: CCN1CCN(C(=O)N[C@@H](C(=O)N[C@H]2Cc3cccc(C(=O)O)c3OB2O)c2ccc(O)c(O)c2)C(=O)C1=O] | 540.3 | 541 |
| 40 | 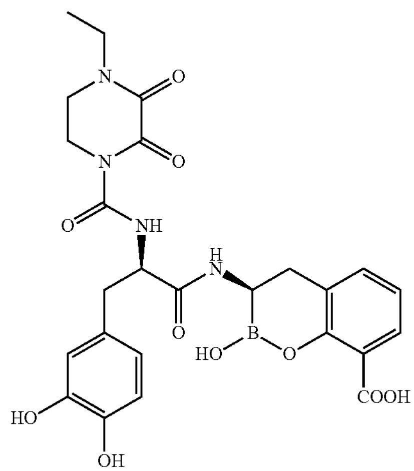 [SMILES: CCN1CCN(C(=O)N[C@H](Cc2ccc(O)c(O)c2)C(=O)N[C@H]2Cc3cccc(C(=O)O)c3OB2O)C(=O)C1=O] | 554.2 | 555.2 |
| 41 | 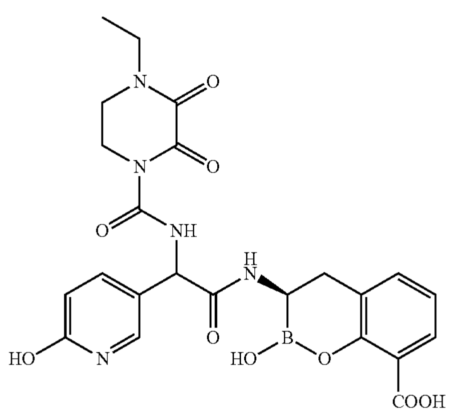 | 525.3 | 526.2 |

TABLE 1-continued

Example compounds.

| Ex. | Structure | MW | ESI-MS (m/z) for [MH]+ |
|---|---|---|---|
| 42 | 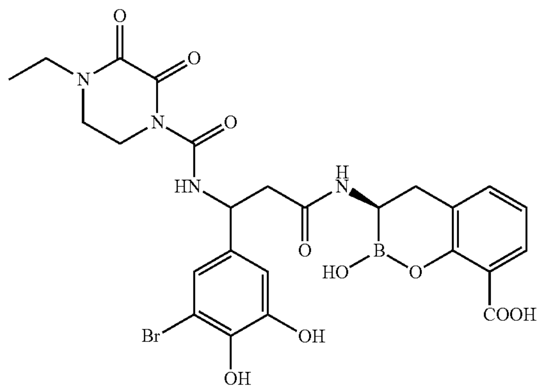 | 633.2 | 633/635 |
| 43 | 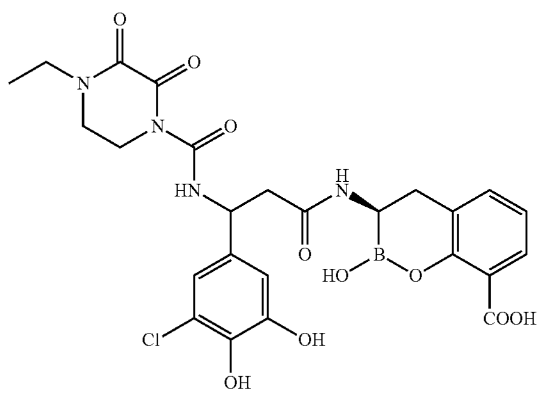 [SMILES: CCN1CCN(C(=O)NC(CC(=O)N[C@H]2Cc3cccc(C(=O)O)c3OB2O)c2cc(O)c(O)c(Cl)c2)C(=O)C1=O] | 588.8 | 589/591 |
| 44 | 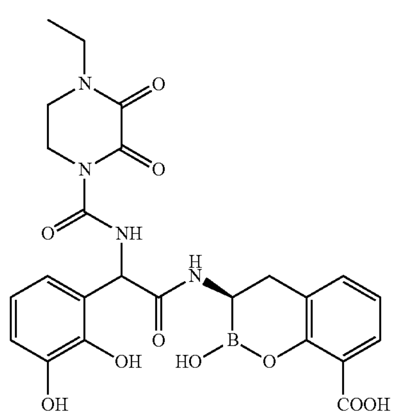 [SMILES: CCN1CCN(C(=O)NC(C(=O)N[C@H]2Cc3cccc(C(=O)O)c3OB2O)c2cccc(O)c2O)C(=O)C1=O] | 540.3 | 541 |

TABLE 1-continued
Example compounds.
| Ex. | Structure | MW | ESI-MS (m/z) for [MH]+ |
|---|---|---|---|
| 45 | 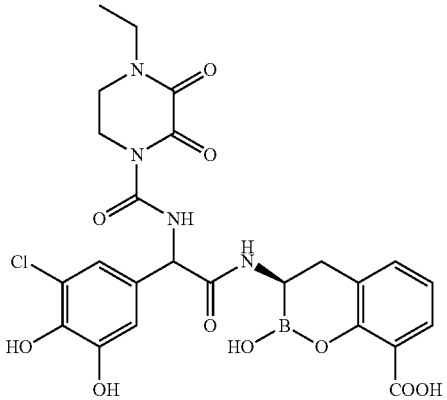 | 574.7 | 575/577 |
| 46 | 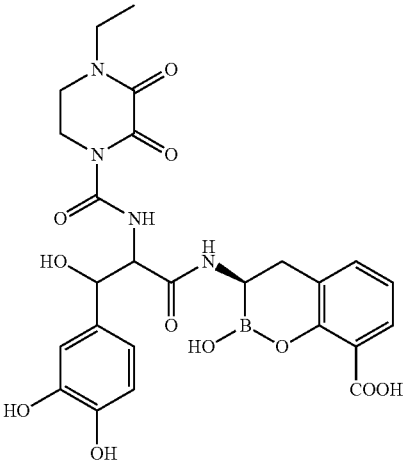 [SMILES: CCN1CCN(C(=O)NC(C(=O)N[C@H]2Cc3cccc(C(=O)O)c3OB2O)C(O)c2ccc(O)c(O)c2)C(=O)C1=O] | 570.3 | 571 |
| 47 | 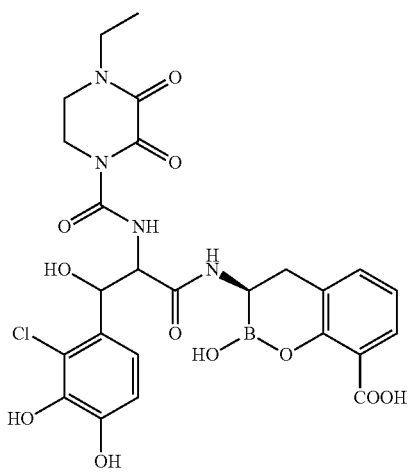 [SMILES: CCN1CCN(C(=O)NC(C(=O)N[C@H]2Cc3cccc(C(=O)O)c3OB2O)C(O)c2ccc(O)c(O)c2Cl)C(=O)C1=O] | 604.3 | 605 |

TABLE 1-continued
Example compounds.
| Ex. | Structure | MW | ESI-MS (m/z) for [MH]+ |
|---|---|---|---|
| 48 | 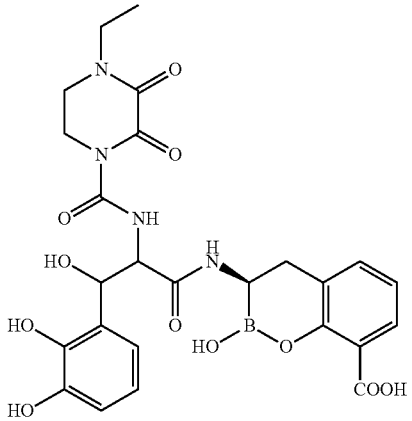 [SMILES: CCN1CCN(C(=O)NC(C(=O)N[C@H]2Cc3cccc(C(=O)O)c3OB2O)C(O)c2cccc(O)c2O)C(=O)C1=O] | 570.3 | 571 |
| 49 | 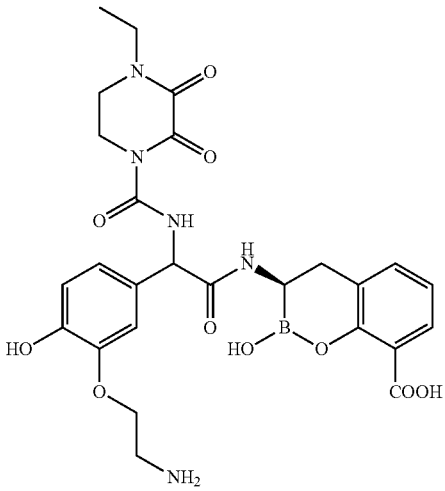 [SMILES: CCN1CCN(C(=O)NC(C(=O)N[C@H]2Cc3cccc(C(=O)O)c3OB2O)c2ccc(O)c(OCCN)c2)C(=O)C1=O] | 583.4 | 584 |
| 50 | 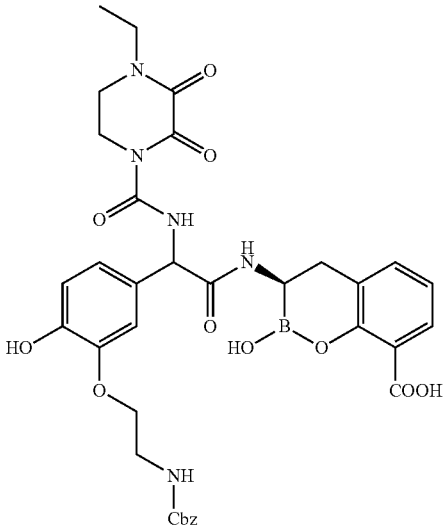 [SMILES: CCN1CCN(C(=O)NC(C(=O)N[C@H]2Cc3cccc(C(=O)O)c3OB2O)c2ccc(O)c(OCCNC(=O)OCc3ccccc3)c2)C(=O)C1=O] | 717.5 | 718 |

TABLE 1-continued

Example compounds.

| Ex. | Structure | MW | ESI-MS (m/z) for [MH]+ |
|---|---|---|---|
| 51 | 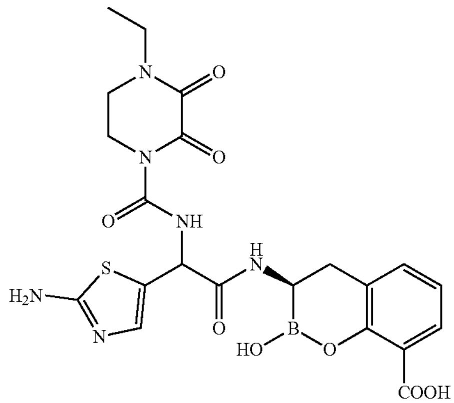 [SMILES: CCN1CCN(C(=O)NC(C(=O)N[C@H]2Cc3cccc(C(=O)O)c3OB2O)c2cnc(N)s2)C(=O)C1=O] | 530.3 | 531 |
| 52 | 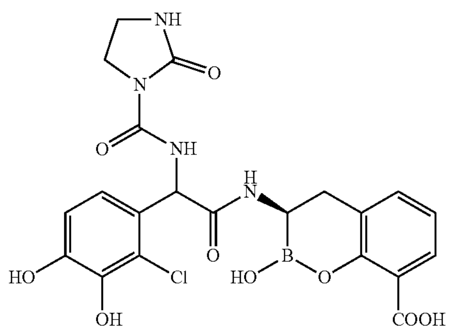 [SMILES: O=C(O)c1cccc2c1OB(O)[C@@H](NC(=O)C(NC(=O)N1CCNC1=O)c1ccc(O)c(O)c1Cl)C2] | 518.1, 520.1 | 519, 521 |
| 53 | 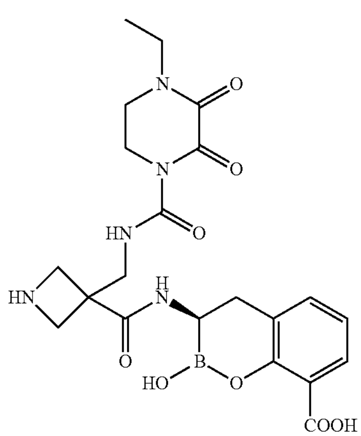 [SMILES: CCN1CCN(C(=O)NCC2(C(=O)N[C@H]3Cc4cccc(C(=O)O)c4OB3O)CNC2)C(=O)C1=O] | 487.3 | 488 |

TABLE 1-continued
Example compounds.
| Ex. | Structure | MW | ESI-MS (m/z) for [MH]+ |
|---|---|---|---|
| 54 | 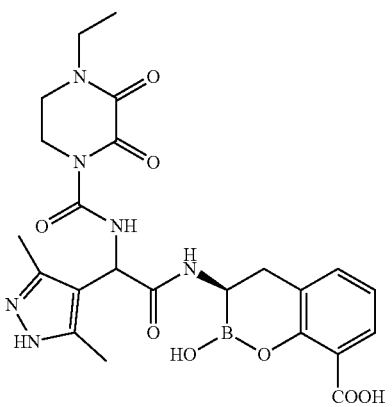 [SMILES: CCN1CCN(C(=O)NC(C(=O)N[C@H]2Cc3cccc(C(=O)O)c3OB2O)c2c(C)n[nH]c2C)C(=O)C1=O] | 526.3 | 527 |
| 55 | 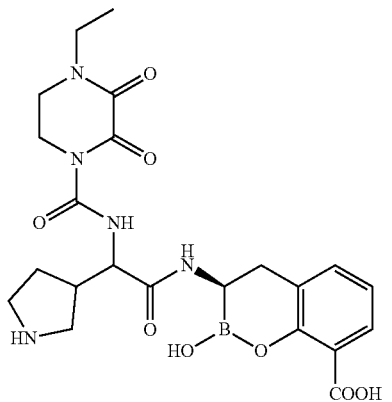 [SMILES: CCN1CCN(C(=O)NC(C(=O)N[C@H]2Cc3cccc(C(=O)O)c3OB2O)C2CCNC2)C(=O)C1=O] | 501.3 | 502 |
| 56 | 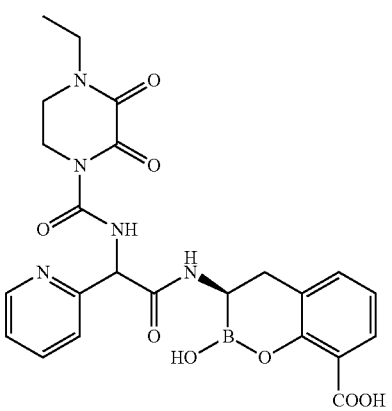 [SMILES: CCN1CCN(C(=O)NC(C(=O)N[C@H]2Cc3cccc(C(=O)O)c3OB2O)c2ccccn2)C(=O)C1=O] | 509.3 | 510 |

TABLE 1-continued

Example compounds.

| Ex. | Structure | MW | ESI-MS (m/z) for [MH]+ |
|---|---|---|---|
| 57 | 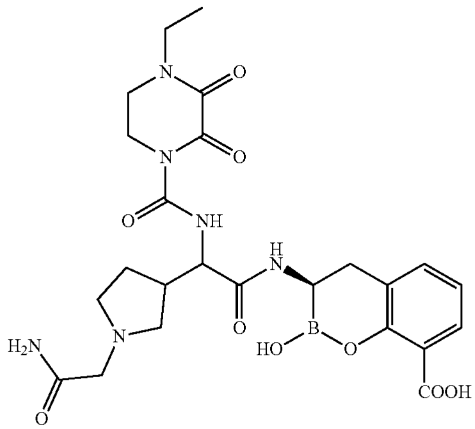 [SMILES: CCN1CCN(C(=O)NC(C(=O)N[C@H]2Cc3cccc(C(=O)O)c3OB2O)C2CCN(CC(N)=O)C2)C(=O)C1=O] | 558.4 | 559 |
| 58 | 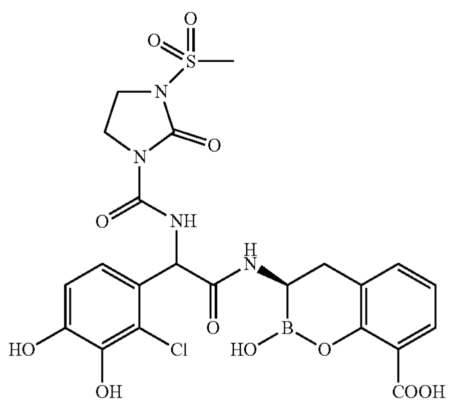 [SMILES: CS(=O)(=O)N1CCN(C(=O)NC(C(=O)N[C@H]2Cc3cccc(C(=O)O)c3OB2O)c2ccc(O)c(O)c2Cl)C1=O] | 596.8 | 597 |
| 59 | 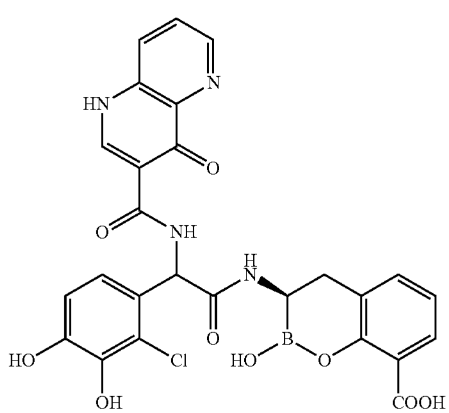 [SMILES: O=C(O)c1cccc2c1OB(O)[C@@H](NC(=O)C(NC(=O)c1c[nH]c3cccnc3c1=O)c1ccc(O)c(O)c1Cl)C2] | 578.7 | 580 |

TABLE 1-continued

Example compounds.

| Ex. | Structure | MW | ESI-MS (m/z) for [MH]+ |
|---|---|---|---|
| 60 | 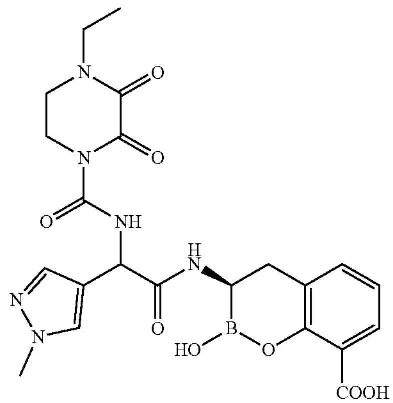 [SMILES: CCN1CCN(C(=O)NC(C(=O)N[C@H]2Cc3cccc(C(=O)O)c3OB2O)c2cnn(C)c2)C(=O)C1=O] | 512.3 | 513 |
| 61 | 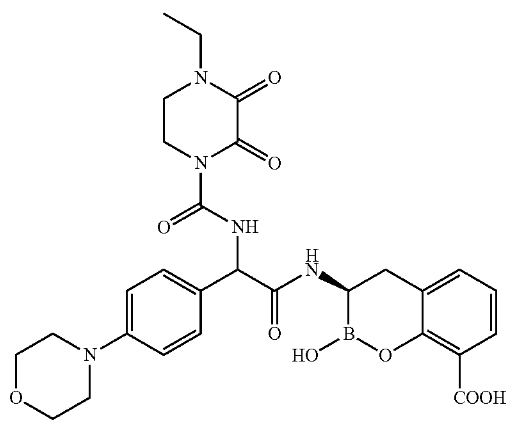 [SMILES: CCN1CCN(C(=O)NC(C(=O)N[C@H]2Cc3cccc(C(=O)O)c3OB2O)c2ccc(N3CCOCC3)cc2)C(=O)C1=O] | 593.4 | 594 |
| 62 | 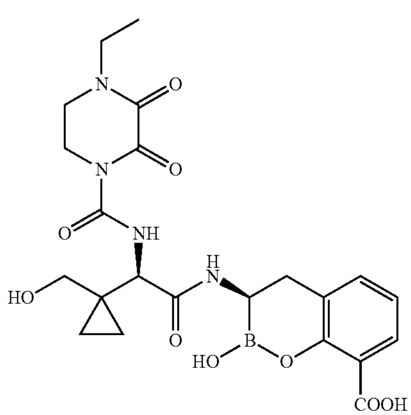 [SMILES: CCN1CCN(C(=O)N[C@@H](C(=O)N[C@H]2Cc3cccc(C(=O)O)c3OB2O)C2(CO)CC2)C(=O)C1=O] | 502.3 | 503 |

TABLE 1-continued

Example compounds.

| Ex. | Structure | MW | ESI-MS (m/z) for [MH]+ |
|---|---|---|---|
| 63 | 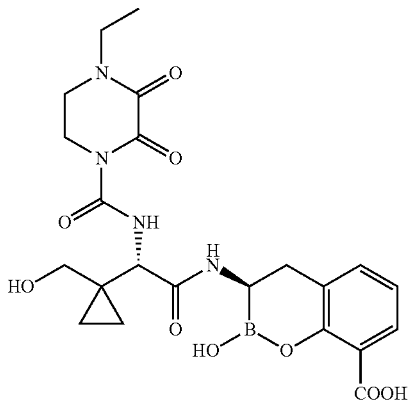 [SMILES: CCN1CCN(C(=O)N[C@H](C(=O)N[C@H]2Cc3cccc(C(=O)O)c3OB2O)C2(CO)CC2)C(=O)C1=O] | 502.3 | 503 |
| 64 | 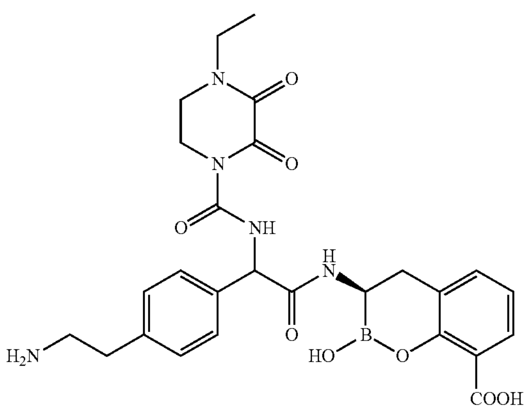 [SMILES: CCN1CCN(C(=O)NC(C(=O)N[C@H]2Cc3cccc(C(=O)O)c3OB2O)c2ccc(CCN)cc2)C(=O)C1=O] | 551.4 | 552 |
| 65 | 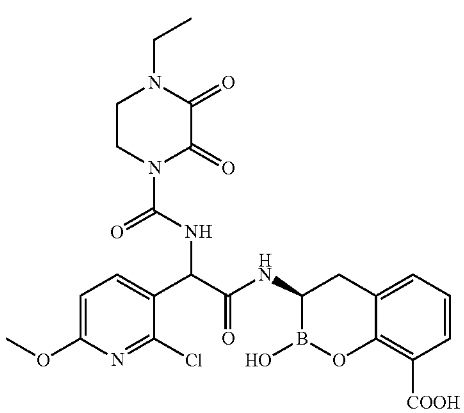 [SMILES: CCN1CCN(C(=O)NC(C(=O)N[C@H]2Cc3cccc(C(=O)O)c3OB2O)c2ccc(OC)nc2Cl)C(=O)C1=O] | 573.8 | 575 |

TABLE 1-continued

Example compounds.

| Ex. | Structure | MW | ESI-MS (m/z) for [MH]+ |
|---|---|---|---|
| 66 | 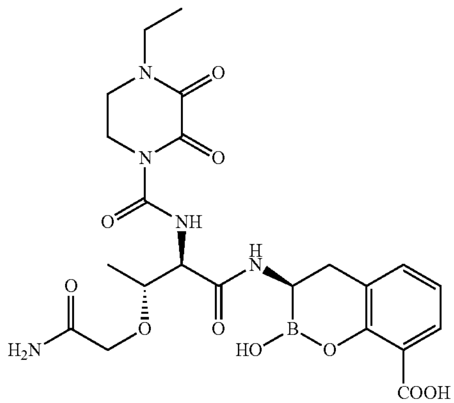 [SMILES: CCN1CCN(C(=O)N[C@@H](C(=O)N[C@H]2Cc3cccc(C(=O)O)c3OB2O)[C@@H](C)OCC(N)=O)C(=O)C1=O] | 533.3 | 534 |
| 67 | 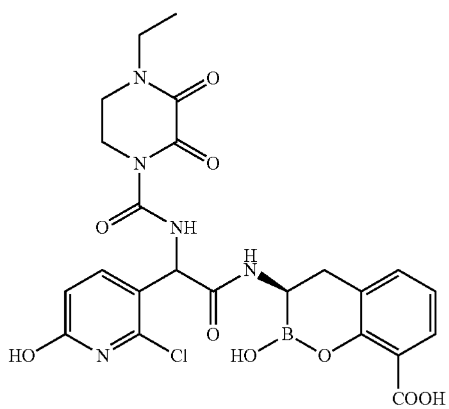 [SMILES: CCN1CCN(C(=O)NC(C(=O)N[C@H]2Cc3cccc(C(=O)O)c3OB2O)c2ccc(O)nc2Cl)C(=O)C1=O] | 559.7 | 561 |
| 68 | 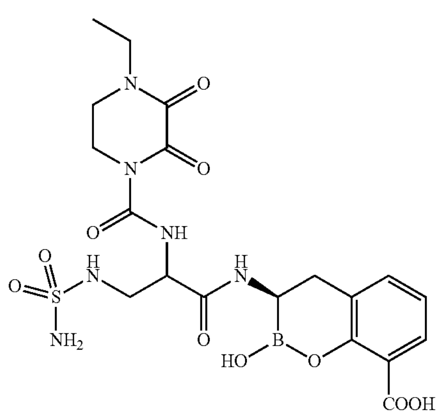 [SMILES: CCN1CCN(C(=O)NC(CNS(N)(=O)=O)C(=O)N[C@H]2Cc3cccc(C(=O)O)c3OB2O)C(=O)C1=O] | 540.3 | 541 |

TABLE 1-continued
Example compounds.
| Ex. | Structure | MW | ESI-MS (m/z) for [MH]+ |
|---|---|---|---|
| 69 | 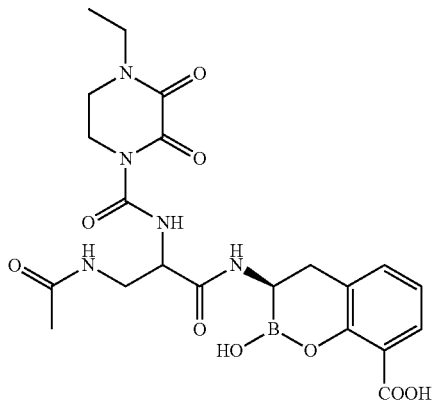 [SMILES: CCN1CCN(C(=O)NC(CNC(C)=O)C(=O)N[C@H]2Cc3cccc(C(=O)O)c3OB2O)C(=O)C1=O] | 503.3 | 504 |
| 70 | 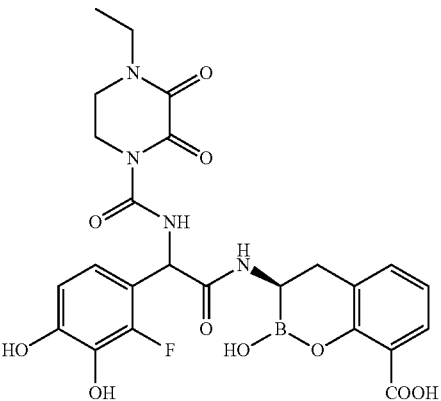 | 558.3 | 559 |
| 71 | 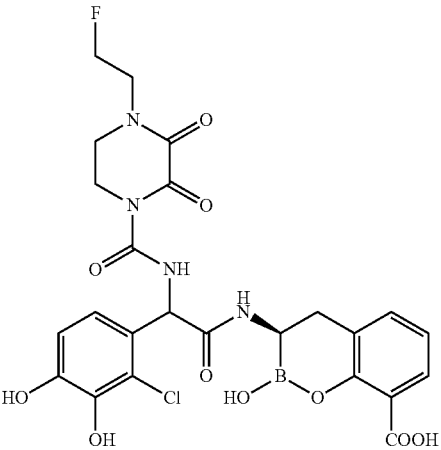 [SMILES: O=C(O)c1cccc2c1OB(O)[C@@H](NC(=O)C(NC(=O)N1CCN(CCF)C(=O)C1=O)c1ccc(O)c(O)c1Cl)C2] | 592.7 | 594 |

TABLE 1-continued

Example compounds.

| Ex. | Structure | MW | ESI-MS (m/z) for [MH]$^+$ |
|---|---|---|---|
| 72 | 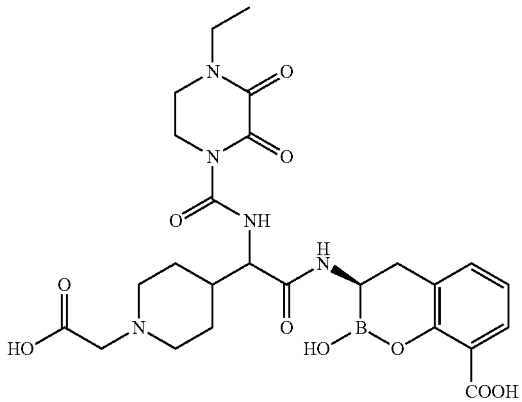 [SMILES: CCN1CCN(C(=O)NC(C(=O)N[C@H]2Cc3cccc(C(=O)O)c3OB2O)C2CCN(CC(=O)O)CC2)C(=O)C1=O] | 573.4 | 574 |
| 73 | 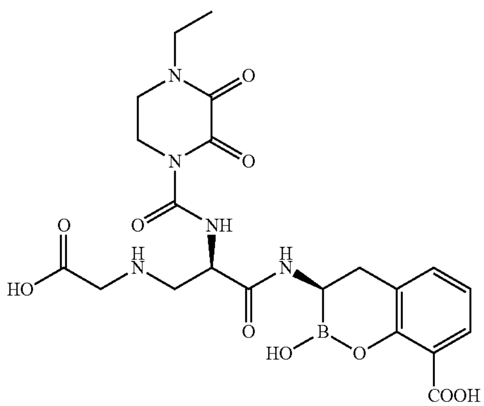 [SMILES: CCN1CCN(C(=O)N[C@H](CNCC(=O)O)C(=O)N[C@H]2Cc3cccc(C(=O)O)c3OB2O)C(=O)C1=O] | 519.3 | 520 |
| 74 | 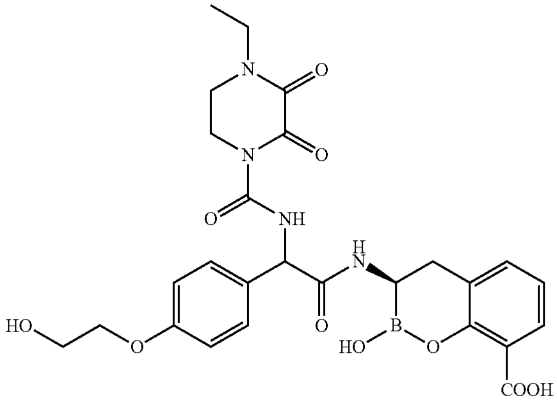 [SMILES: CCN1CCN(C(=O)NC(C(=O)N[C@H]2Cc3cccc(C(=O)O)c3OB2O)c2ccc(OCCO)cc2)C(=O)C1=O] | 568.3 | 569 |

TABLE 1-continued

Example compounds.

| Ex. | Structure | MW | ESI-MS (m/z) for [MH]+ |
|---|---|---|---|
| 75 | 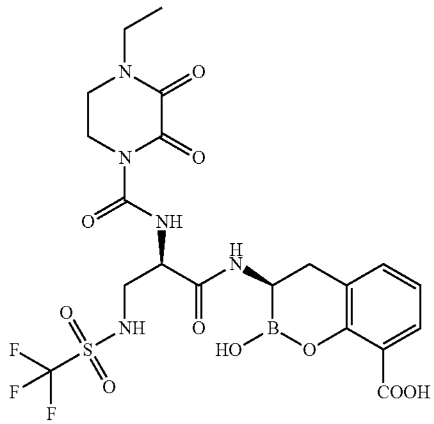 [SMILES: CCN1CCN(C(=O)N[C@H](CNS(=O)(=O)C(F)(F)F)C(=O)N[C@H]2Cc3cccc(C(=O)O)c3OB2O)C(=O)C1=O] | 593.3 | 594 |
| 76 | 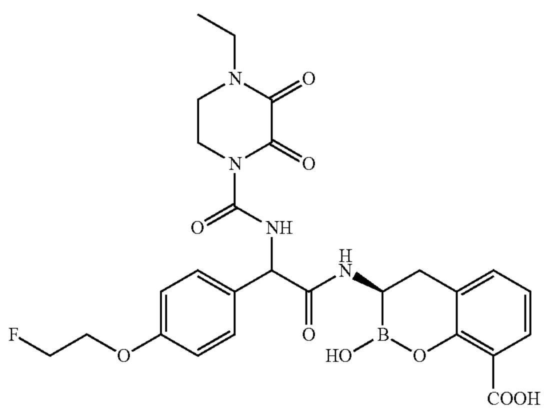 [SMILES: CCN1CCN(C(=O)NC(C(=O)N[C@H]2Cc3cccc(C(=O)O)c3OB2O)c2ccc(OCCF)cc2)C(=O)C1=O] | 570.3 | 571 |
| 77 | 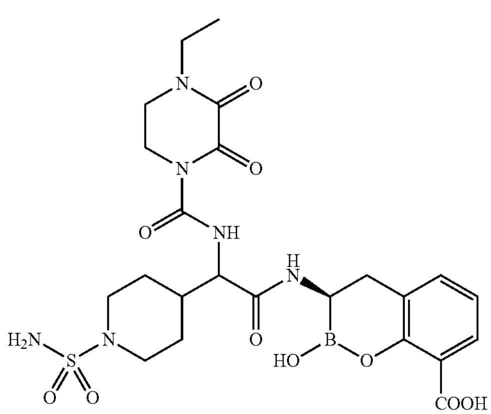 [SMILES: CCN1CCN(C(=O)NC(C(=O)N[C@H]2Cc3cccc(C(=O)O)c3OB2O)C2CCN(S(N)(=O)=O)CC2)C(=O)C1=O] | 594.4 | 595 |

TABLE 1-continued

Example compounds.

| Ex. | Structure | MW | ESI-MS (m/z) for [MH]+ |
|---|---|---|---|
| 78 | 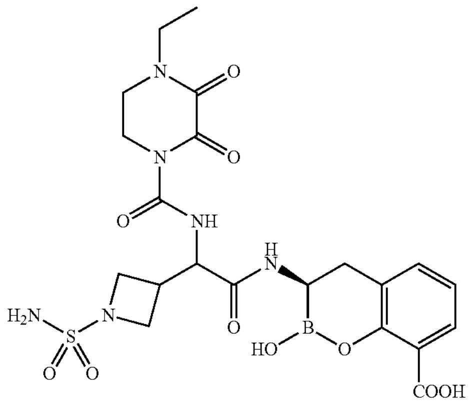 [SMILES: CCN1CCN(C(=O)NC(C(=O)N[C@H]2Cc3cccc(C(=O)O)c3OB2O)C2CN(S(N)(=O)=O)C2)C(=O)C1=O] | 566.3 | 567 |
| 79 | 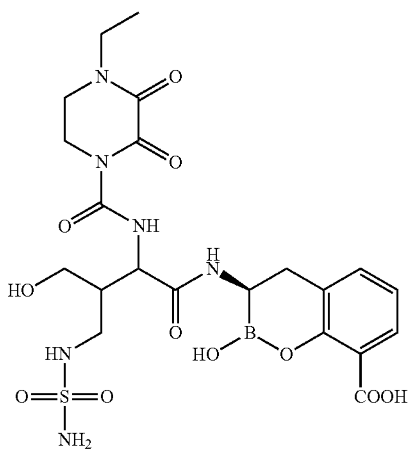 [SMILES: CCN1CCN(C(=O)NC(C(=O)N[C@H]2Cc3cccc(C(=O)O)c3OB2O)C(CO)CNS(N)(=O)=O)C(=O)C1=O] | 584.4 | 585 |
| 80 | 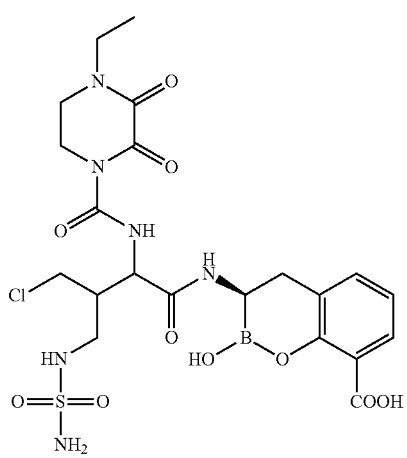 [SMILES: CCN1CCN(C(=O)NC(C(=O)N[C@H]2Cc3cccc(C(=O)O)c3OB2O)C(CCl)CNS(N)(=O)=O)C(=O)C1=O] | 602.8 | 604 |

TABLE 1-continued
Example compounds.
| Ex. | Structure | MW | ESI-MS (m/z) for [MH]+ |
|---|---|---|---|
| 81 | 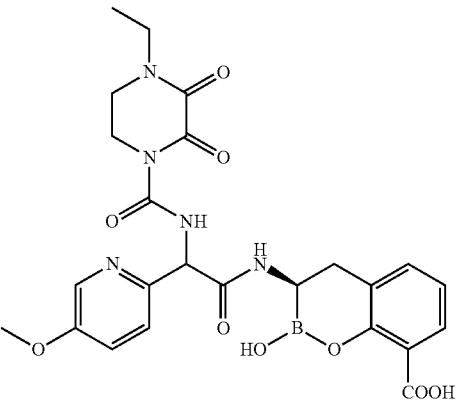 [SMILES: CCN1CCN(C(=O)NC(C(=O)N[C@H]2Cc3cccc(C(=O)O)c3OB2O)c2ccc(OC)cn2)C(=O)C1=O] | 539.3 | 540 |
| 82 | 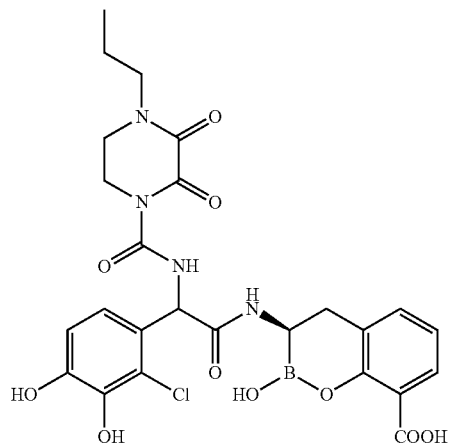 [SMILES: CCCN1CCN(C(=O)NC(C(=O)N[C@H]2Cc3cccc(C(=O)O)c3OB2O)c2ccc(O)c(O)c2Cl)C(=O)C1=O] | 588.8 | 590 |
| 83 | 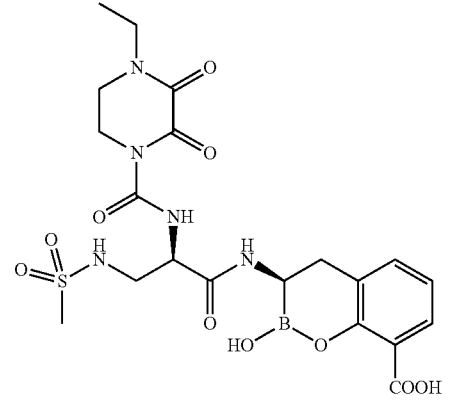 [SMILES: CCN1CCN(C(=O)N[C@H](CNS(C)(=O)=O)C(=O)N[C@H]2Cc3cccc(C(=O)O)c3OB2O)C(=O)C1=O] | 539.3 | 540 |

TABLE 1-continued

Example compounds.

| Ex. | Structure | MW | ESI-MS (m/z) for [MH]+ |
|---|---|---|---|
| 84 | 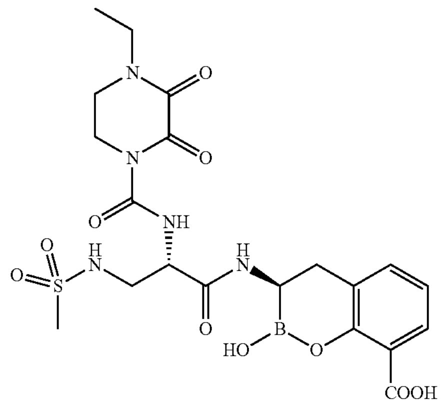 [SMILES: CCN1CCN(C(=O)N[C@@H](CNS(C)(=O)=O)C(=O)N[C@H]2Cc3cccc(C(=O)O)c3OB2O)C(=O)C1=O] | 539.3 | 540 |
| 85 | 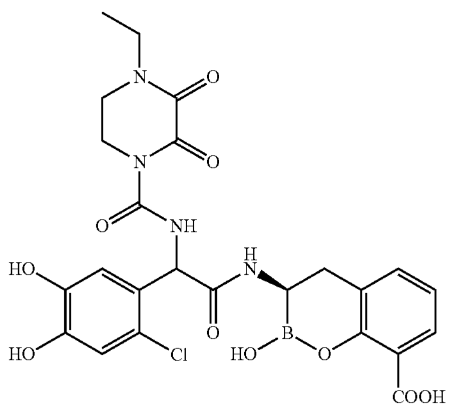 | 574.7 | 575 |
| 86 | 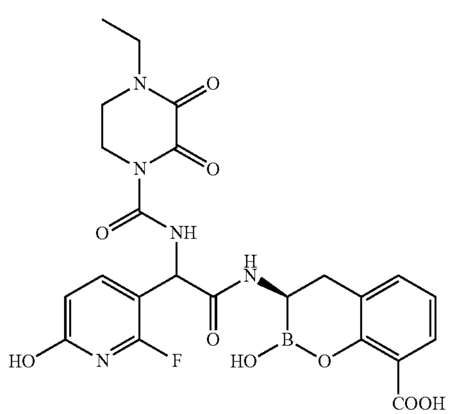 [SMILES: CCN1CCN(C(=O)NC(C(=O)N[C@H]2Cc3cccc(C(=O)O)c3OB2O)c2ccc(O)nc2F)C(=O)C1=O] | 543.3 | 544 |

TABLE 1-continued

Example compounds.

| Ex. | Structure | MW | ESI-MS (m/z) for [MH]+ |
|---|---|---|---|
| 87 | 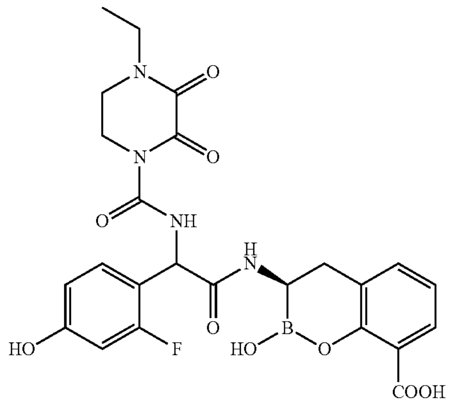 | 542.3 | 543 |
| 88 | 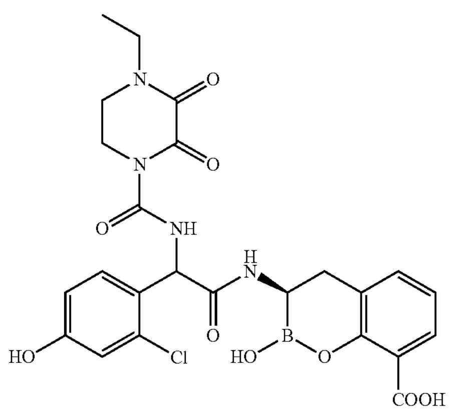 | 558.7 | 559 |
| 89 | 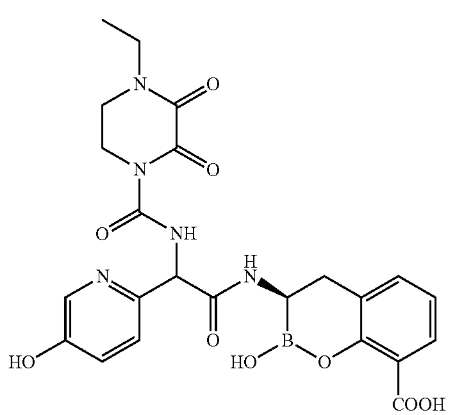 [SMILES: CCN1CCN(C(=O)NC(C(=O)N[C@H]2Cc3cccc(C(=O)O)c3OB2O)c2ccc(O)cn2)C(=O)C1=O] | 525.3 | 526 |

TABLE 1-continued

Example compounds.

| Ex. | Structure | MW | ESI-MS (m/z) for [MH]+ |
|---|---|---|---|
| 90 | 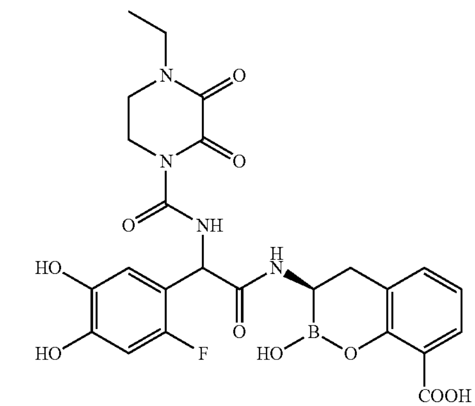 | 558.3 | 559 |
| 91 | Diastereomer 1 | 557.4 | 558 |
| 92 | Diastereomer 2 | 557.4 | 558 |

TABLE 1-continued

Example compounds.

| Ex. | Structure | MW | ESI-MS (m/z) for [MH]+ |
|---|---|---|---|
| 93 | 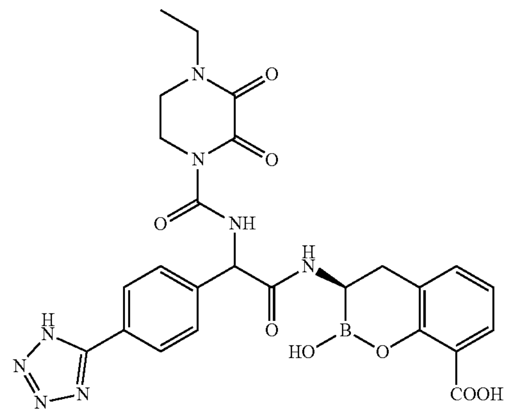 [SMILES: CCN1CCN(C(=O)NC(C(=O)N[C@H]2Cc3cccc(C(=O)O)c3OB2O)c2ccc(-c3nnn[nH]3)cc2)C(=O)C1=O] | 576.3 | 577 |
| 94 | 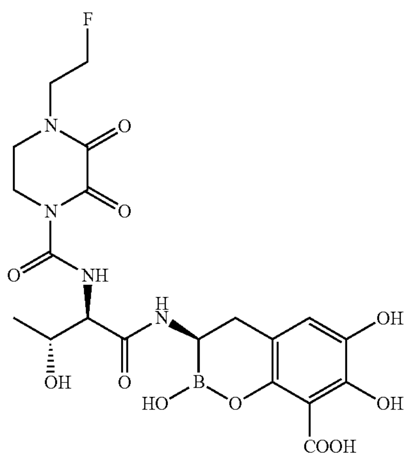 [SMILES: C[C@@H](O)[C@@H](NC(=O)N1CCN(CCF)C(=O)C1=O)C(=O)N[C@H]1Cc2cc(O)c(O)c(C(=O)O)c2OB1O] | 526.2 | 527 |
| 95 | 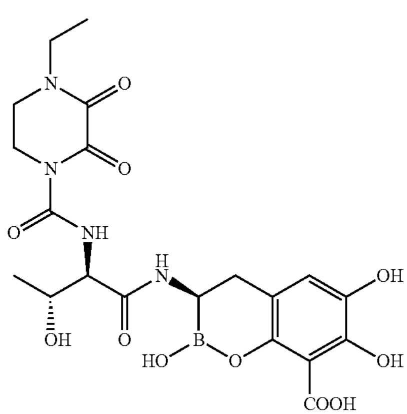 [SMILES: CCN1CCN(C(=O)N[C@@H](C(=O)N[C@H]2Cc3cc(O)c(O)c(C(=O)O)c3OB2O)[C@@H](C)O)C(=O)C1=O] | 508.2 | 509 |

TABLE 1-continued

Example compounds.

| Ex. | Structure | MW | ESI-MS (m/z) for [MH]+ |
|---|---|---|---|
| 96 | 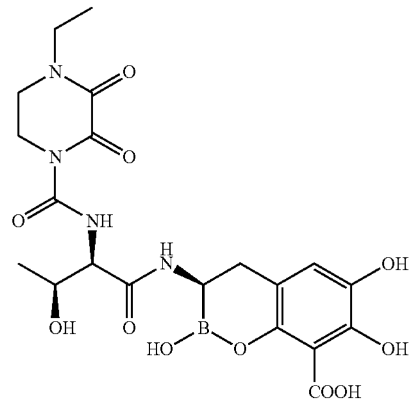 [SMILES: CCN1CCN(C(=O)N[C@@H](C(=O)N[C@H]2Cc3cc(O)c(O)c(C(=O)O)c3OB2O)[C@H](C)O)C(=O)C1=O] | 508.2 | 509 |
| 97 | 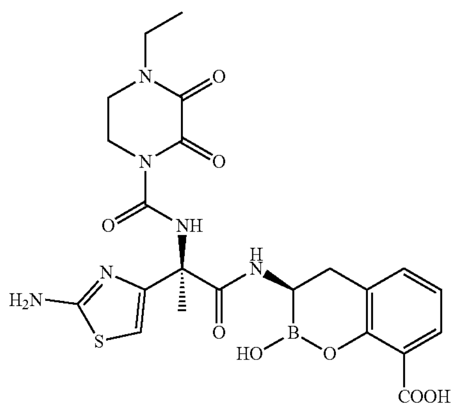 | 544.3 | 545 |
| 98 | 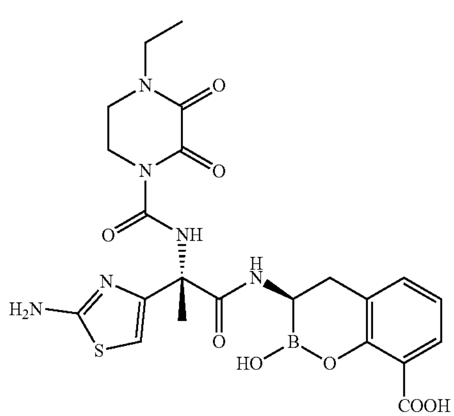 | 544.3 | 545 |

TABLE 1-continued

Example compounds.

| Ex. | Structure | MW | ESI-MS (m/z) for [MH]+ |
|---|---|---|---|
| 99 | 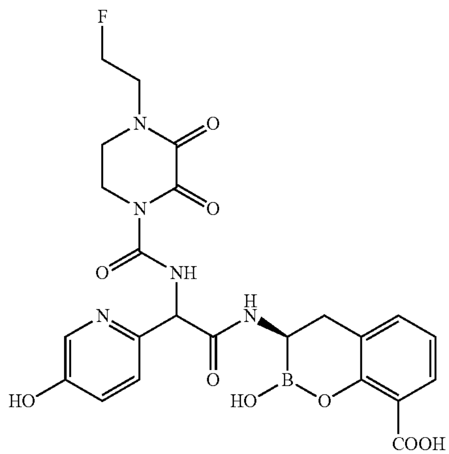 [SMILES: O=C(O)c1cccc2c1OB(O)[C@@H](NC(=O)C(NC(=O)N1CCN(CCF)C(=O)C1=O)c1ccc(O)cn1)C2] | 543.3 | 544 |
| 100 | 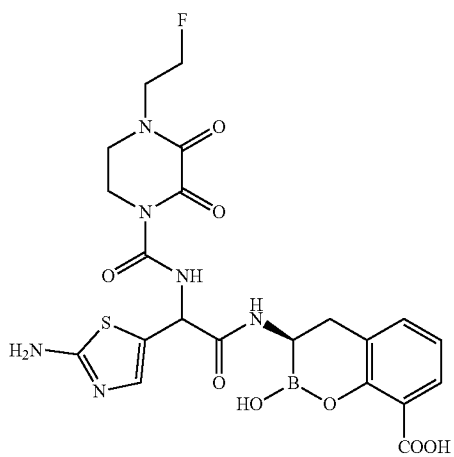 [SMILES: Nc1ncc(C(NC(=O)N2CCN(CCF)C(=O)C2=O)C(=O)N[C@H]2Cc3cccc(C(=O)O)c3OB2O)s1] | 548.3 | 549 |
| 101 | 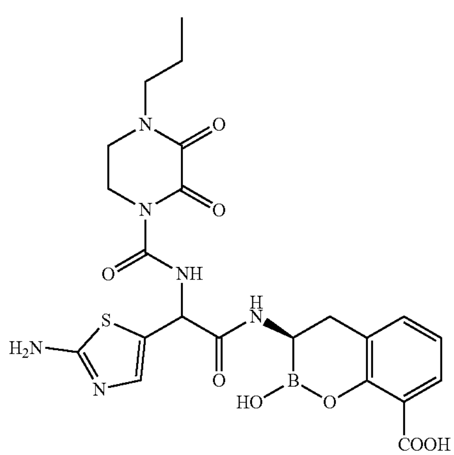 [SMILES: CCCN1CCN(C(=O)NC(C(=O)N[C@H]2Cc3cccc(C(=O)O)c3OB2O)c2cnc(N)s2)C(=O)C1=O] | 544.3 | 545 |

TABLE 1-continued

Example compounds.

| Ex. | Structure | MW | ESI-MS (m/z) for [MH]+ |
|-----|-----------|-----|------------------------|
| 102 | 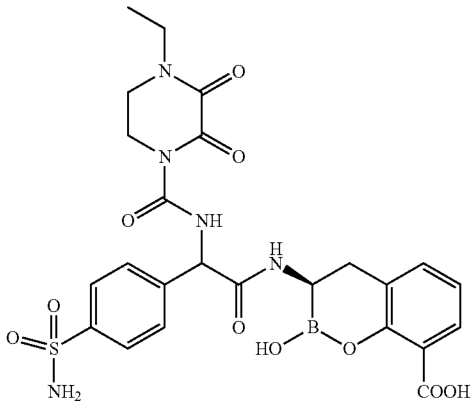 [SMILES: CCN1CCN(C(=O)NC(C(=O)N[C@H]2Cc3cccc(C(=O)O)c3OB2O)c2ccc(S(N)(=O)=O)cc2)C(=O)C1=O] | 587.4 | 588 |
| 103 | 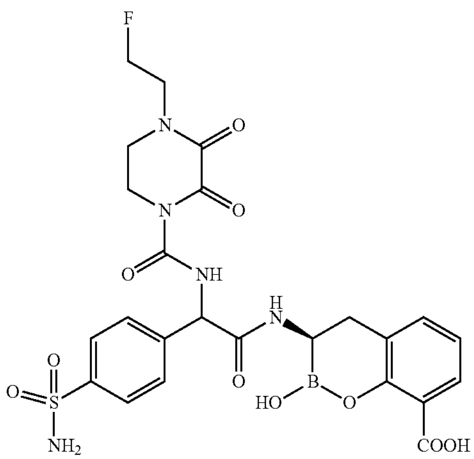 [SMILES: NS(=O)(=O)c1ccc(C(NC(=O)N2CCN(CCF)C(=O)C2=O)C(=O)N[C@H]2Cc3cccc(C(=O)O)c3OB2O)cc1] | 605.4 | 606 |
| 104 | 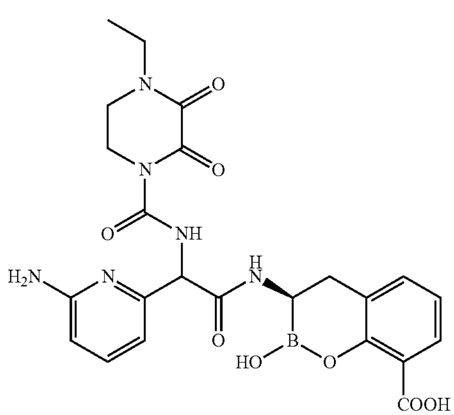 [SMILES: CCN1CCN(C(=O)NC(C(=O)N[C@H]2Cc3cccc(C(=O)O)c3OB2O)c2cccc(N)n2)C(=O)C1=O] | 524.3 | 525 |

TABLE 1-continued

Example compounds.

| Ex. | Structure | MW | ESI-MS (m/z) for [MH]+ |
|---|---|---|---|
| 105 | 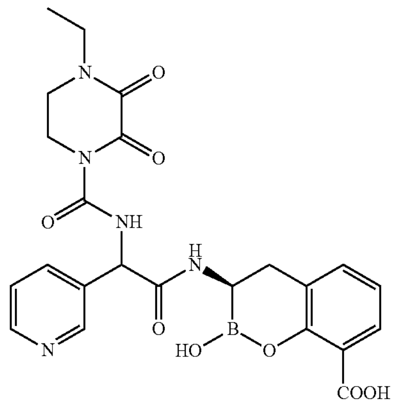 [SMILES: CCN1CCN(C(=O)NC(C(=O)N[C@H]2Cc3cccc(C(=O)O)c3OB2O)c2cccnc2)C(=O)C1=O] | 509.3 | 510 |
| 106 | 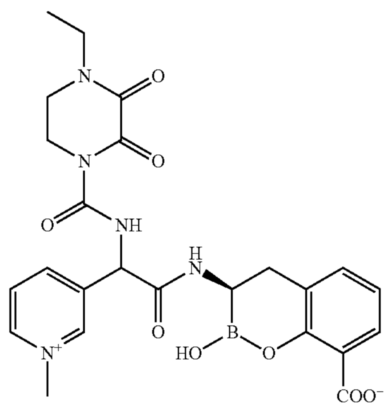 | 523.3 | 524 |
| 107 | 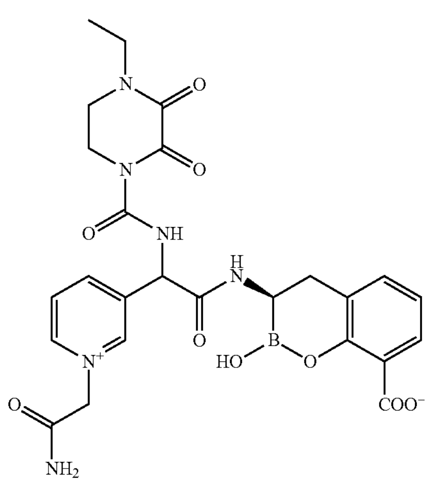 | 566.3 | 567 |

TABLE 1-continued

Example compounds.

| Ex. | Structure | MW | ESI-MS (m/z) for [MH]+ |
|---|---|---|---|
| 108 | 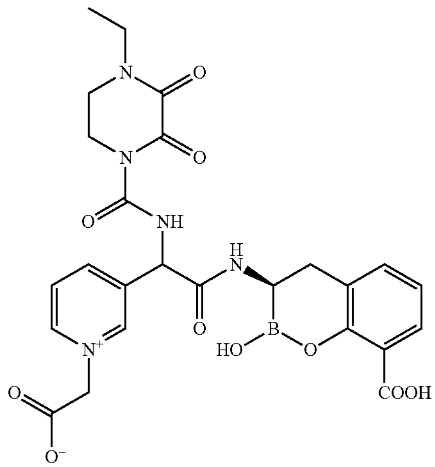 [SMILES: CCN1CCN(C(=O)NC(C(=O)N[C@H]2Cc3cccc(C(=O)O)c3OB2O)c2ccc[n+](CC(=O)[O-])c2)C(=O)C1=O] | 567.3 | 568 |
| 109 | 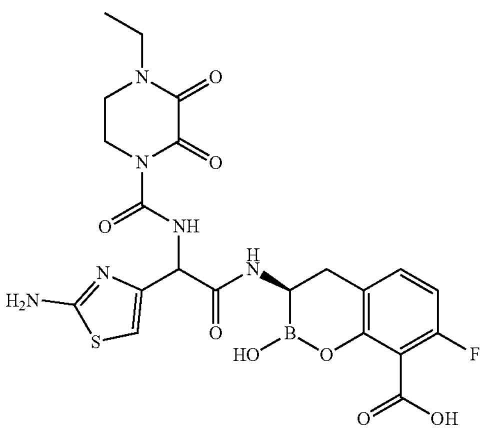 [SMILES: CCN1CCN(C(=O)NC(C(=O)N[C@H]2Cc3ccc(F)c(C(=O)O)c3OB2O)c2csc(N)n2)C(=O)C1=O] | 548.3 | 549 |
| 110 | 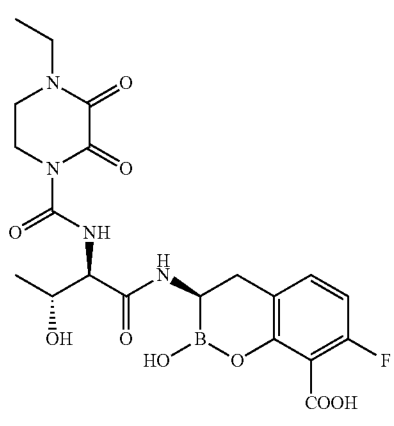 [SMILES: CCN1CCN(C(=O)N[C@@H](C(=O)N[C@H]2Cc3ccc(F)c(C(=O)O)c3OB2O)[C@@H](C)O)C(=O)C1=O] | 494.2 | 495 |

TABLE 1-continued
Example compounds.
| Ex. | Structure | MW | ESI-MS (m/z) for [MH]+ |
|---|---|---|---|
| 111 | 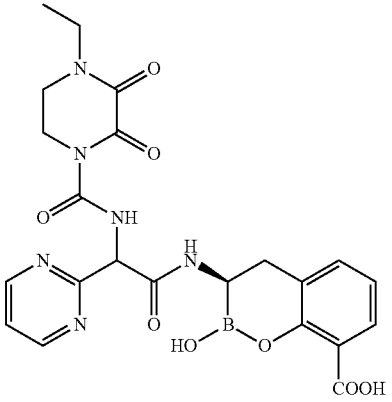 | 510.3 | 511 |
| 112 | 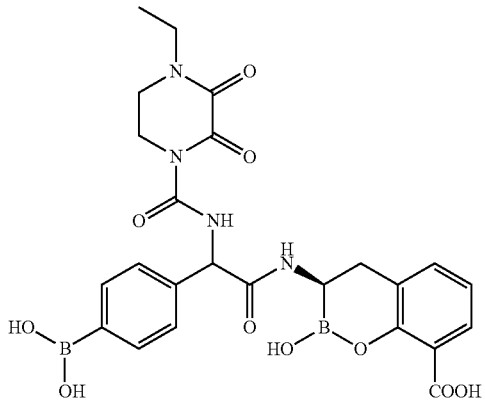 [SMILES: CCN1CCN(C(=O)NC(C(=O)N[C@H]2Cc3cccc(C(=O)O)c3OB2O)c2ccc(B(O)O)cc2)C(=O)C1=O] | 552.1 | 553 |
| 113 | 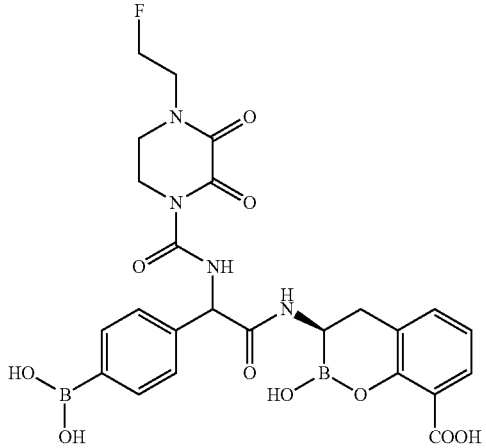 [SMILES: O=C(O)c1cccc2c1OB(O)[C@@H](NC(=O)C(NC(=O)N1CCN(CCF)C(=O)C1=O)c1ccc(B(O)O)cc1)C2] | 570.1 | 571 |

TABLE 1-continued

Example compounds.

| Ex. | Structure | MW | ESI-MS (m/z) for [MH]+ |
|---|---|---|---|
| 114 | 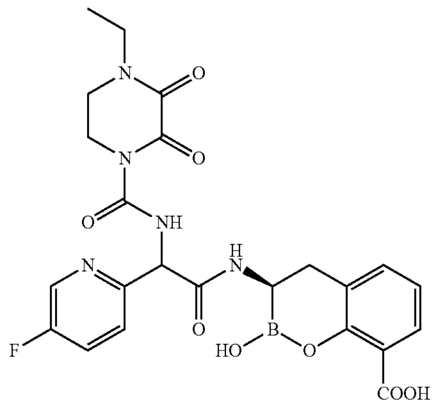 [SMILES: CCN1CCN(C(=O)NC(C(=O)N[C@H]2Cc3cccc(C(=O)O)c3OB2O)c2ccc(F)cn2)C(=O)C1=O] | 527.3 | 528 |
| 115 | 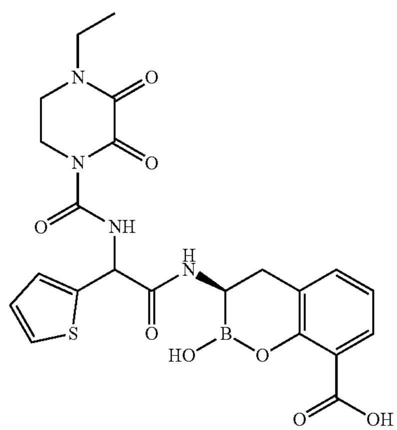 [SMILES: CCN1CCN(C(=O)NC(C(=O)N[C@H]2Cc3cccc(C(=O)O)c3OB2O)c2cccs2)C(=O)C1=O] | 514.3 | 515 |
| 116 | 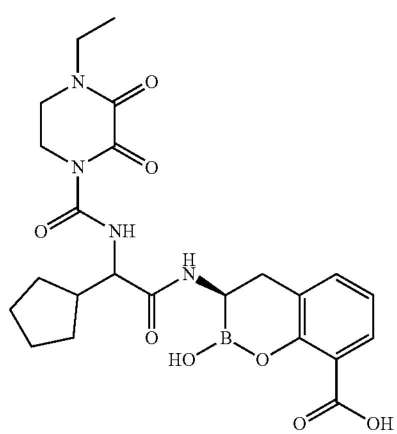 [SMILES: CCN1CCN(C(=O)NC(C(=O)N[C@H]2Cc3cccc(C(=O)O)c3OB2O)C2CCCC2)C(=O)C1=O] | 500.3 | 501 |

TABLE 1-continued
Example compounds.
| Ex. | Structure | MW | ESI-MS (m/z) for [MH]+ |
|---|---|---|---|
| 117 | 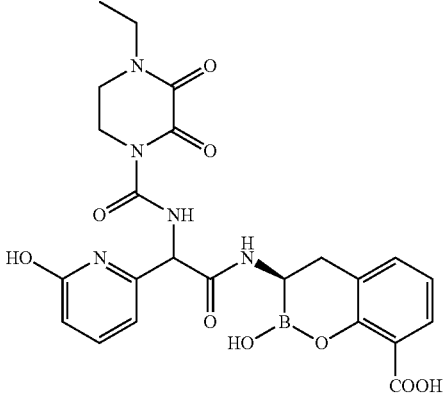 [SMILES: CCN1CCN(C(=O)NC(C(=O)N[C@H]2Cc3cccc(C(=O)O)c3OB2O)c2cccc(O)n2)C(=O)C1=O] | 525.3 | 526 |
| 118 | 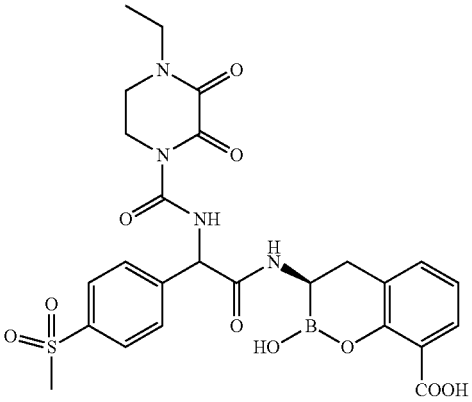 [SMILES: CCN1CCN(C(=O)NC(C(=O)N[C@H]2Cc3cccc(C(=O)O)c3OB2O)c2ccc(S(C)(=O)=O)cc2)C(=O)C1=O] | 586.4 | 587 |
| 119 | 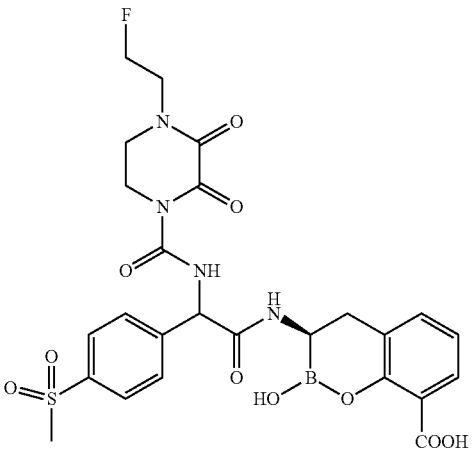 [SMILES: CS(=O)(=O)c1ccc(C(NC(=O)N2CCN(CCF)C(=O)C2=O)C(=O)N[C@H]2Cc3cccc(C(=O)O)c3OB2O)cc1] | 604.4 | 605 |

TABLE 1-continued
Example compounds.
| Ex. | Structure | MW | ESI-MS (m/z) for [MH]+ |
|---|---|---|---|
| 120 | 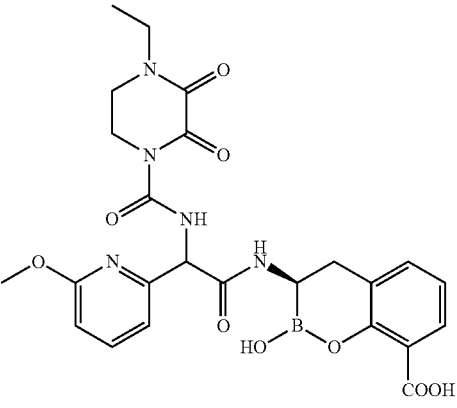 [SMILES: CCN1CCN(C(=O)NC(C(=O)N[C@H]2Cc3cccc(C(=O)O)c3OB2O)c2cccc(OC)n2)C(=O)C1=O] | 539.3 | 540 |
| 121 | 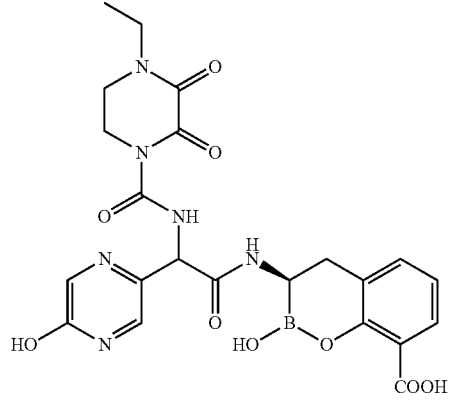 [SMILES: CCN1CCN(C(=O)NC(C(=O)N[C@H]2Cc3cccc(C(=O)O)c3OB2O)c2cnc(O)cn2)C(=O)C1=O] | 526.3 | 527 |
| 122 | 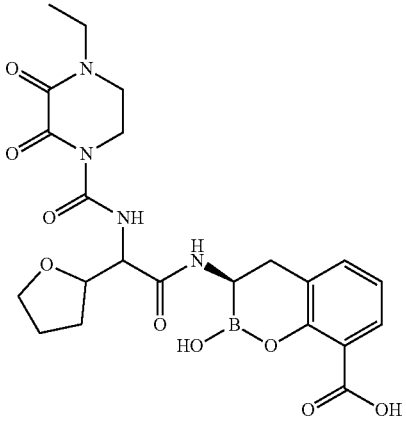 [SMILES: CCN1CCN(C(=O)NC(C(=O)N[C@H]2Cc3cccc(C(=O)O)c3OB2O)C2CCCO2)C(=O)C1=O] | 502.3 | 503 |

TABLE 1-continued

Example compounds.

| Ex. | Structure | MW | ESI-MS (m/z) for [MH]+ |
|---|---|---|---|
| 123 | 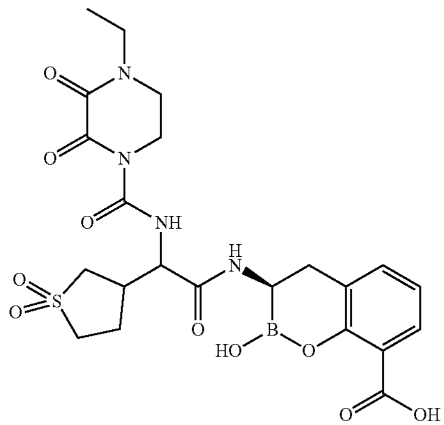 [SMILES: CCN1CCN(C(=O)NC(C(=O)N[C@H]2Cc3cccc(C(=O)O)c3OB2O)C2CCS(=O)(=O)C2)C(=O)C1=O] | 550.3 | 551 |
| 124 | 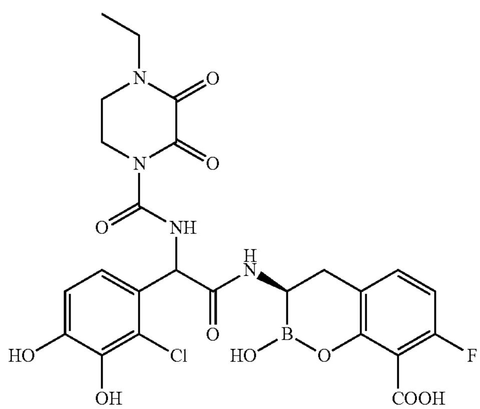 [SMILES: CCN1CCN(C(=O)NC(C(=O)N[C@H]2Cc3ccc(F)c(C(=O)O)c3OB2O)c2ccc(O)c(O)c2Cl)C(=O)C1=O] | 592.7 | 593/595 |
| 125 | 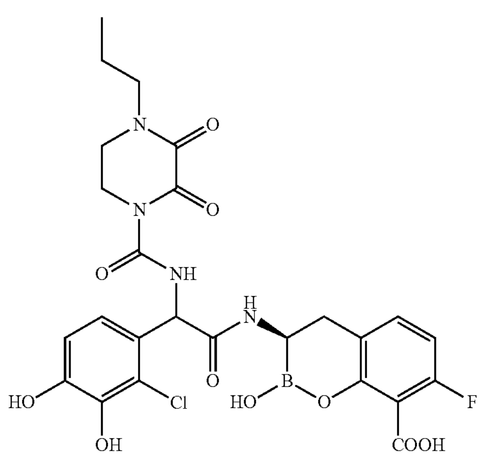 [SMILES: CCCN1CCN(C(=O)NC(C(=O)N[C@H]2Cc3ccc(F)c(C(=O)O)c3OB2O)c2ccc(O)c(O)c2Cl)C(=O)C1=O] | 606.8 | 607/609 |

TABLE 1-continued
Example compounds.
| Ex. | Structure | MW | ESI-MS (m/z) for [MH]+ |
|---|---|---|---|
| 126 | 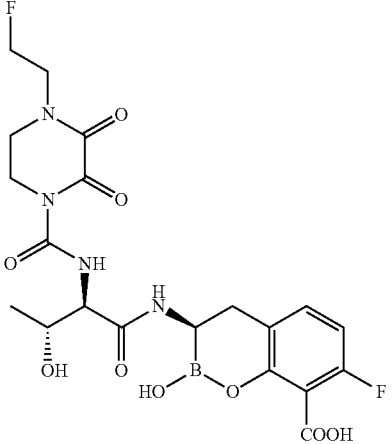 [SMILES: C[C@@H](O)[C@@H](NC(=O)N1CCN(CCF)C(=O)C1=O)C(=O)N[C@H]1Cc2ccc(F)c(C(=O)O)c2OB1O] | 512.2 | 513 |
| 127 | 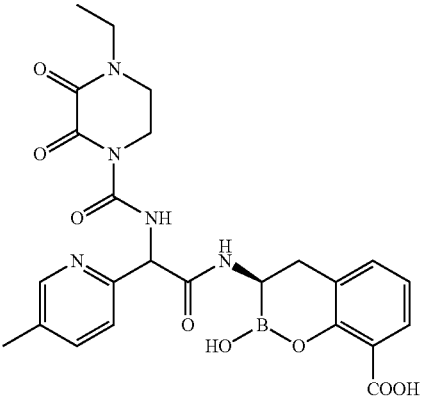 [SMILES: CCN1CCN(C(=O)NC(C(=O)N[C@H]2Cc3cccc(C(=O)O)c3OB2O)c2ccc(C)cn2)C(=O)C1=O] | 523.3 | 524 |
| 128 | 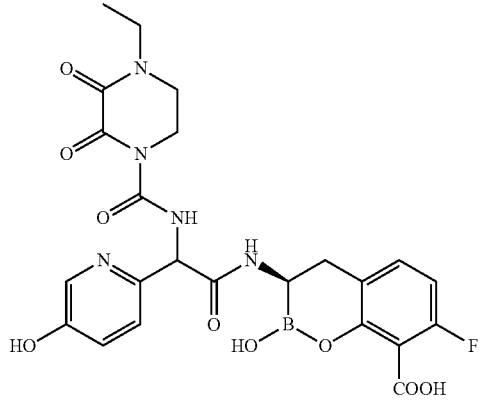 [SMILES: CCN1CCN(C(=O)NC(C(=O)N[C@H]2Cc3ccc(F)c(C(=O)O)c3OB2O)c2ccc(O)cn2)C(=O)C1=O] | 543.3 | 544 |

TABLE 1-continued

Example compounds.

| Ex. | Structure | MW | ESI-MS (m/z) for [MH]+ |
|---|---|---|---|
| 129 | 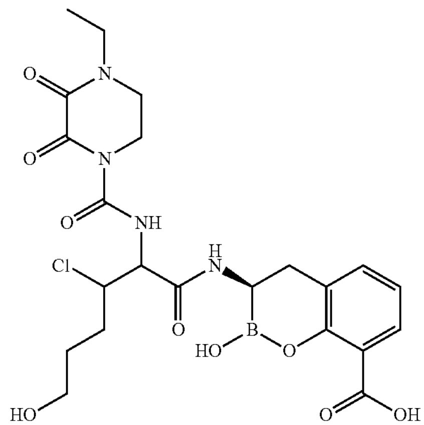 [SMILES: CCN1CCN(C(=O)NC(C(=O)N[C@H]2Cc3cccc(C(=O)O)c3OB2O)C(Cl)CCCO)C(=O)C1=O] | 538.7 | 539.2 |
| 130 | 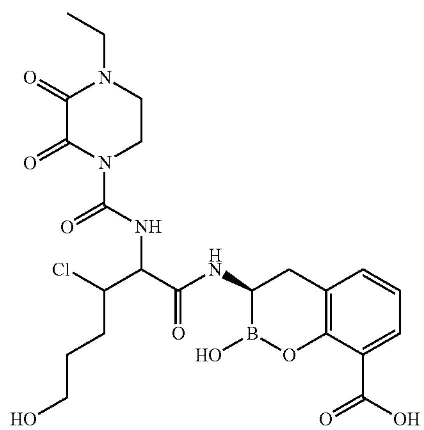 [SMILES: CCN1CCN(C(=O)NC(C(=O)N[C@H]2Cc3cccc(C(=O)O)c3OB2O)C(Cl)CCCO)C(=O)C1=O] | 538.7 | 539.2 |
| 131 | 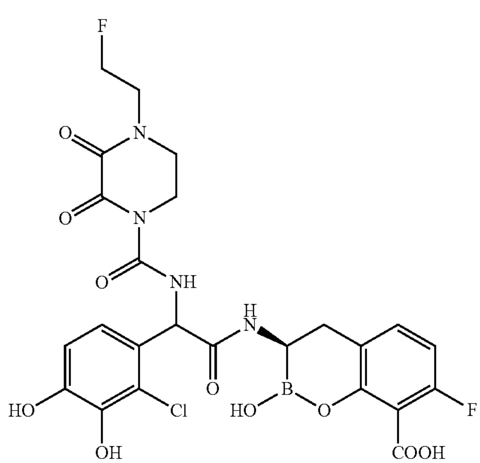 [SMILES: O=C(O)c1c(F)ccc2c1OB(O)[C@@H](NC(=O)C(NC(=O)N1CCN(CCF)C(=O)C1=O)c1ccc(O)c(O)c1Cl)C2] | 610.7 | 611/613 |

TABLE 1-continued
Example compounds.
| Ex. | Structure | MW | ESI-MS (m/z) for [MH]+ |
|---|---|---|---|
| 132 | 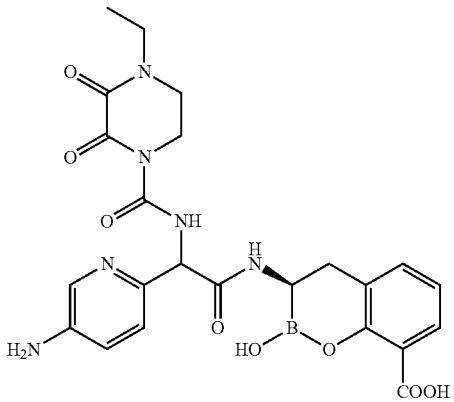 [SMILES: CCN1CCN(C(=O)NC(C(=O)N[C@H]2Cc3cccc(C(=O)O)c3OB2O)c2ccc(N)cn2)C(=O)C1=O] | 524.3 | 525 |
| 133 | 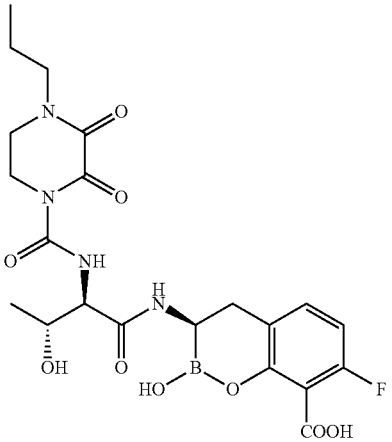 [SMILES: CCCN1CCN(C(=O)N[C@@H](C(=O)N[C@H]2Cc3ccc(F)c(C(=O)O)c3OB2O)[C@@H](C)O)C(=O)C1=O] | 508.3 | 509.1 |

TABLE 1-continued

Example compounds.

| Ex. | Structure | MW | ESI-MS (m/z) for [MH]+ |
|---|---|---|---|
| 134 | 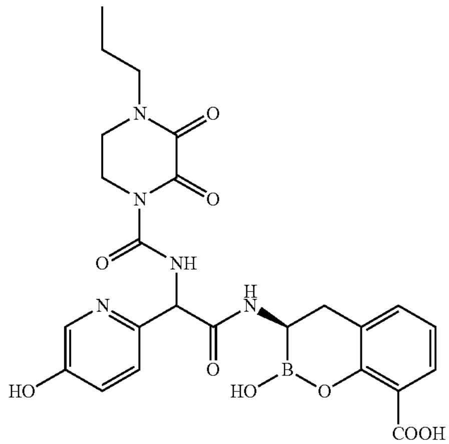 [SMILES: CCCN1CCN(C(=O)NC(C(=O)N[C@H]2Cc3cccc(C(=O)O)c3OB2O)c2ccc(O)cn2)C(=O)C1=O] | 539.3 | 540 |
| 135 | 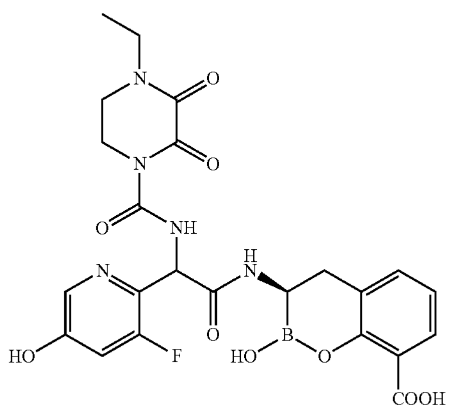 | 543.3 | 544 |
| 136 | 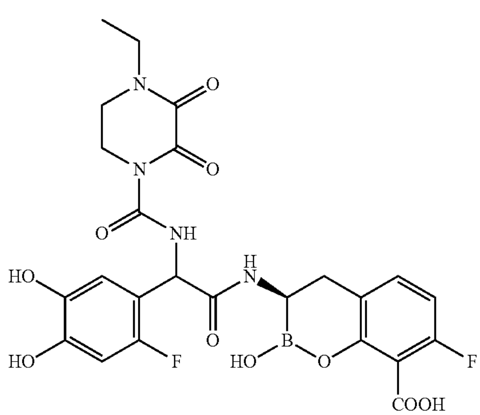 [SMILES: CCN1CCN(C(=O)NC(C(=O)N[C@H]2Cc3ccc(F)c(C(=O)O)c3OB2O)c2cc(O)c(O)cc2F)C(=O)C1=O] | 576.3 | 577 |

TABLE 1-continued

Example compounds.

| Ex. | Structure | MW | ESI-MS (m/z) for [MH]+ |
|---|---|---|---|
| 137 | 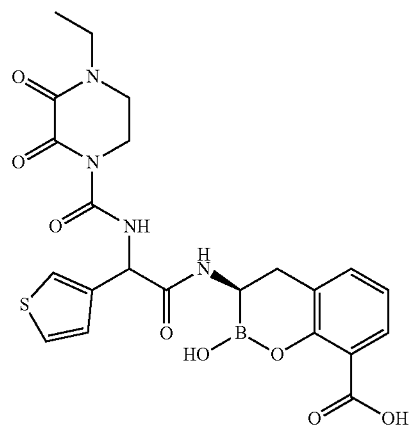 [SMILES: CCN1CCN(C(=O)NC(C(=O)N[C@H]2Cc3cccc(C(=O)O)c3OB2O)c2ccsc2)C(=O)C1=O] | 514.3 | 515.1 |
| 138 | 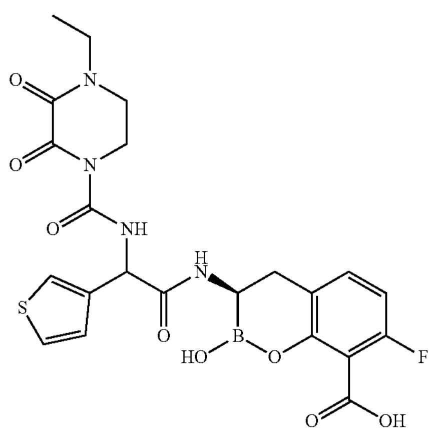 | 532.3 | 533.1 |
| 139 | 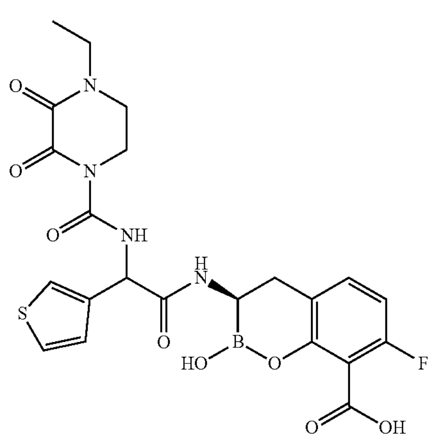 | 532.3 | 533.1 |

TABLE 1-continued

Example compounds.

| Ex. | Structure | MW | ESI-MS (m/z) for [MH]+ |
|---|---|---|---|
| 140 | 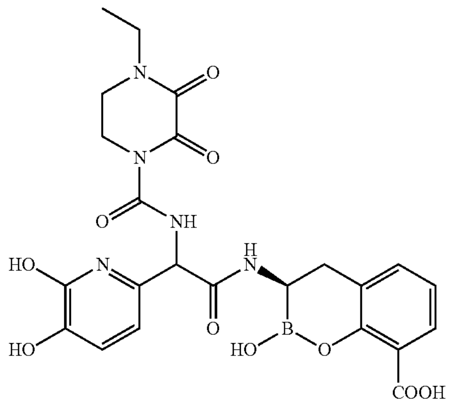 [SMILES: CCN1CCN(C(=O)NC(C(=O)N[C@H]2Cc3cccc(C(=O)O)c3OB2O)c2ccc(O)c(O)n2)C(=O)C1=O] | 541.3 | 542 |
| 141 | 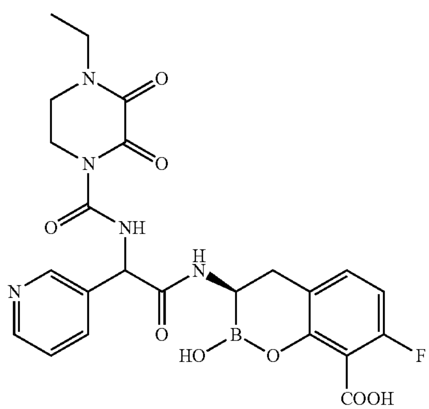 [SMILES: CCN1CCN(C(=O)NC(C(=O)N[C@H]2Cc3ccc(F)c(C(=O)O)c3OB2O)c2cccnc2)C(=O)C1=O] | 527.3 | 528 |
| 142 | 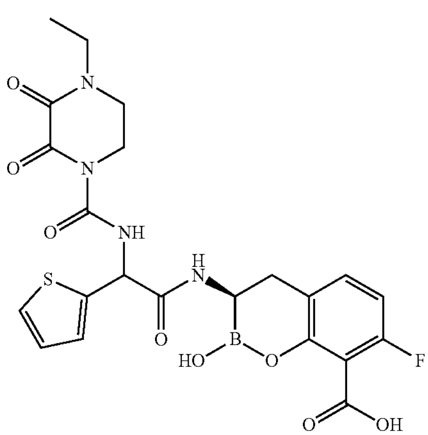 [SMILES: CCN1CCN(C(=O)NC(C(=O)N[C@H]2Cc3ccc(F)c(C(=O)O)c3OB2O)c2cccs2)C(=O)C1=O] | 532.3 | 533.2 |

TABLE 1-continued

Example compounds.

| Ex. | Structure | MW | ESI-MS (m/z) for [MH]+ |
|---|---|---|---|
| 143 | 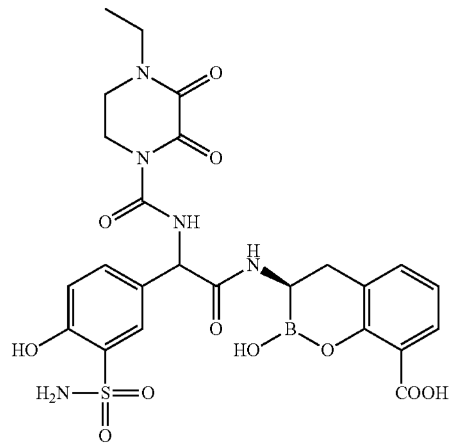 [SMILES: CCN1CCN(C(=O)NC(C(=O)N[C@H]2Cc3cccc(C(=O)O)c3OB2O)c2ccc(O)c(S(N)(=O)=O)c2)C(=O)C1=O] | 603.4 | 587 |
| 144 | 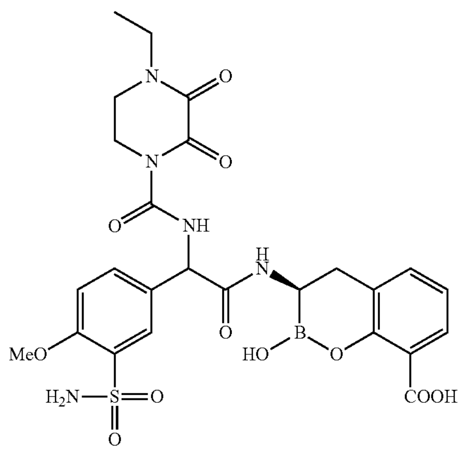 [SMILES: CCN1CCN(C(=O)NC(C(=O)N[C@H]2Cc3cccc(C(=O)O)c3OB2O)c2ccc(OC)c(S(N)(=O)=O)c2)C(=O)C1=O] | 617.4 | 587 |
| 145 | 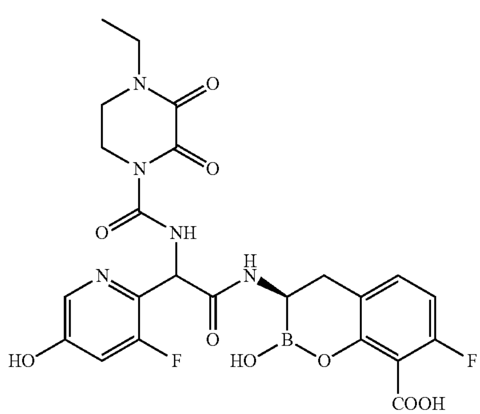 | 561.3 | 562 |

TABLE 1-continued
Example compounds.
| Ex. | Structure | MW | ESI-MS (m/z) for [MH]+ |
|---|---|---|---|
| 146 | 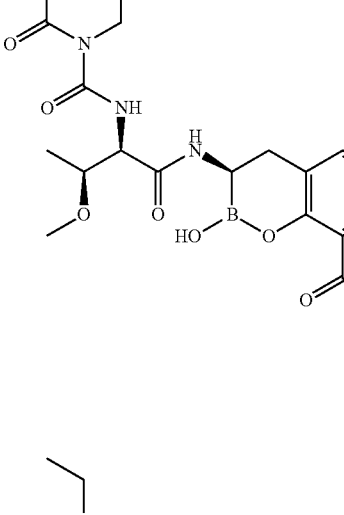 | 490.3 | 491.2 |
| 147 | 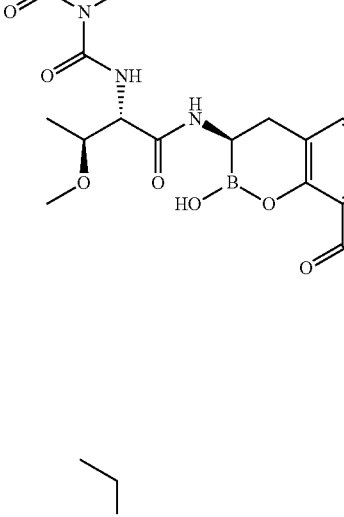 | 490.3 | 491.1 |
| 148 | 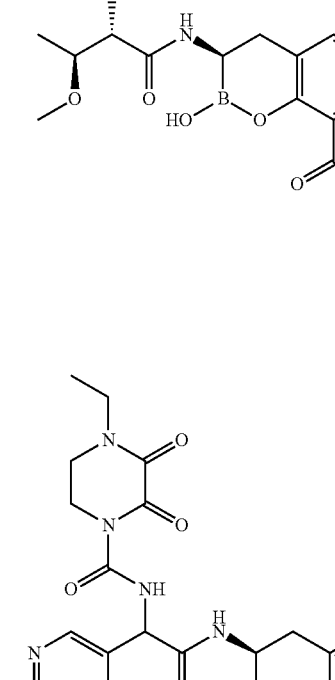 | 524.3 | 525 |

TABLE 1-continued

Example compounds.

| Ex. | Structure | MW | ESI-MS (m/z) for [MH]+ |
|---|---|---|---|
| 149 | 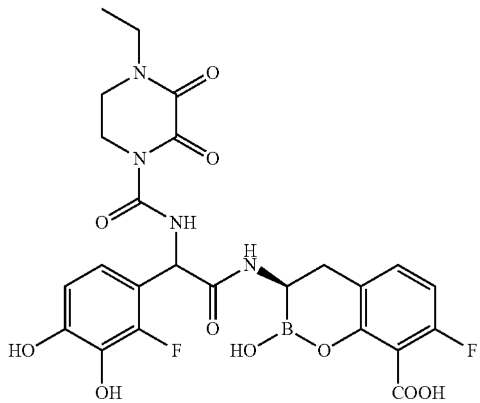 [SMILES: CCN1CCN(C(=O)NC(C(=O)N[C@H]2Cc3ccc(F)c(C(=O)O)c3OB2O)c2ccc(O)c(O)c2F)C(=O)C1=O] | 576.3 | 577 |
| 150 | 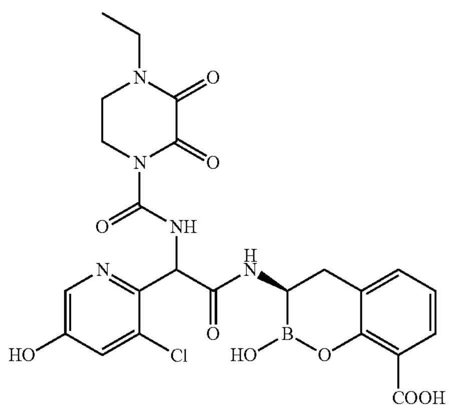 | 559.7 | 560 |
| 151 | 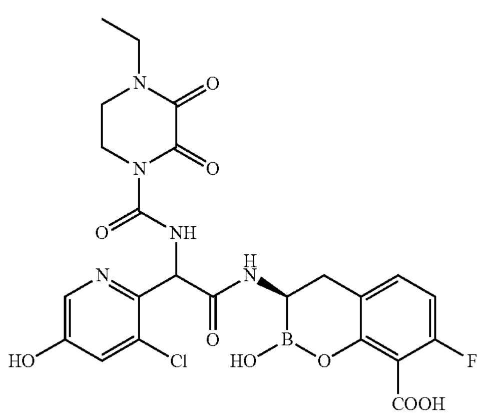 [SMILES: CCN1CCN(C(=O)NC(C(=O)N[C@H]2Cc3ccc(F)c(C(=O)O)c3OB2O)c2ncc(O)cc2Cl)C(=O)C1=O] | 577.7 | 578 |

TABLE 1-continued
Example compounds.
| Ex. | Structure | MW | ESI-MS (m/z) for [MH]+ |
|---|---|---|---|
| 152 | 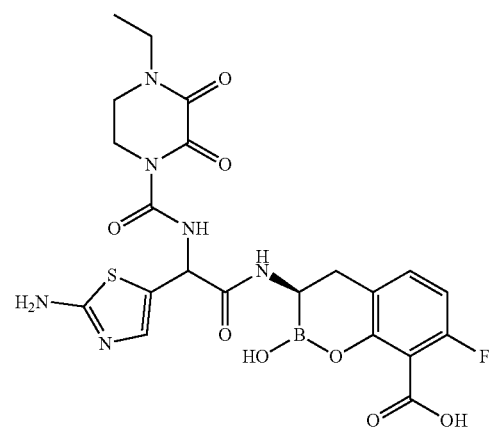 [SMILES: CCN1CCN(C(=O)NC(C(=O)N[C@H]2Cc3ccc(F)c(C(=O)O)c3OB2O)c2cnc(N)s2)C(=O)C1=O] | 548.3 | 549 |
| 153 | 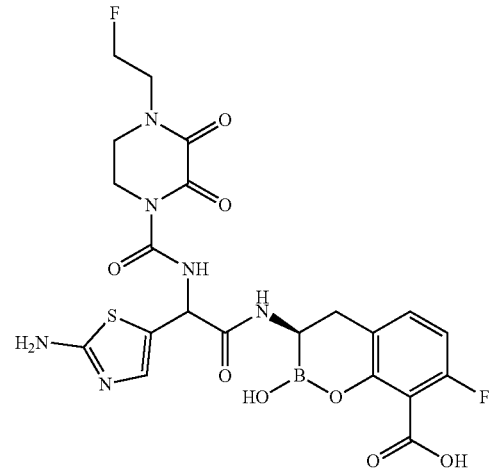 [SMILES: Nc1ncc(C(NC(=O)N2CCN(CCF)C(=O)C2=O)C(=O)N[C@H]2Cc3ccc(F)c(C(=O)O)c3OB2O)s1] | 566.3 | 567 |
| 154 | 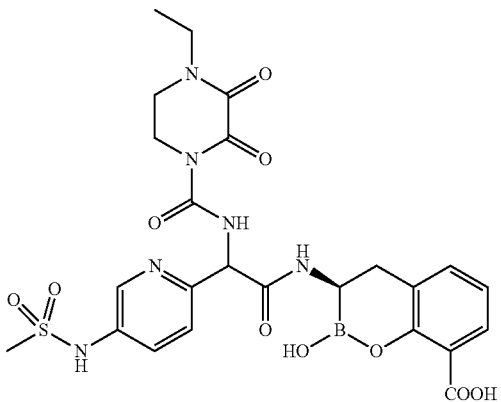 [SMILES: CCN1CCN(C(=O)NC(C(=O)N[C@H]2Cc3cccc(C(=O)O)c3OB2O)c2ccc(NS(C)(=O)=O)cn2)C(=O)C1=O] | 602.4 | 603 |

TABLE 1-continued

Example compounds.

| Ex. | Structure | MW | ESI-MS (m/z) for [MH]⁺ |
|---|---|---|---|
| 155 | 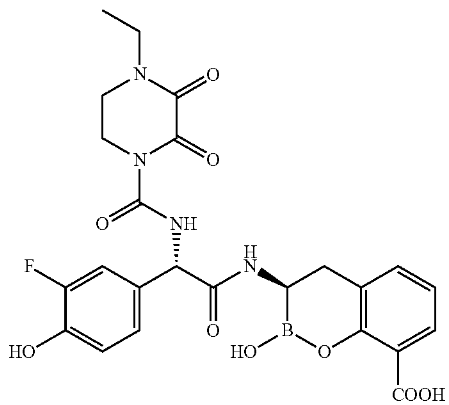 [SMILES: CCN1CCN(C(=O)N[C@H](C(=O)N[C@H]2Cc3cccc(C(=O)O)c3OB2O)c2ccc(O)c(F)c2)C(=O)C1=O] | 542.3 | 543 |
| 156 | 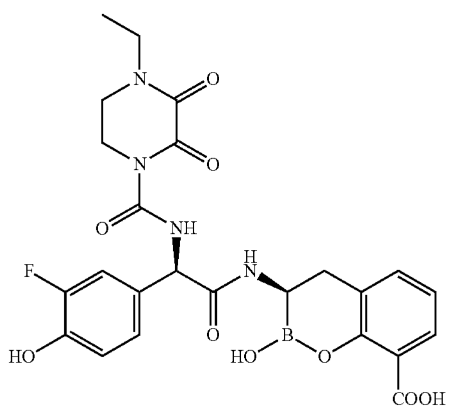 [SMILES: CCN1CCN(C(=O)N[C@@H](C(=O)N[C@H]2Cc3cccc(C(=O)O)c3OB2O)c2ccc(O)c(F)c2)C(=O)C1=O] | 542.3 | 543 |
| 157 | 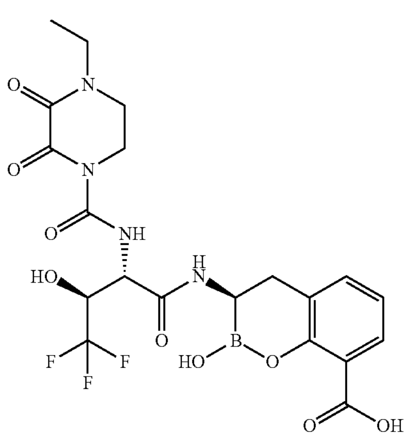 | 530.2 | 531.1 |

TABLE 1-continued

Example compounds.

| Ex. | Structure | MW | ESI-MS (m/z) for [MH]+ |
|---|---|---|---|
| 158 | 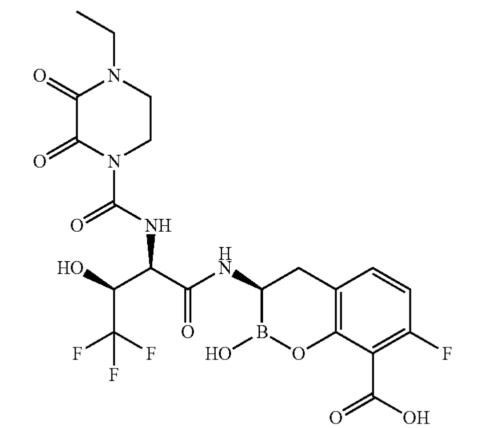 [SMILES: CCN1CCN(C(=O)N[C@@H](C(=O)N[C@H]2Cc3ccc(F)c(C(=O)O)c3OB2O)[C@H](O)C(F)(F)F)C(=O)C1=O] | 548.2 | 549.1 |
| 159 | 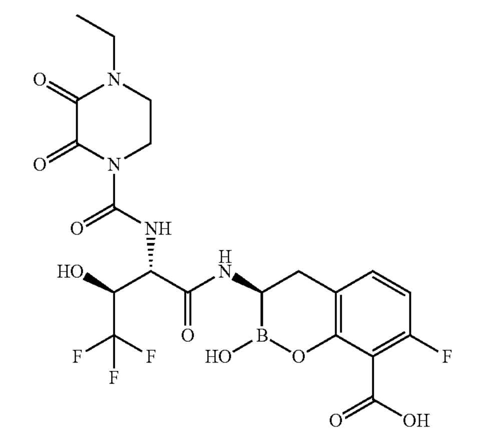 [SMILES: CCN1CCN(C(=O)N[C@H](C(=O)N[C@H]2Cc3ccc(F)c(C(=O)O)c3OB2O)[C@H](O)C(F)(F)F)C(=O)C1=O] | 548.2 | 549.1 |
| 160 | 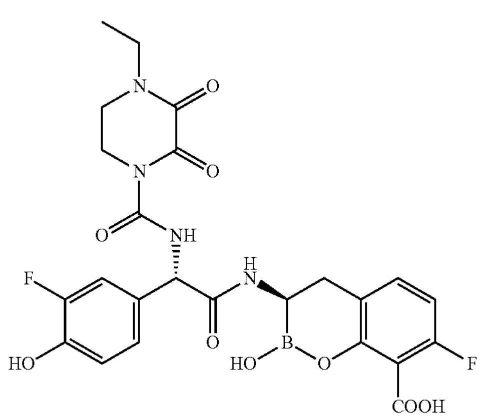 [SMILES: CCN1CCN(C(=O)N[C@H](C(=O)N[C@H]2Cc3ccc(F)c(C(=O)O)c3OB2O)c2ccc(O)c(F)c2)C(=O)C1=O] | 560.3 | 561 |

TABLE 1-continued

Example compounds.

| Ex. | Structure | MW | ESI-MS (m/z) for [MH]+ |
|---|---|---|---|
| 161 | 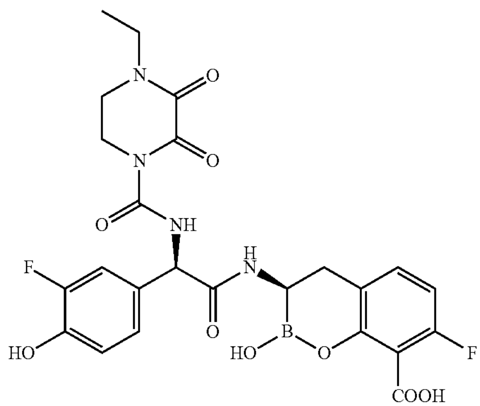 [SMILES: CCN1CCN(C(=O)N[C@@H](C(=O)N[C@H]2Cc3ccc(F)c(C(=O)O)c3OB2O)c2ccc(O)c(F)c2)C(=O)C1=O] | 560.3 | 561 |
| 162 | 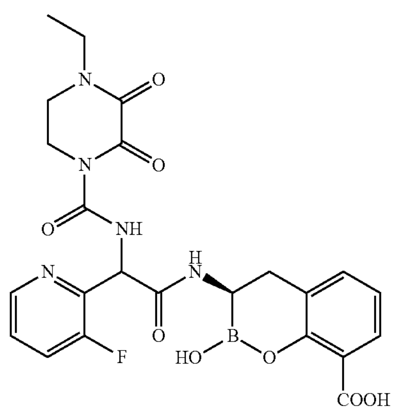 [SMILES: CCN1CCN(C(=O)NC(C(=O)N[C@H]2Cc3cccc(C(=O)O)c3OB2O)c2ncccc2F)C(=O)C1=O] | 527.3 | 528 |
| 163 | 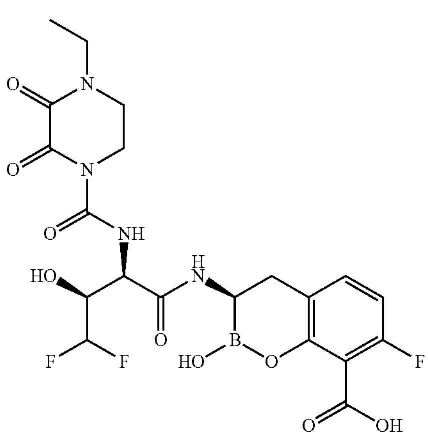 [SMILES: CCN1CCN(C(=O)N[C@@H](C(=O)N[C@H]2Cc3ccc(F)c(C(=O)O)c3OB2O)[C@H](O)C(F)F)C(=O)C1=O] | 530.2 | 531.1 |

TABLE 1-continued

Example compounds.

| Ex. | Structure | MW | ESI-MS (m/z) for [MH]+ |
|---|---|---|---|
| 164 | 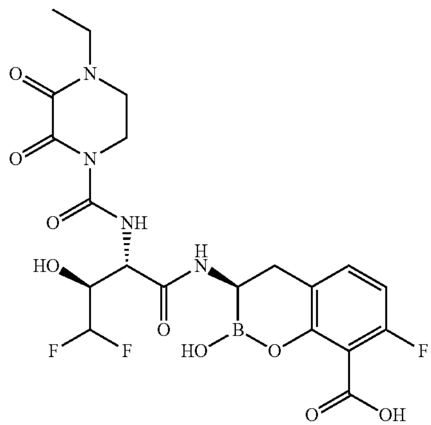 [SMILES: CCN1CCN(C(=O)N[C@H](C(=O)N[C@H]2Cc3ccc(F)c(C(=O)O)c3OB2O)[C@H](O)C(F)F)C(=O)C1=O] | 530.2 | 531.1 |
| 165 | 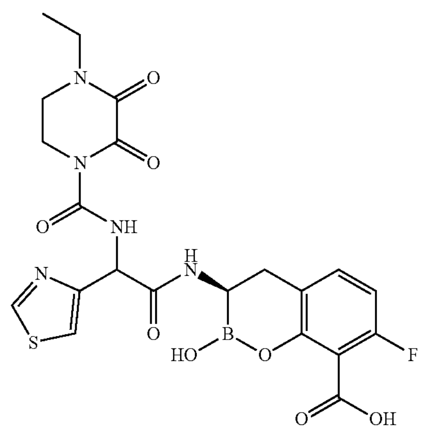 [SMILES: CCN1CCN(C(=O)NC(C(=O)N[C@H]2Cc3ccc(F)c(C(=O)O)c3OB2O)c2cscn2)C(=O)C1=O] | 533.3 | 534 |
| 166 | 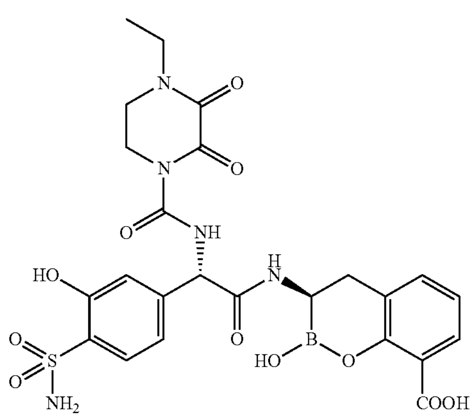 | 603.4 | 604 |

TABLE 1-continued

Example compounds.

| Ex. | Structure | MW | ESI-MS (m/z) for [MH]+ |
|---|---|---|---|
| 167 | 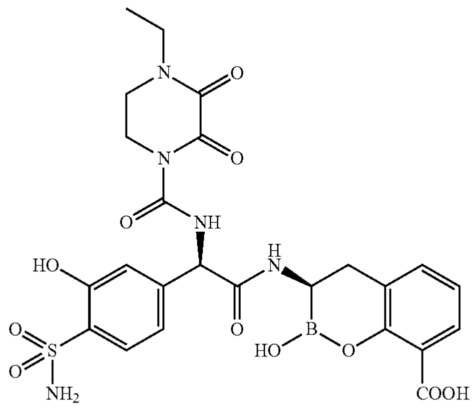 | 603.4 | 604 |
| 168 | 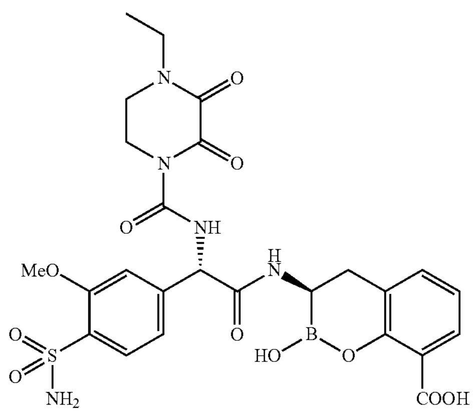 | 617.4 | 618 |
| 169 | 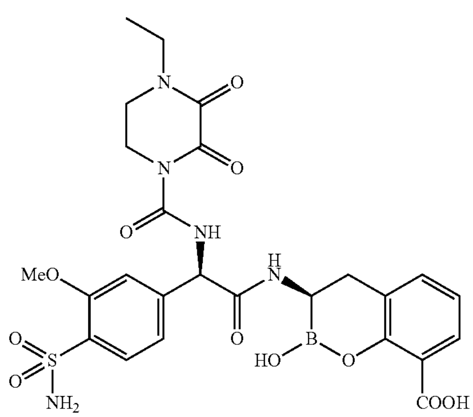 | 617.4 | 618 |

TABLE 1-continued

Example compounds.

| Ex. | Structure | MW | ESI-MS (m/z) for [MH]+ |
|---|---|---|---|
| 170 | 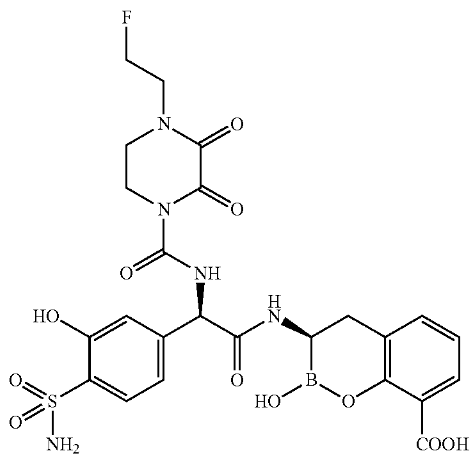 | 621.4 | 622 |
| 171 | 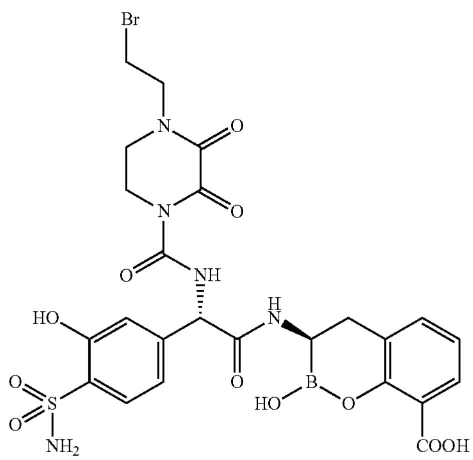 [SMILES: NS(=O)(=O)c1ccc([C@H](NC(=O)N2CCN(CCBr)C(=O)C2=O)C(=O)N[C@H]2Cc3cccc(C(=O)O)c3OB2O)cc1O] | 682.3 | 682/684 |
| 172 | 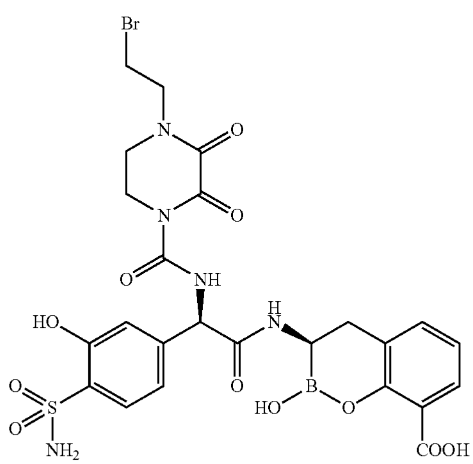 | 682.3 | 682/684 |

TABLE 1-continued

Example compounds.

| Ex. | Structure | MW | ESI-MS (m/z) for [MH]+ |
|---|---|---|---|
| 173 | 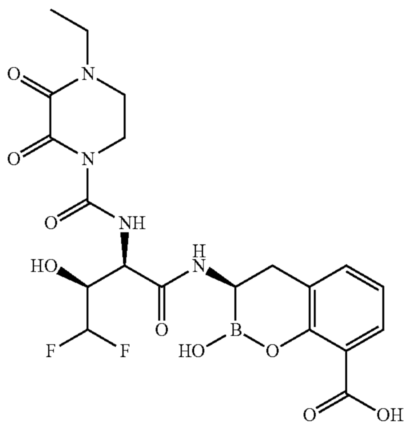 [SMILES: CCN1CCN(C(=O)N[C@@H](C(=O)N[C@H]2Cc3cccc(C(=O)O)c3OB2O)[C@H](O)C(F)F)C(=O)C1=O] | 512.2 | 513.1 |
| 174 | 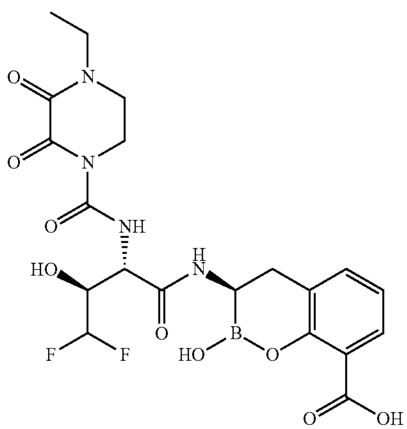 [SMILES: CCN1CCN(C(=O)N[C@H](C(=O)N[C@H]2Cc3cccc(C(=O)O)c3OB2O)[C@H](O)C(F)F)C(=O)C1=O] | 512.2 | 513.1 |
| 175 | 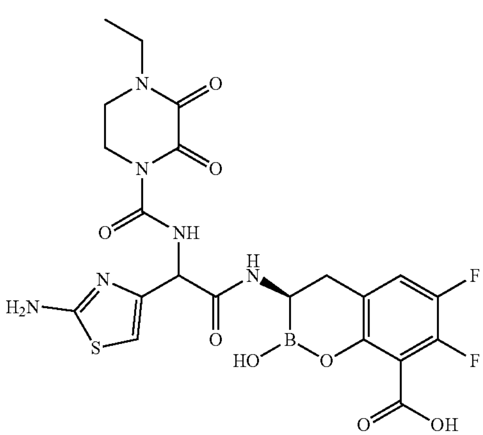 [SMILES: CCN1CCN(C(=O)NC(C(=O)N[C@H]2Cc3cc(F)c(F)c(C(=O)O)c3OB2O)c2csc(N)n2)C(=O)C1=O] | 566.3 | 567.1 |

TABLE 1-continued

Example compounds.

| Ex. | Structure | MW | ESI-MS (m/z) for [MH]+ |
|---|---|---|---|
| 176 | 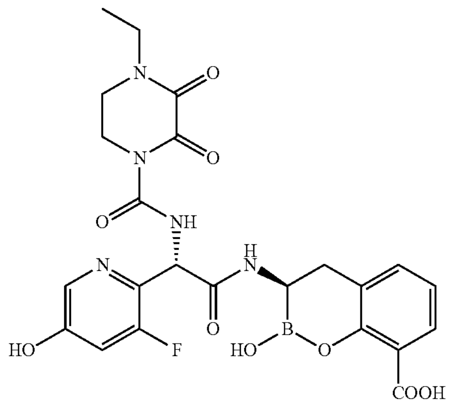 [SMILES: CCN1CCN(C(=O)N[C@H](C(=O)N[C@H]2Cc3cccc(C(=O)O)c3OB2O)c2ncc(O)cc2F)C(=O)C1=O] | 543.3 | 544 |
| 177 | 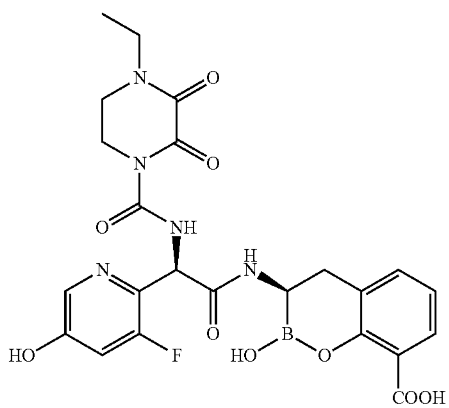 [SMILES: CCN1CCN(C(=O)N[C@@H](C(=O)N[C@H]2Cc3cccc(C(=O)O)c3OB2O)c2ncc(O)cc2F)C(=O)C1=O] | 543.3 | 544 |
| 178 | 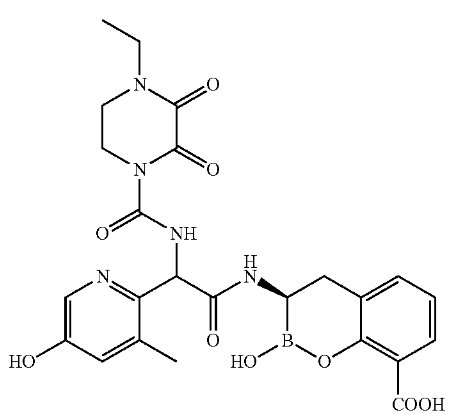 [SMILES: CCN1CCN(C(=O)NC(C(=O)N[C@H]2Cc3cccc(C(=O)O)c3OB2O)c2ncc(O)cc2C)C(=O)C1=O] | 539.3 | 540 |

TABLE 1-continued

Example compounds.

| Ex. | Structure | MW | ESI-MS (m/z) for [MH]+ |
|---|---|---|---|
| 179 | 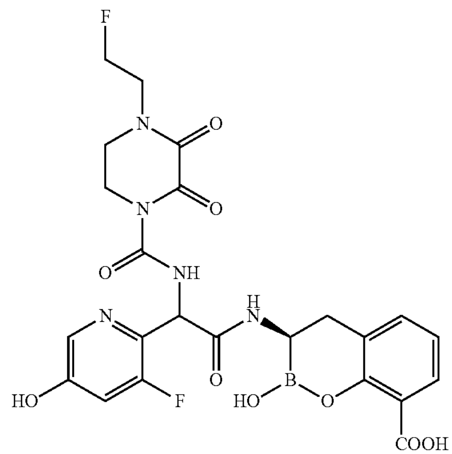 [SMILES: O=C(O)c1cccc2c1OB(O)[C@@H](NC(=O)C(NC(=O)N1CCN(CCF)C(=O)C1=O)c1ncc(O)cc1F)C2] | 561.3 | 562 |
| 180 | 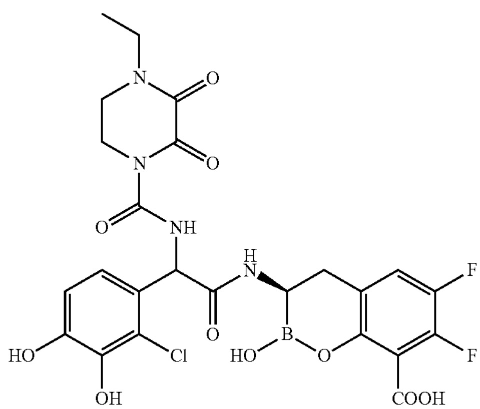 [SMILES: CCN1CCN(C(=O)NC(C(=O)N[C@H]2Cc3cc(F)c(F)c(C(=O)O)c3OB2O)c2ccc(O)c(O)c2Cl)C(=O)C1=O] | 610.7 | 611/613 |
| 181 | 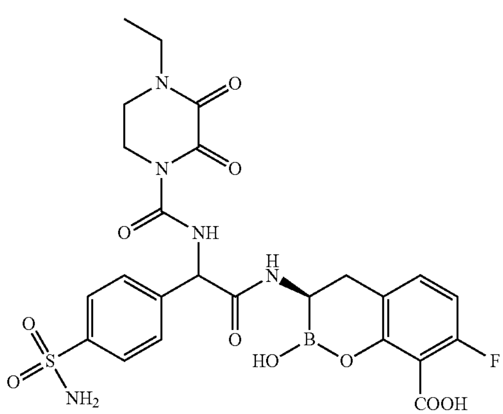 [SMILES: CCN1CCN(C(=O)NC(C(=O)N[C@H]2Cc3ccc(F)c(C(=O)O)c3OB2O)c2ccc(S(N)(=O)=O)cc2)C(=O)C1=O] | 605.4 | 606 |

TABLE 1-continued

Example compounds.

| Ex. | Structure | MW | ESI-MS (m/z) for [MH]+ |
|---|---|---|---|
| 182 | 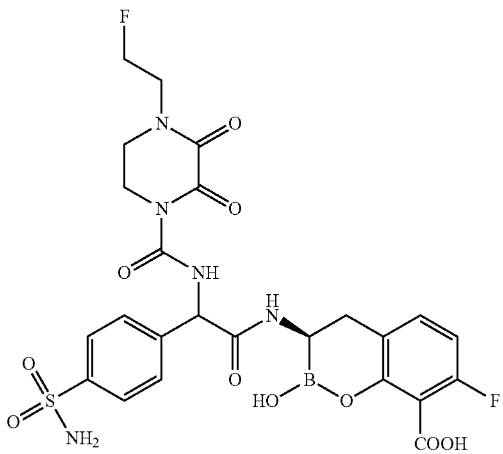 [SMILES: NS(=O)(=O)c1ccc(C(NC(=O)N2CCN(CCF)C(=O)C2=O)C(=O)N[C@H]2Cc3ccc(F)c(C(=O)O)c3OB2O)cc1] | 623.3 | 624 |
| 183 | 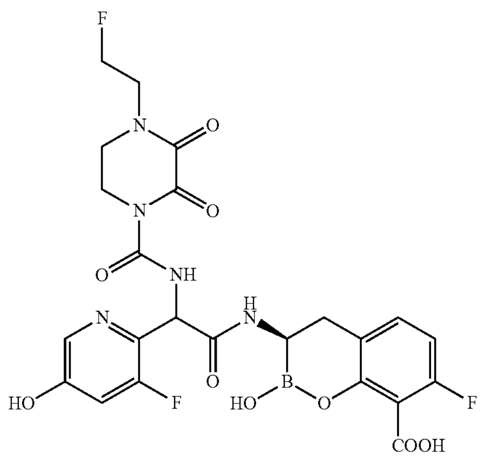 [SMILES: O=C(O)c1c(F)ccc2c1OB(O)[C@@H](NC(=O)C(NC(=O)N1CCN(CCF)C(=O)C1=O)c1ncc(O)cc1F)C2] | 579.3 | 580 |
| 184 | 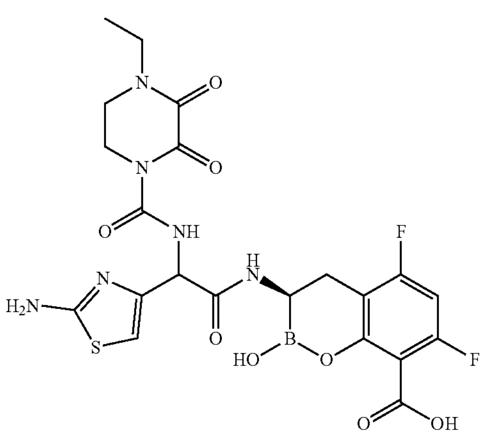 [SMILES: CCN1CCN(C(=O)NC(C(=O)N[C@H]2Cc3c(F)cc(F)c(C(=O)O)c3OB2O)c2csc(N)n2)C(=O)C1=O] | 566.3 | 567 |

TABLE 1-continued

Example compounds.

| Ex. | Structure | MW | ESI-MS (m/z) for [MH]+ |
|---|---|---|---|
| 185 | 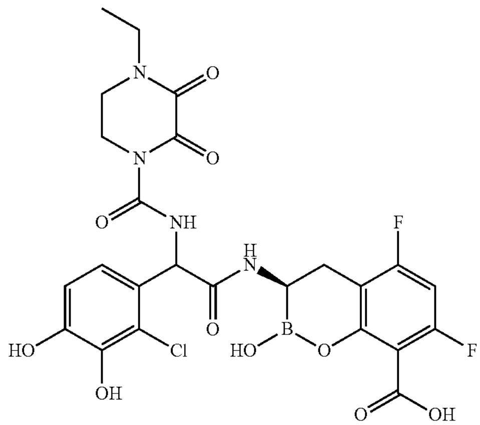 [SMILES: CCN1CCN(C(=O)NC(C(=O)N[C@H]2Cc3c(F)cc(F)c(C(=O)O)c3OB2O)c2ccc(O)c(O)c2Cl)C(=O)C1=O] | 610.7 | 611/613 |
| 186 | 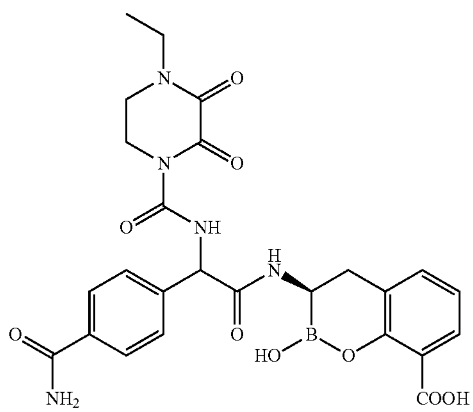 [SMILES: CCN1CCN(C(=O)NC(C(=O)N[C@H]2Cc3cccc(C(=O)O)c3OB2O)c2ccc(C(N)=O)cc2)C(=O)C1=O] | 551.3 | 552 |
| 187 | 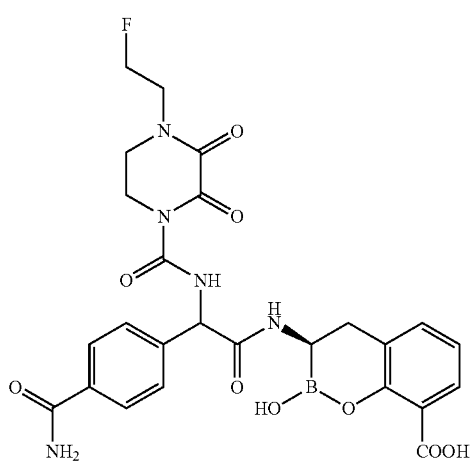 [SMILES: NC(=O)c1ccc(C(NC(=O)N2CCN(CCF)C(=O)C2=O)C(=O)N[C@H]2Cc3cccc(C(=O)O)c3OB2O)cc1] | 569.3 | 570 |

TABLE 1-continued

Example compounds.

| Ex. | Structure | MW | ESI-MS (m/z) for [MH]+ |
|---|---|---|---|
| 188 | 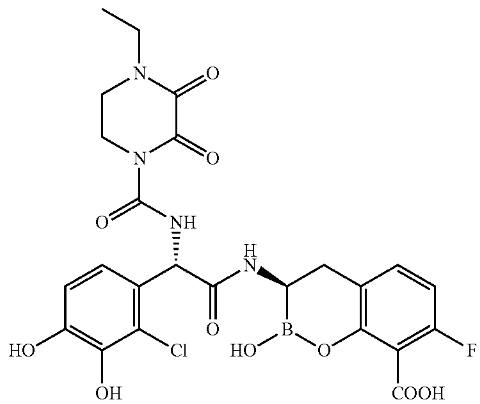 [SMILES: CCN1CCN(C(=O)N[C@H](C(=O)N[C@H]2Cc3ccc(F)c(C(=O)O)c3OB2O)c2ccc(O)c(O)c2Cl)C(=O)C1=O] | 592.7 | 593/595 |
| 189 | 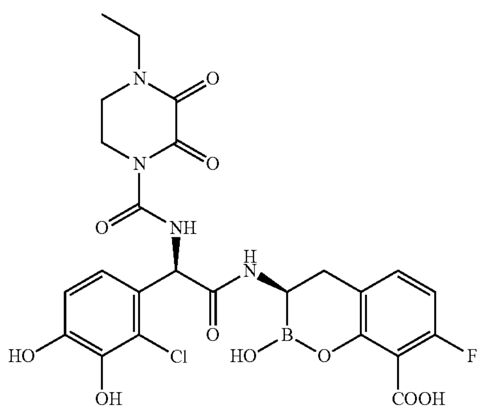 [SMILES: CCN1CCN(C(=O)N[C@@H](C(=O)N[C@H]2Cc3ccc(F)c(C(=O)O)c3OB2O)c2ccc(O)c(O)c2Cl)C(=O)C1=O] | 592.7 | 593/595 |
| 190 | 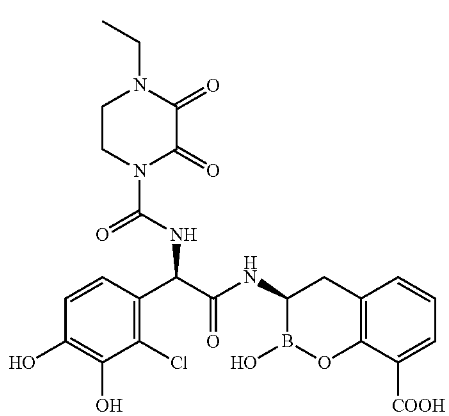 [SMILES: CCN1CCN(C(=O)N[C@@H](C(=O)N[C@H]2Cc3cccc(C(=O)O)c3OB2O)c2ccc(O)c(O)c2Cl)C(=O)C1=O] | 574.7 | 575/577 |

TABLE 1-continued

Example compounds.

| Ex. | Structure | MW | ESI-MS (m/z) for [MH]+ |
|---|---|---|---|
| 191 | 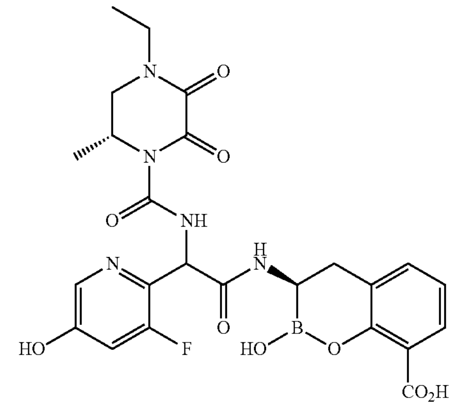 [SMILES: CCN1C[C@@H](C)N(C(=O)NC(C(=O)N[C@H]2Cc3cccc(C(=O)O)c3OB2O)c2ncc(O)cc2F)C(=O)C1=O] | 557.3 | 558 |
| 192 | 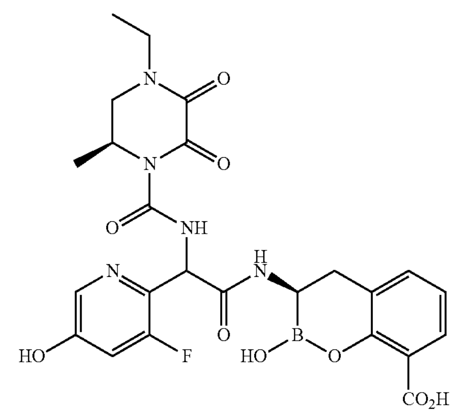 [SMILES: CCN1C[C@H](C)N(C(=O)NC(C(=O)N[C@H]2Cc3cccc(C(=O)O)c3OB2O)c2ncc(O)cc2F)C(=O)C1=O] | 557.3 | 558 |
| 193 | 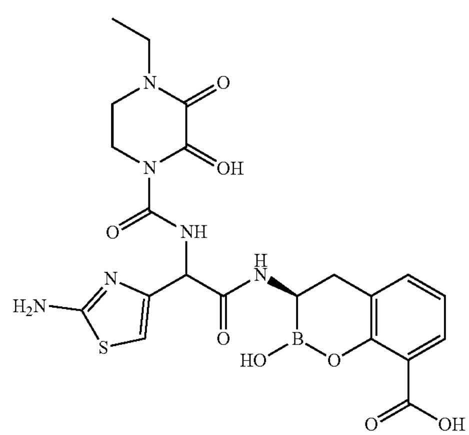 [SMILES: CCN1CCN(C(=O)NC(C(=O)N[C@H]2Cc3cccc(C(=O)O)c3OB2O)c2csc(N)n2)C(=O)C1=O] | 532.3 | 533 |

TABLE 1-continued

Example compounds.

| Ex. | Structure | MW | ESI-MS (m/z) for [MH]⁺ |
|---|---|---|---|
| 194 | 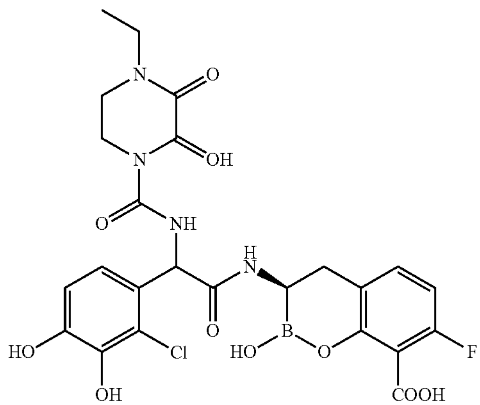 [SMILES: CCN1CCN(C(=O)NC(C(=O)N[C@H]2Cc3ccc(F)c(C(=O)O)c3OB2O)c2ccc(O)c(O)c2Cl)C(=O)C1=O] | 594.7 | 617 [M + Na]⁺ |
| 195 | 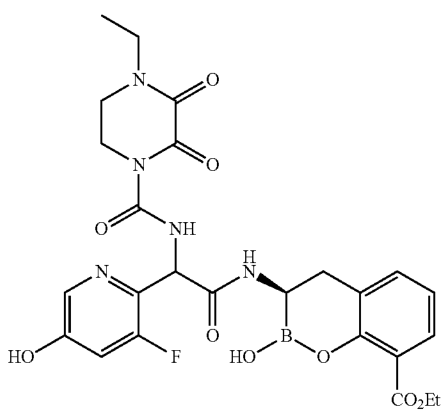 [SMILES: CCOC(=O)c1cccc2c1OB(O)[C@@H](NC(=O)C(NC(=O)N1CCN(CC)C(=O)C1=O)c1ncc(O)cc1F)C2] | 571.3 | 572 |
| 196 | 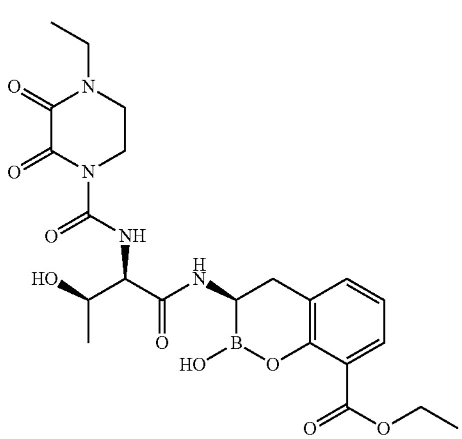 [SMILES: CCOC(=O)c1cccc2c1OB(O)[C@@H](NC(=O)[C@H](NC(=O)N1CCN(CC)C(=O)C1=O)[C@@H](C)O)C2] | 504.3 | 505.2 |

TABLE 1-continued
Example compounds.
| Ex. | Structure | MW | ESI-MS (m/z) for [MH]+ |
|---|---|---|---|
| 197 | 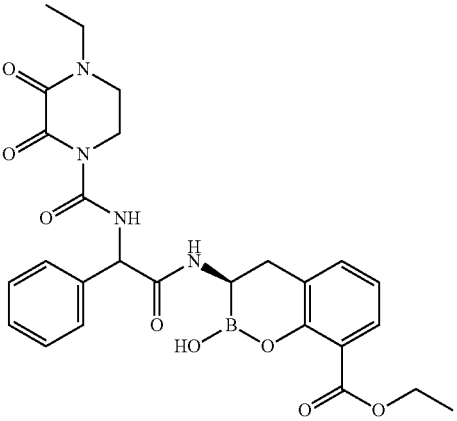 [SMILES: CCOC(=O)c1cccc2c1OB(O)[C@@H](NC(=O)C(NC(=O)N1CCN(CC)C(=O)C1=O)c1ccccc1)C2] | 536.3 | 537.2 |
| 198 | 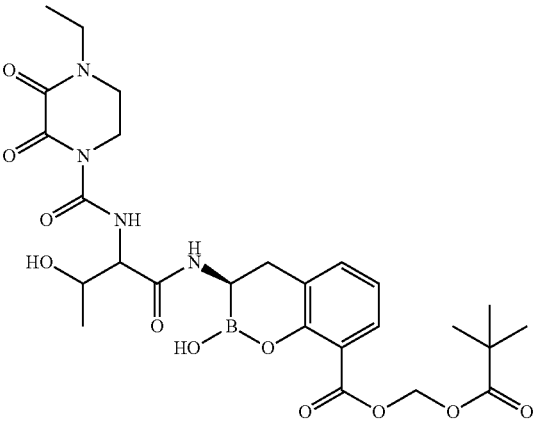 [SMILES: CCN1CCN(C(=O)NC(C(=O)N[C@H]2Cc3cccc(C(=O)OCOC(=O)C(C)(C)C)c3OB2O)C(C)O)C(=O)C1=O] | 590.4 | 591.3 |
| 199 | 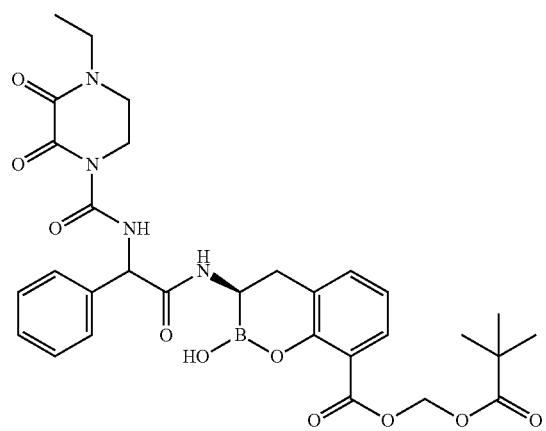 [SMILES: CCN1CCN(C(=O)NC(C(=O)N[C@H]2Cc3cccc(C(=O)OCOC(=O)C(C)(C)C)c3OB2O)c2ccccc2)C(=O)C1=O] | 622.4 | 539.2 [(M − (Piv)) + H]+ |

TABLE 1-continued

Example compounds.

| Ex. | Structure | MW | ESI-MS (m/z) for [MH]+ |
|---|---|---|---|
| 200 | 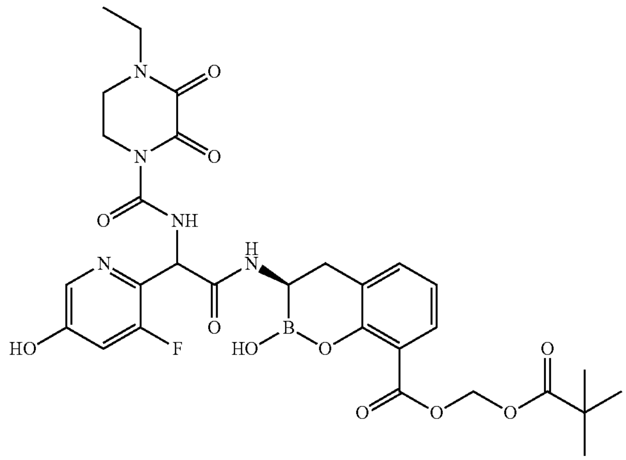 [SMILES: CCN1CCN(C(=O)NC(C(=O)N[C@H]2Cc3cccc(C(=O)OCOC(=O)C(C)(C)C)c3OB2O)c2ncc(O)cc2F)C(=O)C1=O] | 657.4 | 658 |
| 201 | 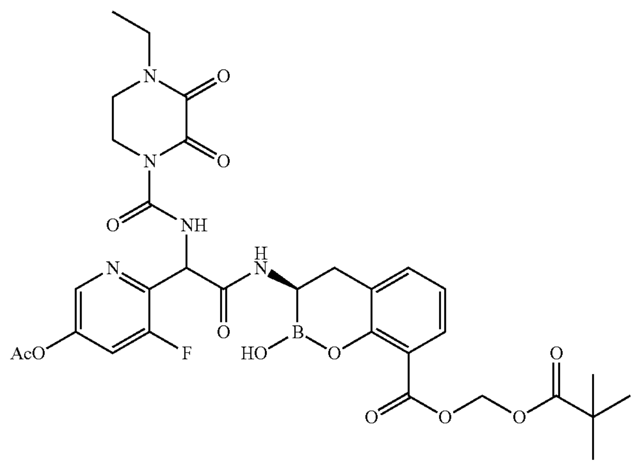 [SMILES: CCN1CCN(C(=O)NC(C(=O)N[C@H]2Cc3cccc(C(=O)OCOC(=O)C(C)(C)C)c3OB2O)c2ncc(OC(C)=O)cc2F)C(=O)C1=O] | 699.5 | 700 |
| 202 | 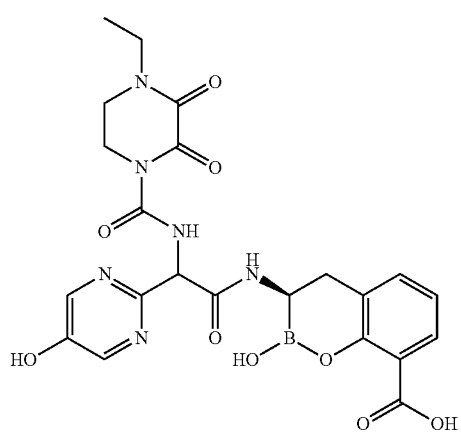 [SMILES: CCN1CCN(C(=O)NC(C(=O)N[C@H]2Cc3cccc(C(=O)O)c3OB2O)c2ncc(O)cn2)C(=O)C1=O] | 526.3 | 700 |

TABLE 1-continued
Example compounds.
| Ex. | Structure | MW | ESI-MS (m/z) for [MH]+ |
|---|---|---|---|
| 203 | 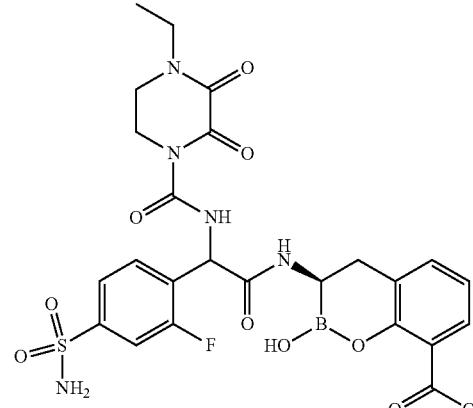 | 605.4 | 527 |
| 204 | 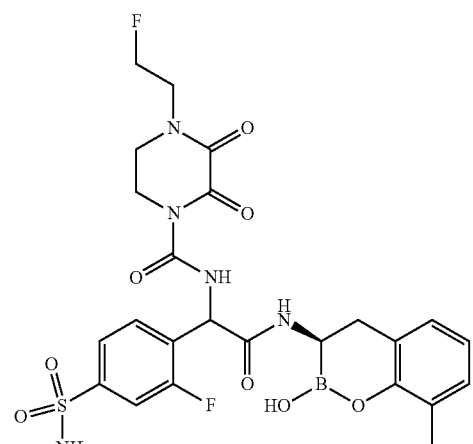 | 623.3 | 624 |
| 205 | 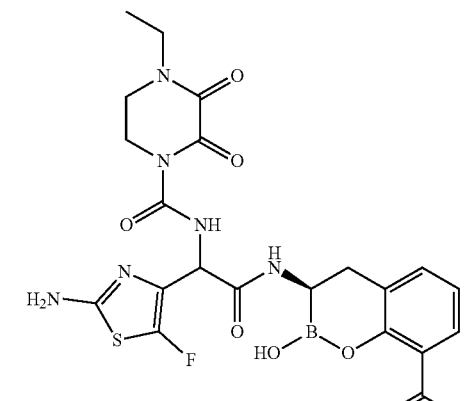 | 548.3 | 549 |

TABLE 1-continued

Example compounds.

| Ex. | Structure | MW | ESI-MS (m/z) for [MH]+ |
|---|---|---|---|
| 206 | 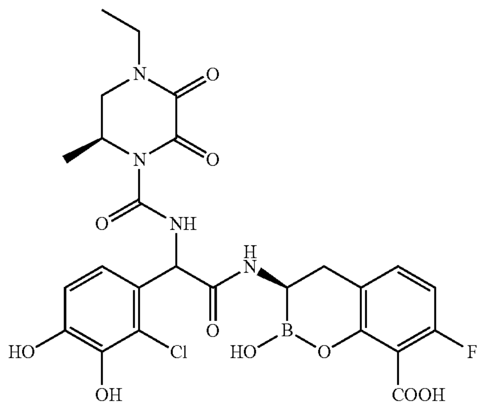 [SMILES: CCN1C[C@H](C)N(C(=O)NC(C(=O)N[C@H]2Cc3ccc(F)c(C(=O)O)c3OB2O)c2ccc(O)c(O)c2Cl)C(=O)C1=O] | 606.8 | 607/609 |
| 207 | 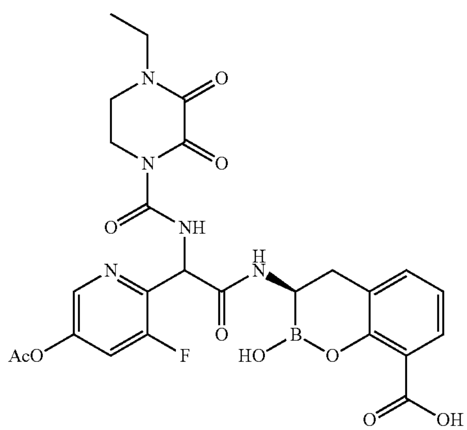 [SMILES: CCN1CCN(C(=O)NC(C(=O)N[C@H]2Cc3cccc(C(=O)O)c3OB2O)c2ncc(OC(C)=O)cc2F)C(=O)C1=O] | 585.3 | 586 |
| 208 | 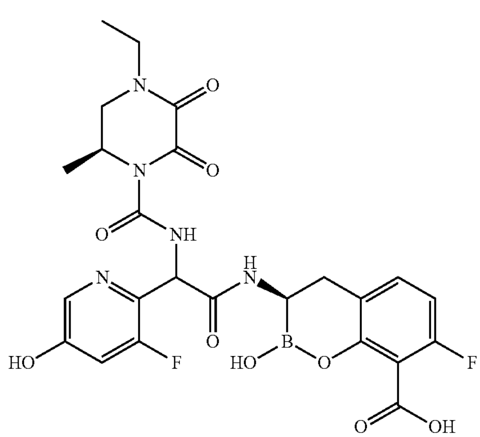 [SMILES: CCN1C[C@H](C)N(C(=O)NC(C(=O)N[C@H]2Cc3ccc(F)c(C(=O)O)c3OB2O)c2ncc(O)cc2F)C(=O)C1=O] | 575.3 | 576 |

TABLE 1-continued

Example compounds.

| Ex. | Structure | MW | ESI-MS (m/z) for [MH]+ |
|---|---|---|---|
| 209 | 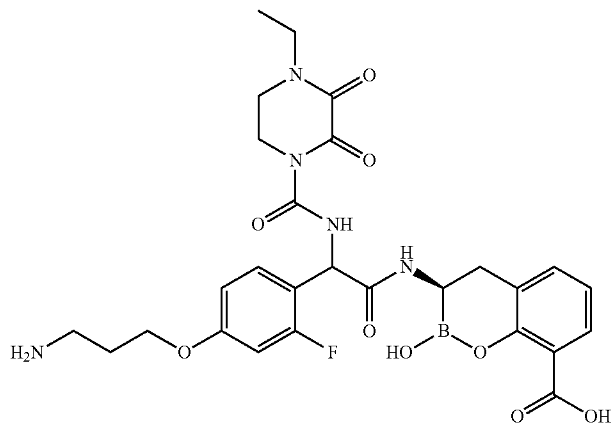 [SMILES: CCN1CCN(C(=O)NC(C(=O)N[C@H]2Cc3cccc(C(=O)O)c3OB2O)c2ccc(OCCCN)cc2F)C(=O)C1=O] | 599.4 | 600 |
| 210 | 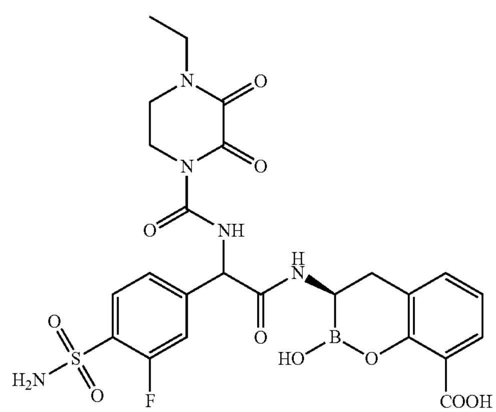 [SMILES: CCN1CCN(C(=O)NC(C(=O)N[C@H]2Cc3cccc(C(=O)O)c3OB2O)c2ccc(S(N)(=O)=O)c(F)c2)C(=O)C1=O] | 605.4 | 606 |
| 211 | 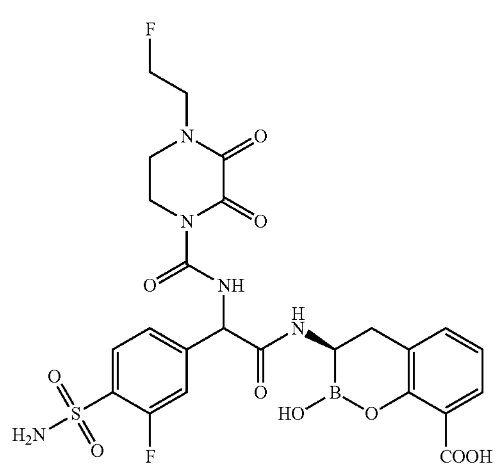 [SMILES: NS(=O)(=O)c1ccc(C(NC(=O)N2CCN(CCF)C(=O)C2=O)C(=O)N[C@H]2Cc3cccc(C(=O)O)c3OB2O)cc1F] | 623.3 | 624 |

TABLE 1-continued
Example compounds.
| Ex. | Structure | MW | ESI-MS (m/z) for [MH]+ |
|---|---|---|---|
| 212 | 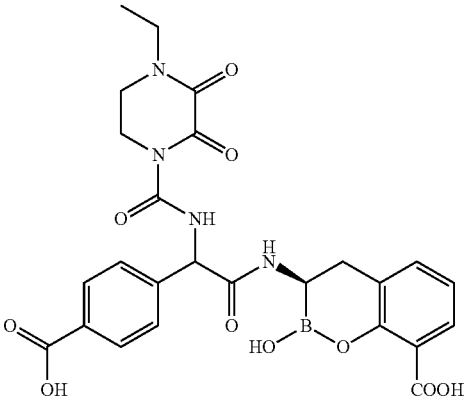 [SMILES: CCN1CCN(C(=O)NC(C(=O)N[C@H]2Cc3cccc(C(=O)O)c3OB2O)c2ccc(C(=O)O)cc2)C(=O)C1=O] | 552.3 | 533 |
| 213 | 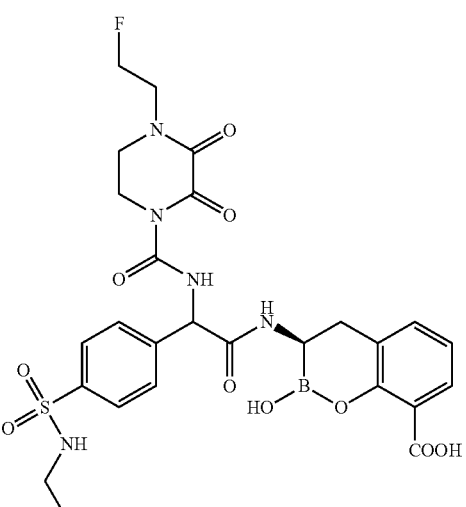 | 649.4 | 650 |
| 214 | 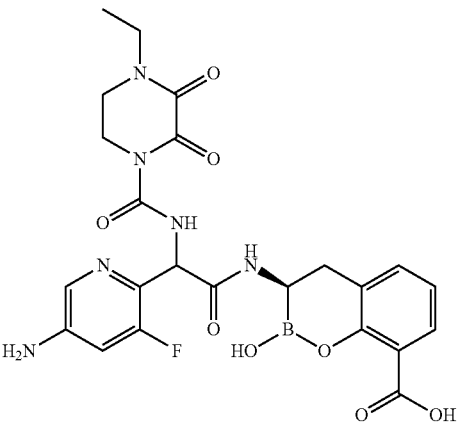 [SMILES: CCN1CCN(C(=O)NC(C(=O)N[C@H]2Cc3cccc(C(=O)O)c3OB2O)c2ncc(N)cc2F)C(=O)C1=O] | 542.3 | 543 |

TABLE 1-continued

Example compounds.

| Ex. | Structure | MW | ESI-MS (m/z) for [MH]$^+$ |
|---|---|---|---|
| 215 | 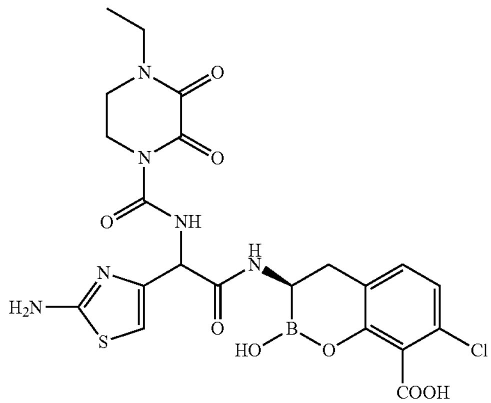 [SMILES: CCN1CCN(C(=O)NC(C(=O)N[C@H]2Cc3ccc(Cl)c(C(=O)O)c3OB2O)c2csc(N)n2)C(=O)C1=O] | 564.8 | 565.1 |
| 216 | 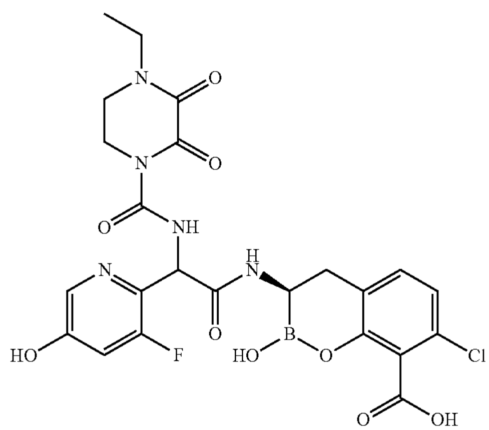 [SMILES: CCN1CCN(C(=O)NC(C(=O)N[C@H]2Cc3ccc(Cl)c(C(=O)O)c3OB2O)c2ncc(O)cc2F)C(=O)C1=O] | 577.7 | 578 |
| 217 | 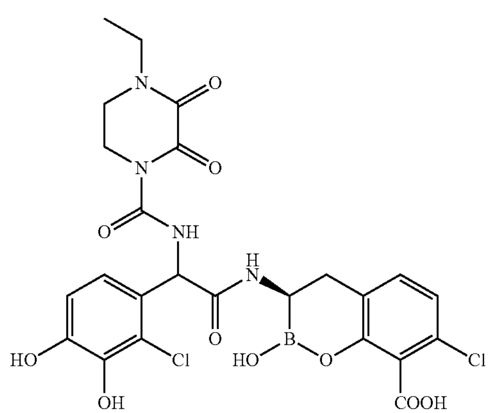 [SMILES: CCN1CCN(C(=O)NC(C(=O)N[C@H]2Cc3ccc(Cl)c(C(=O)O)c3OB2O)c2ccc(O)c(O)c2Cl)C(=O)C1=O] | 609.2 | 609/611/613 |

TABLE 1-continued
Example compounds.
| Ex. | Structure | MW | ESI-MS (m/z) for [MH]+ |
|---|---|---|---|
| 218 | 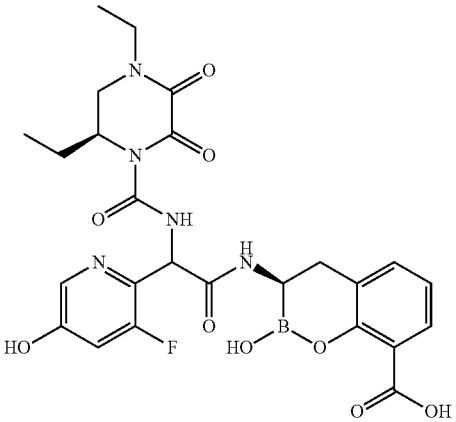 [SMILES: CC[C@H]1CN(CC)C(=O)C(=O)N1C(=O)NC(C(=O)N[C@H]1Cc2cccc(C(=O)O)c2OB1O)c1ncc(O)cc1F] | 571.3 | 572 |
| 219 | 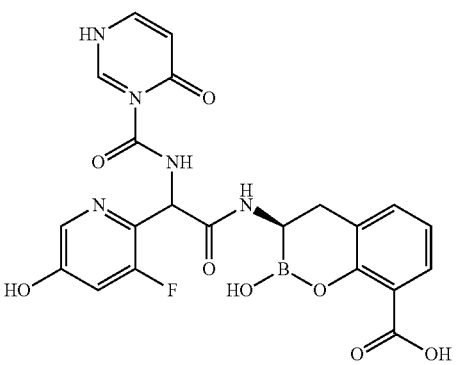 | 496.2 | 497 |
| 220 | 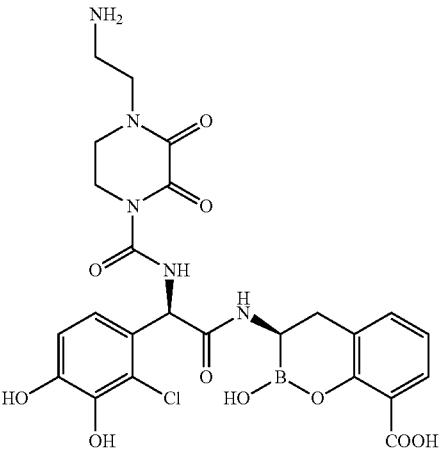 | 589.8 | 704/706 |

TABLE 1-continued

Example compounds.

| Ex. | Structure | MW | ESI-MS (m/z) for [MH]+ |
|---|---|---|---|
| 221 | 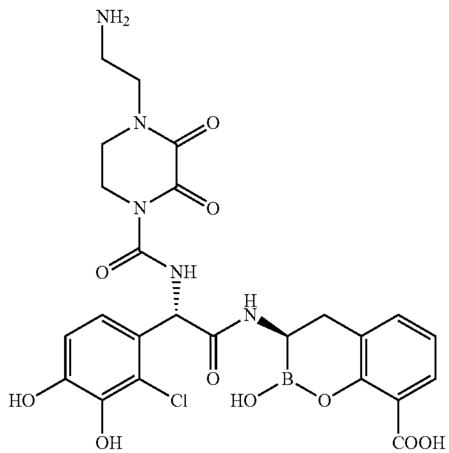 | 589.8 | 704/706 |
| 222 | 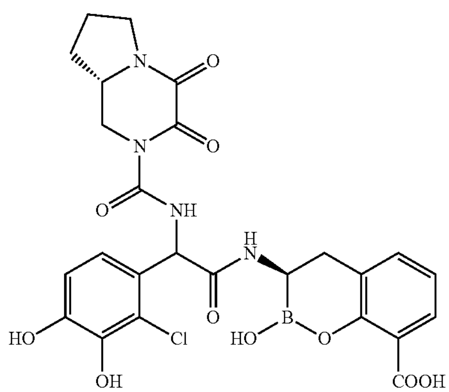 | 586.8 | 587/589 |
| 223 | 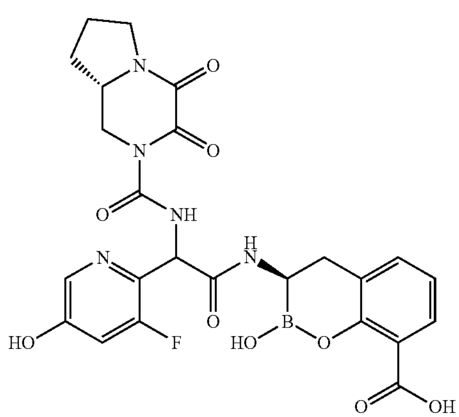 [SMILES: O=C(O)c1cccc2c1OB(O)[C@@H](NC(=O)C(NC(=O)N1C[C@@H]3CCCN3C(=O)C1=O)c1ncc(O)cc1F)C2] | 555.3 | 556 |

TABLE 1-continued
Example compounds.
| Ex. | Structure | MW | ESI-MS (m/z) for [MH]+ |
|---|---|---|---|
| 224 | 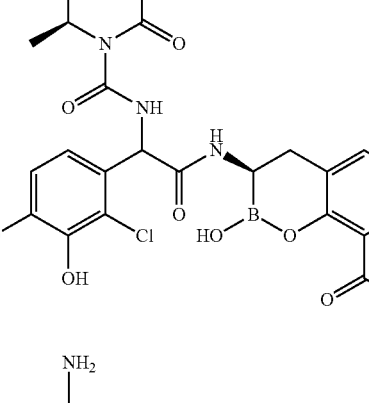 | 604.8 | 605.2 |
| 225 | 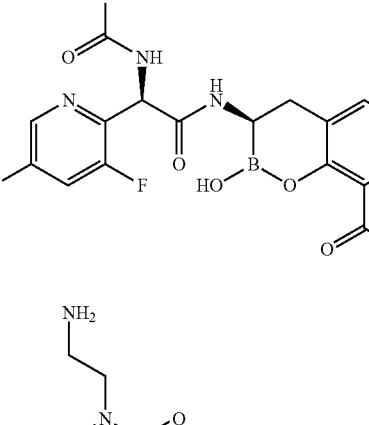 | 558.3 | 577 |
| 226 | 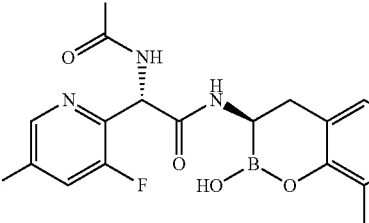 | 558.3 | 559 |

TABLE 1-continued

Example compounds.

| Ex. | Structure | MW | ESI-MS (m/z) for [MH]+ |
|---|---|---|---|
| 227 | 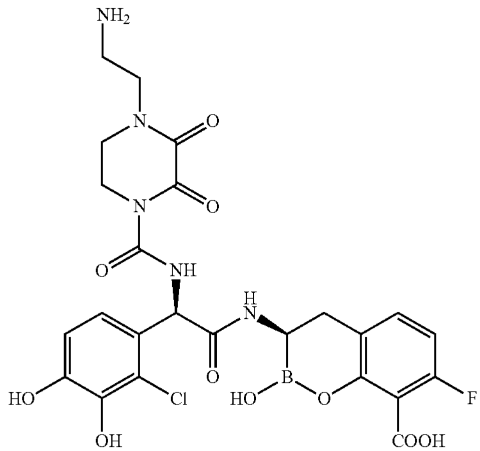 [SMILES: NCCN1CCN(C(=O)N[C@@H](C(=O)N[C@H]2Cc3ccc(F)c(C(=O)O)c3OB2O)c2ccc(O)c(O)c2Cl)C(=O)C1=O] | 607.7 | 608/610 |
| 228 | 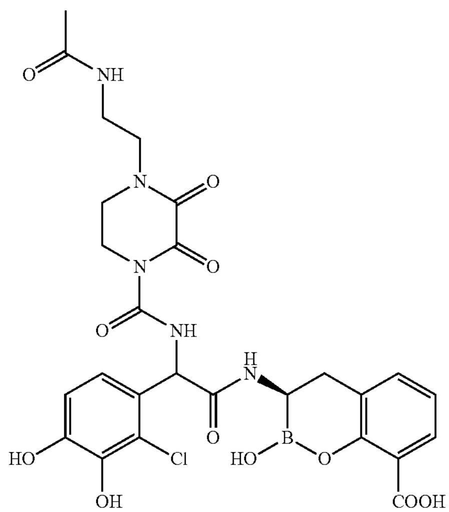 [SMILES: CC(=O)NCCN1CCN(C(=O)NC(C(=O)N[C@H]2Cc3cccc(C(=O)O)c3OB2O)c2ccc(O)c(O)c2Cl)C(=O)C1=O] | 631.8 | 632/634 |
| 229 | 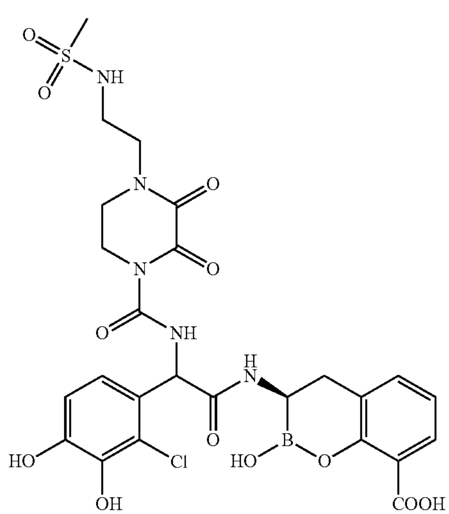 [SMILES: CS(=O)(=O)NCCN1CCN(C(=O)NC(C(=O)N[C@H]2Cc3cccc(C(=O)O)c3OB2O)c2ccc(O)c(O)c2Cl)C(=O)C1=O] | 667.8 | 668/670 |

TABLE 1-continued

Example compounds.

| Ex. | Structure | MW | ESI-MS (m/z) for [MH]+ |
|---|---|---|---|
| 230 | 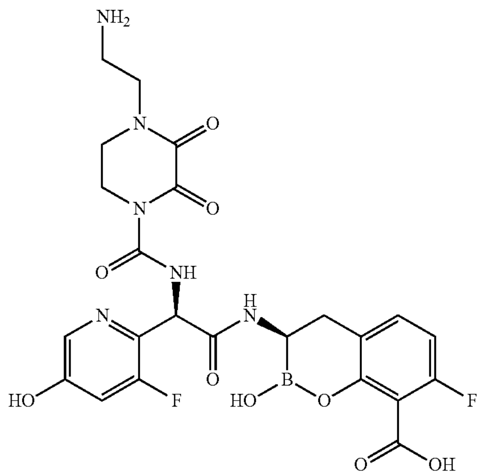 [SMILES: NCCN1CCN(C(=O)N[C@@H](C(=O)N[C@H]2Cc3ccc(F)c(C(=O)O)c3OB2O)c2ncc(O)cc2F)C(=O)C1=O] | 576.3 | 577 |
| 231 | 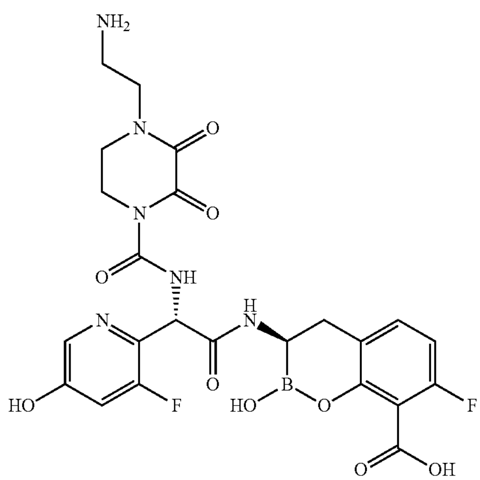 [SMILES: NCCN1CCN(C(=O)N[C@H](C(=O)N[C@H]2Cc3ccc(F)c(C(=O)O)c3OB2O)c2ncc(O)cc2F)C(=O)C1=O] | 576.3 | 577 |
| 232 | 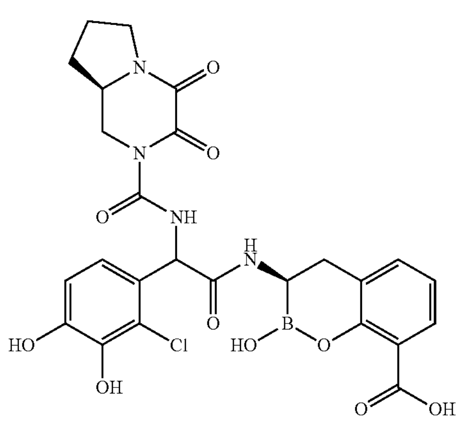 [SMILES: O=C(O)c1cccc2c1OB(O)[C@@H](NC(=O)C(NC(=O)N1C[C@H]3CCCN3C(=O)C1=O)c1ccc(O)c(O)c1Cl)C2] | 586.7 | 587.1 |

TABLE 1-continued

Example compounds.

| Ex. | Structure | MW | ESI-MS (m/z) for [MH]+ |
|---|---|---|---|
| 233 | 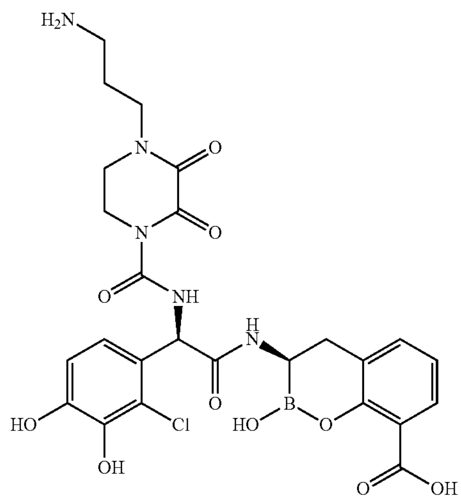 [SMILES: NCCCN1CCN(C(=O)N[C@@H](C(=O)N[C@H]2Cc3cccc(C(=O)O)c3OB2O)c2ccc(O)c(O)c2Cl)C(=O)C1=O] | 603.8 | 604.2 |
| 234 | 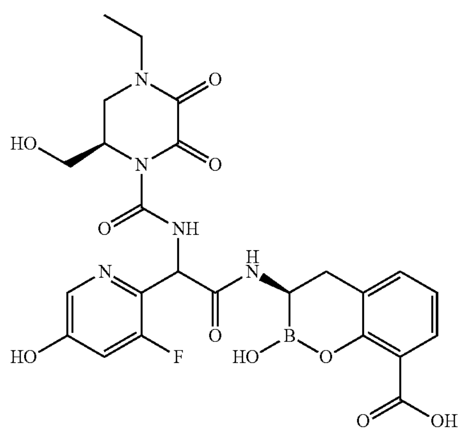 [SMILES: CCN1C[C@H](CO)N(C(=O)NC(C(=O)N[C@H]2Cc3cccc(C(=O)O)c3OB2O)c2ncc(O)cc2F)C(=O)C1=O] | 573.3 | 574 |
| 235 | 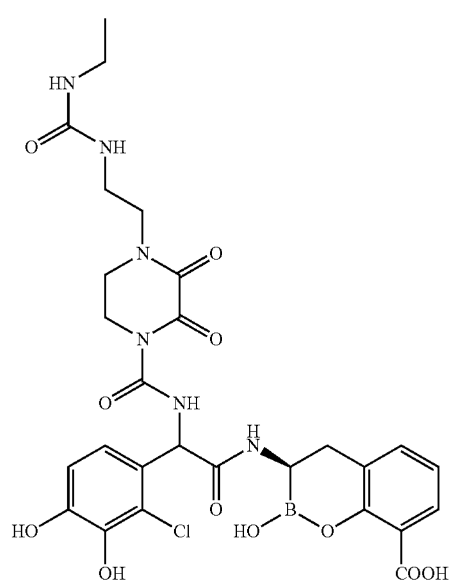 [SMILES: CCNC(=O)NCCN1CCN(C(=O)NC(C(=O)N[C@H]2Cc3cccc(C(=O)O)c3OB2O)c2ccc(O)c(O)c2Cl)C(=O)C1=O] | 660.8 | 661/663 |

TABLE 1-continued
Example compounds.
| Ex. | Structure | MW | ESI-MS (m/z) for [MH]+ |
|---|---|---|---|
| 236 | 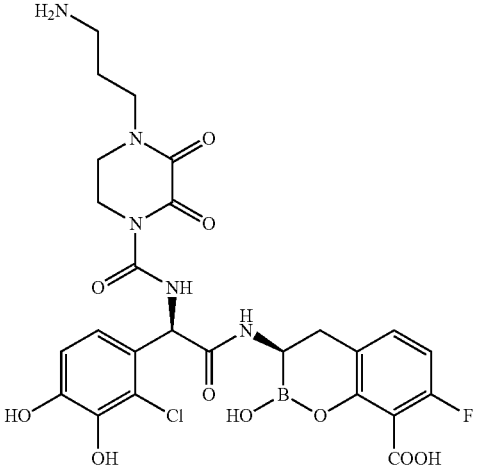 [SMILES: NCCCN1CCN(C(=O)N[C@@H](C(=O)N[C@H]2Cc3ccc(F)c(C(=O)O)c3OB2O)c2ccc(O)c(O)c2Cl)C(=O)C1=O] | 621.8 | 622/624 |
| 237 | 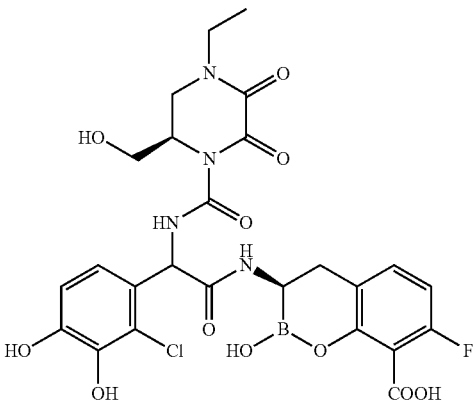 [SMILES: CCN1C[C@H](CO)N(C(=O)NC(C(=O)N[C@H]2Cc3ccc(F)c(C(=O)O)c3OB2O)c2ccc(O)c(O)c2Cl)C(=O)C1=O] | 622.8 | 623/625 |
| 238 | 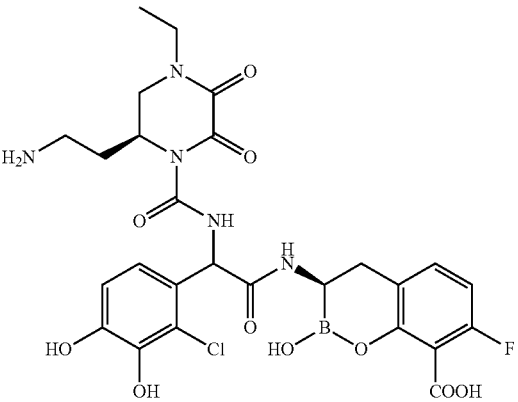 [SMILES: CCN1C[C@H](CCN)N(C(=O)NC(C(=O)N[C@H]2Cc3ccc(F)c(C(=O)O)c3OB2O)c2ccc(O)c(O)c2Cl)C(=O)C1=O] | 635.8 | 636/638 |

TABLE 1-continued
Example compounds.
| Ex. | Structure | MW | ESI-MS (m/z) for [MH]+ |
|---|---|---|---|
| 239 | 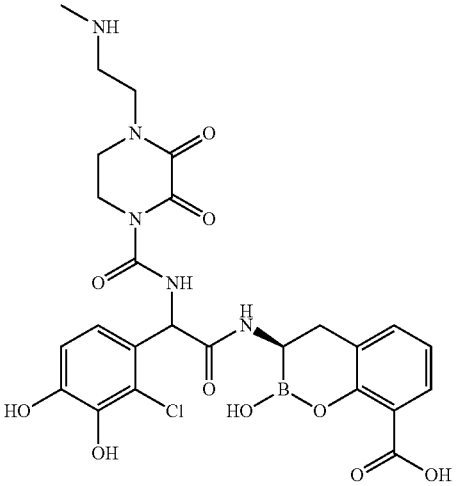 [SMILES: CNCCN1CCN(C(=O)NC(C(=O)N[C@H]2Cc3cccc(C(=O)O)c3OB2O)c2ccc(O)c(O)c2Cl)C(=O)C1=O] | 603.8 | 604.2 |
| 240 | 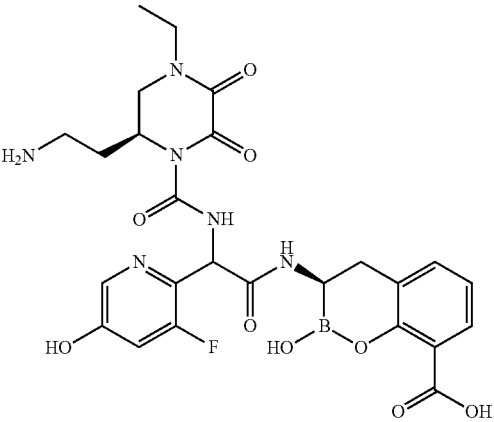 [SMILES: CCN1C[C@H](CCN)N(C(=O)NC(C(=O)N[C@H]2Cc3cccc(C(=O)O)c3OB2O)c2ncc(O)cc2F)C(=O)C1=O] | 586.3 | 587 |
| 241 | 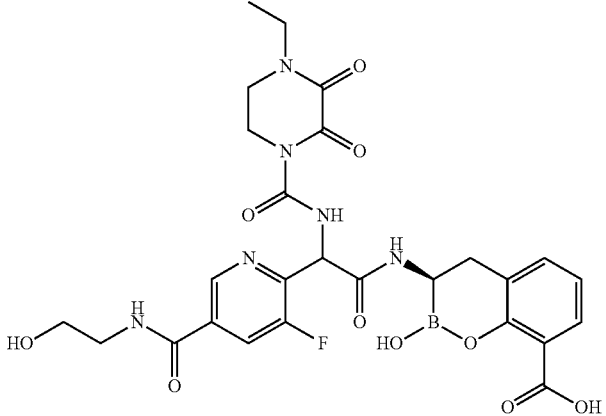 [SMILES: CCN1CCN(C(=O)NC(C(=O)N[C@H]2Cc3cccc(C(=O)O)c3OB2O)c2ncc(C(=O)NCCO)cc2F)C(=O)C1=O] | 614.4 | 615 |

TABLE 1-continued

Example compounds.

| Ex. | Structure | MW | ESI-MS (m/z) for [MH]+ |
|---|---|---|---|
| 242 | 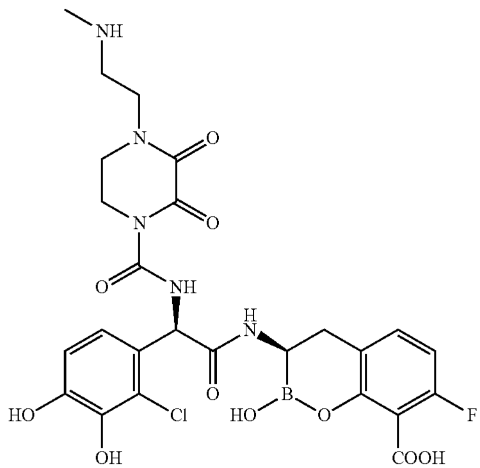 [SMILES: CNCCN1CCN(C(=O)N[C@@H](C(=O)N[C@H]2Cc3ccc(F)c(C(=O)O)c3OB2O)c2ccc(O)c(O)c2Cl)C(=O)C1=O] | 621.8 | 622/624 |
| 243 | 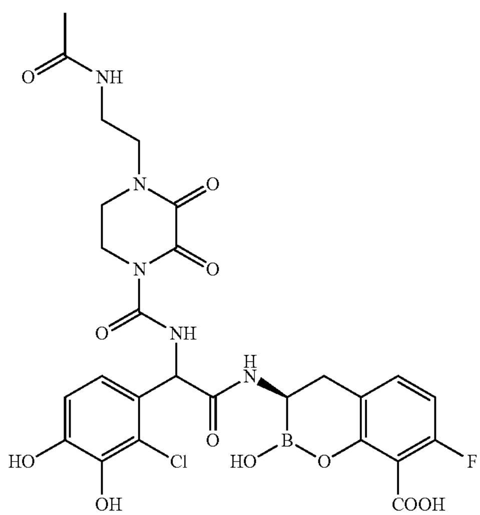 [SMILES: CC(=O)NCCN1CCN(C(=O)NC(C(=O)N[C@H]2Cc3ccc(F)c(C(=O)O)c3OB2O)c2ccc(O)c(O)c2Cl)C(=O)C1=O] | 649.8 | 650/652 |
| 244 | 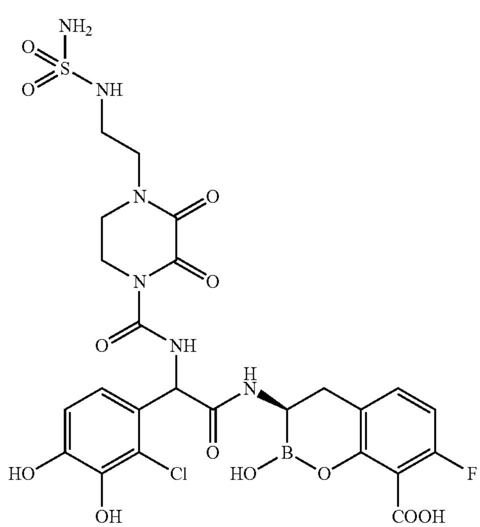 [SMILES: NS(=O)(=O)NCCN1CCN(C(=O)NC(C(=O)N[C@H]2Cc3ccc(F)c(C(=O)O)c3OB2O)c2ccc(O)c(O)c2Cl)C(=O)C1=O] | 686.8 | 687/689 |

TABLE 1-continued

Example compounds.

| Ex. | Structure | MW | ESI-MS (m/z) for [MH]+ |
|---|---|---|---|
| 245 | 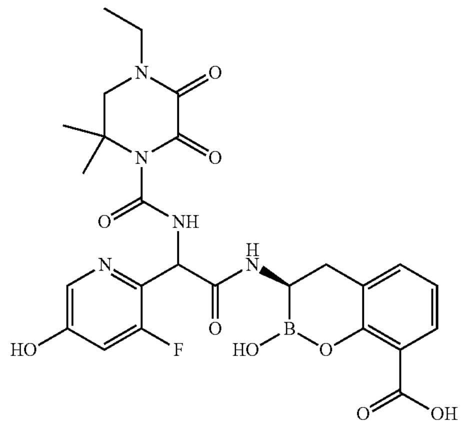 [SMILES: CCN1CC(C)(C)N(C(=O)NC(C(=O)N[C@H]2Cc3cccc(C(=O)O)c3OB2O)c2ncc(O)cc2F)C(=O)C1=O] | 571.3 | 572 |
| 246 | 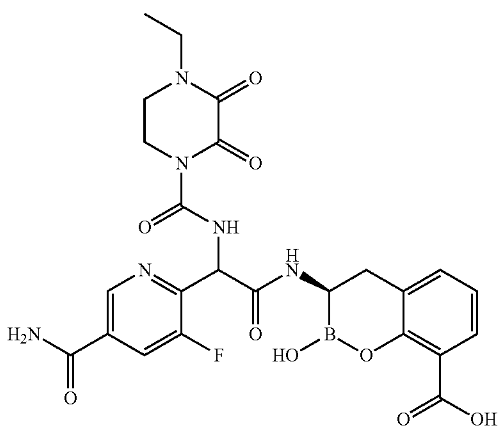 [SMILES: CCN1CCN(C(=O)NC(C(=O)N[C@H]2Cc3cccc(C(=O)O)c3OB2O)c2ncc(C(N)=O)cc2F)C(=O)C1=O] | 570.3 | 571 |
| 247 | 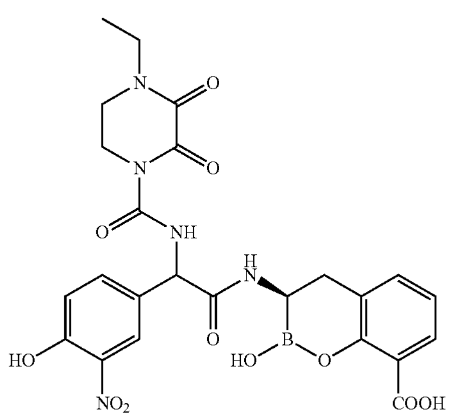 | 569.3 | 570 |

TABLE 1-continued
Example compounds.
| Ex. | Structure | MW | ESI-MS (m/z) for [MH]+ |
|---|---|---|---|
| 248 | 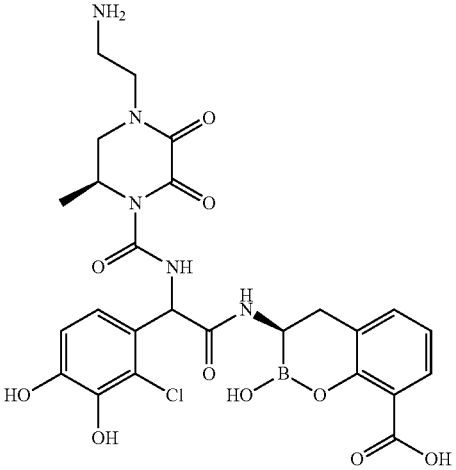 | 603.8 | 604.2 |
| 249 | 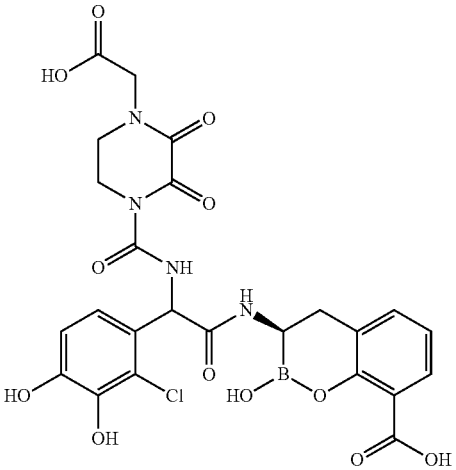 [SMILES: O=C(O)CN1CCN(C(=O)NC(C(=O)N[C@H]2Cc3cccc(C(=O)O)c3OB2O)c2ccc(O)c(O)c2Cl)C(=O)C1=O] | 604.7 | 605.1 |
| 250 | 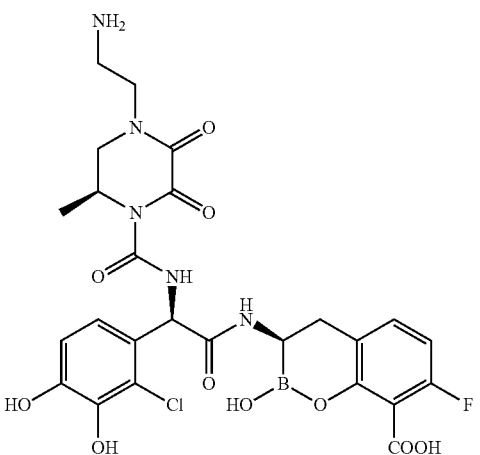 [SMILES: C[C@H]1CN(CCN)C(=O)C(=O)N1C(=O)N[C@@H](C(=O)N[C@H]1Cc2ccc(F)c(C(=O)O)c2OB1O)c1ccc(O)c(O)c1Cl] | 621.8 | 608/610 |

TABLE 1-continued

Example compounds.

| Ex. | Structure | MW | ESI-MS (m/z) for [MH]+ |
|---|---|---|---|
| 251 | 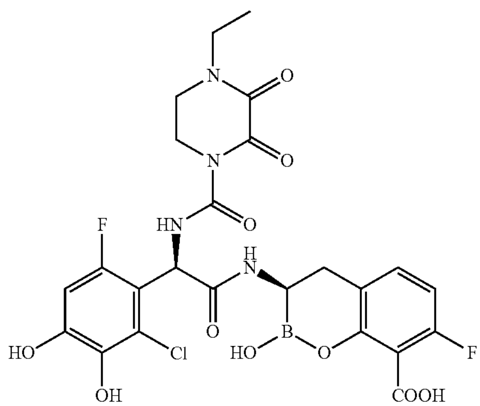 [SMILES: CCN1CCN(C(=O)N[C@@H](C(=O)N[C@H]2Cc3ccc(F)c(C(=O)O)c3OB2O)c2c(F)cc(O)c(O)c2Cl)C(=O)C1=O] | 610.7 | 611/613 |
| 252 | 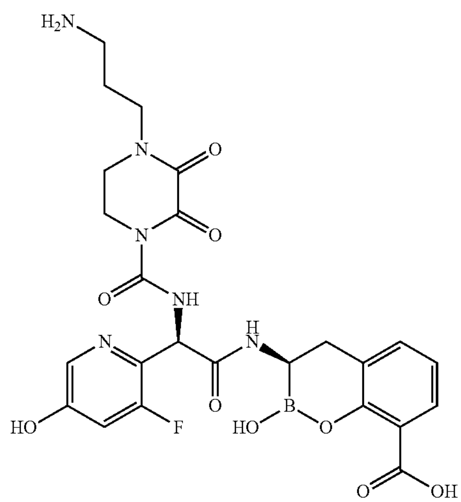 [SMILES: NCCCN1CCN(C(=O)N[C@@H](C(=O)N[C@H]2Cc3cccc(C(=O)O)c3OB2O)c2ncc(O)cc2F)C(=O)C1=O] | 572.3 | 573 |
| 253 | 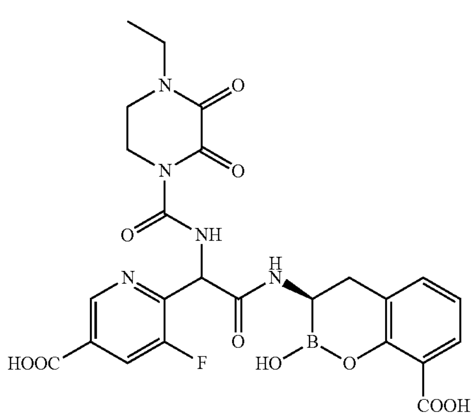 [SMILES: CCN1CCN(C(=O)NC(C(=O)N[C@H]2Cc3cccc(C(=O)O)c3OB2O)c2ncc(C(=O)O)cc2F)C(=O)C1=O] | 571.3 | |

TABLE 1-continued

Example compounds.

| Ex. | Structure | MW | ESI-MS (m/z) for [MH]+ |
|---|---|---|---|
| 254 | 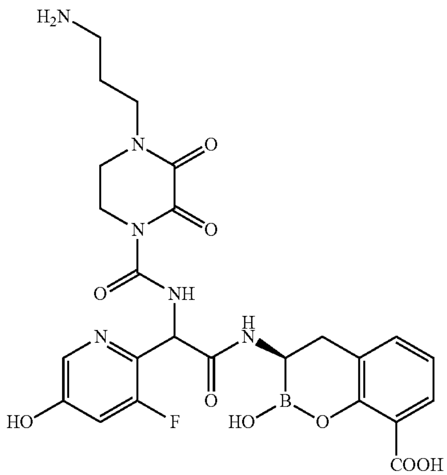 [SMILES: NCCCN1CCN(C(=O)NC(C(=O)N[C@H]2Cc3cccc(C(=O)O)c3OB2O)c2ncc(O)cc2F)C(=O)C1=O] | 572.3 | |
| 255 | 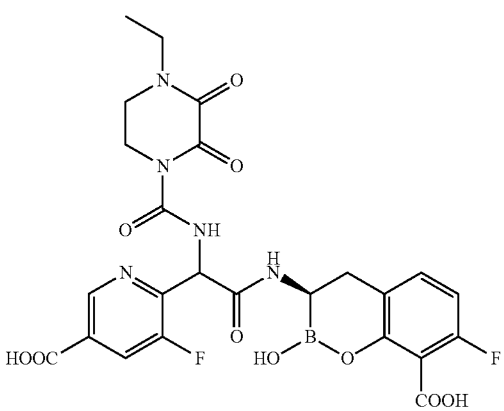 [SMILES: CCN1CCN(C(=O)NC(C(=O)N[C@H]2Cc3ccc(F)c(C(=O)O)c3OB2O)c2ncc(C(=O)O)cc2F)C(=O)C1=O] | 589.3 | |
| 256 | 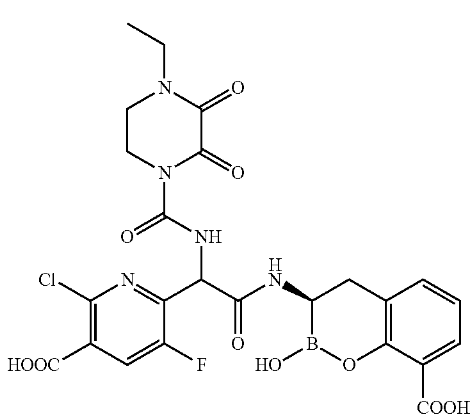 [SMILES: CCN1CCN(C(=O)NC(C(=O)N[C@H]2Cc3cccc(C(=O)O)c3OB2O)c2nc(Cl)c(C(=O)O)cc2F)C(=O)C1=O] | 605.7 | |

TABLE 1-continued

Example compounds.

| Ex. | Structure | MW | ESI-MS (m/z) for [MH]+ |
|---|---|---|---|
| 257 | 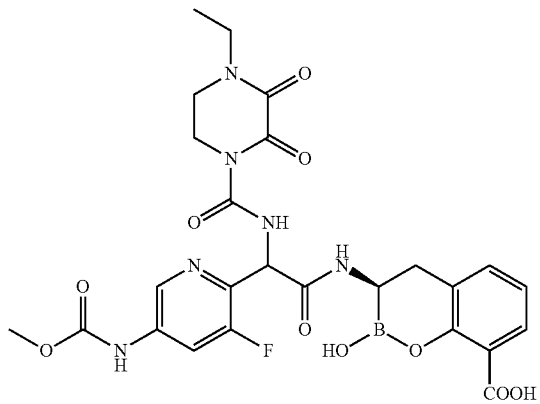 [SMILES: CCN1CCN(C(=O)NC(C(=O)N[C@H]2Cc3cccc(C(=O)O)c3OB2O)c2ncc(NC(=O)OC)cc2F)C(=O)C1=O] | 600.3 | |
| 258 | 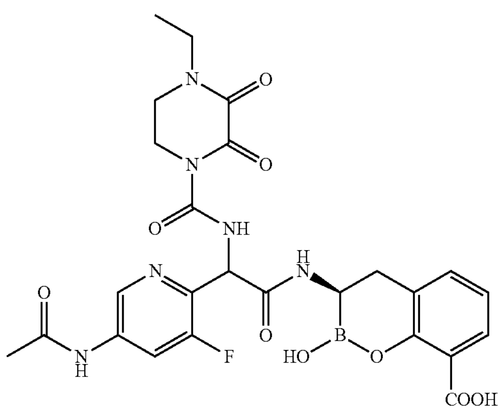 [SMILES: CCN1CCN(C(=O)NC(C(=O)N[C@H]2Cc3cccc(C(=O)O)c3OB2O)c2ncc(NC(C)=O)cc2F)C(=O)C1=O] | 584.3 | |
| 259 | 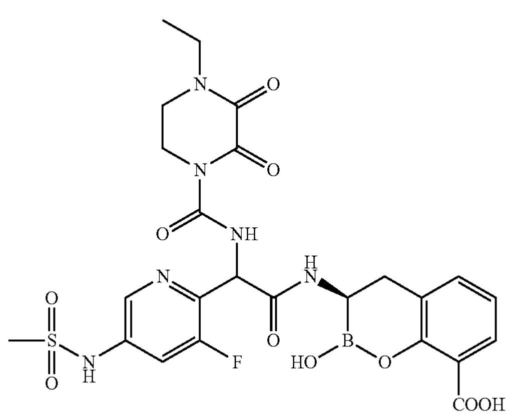 [SMILES: CCN1CCN(C(=O)NC(C(=O)N[C@H]2Cc3cccc(C(=O)O)c3OB2O)c2ncc(NS(C)(=O)=O)cc2F)C(=O)C1=O] | 620.4 | |

TABLE 1-continued

Example compounds.

| Ex. | Structure | MW | ESI-MS (m/z) for [MH]+ |
|---|---|---|---|
| 260 | 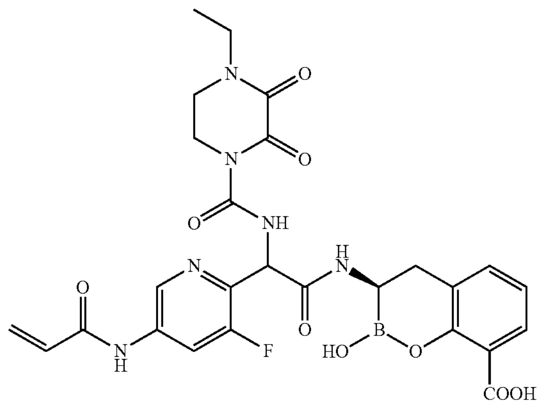 [SMILES: C=CC(=O)Nc1cnc(C(NC(=O)N2CCN(CC)C(=O)C2=O)C(=O)N[C@H]2Cc3cccc(C(=O)O)c3OB2O)c(F)c1] | | 596.3 |
| 261 | 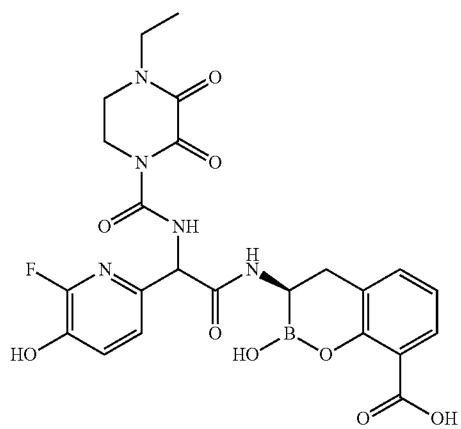 [SMILES: CCN1CCN(C(=O)NC(C(=O)N[C@H]2Cc3cccc(C(=O)O)c3OB2O)c2ccc(O)c(F)n2)C(=O)C1=O] | | 543.3 |
| 262 | 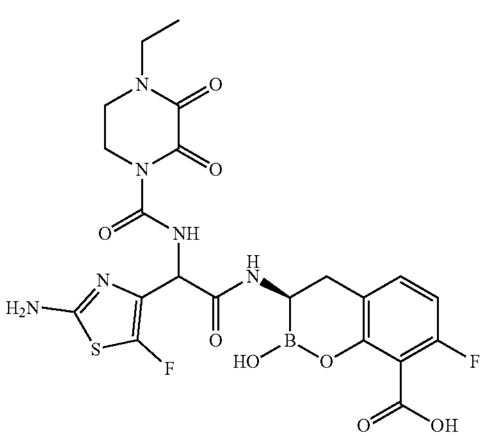 [SMILES: CCN1CCN(C(=O)NC(C(=O)N[C@H]2Cc3ccc(F)c(C(=O)O)c3OB2O)c2nc(N)sc2F)C(=O)C1=O] | | 566.3 |

TABLE 1-continued

Example compounds.

| Ex. | Structure | MW | ESI-MS (m/z) for [MH]+ |
|-----|-----------|-----|------------------------|
| 263 | 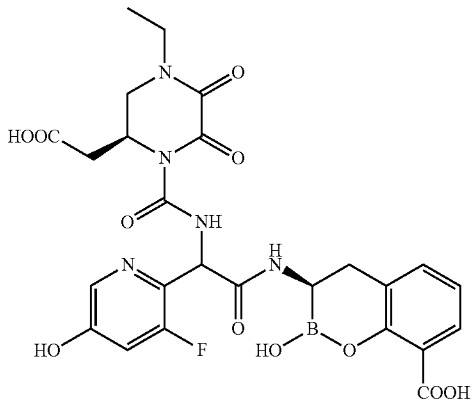 [SMILES: CCN1C[C@H](CC(=O)O)N(C(=O)NC(C(=O)N[C@H]2Cc3cccc(C(=O)O)c3OB2O)c2ncc(O)cc2F)C(=O)C1=O] | 601.3 | |
| 264 | 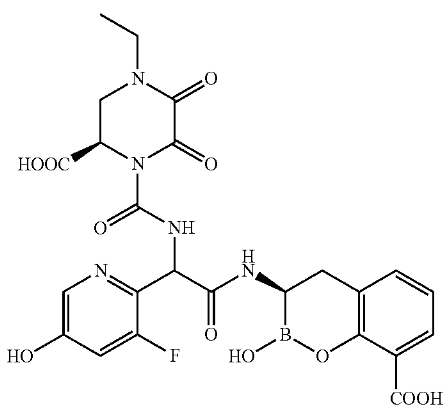 [SMILES: CCN1C[C@H](C(=O)O)N(C(=O)NC(C(=O)N[C@H]2Cc3cccc(C(=O)O)c3OB2O)c2ncc(O)cc2F)C(=O)C1=O] | 587.3 | |
| 265 | 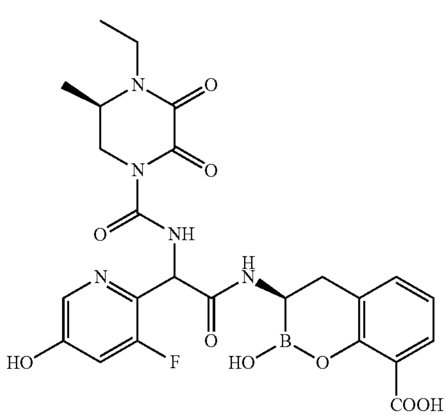 [SMILES: CCN1C(=O)C(=O)N(C(=O)NC(C(=O)N[C@H]2Cc3cccc(C(=O)O)c3OB2O)c2ncc(O)cc2F)C[C@H]1C] | 557.3 | |

TABLE 1-continued

Example compounds.

| Ex. | Structure | MW | ESI-MS (m/z) for [MH]+ |
|---|---|---|---|
| 266 | 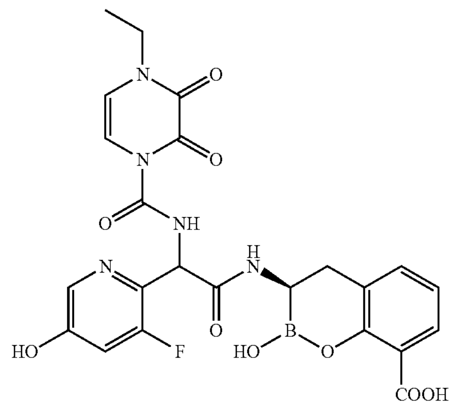 | 541.3 | |
| 267 | 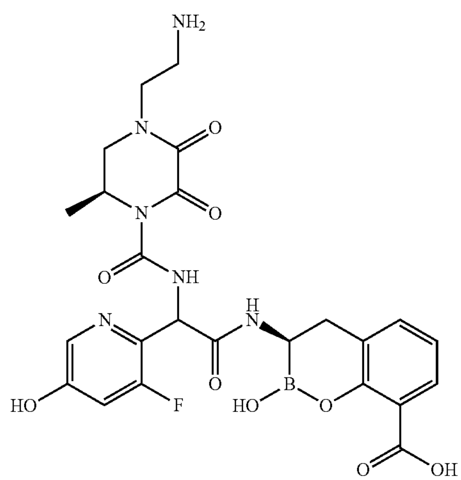 [SMILES: C[C@H]1CN(CCN)C(=O)C(=O)N1C(=O)NC(C(=O)N[C@H]1Cc2cccc(C(=O)O)c2OB1O)c1ncc(O)cc1F] | 572.3 | 573 |
| 268 | 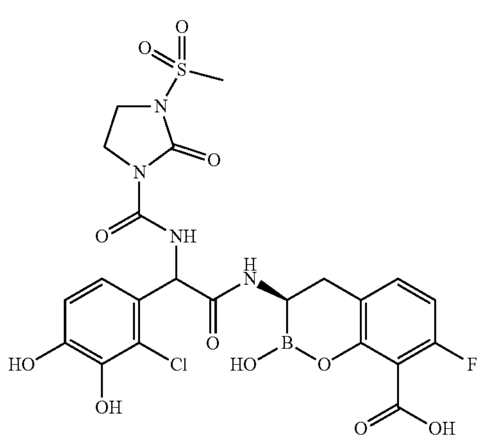 [SMILES: CS(=O)(=O)N1CCN(C(=O)NC(C(=O)N[C@H]2Cc3ccc(F)c(C(=O)O)c3OB2O)c2ccc(O)c(O)c2Cl)C1=O] | 614.7 | |

TABLE 1-continued

Example compounds.

| Ex. | Structure | MW | ESI-MS (m/z) for [MH]+ |
|---|---|---|---|
| 269 | 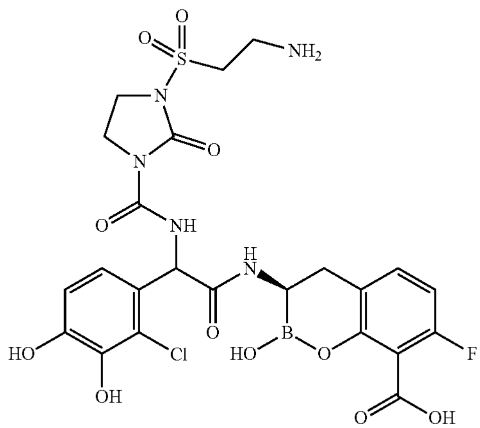 [SMILES: NCCS(=O)(=O)N1CCN(C(=O)NC(C(=O)N[C@H]2Cc3ccc(F)c(C(=O)O)c3OB2O)c2ccc(O)c(O)c2Cl)C1=O] | 643.8 | |
| 270 | 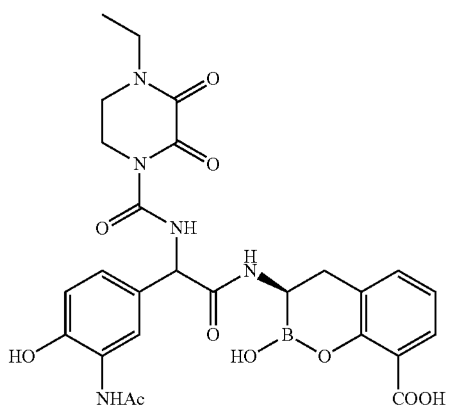 | 581.3 | |
| 271 | 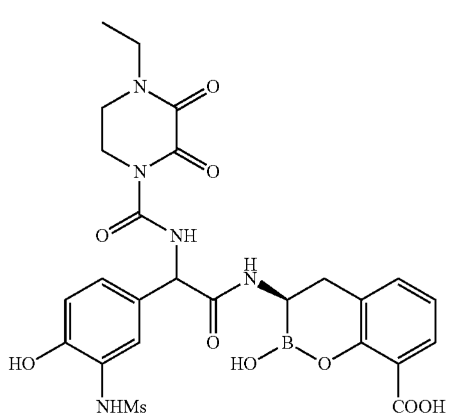 | 617.4 | |

TABLE 1-continued

Example compounds.

| Ex. | Structure | MW | ESI-MS (m/z) for [MH]+ |
|---|---|---|---|
| 272 | 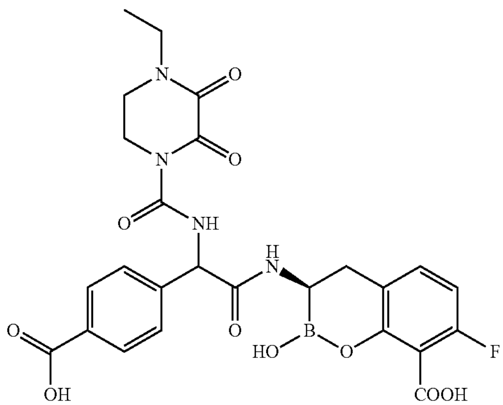 [SMILES: CCN1CCN(C(=O)NC(C(=O)N[C@H]2Cc3ccc(F)c(C(=O)O)c3OB2O)c2ccc(C(=O)O)cc2)C(=O)C1=O] | 570.3 | 571 |
| 273 | 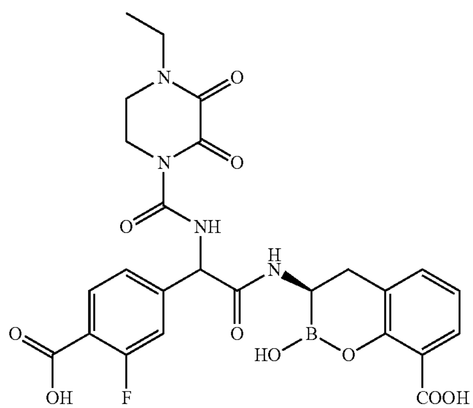 [SMILES: CCN1CCN(C(=O)NC(C(=O)N[C@H]2Cc3cccc(C(=O)O)c3OB2O)c2ccc(C(=O)O)c(F)c2)C(=O)C1=O] | 570.3 | |
| 274 | 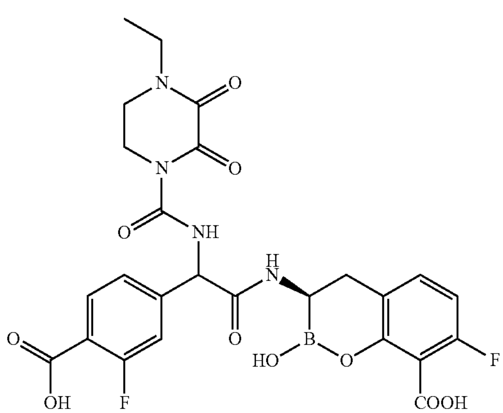 [SMILES: CCN1CCN(C(=O)NC(C(=O)N[C@H]2Cc3ccc(F)c(C(=O)O)c3OB2O)c2ccc(C(=O)O)c(F)c2)C(=O)C1=O] | 588.3 | |

TABLE 1-continued

Example compounds.

| Ex. | Structure | MW | ESI-MS (m/z) for [MH]+ |
|---|---|---|---|
| 275 | 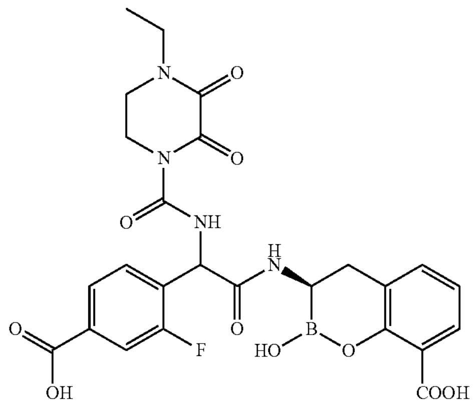 [SMILES: CCN1CCN(C(=O)NC(C(=O)N[C@H]2Cc3cccc(C(=O)O)c3OB2O)c2ccc(C(=O)O)cc2F)C(=O)C1=O] | 570.3 | |
| 276 | 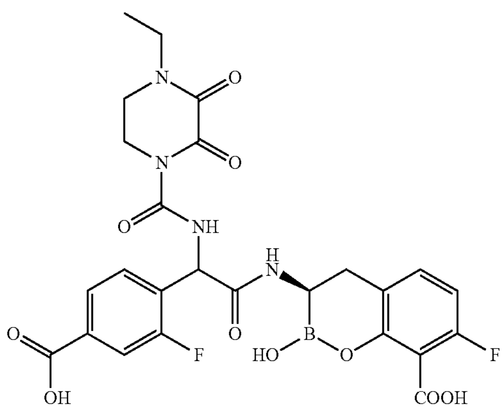 [SMILES: CCN1CCN(C(=O)NC(C(=O)N[C@H]2Cc3ccc(F)c(C(=O)O)c3OB2O)c2ccc(C(=O)O)cc2F)C(=O)C1=O] | 588.3 | |
| 277 | 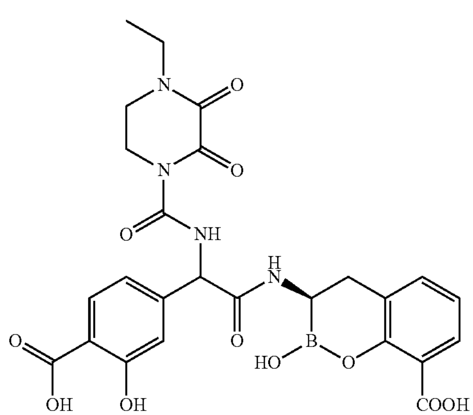 [SMILES: CCN1CCN(C(=O)NC(C(=O)N[C@H]2Cc3cccc(C(=O)O)c3OB2O)c2ccc(C(=O)O)c(O)c2)C(=O)C1=O] | 568.3 | |

TABLE 1-continued

Example compounds.

| Ex. | Structure | MW | ESI-MS (m/z) for [MH]+ |
|---|---|---|---|
| 278 | 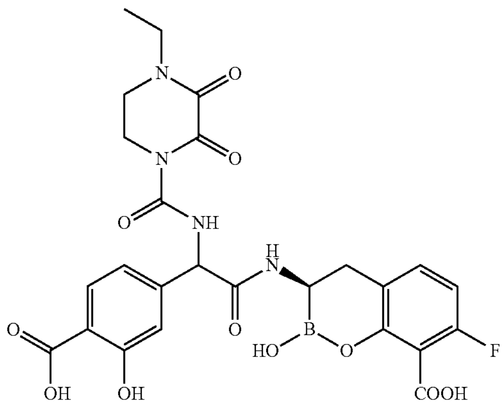 [SMILES: CCN1CCN(C(=O)NC(C(=O)N[C@H]2Cc3ccc(F)c(C(=O)O)c3OB2O)c2ccc(C(=O)O)c(O)c2)C(=O)C1=O] | | 586.3 |
| 279 | 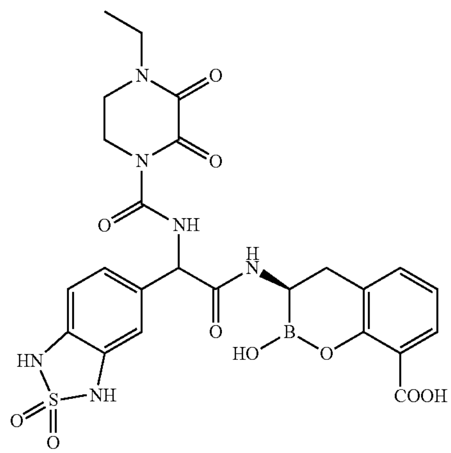 [SMILES: CCN1CCN(C(=O)NC(C(=O)N[C@H]2Cc3cccc(C(=O)O)c3OB2O)c2ccc3c(c2)NS(=O)(=O)N3)C(=O)C1=O] | | 600.4 |
| 280 | 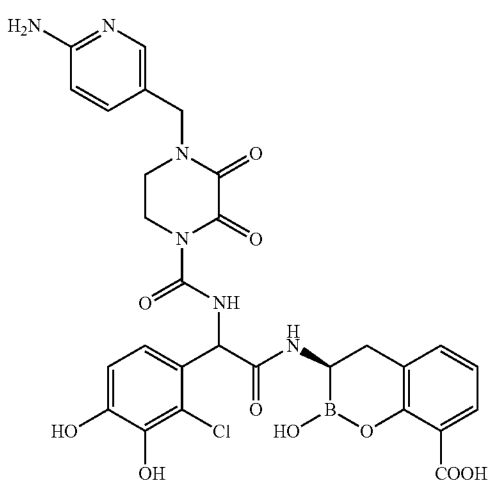 [SMILES: Nc1ccc(CN2CCN(C(=O)NC(C(=O)N[C@H]3Cc4cccc(C(=O)O)c4OB3O)c3ccc(O)c(O)c3Cl)C(=O)C2=O)cn1] | | 652.8 |

TABLE 1-continued

Example compounds.

| Ex. | Structure | MW | ESI-MS (m/z) for [MH]+ |
|---|---|---|---|
| 281 | 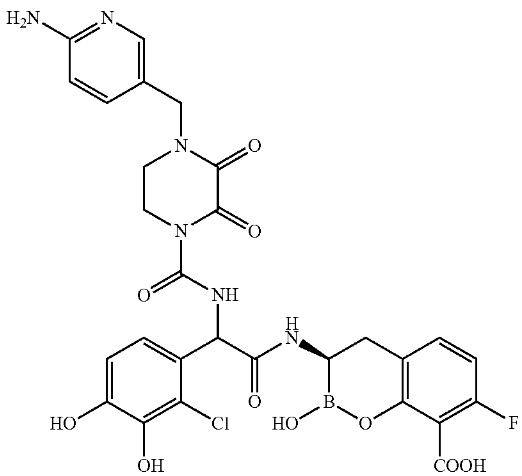 [SMILES: Nc1ccc(CN2CCN(C(=O)NC(C(=O)N[C@H]3Cc4ccc(F)c(C(=O)O)c4OB3O)c3ccc(O)c(O)c3Cl)C(=O)C2=O)cn1] | 670.8 | |
| 282 | 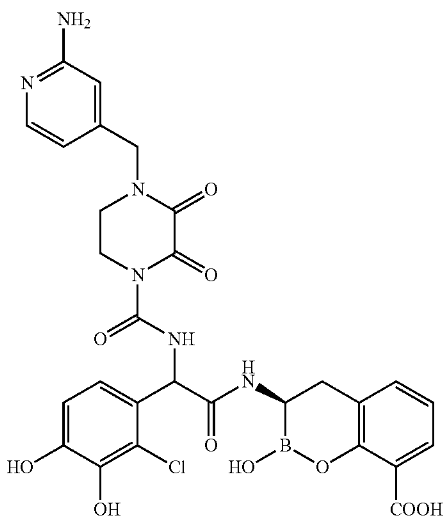 [SMILES: Nc1cc(CN2CCN(C(=O)NC(C(=O)N[C@H]3Cc4cccc(C(=O)O)c4OB3O)c3ccc(O)c(O)c3Cl)C(=O)C2=O)ccn1] | 652.8 | |
| 283 | 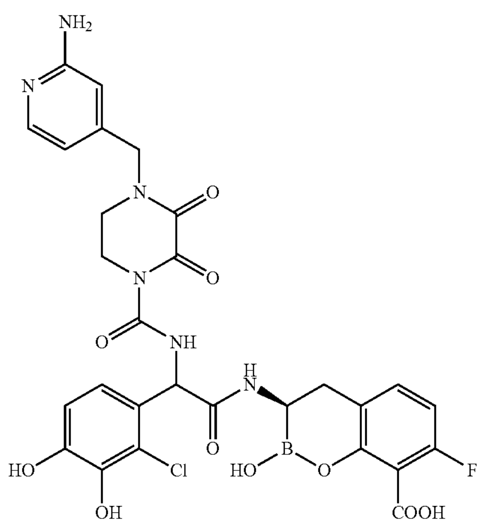 [SMILES: Nc1cc(CN2CCN(C(=O)NC(C(=O)N[C@H]3Cc4ccc(F)c(C(=O)O)c4OB3O)c3ccc(O)c(O)c3Cl)C(=O)C2=O)ccn1] | 670.8 | |

Example A1: Parenteral Composition of a Compounds of Formula Formula (Ia), (IIa), (IIa-1), (Ib), (IIb), or (IIb-1)

To prepare a parenteral pharmaceutical composition suitable for administration by injection, 100 mg of a compound of Formula Formula (Ia), (IIa), (IIa-1), (Ib), (IIb), or (IIb-1), or or a pharmaceutically acceptable salt, solvate, stereoisomer, tautomer, N-oxide, dimer, or timer thereof, is dissolved in DMSO and then mixed with 10 ml of 0.9% sterile saline solution. The mixture is incorporated into a dosage unit suitable for administration by injection.

Example A2: Oral Composition of a Compounds of Formula Formula (Ia), (IIa), (IIa-1), (Ib), (IIb), or (IIb-1)

To prepare a pharmaceutical composition for oral delivery, 400 mg of compound of Formula Formula (Ia), (IIa), (IIa-1), (Ib), (IIb), or (IIb-1) and the following ingredients are mixed intimately and pressed into single scored tablets Tablet Formulation

| Ingredient | Quantity per tablet (mg) |
|---|---|
| compound | 400 |
| cornstarch | 50 |
| croscarmellose sodium | 25 |
| lactose | 120 |
| magnesium stearate | 5 |

The following ingredients are mixed intimately and loaded into a hard-shell gelatin capsule Capsule Formulation

| Ingredient | Quantity per capsule (mg) |
|---|---|
| compound | 200 |
| lactose spray dried | 148 |
| magnesium stearate | 2 |

BIOLOGICAL EXAMPLES

Example I: Experimental Method for *E. coli* Penicillin-Binding Protein-3 Binding Assay with Bocillin-FL Via Fluorescence Polarization To determine the ability of boronic acid-based test PBP inhibitors to bind Penicillin Binding Proteins (PBPs), Bocillin-FL (fluorescently-labeled penicillin V; ThermoFisher Scientific) was used in a fluorescence polarization (FP) competition binding assay to assess inhibitor binding to PBP2, PBP3 or PBP4 from *Escherichia coli*. PBPs were cloned and purified as described previously (King, D. T, et al., *ACS Infectious Diseases* 2015, 1, 175-184). To establish assay conditions for competition binding, an enzyme titration/saturation binding experiment was initially performed. Bocillin-FL was prepared at 0.2 µM in a buffer comprised of 50 mM Hepes (pH 8.0), 300 mM NaCl and 5% (v/v) glycerol. Saturation binding was performed by mixing 40 µl of PBP solutions in concentrations from 0-12 µM with 40 µl of the 0.2 µM Bocillin-FL solution, in individual wells of a black 384-well microplate. FP was measured immediately upon mixing (Excitation, 490 nm; Emission, 520 nm; g-factor, 0.96), using a Cytation3 (BioTek) microplate reader and measured continuously for up to 120 minutes. The FP response became stable after 30 minutes (80 minutes for PBP2), and showed a dose dependence on PBP concentration. For all PBPs the FP signal approached saturation with 1.5 µM PBP (final concentration). The competition binding assay was validated using beta-lactams ampicillin, aztreonam, mecillinam or meropenem. Assays (80 µl final volume) were performed with PBPs at a final concentration of 1.5 µM, Bocillin-FL at 0.1 µM and beta-lactam concentrations that ranged from 0-1000 µM. PBP3 was incubated with increasing concentrations of ampicillin or aztreonam in a black 384-well microplate (Corning) for 30 minutes, and PBP2 and PBP4 were likewise incubated with increasing concentrations of mecillinam and meropenem, respectively. Bocillin-FL was added and the FP immediately measured for 60 minutes (90 minutes for PBP2). The beta-lactam potency was reported as the concentration of beta-lactam required to reduce binding of Bocillin-FL by 500% ($EC_{50}$). The $EC_{50}$ for PBP3 with ampicillin was determined to be 1.4 µM, while that of the PBP3-specific beta-lactam aztreonam was determined to be 0.8 µM. The $EC_{50}$ for mecillinam with PBP2 was found to be 2.1 µM, and the $EC_{50}$ for meropenem with PBP4 was found to be <2 µM. Binding assays for boronic acid PBP inhibitors were performed in an identical fashion.

Representative results for binding to *E. coli* PBP3 are shown in Table 2, where A represents a potency of >500 µM, B represents a potency between 30 µM and 500 µM inclusive, and C represents a potency of <30 µM. NT=Not Tested

TABLE 2

Binding affinity to *E. coli* PBP3 by Exemplary Compounds in fluorescence polarization competition binding assay using Bocillin-FL.

| Ex. | *E. coli* K12 PBP3 Potency | Ex. | *E. coli* K12 PBP3 Potency | Ex. | *E. coli* K12 PBP3 Potency |
|---|---|---|---|---|---|
| 13 | B | 16 | B | 17 | A |
| 18 | B | 20 | B | 21 | B |
| 22 | C | 23 | A | 24 | A |
| 26 | B | 27 | B | 29 | A |
| 31 | B | 33 | A | 34 | B |
| 35 | A | 36 | A | 37 | C |
| 38 | B | 40 | B | 41 | B |
| 42 | B | 43 | B | 44 | A |
| 45 | C | 46 | B | 47 | A |
| 48 | A | 49 | B | 50 | B |
| 51 | B | 54 | B | 55 | A |
| 57 | A | 60 | B | 63 | A |
| 64 | A | 66 | B | 67 | B |
| 68 | A | 69 | A | 70 | C |
| 71 | C | 72 | B | 73 | A |
| 74 | B | 75 | A | 76 | B |
| 77 | B | 81 | B | 82 | C |
| 83 | A | 84 | B | 86 | B |
| 87 | C | 88 | C | 89 | C |
| 90 | C | 91 | A | 92 | A |
| 93 | C | 94 | A | 95 | A |
| 96 | A | 97 | A | 98 | A |
| 99 | C | 100 | B | 101 | B |
| 102 | C | 103 | C | 104 | C |
| 105 | B | 106 | A | 107 | A |
| 108 | B | 109 | C | 110 | B |
| 111 | B | 112 | B | 113 | B |
| 114 | B | 115 | C | 116 | C |
| 117 | B | 118 | C | 119 | B |
| 120 | B | 121 | B | 122 | B |
| 123 | A | 124 | B | 125 | B |
| 126 | A | 127 | A | 128 | B |
| 129 | A | 130 | A | 131 | B |

TABLE 2-continued

Binding affinity to *E. coli* PBP3 by Exemplary Compounds in fluorescence polarization competition binding assay using Bocillin-FL.

| Ex. | *E. coli* K12 PBP3 Potency | Ex. | *E. coli* K12 PBP3 Potency | Ex. | *E. coli* K12 PBP3 Potency |
|---|---|---|---|---|---|
| 132 | C | 133 | A | 134 | C |
| 135 | C | 136 | C | 137 | B |
| 138 | C | 139 | B | 140 | B |
| 141 | B | 142 | B | 143 | C |
| 144 | B | 145 | C | 146 | B |
| 147 | A | 148 | B | 149 | B |
| 150 | C | 151 | C | 152 | B |
| 153 | B | 154 | B | 155 | B |
| 156 | C | 157 | A | 158 | B |
| 159 | A | 160 | B | 161 | C |
| 162 | B | 163 | C | 164 | A |
| 165 | B | 166 | B | 167 | C |
| 168 | B | 169 | B | 171 | B |
| 172 | C | 173 | A | 174 | A |
| 175 | B | 176 | C | 177 | C |
| 178 | B | 179 | C | 180 | C |
| 181 | B | 182 | B | 183 | C |
| 184 | B | 185 | B | 186 | B |
| 187 | B | 188 | B | 189 | C |
| 190 | B | 191 | B | 192 | C |
| 193 | B | 194 | B | 195 | A |
| 202 | B | 203 | C | 204 | C |
| 205 | C | 206 | C | 208 | C |
| 209 | B | 210 | B | 211 | B |
| 212 | C | 213 | B | 214 | B |
| 215 | B | 216 | C | 217 | B |
| 218 | C | 219 | C | 220 | C |
| 221 | B | 222 | B | 223 | B |
| 224 | B | 225 | C | 226 | B |
| 227 | B | 228 | B | 229 | C |
| 230 | C | 231 | B | 232 | B |
| 233 | B | 234 | C | 235 | C |
| 236 | B | 237 | C | 238 | B |
| 239 | B | 246 | B | 247 | C |

Representative results for binding to *E. coli* PBP2 are shown in Table 3, where A represents a potency of >500 μM, B represents a potency between 30 PM and 500 μM inclusive, and C represents a potency of <30 μM. NT=Not Tested

TABLE 3

Binding affinity to *E. coli* PBP2 by Exemplary Compounds in fluorescence polarization competition binding assay using Bocillin-FL.

| Ex. | *E. coli* K12 PBP2 Potency (EC$_{50}$) | Ex. | *E. coli* K12 PBP2 Potency (EC$_{50}$) | Ex. | *E. coli* K12 PBP2 Potency (EC$_{50}$) |
|---|---|---|---|---|---|
| 5 | B | 16 | A | 20 | A |
| 27 | A | 34 | A | 51 | A |
| 81 | B | 87 | A | 89 | B |
| 90 | A | 101 | A | 102 | A |
| 103 | A | 104 | B | 109 | A |
| 110 | A | 114 | A | 117 | A |
| 121 | A | 126 | A | 131 | A |
| 135 | B | 138 | B | 142 | A |
| 148 | A | 150 | A | 151 | A |
| 154 | B | 156 | A | | |

Representative results for binding to *E. coli* PBP4 are shown in Table 4, where A represents a potency of >500 μM, B represents a potency between 30 μM and 500 μM inclusive, and C represents a potency of <30 μM. NT=Not Tested

TABLE 4

Binding affinity to *E. coli* PBP4 by Exemplary Compounds in fluorescence polarization competition binding assay using Bocillin-FL.

| Ex. | *E. coli* K12 PBP4 Potency (EC$_{50}$) | Ex. | *E. coli* K12 PBP4 Potency (EC$_{50}$) | Ex. | *E. coli* K12 PBP4 Potency (EC$_{50}$) |
|---|---|---|---|---|---|
| 5 | A | 16 | A | 20 | A |
| 27 | A | 37 | A | 40 | B |
| 51 | A | 82 | A | 87 | A |
| 89 | B | 90 | A | 110 | A |
| 117 | A | 121 | A | 131 | B |
| 136 | A | 145 | A | | |

Example II: Experimental Method to Assess Binding to Penicillin-Binding Proteins: Radioligand Competition Binding Assay To determine the ability of boronic acid-based test PBP inhibitors to bind Penicillin Binding Proteins (PBPs), a radio-labelled boronic acid PBP inhibitor

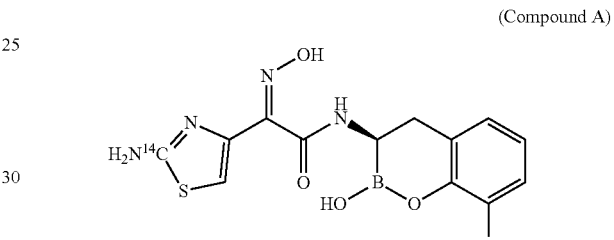

(Compound A)

was used in competition binding assays to determine boronic acid PBP inhibitor binding to PBP1a or PBP1b from *Escherichia coli*. PBP1a and PBP1b were purified as described previously (Bertsche, U.; et al., *J. Biol. Chem.* 2005, 280 (45), 38096-38101; Born, P.; et al., *J. Biol. Chem.* 2006. 281 (37), 26985-26993). To establish assay conditions for competition binding, an enzyme titration/saturation binding experiment was performed. Saturation binding was performed in a buffer comprised of 20 mM Tris (pH 7.5), 500 mM NaCl and 0.1% (v/v) TritonX-100, with PBP1a/PBP1b at a final concentration of 0.1 μM and Compound A at final concentrations ranging from 0-100 μM. Mixtures were incubated for 60 minutes, then applied to Zeba Spin Desalting columns or plates (ThermoFisher Scientific) and centrifuged at 1000-1500×g for 2 minutes. The flow through, containing PBP bound with Compound A, was recovered and 100 μL mixed with 5 mL of UltimaGold liquid scintillation cocktail (Perkin Elmer), and the radioactivity counted using a Beckman Coulter LS 6500 Multipurpose scintillation counter. PBP binding of Compound A approached saturation at 20 μM of $^{14}$C-labeled probe. The competition binding assay was validated using the beta-lactam ampicillin, with Compound A at a final concentration of 20 μM, PBP1a/PBP1b at a final concentration of 0.1 μM. PBP1a/PBP1b was incubated with ampicillin in a 96-well microplate for 60 minutes, then Compound A was added and the mixtures incubated for an additional 60 minutes. The mixtures were then applied to Zeba Spin desalting plates and centrifuged at 1000×g for 2 minutes. The flow through was recovered and 100 μl mixed with 5 ml of UltimaGold liquid scintillation cocktail and the radioactivity counted. Ampicillin inhibited binding of Compound A with an EC$_{50}$ (the concentration of inhibitor required to reduce binding of Compound A by 50%) of less than 0.5 μM. Binding assays with boronic acid PBP inhibitors were performed in an identical fashion. The potency of boronic acid PBP inhibitors was reported as the $EC_{50}$ value.

Representative results for binding to *E. coli* PBP1a and PBP1b are shown in Table 5, where A represents a potency of >100 μM, B represents a potency between 10 μM and 100 μM inclusive, and C represents a potency of <10 μM. NT=Not Tested

TABLE 5

Binding affinity to *E. coli* PBP1a and PBP1b by Exemplary Compounds in competition binding assay using $^{14}$C-labeled boronic acid probe.

| Ex. | *E. coli* K12 PBP1a $EC_{50}$ | *E. coli* K12 PBP1b $EC_{50}$ | Ex. | *E. coli* K12 PBP1a $EC_{50}$ | *E. coli* K12 PBP1b $EC_{50}$ |
|---|---|---|---|---|---|
| 5 | C | C | 11 | NT | C |
| 17 | C | NT | 20 | C | NT |
| 22 | C | C | 23 | NT | A |
| 24 | NT | A | 25 | NT | C |
| 26 | C | NT | 27 | C | NT |
| 29 | NT | A | 31 | NT | B |
| 33 | NT | C | 34 | C | NT |
| 35 | NT | C | 36 | NT | C |
| 41 | NT | C | 43 | NT | B |
| 45 | C | C | 46 | C | NT |
| 47 | NT | B | 48 | NT | C |
| 49 | C | NT | 51 | NT | B |
| 56 | NT | A | 60 | NT | B |
| 63 | NT | C | 64 | NT | B |
| 67 | NT | B | 68 | NT | C |
| 69 | NT | C | 70 | C | NT |
| 71 | C | C | 72 | NT | C |
| 73 | NT | A | 74 | NT | A |
| 76 | C | NT | 77 | NT | C |
| 78 | NT | A | 82 | NT | B |
| 84 | NT | C | 85 | C | C |
| 86 | C | NT | 88 | NT | C |
| 91 | NT | C | 92 | NT | C |
| 99 | B | NT | 100 | B | NT |
| 102 | B | NT | 103 | B | NT |
| 104 | NT | A | 105 | NT | A |
| 106 | NT | C | 107 | NT | A |
| 108 | NT | B | 109 | NT | A |
| 110 | NT | A | 111 | NT | A |
| 112 | NT | A | 113 | NT | A |
| 114 | NT | A | 115 | NT | A |
| 116 | NT | B | 117 | NT | A |
| 118 | NT | A | 119 | NT | A |
| 121 | NT | A | 123 | NT | A |
| 124 | NT | C | 125 | NT | C |
| 127 | NT | A | 129 | NT | A |
| 130 | NT | A | 131 | NT | B |
| 132 | NT | B | 136 | NT | B |
| 145 | NT | A | | | |

Example III: In Vitro Antibacterial Assays

To determine the ability of test compounds to potentiate the inhibition of the growth of bacterial strains, classic cell based broth microdilution minimum inhibitory concentration (MIC) assays were employed. MIC assays are performed according to CLSI methods except where otherwise noted (CLSI, 2011 and CLSI, 2009). The reference type strain *E. coli* ATCC 25922, the wild-type parent strain *E. coli* AG100, the hyper-permeable *E. coli* 901C and *E. coli* D22 and the *E. coli* AG100A strain lacking the acrAB efflux pump encoding genes were used to determine the ability of the PBP inhibitors to penetrate the outer membrane of gram-negative bacteria and inhibit bacterial growth. Three additional challenge isolates of *Klebsiella pneumoniae* (*K. pneumoniae* 848844 producing SHV-11 and KPC-2, *K. pneumoniae* UMM producing SHV-5 and KPC-2 and *K. pneumoniae* SI-117 producing VIM-1) were used to further assess antibacterial activity in Enterobacteriaceae and demonstrate activity of the PBP inhibitors irrespective of the beta-lactamase content of these organisms. The *P. aeruginosa* PAO1, *P. aeruginosa* ATCC 27853 and *A. baumannii* ATCC 19606, along with the hyper-permeable *P. aeruginosa* ATCC 35151 and an engineered efflux pump-compromised strain of *P. aeruginosa* (ΔmexAB-oprM) were used to determine the ability of PBP inhibitors to penetrate the outer membrane of *P. aeruginosa* and *A. baumannii* and assess antibacterial activity against these important gram-negative organisms.

Briefly, cryo-preserved bacterial cultures of challenge strains are streaked for isolation on appropriate agar medium, in this case Mueller Hinton II agar. Following incubation to allow growth of the colonies, plates are sealed with parafilm and stored refrigerated for up to two weeks. For preparation of assay inoculum and to ensure low variability, at least 5 colonies are picked from the agar plates with an inoculating loop and aseptically transferred to a culture tube containing 3 mL of Mueller-Hinton Broth (supplemented with divalent cations to required levels based on Manufacturers' certification). The broth culture is grown for 3-5 hours at 37° C. with shaking at 200 rpm. Meanwhile, 2-fold serial dilutions of test compounds are conducted in a 96 well plate with a final volume of 75 μL per well at 2-fold the final desired concentration. After the dilution plates are set up the growing cultures are then diluted in a cuvette containing MH II broth and the optical density is measured at 600 nm. The Inoculum is diluted such that 75 μL of this culture in Mueller-Hinton Broth results in a starting bacterial concentration of $5 \times 10^5$ CFU/mL when added to the dilution plates. The plates are incubated for 16-20 hours at 37° C. The MIC values are read visually as the lowest concentration well with no bacterial growth.

Additional antibacterial testing of the series was performed in wild-type reference strains of *N. gonorrhoeae* (ATCC 49226, FA1090, WHO F and FA19). Liquid broth-based assays were used for antibacterial testing of PBP inhibitors in *Neisseria gonorrhoeae*. Briefly, cryo-preserved bacterial cultures of clinical strains are streaked for isolation on GC Base agar (BD #228950 at 36 g/L autoclaved at 121° C. for 20 minutes to sterilize) with 1% Kellogg's supplement (40 g glucose, 0.5 g glutamine, 0.05 g ferric nitrate and 2 mg cocarboxylase per 100 mL deionized water filter sterilized through 0.2 μm syringe filters). Following incubation at 36° C. and 5% $CO_2$ to allow growth of colonies, strains are aseptically sub-cultured from original agar plate onto 3 agar plates per strain 24 hours before inoculum preparation. 2-fold serial dilutions of test compounds are conducted in a 96 well plate with a final volume of 150 μL per well at 4/3-fold the final desired concentration. For preparation of assay inoculum, a direct suspension is prepared by aseptically swabbing all colonies from sub-cultured agar plates into culture tubes containing 2 mL of fresh GC broth with 100 Kellogg's supplement. After the dilution plates are set up, direct suspensions are then diluted in a cuvette containing GC broth (15 g proteose peptone 43, 1 g corn starch, 4 g dipotassium phosphate, 1 g monopotassium phosphate and 5 g sodium chloride per liter of deionized water are mixed on a stir plate for 20 minutes, pH adjusted to 7.2+/−0.2 pH units with 1 N HCl, centrifuged at 10,000×g for 20 minutes to pellet undissolved corn starch and then autoclaved at 121° C. for 20 minutes to sterilize) and the optical density is measured at 600 nm. Inocula are diluted such that 50 µL of this culture in Mueller-Hinton Broth results in a starting bacterial concentration of $5 \times 10^5$ CFU/mL when added to the dilution plates. The plates are incubated 40-42 hours at 36° C. and 5% $CO_2$. The MIC is read visually as the lowest concentration well with no bacterial growth.

Representative results for MIC testing in Enterobacteriaceae are shown in Table 6, where A represents an MIC≥128 µg/mL, B represents an MIC of 32 to 64 µg/mL, C represents an MIC from 8 to 16 µg/mL, D represents an MIC from 2 to 4 µg/mL, E represents an MIC from 0.5 to 1 µg/mL, and F represents an MIC≤0.25 µg/mL. NT=Not Tested

TABLE 6

Inhibition of bacterial growth. Minimum Inhibitory Concentrations of Exemplary Compounds for Enterobacteriaceae.

| Ex. | E. coli 25922 | E. coli 901C | E. coli D22 | E. coli AG100 | E. coli AG100A | K. pneumoniae 848844 | K. pneumoniae UMM | K. pneumoniae SI-117 |
|---|---|---|---|---|---|---|---|---|
| 5 | C | F | D | C | D | B | C | C |
| 6 | A | C | NT | A | C | NT | A | NT |
| 7 | A | C | NT | A | B | NT | A | NT |
| 8 | A | A | NT | A | A | NT | A | A |
| 9 | A | A | NT | A | A | NT | A | NT |
| 10 | C | E | NT | B | D | NT | C | NT |
| 13 | B | F | NT | B | D | NT | B | NT |
| 16 | B | E | C | B | D | B | B | B |
| 22 | C | E | NT | C | D | NT | C | NT |
| 27 | B | E | C | B | D | A | B | B |
| 37 | B | E | NT | B | D | NT | C | NT |
| 39 | C | E | NT | C | D | NT | C | NT |
| 45 | C | E | NT | C | C | NT | C | NT |
| 51 | C | E | NT | B | C | NT | B | NT |
| 58 | B | D | C | B | C | C | C | A |
| 70 | D | E | D | D | E | C | E | C |
| 71 | C | E | NT | D | D | NT | B | NT |
| 82 | B | D | D | B | D | A | B | B |
| 85 | C | E | NT | C | C | NT | B | NT |
| 89 | C | E | NT | B | D | NT | C | NT |
| 90 | C | E | C | C | D | B | C | A |
| 99 | B | F | NT | B | D | NT | C | NT |
| 100 | B | E | C | B | D | B | C | C |
| 102 | B | F | NT | C | D | NT | B | NT |
| 103 | B | F | NT | C | D | NT | B | NT |
| 104 | C | F | D | B | E | A | B | B |
| 105 | B | F | C | B | D | A | B | A |
| 107 | B | C | B | B | C | B | B | B |
| 108 | B | C | C | A | B | A | B | A |
| 109 | C | E | D | C | C | B | C | C |
| 110 | C | D | C | C | C | B | C | C |
| 111 | B | E | C | B | D | A | B | A |
| 112 | B | F | D | B | D | A | B | A |
| 113 | B | F | C | B | D | A | B | A |
| 115 | B | F | C | B | D | A | B | B |
| 117 | B | E | C | A | D | B | B | A |
| 121 | B | E | C | B | D | A | C | B |
| 124 | C | F | E | E | E | A | C | C |
| 125 | D | E | E | D | D | S | B | D |
| 126 | C | D | D | C | C | B | C | C |
| 128 | B | E | D | C | D | B | C | C |
| 131 | D | E | D | C | D | B | C | C |
| 134 | B | D | C | B | C | B | B | B |
| 135 | D | F | E | C | D | B | C | B |
| 136 | C | E | D | D | D | B | C | A |
| 140 | C | E | D | B | D | B | C | B |
| 141 | A | D | C | A | B | A | B | A |
| 143 | B | F | D | B | D | A | B | A |
| 144 | A | E | C | C | C | A | B | A |
| 145 | C | E | D | C | D | B | C | B |
| 148 | C | E | D | B | D | B | B | B |
| 149 | C | E | D | D | E | D | D | D |
| 150 | B | E | D | B | D | A | B | A |
| 151 | A | E | C | B | C | A | B | B |
| 154 | A | E | C | A | C | A | A | A |
| 155 | A | E | C | A | C | A | A | A |
| 156 | B | F | D | B | D | B | B | B |
| 160 | A | D | B | A | A | A | A | A |
| 161 | A | E | D | A | B | A | B | A |
| 162 | B | E | C | B | D | A | B | B |

TABLE 6-continued

Inhibition of bacterial growth. Minimum Inhibitory Concentrations of Exemplary Compounds for Enterobacteriaceae.

| Ex. | E. coli 25922 | E. coli 901C | E. coli D22 | E. coli AG100 | E. coli AG100A | K. pneumoniae 848844 | K. pneumoniae UMM | K. pneumoniae SI-117 |
|---|---|---|---|---|---|---|---|---|
| 166 | B | F | D | B | D | A | B | A |
| 167 | B | F | D | B | D | A | B | A |
| 168 | A | E | C | A | C | A | A | A |
| 169 | B | F | D | B | C | A | A | A |
| 170 | C | F | E | C | D | B | C | B |
| 171 | B | E | E | B | C | A | B | A |
| 172 | B | E | C | B | C | A | B | A |
| 176 | B | F | D | B | D | A | B | B |
| 177 | C | F | E | C | E | B | C | B |
| 178 | A | C | B | A | B | A | A | A |
| 179 | C | F | E | C | E | B | D | C |
| 180 | C | E | D | D | E | D | E | D |
| 181 | A | E | C | A | B | B | B | A |
| 182 | A | E | D | A | B | A | B | A |
| 183 | B | F | D | C | D | A | C | B |
| 185 | C | E | D | D | D | E | D | D |
| 186 | B | F | E | C | D | A | B | A |
| 187 | B | F | E | C | D | A | B | A |
| 188 | B | D | C | C | C | C | A | B |
| 189 | D | E | E | D | E | D | E | E |
| 190 | D | F | E | E | F | E | E | D |
| 191 | A | E | C | A | C | A | A | A |
| 192 | D | F | E | C | E | B | C | B |
| 194 | B | C | C | C | C | C | C | C |
| 195 | A | B | A | A | A | A | A | A |
| 202 | B | E | C | B | D | A | B | B |
| 203 | B | F | D | B | D | A | B | A |
| 204 | B | F | D | B | D | A | B | A |
| 205 | D | F | E | C | E | B | A | B |
| 206 | D | F | E | E | F | D | D | D |
| 207 | C | F | E | C | E | B | C | B |
| 208 | C | F | D | C | D | B | C | B |
| 209 | C | F | D | B | E | A | B | A |
| 210 | C | F | D | B | D | A | B | A |
| 211 | B | F | D | B | D | A | B | A |
| 212 | B | F | D | B | C | A | B | A |
| 213 | A | E | D | B | C | A | B | A |
| 214 | C | E | D | B | D | B | B | B |
| 216 | B | E | D | B | C | B | B | B |
| 217 | C | D | D | D | D | D | D | D |
| 218 | B | F | D | B | D | A | B | A |
| 219 | A | D | C | A | C | A | B | B |
| 220 | C | E | E | E | E | E | E | D |
| 221 | A | C | C | C | C | B | C | B |
| 222 | A | B | A | B | B | A | B | A |
| 223 | A | C | B | A | B | A | A | A |
| 224 | D | E | D | D | E | D | D | D |
| 225 | C | E | D | C | E | B | C | C |
| 226 | A | D | C | B | C | A | B | A |
| 227 | E | F | E | F | F | E | E | E |
| 228 | C | E | D | D | E | D | E | D |
| 229 | C | E | D | D | E | D | C | C |
| 230 | C | E | D | C | D | B | C | C |
| 231 | B | D | C | B | C | B | B | B |
| 232 | A | C | C | C | C | C | B | B |
| 233 | C | E | E | E | E | D | D | D |
| 234 | A | D | C | A | C | A | B | A |
| 235 | B | D | D | C | D | D | D | C |
| 236 | E | E | E | E | E | E | E | E |
| 237 | D | F | F | E | F | D | D | D |
| 238 | B | D | C | D | D | C | C | C |
| 239 | B | D | D | D | D | D | D | A |
| 240 | A | C | C | A | C | A | A | A |
| 241 | A | E | C | A | C | A | A | A |
| 242 | C | E | E | E | E | E | E | D |
| 243 | C | E | D | D | E | D | D | D |
| 244 | C | E | E | D | E | D | E | D |
| 245 | A | C | A | B | B | A | A | A |
| 246 | A | D | B | A | B | NT | A | A |
| 247 | B | F | D | B | D | NT | A | A |
| 248 | C | E | D | D | E | D | D | D |
| 249 | B | D | C | C | C | D | C | C |
| 250 | D | E | E | E | E | E | E | D |

TABLE 6-continued

Inhibition of bacterial growth. Minimum Inhibitory Concentrations of Exemplary Compounds for Enterobacteriaceae.

| Ex. | E. coli 25922 | E. coli 901C | E. coli D22 | E. coli AG100 | E. coli AG100A | K. pneumoniae 848844 | K. pneumoniae UMM | K. pneumoniae SI-117 |
|---|---|---|---|---|---|---|---|---|
| 251 | D | E | E | E | E | D | E | D |
| 252 | C | E | D | C | E | B | C | B |

Representative results for testing in *P. aeruginosa* and *A. baumannii* strains are shown in Table 7, where A represents an MIC≥128 μg/mL, B represents an MIC of 32 to 64 Tg/mL, C represents an MIC from 8 to 16 μg/mL, D represents an MIC from 2 to 4 μg/mL, E represents an MIC 1 from 0.5 to 1 μg/mL, and F represents an MIC≤0.25 μg/mL. NT=Not Tested

TABLE 7

Inhibition of bacterial growth. Minimum Inhibitory Concentrations of Exemplary Compounds for *P. aeruginosa* and *A. baumannii* strains.

| Ex. | P. aeruginosa PAO1 | P. aeruginosa ATCC 27853 | P. aeruginosa ATCC 35151 | P. aeruginosa ΔmexAB-OprM | A. baumannii ATCC 19606 |
|---|---|---|---|---|---|
| 58 | C | NT | F | F | D |
| 65 | A | NT | C | B | NT |
| 70 | C | NT | F | E | E |
| 71 | B | NT | E | D | E |
| 124 | E | NT | F | F | E |
| 125 | E | NT | F | F | F |
| 128 | A | NT | E | C | A |
| 131 | E | NT | F | F | C |
| 136 | C | NT | E | E | D |
| 138 | A | NT | E | B | A |
| 145 | A | NT | C | C | A |
| 149 | D | NT | F | F | C |
| 151 | A | NT | F | C | A |
| 150 | A | NT | D | B | A |
| 161 | A | NT | F | C | A |
| 169 | A | NT | E | C | A |
| 170 | A | NT | F | C | A |
| 172 | A | NT | F | D | A |
| 177 | A | NT | E | D | A |
| 181 | A | NT | E | C | A |
| 182 | A | NT | E | C | A |
| 183 | A | NT | F | B | A |
| 185 | A | NT | F | E | A |
| 188 | C | NT | E | E | B |
| 189 | F | NT | F | F | F |
| 190 | E | NT | F | F | F |
| 191 | A | NT | D | B | A |
| 194 | C | NT | F | E | E |
| 203 | A | NT | E | C | A |
| 204 | A | NT | E | C | A |
| 205 | A | NT | F | D | B |
| 206 | D | NT | F | F | F |
| 208 | A | NT | F | B | A |
| 210 | A | NT | E | D | A |
| 212 | B | NT | F | C | A |
| 213 | A | NT | D | C | A |
| 216 | A | NT | F | B | A |
| 217 | D | NT | F | F | E |
| 218 | A | NT | D | B | A |
| 220 | E | NT | F | F | F |
| 222 | C | NT | F | F | B |
| 224 | C | NT | F | E | F |
| 225 | A | NT | E | D | A |
| 227 | F | NT | F | F | F |
| 228 | E | NT | F | F | E |
| 229 | D | NT | F | F | F |
| 230 | B | NT | F | D | A |

TABLE 7-continued

Inhibition of bacterial growth. Minimum Inhibitory Concentrations of Exemplary Compounds for *P. aeruginosa* and *A. baumannii* strains.

| Ex. | P. aeruginosa PAO1 | P. aeruginosa ATCC 27853 | P. aeruginosa ATCC 35151 | P. aeruginosa ΔmexAB-OprM | A. baumannii ATCC 19606 |
|---|---|---|---|---|---|
| 231 | A | NT | E | C | A |
| 232 | B | NT | F | F | A |
| 233 | NT | D | F | F | D |
| 234 | NT | A | C | B | A |
| 235 | NT | C | F | F | E |
| 236 | NT | E | F | F | F |
| 237 | NT | E | F | F | F |
| 238 | NT | D | F | F | E |
| 239 | NT | C | F | F | E |
| 240 | NT | A | C | A | A |
| 242 | NT | E | F | F | E |
| 243 | NT | F | F | F | E |
| 244 | NT | F | F | F | F |
| 245 | NT | A | B | A | A |
| 246 | NT | A | D | B | A |
| 247 | NT | A | E | C | A |
| 248 | NT | B | F | F | E |
| 249 | NT | E | F | F | E |
| 250 | NT | E | F | F | F |
| 251 | NT | E | F | F | E |
| 252 | NT | B | F | C | A |

Representative results for testing in *N. gonorrhoeae* strains are shown in Table 8, where A represents an MIC≥64 μg/mL, B represents an MIC of 16 to 32 μg/mL, C represents an MIC from 4 to 8 μg/mL, D represents an MIC from 1 to 2 μg/mL, E represents an MIC from 0.25 to 0.5 μg/mL, and F represents an MIC≤0.125 μg/mL. NT=Not Tested

TABLE 8

Inhibition of bacterial growth. Minimum Inhibitory Concentrations of Exemplary Compounds for *N. gonorrhoeae* strains.

| Ex. | N. gonorrhoeae ATCC 49226 | N. gonorrhoeae FA1090 | N. gonorrhoeae WHO F | N. gonorrhoeae FA19 |
|---|---|---|---|---|
| 5 | D | F | F | D |
| 37 | C | D | D | C |
| 39 | D | F | E | D |
| 52 | E | F | F | A |
| 58 | C | C | D | C |
| 70 | E | F | F | D |
| 87 | D | F | F | C |
| 93 | C | E | F | C |
| 101 | D | F | F | D |
| 102 | D | F | F | D |
| 103 | D | F | F | D |
| 109 | D | E | E | C |
| 112 | D | F | F | D |
| 113 | D | F | F | D |
| 124 | D | D | F | C |
| 125 | C | D | E | B |
| 131 | C | E | E | C |

TABLE 8-continued

Inhibition of bacterial growth. Minimum Inhibitory Concentrations of Exemplary Compounds for *N. gonorrhoeae* strains.

| Ex. | *N. gonorrhoeae* ATCC 49226 | *N. gonorrhoeae* FA1090 | *N. gonorrhoeae* WHO F | *N. gonorrhoeae* FA19 |
|---|---|---|---|---|
| 135 | D | F | F | D |
| 136 | D | D | D | C |
| 137 | D | F | F | C |
| 142 | E | F | F | D |
| 145 | E | F | F | D |
| 149 | D | E | F | D |
| 150 | C | E | E | C |
| 151 | D | E | F | C |
| 152 | D | E | E | D |
| 153 | D | E | E | D |
| 160 | B | E | E | B |
| 161 | D | F | F | D |
| 170 | C | E | F | C |
| 177 | C | F | F | C |
| 179 | E | F | F | C |
| 181 | C | D | E | C |
| 182 | C | D | D | C |
| 183 | E | E | F | D |
| 186 | D | F | F | D |
| 187 | E | F | F | E |
| 188 | B | C | C | B |
| 189 | D | E | E | D |
| 190 | D | E | E | C |
| 191 | A | E | D | B |
| 192 | D | F | F | D |
| 194 | B | C | C | C |
| 202 | C | E | E | C |
| 293 | D | F | E | D |
| 204 | D | E | E | D |
| 205 | F | F | F | F |
| 206 | C | E | E | C |
| 207 | E | F | F | D |
| 208 | C | E | F | C |
| 210 | C | F | F | D |
| 211 | C | E | E | C |
| 212 | E | F | F | E |
| 213 | C | E | E | B |
| 214 | C | F | F | C |
| 215 | C | D | E | C |
| 216 | D | E | F | D |
| 217 | B | D | E | C |
| 218 | B | E | E | B |
| 220 | B | C | D | A |
| 223 | A | D | D | A |
| 224 | A | D | C | A |
| 225 | B | E | E | C |
| 227 | C | D | D | C |
| 228 | A | D | C | A |
| 229 | A | C | C | A |
| 230 | C | D | E | C |
| 233 | A | D | C | B |
| 234 | B | E | E | B |
| 235 | A | D | D | A |
| 236 | B | D | D | C |
| 237 | C | D | E | C |
| 238 | A | C | C | A |
| 239 | A | C | C | A |

Example IV: Boronate Penicillin-Binding Protein (PBP) Inhibitors are not Impacted by CTX-M15 β-lactamase To determine if test compounds were affected by CTX-M15, the most abundant extended spectrum β-lactamase in clinical settings worldwide, the inhibition of the growth of an engineered strain of *Escherichia coli* harboring CTX-M15 was tested. This strain was constructed by cloning the gene encoding CTX-M15 into the NdeI and BamHI restriction endonuclease sites of plasmid pLBII, placing the gene(s) under the control of the Lac promoter. The constructed expression plasmid for CTX-M15 was used to transform competent *E. coli* DH5α cells to make the engineered strain, including an empty pLBII vector control strain. The classic cell based broth microdilution MIC assay was employed as described above with the addition of control antibiotics, known to be degraded by β-lactamases (Ceftazidime, piperacillin and piperacillin+tazobactam). Examples 1 through 128 display for the most part the same MIC values in both strains regardless of the presence of CTX-M 15 β-lactamase, whereas β-lactams antibiotics, ceftazidime and piperacillin have weaker MICs in the CTX-M15 producer, and the protected piperacillin+tazobactam shows similar activity between the CTX-M15 producer and the parent strain with the empty pLBII plasmid.

Representative results are shown in Table 9, where A represents an MIC≥512 µg/mL, B represents an MIC of 128 to 256 µg/mL, C represents an MIC from 32 to 64 µg/mL, D represents an MIC from 8 to 16 µg/mL, E represents an MIC from 2 to 4 µg/mL, and F represents an MIC<1 µg/mL. NT=Not Tested.

TABLE 9

Inhibition of growth of engineered *Escherichia coli* producing CTX-M15. Minimum Inhibitory Concentrations of exemplary compounds as compared to β-lactams antibiotics.

| | Microbiological Activity (MIC in mg/L) | |
|---|---|---|
| Example | *E. coli* DH5α/pLBII | *E. coli* DH5α/pLBII-CTX-M15 |
| 9 | A | A |
| 28 | A | A |
| 10 | D | D |
| 11 | B | B |
| 12 | A | A |
| 13 | D | D |
| 14 | A | A |
| 15 | A | A |
| 53 | A | A |
| 16 | C | C |
| 17 | A | B |
| 18 | B | B |
| 19 | A | A |
| 20 | C | C |
| 21 | B | B |
| 22 | D | D |
| 23 | A | A |
| 24 | A | A |
| 25 | A | A |
| 26 | B | B |
| 27 | D | D |
| 29 | B | B |
| 30 | A | A |
| 31 | A | A |
| 32 | A | A |
| 33 | A | A |
| 34 | B | B |
| 35 | A | A |
| 36 | A | A |
| 37 | D | D |
| 38 | E | E |
| 41 | C | C |
| 45 | D | D |
| 49 | C | N.T. |
| 51 | D | N.T. |
| 52 | NT | B |
| 53 | A | B |
| 54 | NT | B |
| 55 | NT | B |
| 57 | NT | B |
| 58 | NT | C |
| 59 | NT | B |
| 60 | NT | C |
| 61 | NT | B |
| 62 | NT | C |

TABLE 9-continued

Inhibition of growth of engineered *Escherichia coli* producing CTX-M15. Minimum Inhibitory Concentrations of exemplary compounds as compared to β-lactams antibiotics.

| | Microbiological Activity (MIC in mg/L) | |
|---|---|---|
| Example | *E. coli* DH5α/pLBII | *E. coli* DH5α/pLBII-CTX-M15 |
| 63 | NT | B |
| 64 | NT | B |
| 65 | NT | B |
| 66 | NT | C |
| 67 | NT | B |
| 68 | NT | C |
| 69 | NT | B |
| 70 | NT | C |
| 71 | NT | D |
| 72 | NT | B |
| 73 | NT | B |
| 74 | NT | B |
| 75 | NT | B |
| 76 | NT | B |
| 77 | NT | B |
| 78 | NT | B |
| 79 | NT | C |
| 80 | NT | B |
| 81 | NT | B |
| 82 | NT | C |
| 83 | NT | C |
| 84 | NT | B |
| 85 | NT | C |
| 86 | NT | B |
| 87 | NT | C |
| 88 | NT | B |
| 89 | NT | D |
| 90 | NT | D |
| 91 | NT | B |
| 92 | NT | B |
| 93 | NT | C |
| 94 | NT | B |
| 95 | NT | B |
| 96 | NT | B |
| 97 | NT | B |
| 98 | NT | B |
| 99 | NT | C |
| 100 | NT | D |
| 101 | NT | C |
| 102 | NT | D |
| 103 | NT | B |
| 103 | NT | D |
| 104 | NT | B |
| 104 | NT | C |
| 105 | NT | C |
| 106 | NT | C |
| 107 | NT | C |
| 108 | NT | C |
| 109 | NT | E |
| 110 | NT | D |
| 111 | NT | C |
| 112 | NT | C |
| 113 | NT | C |
| 114 | NT | B |
| 115 | NT | C |
| 116 | NT | B |
| 117 | NT | C |
| 118 | NT | B |
| 119 | NT | C |
| Ceftazidime | G | D |
| Piperacillin | F | B |
| Piperacillin + Tazobactam | F | F |

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A compound or a pharmaceutically acceptable salt, solvate, stereoisomer, tautomer, or N-oxide thereof; having one of the following formulas:

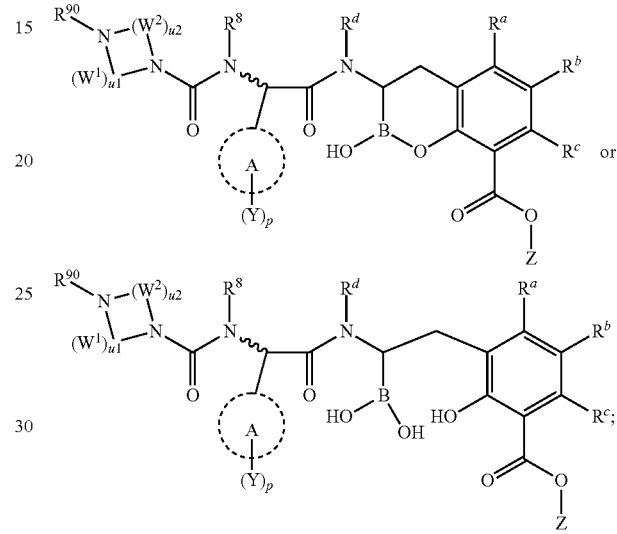

wherein:
Ring A is a 6-membered heteroaryl;
each Y is independently halogen, optionally substituted alkyl, —OH, —OR$^{34}$, —OC(=O)R$^{34}$, —NR$^{32}$R$^{33}$, —NR$^{32}$C(=O)R$^{34}$, —NR$^{32}$C(=O)OR$^{34}$, —NR$^{32}$S(=O)$_{0,1,2}$NR$^{32}$R$^{33}$, —NR$^{32}$S(=O)$_{0,1,2}$R$^{34}$, —C(=O)OH, —C(=O)OR$^{34}$, or —C(=O)NR$^{32}$R$^{33}$;
R$^{32}$ and R$^{33}$ are independently hydrogen or optionally substituted alkyl;
R$^{34}$ is optionally substituted alkyl;
p is 1-3;
R is hydrogen or alkyl;
each W$^1$ and W$^2$ is independently —C(=O)— or —C(R$^{91}$)$_2$—;
R$^{90}$ is hydrogen or optionally substituted alkyl;
each R$^{91}$ is independently hydrogen or optionally substituted alkyl;
u1 is 1 or 2;
u2 is 1 or 2;
R$^a$, R$^b$, and R$^c$ are independently hydrogen, halogen, cyano, alkyl, or —OH;
R$^d$ is hydrogen or alkyl;
Z is hydrogen, R$^{61}$, —R$^{60}$OC(=O)R$^{61}$, or —R$^{60}$OC(=O)OR$^{61}$;
each R$^{60}$ is independently —CH$_2$— or —CH(CH$_3$)—; and
each R$^{61}$ is independently optionally substituted alkyl.

2. The compound of claim 1, wherein:
u1 is 2; each W$^1$ is —C(R$^{91}$)$_2$—; u2 is 2; and each W$^2$ is —C(=O)—; or
u1 is 2; each W$^1$ is —C(R$^{91}$)$_2$—; u2 is 1; and W$^2$ is —C(=O)—.

3. The compound of claim 1, wherein $R^{90}$ is optionally substituted alkyl.

4. The compound of claim 1, wherein each $R^{91}$ is independently hydrogen.

5. The compound of claim 1, wherein Ring A is pyridine, pyrimidine, pyrazine, or pyridazine.

6. The compound of claim 1, wherein each Y is independently halogen, optionally substituted alkyl, —OH, or —OR$^{34}$.

7. The compound of claim 1, wherein each Y is independently halogen, —OH, or —OR$^{34}$.

8. The compound of claim 1, wherein each Y is halogen or —OH.

9. The compound of claim 1, wherein p is 2 or 3.

10. The compound of claim 1, wherein $R^a$, $R^b$, and $R^c$ are independently hydrogen or fluoro.

11. The compound of claim 1, wherein $R^d$ is hydrogen.

12. The compound of claim 1, wherein Z is hydrogen.

13. The compound of claim 1 selected from:

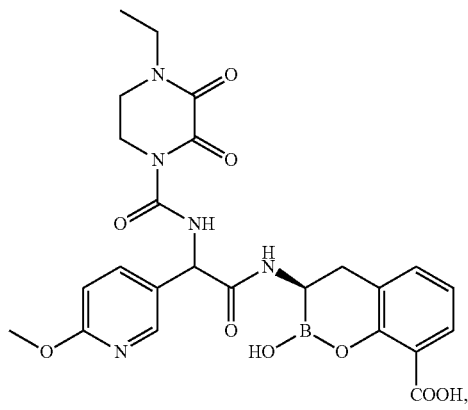

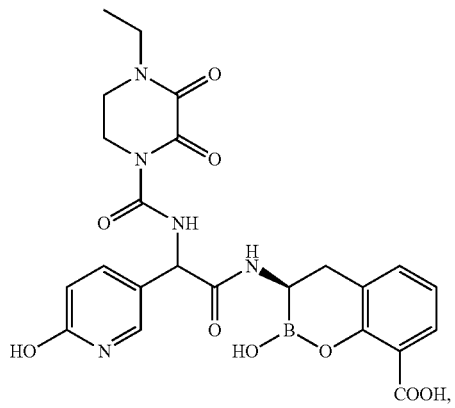

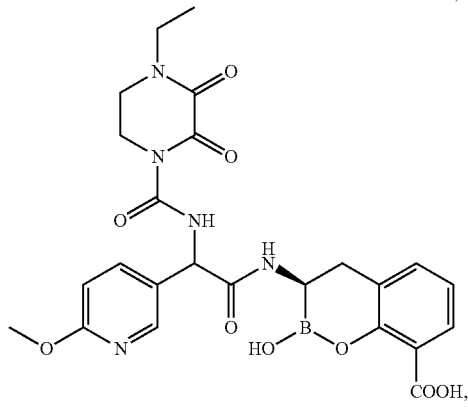

-continued

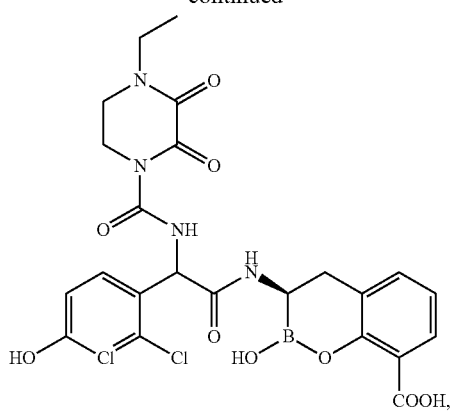

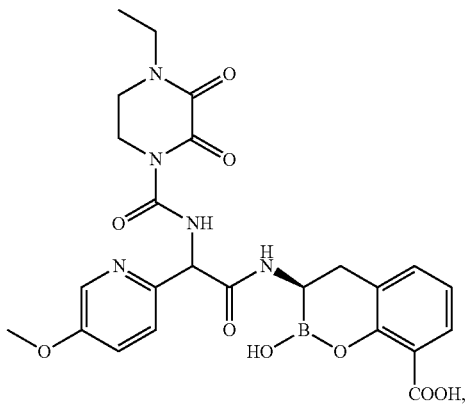

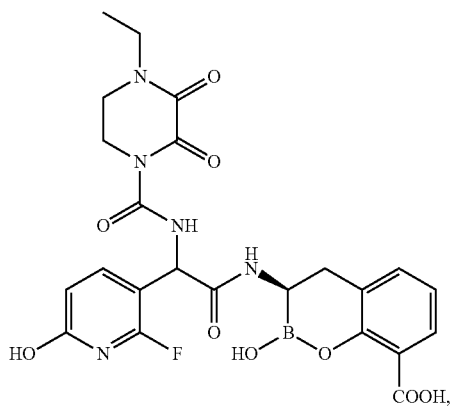

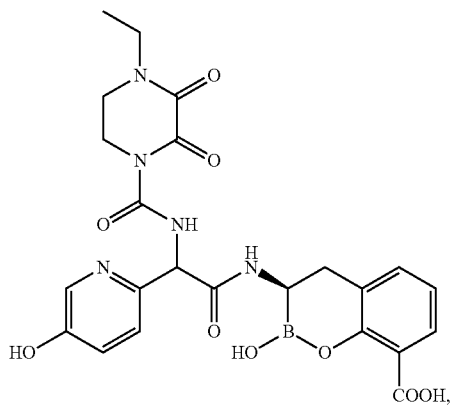

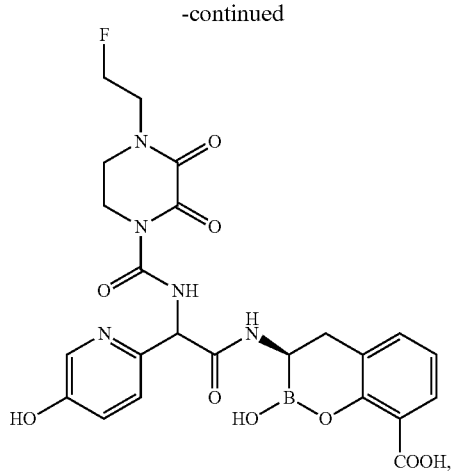
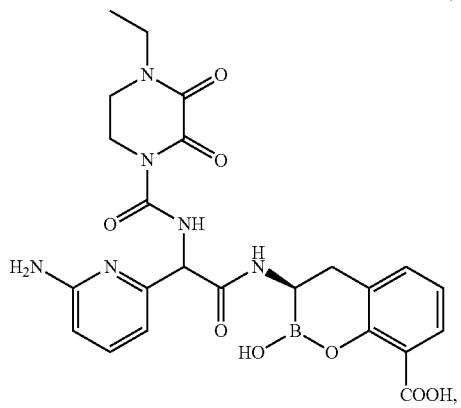
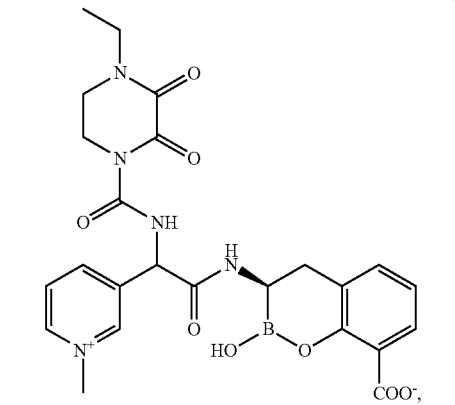
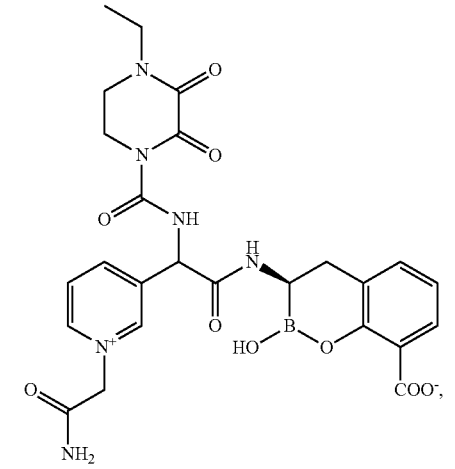
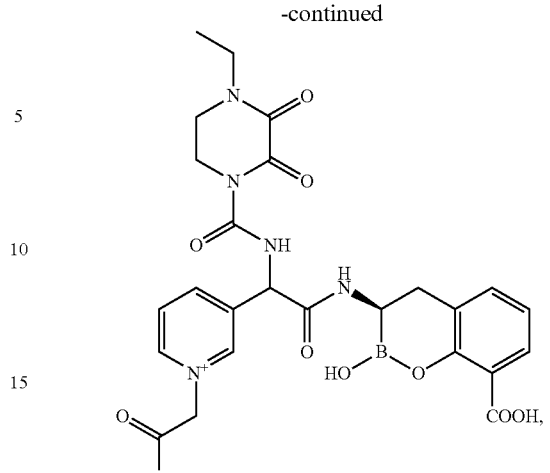
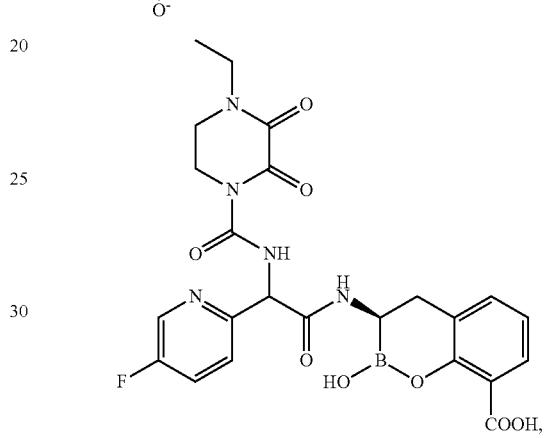
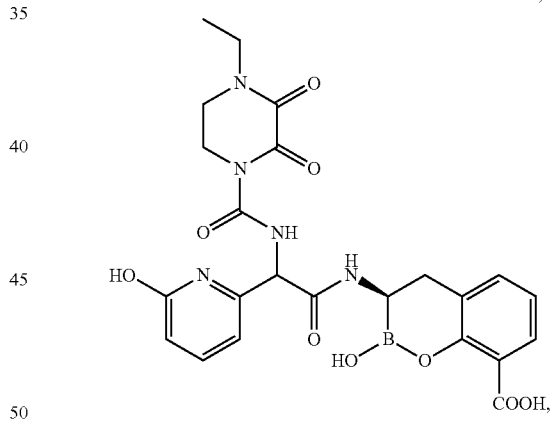
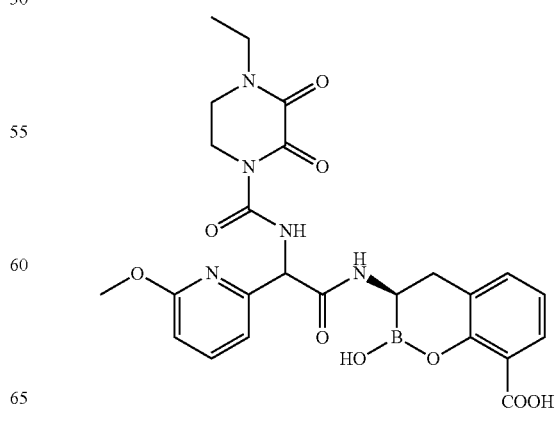

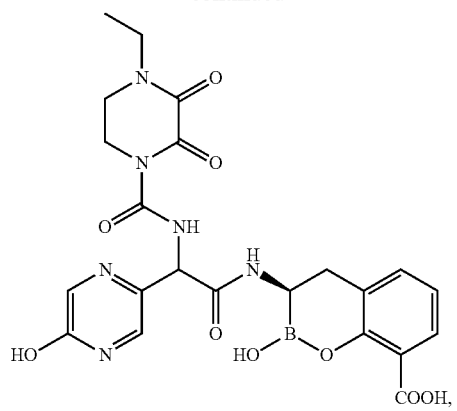
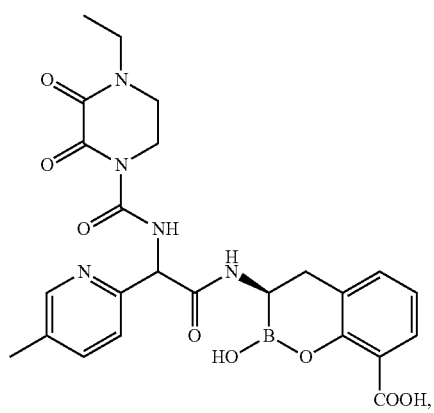
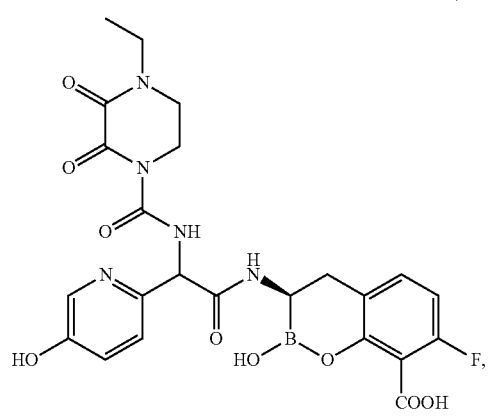
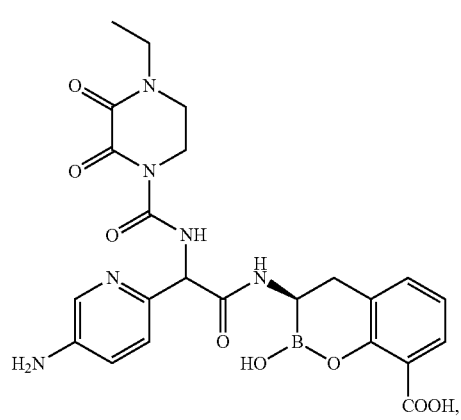
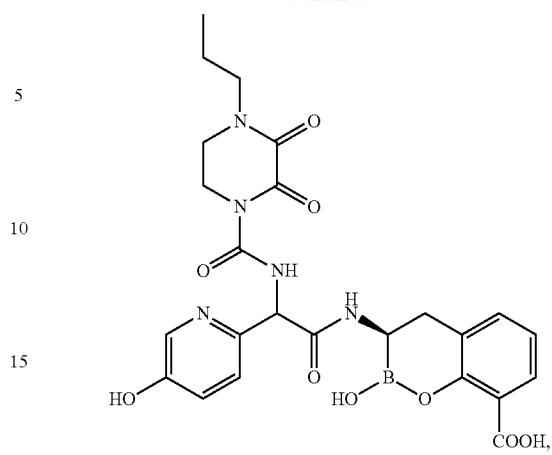
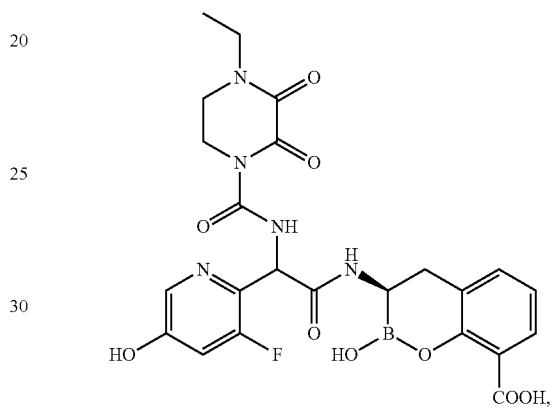
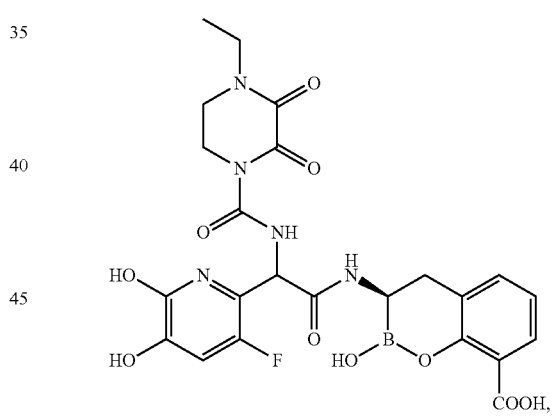
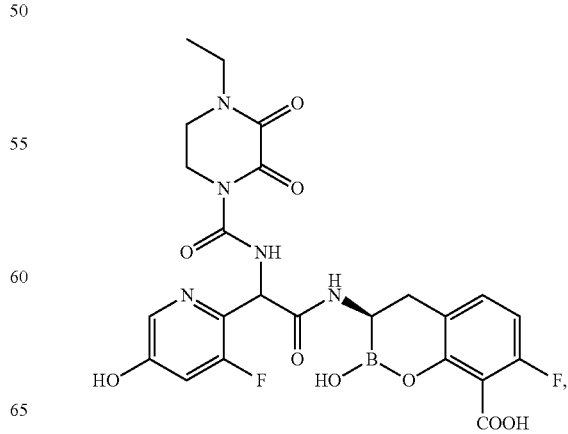

543
-continued
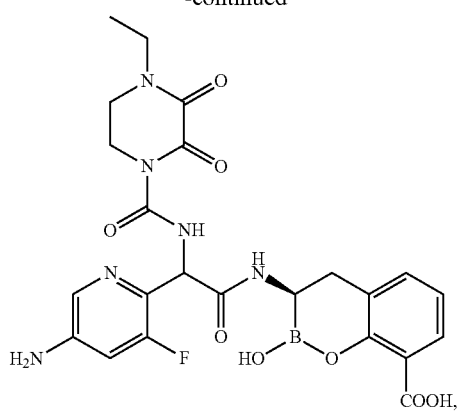
544
-continued
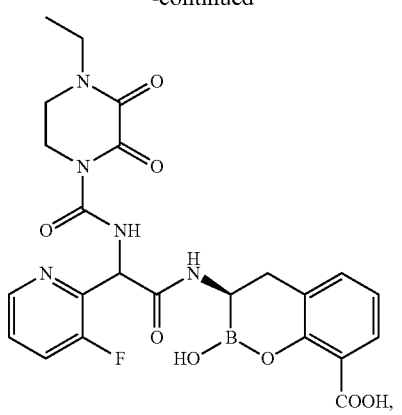

545
-continued
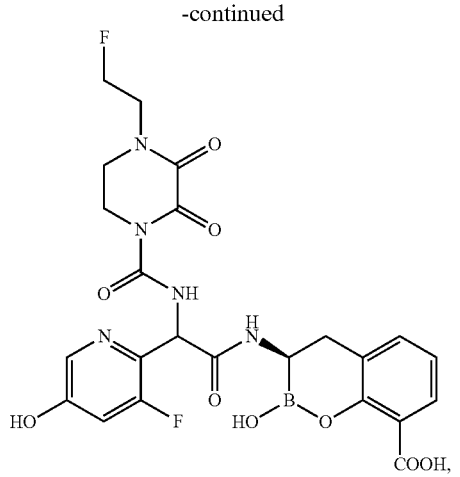
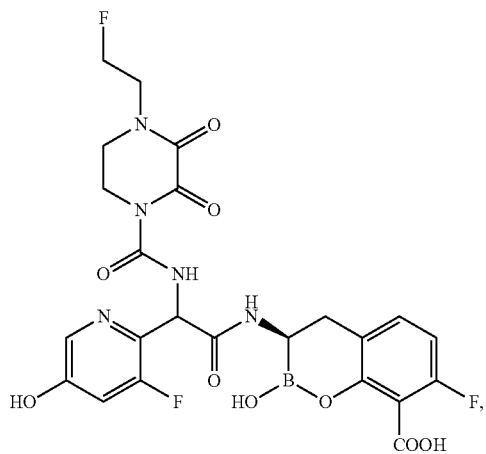
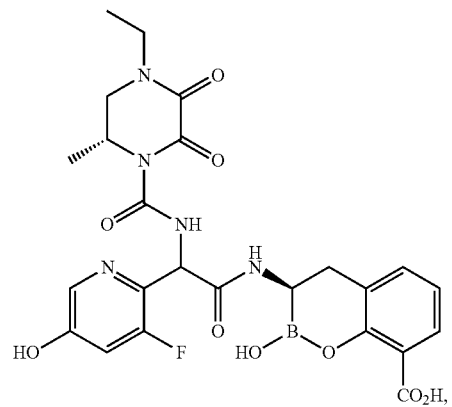
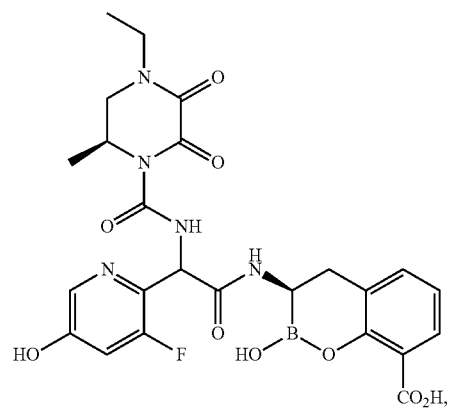
546
-continued
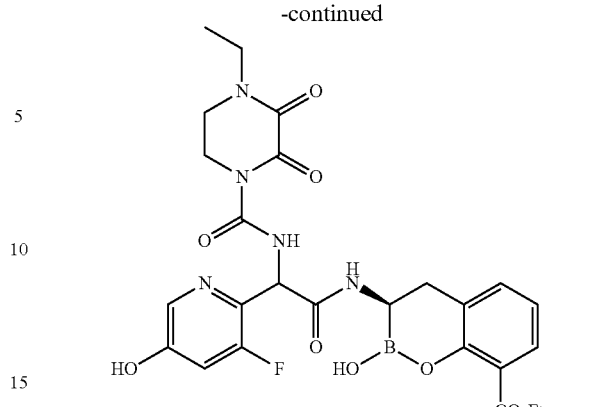
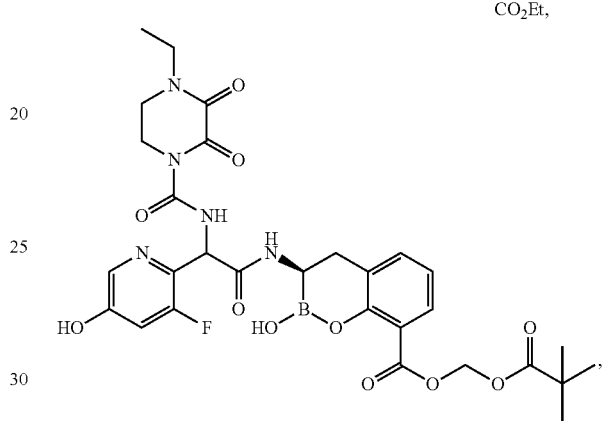

547
-continued
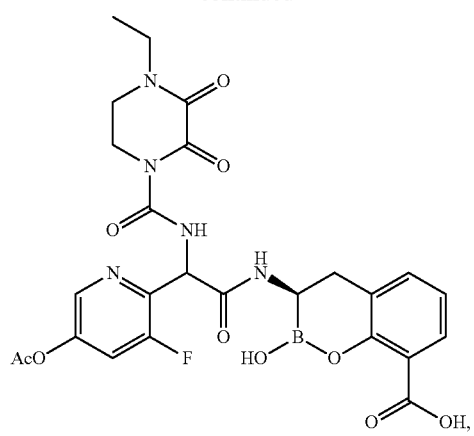
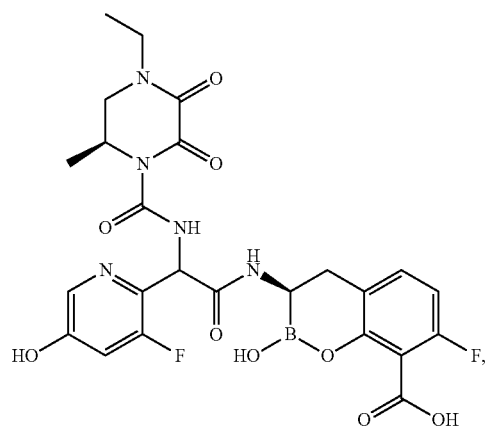
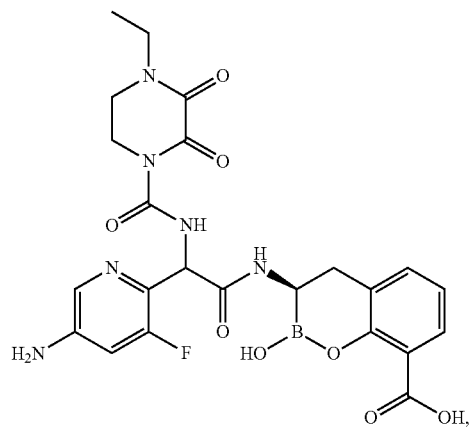
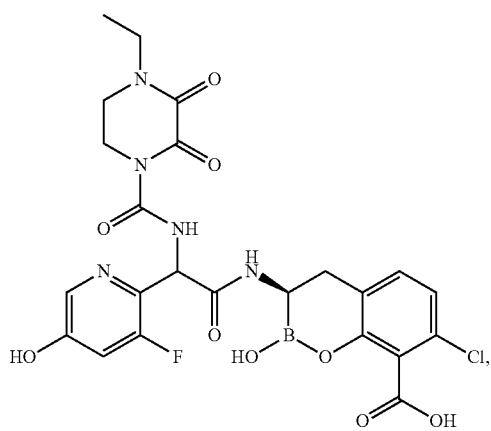
548
-continued
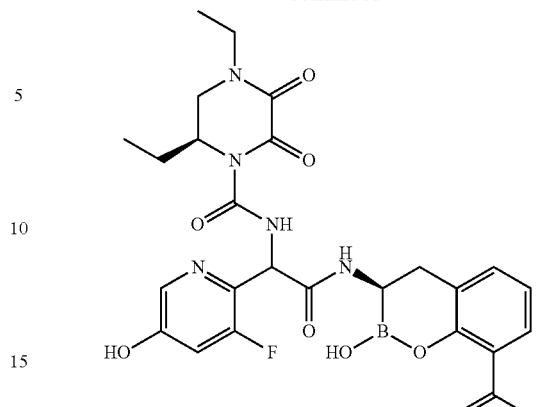
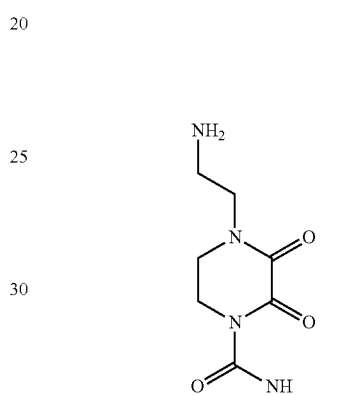
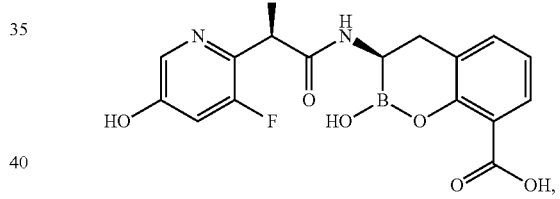
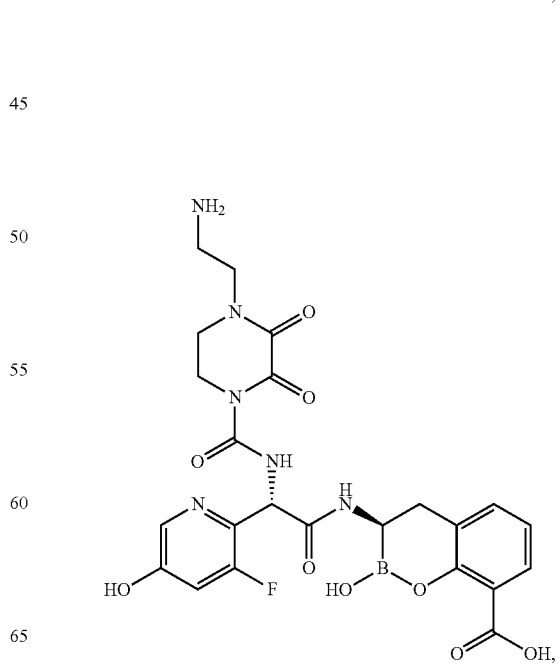

549
-continued
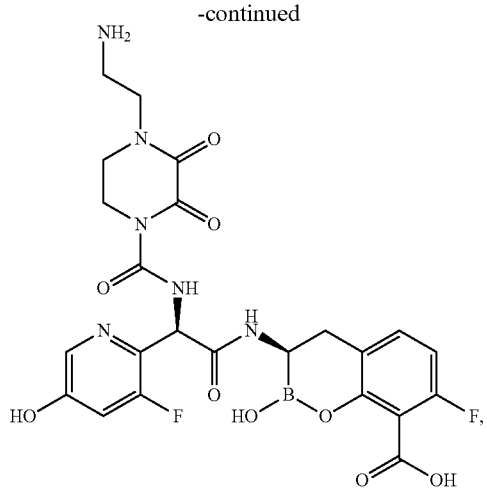
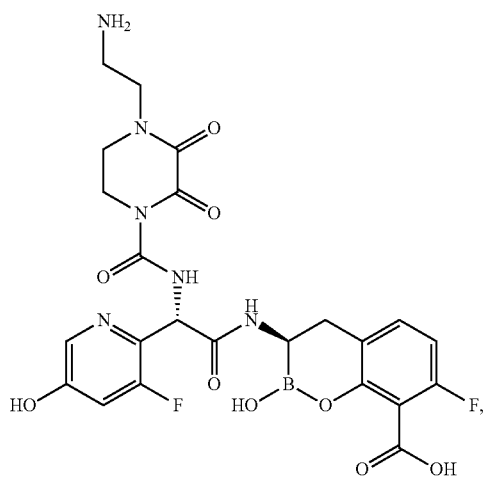
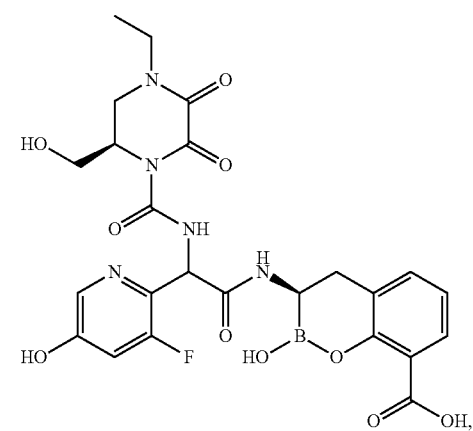
550
-continued
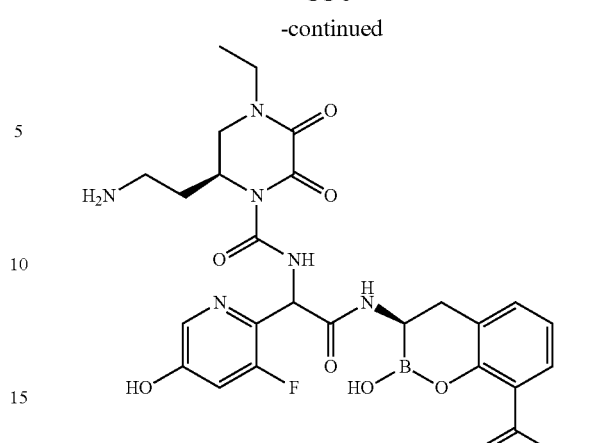
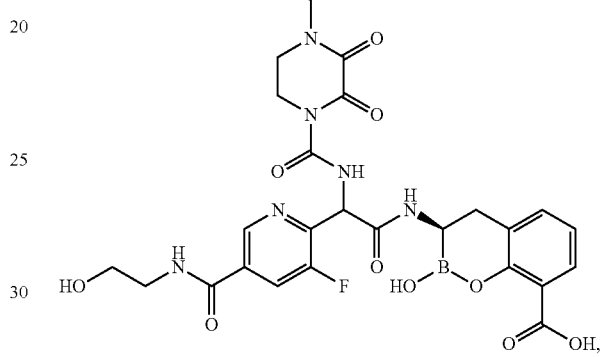
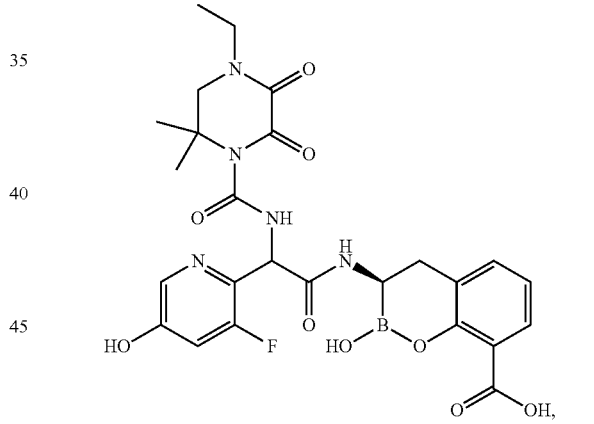
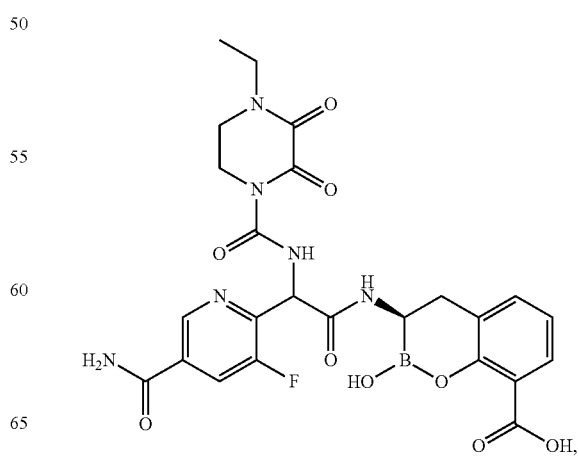

551
-continued
552
-continued
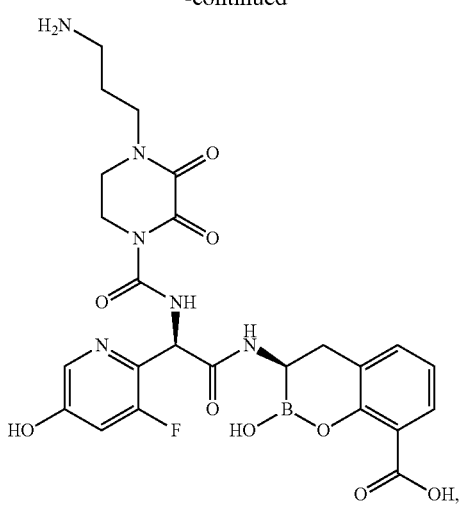
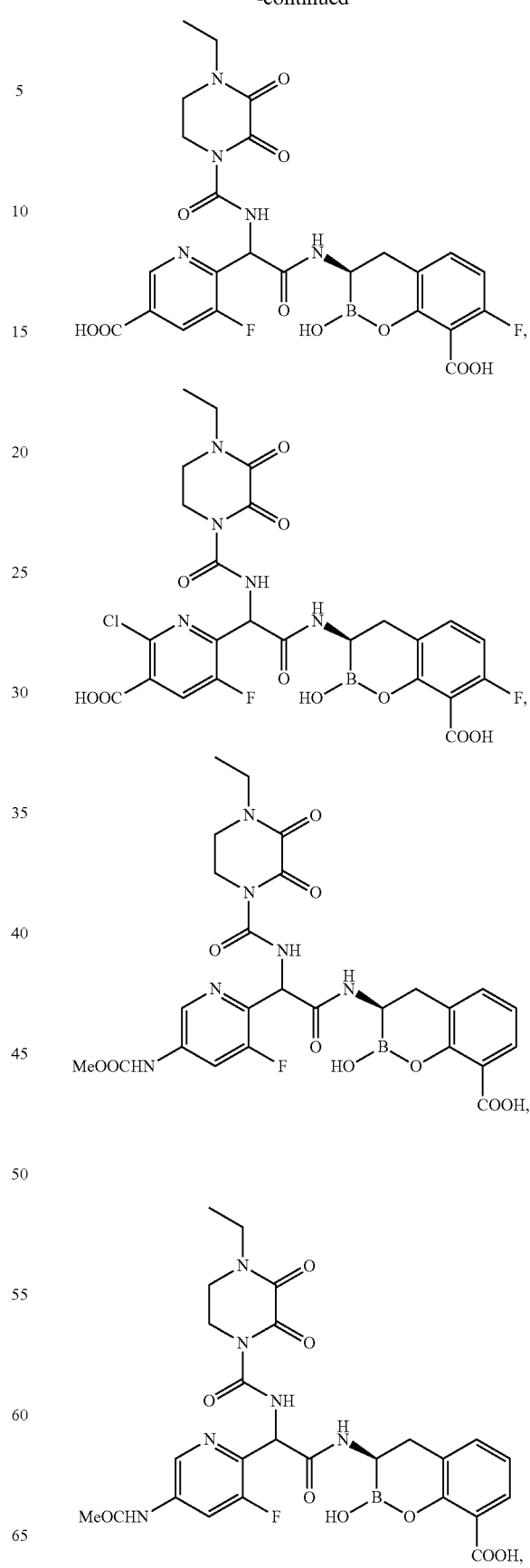

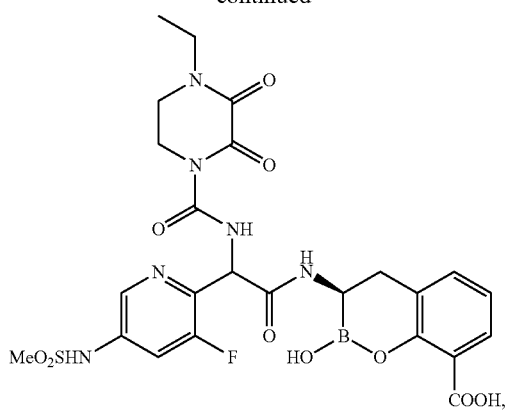

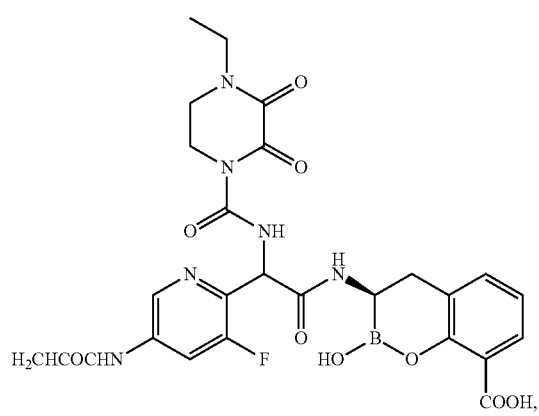

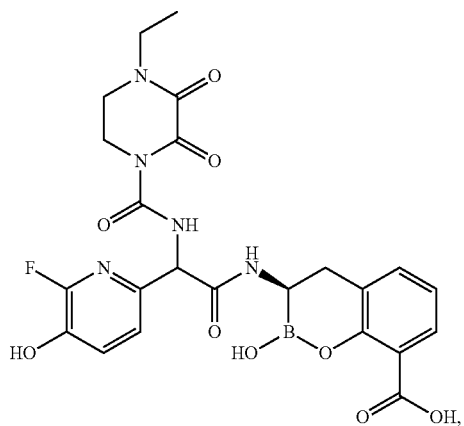

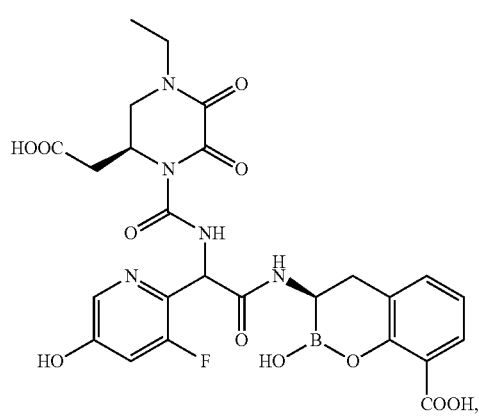

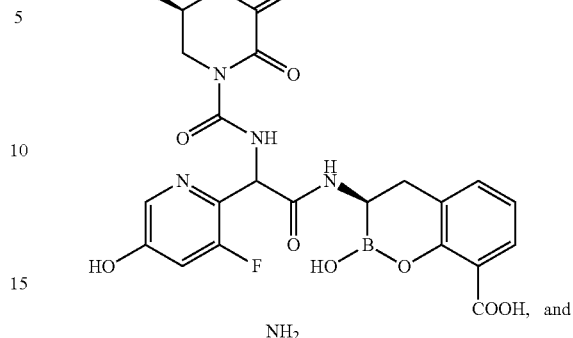

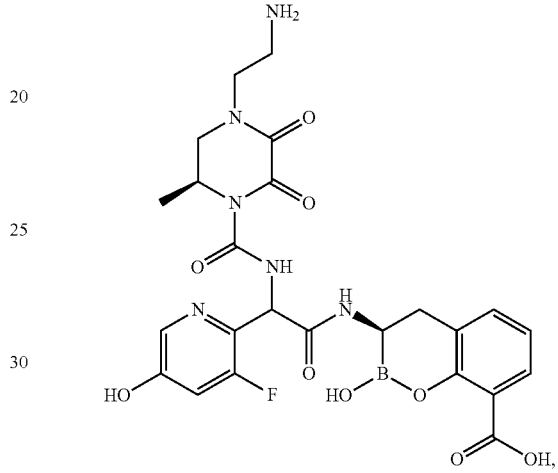

or a pharmaceutically acceptable salt, solvate, stereoisomer, tautomer, N-oxide, dimer, or trimer thereof.

14. A pharmaceutical composition comprising the compound of claim 1, or a pharmaceutically acceptable salt, solvate, stereoisomer, tautomer, or N-oxide thereof, and a pharmaceutically acceptable excipient.

15. A method of treating a bacterial infection in a subject, comprising administering to the subject an effective amount of the compound of claim 1, or a pharmaceutically acceptable salt, solvate, stereoisomer, tautomer, or N-oxide thereof.

16. The compound of claim 1, wherein $R^{90}$ is —H,

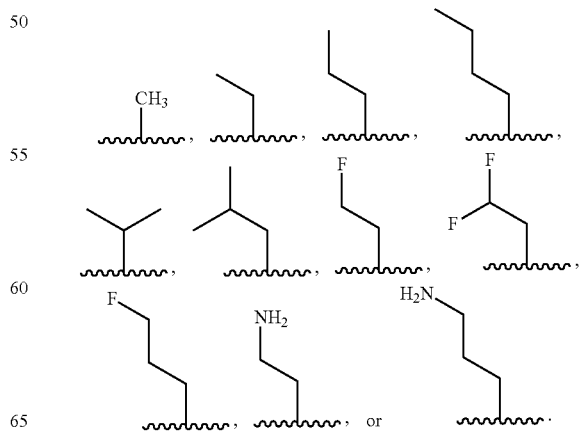

17. The compound of claim 1, wherein $R^{90}$ is

UNITED STATES PATENT AND TRADEMARK OFFICE
CERTIFICATE OF CORRECTION

PATENT NO. : 12,173,018 B2
APPLICATION NO. : 17/057593
DATED : December 24, 2024
INVENTOR(S) : Christopher J. Burns et al.

Page 1 of 3

It is certified that error appears in the above-identified patent and that said Letters Patent is hereby corrected as shown below:

In the Claims

Claim 1, Column 536, Line 47:
Replace "R is hydrogen or alkyl" with --$R^8$ is hydrogen or alkyl--

Claim 13, Column 537, Lines 50-65:

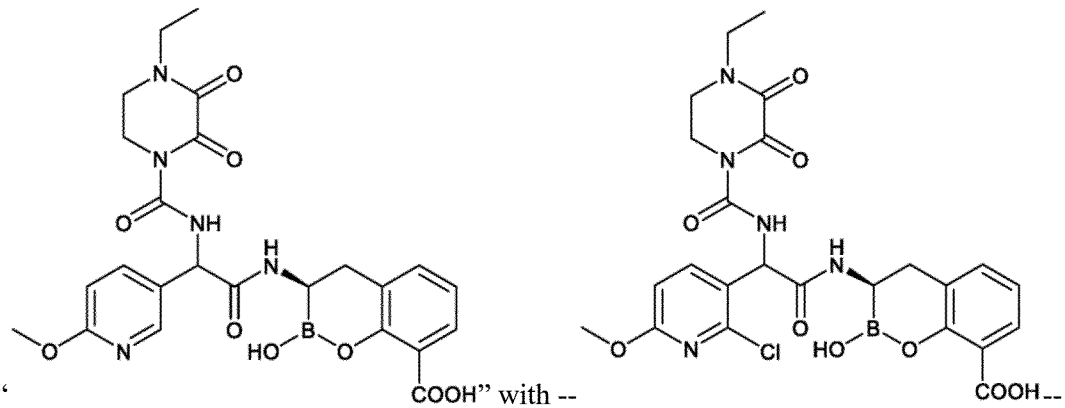

Replace " [structure] COOH" with -- [structure] COOH --

Signed and Sealed this
Eleventh Day of March, 2025

Coke Morgan Stewart
*Acting Director of the United States Patent and Trademark Office*

CERTIFICATE OF CORRECTION (continued)
U.S. Pat. No. 12,173,018 B2

Claim 13, Column 538, Lines 1-15:

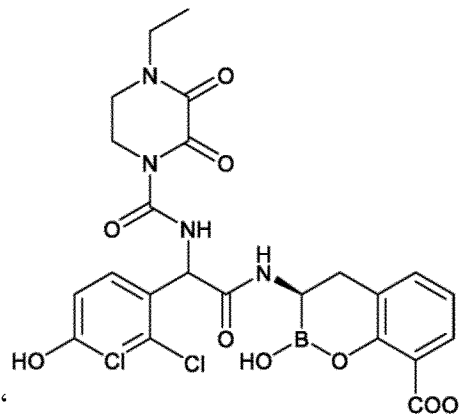

Replace " " with --   --

Claim 13, Column 542, Lines 35-50:

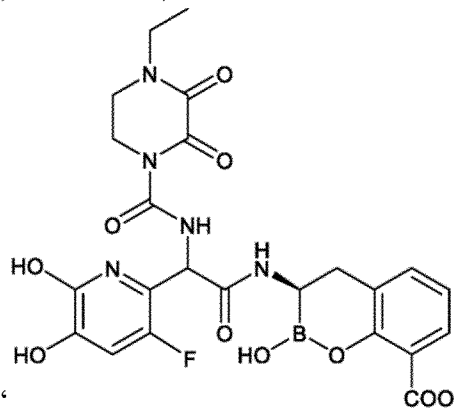

Replace " " with --   --

Claim 13, Column 543, Lines 1-15:

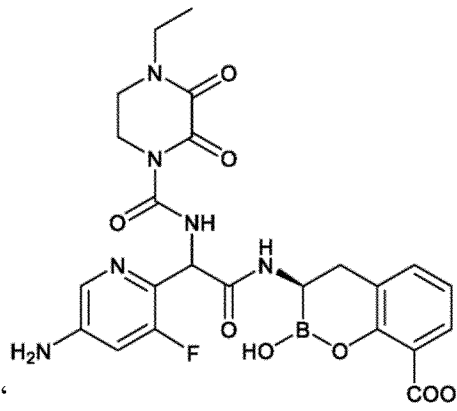

Replace " " with --   --

CERTIFICATE OF CORRECTION (continued)
U.S. Pat. No. 12,173,018 B2

Claim 13, Column 552, Lines 17-32:

Replace " 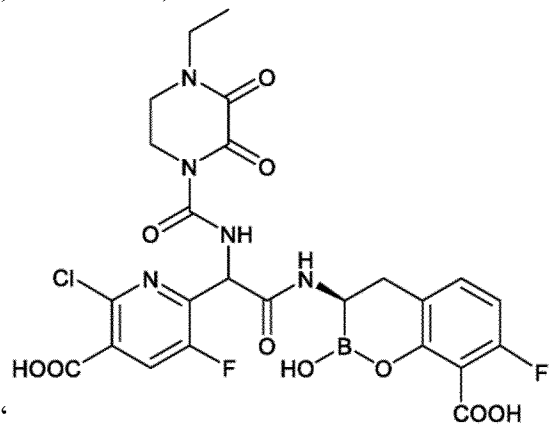 " with

-- 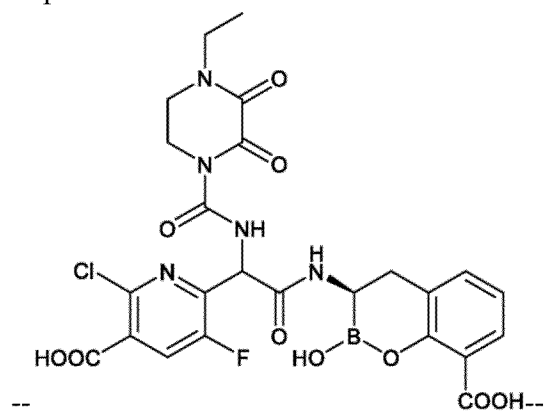 --